United States Patent
Uchida et al.

(10) Patent No.: US 9,200,008 B2
(45) Date of Patent: Dec. 1, 2015

(54) HETEROCYCLIC COMPOUND AND P27$^{Kip1}$ DEGRADATION INHIBITOR

(75) Inventors: Hiroshi Uchida, Kawasaki (JP); Akira Asagarasu, Kawasaki (JP); Teruaki Matsui, Tokyo (JP)

(73) Assignee: ASKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 13/701,896

(22) PCT Filed: Jul. 1, 2011

(86) PCT No.: PCT/JP2011/065148
§ 371 (c)(1),
(2), (4) Date: Dec. 4, 2012

(87) PCT Pub. No.: WO2012/002527
PCT Pub. Date: Jan. 5, 2012

(65) Prior Publication Data
US 2013/0079306 A1    Mar. 28, 2013

(30) Foreign Application Priority Data

Jul. 2, 2010    (JP) .................... 2010-152533

(51) Int. Cl.
| | |
|---|---|
| *C07D 471/04* | (2006.01) |
| *C07D 498/04* | (2006.01) |
| *C07D 207/34* | (2006.01) |
| *C07D 231/40* | (2006.01) |
| *C07D 277/20* | (2006.01) |
| *C07D 277/42* | (2006.01) |
| *C07D 307/68* | (2006.01) |
| *C07D 403/12* | (2006.01) |
| *C07D 405/14* | (2006.01) |
| *C07D 409/12* | (2006.01) |
| *C07D 417/12* | (2006.01) |
| *C07D 417/14* | (2006.01) |
| *C07D 487/04* | (2006.01) |
| *C07D 491/052* | (2006.01) |
| *C07F 5/02* | (2006.01) |

(52) U.S. Cl.
CPC ............ *C07D 498/04* (2013.01); *C07D 207/34* (2013.01); *C07D 231/40* (2013.01); *C07D 277/20* (2013.01); *C07D 277/42* (2013.01); *C07D 307/68* (2013.01); *C07D 403/12* (2013.01); *C07D 405/14* (2013.01); *C07D 409/12* (2013.01); *C07D 417/12* (2013.01); *C07D 417/14* (2013.01); *C07D 471/04* (2013.01); *C07D 487/04* (2013.01); *C07D 491/052* (2013.01); *C07F 5/025* (2013.01)

(58) Field of Classification Search
None
See application file for complete search history.

(56) References Cited

U.S. PATENT DOCUMENTS

| | | | |
|---|---|---|---|
| 6,440,440 B1* | 8/2002 | Meerpoel et al. ............. 424/405 |
| 2003/0114505 A1 | 6/2003 | Ueno et al. |
| 2005/0148643 A1 | 7/2005 | Rui et al. |
| 2006/0030617 A1 | 2/2006 | McKenna et al. |
| 2006/0142352 A1 | 6/2006 | McKenna et al. |
| 2006/0194843 A1 | 8/2006 | Berdini et al. |
| 2006/0194850 A1 | 8/2006 | Yamamoto et al. |
| 2008/0200509 A1 | 8/2008 | Berdini et al. |
| 2008/0269206 A1* | 10/2008 | Russell et al. ............. 514/226.2 |
| 2008/0269207 A1 | 10/2008 | Berdini et al. |
| 2009/0170911 A1 | 7/2009 | Yamamoto et al. |
| 2011/0003799 A1 | 1/2011 | Berdini et al. |

FOREIGN PATENT DOCUMENTS

| | | |
|---|---|---|
| JP | 2006-528163 | 12/2006 |
| WO | WO 9941239 A1 * | 8/1999 |
| WO | 00/26202 | 5/2000 |

(Continued)

OTHER PUBLICATIONS

"Study of Amino-Imino Tautomerism in Derivatives of 2-, 4- and 66Aminonicotinic Acid" by Smrckova et al., Collect. Czech. Chem. Commun., 2057-68 (1994).*

(Continued)

*Primary Examiner* — Theodore R West
(74) *Attorney, Agent, or Firm* — Wenderoth, Lind & Ponack, L.L.P.

(57) ABSTRACT

A novel heterocyclic compound or a salt thereof useful for selectively inhibiting the degradation of p27$^{Kip1}$ is provided. The compound or the salt thereof is represented by the following formula (1):

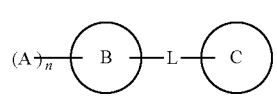

(1)

wherein A represents an alkyl group, a cycloalkyl group, an aryl group or a heterocyclic group, the group A may have a substituent; the ring B represents a 5- to 8-membered monocyclic heterocyclic ring or a condensed ring containing the monocyclic heterocyclic ring, the ring B may have a substituent; the ring C represents an aromatic ring, the ring C may have a substituent; L represents a linker comprising a main chain having 3 to 5 atoms selected from the group consisting of a carbon atom, a nitrogen atom, an oxygen atom and a sulfur atom, wherein at least one atom in the main chain is a hetero atom selected from the group consisting of a nitrogen atom, an oxygen atom and a sulfur atom, the linker L may have a substituent; and n is 0 or 1.

7 Claims, 5 Drawing Sheets

(56) References Cited

FOREIGN PATENT DOCUMENTS

| WO | 01/60819 | 8/2001 |
|---|---|---|
| WO | 03/105774 | 12/2003 |
| WO | 2005/012256 | 2/2005 |
| WO | 2005/012269 | 2/2005 |
| WO | 2006/091246 | 8/2006 |
| WO | 2007/008926 | 1/2007 |
| WO | WO 2008107677 A2 * | 9/2008 |
| WO | 2010/134082 | 11/2010 |

OTHER PUBLICATIONS

"2-(2-Thienyl)-5,6-dihydroxy-4-carboxypyrimidines as Inhibitors of the Hepatitis C Virus NS5B Polymerase: Discovery, SAR, Modeling, and Mutagenesis" by Koch et al., J. Med. Chem. 49, 1693-705 (2006).*

Japanese Patent Publication No. 2004-043438-A by Kobayashi et al. (CAPLUS Abstract, retrieved Feb. 2014).*

"Natural products in cancer chemotherapy: past, present and future" by Mann, Nature Rev. Cancer 2, 143-48 (2002).*

"Development of a sphingosine kinase 1 specific small-molecule inhibitor" by Hengst et al., Bioorg. Med. Chem. Lett. 20, 7498-502 (2010).*

International Search Report issued Oct. 25, 2011 in International (PCT) Application No. PCT/JP2011/065148.

English translation of the International Preliminary Report on Patentability and Written Opinion dated Feb. 12, 2013.

Supplementary European Search Report issued Oct. 24, 2013 in corresponding European Patent Application No. 11 80 0989.

Supplementary European Communication issued Jun. 2, 2015 in corresponding European Application No. 11 800 989.3.

* cited by examiner

Effects on expression kinetics of various substrate proteins

Effects on expression kinetics of various substrate proteins

Effects on expression kinetics of various substrate proteins

Apoptosis-inducing action (flow cytometry)

Apoptosis-inducing action (flow cytometry)

Apoptosis-inducing action (flow cytometry)

HETEROCYCLIC COMPOUND AND P27$^{Kip1}$ DEGRADATION INHIBITOR

This application is a U.S. national stage of International Application No. PCT/JP2011/065148 filed Jul. 1, 2011.

TECHNICAL FIELD

The present invention relates to a heterocyclic compound that specifically binds to the component protein Skp2 of ubiquitin ligase (SCF$^{Skp2}$) and, for example, inhibits the dissociation of p27$^{Kip1}$ from SCF$^{Skp2}$ complex, and that is useful for subsequently inhibiting the progression of the ubiquitination of p27$^{Kip1}$ and inhibiting the degradation of p27$^{Kip1}$ by a proteasome; a p27$^{Kip1}$ ubiquitination inhibitor (or a p27$^{Kip1}$ degradation inhibitor) containing the compound; and an agent for preventing and/or treating a cell proliferative disease (for example, an anticancer agent).

BACKGROUND ART p27$^{Kip1}$ is one of cyclin-dependent kinase inhibitors (CDK Inhibitors) that are a factor negatively regulating cell cycle progression. Clinical studies have revealed that the accelerated degradation of p27$^{Kip1}$ decreases the expression amount of p27$^{Kip1}$ in highly malignant cancer cells. Moreover, clinical studies suggest that the decrease in the expression amount of p27$^{Kip1}$ closely relates to the progression, recurrence and metastasis of cancer and the decrease of survival ratio of patients with cancer.

p27$^{Kip1}$ is mainly decomposed by ubiquitin-proteasome system to decrease in the amount of expression. More specifically, if threonine 187 of p27$^{Kip1}$ is phosphorylated, p27$^{Kip1}$ is isolated from a cyclin-CDK complex to specifically bind to F-box protein (Skp2) of a ubiquitin ligase comprising a SCF (Skp1/Cullin1/F-box) complex. Whereas, a ubiquitin conjugating enzyme (E2) binds to the ubiquitin ligase complex through Rbx1 in the complex, and p27$^{Kip1}$ binding to Skp2 is ubiquitinated through the enzyme. By the repetition of the ubiquitination reaction, the polyubiquitinated p27$_{Kip1}$ is recognized by a proteasome to be decomposed.

Thus the degradation mechanism of p27$^{Kip1}$ has been explained molecular-biologically, but an effective p27$^{Kip1}$ degradation inhibitor is still not known.

Incidentally, WO2005/012269 (Patent Document 1) discloses a compound represented by following formula as a physiologically active inhibitor of LPA acting as an intercellular messenger.

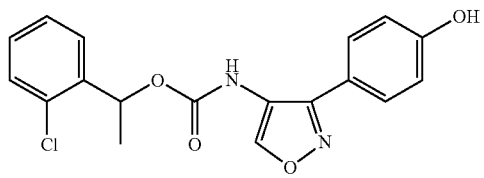 [SMILES: CC(OC(=O)Nc1conc1-c1ccc(O)cc1)c1ccccc1Cl]

This document also discloses that the compound is useful as a treating or preventing agent for a cell proliferative disease, which is one of diseases in which a LPA receptor participates. The document, however, is silent on the relationship between the compound and an intracellular protein.

RELATED ART DOCUMENTS

Patent Documents

Patent Document 1: WO2005/012269 (Claims, Examples)

SUMMARY OF THE INVENTION

Problems to be Solved by the Invention

It is therefore an object of the present invention to provide a novel heterocyclic compound or a salt thereof, a degradation inhibitor of p27$^{Kip1}$, a ubiquitination inhibitor of p27$^{Kip1}$, a preventing and/or treating agent for a cell proliferative disease, and a pharmaceutical composition.

Another object of the present invention is to provide a novel heterocyclic compound or a salt thereof effective in selectively inhibiting the degradation of p27$^{Kip1}$, a degradation inhibitor of p27$^{Kip1}$, a ubiquitination inhibitor of p27$^{Kip1}$, a preventing and/or treating agent for a cell proliferative disease, and a pharmaceutical composition.

It is still another object of the present invention to provide a novel heterocyclic compound or a salt thereof effective in selectively inhibiting the ubiquitination of p27$^{Kip1}$, a degradation inhibitor of p27$^{Kip1}$, a ubiquitination inhibitor of p27$^{Kip1}$, a preventing and/or treating agent for a cell proliferative disease, and a pharmaceutical composition.

Means to Solve the Problems

As a compound acting on the ubiquitin-proteasome system, a proteasome inhibitor VELCADE (registered trademark) (manufactured by Millennium, generic name "Bortezomib") non-selectively inhibits substrate proteins because a proteasome has a function to decompose various ubiquitinated substrate proteins. Moreover, MLN4924, which has been reported as an inhibitor of NAE (NEDD8-activating enzyme), acts on all of Cullin-RING ligases (CRLs) containing Cullin protein as a constituent element, thereby inhibiting the degradation of all substrate proteins to be ubiquitinated.

Thus, the inventors of the present invention made intensive studies to achieve the above objects based on the knowledge and finally found that a heterocyclic compound or a salt thereof having a plurality of rings linked to each other through a specific linker (1) specifically binds to the component protein Skp2 of the ubiquitin ligase (SCF$^{Skp2}$) and, for example, inhibits the dissociation p27$^{Kip1}$ from SCF$^{Skp2}$ complex, as a result can inhibit the ubiquitination of p27$^{Kip1}$ and the degradation of p27$^{Kip1}$ by the proteasome followed by the ubiquitination, (2) can selectively inhibit the degradation of p27$^{Kip1}$ at a high activity, recover the expression amount of p27$^{Kip1}$, and thus avoid increase in the non-selective expression of proteins other than p27$^{Kip1}$, and (3) can induce cell death (apoptosis) of cells having a decreased expression amount of p27$^{Kip1}$ (such as cancer cells). The present invention was accomplished based on the above findings.

That is, the heterocyclic compound or the salt thereof of the present invention is represented by the following formula (1) or a salt thereof.

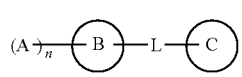

(1)

In the formula, A represents an alkyl group, a cycloalkyl group, an aryl group or a heterocyclic group, the group A may have a substituent; the ring B represents a 5- to 8-membered monocyclic heterocyclic ring or a condensed ring containing the monocyclic heterocyclic ring, the ring B may have a substituent; the ring C represents an aromatic ring, the ring C may have a substituent; L represents a linker comprising a main chain having 3 to 5 atoms selected from the group consisting of a carbon atom, a nitrogen atom, an oxygen atom and a sulfur atom, wherein at least one atom in the main chain is a hetero atom selected from the group consisting of a nitrogen atom, an oxygen atom and a sulfur atom, the linker L may have a substituent; and n is 0 or 1.

With the proviso that (i) when n is 0, the ring B is a condensed ring containing a 5- to 8-membered monocyclic heterocyclic ring,
(ii) when the ring C is a monocyclic arene ring, the ring C has a substituent,
(iii) when the linker L is a linker represented by the following formula (1-a1):

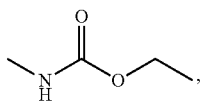

(1-a1)

the group A is a group other than 2-methylaminopyrimidin-4-yl group and the ring C is a ring other than 9-fluorenyl group,
(iv) when linker L is a linker represented by the following formula (1-a2):

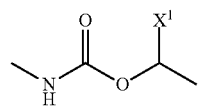

(1-a2)

wherein $X^1$ represents methyl group and the ring C is a benzene ring having a halogen atom as a substituent,
the ring B is a ring other than 3,4-isoxazole-diyl group.

In the formula (1), the linker L may contain a urethane bond or linkage [—NH—C(O)—O— or —O—C(O)—NH—]. For example, the linker L may be a linker represented by each one of the following formulae (1-a1) to (1-a6):

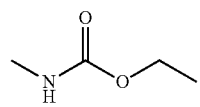

(1-a1)

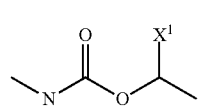

(1-a2)

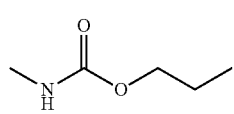

(1-a3)

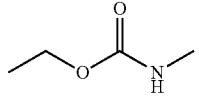

(1-a4)

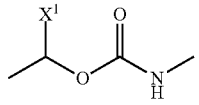

(1-a5)

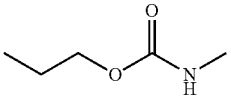

(1-a6)

wherein $X^1$ represents an alkyl group.

In the formula (1), the group A may be an aryl or heterocyclic group having at least one substituent selected from the group consisting of a halogen atom, an alkyl group, a hydroxyl group, an alkoxy group, a mercapto group and an alkylthio group, for example, may be a phenyl group having substituent(s) on 2-position and/or 4-position.

In the formula (1), the ring B may be an aromatic heterocyclic ring containing at least one hetero atom selected from the group consisting of a nitrogen atom (N), an oxygen atom (O) and a sulfur atom (S) as a constituent atom thereof. For example, the ring B may be an aromatic heterocyclic ring selected from the group consisting of a pyrrole ring, a furan ring, a thiophene ring, an imidazole ring, a pyrazole ring, a thiazole ring, an isothiazole ring, an oxazole ring, an isoxazole ring, a thiadiazole ring, a pyridine ring, a pyrimidine ring and a quinoline ring (in particular, a 5- or 6-membered monocyclic heterocyclic ring such as a thiazole ring, an isothiazole ring or a pyrazole ring).

In the formula (1), the aromatic ring represented by the ring C is not particularly limited to a specific one. For example, the aromatic ring is practically a monocyclic (non-condensed) arene ring having a substituent, a condensed arene ring which may have a substituent, or a monocyclic (non-condensed) or condensed heterocyclic ring which may have a substituent. The ring C may for example be each one of the following formulae (4-a) to (4-c):

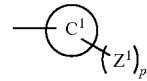

(4-a)

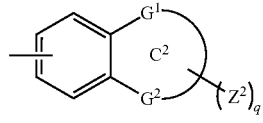

(4-b)

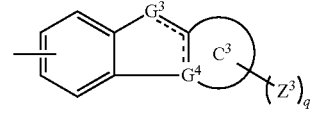

(4-c)

wherein $Z^1$ represents a halogen atom, an alkyl group, a hydroxyl group, an alkoxy group, a mercapto group, an alkylthio group, an N-alkyl-substituted amino group (such as an N,N-dialkylamino group) or an N-acyl-substituted amino group (such as an N,N-diacylamino group); $Z^2$ represents an alkyl group or an acyl group; $Z^3$ represents an alkyl group or an acyl group; the ring $C^1$ represents a $C_{6-10}$ arene ring; the ring $C^2$ represents a 5- to 8-membered heterocyclic ring comprising $G^1$ and $G^2$, the ring containing at least one hetero atom selected from the group consisting of a nitrogen atom (N), an oxygen atom (O) and a sulfur atom (S) as a constituent atom thereof; the ring $C^3$ represents a 5- to 8-membered heterocyclic ring comprising $G^4$ of the ring adjacent thereto, the ring $C^3$ containing at least one hetero atom selected from the group consisting of a nitrogen atom (N), an oxygen atom (O) and a sulfur atom (S) as a constituent atom thereof; $G^1$ to $G^3$ each represent a nitrogen atom (N), an oxygen atom (O), a sulfur atom (S), NH, CH or $CH_2$ depending on the aromaticity or nonaromaticity of the ring $C^2$ or that of the 5-membered ring adjacent to the ring $C^3$; $G^4$ represents a nitrogen atom (N), a carbon atom (C) or CH depending on the aromaticity or nonaromaticity of the 5-membered ring adjacent to the ring $C^3$; p is an integer of 1 to 5, and q is an integer of 0 to 6.

In the 5-membered ring which is adjacent to the ring $C^3$ and contains $G^3$ and $G^4$, the broken line indicates that the 5-membered ring may be an aromatic ring or a nonaromatic (aliphatic) ring.

As concrete examples of the compound or the salt thereof, there may be mentioned compounds or salts thereof, each represented by any one of the following formulae (6-a) to (6-c):

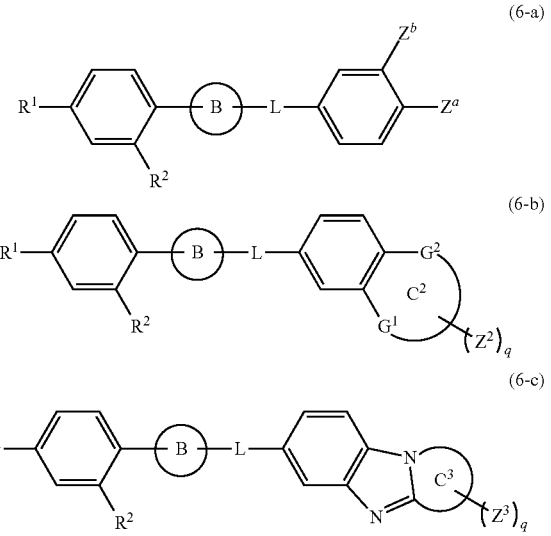

wherein $R^1$ and $R^2$ are the same or different and each represent a halogen atom, an alkyl group, a hydroxyl group, an alkoxy group, a mercapto group or an alkylthio group; the ring B represents a thiazole ring, an isothiazole ring or a pyrazole ring, the ring B may have at least one substituent selected from the group consisting of an alkyl group, a haloalkyl group, a cycloalkyl group, an aryl group, an aralkyl group and an acyl group; L represents a linker selected from the group consisting of the formulae (1-a1) to (1-a6); $Z^a$ represents a hydroxyl group, an alkoxy group, a mercapto group, an alkylthio group, an N-alkyl-substituted amino group (such as an N,N-dialkylamino group) or an N-acyl-substituted amino group (such as an N,N-diacylamino group); $Z^b$ represents a hydrogen atom, an alkyl group, a hydroxyl group or an alkoxy group; $G^1$ represents a nitrogen atom (N), CH or $CH_2$ depending on the aromaticity or non-aromaticity of the ring $C^2$; $G^2$ represents a nitrogen atom (N), an oxygen atom (O) or NH; the ring $C^2$, the ring $C^3$, $Z^2$, $Z^3$ and q have the same meanings as defined above.

The pharmaceutical composition of the present invention comprises the compound or a pharmaceutically (or physiologically) acceptable salt thereof and a carrier.

The heterocyclic compound or the salt thereof represented by the following formula (1):

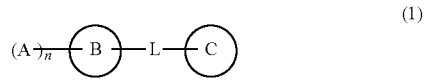
(1)

wherein A represents an alkyl group, a cycloalkyl group, an aryl group or a heterocyclic group, the group A may have a substituent; the ring B represents a 5- to 8-membered monocyclic heterocyclic ring or a condensed ring containing the monocyclic heterocyclic ring, the ring B may have a substituent; the ring C represents an aromatic ring, the ring C may have a substituent; L represents a linker comprising a main chain having 3 to 5 atoms selected from the group consisting of a carbon atom, a nitrogen atom, an oxygen atom and a sulfur atom, wherein at least one atom in the main chain is a hetero atom selected from the group consisting of a nitrogen atom, an oxygen atom and a sulfur atom, the linker L may have a substituent; and n is 0 or 1;

with the proviso that (i) when n is 0, the ring B is a condensed ring containing a 5- to 8-membered monocyclic heterocyclic ring,
(ii) when the ring C is a monocyclic arene ring, the ring C has a substituent;
specifically binds to the component protein Skp2 of ubiquitin ligase ($SCF^{Skp2}$) and, for example, inhibits the dissociation of $p27^{Kip1}$ from $SCF^{Skp2}$ complex, and as a result can effectively inhibit the ubiquitination of $p27^{Kip1}$ and the degradation of $p27^{Kip1}$ by the proteasome followed by the ubiquitination. Thus, the present invention includes a $p27^{Kip1}$ ubiquitination inhibitor or degradation inhibitor containing the compound or a pharmaceutically (or physiologically) acceptable salt thereof as an effective ingredient.

Further, the heterocyclic compound or the salt thereof represented by the following formula (1):

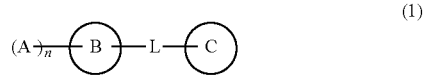
(1)

wherein A represents an alkyl group, a cycloalkyl group, an aryl group or a heterocyclic group, the group A may have a substituent; the ring B represents a 5- to 8-membered monocyclic heterocyclic ring or a condensed ring containing the monocyclic heterocyclic ring, the ring B may have a substituent; the ring C represents an aromatic ring, the ring C may have a substituent; L represents a linker comprising a main chain having 3 to 5 atoms selected from the group consisting of a carbon atom, a nitrogen atom, an oxygen atom and a sulfur atom, wherein at least one atom in the main chain is a hetero atom selected from the group consisting of a nitrogen atom, an oxygen atom and a sulfur atom, the linker L may have a substituent; n is 0 or 1;

with the proviso that (i) when n is 0, the ring B is a condensed ring containing a 5- to 8-membered monocyclic heterocyclic ring,
(ii) when the ring C is a monocyclic arene ring, the ring C has a substituent, (iii) when the linker L is a linker represented by the following formula (1-a2):

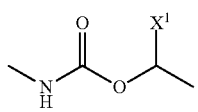
(1-a2)

wherein $X^1$ represents methyl group and the ring C is a benzene ring having a halogen atom as a substituent, the ring B is a ring other than 3,4-isoxazole-diyl group; can inhibit the decomposition of the p27$^{Kip1}$ effectively and recover the expression amount of the p27$^{Kip1}$. Thus, the compound or the salt thereof is effective in preventing and/or treating a cell proliferative disease (for example, cancer, rheumatism, diabetes, adiposis, endometriosis, prostatomegaly, and inflammation). The present invention therefore includes an agent for preventing and/or treating a cell proliferative disease, containing the compound or the pharmaceutically (or physiologically) acceptable salt thereof as an effective ingredient.

Effects of the Invention

The compound or the salt thereof of the present invention specifically binds to the component protein Skp2 of the ubiquitin ligase (SCF$^{Skp2}$) and, for example, inhibits the dissociation of p27$^{Kip1}$ from SCF$^{Skp2}$ complex, as a result can inhibit the ubiquitination of p27$^{Kip1}$ and the degradation of p27$^{Kip1}$ by the proteasome followed by the ubiquitination. Moreover, since, differently from proteasome inhibitor or the like, the compound or the salt thereof can selectively inhibit the degradation of p27$^{Kip1}$, the degradation or increased expression of proteins other than p27$^{Kip1}$ can be avoided. Further, since the action of the compound or the salt thereof of the present invention on cells having a decreased expression of p27$^{Kip1}$ (such as cancer cells) allows the expression amount of p27$^{Kip1}$ to be recovered to induce the cell death (apoptosis). The compound or the salt thereof is useful for preventing and/or treating a cell proliferative disease (for example, cancer, rheumatism, diabetes, adiposis, endometriosis, prostatomegaly, and inflammation).

There is a report that the component protein Skp2 of the ubiquitin ligase (SCF$^{Skp2}$) is overexpressed in highly malignant cancer cells in which the degradation of p27$^{Kip1}$ is accelerated. For such highly malignant cancer cells, the compound or the salt thereof of the present invention binds to Skp2 due to a high activity thereof and can selectively inhibit the ubiquitination of p27$^{Kip1}$, effectively induce apoptosis accompanied by the expression amount of p27$^{Kip1}$ and show a high anticancer action.

DESCRIPTION OF EMBODIMENTS

Figure 1:
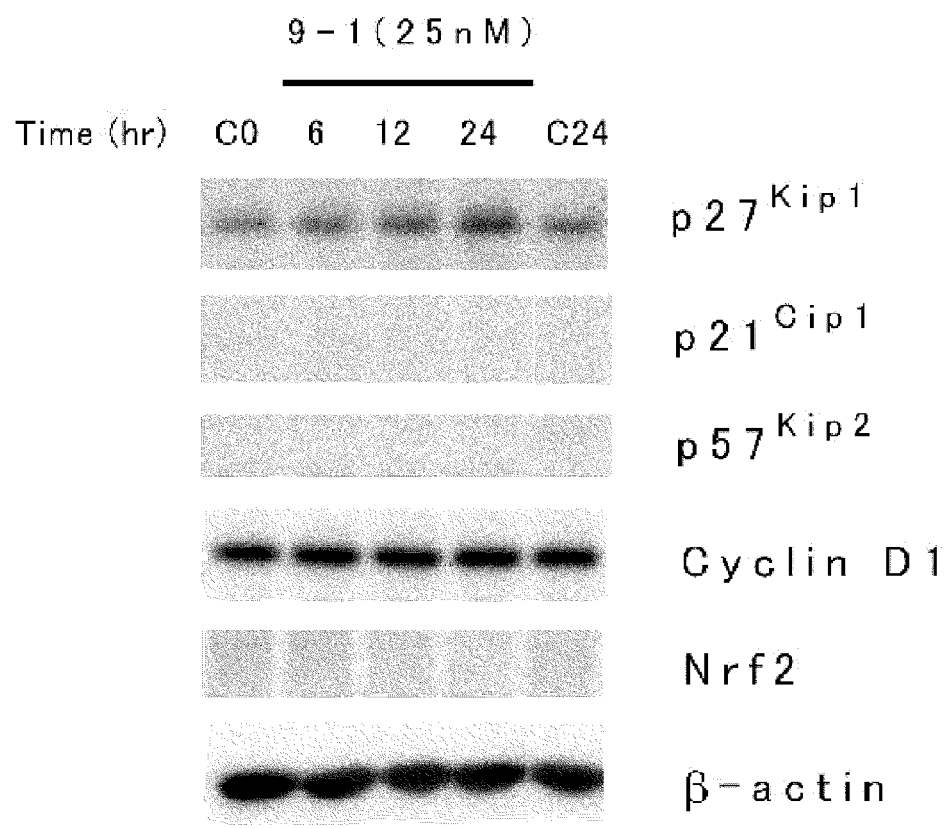
FIG. 1 shows results of the compound of Example 9-1 in Test Example 3.

In the formula (1), the alkyl group represented by the group A may include, for example, a straight chain or branched chain alkyl group (for example, a $C_{1-10}$alkyl group, preferably a $C_{1-6}$alkyl group, and more preferably a $C_{1-4}$alkyl group) such as methyl, ethyl, propyl, isopropyl, butyl, t-butyl, pentyl, hexyl, 2-ethylhexyl, heptyl or octyl group.

As the cycloalkyl group represented by the group A, there may be mentioned a $C_{3-10}$cycloalkyl group (preferably a $C_{4-8}$cycloalkyl group, and more preferably a $C_{5-6}$cycloalkyl group) such as cyclopropyl, cyclobutyl, cyclopentyl, cyclohexyl, cycloheptyl or cyclooctyl group; a crosslinked cyclic cycloalkyl group (e.g., abi- or tricycloalkyl group) such as adamantly group or norbornyl group.

The aryl group represented by the group A may include, for example, a $C_{6-10}$aryl group such as phenyl or naphthyl group.

The heterocyclic group represented by the group A may include various heterocyclic groups, each having an aromatic or nonaromatic 5- to 8-membered heterocyclic ring, for example, a heterocyclic group containing at least one hetero atom selected from the group consisting of a nitrogen atom, an oxygen atom and a sulfur atom [for example, a 5- or 6-membered heterocyclic group, and a condensed ring group of a 5- or 6-membered heterocyclic ring and a carbocyclic (hydrocarbon) ring]. As the 5- or 6-membered heterocyclic group, for example, there may be mentioned a heterocyclic group containing an oxygen atom as a hetero atom, such as a furyl group (such as 2- or 3-furyl group); a heterocyclic group containing a sulfur atom as a hetero atom, such as a thienyl group (such as 2- or 3-thienyl group); a heterocyclic group containing a nitrogen atom as a hetero atom, such as a pyridyl group (such as 2-, 3- or 4-pyridyl group) or a pyrazolyl group (such as pyrazol-2-yl group); and a heterocyclic group containing sulfur atom and nitrogen atom as hetero atoms, such as a thiazolyl group (such as thiazol-5-yl group). The condensed ring group of a 5- or 6-membered heterocyclic ring and a carbocyclic ring (such as a benzene ring) may include, for example, a condensed ring group of a heterocyclic ring containing a sulfur atom as a hetero atom and a carbocyclic ring (such as a benzene ring) [e.g., a benzothienyl group (or thianaphthenyl group) (such as benzo[b]thiophen-3-yl group (or thianaphthen-3-yl group))]; a condensed ring group of a heterocyclic ring containing a nitrogen atom as a hetero atom and a carbocyclic ring (such as a benzene ring) [e.g., an isoquinolyl group (such as isoquinolin-1-yl group)]; and a condensed ring group of a heterocyclic ring containing an oxygen atom as a hetero atom and a carbocyclic ring (such as a benzene ring) [e.g., a coumaryl group (such as coumaran-5- or 7-yl group) and an alkylenedioxyphenyl group (e.g., a $C_{1-4}$alkylenedioxyphenyl group such as 2,3-ethylenedioxyphenyl group)].

The group A may have a substituent. The substituent may include a halogen atom, an alkyl group, a cycloalkyl group, an aryl group, a hydroxyl group, an alkoxy group, a mercapto group, an alkylthio group, an amino group, an N-substituted amino group, and others. The substituent may further have a substituent (such as a halogen atom) to form a haloalkyl group, a haloalkoxy group, and others.

The halogen atom as the substituent of the group A may include a fluorine atom and a chlorine atom.

The alkyl group as the substituent of the group A may include the above-mentioned $C_{1-6}$alkyl group (preferably a $C_{1-4}$alkyl group). As the haloalkyl group as the substituent of the group A, there may be mentioned a straight chain or branched chain haloC$_{1-6}$alkyl group, for example, a mono- to per-fluoroC$_{1-6}$alkyl group (preferably a mono- to per-fluoroC$_{1-4}$alkyl group) such as a fluoromethyl group (e.g., trifluoromethyl group), a fluoroethyl group (e.g., 2,2,2-trifluoroethyl group and perfluoroethyl group), or a fluoropropyl group (e.g., 3,3,3,2,2-pentafluoropropyl group and perfluoropropyl group); and chloroalkyl groups corresponding to these fluoroalkyl groups.

As the substituent of the group A, the cycloalkyl group may include a C$_{3-10}$cycloalkyl group (preferably a C$_{4-8}$cycloalkyl group, and more preferably a C$_{5-6}$cycloalkyl group) such as cyclopentyl or cyclohexyl group; the aryl group may include a C$_{6-10}$aryl group such as phenyl or naphthyl group.

The alkoxy group as the substituent of the group A may include a straight chain or branched chain alkoxy group (e.g., a C$_{1-10}$alkoxy group, preferably a C$_{1-6}$alkoxy group, and more preferably a C$_{1-4}$alkoxy group) such as methoxy, ethoxy, propoxy, isopropoxy, n-butoxy, or t-butoxy group. The haloalkoxy group as the substituent of the group A may include a straight chain or branched chain haloC$_{1-6}$alkoxy group, for example, a mono- to per-fluoroC$_{1-6}$alkoxy group (preferably a mono- to per-fluoroC$_{1-4}$alkoxy group) such as a fluoromethoxy group (e.g., trifluoromethoxy group), a fluoroethoxy group (e.g., 2,2,2-trifluoroethoxy group and perfluoroethoxy group), or a fluoropropoxy group (e.g., 3,3,3,2,2-pentafluoropropoxy group and perfluoropropoxy group); and chloroalkoxy groups corresponding to these fluoroalkoxy groups.

The alkylthio group as the substituent of the group A may include a straight chain or branched chain alkylthio group (e.g., a C$_{1-10}$alkylthio group, preferably a C$_{1-6}$alkylthio group, and more preferably a C$_{1-4}$alkylthio group) such as methylthio, ethylthio, propylthio, isopropylthio, butylthio, or t-butylthio group.

The N-substituted amino group as the substituent of the group A may include an N-monosubstituted amino group [for example, an N-alkylamino group (e.g., an N—C$_{1-6}$alkylamino group, and preferably an N—C$_{1-4}$alkylamino group) such as N-methylamino or N-ethylamino group; and an N-acylamino group (e.g., an N—(C$_{1-6}$alkyl-carbonyl)amino group, and preferably an N—(C$_{1-4}$alkyl-carbonyl)amino group) such as N-acetylamino or N-propionylamino group]; an N,N-disubstituted amino group [for example, an N,N-dialkylamino group (e.g., an N,N-diC$_{1-6}$alkylamino group, and preferably an N,N-diC$_{1-4}$alkylamino group) such as N,N-dimethylamino, N,N-diethylamino, or N-methyl-N-ethylamino group; and an N,N-diacylamino group (e.g., an N,N-di(C$_{1-6}$alkyl-carbonyl)amino group, and preferably an N,N-di(C$_{1-4}$alkyl-carbonyl)amino group) such as N,N-diacetylamino group]; and others.

The alkyl group having a substituent may include an alkyl group having at least one substituent selected from the group consisting of a halogen atom and an aryl group, for example, a haloC$_{1-6}$alkyl group (preferably a haloC$_{1-4}$alkyl group) as exemplified above and an arylalkyl group (or aralkyl group) [e.g., a C$_{6-10}$arylC$_{1-6}$alkyl group (preferably a C$_{6-10}$arylC$_{1-4}$alkyl group) such as benzyl or phenethyl group].

As the cycloalkyl group having a substituent, there may be mentioned an alkylcycloalkyl group [for example, a C$_{1-6}$alkylC$_{5-6}$cycloalkyl group (preferably a C$_{1-4}$alkylC$_{5-6}$cycloalkyl group) such as 2-methylcyclohexyl group or 2-ethylcyclohexyl group], and others.

The aryl group having a substituent may include, for example, an aryl group (e.g., a C$_{6-24}$aryl group, preferably a C$_{6-20}$aryl group, and more preferably a C$_{6-18}$aryl group) having at least one substituent selected from the group consisting of a halogen atom, an alkyl group, a haloalkyl group, a hydroxyl group, an alkoxy group, a haloalkoxy group, a mercapto group, an alkylthio group and an N-substituted amino group.

Concretely, the monosubstituted aryl group may include an aryl group having one substituent selected from the group consisting of a halogen atom, an alkyl group, a haloalkyl group, a hydroxyl group, an alkoxy group, a haloalkoxy group, and an N-alkyl-substituted amino group [for example, a haloaryl group (e.g., a haloC$_{6-10}$aryl group) such as 2-, 3- or 4-chlorophenyl group or 2-, 3- or 4-fluorophenyl group; an alkylaryl group (e.g., a C$_{1-6}$alkylC$_{6-10}$aryl group, and preferably a C$_{1-4}$alkylC$_{6-10}$aryl group) such as 2-, 3- or 4-methylphenyl group or 2-, 3- or 4-ethylphenyl group; a mono- to per-haloC$_{1-6}$alkylC$_{6-10}$aryl group (e.g., a mono- to per-fluoroC$_{1-6}$alkylC$_{6-10}$aryl group, and preferably a mono- to per-fluoroC$_{1-4}$alkylC$_{6-10}$aryl group) such as 2- or 4-trifluoromethylphenyl group or 2- or 4-trichloromethylphenyl group; a hydroxyaryl group (e.g., a hydroxyC$_{6-10}$aryl group) such as 2- or 4-hydroxyphenyl group; an alkoxyaryl group (e.g., a C$_{1-6}$alkoxyC$_{6-10}$aryl group, and preferably a C$_{1-4}$alkoxyC$_{6-10}$aryl group) such as 2- or 4-methoxyphenyl group, 2- or 4-ethoxyphenyl group, or 2- or 4-propoxyphenyl group; a haloC$_{1-6}$alkoxyC$_{6-10}$aryl group (a mono- to per-fluoroC$_{1-6}$alkoxyC$_{6-10}$aryl group, and preferably a mono- to per-fluoroC$_{1-4}$alkoxyC$_{6-10}$aryl group); and an N,N-dialkylaminoaryl group (e.g., an N,N-diC$_{1-6}$alkylaminoC$_{6-10}$aryl group, and preferably an N,N-diC$_{1-4}$alkylaminoC$_{6-10}$aryl group) such as 4-(N,N-dimethylamino)phenyl group].

As the disubstituted aryl group, for example, there may be mentioned an aryl group having two substituents, which may be the same or different from each other, selected from the group consisting of a halogen atom, an alkyl group, a hydroxyl group, an alkoxy group, a mercapto group and an alkylthio group [for example, a dihaloaryl group (e.g., a dihaloC$_{6-10}$aryl group) such as 2,3-, 2,4- or 3,4-dichlorophenyl group, 2,3-, 2,4- or 3,4-difluorophenyl group, 2-chloro-4-fluorophenyl group or 2-fluoro-4-chlorophenyl group; a dialkylaryl group (e.g., a diC$_{1-6}$alkylC$_{6-10}$aryl group, and preferably a diC$_{1-4}$alkylC$_{6-10}$aryl group) such as 2,3-, 2,4- or 2,5-dimethylphenyl group; a dihydroxyaryl group (e.g., a dihydroxyC$_{6-10}$aryl group) such as 2,3-, 2,4-, 2,6- or 3,4-dihydroxyphenyl group; a dialkoxyaryl group (e.g., a diC$_{1-6}$alkoxyC$_{6-10}$aryl group, and preferably a diC$_{1-4}$alkoxyphenyl group) such as 2,3-, 2,4-, 2,6- or 3,4-dimethoxyphenyl group; an alkyl-haloaryl group (e.g., a C$_{1-6}$alkyl-haloC$_{6-10}$aryl group, and preferably a C$_{1-4}$alkyl-haloC$_{6-10}$aryl group) such as 2-methyl-3- (or 4-)chlorophenyl group or 2-methyl-3- (or 4-)fluorophenyl group; a hydroxy-haloaryl group (e.g., a hydroxy-haloC$_{6-10}$aryl group) such as 2-hydroxy-4-chlorophenyl group, 2-hydroxy-4-fluorophenyl group, 2-chloro-4-hydroxyphenyl group or 2-fluoro-4-hydroxyphenyl group; an alkoxy-haloaryl group (e.g., a C$_{1-6}$alkoxy-haloC$_{6-10}$aryl group, and preferably a C$_{1-4}$alkoxy-haloC$_{6-10}$aryl group) such as 2-methoxy-4-chlorophenyl group, 2-methoxy-4-fluorophenyl group, 2-chloro-4-methoxyphenyl group or 2-fluoro4-methoxyphenyl group; an alkyl-hydroxyaryl group (e.g., a C$_{1-6}$alkyl-hydroxyC$_{6-10}$aryl group, and preferably a C$_{1-4}$alkyl-hydroxyC$_{6-10}$aryl group) such as 2-methyl-3- (or 4-)hydroxyphenyl group or 2-hydroxy-4-methylphenyl group; and an alkyl-alkoxyaryl group (e.g., a C$_{1-6}$alkyl-C$_{1-6}$alkoxyC$_{6-10}$aryl group, and preferably a C$_{1-4}$alkyl-C$_{1-4}$alkoxyC$_{6-10}$aryl group) such as 2-methyl-3- (or 4-)methoxyphenyl group or 2-methoxy-4-methylphenyl group.

The heterocyclic group having a substituent may include a group comprising a heterocyclic ring (e.g., a 5- to 8-membered ring, preferably a 5- to 7-membered heterocyclic group, more preferably a 5- or 6-membered heterocyclic group) that is a heterocyclic ring (e.g., an aromatic heterocyclic ring) containing at least one hetero atom selected from the group consisting of a nitrogen atom, an oxygen atom and a sulfur atom and having at least one substituent selected from the group consisting of a halogen atom, an alkyl group, a hydroxyl group, an alkoxy group, a mercapto group and an alkylthio group. Concretely, there may be mentioned a heterocyclic group having a halogen atom and/or an alkyl group as substituent(s), for example, a heterocyclic group having a halogen atom as a substituent [for example, a 5- or 6-membered heterocyclic group containing a nitrogen atom as a hetero atom, e.g., a halopyridyl group (e.g., a chloropyridyl group such as 3-chloropyridin-2-yl group, and a fluoropyridyl group corresponding to each of the chloropyridyl groups); a 5- or 6-membered heterocyclic group containing an oxygen atom as a hetero atom, e.g., a halofuryl group (e.g., a chlorofuryl group such as 3-chlorofuran-2-yl group, and a fluorofuryl group corresponding to each of the chlorofuryl groups); and a 5- or 6-membered heterocyclic group containing a sulfur atom as a hetero atom, e.g., a halothienyl group (e.g., a chlorothienyl group such as 3- or 5-chlorothiophen-2-yl group or 3,5-dichlorothiophen-2-yl group, and a fluorothienyl group corresponding to each of the chlorothienyl groups)] and a heterocyclic group having an alkyl group as a substituent [for example, a 5- or 6-membered heterocyclic group containing a nitrogen atom as a hetero atom, e.g., an alkylpyridyl group (e.g., a mono- or di-$C_{1-4}$alkylpyridyl group such as 3-methylpyridin-2-yl group or 4-methylpyridin-3-yl group) and an alkylpyrazolyl group (e.g., a mono- or di-$C_{1-4}$alkylpyrazolyl group such as (1,4-dimethyl)pyrazol-2-yl group); and a 5- or 6-membered heterocyclic group containing a sulfur atom and a nitrogen atom as hetero atoms, e.g., an alkylthiazolyl group (e.g., a mono- or di-$C_{1-4}$alkylthiazolyl group such as (4-methyl)thiazol-5-yl group or (2,4-dimethyl)thiazol-5-yl group)].

The preferred group A includes an aryl or heterocyclic group having a substituent (for example, an aryl or heterocyclic group having at least one substituent selected from the group consisting of a halogen atom, an alkyl group, a hydroxyl group, an alkoxy group, a mercapto group and an alkylthio group). The number of substituents of the aryl or heterocyclic group is, for example, about 1 to 5, preferably about 1 to 4, and more preferably about 1 to 3 (e.g., 1 or 2), depending on the species of the aryl or heterocyclic group. There is no particular limitation as to the position of the substituent in the aryl or heterocyclic group. For example, for a phenyl group or a 5- or 6-membered heterocyclic group, the substituent may be located at 2-, 3-, or 4-position. If the number of substituents is not less than 2, the position of the substituent practically contains at least 2-position and/or 4-position.

The further preferred group A includes a $C_{6-10}$aryl group having a substituent, for example, a group represented by the following formula (2):

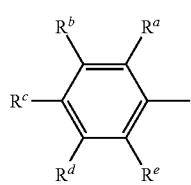

(2)

wherein $R^a$ to $R^e$ are the same or different and each represent a hydrogen atom, a halogen atom, an alkyl group, a haloalkyl group, a hydroxyl group, an alkoxy group, a haloalkoxy group, a mercapto group or an alkylthio group; with the proviso that groups in which all of $R^a$ to $R^e$ are hydrogen atoms are excluded.

The halogen atom, alkyl group, haloalkyl group, alkoxy group, haloalkoxy group or alkylthio group represented by each of $R^a$ to $R^e$ may include the same halogen atom (such as a fluorine atom or a chlorine atom), $C_{1-4}$alkyl group (such as a $C_{1-2}$alkyl group), fluoro$C_{1-4}$alkyl group (such as a fluoro$C_{1-2}$alkyl group), $C_{1-4}$alkoxy group (such as a $C_{1-2}$alkoxy group), fluoro$C_{1-4}$alkoxy group (such as a fluoro$C_{1-2}$alkoxy group) and $C_{1-4}$alkylthio group (such as a $C_{1-2}$alkylthio group) as the substituent of the group A.

The particularly preferred group A includes a mono- or di-substituted aryl group (such as a mono- or di-substituted $C_{6-10}$aryl group), for example, a phenyl group having substituent (s) at 2-position and/or 4-position. That is, the preferred one includes a group represented by the formula (2) in which each of $R^b$, $R^d$ and $R^e$ is a hydrogen atom and at least one of $R^a$ and $R^c$ is a halogen atom, an alkyl group, a haloalkyl group, a hydroxyl group, an alkoxy group, a haloalkoxy group, a mercapto group or an alkylthio group [for example, a group represented by the formula (2) in which each of $R^b$, $R^d$ and $R^e$ is a hydrogen atom and the combination of $R^a$ and $R^c$ ($R^a$, $R^c$) is (a halogen atom, a halogen atom), (an alkyl group, an alkyl group), (a hydroxyl group, a hydroxyl group), (an alkoxy group, an alkoxy group), (an alkyl group, a halogen atom), (a hydroxyl group, a halogen atom), (an alkoxy group, a halogen atom), (a hydroxyl group, an alkyl group) or (an alkoxy group, an alkyl group)]. Concretely, the group A is preferably a 2,4-dihalophenyl group, a 2,4-di$C_{1-4}$alkylphenyl group, a 2,4-dihydroxyphenyl group, a 2,4-di$C_{1-4}$alkoxyphenyl group, a 2-$C_{1-4}$alkyl-4-halophenyl group, a 2-hydroxy-4-halophenyl group, a 2-$C_{1-4}$alkoxy-4-halophenyl group, a 2-hydroxy-4-$C_{1-4}$alkylphenyl group, a 2-$C_{1-4}$alkoxy-4-$C_{1-4}$alkylphenyl group, or the like.

In the formula (1), it is preferable that n be 0 or 1 (the group A be not essential) and particularly preferable that n be 1 (the formula (1) have the group A).

The heterocyclic ring represented by the ring B may be a nonaromatic heterocyclic ring or an aromatic heterocyclic ring or may be a monocyclic heterocyclic ring or a condensed heterocyclic ring. The heterocyclic ring represented by the ring B is not particularly limited to a specific one and may for example be a heterocyclic ring (e.g., an aromatic heterocyclic ring) containing at least one hetero atom selected from the group consisting of a nitrogen atom (N), an oxygen atom (O) and a sulfur atom (S), as a constituent atom thereof. The number of hetero atoms is not particularly limited to a specific one and may for example be about 1 to 4 (preferably about 1 to 3, particularly about 1 to 2).

The monocyclic heterocyclic ring is, for example, a 5- to 8-membered heterocyclic ring, preferably a 5- to 7-membered heterocyclic ring, and more preferably a 5- or 6-membered heterocyclic ring.

The 5-membered monocyclic heterocyclic ring may include a heterocyclic ring containing one hetero atom as a constituent atom thereof (e.g., pyrrole, furan, and thiophene), a heterocyclic ring containing a plurality of (e.g., 2 to 3) hetero atoms as constituent atoms thereof (e.g., a heterocyclic ring containing a nitrogen atom, such as imidazole, pyrazole or triazole; a heterocyclic ring containing an oxygen atom and a nitrogen atom, such as oxazole, isoxazole or oxadiazole (or furazan); and a heterocyclic ring containing a sulfur atom and a nitrogen atom, such as triazole, isothiazole or thiadiazole), hydrogenated products of these rings, and others.

As the 6-membered heterocyclic ring, there may be mentioned a heterocyclic ring containing one hetero atom as a constituent atom thereof (e.g., pyridine and pyran), a heterocyclic ring containing a plurality of (e.g., 2 to 4) hetero atoms as constituent atoms thereof (e.g., a heterocyclic ring containing a nitrogen atom, such as pyridazine, pyrimidine, pyrazine, triazine or tetrazine), hydrogenated products of these rings, and others.

The condensed heterocyclic ring may include a condensed ring (e.g., a 6 to 15-membered ring, and preferably a 8 to 13-membered ring) containing the monocyclic 5- to 8-membered heterocyclic ring, for example, a condensed ring of (i) a benzene ring, (ii) a $C_{4-8}$aliphatic carbocyclic ring or a 5- to 8-membered heterocyclic ring containing at least an oxygen atom as a hetero atom, and (iii) a 5- to 8-membered heterocyclic ring containing at least a nitrogen atom as a hetero atom [for example, a condensed ring of (i) a benzene ring, (ii) a cycloalkane ring (e.g., a $C_{4-8}$cycloalkane ring such as cyclohexane ring), a cycloalkene ring (e.g., a $C_{4-8}$cycloalkene ring such as cyclohexene ring) or a 5- or 6-membered ring selected from the group consisting of a chroman ring, a isochroman ring, chromene ring and an isochromene ring, and (iii) a pyrrole ring (e.g., indenopyrazole and chromenopyrazole); and hydrogenated product of these rings]. Adjacent two substituents of the monocyclic 5- to 8-membered heterocyclic ring may be bonded to each other to form the condensed heterocyclic ring. Moreover, the condensed heterocyclic ring may be formed by bonding the substituent of the ring A and the substituent on the monocyclic 5- to 8-membered heterocyclic ring to each other [in this case, n is 0 in the formula (1)].

The hetero atom (particularly a nitrogen atom) or carbon atom of the ring B may have a substituent. The substituent may include an alkyl group, a cycloalkyl group, an aryl group, an aralkyl group, an acyl group, an amino group, an N-substituted amino group, and other groups. If necessary, the substituents may further have a substituent [e.g., a halogen atom, a hydroxyl group, and an alkoxy group (a straight chain or branched chain $C_{1-4}$alkoxy group)] to form a haloalkyl group, a hydroxyaryl group, an alkoxyaryl group, or the like. The amino group and the N-substituted amino group are practically located at a carbon atom of the heterocyclic ring of the ring B.

The alkyl group, cycloalkyl group, aryl group and aralkyl group as the substituent of the ring B may include the same straight chain or branched chain $C_{1-6}$alkyl group, $C_{3-10}$cycloalkyl group, $C_{6-10}$aryl group and $C_{6-10}$aryl$C_{1-6}$alkyl group as the group A, respectively.

The acyl group as the substituent of the ring B may include, for example, formyl group, a straight chain or branched chain $C_{1-10}$alkyl-carbonyl group (preferably a $C_{1-6}$alkyl-carbonyl group, and more preferably a $C_{1-4}$alkyl-carbonyl group) such as acetyl, propionyl or butylyl group; a $C_{3-10}$cycloalkyl-carbonyl group such as cyclohexylcarbonyl group; a $C_{6-10}$arylcarbonyl group such as benzoyl group; and a $C_{6-10}$aryl-$C_{1-4}$alkylcarbonyl group such as benzylcarbonyl group.

As the N-substituted amino group as the substituent of the ring B, there may be mentioned the same N-monosubstituted amino group [for example, an N—$C_{1-6}$alkylamino group and an N—($C_{1-6}$alkyl-carbonyl)amino group] and N,N-disubstituted amino group [for example, an N,N-di$C_{1-6}$alkylamino group and an N,N-di($C_{1-6}$alkyl-carbonyl)amino group] as the substituent of the group A.

Examples of the haloalkyl group as the substituent of the ring B may include the same straight chain or branched chain halo$C_{1-6}$alkyl group as the group A. Moreover, as the substituent of the ring B, the hydroxyaryl group may include a hydroxy$C_{6-10}$aryl group such as hydroxyphenyl or hydroxynaphthyl group; the alkoxyaryl group may include a $C_{1-6}$alkoxy$C_{6-10}$aryl group such as methoxyphenyl, methoxynaphthyl, ethoxyphenyl or ethoxynaphthyl group.

Among these substituents, an alkyl group, a haloalkyl group, a cycloalkyl group, an aryl group, an aralkyl group, a hydroxyaryl group, an alkoxyaryl group, and an acyl group are preferred. As the alkyl group, a $C_{1-4}$alkyl group such as methyl, ethyl, propyl or isopropyl group is preferred. The preferred haloalkyl group includes a halo$C_{1-4}$alkyl group [for example, a mono- to per-fluoro$C_{1-3}$alkyl group (e.g., a mono- to per-fluoro$C_{1-2}$alkyl group)] such as trihalomethyl group. The cycloalkyl group preferably includes a $C_{3-6}$cycloalkyl group such as cyclopropyl group. As the aryl group, a $C_{6-10}$aryl group such as phenyl group is preferred. As the aralkyl group, the preferred one includes a $C_{6-10}$aryl$C_{1-4}$alkyl group (e.g., a $C_{6-10}$aryl$C_{1-2}$alkyl group) such as benzyl group. The hydroxyaryl group preferably includes a hydroxy$C_{6-10}$aryl group such as hydroxyphenyl group. As the alkoxyaryl group, a $C_{1-4}$alkoxy$C_{6-10}$aryl group (e.g., a $C_{1-2}$alkoxy$C_{6-10}$aryl group) such as methoxyphenyl group is preferred. The acyl group preferably includes a $C_{1-4}$alkyl-carbonyl group (e.g., a $C_{1-2}$alkyl-carbonyl group) such as acetyl group.

There is no particular limitation as to the position of the substituent. Depending on the species of the ring B, for example, the substituent may be located at 1-, 2-, or 3-position to a nitrogen atom or may be located at 3- or 4-position to a sulfur atom or an oxygen atom. The position of the substituent practically contains at least 1-position and/or 4-position.

The position of the ring B to be linked to the ring A and that to be linked to the linker L are not particularly limited. The ring A and the linker L may bond to the ring B at adjacent position or non-adjacent position (for example, 2,4-positions, 2,5-positions, 3,5-positions, or 3,6-positions) and are practically located at 2,5-positions or 3,5-positions with respect to a hetero atom constituting the ring B.

The preferred ring B includes a pyrrole ring, a furan ring, a thiophene ring, an imidazole ring, a pyrazole ring, a thiazole ring, an isothiazole ring, an oxazole ring, an isoxazole ring, a thiadiazole ring, a pyridine ring, a pyrimidine ring, and a quinoline ring. Concretely, the ring B includes groups (linking units or joining units) represented by the following formulae (3-1) to (3-18).

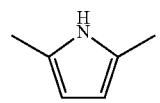

(3-1)

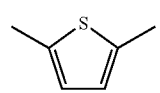

(3-2)

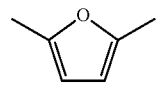

(3-3)

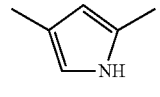

(3-4)

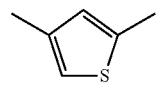

(3-5)

-continued

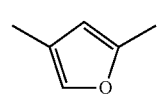 (3-6)

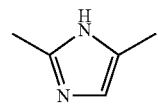 (3-7)

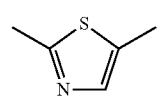 (3-8)

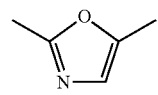 (3-9)

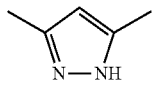 (3-10)

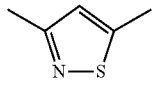 (3-11)

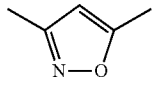 (3-12)

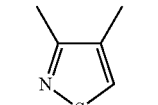 (3-13)

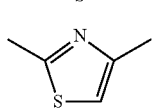 (3-14)

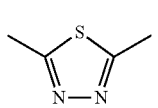 (3-15)

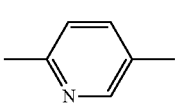 (3-16)

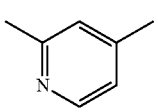 (3-17)

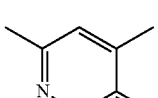 (3-18)

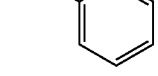

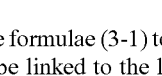

In each one of the formulae (3-1) to (3-18), the left end and the right end may be linked to the linker L and the ring A, respectively; or the left end and the right end may be linked to the ring A and the linker L, respectively. Each one of these rings may have a substituent. That is, each hydrogen atom bonding to carbon atom and/or nitrogen atom constituting the ring may be replaced with the above-exemplified substituent (for example, an alkyl group, a haloalkyl group, a cycloalkyl group, an aryl group, an aralkyl group, and an acyl group). As the ring B with or without a substituent, the group represented by any one of the following formulae (3-a) to (3-p) is preferred.

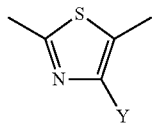 (3-a)

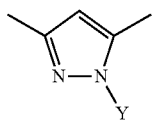 (3-b)

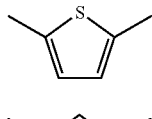 (3-c)

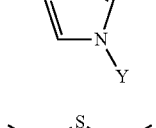 (3-d)

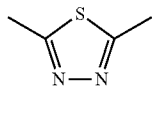 (3-e)

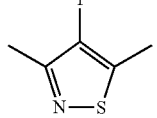 (3-f)

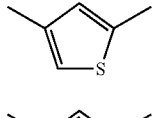 (3-g)

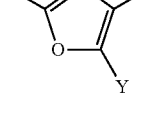 (3-h)

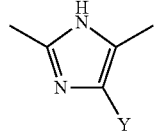 (3-i)

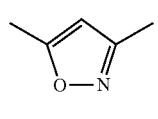 (3-j)

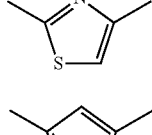 (3-k)

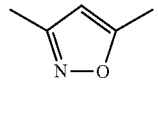 (3-l)

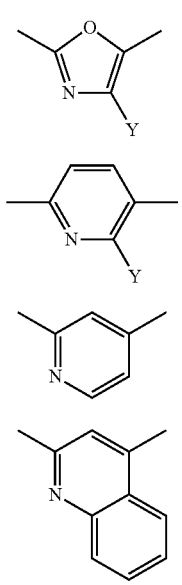

(3-m)

(3-n)

(3-o)

(3-p)

In the formulae, Y represents a hydrogen atom, an alkyl group, a haloalkyl group, a cycloalkyl group, an aryl group, an aralkyl group, or an acyl group.

In each one of the formulae (3-a) to (3-p), it is preferable that the left end and the right end be linked to the ring A and the linker L, respectively.

In the formulae (3-a), (3-b), (3-d), (3-f), (3-h), (3-i), (3-m) and (3-n), the alkyl group, haloalkyl group, cycloalkyl group, aryl group, aralkyl group and acyl group, each represented by the group Y, may include the same groups as the substituent of the ring B, for example, a $C_{1-4}$alkyl group, a halo$C_{1-4}$alkyl group (e.g., a fluoro$C_{1-4}$alkyl group), a $C_{3-6}$cycloalkyl group, a $C_{6-10}$aryl group, a $C_{6-10}$aryl$C_{1-4}$alkyl group and $C_{1-4}$alkylcarbonyl group, respectively. The group Y is practically an alkyl group or an acyl group.

The further preferred ring B may include a 5-membered heterocyclic ring containing two or more hetero atoms as constituent atoms thereof, wherein at least one hetero atom is a nitrogen atom; particularly, a thiazole ring, isothiazole ring or pyrazole ring which may have a substituent (such as an alkyl group or an acyl group) [for example, a ring represented by the formula (3-a), (3-b) or (3-f)].

In the formula (1), the aromatic ring represented by the ring C is not particularly limited to a specific one, and may be a carbocyclic ring or a heterocyclic ring.

The aromatic carbocyclic ring may be a monocyclic or condensed cyclic arene ring (for example, a condensed bi- to tetra-cyclic arene ring). The aromatic carbocyclic ring may include, for example, a $C_{6-24}$arene ring (preferably a $C_{6-20}$arene ring, and more preferably a $C_{6-18}$arene ring) such as benzene, indan, indene, naphthalene, fluorene, phenanthrene or anthracene.

The aromatic heterocyclic ring is not particularly limited to a specific one and usually contains at least one hetero atom selected from the group consisting of a nitrogen atom (N), an oxygen atom (O) and a sulfur atom (S), as a constituent atom thereof. The aromatic heterocyclic ring may be a non-condensed ring (a monocyclic heterocyclic ring) or may be a condensed ring (a condensed ring of a heterocyclic ring and a heterocyclic ring, a condensed ring of a carbocyclic ring and a heterocyclic ring).

The non-condensed ring may include a 5- to 8-membered heterocyclic ring, preferably a 5- to 7-membered heterocyclic ring, and more preferably a 5- or 6-membered heterocyclic ring. As representative examples of the non-condensed ring, there may be mentioned a 5- or 6-membered ring containing a nitrogen atom as a hetero atom, e.g., pyrrole, imidazole, pyrazole, triazole, pyridine, pyridazine, pyrimidine, pyrazine, triazine, and tetrazine; a 5- or 6-membered ring containing an oxygen atom as a hetero atom, e.g., furan; a 5- or 6-membered ring containing a sulfur atom as a hetero atom, e.g., thiophene; a 5- or 6-membered ring containing a nitrogen atom and an oxygen atom as hetero atoms, e.g., oxazole, isoxazole, and oxazine; and a 5- or 6-membered ring containing a nitrogen atom and a sulfur atom as hetero atoms, e.g., triazole, isothiazole, and thiazine.

As the condensed ring, there may be mentioned a condensed ring (for example, a 6 to 15-membered ring, and preferably a 8 to 13-membered ring) containing at least a 5- to 8-membered monocyclic heterocyclic ring (for example, a 5- to 7-membered heterocyclic ring, and particularly a 5- or 6-membered heterocyclic ring). Specifically, the condensed ring may include a condensed ring containing a 5- or 6-membered monocyclic heterocyclic ring having a nitrogen atom as a hetero atom [for example, a bicyclic condensed ring such as indole, indoline, isoindole, isoindoline, indolizine, indazole, benzimidazole, benzotriazole, purine, quinoline, isoquinoline, quinolizine, cinnoline, quinazoline, quinoxaline, phthalazine, naphthyridine or pteridine; and a tricyclic condensed ring such as carbazole, acridine, phenazine, benzocinnoline (or phenazone), benzopyrroloimidazole, benzimidazopyridine or benzimidazoazepine], a condensed ring containing a 5- or 6-membered monocyclic heterocyclic ring having an oxygen atom as a hetero atom [for example, a bicyclic condensed ring such as benzofuran, isobenzofuran, coumaran, coumarin, chromene, isochromene, chroman, isochroman or an alkylenedioxybenzene (a $C_{1-4}$alkylenedioxybenzene such as methylenedioxybenzene); and a tricyclic condensed ring such as dibenzofuran or xanthene], a condensed ring containing a 5- or 6-membered monocyclic heterocyclic ring having a sulfur atom as a hetero atom [for example, a bicyclic condensed ring such as benzothiophene (or thionaphthene) or an alkylenedithiobenzene (a $C_{1-4}$alkylenedithiobenzene such as methylenedithiobenzene); and a tricyclic condensed ring such as dibenzothiopyran or thianthrene], a condensed ring containing a 5- or 6-membered monocyclic heterocyclic ring having a nitrogen atom and an oxygen atom as hetero atoms [for example, a bicyclic condensed ring such as benzoxazole; and a tricyclic condensed ring such as phenoxazine or oxadiazafluorene (or benzimidazomorpholine)], a condensed ring containing a 5- or 6-membered monocyclic heterocyclic ring having a nitrogen atom and a sulfur atom as hetero atoms [for example, a bicyclic condensed ring such as benzothiazoline or benzothiazole; and a tricyclic condensed ring such as phenothiazine or thiadiazafluorene], and a condensed ring containing a 5- or 6-membered monocyclic heterocyclic ring having an oxygen atom and a sulfur atom as hetero atoms [for example, a tricyclic condensed ring such as phenoxathiin ring]; or hydrogenated products of these rings. Among these condensed heterocyclic rings, the condensed ring practically includes a condensed ring containing a benzene ring and a heterocyclic ring (e.g., a 5 to 15-membered ring, and preferably a 5 to 10-membered ring) having at least one hetero atom selected from the group consisting of a nitrogen atom (N), an oxygen atom (O) and a sulfur atom (S) [for example, a bicyclic condensed ring of a benzene ring and a 5- to 8-membered monocyclic heterocyclic ring, and a condensed ring of a benzene ring and a 6- to 15-membered (e.g., 7- to 13-membered, preferably 8- to 10-membered) bicyclic heterocyclic ring (e.g., a tricyclic condensed ring of a benzene ring and two 5- to 8-membered monocyclic heterocyclic rings which may be the same or different from each other)].

The ring C may have a substituent. When the ring C is a monocyclic arene ring (for example, a benzene ring), the ring C practically has a substituent from the viewpoint of the pharmacological activity. Specifically, in many cases, the ring C is a monocyclic arene ring having a substituent, a condensed cyclic arene ring which may have a substituent, or a monocyclic or condensed cyclic heterocyclic ring which may have a substituent.

The substituent may include a halogen atom, an alkyl group, a cycloalkyl group, an aryl group, a hydroxyl group, an alkoxy group, a carboxyl group, an acyl group, a carbamoyl group, an N-substituted carbamoyl group, a dihydroxyboryl group, a mercapto group, an alkylthio group, a sulfonic acid group, an amino group, an N-substituted amino group, a cyano group, a nitro group, and a heterocyclic group. If necessary, the substituent may further have a substituent [e.g., a halogen atom, an aryl group (such as a $C_{6-10}$aryl group), a hydroxyl group, an alkoxy group (such as a straight chain or branched chain $C_{1-4}$alkoxy group), a mercapto group, and an alkylthio group (such as a straight chain or branched chain $C_{1-4}$alkylthio group)] to form a haloalkyl group, a haloalkoxy group, an aralkyl group, an aryloxy group, an aralkyloxy group, a hydroxyalkyl group, an alkoxyalkyl group, an alkoxycarbonyl group, a mercaptoalkyl group, an alkylthioalkyl group, or the like.

The halogen atom, alkyl group, cycloalkyl group, aryl group, alkoxy group and acyl group, as the substituent of the ring C, may include the same halogen atom (such as a fluorine atom or a chlorine atom), straight chain or branched chain $C_{1-6}$alkyl group, $C_{3-10}$cycloalkyl group, $C_{6-10}$aryl group, $C_{1-6}$alkoxy group and $C_{1-6}$alkyl-carbonyl group, respectively, as the substituent on the group A or the ring B.

The N-substituted carbamoyl group as the substituent of the ring C may include an N-mono$C_{1-6}$alkylcarbamoyl group, an N-mono$C_{1-6}$acyl-carbamoyl group, an N,N-di$C_{1-6}$alkyl-carbamoyl group, and an N,N-di$C_{1-6}$acyl-carbamoyl group.

The alkylthio group as the substituent of the ring C may include the same straight chain or branched chain $C_{1-6}$alkylthio group (preferably a $C_{1-4}$alkylthio group) as the substituent of the group A.

The N-substituted amino group as the substituent of the ring C may include the same N-monosubstituted amino group [for example, an N—$C_{1-6}$alkylamino group and an N—($C_{1-6}$alkyl-carbonyl)amino group] and N,N-disubstituted amino group [for example, an N,N-di$C_{1-6}$alkylamino group and an N,N-di($C_{1-6}$alkyl-carbonyl)amino group] as the substituent of the group A.

The heterocyclic group as the substituent of the ring C may include various heterocyclic groups, each containing an aromatic or nonaromatic 5- to 8-membered heterocyclic ring (for example, a 5 to 7-membered ring, and preferably a 5- or 6-membered ring); for example, a group containing a 5- or 6-membered heterocyclic ring having at least one hetero atom selected from the group consisting of a nitrogen atom, an oxygen atom, a sulfur atom and a boron atom [e.g., a 5- or 6-membered heterocyclic group having a nitrogen atom and an oxygen atom as hetero atoms, such as a morpholyl group (e.g., 4-morpholyl group); and a 5- or 6-membered heterocyclic group containing a boron atom and an oxygen atom as hetero atoms, such as 1,3,2-dioxaborinan-2-yl group].

The haloalkyl group, haloalkoxy group and aralkyl group (arylalkyl group) as the substituent of the ring C may include the same straight chain or branched chain halo$C_{1-6}$alkyl group, (preferably a halo$C_{1-4}$alkyl group), straight chain or branched chain halo$C_{1-6}$alkoxy group (preferably, e.g., a mono- to per-fluoro$C_{1-4}$alkoxy group such as difluoromethyloxy or trifluoromethyloxy group, and chloro$C_{1-4}$alkoxy groups corresponding to these fluoro$C_{1-4}$alkoxy groups) and $C_{6-10}$aryl$C_{1-6}$alkyl group (preferably a $C_{6-10}$aryl$C_{1-4}$alkyl group), respectively, as substituent on the group A or the ring B.

The aryloxy group as the substituent of the ring C may include a $C_{6-10}$ aryloxy group such as phenyloxy or naphthyloxy group; the aralkyloxy group as the substituent of the ring C may include a $C_{6-10}$aryl$C_{1-6}$alkyloxy group (preferably a $C_{6-10}$aryl$C_{1-4}$alkyloxy group) such as benzyloxy or phenethyloxy group.

The hydroxyalkyl group as the substituent of the ring C may include a hydroxyl-straight chain or branched chain $C_{1-6}$alkyl group (preferably a hydroxy$C_{1-4}$alkyl group) such as hydroxymethyl, 2-hydroxyethyl or 3-hydroxypropyl group.

The alkoxyalkyl group as the substituent of the ring C may include a straight chain or branched chain $C_{1-6}$alkoxy$C_{1-6}$alkyl group (preferably a $C_{1-4}$alkoxy$C_{1-4}$alkyl group) such as methoxymethyl, methoxyethyl, ethoxymethyl or ethoxyethyl group.

The alkoxycarbonyl group as the substituent of the ring C may include a straight chain or branched chain $C_{1-6}$alkoxy-carbonyl group (preferably, e.g., a $C_{1-4}$alkoxy-carbonyl group) such as methoxycarbonyl or ethoxycarbonyl group.

The mercaptoalkyl group as the substituent of the ring C may include a mercapto-straight chain or branched chain $C_{1-6}$alkyl group corresponding to the hydroxyalkyl group. The alkylthioalkyl group may include a straight chain or branched chain $C_{1-6}$alkylthio$C_{1-6}$alkyl group corresponding to the alkoxyalkyl group.

The monocyclic or condensed cyclic arene ring having a substituent may include, for example, an arene ring (a $C_{6-24}$arene ring such as benzene or naphthalene) having at least one substituent selected from the group consisting of a halogen atom, an alkyl group, a haloalkyl group, a cycloalkyl group, an aryl group, an aralkyl group, a hydroxyl group, an alkoxy group, a haloalkoxy group, an aryloxy group, an aralkyloxy group, a dihydroxyboryl group, a carboxyl group, an alkoxycarbonyl group, a mercapto group, an alkylthio group, a nitro group, an amino group, an N-substituted amino group and a heterocyclic group.

The combination of the substituents is not particularly limited to a specific one. For the disubstituted arene ring, two substituents may be the same or different from each other and may for example be selected from the group consisting of a halogen atom, an alkyl group, a hydroxyl group, an alkoxy group, a haloalkoxy group, a dihydroxyboryl group and a nitro group. For the trisubstituted arene ring, three substituents may be the same or different from one another and may for example be selected from the group consisting of a halogen atom, an alkyl group, a hydroxyl group and an alkoxy group. There is no particular limitation as to the position of the substituent. For example, for a monosubstituted benzene, the substituent may be located at 2-, 3-, or 4-position; for a disubstituted benzene, the substituents may be located at 2,3-, 2,4-, 2,5-, 3,4-, or 3,5-positions; for a trisubstituted benzene, the substituents may be located at 2,3,4- or 3,4,5-positions.

The monocyclic heterocyclic ring having a substituent may include a 5- to 8-membered heterocyclic ring having at least one substituent selected from the group consisting of a hydroxyl group, an alkoxy group (e.g., a $C_{1-6}$alkoxy group), a mercapto group and an alkylthio group (e.g., a $C_{1-6}$alkylthio group) {for example, a 5- or 6-membered heterocyclic ring containing at least one hetero atom selected from the group consisting of a nitrogen atom, an oxygen atom and a sulfur atom [e.g., an alkoxypyridine (e.g., a $C_{1-4}$alkoxypyridine such as 2-methoxypyridine)]}.

The condensed heterocyclic ring having a substituent may include the above-mentioned condensed heterocyclic ring having at least one substituent selected from the group consisting of an alkyl group, a hydroxyalkyl group, an alkoxyalkyl group, a hydroxyl group, an alkoxy group and an acyl group.

The preferred ring C includes a monocyclic or condensed ring having at least a benzene skeleton and may for example be any one of the following formulae (4-a) to (4-c):

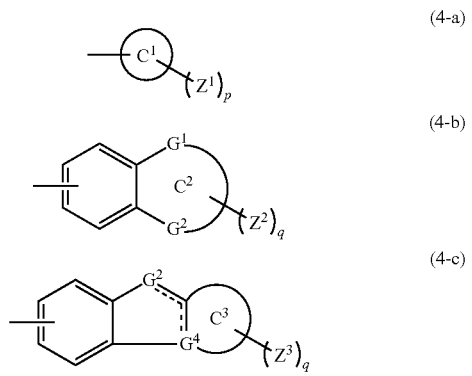

wherein $Z^1$ represents a halogen atom, an alkyl group, a hydroxyl group, an alkoxy group, a mercapto group, an alkylthio group, an N-alkyl-substituted amino group or an N-acyl-substituted amino group; $Z^2$ represents an alkyl group, a hydroxyalkyl group, an alkoxyalkyl group or an acyl group; $Z^3$ represents an alkyl group, a hydroxyl group, an alkoxy group or an acyl group; the ring $C^1$ represents a $C_{6-10}$arene ring; the ring $C^2$ represents a 5- to 8-membered heterocyclic ring containing $G^1$ and $G^2$, the ring containing at least one hetero atom selected from the group consisting of a nitrogen atom (N), an oxygen atom (O) and a sulfur atom (S) as a constituent atom thereof; the ring $C^3$ represents a 5- to 8-membered heterocyclic ring containing $G^4$ of the ring adjacent thereto, the ring $C^3$ containing at least one hetero atom selected from the group consisting of a nitrogen atom (N), an oxygen atom (O) and a sulfur atom (S) as a constituent atom thereof; $G^1$ to $G^3$ each represent a nitrogen atom (N), an oxygen atom (O), a sulfur atom (S), NH, CH or $CH_2$ depending on the aromaticity or nonaromaticity of the ring $C^2$ or that of the 5-membered ring adjacent to the ring $C^3$; $G^4$ represents a nitrogen atom (N), a carbon atom (C) or CH depending on the aromaticity or nonaromaticity of the 5-membered ring adjacent to the ring $C^3$; p is an integer of 1 to 5, and q is an integer of 0 to 6.

In the formula (4-c), the chemical bond represented as follows:

------ represents a single bond or a double bond.

In the formula (4-a), the arene ring represented by the ring $C^1$ may include a $C_{6-10}$arene ring such as benzene or naphthalene.

The halogen atom, alkyl group, alkoxy group, alkylthio group, N-alkyl-substituted amino group and N-acyl-substituted amino group, each represented by $Z^1$, may include the halogen atom (such as a fluorine atom or a chlorine atom), $C_{1-6}$alkyl group, $C_{1-6}$alkoxy group, $C_{1-6}$alkylthio group, N—$C_{1-6}$alkyl-substituted amino group and N—($C_{1-6}$alkyl-carbonyl) substituted amino group, respectively, each exemplified as the substituent on the ring C. When p is an integer of not less than 2, the species of $Z^1$ may be the same or different from each other.

The coefficient p (the number p) of $Z^1$ is about 1 to 5, preferably about 1 to 4, and more preferably about 1 to 3 (e.g., 1 to 2). Moreover, there is no particular limitation as to the position of the substituent $Z^1$. For example, when the ring $C^1$ is a benzene ring, the position of the substituent $Z^1$ may be 2-, 3-, 4-, or 5-position in the ring, and is preferably at least 3- and/or 4-position (in particular, at least 4-position) in the ring.

The group represented by the formula (4-a) preferably includes, for example, a group represented by the following formula (4-a2):

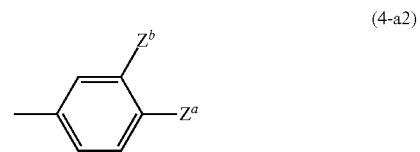

wherein $Z^a$ represents a hydroxyl group, an alkoxy group, a mercapto group, an alkylthio group, an N,N-dialkylamino group or an N,N-diacylamino group; $Z^b$ represents a hydrogen atom, an alkyl group, a hydroxyl group or an alkoxy group.

In the formula (4-a2), the alkoxy group, alkylthio group, N,N-dialkylamino group or N,N-diacylamino group represented by $Z^a$ may include the same $C_{1-6}$alkoxy group (preferably a $C_{1-4}$alkoxy group), $C_{1-6}$alkylthio group (preferably a $C_{1-4}$alkylthio group), N,N-di$C_{1-6}$alkylamino group (preferably an N,N-di$C_{1-4}$alkylamino group) or N,N-di($C_{1-6}$alkyl-carbonyl)amino group [preferably an N,N-di($C_{1-4}$alkyl-carbonyl)amino group] as the above-exemplified group. The alkyl group or alkoxy group represented by $Z^b$ may include the same $C_{1-6}$alkyl group (preferably a $C_{1-4}$alkyl group) or $C_{1-6}$alkoxy group (preferably a $C_{1-4}$alkoxy group) as the above-exemplified group.

When $Z^a$ is a hydroxyl group or an alkoxy group, $Z^b$ is practically an alkyl group, a hydroxyl group or an alkoxy group.

In the formula (4-b), the ring $C^2$ is a 5- to 8-membered heterocyclic ring (for example, a 5- to 7-membered heterocyclic ring, and preferably a 5- or 6-membered heterocyclic ring) containing $G^1$ and $G^2$ as constituent atoms thereof, and is usually a heterocyclic ring containing at least one hetero atom selected from the group consisting of a nitrogen atom (N), an oxygen atom (O) and a sulfur atom (S) as a constituent atom thereof. The ring $C^2$ may for example be a ring (a heterocyclic ring) of the above-exemplified bicyclic condensed heterocyclic ring [that is, a residue obtained by removing a benzene ring from a condensed ring of the benzene ring and a heterocyclic ring containing at least one hetero atom selected from the group consisting of a nitrogen atom (N), an oxygen atom (O) and a sulfur atom (S) as a constituent atom thereof (for example, a nitrogen-atom-containing heterocyclic ring such as indole, indoline, isoindole, isoindoline, indazole, benzimidazole, benzotriazole, quinoline, isoquinoline, cinnoline, quinazoline, quinoxaline or phthalazine; and an oxygen-atom-containing heterocyclic ring such as benzofuran, isobenzofuran, coumaran, coumarin, chromene, isochromene, chroman, isochroman or an alkylenedioxybenzene)].

In the formula (4-c), the ring $C^3$ is a 5 to 8-membered ring (e.g., a 5 to 7-membered ring) containing $G^4$ as a constituent atom thereof, and is usually a heterocyclic ring containing at least one hetero atom selected from the group consisting of a nitrogen atom (N), an oxygen atom (O) and a sulfur atom (S) as a constituent atom thereof. The ring $C^3$ may for example be a ring of the above-exemplified tricyclic condensed heterocyclic ring {e.g., a residue obtained by removing a benzene ring and a 5-membered monocyclic ring adjacent to the benzene ring from a tricyclic condensed heterocyclic ring, having a benzene skeleton at an end thereof, of the benzene ring, the 5-membered monocyclic carbocyclic or heterocyclic ring and a 5- to 8-membered heterocyclic ring [for example, a condensed ring of a benzene ring, an imidazole ring and a ring selected from the group consisting of a pyrrole ring, a pyridine ring, an azepine ring and a morpholine ring (e.g., benzopyrroloimidazole, benzimidazopyridine, benzimidazoazepine, and benzimidazomorpholine), or hydrogenated products of these rings]}.

The alkyl group or acyl group represented by $Z^2$ and $Z^3$ may include the $C_{1-6}$alkyl group (preferably a $C_{1-4}$alkyl group) or $C_{1-6}$alkyl-carbonyl group (preferably a $C_{1-4}$alkyl-carbonyl group) exemplified as the substituent of the ring C. The hydroxyalkyl group or alkoxyalkyl group represented by $Z^2$ may include the hydroxy$C_{1-6}$alkyl group (preferably a hydroxy$C_{1-4}$alkyl group) or $C_{1-6}$alkoxy$C_{1-6}$alkyl group (preferably a $C_{1-4}$alkoxy$C_{1-4}$alkyl group) exemplified as the substituent of the ring C. The alkoxy group represented by $Z^3$ may include the $C_{1-6}$alkoxy group (preferably a $C_{1-4}$alkoxy group) exemplified as the substituent of the ring C. Each one of these substituents $Z^2$ and $Z^3$ is practically an alkyl group, an acyl group, or the like. When q is an integer of not less than 2, the species of the substituent $Z^2$ (or $Z^3$) may be the same or different from each other.

The coefficient q of $Z^2$ (or $Z^3$) is, for example, 0 to 6, preferably about 0 to 4, more preferably about 0 to 3, and particularly about 0 to 2.

The group represented by the formula (4-b) may include a group comprising a condensed ring of a benzene ring and a 5- to 8-membered monocyclic heterocyclic ring containing at least one hetero atom selected from the group consisting of a nitrogen atom (N), an oxygen atom (O) and a sulfur atom (S) as a constituent atom thereof, for example, a condensed ring group of a 5- or 6-membered heterocyclic ring containing an oxygen atom as a hetero atom and a benzene ring, such as a benzofuryl group (e.g., benzofuran-5-yl group), a coumaryl group (e.g., coumaran-5-yl group), a coumarinyl group (e.g., coumarin-5-yl group), or an alkylenedioxyphenyl group (e.g., a $C_{1-4}$alkylenedioxyphenyl group such as 3,4-methylenedioxyphenyl group); a condensed ring group of a 5- or 6-membered heterocyclic ring containing a nitrogen atom as a hetero atom and a benzene ring, such as an indolyl group [e.g., indol-4- (or 5-, 6-, 7-)yl group], an alkylindolyl group [e.g., a $C_{1-4}$alkylindolyl group such as 1-methylindol-5- (or 6-)yl group], an indazolyl group [e.g., 1H- (or 2H-)indazol-5- (or 6-)yl group], an alkylindazolyl group [e.g., a $C_{1-4}$alkylindazolyl group such as 1-methyl (or 1-ethyl)-1H-indazol-5-yl group, 1-methyl (or 1-ethyl)-1H-indazol-6-yl group or 2-methyl (or 2-ethyl)-2H-indazol-5-yl group], a benzimidazolyl group [e.g., benzimidazol-5-yl group], an alkylbenzimidazolyl group [e.g., a mono- or di-$C_{1-4}$alkylbenzimidazolyl group such as 1-methyl (or 1-ethyl, 1-propyl, 1-isopropyl) benzimidazol-5-yl group, 1,2-dimethylbenzimidazol-5-yl group, 1-methyl-2-ethyl-benzimidazol-5-yl group or 1-ethyl-2-methyl-benzimidazol-5-yl group], a benzotriazolyl group [e.g., benzotriazol-5-yl group], an alkylbenzotriazolyl group [e.g., a $C_{1-4}$alkylbenzotriazolyl group such as 1-methyl (or 1-ethyl)benzotriazol-5-yl group], a quinolyl group [e.g., quinolin-6-yl group], a quinoxalinyl group [e.g., quinoxalin-6-yl group], or an alkylquinoxalinyl group [e.g., a mono- or di-$C_{1-4}$alkylquinoxalinyl group such as 2,3-dimethylquinoxalin-6-yl group]; a condensed ring group of a 5- or 6-membered heterocyclic ring containing a nitrogen atom and an oxygen atom as hetero atoms and a benzene ring, such as a benzoxazolyl group [e.g., benzoxazol-6-yl group] or a dihydrobenzoxazinyl group [e.g., 2,3-dihydro-1,4-benzoxazin-6-yl group]; and others.

The group represented by the formula (4-c) may include a condensed ring group of a benzene ring, a 5-membered monocyclic heterocyclic ring containing at least one hetero atom selected from the group consisting of a nitrogen atom (N), an oxygen atom (O) and a sulfur atom (S), and a 5- to 8-membered monocyclic heterocyclic ring containing at least one hetero atom selected from the group consisting of a nitrogen atom (N), an oxygen atom (O) and a sulfur atom (S), for example, a condensed ring group of a benzene ring, an imidazole ring, and a ring selected from the group consisting of a pyrrole ring, a pyridine ring, an azepine ring and a morpholine ring {e.g., a benzopyrroloimidazolyl group or a group containing a hydrogenated product thereof such as 2,3-dihydro-1H-benzo[d]pyrrolo[1,2-a]imidazolyl group; a benzimidazopyridyl group or a group containing a hydrogenated product thereof such as 1,2,3,4-tetrahydrobenzo[4,5]imidazo[1,2-a]pyridyl group; a benzimidazoazepinyl group or a group containing a hydrogenated product thereof such as 7,8,9,10-tetrahydro-6H-benzo[4,5]imidazo[1,2-a]azepinyl group; and a 2-oxa-4-a, 9-diazafluorenyl group or a group containing a hydrogenated product thereof such as 3,4-dihydro-1H-2-oxa-4a,9-diazafluorenyl group}.

Among the groups represented by the formula (4-b) or (4-c), a group represented by the following formula (4-b2) or (4-c2) is preferred.

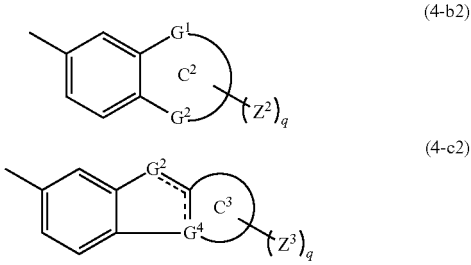

In the formulae, the ring $C^2$ represents a 5- to 8-membered heterocyclic ring (e.g., a 5- to 7-membered heterocyclic ring, and preferably a 5- or 6-membered heterocyclic ring) having $G^1$ and $G^2$, and contains at least one (e.g., about 1 to 3) hetero atom selected from the group consisting of a nitrogen atom (N) and an oxygen atom (O) as a constituent atom thereof; the ring $C^3$ represents a 5- to 8-membered heterocyclic ring (e.g., a 5- to 7-membered heterocyclic ring) having $G^4$ of the ring adjacent thereto, and contains at least one hetero atom (e.g., about 1 to 2) selected from the group consisting of a nitrogen atom (N) and an oxygen atom (O) as a constituent atom thereof; $G^2$ represents an oxygen atom (O), a nitrogen atom (N) or NH depending on the aromaticity or nonaromaticity of the ring $C^2$; $G^4$ represents a nitrogen atom (N); and the group $Z^2$, the group $Z^3$, $G^1$, $G^3$ and q have the same meanings as defined above.

In the formula (4-c2), the broken line indicates that the 5-membered ring which is adjacent to the ring C³ and contains G³ and G⁴ may be an aromatic ring or a nonaromatic (aliphatic) ring.

Concretely, the group represented by the formula (4-b2) or (4-c2) include groups represented by any one of following formulae (4-b3) to (4-b6), (4-c2) and (4-c3):

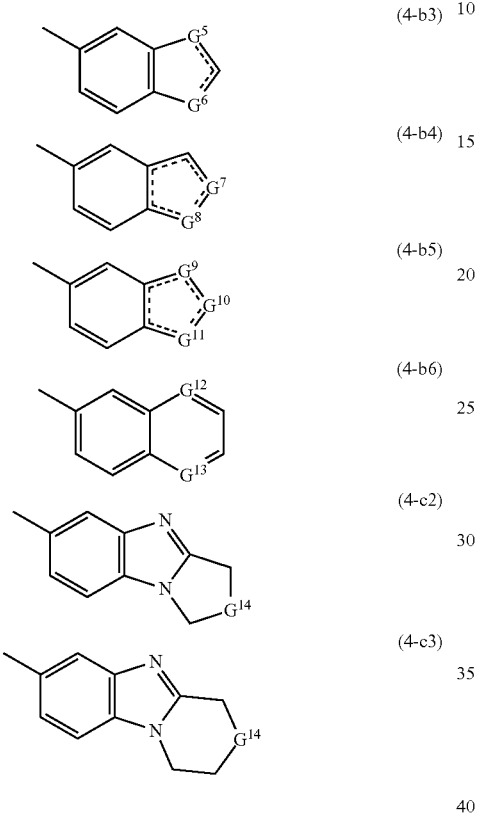

wherein G⁵ represents N, NH, S, O, CH or CH₂; G⁶ represents N, NH, S or O; G⁷ represents N or NH; G⁸ represents N, NH, S or O; G⁹ to G¹¹ each represent N or NH; G¹² represents CH or N; G¹³ represents N; and G¹⁴ represents NH, O, S or CH₂.

Each one of the groups represented by the formulae (4-b3) to (4-b6), (4-c2) and (4-c3) may have a substituent. That is, each hydrogen atom bonding to carbon atom and/or nitrogen atom constituting the ring may be replaced with the above-exemplified substituent (for example, an alkyl group and an acyl group).

As the group included in the formula (4-b2), a group represented by the formula (4-b2) in which G¹ is a nitrogen atom (N), CH or CH₂ is preferred. As the group included in the formula (4-c2), a group represented by the formula in which G³ is a nitrogen atom (N) or NH is preferred. In particular, it is preferable that the group be represented by any one of the following formulae (5-a) to (5-k):

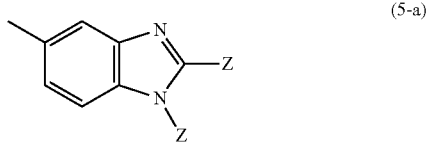

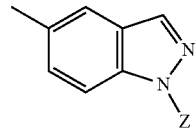

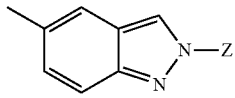

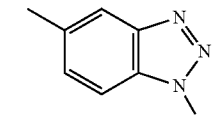

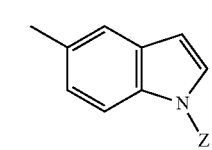

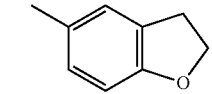

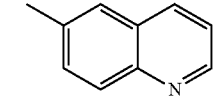

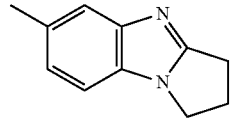

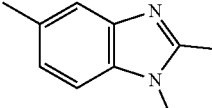

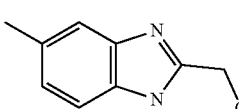

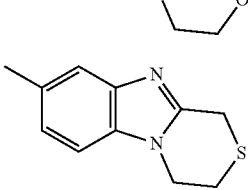

wherein Z represents a hydrogen atom, an alkyl group, or an acyl group.

In the formulae (5-a) to (5-e), the alkyl group and the acyl group, each represented by Z may include the $C_{1-6}$alkyl group (preferably a $C_{1-4}$alkyl group) and the $C_{1-6}$alkyl-carbonyl group (preferably a $C_{1-4}$alkyl-carbonyl group), respectively, exemplified as the substituent of the ring C. In the formula (5-a), the species of two substituents Z may be the same or different from each other.

In the formula (1), the linker represented by L is not particularly limited to a specific one as far as the ring B and the ring C can be linked (or joined) through the linker. For example, the linker has a main chain containing about 3 to 5 (particularly 4 to 5) atoms, each selected from the group consisting of a carbon atom (C), a nitrogen atom (N), an oxygen atom (O) and a sulfur atom (S). The main chain of the linker usually comprises at least one carbon atom and at least one hetero atom selected from the group consisting of a nitrogen atom, an oxygen atom and a sulfur atom. Moreover, each hydrogen atom bonding to the carbon atom of the main chain may be replaced with a group selected from the group consisting of an oxygen atom (or oxo group or group =O), a sulfur atom (or thioxo group or group =S), an alkyl group and an acyl group; each hydrogen atom bonding to the nitrogen atom of the main chain may be replaced with a group selected from the group consisting of an alkyl group and an acyl group. The bonding manner of the atoms of the main chain is not particularly limited to a specific one. For example, the linker may include a linker containing at least one chemical bond selected from the group consisting of an amide bond, a urethane bond, a thioamide bond, a thiourethane bond and an ether bond. Concretely, the linker may contain at least any one of basic skeletons (basic units) represented by following formulae (1-a) to (1-i):

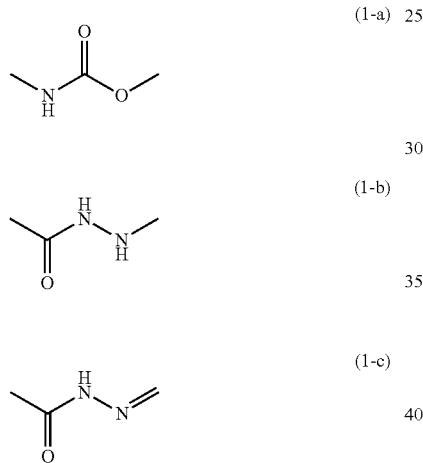

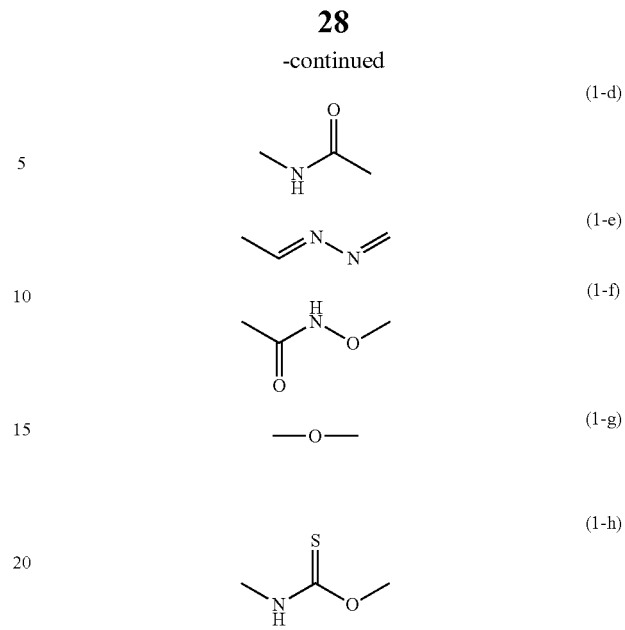

In these basic skeletons (1-a) to (1-i), the hydrogen atom of the —NH— group may be replaced with a group such as an alkyl group or an acyl group. The alkyl group may include the same straight chain or branched chain $C_{1-6}$alkyl group (preferably a $C_{1-4}$alkyl group) as the group A. The acyl group may include the same straight chain or branched chain $C_{1-6}$alkyl-carbonyl group (preferably a $C_{1-4}$alkyl-carbonyl group) as the substituent of the ring B.

Among these linkers, representative linkers are shown in Table 1.

TABLE 1

TABLE 1-continued

| Basic skeltons | Representative examples | | | |
|---|---|---|---|---|
| (1-c) | (1-c1) | (1-c2) | (1-c3) | |
| (1-d) | (1-d1) | (1-d2) | (1-d3) | |
| (1-e) | (1-e1) | (1-e2) | | |
| (1-f) | (1-f1) | | | |
| —O— (1-g) | (1-g1) | (1-g2) | | |
| (1-h) | (1-h1) | | | |
| (1-i) | (1-i1) | | | |

In the formulae shown in Table 1, $X^1$ represents an alkyl group, and $X^2$ represents an alkyl group or an acyl group. The alkyl group represented by $X^1$ or $X^2$ may include the same $C_{1-4}$alkyl group (e.g., a $C_{1-2}$alkyl group) as the above-exemplified group; the acyl group represented by $X^2$ may include the same $C_{1-4}$alkyl-carbonyl group (e.g., a $C_{1-2}$alkyl-carbonyl group) as the above-exemplified group.

In the basic skeleton and representative linker shown in Table 1, the left end and the right end may be linked to the ring C and the ring B, respectively. It is preferable that the left end and the right end be linked to the ring B and the ring C, respectively.

Among these linkers, a linker containing any one of the basic skeletons represented by the formulae (1-a) to (1-c) is preferred. In particular, a linker containing the urethane bond (—NHC(O)O— or —OC(O)NH—) represented by the formula (1-a) [for example, a linker represented by each of the formulae (1-a1) to (1-a6)] is preferred.

When the linker L is a linker represented by the formula (1-a1), in many cases the group A is a group other than 2-methylaminopyrimidin-4-yl group and the ring C is a ring other than 9-fluorenyl group. When the linker L is a linker represented by the formula (1-a2) in which $X^1$ is methyl group and the ring C is a benzene ring having a halogen atom as a substituent, the ring B is a ring other than an isoxazole-diyl group (particularly, 3,4-isoxazole-diyl group) in many cases.

The heterocyclic compound represented by the formula (1) or the salt thereof according to the present invention is novel. Moreover, the heterocyclic compound having any combination of the groups (or biological equivalents) exemplified in each item of the group A, the ring B, the linker L and the ring C, or the pharmaceutically (or physiologically) acceptable salt thereof is novel as a $p27^{Kip1}$ ubiquitination inhibitor (or degradation inhibitor). Further, the heterocyclic compound having any combination of the groups (or biological equivalents) exemplified in each item of the group A, the ring B, the linker L and the ring C, or the pharmaceutically (or physiologically) acceptable salt thereof [with the proviso that when the linker L is a linker represented by the formula (1-a2) in which $X^1$ is methyl group and the ring C is a benzene ring having a halogen atom as a substituent, the ring B is a ring other than an isoxazole-diyl group (particularly, 3,4-isoxazole-diyl group)] is novel as a preventing and/or treating agent for a cell proliferative disease.

The compound represented by the formula (1) or the salt thereof is not particularly limited to a specific one as far as the compound or the salt thereof is the compound having any combination of the groups exemplified in each item of the group A, the ring B, the linker L and the ring C or the salt thereof; for example, from the viewpoint of the binding property to the Skp2, the ability to inhibit $p27^{Kip1}$ ubiquitination, the ability to inhibit $p27^{Kip1}$ degradation, the ability to inhibit cell proliferation, and the ability to induce apoptosis, the following compound or a salt thereof is preferred:

(1-1) a compound in which the linker L contains the basic skeleton of the formula (1-a) [for example, the compound (1) in which the linker L is any one of the formulae (1-a1) to (1-a6), the group A is an aryl group having a substituent (e.g., a group represented by the formula (2)), the ring B is a thiazole, isothiazole or pyrazole ring which may have a substituent, and the ring C is any one of the formulae (4-a) to (4-c)] or a salt thereof;

(1-2) a compound in which the linker L contains the basic skeleton of the formula (1-b) [for example, the compound (1) in which the linker L is the formula (1-b1) or (1-b2), the group A is an aryl group having a substituent (e.g., a group represented by the formula (2)), the ring B is a thiazole ring, pyrazole ring or furan ring which may have a substituent, and the ring C is an aryl group represented by the formula (4-a) or a heterocyclic group represented by the formula (4-b) or (4-b2)] or a salt thereof;

(1-3) a compound in which the linker L contains the basic skeleton of the formula (1-c) [for example, the compound (1) in which the linker L is any one of the formulae (1-c1) to (1-c3), the ring A is an aryl group having no substituent, an aryl group having a substituent (e.g., a group represented by the formula (2)) or a heterocyclic group having a substituent (e.g., a 5- to 8-membered heterocyclic group containing at least a nitrogen atom as a hetero atom, such as pyridyl group), the ring B is a thiazole ring, isothiazole ring, pyrazole ring, pyrrole ring, imidazole ring or oxazole ring which may have a substituent, and the ring C is an aryl group represented by the formula (4-a) (wherein $Z^1$ may be a boronic acid group) or a heterocyclic group represented by the formula (4-b) or (4-b2)] or a salt thereof;

(1-4) a compound in which the linker L contains the basic skeleton of the formula (1-d) [for example, the compound (1) in which the linker L is anyone of the formulae (1-d1) to (1-d3), the group A is an aryl group having a substituent (e.g., a group represented by the formula (2)), the ring B is a thiazole ring or pyrazole ring which may have a substituent, and the ring C is an aryl group represented by the formula (4-a)] or a salt thereof;

(1-5) a compound in which the linker L contains the basic skeleton of the formula (1-e) [for example, the compound (1) in which the linker L is the formula (1-e1) or (1-e2), the group A is an aryl group having substituent (e.g., a group represented by the formula (2)), the ring B is a thiazole ring or pyrazole ring which may have a substituent, and the ring C is an aryl group represented by the formula (4-a)] or a salt thereof;

(1-6) a compound in which the linker contains the basic skeleton of the formula (1-g) [for example, the compound (1) in which the linker L is the formula (1-g1) or (1-g2), the group A is an aryl group having a substituent (e.g., a group represented by the formula (2)), the ring B is a thiazole ring or pyrazole ring which may have a substituent, and the ring C is an aryl group represented by the formula (4-a)] or a salt thereof; and (1-7) a compound in which the linker contains the basic skeleton of the formula (1-h) [for example, the compound (1) in which the linker L is the formula (1-h1), the group A is aryl group having a substituent (e.g., a group represented by the formula (2)), the ring B is a thiazole ring or pyrazole ring which may have a substituent, and the ring C is an aryl group represented by the formula (4-a)].

As the compound represented by the formula (1) or the salt thereof, a compound represented by any one of the following formulae (6-a) to (6-c) or a salt thereof is preferred, in particular, from the viewpoint of the ability to inhibit $p27^{Kip1}$ degradation and the ability to induce apoptosis.

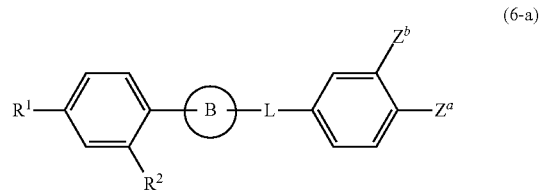

(6-a)

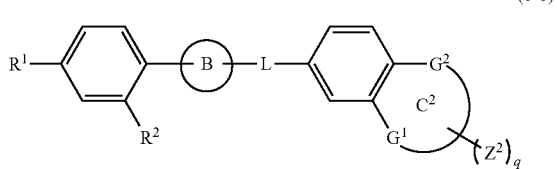

(6-b)

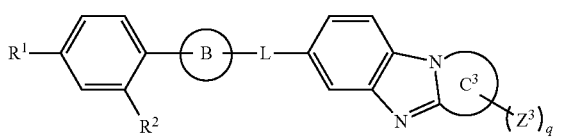

(6-c)

In the formulae, $R^1$ and $R^2$ are the same or different and each represent a halogen atom, an alkyl group, a hydroxyl group, an alkoxy group, a mercapto group or an alkylthio group; the ring B is a thiazole ring, an isothiazole ring or a pyrazole ring, and the ring B may have at least one substituent selected from the group consisting of an alkyl group, a haloalkyl group, a cycloalkyl group, an aryl group, an aralkyl group and an acyl group; $Z^a$ represents a hydroxyl group, an alkoxy group, a mercapto group, an alkylthio group, an N-alkyl-substituted amino group (e.g., an N,N-dialkylamino group) or an N-acyl-substituted amino group (e.g., an N,N-diacylamino group); $Z^b$ represents a hydrogen atom, an alkyl group, a hydroxyl group or an alkoxy group; the ring $C^2$ represents a 5 to 8-membered ring (e.g., a 5 to 7-membered ring, and preferably a 5- or 6-membered ring) having $G^1$ and $G^2$, and contains at least one hetero atom selected from the group consisting of a nitrogen atom (N), an oxygen atom (O) and a sulfur atom (S) as a constituent atom thereof; $G^1$ represents a nitrogen atom (N), CH or $CH_2$ depending on the aromaticity or nonaromaticity of the ring $C^2$; $G^2$ represents a nitrogen atom (N), an oxygen atom (O) or NH; the ring $C^3$ represents a 5 to 8-membered ring (e.g., a 5 to 7-membered ring) having a nitrogen atom and optionally at least one hetero atom selected from the group consisting of an oxygen atom (O) and a sulfur atom (S) as constituent atom(s) thereof; L represents a linker selected from the group consisting of the formulae (1-a1) to (1-a6); $Z^2$, $Z^3$ and q have the same meanings as defined above.

The halogen atom, alkyl group, alkoxy group or alkylthio group, each represented by and $R^2$, may include the same halogen atom (e.g., a fluorine atom and a chlorine atom), $C_{1-6}$alkyl group (e.g., a $C_{1-4}$alkyl group), $C_{1-6}$alkoxy group (e.g., a $C_{1-4}$alkoxy group) or $C_{1-6}$alkylthio group (e.g., a $C_{1-4}$alkylthio group) as the groups exemplified in the group R.

Concretely, the compounds represented by the formula (1) include, for example, compounds shown in Tables 2 to 4.

TABLE 2

| | $R^1$ | $R^2$ | Ring B | Linker L | Ring C | Representative compounds |
|---|---|---|---|---|---|---|
| Compound of formula (6-b) | Halogen atom | Alkyl group | 4-Alkyl thiazole-2,5-diyl | Formula (1-a1) | Formula (5-a) | [2-(4-halo-2-$C_{1-4}$alkylphenyl)-4-$C_{1-4}$alkylthiazol-5-yl]carbamic acid 1-$C_{1-4}$alkyl-1H-benzimidazol-5-ylmethyl ester, etc. |
| | Halogen atom | Alkoxy group | | | Formula (5-a), (5-b) or (5-d) | [2-(4-halo-2-$C_{1-4}$alkoxyphenyl)-4-$C_{1-4}$alkylthiazol-5-yl]carbamic acid 1-$C_{1-4}$alkyl-1H-benzimidazol-5-ylmethyl ester, [2-(4-halo-2-$C_{1-4}$alkoxyphenyl)-4-$C_{1-4}$alkylthiazol-5-yl]carbamic acid 1-$C_{1-4}$alkyl-1H-indazol-5-ylmethyl ester, [2-(4-halo-2-$C_{1-4}$alkoxyphenyl)-4-$C_{1-4}$alkylthiazol-5-yl]carbamic acid 1-$C_{1-4}$alkyl-1H-benzotriazol-5-ylmethyl ester, etc. |
| | Alkyl group | Alkyl group | | | Formula (5-a) | [2-(2,4-di$C_{1-4}$alkylphenyl)-4-$C_{1-4}$alkylthiazol-5-yl]carbamic acid 1-$C_{1-4}$alkyl-1H-benzimidazol-5-ylmethyl ester, etc. |
| | Alkyl group | Alkoxy group | | | Formula (5-a), (5-b) or (5-d) | [2-(2-$C_{1-4}$alkoxy-4-$C_{1-4}$alkylphenyl)-4-$C_{1-4}$alkylthiazol-5-yl]carbamic acid 1-$C_{1-4}$alkyl-1H-benzimidazol-5-ylmethyl ester, [2-(2-$C_{1-4}$alkoxy-4-$C_{1-4}$alkylphenyl)-4-$C_{1-4}$alkylthiazol-5-yl]carbamic acid 1-$C_{1-4}$alkyl-1H-indazol-5-ylmethyl ester, [2-(2-$C_{1-4}$alkoxy-4-$C_{1-4}$alkylphenyl)-4-$C_{1-4}$alkylthiazol-5-yl]carbamic acid 1-$C_{1-4}$alkyl-1H-benzotriazol-5-ylmethyl ester, etc. |
| | Alkoxy group | Alkoxy group | | | Formula (5-a) | [2-(2,4-di$C_{1-4}$alkoxyphenyl)-4-$C_{1-4}$alkylthiazol-5-yl]carbamic acid 1-$C_{1-4}$alkyl-1H-benzimidazol-5-ylmethyl ester, etc. |
| | Halogen atom | Alkoxy group | 2-Alkyl-2H-pyrazole-3,5-diyl | | Formula (5-a), (5-b) or (5-c) | [5-(4-halo-2-$C_{1-4}$alkoxyphenyl)-2-$C_{1-4}$alkyl-2H-pyrazol-3-yl]carbamic acid 1-$C_{1-4}$alkyl-1H-benzimidazol-5-ylmethyl ester, [5-(4-halo-2-$C_{1-4}$alkoxyphenyl)-2-$C_{1-4}$alkyl-2H-pyrazol-3-yl]carbamic acid 1-$C_{1-4}$alky-1H-indazol-5-ylmethyl ester, [5-(4-halo-2-$C_{1-4}$alkoxyphenyl)-2-$C_{1-4}$alkyl-2H-pyrazol-3-yl]carbamic acid 2-$C_{1-4}$alkyl-2H-indazol-6-ylmethyl ester, etc. |
| | Alkyl group | Alkyl group | | | Formula (5-a) | [5-(2,4-di$C_{1-4}$alkylphenyl)-2-$C_{1-4}$alkyl-2H-pyrazol-3-yl]carbamic acid 1-$C_{1-4}$alkyl-1H-benzimidazol-5-ylmethyl ester, |
| | Alkyl group | Alkoxy group | | | | [5-(2-$C_{1-4}$alkoxy-4-$C_{1-4}$alkylphenyl)-2-$C_{1-4}$alkyl-2H-pyrazol-3-yl]carbamic acid (1-$C_{1-4}$alkyl-1H-benzimidazol-5-yl)methyl ester, etc. |
| | Halogen atom | Alkyl group | 4-Alkyl thiazole-2,5-diyl | Formula (1-a4) | Formula (5-a) | (1-$C_{1-4}$alkyl-1H-benzimidazol-5-yl)carbamic acid 2-(4-halo-2-$C_{1-4}$alkylphenyl)-4-$C_{1-4}$alkylthiazol-5-ylmethyl ester, etc. |

TABLE 3

| | $R^1$ | $R^2$ | Ring B | Linker L | Ring C | Representative compounds |
|---|---|---|---|---|---|---|
| Compound of formula (6-b) | Alkyl group | Alkoxy group | Isothiazole-3,5-diyl | Formula (1-a4) | Formula (5-a) | (1-$C_{1-4}$alkyl-1H-benzimidazol-5-yl)carbamic acid 3-(2-$C_{1-4}$alkoxy-4-$C_{1-4}$alkylphenyl)isothiazol-5-ylmethyl ester, |
| | Halogen atom | Alkoxy group | | | | (1-$C_{1-4}$alkyl-1H-benzimidazol-5-yl)carbamic acid 3-(4-halo-2-$C_{1-4}$alkoxyphenyl)isothiazol-5-ylmethyl ester, etc. |
| | Halogen atom | Alkoxy group | 2-Alkyl-2H-pyrazole-3,5-diyl | | Formula (5-a) or (5-c) | (1-$C_{1-4}$alkyl-1H-benzimidazol-5-yl)carbamic acid 5-(4-halo-2-$C_{1-4}$alkoxyphenyl)-2-$C_{1-4}$alkyl-2H-pyrazol-3-ylmethyl ester, (2-$C_{1-4}$alkyl-2H-indazol-5-yl)carbarmic acid 5-(4-halo-2-$C_{1-4}$alkoxyphenyl)-2-$C_{1-4}$alkyl-2H-pyrazol-3-ylmethyl ester, etc. |
| | Alkyl group | Alkyl group | | | Formula (5-a) | (1-$C_{1-4}$alkyl-1H-benzimidazol-5-yl) carbamic acid 5-(2,4-di$C_{1-4}$alkylphenyl)-2-$C_{1-4}$alkyl-2H-pyrazol-3-ylmethyl ester, |
| | Alkyl group | Alkoxy group | | | | (1-$C_{1-4}$alkyl-1H-benzimidazol-5-yl)carbamic acid 5-(2-$C_{1-4}$alkoxy-4-$C_{1-4}$alkylphenyl)-2-$C_{1-4}$alkyl-2H-pyrazol-3-ylmethyl ester, etc. |
| Compound of formula (6-c) | Halogen atom | Alkyl group | 4-Alkyl thiazole-2,5-diyl | Formula (1-a1) | Formula (5-j) | [2-(4-halo-2-$C_{1-4}$alkylphenyl)-4-$C_{1-4}$alkylthiazol-5-yl]carbamic acid 3,4-dihydro-1H-2-oxa-4a,9-diazafluoren-7-ylmethyl ester, etc. |
| | Halogen atom | Alkoxy group | | | Formula (5-h) or (5-j) | [2-(4-halo-2-$C_{1-4}$alkoxyphenyl)-4-$C_{1-4}$alkylthiazol-5-yl]carbamic acid 2,3-dihydro-1H-benzo[d]pyrrolo[1,2-a]imidazol-6-ylmethyl ester, [2-(4-halo-2-$C_{1-4}$alkoxyphenyl)-4-$C_{1-4}$alkylthiazol-5-yl]carbamic acid 3,4-dihydro-1H-2-oxa-4a,9-diazafluoren-7-ylmethyl ester, etc. |
| | Alkyl group | Alkyl group | | | Formula (5-j) | [2-(2,4-di$C_{1-4}$alkylphenyl)-4-$C_{1-4}$alkylthiazol-5-yl]carbamic acid 3,4-dihydro-1H-2-oxa-4a,9-diazafluoren-7-ylmethyl ester, etc. |
| | Alkyl group | Alkoxy group | | | Formula (5-j) | [2-(2-$C_{1-4}$alkoxy-4-$C_{1-4}$alkylphenyl)-4-$C_{1-4}$alkylthiazol-5-yl]carbamic acid 3,4-dihydro-1H-2-oxa-4a,9-diazafluoren-7-ylmethyl ester, etc. |
| | Halogen atom | Alkoxy group | 2-Alkyl-2H-pyrazole-3,5-diyl | | Formula (5-j) | [5-(4-halo-2-$C_{1-4}$alkoxyphenyl)-2-$C_{1-4}$alkyl-2H-pyrazol-3-yl]carbamic acid 3,4-dihydro-1H-2-oxa-4a,9-diazafluoren-7-ylmethyl ester, |
| | Alkyl group | Alkoxy group | | | | [5-(2-$C_{1-4}$alkoxy-4-$C_{1-4}$alkylphenyl)-2-$C_{1-4}$alkyl-2H-pyrazol-3-yl]carbamic acid 3,4-dihydro-1H-2-oxa-4a,9-diazafluoren-7-ylmethyl ester, etc. |

TABLE 4

| | R¹ | R² | Ring B | Linker L | Ring C | Representative compounds |
|---|---|---|---|---|---|---|
| Compound of formula (6-c) | Halogen atom | Alkyl group | 4-Alkyl thiazole-2,5-diyl | Formula (1-a4) | Formula (5-j) | (3,4-dihydro-1H-2-oxa-4a,9-diazafluoren-7-yl)carbamic acid 2-(4-halo-2-$C_{1-4}$alkylphenyl)-4-$C_{1-4}$alkylthiazol-5-ylmethyl ester, etc. |
| | Halogen atom | Alkoxy group | Isothiazole-3,5-diyl | | Formula (5-i) or (5-j) | (1,2,3,4-tetrahydrobenzo[4,5]imidazo[1,2-a]pyridin-7-yl)carbamic acid 3-(4-halo-2-$C_{1-4}$alkoxyphenyl)isothiazol-5-ylmethyl ester, (3,4-dihydro-1H-2-oxa-4a,9-diazafluoren-7-yl)carbamic acid 3-(4-halo-2-$C_{1-4}$alkoxyphenyl)isothiazol-5-ylmethyl ester, etc. |
| | Halogen atom | Alkoxy group | 2-Alkyl-2H-pyrazole-3,5-diyl | | Formula (5-h), (5-i) or (5-j) | (2,3-dihydro-1H-benzo[d]pyrrolo[1,2-a]imidazol-6-yl)carbamic acid 5-(4-halo-2-$C_{1-4}$alkoxyphenyl)-2-$C_{1-4}$alkyl-2H-pyrazol-3-ylmethyl ester, (1,2,3,4-tetrahydrobenzo[4,5]imidazo[1,2-a]pyridin-7-yl)carbamic acid 5-(4-halo-2-$C_{1-4}$alkoxyphenyl)-2-$C_{1-4}$alkyl-2H-pyrazol-3-ylmethyl ester, (3,4-dihydro-1H-2-oxa-4a,9-diazafluoren-7-yl)carbamic acid 5-(4-halo-2-$C_{1-4}$alkoxyphenyl)-2-$C_{1-4}$alkyl-2H-pyrazol-3-ylmethyl ester, etc. |
| | Alkyl group Alkyl group | Alkyl group Alkoxy group | | | Formula (5-h) or (5-j) | (2,3-dihydro-1H-benzo[d]pyrrolo[1,2-a]imidazol-6-yl)carbamic acid 5-(2,4-di$C_{1-4}$alkylphenyl)-2-$C_{1-4}$alkyl-2H-pyrazol-3-ylmethyl ester, (3,4-dihydro-1H-2-oxa-4a,9-diazafluoren-7-yl)carbamic acid 5-(2,4-di$C_{1-4}$alkylphenyl)-2-$C_{1-4}$alkyl-2H-pyrazol-3-ylmethyl ester, (2,3-dihydro-1H-benzo[d]pyrrolo[1,2-a]imidazol-6-yl)carbamic acid 5-(2-$C_{1-4}$alkoxy-4-$C_{1-4}$alkylphenyl)-2-$C_{1-4}$alkyl-2H-pyrazol-3-ylmethyl ester, (3,4-dihydro-1H-2-oxa-4a,9-diazafluoren-7-yl)carbamic acid 5-(2-$C_{1-4}$alkoxy-4-$C_{1-4}$alkylphenyl)-2-$C_{1-4}$alkyl-2H-pyrazol-3-ylmethyl ester, etc. |

The present invention also includes a salt (e.g., a salt with a pharmacologically or physiologically acceptable acid or base) of the compound represented by the formula (1). The acid for forming such a salt may include an inorganic acid (e.g., hydrochloric acid, hydrobromic acid, sulfuric acid, nitric acid, and phosphoric acid) and an organic acid (e.g., an organic carboxylic acid such as acetic acid, propionic acid, trichloroacetic acid, trifluoroacetic acid, oxalic acid, succinic acid, fumaric acid, or maleic acid; an hydroxycarboxylic acid such as lactic acid, malic acid, tartaric acid, or citric acid; and a sulfonic acid such as methanesulfonic acid or toluenesulfonic acid). As the base, there may be mentioned, for example, an inorganic base (such as ammonia; an alkali metal hydroxide such as sodium hydroxide or potassium hydroxide; an alkali metal carbonate; an alkaline earth metal hydroxide such as calcium hydroxide or magnesium hydroxide; and an alkaline earth metal carbonate such as calcium carbonate) and an organic base [for example, an aliphatic amine (e.g., an alkylamine such as triethylamine; an alkanolamine such as ethanolamine; and a polyamine such as an alkylenediamine), an alicyclic amine (e.g., a dicycloalkylamine such as dicyclohexylamine), an aromatic amine (e.g., an N-alkyl-substituted aniline such as N,N-dimethylaniline), and a heterocyclic amine (e.g., a 5- or 6-membered ring such as pyrrolidine, pyridine, or morpholine)]. These acids or bases may be used alone or in combination.

The compound or the salt thereof of the present invention may be an anhydride or a hydrate or may be a solvate (e.g., a solvate of an organic solvent such as ethanol). Moreover, the compound or the salt thereof of the present invention also includes a hydrate or solvate of the compound of the formula (1) or the salt thereof, and in addition, an isolated crystal (e.g., a polymorphic crystalline substance). Moreover, the compound or the salt thereof according to the present invention also includes a tautomer, optically active substance having an asymmetric carbon atom (such as (R)-body, (S)-body, diastereomer), or racemic body of the compound of the formula (1) or the salt thereof, or a mixture of these compounds. Further, the end group or heterocyclic group, or other groups of the compound or the salt thereof may be modified for forming a pro-drug which expresses an activity in a living body (or an active metabolite). The pro-drug may include, for example, a compound which expresses an activity by metabolism such as hydrolysis, oxidation, reduction, or transesterification (for example, an ester body, ether body, alcohol body, or amide body of the compound of the formula (1)). The compound or the salt thereof of the present invention has a high safety.

[Production Process]

The compound represented by the formula (1) or the salt thereof can be produced by linking a unit represented by the group A, a unit represented by the ring B, a unit represented by the linker L, and a unit represented by the ring C, and the order to be linked is not particularly limited to a specific one. For example, the compound or the salt thereof can be produced according to the following reaction scheme (i):

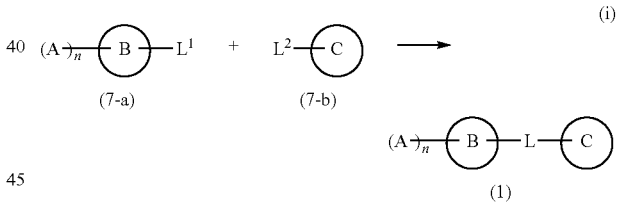

wherein $L^1$ and $L^2$ represent groups which allow to react with each other to form the linker L; the group A, the ring B, the ring C, L and n have the same meanings as defined above.

In the reaction step (i), the groups represented by $L^1$ and $L^2$ are not particularly limited to a specific one as far as these groups allow to react with each other to form the linker L. The groups $L^1$ and $L^2$ are suitably selected depending on the species of the linker L, and may for example be functional groups which allow to react with each other to form a bond. Each one of the groups $L^1$ and $L^2$ may be the functional group (end group) or a group having the functional group. The functional group may include a haloalkyl group, a hydroxyl group, an aldehyde group (formyl group), a carboxyl group, a carbazoyl group, a hydroxamic acid group, an amino group, a hydrazino group, an aminocyano group, an isocyanate group, an isothiocyanato group, and other groups. In the group having the functional group, the residue that the functional group is removed from the group having the functional group may include an alkylene group.

More specifically, the compound represented by the formula (1) or the salt thereof can be prepared according to the following reaction scheme (ii):

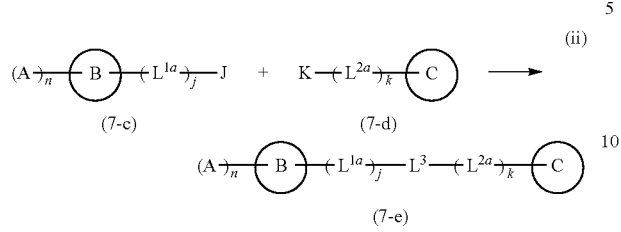

wherein the groups J and K are located at an end of the compound having the ring B and an end of the compound having the ring C, respectively, and allow to react with each other to link the compound having the ring B and the compound having the ring C; $L^{1a}$ and $L^{2a}$ are the same or different and each represent an alkylene group; $L^3$ represents a linker represented by any one of the following formulae (1-a) to (1-i); j and k are the same or different and each are 0 or 1; and the group A, the ring B, the ring C and n have the same meanings as defined above.

In the reaction step (ii), the groups J and K are not particularly limited to a specific one as far as these groups allow to react with each other to link the compound having the ring B and the compound having the ring C. These groups are suitably selected depending on the species of the basic skeleton $L^3$ of the linker L [-($L^{1a}$)$_j$-$L^3$-($L^{2a}$)$_k$-]. Concrete examples of the combination of the groups J and K corresponding to the basic skeleton $L^3$ of the linker L are shown in Table 5.

TABLE 5

| Basic skeleton $L^3$ | End group J | End group K |
|---|---|---|
| (1-a) | Isocyanate group | Hydroxyl group |
| (1-b) | Carboxyl group | Hydrazino group |
| (1-c) | Carbazoyl group [—C(O)—NH—NH$_2$] | Formyl group |
| (1-d) | Amino group | Carboxyl group |
| (1-r) | Aminocyano group [—C═N—NH$_2$] | Formyl group |
| (1-f) | Carboxyl group | Hydroxyamino group |
| —O— (1-g) | Hydroxyl group Haloalkyl group | Haloalkyl group Hydroxyl group |
| (1-h) | Isothiocyanato group | Hydroxyl group |
| (1-i) | Carboxyl group Carbazoyl group | Carbazoyl group Carboxyl group |

In Table 5, as the combination of the groups J and K, the combination in which the left end and the right end of the linker L are linked to the ring B and the ring C, respectively, is shown. Use of the compound of the ring C having the group J and the compound of the ring B having the group K can easily produce the compound in which the left end and the right end of the linker L are linked to the ring C and the ring B, respectively.

The alkylene group (including an alkylidene group) represented by each of $L^{1a}$ and $L^{2a}$ may include a straight chain or branched chain alkylene group (for example, a $C_{1-4}$alkylene group, and preferably a $C_{1-2}$alkylene group) such as methylene, 1,1-ethanediyl, ethylene (1,2-ethanediyl), 1,1-propanediyl, propylene (1,2-propanediyl), trimethylene, or tetramethylene group. The species of $L^{1a}$ and $L^{2a}$ may be the same or different from each other.

In the formation reaction of the linker, the ratio (the amount to be used) of the compound (7-a) [or the compound (7-c)] and the compound (7-b) [or the compound (7-d)] may be the ratio at which $L^1$ (end group J) and $L^2$ (end group K) are equivalent or almost equivalent. The ratio (molar ratio) of the compound (7-a) [or the compound (7-c)] relative to the compound (7-b) [or the compound (7-d)] may for example be about 2/1 to 1/2, preferably about 1.5/1 to 1/1.5, and more preferably about 1.2/1 to 1/1.2 in a ratio of the former/the latter.

The formation reaction of the linker may be carried out in the presence of a solvent. The solvent is not particularly limited to a specific one as far as the solvent is inactive to the reaction. The solvent may suitably be selected depending on the species of the raw material compounds (7-a) to (7-d), the species of the reaction, and others and may include, for example, a hydrocarbon (e.g., an aliphatic hydrocarbon such as pentane or hexane; an alicyclic hydrocarbon such as cyclohexane; and an aromatic hydrocarbon such as benzene, toluene, or xylene), a halogen-containing solvent (e.g., a halogenated hydrocarbon such as methylene chloride, chloroform, carbon tetrachloride, bromoform, or ethylene chloride), an alcohol (e.g., an alkanol such as methanol, ethanol, propanol, isopropanol, butanol, isobutanol, or t-butanol; and a glycol such as ethylene glycol or propylene glycol), an ether (e.g., a chain ether such as ethyl ether or isopropyl ether; and a cyclic ether such as dioxane, tetrahydrofuran, or tetrahydropyran), a cellosolve (e.g., a $C_{1-4}$alkyl cellosolve such as methyl cellosolve or ethyl cellosolve), a cellosolve acetate (e.g., a $C_{1-4}$alkyl cellosolve acetate such as ethyl cellosolve acetate), a carbitol (e.g., methyl carbitol), a ketone (e.g., a dialkyl ketone such as acetone, methyl ethyl ketone, diisopropyl ketone, or isobutyl methyl ketone), an organic carboxylic acid (e.g., acetic acid), an ester (e.g., an acetic acid ester such as methyl acetate, ethyl acetate, butyl acetate), an amide (e.g., formamide; an N-mono- or di-$C_{1-4}$alkylformamide such as N-methylformamide or N,N-dimethylformamide; and an N-mono- or di-$C_{1-4}$alkylacetamide such as N-methylacetamide or N,N-dimethylacetamide), a pyridine (e.g., pyridine and pyridine borane), and a nitrile (e.g., acetonitrile and benzonitrile). These solvents may be used alone or as a mixed solvent.

Moreover, the formation reaction of the linker may be carried out in the presence of a catalyst. The catalyst may include, for example, an acid catalyst [for example, an inorganic acid (e.g., sulfuric acid), an organic acid (e.g., p-toluenesulfonic acid), and Lewis acid], a base catalyst {for example, an inorganic base [e.g., a metal hydroxide (e.g., an alkali metal or alkaline earth metal hydroxide such as sodium hydroxide) and a metal carbonate (e.g., an alkali metal or alkaline earth metal carbonate such as sodium carbonate)], an organic base [for example, an aliphatic amine [for example, a primary to tertiary aliphatic amine, e.g., an aliphatic tertiary amine such as a tri$C_{1-4}$alkylamine (such as triethylamine, diethylmethylamine, diisopropylethylamine, tri-n-propylamine, or tributylamine)], an aromatic amine (for example, a primary to tertiary aromatic amine, e.g., an aromatic tertiary amine such as N,N-dimethylaniline), and a heterocyclic amine (for example, a primary to tertiary heterocyclic amine, e.g., a heterocyclic tertiary amine such as picoline, pyridine, pyrazine, pyrimidine, pyridazine, 1-methylimidazole, triethylenediamine, N,N-dimethylaminopyridine, or 1,8-diazabicyclo[5.4.0]unde-7-cene)]}. These catalysts may be used alone or in combination.

The amount of the catalyst may for example be about 0.0001 to 5 mol and preferably about 0.001 to 1 mol relative to 1 mol of the compound (7-a) [or the compound (7-c)] or the compound (7-b) [or the compound (7-d)].

The formation reaction of the linker may be conducted under a room temperature or a heated condition. Moreover, the reaction can be conducted in air or under an inactive (or inert) gas atmosphere (such as nitrogen, helium, or argon gas). The reaction may be carried out under an atmospheric pressure or an applied pressure. The reaction time is not particularly limited to a specific one and may for example be about 0.1 to 60 hours and preferably about 0.5 to 50 hours.

After the completion of the reaction, the compound represented by the formula (1) [or the formula (7-e)] or the salt thereof may be separated or purified from the reaction mixture by a conventional separation or purification (or isolation) method, for example, filtration, distillation, condensation, precipitation, crystallization, recrystallization, decantation, extraction, drying, washing, chromatography, and a combination thereof.

(Compound Represented by the Formula (7-a))

The compound represented by the formula (7-a) can be prepared according to a conventional method, for example, any one of the following reaction schemes (iii) to (v).

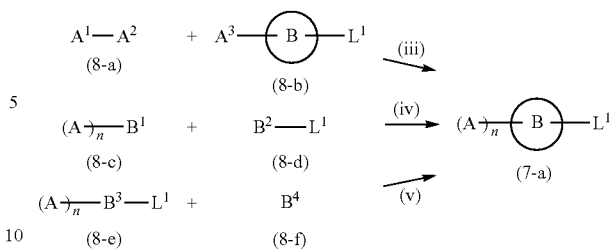

wherein $A^1$ represents the group A or a residue of the group A; the groups $A^2$ and $A^3$ are located at an end of the compound having the group $A^1$ and an end of the compound having the ring B, respectively, and allow to react with each other to link the group A and the ring B; $B^1$ and $B^2$ are groups which allow to react with each other to form the ring B, $B^3$ and $B^4$ are groups which allow to react with each other to form the ring B; the group A, the ring B, the group $L^1$ and n have the same meanings as defined above.

In the reaction step (iii), the method for linking the group A to the ring B is not particularly limited to a specific one, and conventional addition reaction, substitution reaction, coupling reaction (for example, a cross-coupling reaction such as Suzuki coupling reaction), or other reactions can be used. As the combination of $A^2$ and $A^3$, for example, when $A^2$ is a boronic acid group [—$B(OH)_2$] and $A^3$ is a halogen atom, both groups allow to react with each other to link $A^1$ (=A) to the ring B, and the compound represented by the formula (7-a) is obtained.

The compound represented by the formula (8-a) may include a compound in which $A^2$ is a boronic acid group, for example, an arylboronic acid [e.g., a halo-alkoxyarylboronic acid (preferably a halo-$C_{1-6}$alkoxy$C_{6-10}$arylboronic acid) such as 4-chloro-2-methoxyphenylboronic acid].

The compound represented by the formula (8-b) may include a compound in which $A^3$ is a halogen atom and $L^1$ is an alkoxycarbonyl group [e.g., an alkyl 4-halo-1-alkyl-1H-pyrrole-2-carboxylate (preferably a $C_{1-4}$alkyl 4-halo-1-$C_{1-4}$alkyl-1H-pyrrole-2-carboxylate) such as ethyl 4-bromo-1-methyl-1H-pyrrole-2-carboxylate], and others.

The ratio (amount to be used) of the compound represented by the formula (8-a) relative to the compound represented by the formula (8-b) may for example be about 99/1 to 1/99, preferably about 90/10 to 10/90, and more preferably about 85/15 to 15/85 in a molar ratio of the former/the latter.

The reaction of the compound (8-a) and the compound (8-b) may be carried out in the presence of an inorganic base. As the inorganic base, there may be mentioned a metal carbonate (for example, an alkali metal carbonate such as potassium carbonate or sodium carbonate), and others. These inorganic bases may be used alone or in combination. The ratio (the amount to be used) of the inorganic base may for example be about 0.1 to 10 mol and preferably about 0.5 to 5 mol relative to 1 mol of the total of the compound (8-a) and the compound (8-b).

The reaction of the compound (8-a) and the compound (8-b) may be carried out in the presence of a catalyst [for example, a palladium-series catalyst such as tetrakis(triphenylphosphine)palladium]. The ratio (the amount to be used) of the catalyst may be not more than 0.1 mol and preferably not more than 0.01 mol (e.g., about 0.001 to 0.01 mol) relative to 1 mol of the total of the compound represented by the formula (8-a) and the compound represented by the formula (8-b).

The reaction of the compound (8-a) and the compound (8-b) may be carried out in the presence of a solvent. The solvent is not particularly limited to a specific one as far as the solvent is inactive to the reaction. The solvent may include water, a hydrocarbon (e.g., an aliphatic hydrocarbon such as pentane or hexane; an alicyclic hydrocarbon such as cyclohexane; and an aromatic hydrocarbon such as benzene, toluene, or xylene), an amide (e.g., formamide; an N-mono- or di-$C_{1-4}$alkylformamide such as N-methylformamide or N,N-dimethylformamide; and an N-mono- or di-$C_{1-4}$alkylacetamide such as N-methylacetamide or N,N-dimethylacetamide), and others. These solvents may be used alone or as a mixed solvent. Among these solvents, mixed solvent of a water and an amide [for example, a mixed solvent containing water and an amide in a ratio (volume ratio) of 10/90 to 50/50 as the former/the latter] is widely used.

The reaction of the compound (8-a) and the compound (8-b) can be conducted under a room temperature or a heated condition. For example, the reaction can be conducted at a temperature of about 10 to 150° C. (preferably about 20 to 100° C.). Moreover, the reaction can be conducted in air or under an inactive (or inert) gas atmosphere (such as nitrogen, helium, or argon gas). The reaction may be carried out under an atmospheric pressure or an applied pressure. The reaction time is not particularly limited to a specific one and may for example be about 0.1 to 20 hours, preferably about 0.5 to 15 hours, and more preferably about 1 to 10 hours.

In the reaction step (iv), the method for forming the ring B is not particularly limited to a specific one and a known method for producing a heterocyclic ring [for example, a method described in the fourth edition Jikken Kagaku Koza (Experimental Chemistry Lecture) 24, Organic Chemistry VI, Hetero element/representative metal element compounds, edited by The Chemical Society of Japan, published by Maruzen Company, Limited, p. 463 to 549] can be used. For example, a reaction such as a reaction of a thioamide (or an amide, a ketone) and an α-halo ketone (e.g., Hantzsch method, Feist-Benary method), a reaction of a thiosemicarbazide (or a semicarbazide) and an acid halide, or a reaction of a hydroxyiminoacetonitrile and an alkyl thioglycolate can be used for cyclization. In the cyclization reaction, representative combination examples of the compound (8-c) and the compound (8-d) as well as representative examples of the compound (7-a) are shown in Table 6.

TABLE 6

| Compound (8-c) | Compound (8-d) | Compound (7-a) |
|---|---|---|
| $(A)_n$–C(=S)–NH$_2$ | H–C(=O)–CH(Halo)–L$^1$ | $(A)_n$–thiazole–L$^1$ |
| $(A)_n$–C(=O)–NH$_2$ | H–C(=O)–CH(Halo)–L$^1$ | $(A)_n$–oxazole–L$^1$ |
| $(A)_n$–C(=O)–CH$_3$ + NH$_3$ | H–C(=O)–CH(Halo)–L$^1$ | $(A)_n$–pyrrole–L$^1$ |
| $(A)_n$–C(=O)–CH$_3$ | H–C(=O)–CH(Halo)–L$^1$ | $(A)_n$–furan–L$^1$ |
| $(A)_n$–C(=S)–NH–NH$_2$ | Halo–C(=O)–L$^1$ | $(A)_n$–thiadiazole–L$^1$ |
| $(A)_n$–C(=O)–NH–NH$_2$ | Halo–C(=O)–L$^1$ | $(A)_n$–oxadiazole–L$^1$ |
| $(A)_n$–C(CN)=N–O–S(=O)$_2$–C$_6$H$_4$–CH$_3$ | HS–CH$_2$–C(=O)–L$^1$ | $(A)_n$–isothiazole(NH$_2$)–L$^1$ |

In the formulae of Table 6, Halo represents a halogen atom (such as a chlorine atom or a bromine atom); the group A, the group L$^1$ and n have the same meanings as defined above.

In the reaction step (v), the method for forming the ring B is not particularly limited to a specific one and a known method for producing a heterocyclic ring [for example, a method described in the fourth edition Jikken Kagaku Koza (Experimental Chemistry Lecture) 24, Organic Chemistry VI, Hetero element/representative metal element compounds, edited by The Chemical Society of Japan, published by Maruzen Company, Limited, p. 463 to 549] can be used. For example, a cyclization reaction of an α,β-unsaturated ketone (or a 1,2-diketone) and a hydrazine (or a hydroxylamine, an amide) can be used. In the cyclization reaction, representative combination examples of the compound (8-e) and the compound (8-f) as well as representative examples of the compound (7-a) are shown in Table 7.

TABLE 7

| Compound (8-e) | Compound (8-f) | Compound (7-a) | |
|---|---|---|---|
| $(A)_n$—C(=O)—CH$_2$—C(=O)—L$^1$ | H$_2$N—NH$_2$ | $(A)_n$-[pyrazole]-L$^1$ (N—NH) | $(A)_n$-[pyrazole]-L$^1$ (HN—N) |
| $(A)_n$—C(=O)—CH$_2$—C(=O)—L$^1$ | NH$_2$OH | $(A)_n$-[isoxazole]-L$^1$ (O—N) | $(A)_n$-[isoxazole]-L$^1$ (N—O) |
| $(A)_n$—C(=O)—CH$_2$—C(=O)—L$^1$ | NH$_2$—C(=O)—H | $(A)_n$-[pyrimidine]-L$^1$ | |
| $(A)_n$—C(=O)—C(=O)—L$^1$ | NH$_2$—C(=O)—H | $(A)_n$-[imidazole]-L$^1$ | |

In the formulae of Table 7, the group A, the group L$^1$ and n have the same meanings as defined above.

In the reaction steps (iv) and (v), each of the ratio (the amount to be used) of the compound (8-c) relative to the compound (8-d) and the ratio (the amount to be used) of the compound (8-e) relative to the compound (8-f) may be about 90/10 to 10/90, preferably about 80/20 to 20/80, and more preferably about 70/30 to 30/70 in a molar ratio of the former/the latter.

The reaction steps (iv) and (v) may be carried out in the presence of a solvent. The solvent is not particularly limited to a specific one as far as the solvent is inactive to the reaction. The solvent may include, for example, a hydrocarbon (e.g., an aliphatic hydrocarbon such as pentane or hexane; an alicyclic hydrocarbon such as cyclohexane; and an aromatic hydrocarbon such as benzene, toluene, or xylene) and an alcohol (e.g., an alkanol such as methanol or ethanol). These solvents may be used alone or as a mixed solvent. Among these solvents, a $C_{1-4}$alkanol such as ethanol is widely used.

The reaction steps (iv) and (v) can be carried out under a room temperature or a heated condition. For example, the reaction can be conducted at a temperature of about 10 to 150° C. (preferably about 20 to 100° C.). Moreover, the reaction can be conducted in air or under an inactive (or inert) gas atmosphere (such as nitrogen, helium, or argon gas). The reaction may be carried out under an atmospheric pressure or an applied pressure. The reaction time is not particularly limited to a specific one and may for example be about 1 to 50 hours, preferably about 5 to 40 hours, and more preferably about 10 to 30 hours.

(Compound Represented by the Formula (7-b))

The compound represented by the formula (7-b) may for example be any one of the following formulae (7-b1) to (7-b3):

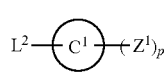

(7-b1)

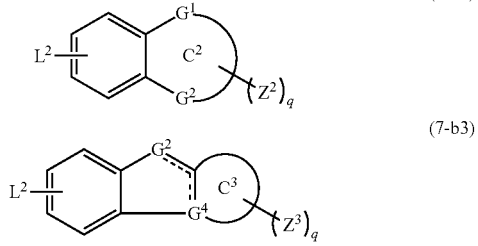

wherein the group L$^2$, the group Z$^1$, the group Z$^2$, the group Z$^3$, the ring C$^1$, the ring C$^2$, the ring C$^3$, G$^1$ to G$^4$, p and q have the same meanings as defined above.

The compound represented by the formula (7-b1) may be synthesized by a conventional method or may be a product on the market. Specifically, the compound represented by the formula (7-b1) may include a compound corresponding to the ring represented by the formula (4-a), for example, a compound in which the end group of L$^2$ (the group K) is a hydroxyl group [e.g., an aralkyl alcohol (preferably a $C_{6-10}$aryl$C_{1-4}$alkyl alcohol) such as benzyl alcohol; a haloaralkyl alcohol (preferably a halo$C_{6-10}$aryl$C_{1-4}$alkyl alcohol) such as 4-fluorobenzyl alcohol; an alkoxy-aralkyl alcohol (preferably a $C_{1-4}$alkoxy-$C_{6-10}$aryl$C_{1-4}$alkyl alcohol) such as 4-methoxybenzyl alcohol or 4-methoxyphenethylalcohol; an alkylthio-aralkyl alcohol (preferably a $C_{1-4}$alkylthio-$C_{6-10}$aryl$C_{1-4}$alkyl alcohol) such as 4-methylthiobenzyl alcohol; an N,N-dialkyl-aralkyl alcohol (preferably an N,N-di$C_{1-4}$alkyl-$C_{6-10}$aryl$C_{1-4}$alkyl alcohol) such as 3- or 4-(N,N-dimethyl)-benzyl alcohol; and a halo-alkoxy-aralkyl alcohol (preferably a halo-$C_{1-4}$alkoxy-$C_{6-10}$aryl$C_{1-4}$alkyl alcohol) such as 3-fluoro-4-methoxybenzyl alcohol], and compounds each of which corresponds to each of these compounds and in each of which the end group of L$^2$ (the group K) is a formyl group, a carboxyl group, a carbazoyl group or other groups.

The compound represented by the formula (7-b2) or (7-b3) may be a product on the market or may be synthesized by a known process for producing a heterocyclic ring (for example, a method described in the fourth edition Jikken Kagaku Koza (Experimental Chemistry Lecture) 24, Organic Chemistry VI, Hetero element/representative metal element compounds, edited by The Chemical Society of Japan, published by Maruzen Company, Limited, p. 463 to 549; a method described in J. Chem. Soc., 1963, 4666-4669; and a method described in J. Chem. Soc. Perkin I, 1979, 1056-1062). For example, the compound represented by the formula (7-b2) or (7-b3) can be prepared according to the following reaction scheme (vi) or (vii):

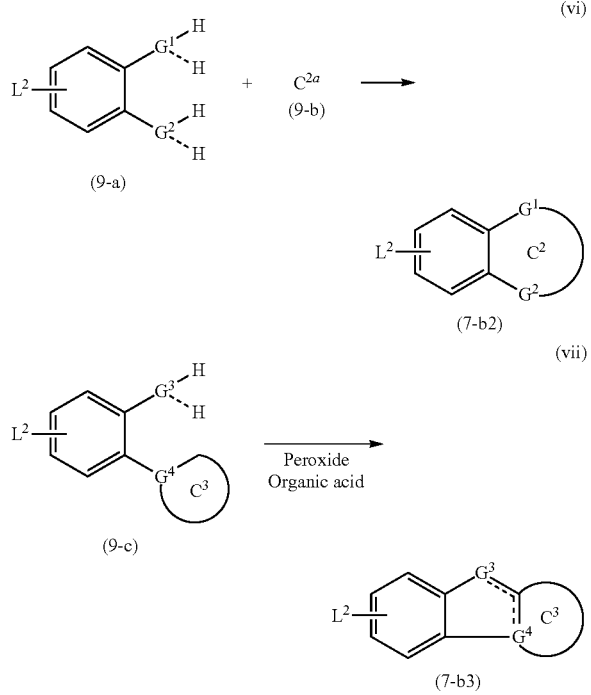

wherein $C^{2a}$ represents a component for forming the ring $C^2$; and the group $L^2$, the ring $C^2$, the ring $C^3$, and $G^1$ to $G^4$ have the same meanings as defined above.

In the formulae (9-a) and (9-b), the broken line indicates that each of $G^1$ to $G^3$ may bind to a hydrogen atom depending on the species of $G^1$ to $G^3$.

The compound (9-b) is not particularly limited to a specific one as far as the compound is a component for forming the ring $C^2$. As the compound (9-b), at least an acid component (an organic acid) is usually employed. The acid component may include an alkanoic acid (e.g., a $C_{1-6}$alkanoic acid) such as formic acid, acetic acid, or propionic acid, or an acid anhydride thereof. In the case where a nitrogen atom is introduced into the ring $C^2$, nitrous acid or a salt (an alkali metal salt such as a sodium salt) thereof or an ester thereof (e.g., a $C_{1-6}$alkyl ester of nitrous acid, such as isoamyl nitrite) is widely used in addition to the acid component.

Representative examples of the combination of the compound (9-a) and the compound (9-b) are shown in Table 8.

TABLE 8

| Compound (9-a) | Compound (9-b) | Compound (7-b2) |
|---|---|---|
| with NH₂ and NH-Z | H—C(=O)—OH | benzimidazole with N-Z |

TABLE 8-continued

| Compound (9-a) | Compound (9-b) | Compound (7-b2) |
|---|---|---|
| SH, NH₂ | H—C(=O)—OH | benzothiazole |
| OH, NH₂ | H—C(=O)—OH | benzoxazole |
| CH₃, NH-Z | (CH₃)₂CH—C₂H₄—ONO | indazole with N-Z |
| NH₂, NH-Z | NaNO₂ | benzotriazole with N-Z |
| NH₂, NH₂ | Z—C(=O)—C(=O)—Z | quinoxaline with Z, Z |

In the formulae of Table 8, the group $L^2$ and the group Z have the same meanings as defined above.

In the cyclization reaction (vi), the ratio (the amount to be used) of the compound (9-a) relative to the compound (9-b) may be about 2/1 to 1/2 and preferably about 1.5/1 to 1/1.5 in a molar ratio of the former/the latter. Since the organic acid such as formic acid also act as a reaction solvent, the molar quantity of the compound (9-b) may be in excess of that of the compound (9-a) [for example, the ratio of the compound (9-a) relative to the compound (9-b) may be about 1/2 to 1/50 in a molar ratio of the compound (9-a)/the compound (9-b)].

In the cyclization reaction (vii), the intramolecular cyclization of the compound (9-c) in the presence of a peroxide (such as hydrogen peroxide solution) and an organic acid (such as formic acid) forms a 5-membered ring adjacent to both the benzene ring and the ring $C^3$. The organic acid such as formic acid acts as a reactant and a reaction solvent; the molar quantity of the organic acid is usually in excess of that of the compound (9-c) [for example, the ratio of the compound (9-c) relative to the organic acid may be about 1/2 to 1/50 in a molar ratio of the compound (9-c)/the organic acid].

The cyclization reactions (vi) and (vii) may be carried out in the presence of a solvent. The solvent may include a hydrocarbon (e.g., an aliphatic hydrocarbon such as pentane or hexane; an alicyclic hydrocarbon such as cyclohexane; and an aromatic hydrocarbon such as benzene, toluene, or xylene), a halogen-containing solvent (e.g., a halogenated hydrocarbon such as methylene chloride, chloroform, carbon tetrachloride, bromoform, or ethylene chloride), and an ether (e.g., a chain ether such as ethyl ether or isopropyl ether; and a cyclic ether such as dioxane, tetrahydrofuran, or tetrahydropyran). These solvents may be used alone or as a mixed solvent.

The cyclization reactions (vi) and (vii) can be carried out under a room temperature or a heated condition. For example, the reaction can be conducted at a temperature of about 10 to 150° C. (preferably about 20 to 100° C.). Moreover, the reaction can be conducted in air or under an inactive (or inert) gas atmosphere (such as nitrogen, helium, or argon gas). The reaction may be carried out under an atmospheric pressure or an applied pressure. The reaction time is not particularly limited to a specific one and may for example be about 1 minute to 50 hours, preferably about 5 minutes to 40 hours, and more preferably about 10 minutes to 30 hours.

In the compound (7-a) [or the compound (7-c)] or the compound (7-b) [or the compound (7-d)], $L^1$ (the end group J) or $L^2$ (the end group K) may be groups which allow to directly react with each other to form a linker, or may be precursor groups of the groups which can form a linker. The precursor groups can be converted into an objective group by using a known reaction (such as an oxidation reaction, a reduction reaction, an addition reaction, a condensation reaction, a hydrolysis reaction, or a rearrangement reaction). For example, an alkoxycarbonyl group can be converted into a carboxyl group by a hydrolysis reaction; a carboxyl group can be (a) converted into an acid azide group by a reaction with a diarylphosphoryl azide, and the acid azide group can be converted into an isocyanate group by Curtius rearrangement reaction, (b) converted into a carbazoyl group by a reaction with hydrazine, (c) converted into a carbamoyl group by a reaction with ammonia, and the carbamoyl group can be converted into an isothiocyanato group by a reaction with thionyl chloride, or (d) converted into an aldehyde group by a reduction reaction, and the aldehyde group can be (d1) converted into an alkyl group by Clemmensen reduction, and the alkyl group can be converted into a haloalkyl group by halogenation or (d2) converted into an aminocyano group by a reaction with hydrazine.

The reaction for converting $L^1$ (the end group J) or $L^2$ (the end group K) into an objective group and the formation reaction of the linker L may be conducted in respective reaction systems or in the same reaction system.

Specifically, one example of the method for producing the linker represented by the formula (1-a) (a method using Curtius rearrangement) is explained in detail as follows. In this method, a compound represented by the formula (7-h) is obtained by a reaction of a carboxylic acid represented by the formula (7-f), an alcohol represented by the formula (7-g) and a diarylphosphoryl azide (a $diC_{6-10}$arylphosphoryl azide such as diphenylphosphoryl azide) in the presence of a base, according to the following reaction scheme:

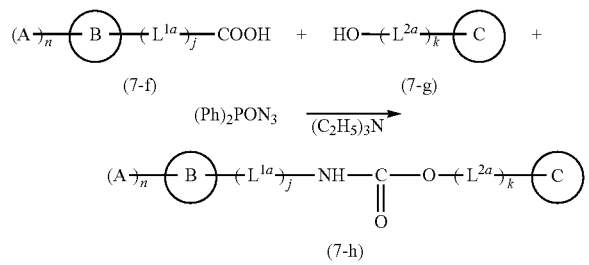

wherein the group A, the ring B, the ring C, the group $L^{1a}$, the group $L^{2a}$, j, k and n have the same meanings as defined above. More specifically, a compound represented by the formula (7-h) is obtained according to the following reaction scheme:

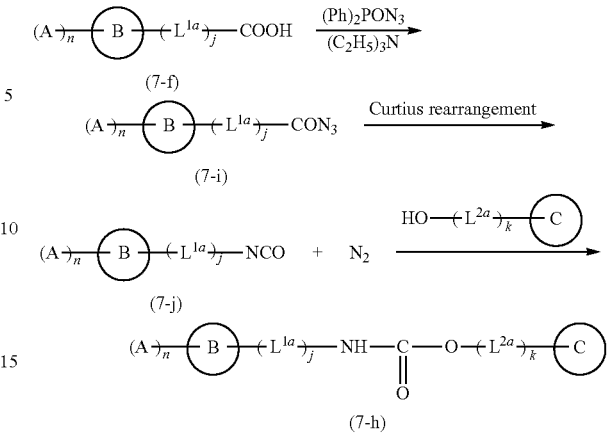

wherein the group A, the ring B, the ring C, the group $L^{1a}$, the group $L^{2a}$, j, k and n have the same meanings as defined above.

That is, the compound represented by the formula (7-h) is obtained by a step for allowing the carboxylic acid represented by the formula (7-f) to react with the diarylphosphoryl azide in the presence of the base to produce a carboxylic acid azide, a step for converting an acid azide group of the carboxylic acid azide into an isocyanate group by Curtius rearrangement to produce an isocyanate represented by the formula (7-j), and a step for allowing the isocyanate to react with the alcohol represented by the formula (7-g).

The ratio (the amount to be used) of the carboxylic acid represented by the formula (7-f) relative to the alcohol represented by the formula (7-g) is not particularly limited to a specific one, and may be the ratio at which the carboxyl group and the hydroxyl group may be equivalent or almost equivalent. For example, the ratio of the carboxylic acid relative to the alcohol may be about 2/1 to 1/2, preferably about 1.5/1 to 1/1.5, and more preferably about 1.2/1 to 1/1.2 in a molar ratio of the former/the latter.

The ratio (the amount to be used) of the diarylphosphoryl azide may for example be about 0.1 to 2 mol, preferably about 0.5 to 1.5 mol, and more preferably 0.8 to 1.2 mol relative to 1 mol of the carboxylic acid represented by the formula (7-f).

The base may be a basic inorganic compound and is usually a basic organic compound. As the basic organic compound, a tertiary amine is widely used. For example, the basic organic compound may include an aliphatic amine (e.g., a $triC_{1-6}alkylamine$ such as trimethylamine or triethylamine; and an N,N,N',N'-$tetraC_{1-4}alkylC_{1-4}alkanediamine$ such as N,N,N',N'-tetramethylethylenediamine or N,N,N',N'-tetramethylpropanediamine), an alicyclic amine (e.g., a $triC_{5-6}cycloalkylamine$ such as tricyclohexylamine; a $diC_{5-6}cycloalkylC_{1-4}alkylamine$ such as dicyclohexylethylamine; and a $diC_{1-4}alkylC_{5-6}cycloalkylamine$ such as diethylcyclohexylamine), and an aromatic amine (e.g., an N,N-$diC_{1-4}alkylaniline$ such as N,N-dimethylaniline or N,N-diethylaniline; and an N-arylpyrrolidine such as N-phenylpyrrolidine). These bases may be used alone or in combination. Among these bases, a $triC_{1-4}alkylamine$ such as triethylamine is widely used.

The ratio (the amount to be used) of the base is, for example, about 0.01 to 1 mol and preferably about 0.1 to 0.5 mol relative to 1 mol of the total of the carboxylic acid represented by the formula (7-f), the alcohol represented by the formula (7-g) and the diarylphosphoryl azide.

The reaction of the compound (7-f) and the compound (7-g) may be carried out in the presence of a solvent. The is not particularly limited to a specific one as far as the solvent is inactive to the reaction. The solvent may include a hydrocarbon (e.g., an aliphatic hydrocarbon such as pentane or hexane; an alicyclic hydrocarbon such as cyclohexane; and an aromatic hydrocarbon such as benzene, toluene, or xylene), a halogen-containing solvent (e.g., a halogenated hydrocarbon such as methylene chloride, chloroform, carbon tetrachloride, bromoform, or ethylene chloride), an ether (e.g., a chain ether such as ethyl ether or isopropyl ether; and a cyclic ether such as dioxane, tetrahydrofuran, or tetrahydropyran), a ketone (e.g., a dialkyl ketone such as acetone, methyl ethyl ketone, diisopropyl ketone, or isobutyl methyl ketone), an ester (e.g., an ester of acetic acid, such as methyl acetate, ethyl acetate, or butyl acetate), and a nitrile (e.g., acetonitrile). These solvents may be used alone or as a mixed solvent. Among these solvents, an aromatic hydrocarbon such as toluene is widely used.

The reaction of the compound (7-f) and the compound (7-g) can be conducted under a room temperature or a heated condition. For example, the reaction can be conducted at a temperature of about 10 to 150° C. (preferably about 20 to 100° C.). Moreover, the reaction can be conducted in air or under an inactive (or inert) gas atmosphere (such as nitrogen, helium, or argon gas). The reaction may be carried out under an atmospheric pressure or an applied pressure. The reaction time is not particularly limited to a specific one and may for example be about 0.1 to 20 hours, preferably about 0.5 to 15 hours, and more preferably about 1 to 10 hours.

After the completion of the reaction, the compound represented by the formula (7-h) or the salt thereof may be separated or purified from the reaction mixture by a conventional separation or purification (or isolation) method, for example, filtration, distillation, condensation, precipitation, crystallization, recrystallization, decantation, extraction, drying, washing, chromatography, and a combination thereof.

[Use and Pharmaceutical Composition]

The compound or the salt thereof of the present invention specifically binds to the component protein Skp2 of ubiquitin ligase and is thus useful as a $p27^{Kip1}$ ubiquitination inhibitor. Since the compound or the salt thereof can inhibit the ubiquitination of $p27^{Kip1}$ at a high activity, for example, by inhibition of the dissociation of $p27^{Kip1}$ from $SCF^{Skp2}$ complex, resulting in effectively inhibiting the degradation of $p27^{Kip1}$ by proteasome, the compound or the salt thereof is also useful as a $p27^{Kip1}$ degradation inhibitor. Moreover, since the compound or the salt thereof of the present invention recovers the expression amount of $p27^{Kip1}$ by inhibiting the degradation of $p27^{Kip1}$ and effectively induces cell death (apoptosis), the compound or the salt thereof is also useful as a cell-death inducer and is useful as a preventing and/or treating agent for a cell proliferative disease, for example, cancer, rheumatism, diabetes, adiposis, endometriosis, prostatomegaly, and inflammation. The compound or the salt thereof of the present invention is useful as a preventing and/or treating agent for various cancers [for example, a solid cancer (e.g., an encephaloma, a cancer of the mouth, a cancer of the pharynx, a cancer of the larynx, a lung cancer, a digestive cancer (e.g., a cancer of the esophagus, a cancer of the stomach, a cancer of the large intestine, a cancer of the liver, and a cancer of the pancreas), a urinary cancer (e.g., a cancer of the kidney, a cancer of the bladder, and a cancer of the prostate), a cancer of the breast, a cancer of the uterus (or the uterine cervix), a cancer of the ovary, a skin cancer, a cancer of the thyroid, and an osteosarcoma), and a blood cancer (e.g., a leukemia and a malignant lymphoma)]. In particular, the compound or the salt thereof of the present invention is useful as a preventing and/or treating agent for a highly malignant (or intractable) cancer, for example, an encephaloma, an oral squamous cell cancer, a lung cancer, a cancer of the stomach, a cancer of the large intestine, a cancer of the liver, a cancer of the bladder, a cancer of the prostate (e.g., a hormone refractory prostate cancer), a cancer of the breast, a cancer of the uterus (or the uterine cervix), a cancer of the ovary, and a blood cancer. The preventing and/or treating agent for the cancer is preferably used due to prevention of the development and proliferation (e.g., progression, recurrence, and metastasis) of the cancer.

The above-mentioned compound may be used as a medicine alone, or the above-mentioned crystal may be used in combination with a carrier (e.g., a pharmacologically or physiologically acceptable carrier) to provide a pharmaceutical composition (or preparation). With respect to the pharmaceutical composition of the present invention, the carrier may be suitably selected depending on the form of the composition or preparation (that is, the dosage form), the route of administration, the application (or use), and others. The dosage form is not particularly limited to a specific one and may be a solid preparation (for example, powdered preparations, powders, granulated preparations (e.g., granules and microfine granules or the like), spherical or spheroidal preparations, pills, tablets, capsules (including soft capsules and hard capsules), dry syrups, and suppositories), a semisolid preparation (for example, creams, ointments, gels, gumdrop-like preparations, and film-like preparations, sheet-like preparations), a liquid preparation (for example, solutions, suspensions, emulsions, syrup, elixir, lotions, injectable solutions (or injections), and drops), and others. Moreover, sprays or aerosols of the powdered preparations and/or the liquid preparation may be also included. Incidentally, the capsules may be a capsule filled with a liquid or a capsule filled with a solid preparation (such as granules). Moreover, the preparation may be a lyophilized preparation. Further, the preparation of the present invention may be a preparation releasing the active ingredient(s) at a controlled rate (a sustained release preparation or a rapid-release preparation). The preparation may be a preparation for oral administration or a preparation for parenteral administration (for example, a nosal preparation (or a collunarium), an inhalant preparation, and a preparation for transdermal administration). Furthermore, the preparation may be a preparation for topical administration (for example, solutions such as injectable solutions (e.g., aqueous injectable solutions and nonaqueous injectable solutions), suspensions, ointments, plasters and pressure sensitive adhesives, and cataplasms). The preparation of the present invention is practically a solid preparation (particularly, a preparation for oral administration) or a liquid preparation (a preparation for parenteral administration, such as injectable solutions). The amount of the compound or the salt thereof in the preparation of the present invention is not particularly limited to a specific one. Depending on the dosage form, the amount of the compound or the salt thereof can for example be selected from the range of about 0.0001 to 99% by weight, and is usually about 0.005 to 60% by weight (e.g., about 0.01 to 50% by weight) for a solid preparation or a semisolid preparation and is about 0.001 to 30% by weight (e.g., about 0.005 to 20% by weight) for a liquid preparation.

The carrier may for example be selected depending on the administration route and the application of preparation, from components (e.g., an excipient, a binder, a disintegrant, a lubricant, and a coating agent) listed in Japanese Pharmacopoeia, (1) Handbook of Pharmaceutical Excipients (Maruzen Company, ltd., (1989)), (2) Japanese Pharmaceutical Excipients Dictionary 2000 (Yakuji Nippo Ltd., issued March, 2002), (3) Japanese Pharmaceutical Excipients Dictionary 2005 (Yakuji Nippo Ltd., issued May, 2005), (4) Pharmaceutics, revised fifth edition (Nankodo, Co., Ltd. (1997)), and (5) Japanese Pharmaceutical Excipients 2003 (Yakuji Nippo Ltd., issued August, 2003). For example, the carrier for a solid preparation is practically at least one member selected from the group consisting of an excipient, a binder, and a disintegrant. Moreover, the pharmaceutical composition may contain a lipid.

The excipient may include a saccharide or a sugar alcohol such as lactose, white sugar or refined sugar, glucose, sucrose, mannitol, sorbitol, or xylitol; a starch such as acorn starch; a polysaccharide such as a crystalline cellulose (including a microcrystalline cellulose); silicon dioxide or a silicate such as a light silicic anhydride or a synthetic aluminum silicate; and others. The binder may include a water-soluble starch such as a pregelatinized starch or a partially pregelatinized starch; a polysaccharide such as agar, gum acacia (or gum arabic), dextrin, sodium alginate, a tragacanth gum, a xanthan gum, a hyaluronic acid, or a sodium chondroitin sulfate; a synthetic polymer such as a polyvinylpyrrolidone, a polyvinyl alcohol, a carboxyvinyl polymer, a polyacrylic polymer, a polylactic acid, or a polyethylene glycol; a cellulose ether such as a methyl cellulose (MC), an ethyl cellulose (EC), a carboxymethyl cellulose (CMC), a carboxymethyl cellulose sodium, a hydroxyethyl cellulose (HEC), a hydroxypropyl cellulose (HPC), or a hydroxypropylmethyl cellulose (HPMC); and others. The disintegrant may include calcium carbonate, a sodium carboxymethyl starch, a carboxymethyl cellulose or a salt thereof (e.g., a carmellose, a carmellose sodium, a carmellose calcium, and a croscarmellose sodium), a crosslinked polyvinylpyrrolidone (crospovidone), a low-substituted hydroxypropyl cellulose, and others. These carriers may be used alone or in combination.

For example, there may be used, as the coating agent, a saccharide or a sugar, a cellulose derivative such as an ethyl cellulose or a hydroxymethyl cellulose, a poly(oxyethylene glycol), a cellulose acetate phthalate, a hydroxypropylmethyl cellulose phthalate, a methyl methacrylate-(meth)acrylic acid copolymer, and eudragit (a copolymer of methacrylic acid and acrylic acid). The coating agent may be an enteric component (e.g., a cellulose phthalate, a hydroxypropylmethyl cellulose phthalate, and a methyl methacrylate-(meth)acrylic acid copolymer) or a gastric soluble component comprising a polymer containing a basic component such as a dialkylaminoalkyl(meth)acrylate (e.g., eudragit). Moreover, the preparation may be a capsule having such an enteric component or gastric soluble component as a capsule shell.

In the carrier of the liquid preparation, an oil-based carrier may include an oil derived from plants or animals (e.g., an oil derived from vegetables such as a jojoba oil, an olive oil, a palm oil, or a cotton seed oil; and an oil derived from animals such as squalene), a mineral oil (e.g., a liquid petrolatum and a silicone oil), and others. An aqueous carrier may include water (e.g., a purified water or a sterile water, a distilled water for injection), a physiological saline, a Ringer's solution, a glucose solution, a water-soluble organic solvent [for example, a lower aliphatic alcohol such as ethanol or isopropanol; a (poly)alkylene glycol (e.g., ethylene glycol and a polyethylene glycol); and glycerin], dimethyl isosorbide, dimethylacetamide, and others. Moreover, the carrier of the semisolid preparation may be selected from the carrier of the solid preparation and/or that of the liquid preparation. Further, the carrier of the semisolid preparation may contain a lipid.

The lipid may include a wax (e.g., a bees wax, a carnauba wax, a lanolin, a paraffin, and a petrolatum), a higher (or long chain) fatty acid ester [e.g., an alkyl ester of a saturated or unsaturated fatty acid, and an ester of a fatty acid with a polyvalent alcohol (such as a polyC$_{2-4}$alkylene glycol, glycerin, or a polyglycerin) (e.g., a glyceride)], a hardened (or hydrogenated) oil, a higher alcohol (e.g., a saturated aliphatic alcohol such as stearyl alcohol and an unsaturated aliphatic alcohol such as oleyl alcohol), a higher fatty acid (e.g., linoleic acid, linoleic acid, stearic acid and oleic acid), a metallic soap (e.g., a metal salt of a fatty acid, such as a sodium salt of palm oil fatty acid or calcium stearate), and others.

In the preparation, known additives can be suitably used depending on an administration route, a dosage form, and others. Such an additive may include, for example, a lubricant (e.g., a talc, magnesium stearate, and a polyethylene glycol 6000), a disintegrant aid, an antioxidation agent or an antioxidant, an emulsifier (e.g., a variety of surfactants such as a nonionic surfactant), a dispersing agent, a suspending agent, a dissolving agent, a dissolution aid, a thickener (e.g., a water-soluble polymer such as a carboxyvinyl polymer, a polyvinyl alcohol, a carrageen, or a gelatin; and a cellulose ether such as a carboxymethyl cellulose), a pH adjusting agent or a buffer (e.g., a citric acid-sodium citrate buffer), a stabilizer, an antiseptic agent or a preservative (e.g., a paraben such as methyl paraben or butyl paraben), a fungicide or antibacterial agent (e.g., a benzoic acid compound such as sodium benzoate), an antistatic agent, a corrigent or a masking agent (e.g., sweetening agent), a coloring agent (e.g., a dye and a pigment such as colcothar), a deodorant or a perfume (e.g., an aromatic substance), an algefacient, an antifoaming agent, an isotonizing agent, and a soothing agent. These additives may be used singly or in combination.

In the injectable solution, usually, the dissolving agent, the dissolution aid, the suspending agent, the buffer, the stabilizer, the preservative, and others may be used as the additive in practical cases. Incidentally, to powders for an injection (lyophilized preparations), which are dissolved or suspended in water (a water for injection) or a transfusion agent (such as a physiological saline, a glucose solution, or a Ringer's solution) before administration, may be added conventional additive (s) used for powders for an injection.

Moreover, in a topically administering preparation such as an inhalant preparation or a transdermal absorption preparation, as the additive, usually, the dissolution aid, the stabilizer, the buffer, the suspending agent, the emulsifier, the preservative, and others may be practically used.

The pharmaceutical composition of the present invention may be prepared by using a carrier component in addition to an effective ingredient, and if necessary, an additive and the like, with a conventional preparation manner (for example, a production process described in Japanese Pharmacopoeia 15$^{th}$ edition or a process in accordance with the production process).

The compound or the salt thereof (including the p27$^{Kip1}$ ubiquitination inhibitor, the p27$^{Kip1}$ degradation inhibitor, the preventing and/or treating agent for a cell proliferative disease, and the pharmaceutical composition) of the present invention is safely administered orally or parenterally (for example, transrectally, intravenously, intramuscularly, and subcutaneously) to human beings and non-humans, usually mammals (e.g., human beings, mice, rats, rabbits, dogs, cats, bovines, horses, pigs, and monkeys). The amount to be administered (or dose) of the compound or the salt thereof of the present invention may suitably be selected according to the subject of administration, the age, body weight, sex, and condition (e.g., a performance status, a condition of a disease, and a presence of a complication) of the subject, the time (or period or schedule) of administration, the dosage form, the method (or route) of administration, and others.

The amount to be administered (or dose) to human beings is, for example, in an oral administration, usually about 0.01 to 1,000 mg a day, preferably about 0.1 to 700 mg a day, and more preferably about 0.2 to 500 mg a day, in a free form of the compound or the salt thereof. Further, in a topically administering agent, the amount to be administered to human beings is usually about 0.01 to 200 mg a day, preferably about 0.05 to 100 mg a day, and more preferably about 0.1 to 80 mg a day, in a free form of the compound or the salt thereof.

EXAMPLES

The following examples are intended to describe this invention in further detail and should by no means be interpreted as defining the scope of the invention.

Synthesis scheme 1

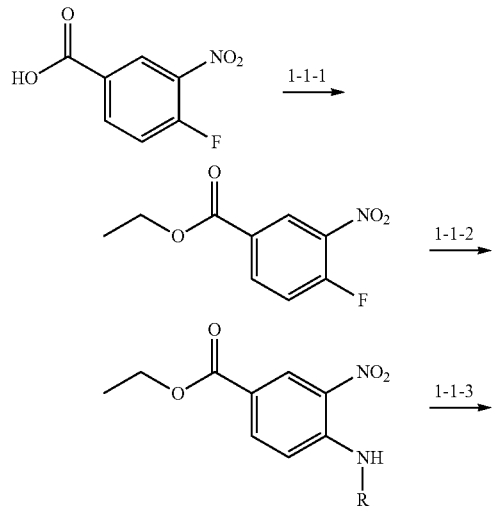

In the formulae, R represents an alkyl group or an alkoxyalkyl group.

Example 1-1

Step 1-1-1

Ethyl 4-fluoro-3-nitrobenzoate

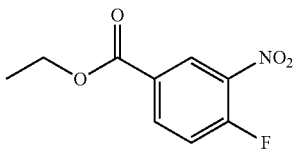

To a suspension of 4-fluoro-3-nitrobenzoic acid (150 g, 0.810 mol) in ethanol (1000 ml), concentrated sulfuric acid (25 ml) was added dropwise, and the mixture was heated under reflux for 8 hours. After being allowed to cool, the mixture was concentrated under a reduced pressure, and water was added thereto under stirring. The precipitate was separated by filtration, washed with water and then subjected to through circulation drying to give the title compound (160 g, 93%) as a yellow solid.

$^1$H-NMR (DMSO-$d_6$) δ: 8.56 (dd, J=2.3, 7.3 Hz, 1H), 8.35-8.31 (m, 1H), 7.76-7.71 (m, 1H), 4.37 (q, J=7.3 Hz, 2H), 1.35 (t, J=7.3 Hz, 3H)

Mass, m/z: 213 (M$^+$), 185, 168 (base)

Step 1-1-2

Ethyl 4-methylamino-3-nitrobenzoate

Ethyl 4-fluoro-3-nitrobenzoate (10.0 g, 46.9 mmol) prepared in the Step 1-1-1 was dissolved in methanol (40 ml), and triethylamine (10 ml, 70.4=01) was added thereto. Under an ice cooling, a 40% methylamine-methanol solution (5.50 g, 70.4 mmol) was added to the mixture. After the resulting mixture was stirred for one hour under an ice cooling, ice water was added thereto. The precipitate was separated by filtration and washed with water. The washed product was subjected to through circulation drying overnight to give the title compound (10.4 g, 99%) as a yellow powder.

$^1$H-NMR (CDCl$_3$) δ: 8.87 (d, J=1.9 Hz, 1H), 8.33 (brs, 1H), 8.08 (dd, J=1.9, 9.2 Hz, 1H), 6.87-6.84 (m, 1H), 4.35 (q, J=6.9 Hz, 2H), 3.08 (d, J=5.0 Hz, 3H), 1.38 (t, J=6.9 Hz, 3H)

Mass, m/z: 224 (M$^+$), 179, 105 (base)

Step 1-1-3

Ethyl 3-amino-4-methylaminobenzoate

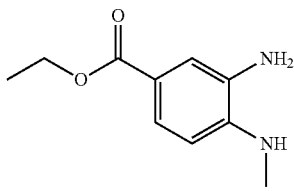 [SMILES: CCOC(=O)c1ccc(NC)c([N+](=O)[O-])c1]

Ethyl 4-methylamino-3-nitrobenzoate (6.80 g, 30.3 mmol) prepared in the Step 1-1-2 was dissolved in methanol (200 ml), and palladium 5% on carbon (1.10 g) was added to the solution. The mixture was stirred under a hydrogen flow at a room temperature overnight. The mixture was filtered, and the filtrate was concentrated to give the title compound (4.85 g, 82%) as a light-brown powder.

$^1$H-NMR (CDCl$_3$) δ: 7.92 (dd, J=1.9, 8.5 Hz, 1H), 7.40 (d, J=1.9 Hz, 1H), 6.58 (d, J=8.5 Hz, 1H), 4.31 (q, J=7.3 Hz, 2H), 3.99 (brs, 1H), 3.22 (brs, 2H), 2.19 (s, 3H), 1.36 (t, J=7.3 Hz, 3H)

Mass, m/z: 194 (M$^+$, base), 149

Step 1-1-4

Ethyl 1-methyl-1H-benzimidazole-5-carboxylate

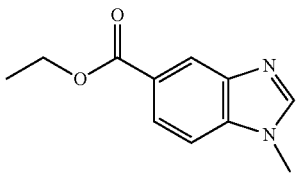

Ethyl 3-amino-4-methylaminobenzoate (24.1 g, 124 mmol) in the Step 1-1-3 was dissolved in formic acid (200 ml), and the solution was heated under reflux for 2 hours. After being cooled by ice, the solution was neutralized with a 25% ammonia water. The solution was subjected to extraction with chloroform, and the extract was dried over anhydrous magnesium sulfate and then concentrated. The concentrate was purified by silica gel column chromatography (chloroform:methanol=20:1) to give the title compound (26.1 g, quantitative) as a light-purple powder.

$^1$H-NMR (CDCl$_3$) δ: 8.52 (d, J=1.5 Hz, 1H), 8.04 (dd, J=1.5, 8.5 Hz, 1H), 7.92 (s, 1H), 7.39 (d, J=8.5 Hz, 1H), 4.40 (q, J=7.3 Hz, 2H), 3.86 (s, 3H), 1.41 (t, J=7.3 Hz, 3H)

Mass, m/z: 204 (M$^+$), 159 (base)

Step 1-1-5

(1-Methyl-1H-benzimidazol-5-yl)methanol

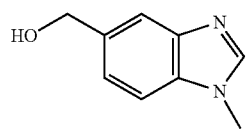

Under an argon gas flow, lithium aluminum hydride (9.70 g, 256 mmol) was suspended in tetrahydrofuran (100 ml); and under an ice cooling, a solution (100 ml) of ethyl 1-methyl-1H-benzimidazole-5-carboxylate (26.1 g, 128 mmol) prepared in the Step 1-1-4 in tetrahydrofuran was slowly added thereto. The mixture was stirred under an ice cooling for one hour. Under an ice cooling, a saturated sodium bicarbonate solution was slowly added to the mixture. The precipitate was removed by filtration, and the residue was concentrated. The concentrate was dissolved in chloroform, and the solution was washed with a saturated sodium bicarbonate solution and then concentrated. The concentrate was purified by silica gel column chromatography (chloroform:methanol=10:1 to 5:1) to give the title compound (11.4 g, 55%) as a light-red powder.

$^1$H-NMR (CDCl$_3$) δ: 7.85 (s, 1H), 7.77 (s, 1H), 7.37-7.34 (m, 2H), 4.80 (s, 2H), 3.84 (s, 3H), 1.92 (brs, 1H)

Mass, m/z: 162 (M$^+$), 133 (base)

Examples 1-2 to 1-6

The objective bicyclic compounds were obtained according to the same procedure as in Example 1-1 except that compounds shown in the following table were used instead of the 40% methylamine-methanol solution as a ring-forming component or ethyl 4-fluoro-3-nitrobenzoate as a monocyclic compound.

TABLE 9

| Ring-forming component | Monocyclic compound | Example | $^1$H-NMR | Mass, m/z |
| --- | --- | --- | --- | --- |
| Ethyl amine | — | Example 1-2 ![structure] | (DMSO-d$_6$) δ: 8.19 (s, 1H), 7.57 (d, J = 0.8 Hz, 1H), 7.53 (d, J = 8.5 Hz, 1H), 7.22 (dd, J = 1.5, 8.5 Hz, 1H), 5.10 (t, J = 5.8 Hz, 1H), 4.59 (d, J = 5.8 Hz, 2H), 4.26 (q, J = 7.3 Hz, 2H), 1.41 (t, J = 7.3 Hz, 3H) | 176 (M$^+$), 147 (base) |

TABLE 9-continued

| Ring-forming component | Monocyclic compound | Example | ¹H-NMR | Mass, m/z |
|---|---|---|---|---|
| 1-Amino propane | — | Example 1-3 | (DMSO-d$_6$) δ: 8.17 (s, 1H), 7.57 (s, 1H), 7.53 (d, J = 8.1 Hz, 1H), 7.22 (dd, J = 1.2, 8.5 Hz, 1H), 5.09 (t, J = 5.8 Hz, 1H), 4.58 (d, J = 5.8 Hz, 2H), 4.19 (t, J = 6.9 Hz, 2H), 1.85-1.76 (m, 2H), 0.83 (t, J = 7.3 Hz, 3H) | 190 (M⁺), 161 (base) |
| Isopropyl amine | — | Example 1-4 | (DMSO-d$_6$) δ: 8.27 (s, 1H), 7.57-7.54 (m, 2H), 7.23-7.20 (m, 1H), 5.10 (t, J = 5.8 Hz, 1H), 4.76-4.70 (m, 1H), 4.58 (d, J = 5.8 Hz, 2H) 1.53 (d, J = 6.7 Hz, 6H) | 232 (M⁺), 187 (base) |
| — | 4-Fluoro-3-nitro-acetophenone | Example 1-5 | (DMSO-d$_6$) δ: 8.12 (s, 1H), 7.58 (d, J = 0.8 Hz, 1H), 7.47 (d, J = 8.5 Hz, 1H), 7.27 (dd, J = 1.5, 8.5 Hz, 1H), 5.08 (d, J = 4.2 Hz, 1H), 4.86-4.81 (m, 1H), 3.82 (s, 3H), 1.37 (d, J = 6.6 Hz, 3H) | 176 (M⁺, base) |
| 2-Methoxy ethyl amine | — | Example 1-6 | (DMSO-d$_6$) δ: 8.12 (s, 1H), 7.56 (s, 1H), 7.54 (d, J = 8.5 Hz, 1H), 7.21 (dd, J = 1.2, 8.5 Hz, 1H), 5.10 (t, J = 5.8 Hz, 1H), 4.58 (d, J = 5.8 Hz, 2H), 4.39 (t, J = 5.4 Hz, 2H), 3.67 (t, J = 5.4 Hz, 2H), 3.22 (s, 3H) | 206 (M⁺), 161 (base) |

Synthesis scheme 2

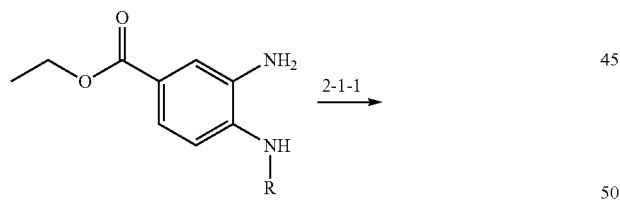

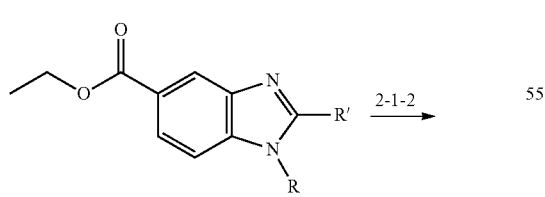

In the formulae, R represents an alkyl group, and R' represents an alkyl group or an alkoxyalkyl group.

Example 2-1

Step 2-1-1

Ethyl 1,2-dimethyl-1H-benzimidazole-5-carboxylate

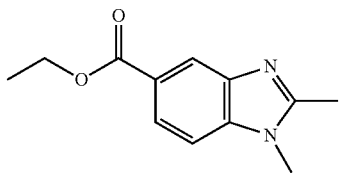 [SMILES: CCOC(=O)c1ccc2c(c1)nc(C)n2C]

Ethyl 3-amino-4-methylaminobenzoate (1.00 g, 5.15 mmol) prepared in the Step 1-1-3 was dissolved in acetic anhydride (4 ml), and the mixture was heated under reflux for 19 hours. After being allowed to cool, the mixture was neutralized with a saturated sodium bicarbonate solution and subjected to extraction with ethyl acetate. The extract was dried over anhydrous magnesium sulfate and then concentrated. The concentrate was purified by silica gel column chromatography (chloroform:methanol=10:1) to give the title compound (1.15 g, quantitative) as a light-brown oily substance.

$^1$H-NMR (CDCl$_3$) δ: 8.39 (d, J=1.5 Hz, 1H), 7.98 (dd, J=1.5, 8.5 Hz, 1H), 7.28 (d, J=8.5 Hz, 1H), 4.39 (q, J=6.9 Hz, 2H), 3.75 (s, 3H), 2.62 (s, 3H), 1.41 (t, J=6.9 Hz, 3H)

Mass, m/z: 218 (M$^+$), 173 (base)

Step 2-1-2

(1,2-dimethyl-1H-benzimidazol-5-yl)methanol

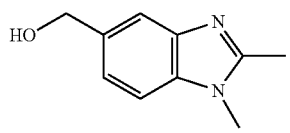

Ethyl 1,2-dimethyl-1H-benzimidazole-5-carboxylate prepared in the Step 2-1-1 was used and subjected to the same procedure as in the Step 1-1-5 to give the title compound.

$^1$H-NMR (DMSO-d$_6$) δ: 7.44 (d, J=0.7 Hz, 1H), 7.39 (d, J=8.5 Hz, 1H), 7.14 (dd, J=1.5, 8.5 Hz, 1H), 5.09 (t, J=5.8 Hz, 1H), 4.56 (d, J=5.8 Hz, 2H), 3.71 (s, 3H), 2.50 (s, 3H)

Mass, m/z: 176 (M$^+$), 147 (base)

Examples 2-2 to 2-4

The objective bicyclic compounds were obtained according to the same procedure as in Example 2-1 except that compounds shown in the following table were used instead of acetic anhydride as a ring-forming component or ethyl 3-amino-4-methylaminobenzoate as a monocyclic compound.

Synthesis scheme 3

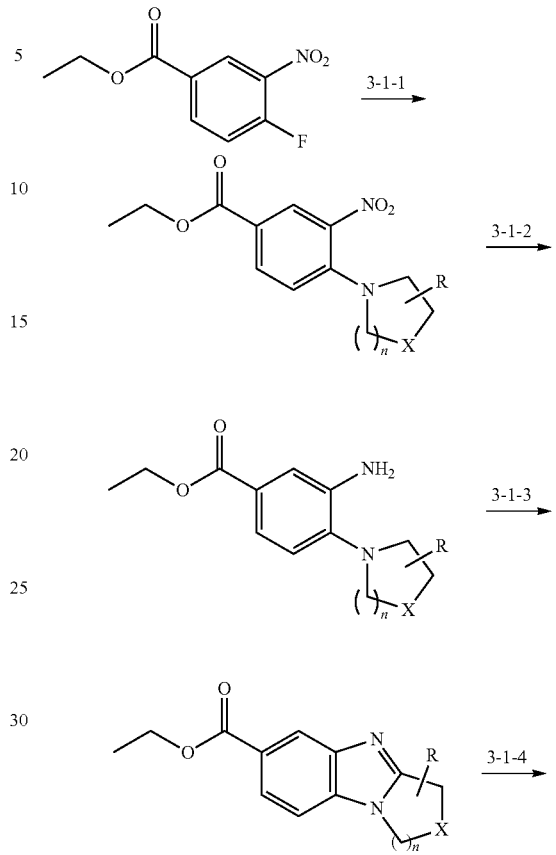

TABLE 10

| Ring-forming component | Mono-cyclic compound | Example | $^1$H-NMR | Mass, m/z |
|---|---|---|---|---|
| Propionic anhydride | — | Example 2-2 | (CDCl$_3$) δ: 7.67 (s, 1H), 7.30-7.27 (m, 2H), 4.77 (s, 2H), 3.72 (s, 3H), 2.90 (q, J = 7.7 Hz, 2H), 1.44 (t, J = 7.7 Hz, 3H) | 190 (M$^+$, base), 161 |
| — | Ethyl 3-amino-4-ethyl amino-benzoate | Example 2-3 | (DMSO-d$_6$) δ: 7.45 (d, J = 0.8 Hz, 1H), 7.41 (d, J = 8.1 Hz, 1H), 7.14 (dd, J = 1.5, 8.5 Hz, 1H), 5.06 (t, J = 5.8 Hz, 1H), 4.56 (d, J = 5.8 Hz, 2H), 4.19 (q, J = 7.3 Hz, 2H), 2.51 (s, 3H), 1.28 (t, J = 7.3 Hz, 3H) | 190 (M$^+$, base), 161 |
| Methoxyacetic acid | — | Example 2-4 | (DMSO-d$_6$) δ: 7.54 (d, J = 0.8 Hz, 1H), 7.48 (dd, J = 8.1 Hz, 1H), 7.23 (dd, J = 1.5, 8.1 Hz, 1H), 4.68 (s, 2H), 4.58 (d, J = 5.8 Hz, 2H), 3.79 (s, 3H), 3.32 (s, 3H) | 206 (M$^+$), 190 (base) |

-continued

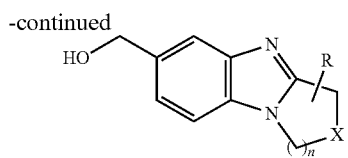

In the formulae, R represents a hydrogen atom, an alkyl group or a hydroxyl group; X represents CH$_2$, NH, O or S; and n is an integer of 1 to 3.

Example 3-1

Step 3-1-1

Ethyl 3-nitro-4-piperidin-1-ylbenzoate

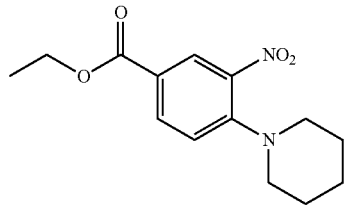 [SMILES: CCOC(=O)c1ccc(N2CCCCC2)c([N+](=O)[O-])c1]

Ethyl 4-fluoro-3-nitrobenzoate (160 g, 0.752 mol) prepared in the Step 1-1-1 was suspended in ethanol (500 ml). Triethylamine (91.4 g, 0.903 mol) was added to the suspension, and under an ice cooling, piperidine (76.9 g, 0.903 mol) was slowly added thereto. After the mixture was stirred at a room temperature for 2 hours, a saturated sodium bicarbonate solution was added to the mixture, and the resulting mixture was subjected to extraction with ethyl acetate. The ethyl acetate layer was washed with a saturated sodium bicarbonate solution and a saturated saline solution in order, and then dried over anhydrous magnesium sulfate and concentrated. The concentrate was purified by silica gel column chromatography (n-hexane:ethyl acetate=4:1 to 3:1) to give the title compound (222 g, quantitative) as a poppy-red oily substance.

$^1$H-NMR (DMSO-d$_6$) δ: 8.26 (d, J=2.3 Hz, 1H), 7.98 (dd, J=2.3, 8.9 Hz, 1H), 7.31 (d, J=9.2 Hz, 1H), 4.30 (q, J=7.3 Hz, 2H), 3.13 (brs, 4H), 1.60 (brs, 6H), 1.31 (t, J=7.3 Hz, 3H)

Mass, m/z: 278 (M$^+$), 261 (base)

Step 3-1-2

Ethyl 3-amino-4-piperidin-1-ylbenzoate

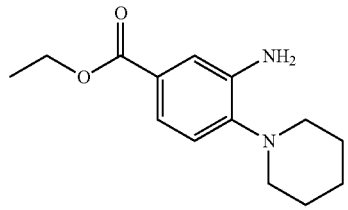 [SMILES: CCOC(=O)c1ccc(N2CCCCC2)c(N)c1]

Ethyl 3-nitro-4-piperidin-1-ylbenzoate (2.83 g, 10.2 mmol) prepared in the Step 3-1-1 was dissolved in methanol (50 ml), and palladium 5% on carbon (500 mg) was added to the solution. The mixture was stirred under a hydrogen flow at a room temperature overnight. The mixture was filtered, and the filtrate was concentrated to give the title compound (2.23 g, 90%) as a blackish-red solid.

$^1$H-NMR (CDCl$_3$) δ: 7.43 (dd, J=2.3, 8.1 Hz, 1H), 7.38 (d, J=2.3 Hz, 1H), 6.95 (d, J=8.1 Hz, 1H), 4.32 (q, J=7.3 Hz, 2H), 3.95 (brs, 2H), 2.95-2.80 (m, 4H), 1.72-1.68 (m, 4H), 1.61-1.57 (m, 2H), 1.36 (t, J=7.3 Hz, 3H)

Mass, m/z: 248 (M$^+$, base)

Step 3-1-3

Ethyl 1,2,3,4-tetrahydrobenzo[4,5]imidazo[1,2-a]pyridine-7-carboxylate

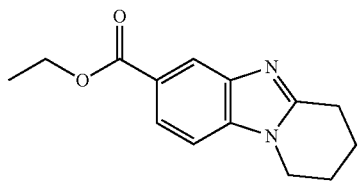 [SMILES: CCOC(=O)c1ccc2c(c1)nc1n2CCCC1]

Ethyl 3-amino-4-piperidin-1-ylbenzoate (5.38 g, 21.7 mmol) prepared in the Step 3-1-2 was dissolved in formic acid (90%, 40 ml). Hydrogen peroxide solution (20 ml) was added to the solution, and the mixture was heated under reflux for 40 minutes. After being allowed to cool, the mixture was neutralized with a saturated sodium bicarbonate solution and a 25% ammonia water and subjected to extraction with ethyl acetate. The extract was dried over anhydrous magnesium sulfate and then concentrated. The residue was purified by silica gel column chromatography (n-hexane:ethyl acetate=1:1) to give the title compound (3.94 g, 74%) as a light-brown powder.

$^1$H-NMR (DMSO-d$_6$) δ: 8.13 (d, J=1.2 Hz, 1H), 7.84 (dd, J=1.5, 8.1 Hz, 1H), 7.57-7.54 (m, 1H), 4.32 (q, J=6.9 Hz, 2H), 4.16-4.13 (m, 2H), 3.02-2.98 (m, 2H), 2.09-2.03 (m, 2H), 1.98-1.92 (m, 2H), 1.35 (t, J=6.9 Hz, 3H)

Mass, m/z: 244 (M$^+$), 199 (base)

Step 3-1-4

(1,2,3,4-Tetrahydrobenzo[4,5]imidazo[1,2-a]pyridine-7-yl)methanol

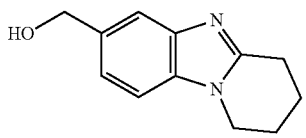 [SMILES: OCc1ccc2c(c1)nc1n2CCCC1]

Lithium aluminum hydride (1.97 g, 51.9 mmol) was suspended in tetrahydrofuran (30 ml); and under an ice cooling, a solution (20 ml) of ethyl 1,2,3,4-tetrahydrobenzo[4,5]imidazo[1,2-a]pyridine-7-carboxylate (6.34 g, 26.0 mmol) prepared in the Step 3-1-3 in tetrahydrofuran was slowly added thereto. After the mixture was stirred under an ice cooling for one hour, a saturated sodium bicarbonate solution (5 ml) was slowly added to the mixture at the same temperature while paying attention to the generation of heat. Further, ethyl acetate was slowly added to the mixture. The mixture was allowed to cool to a room temperature and filtered. The filtrate was thoroughly washed with chloroform. The filtrate was concentrated and purified by silica gel column chromatography (chloroform:methanol=20:1 to 10:1) to give the title compound (4.20 g, 80%) as a white powder.

$^1$H-NMR (DMSO-$d_6$) δ: 7.45 (d, J=0.7 Hz, 1H), 7.37 (d, J=8.1 Hz, 1H), 7.13 (dd, J=1.2, 8.1 Hz, 1H), 5.08 (t, J=5.8 Hz, 1H), 4.57 (d, J=5.8 Hz, 2H), 4.08-4.05 (m, 2H), 2.96-2.93 (m, 2H), 2.07-2.01 (m, 2H), 1.96-1.90 (m, 2H)

Mass, m/z: 202 (M$^+$, base), 185

Examples 3-2 to 3-7

The objective tricyclic compounds were obtained according to the same procedure as in Example 3-1 except that any one of N-containing monocyclic compounds shown in the following table was used instead of piperidine.

TABLE 11

| N-containing monocyclic compound | Example | $^1$H-NMR | Mass, m/z |
|---|---|---|---|
| Pyrrolidine | Example 3-2 | (DMSO-$d_6$) δ: 7.47 (s, 1H), 7.35 (d, J = 8.1 Hz, 1H), 7.12 (dd, J =1.2, 8.1 Hz, 1H), 5.12 (br s, 1H), 4.57 (s, 2H), 4.08 (t, J = 6.9 Hz, 2H), 2.95-2.91 (m, 2H), 2.67-2.58 (m, 2H), 1.35 (t, J = 7.0 Hz, 3H) | 188 (M$^+$), 171, 159 (base) |
| Azepane | Example 3-3 | (DMSO-$d_6$) δ: 7.44 (s, 1H), 7.42 (d, J = 8.1 Hz, 1H), 7.13 (dd, J = 1.2, 8.1 Hz, 1H), 5.08-5.05 (m, 1H), 4.56 (d, J = 5.8 Hz, 2H), 4.12 (t, J = 5.0 Hz, H), 3.01 (t, J = 5.8 Hz, 2H), 1.90-1.84 (m, 2H), 1.74-1.64 (m, 4H) | 216 (M$^+$), 187 (base) |
| 2-Methyl piperidine | Example 3-4 | (DMSO-$d_6$) δ: 7.44 (d, J = 0.8 Hz, 1H), 7.42 (d, J = 8.1 Hz, 1H), 7.13 (dd, J = 1.5, 8.5 Hz, 1H), 5.07 (t, J = 5.8 Hz, 1H), 4.67-4.59 (m, 1H), 4.56 (d, J = 5.8 Hz, 2H), 3.01-2.94 (m, 1H), 2.91-2.82 (m, 1H), 2.18-2.09 (m, 1H), 2.04-1.95 (m, 1H), 1.92-1.84 (m, 2H), 1.42 (d, J = 6.4 Hz, 3H) | 216 (M$^+$), 201, 187 (base) |
| 4-Methyl piperidine | Example 3-5 | (DMSO-$d_6$) δ: 7.45 (d, J = 0.8 Hz, 1H), 7.37 (d, J = 8.1 Hz, 1H), 7.14 (dd, J = 1.2, 8.1 Hz, 1H), 5.08 (t, J = 5.8 Hz, 1H), 4.57 (d, J = 5.4 Hz, 2H), 4.25-4.20 (m, 1H), 3.97-3.90 (m, 1H), 3.07-3.02 (m, 1H), 2.58-2.54 (m, 1H), 2.13-2.07 (m, 2H), 1.78-1.68 (m, 1H), 1.11 (d, J = 6.6 Hz, 3H) | 216 (M$^+$), 187 (base) |
| Morpholine | Example 3-6 | (DMSO-$d_6$) δ: 7.52 (s, 1H), 7.45 (d, J = 8.5 Hz, 1H), 7.20 (dd, J = 1.5, 8.5 Hz, 1H), 5.12 (t, J = 5.8 Hz, 1H), 4.94 (s, 2H), 4.59-4.58 (m, 2H), 4.20-4.14 (m, 4H) | 204 (M$^+$), 187, 175 (base) |
| 3-Hydroxy pyrrolidine | Example 3-7 | (DMSO-$d_6$) δ: 7.49 (s, 1H), 7.37 (d, J = 8.1 Hz, 1H), 7.13 (dd, J = 1.5, 8.1 Hz, 1H), 5.62 (d, J = 4.6 Hz, 1H), 5.09 (t, J = 5.8 Hz, 1H), 5.00-4.95 (m, 1H), 4.57 (d, J = 5.8 Hz, 2H), 4.27 (dd, J = 5.4, 10.8 Hz, 1H), 3.89 (dd, J = 2.3, 10.8 Hz, 1H), 3.25 (dd, J = 6.6, 17.0 Hz, 1H), 2.77 (dd, J = 2.7, 17.0 Hz, 1H) | 204 (M$^+$), 175 (base) |

Example 3-8

7-hydroxymethyl-1,2,3,4-tetrahydrobenzo[4,5]imidazo[1,2-a]pyridin-3-ol

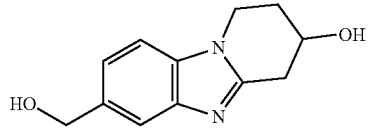 [SMILES: OCc1ccc2c(c1)nc1n2CCC(O)C1]

The title compound was obtained according to the same procedure as in Example 3-1 except that 4-hydroxypiperidine was used instead of piperidine.

$^1$H-NMR (DMSO-d$_6$) δ: 7.45 (s, 1H), 7.38 (d, J=8.5 Hz, 1H), 7.14 (dd, J=1.2, 8.1 Hz, 1H), 5.62 (d, J=3.5 Hz, 1H), 5.08 (t, J=5.8 Hz, 1H), 4.57 (d, J=5.8 Hz, 2H), 4.29-4.23 (m, 1H), 4.12-4.07 (m, 2H), 3.13 (dd, J=4.2, 17.0 Hz, 1H), 2.87 (dd, J=5.4, 17.0 Hz, 1H), 2.18-1.91 (m, 2H)

Mass, m/z: 218 (M$^+$, base)

approximately halved, the mixture was neutralized with a saturated sodium bicarbonate solution. The mixture was subjected to extraction with ethyl acetate, and the extract was dried over anhydrous magnesium sulfate and then concentrated to give the title compound (5.87 g, 99%) as a light-brown solid.

$^1$H-NMR (CDCl$_3$) δ: 7.74 (d, J=2.3 Hz, 1H), 7.72 (d, J=1.9 Hz, 1H), 6.62 (d, J=8.1 Hz, 1H), 4.30 (q, J=7.3 Hz, 2H), 4.00 (brs, 2H), 2.17 (s, 3H), 1.35 (t, J=7.3 Hz, 3H)

Mass, m/z: 179 (M$^+$), 134 (base)

Step 4-1-2

Ethyl 1H-indazole-5-carboxylate

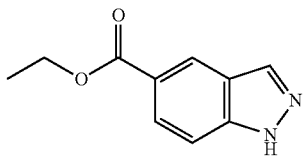

Synthesis scheme 4

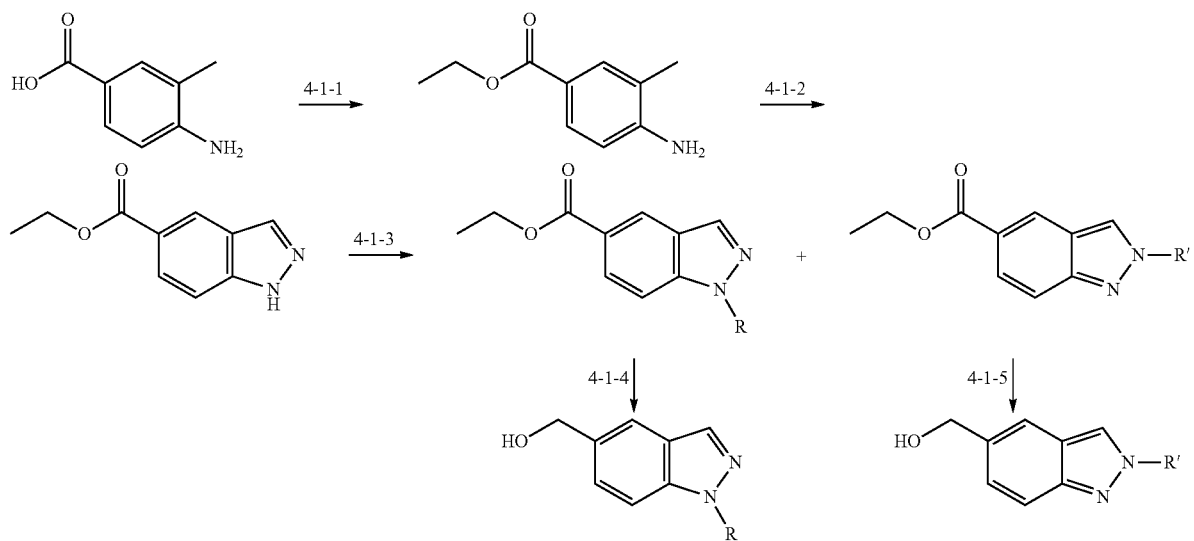

In the formulae, R and R' each represent a hydrogen atom or an alkyl group.

Example 4-1

Step 4-1-1

Ethyl 4-amino-3-methylbenzoate

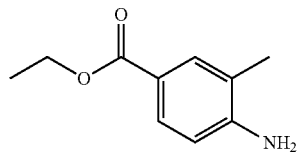

To a suspension of 4-amino-3-methylbenzoic acid (5.00 g, 33.1 mmol) in ethanol (50 ml), concentrated sulfuric acid (5.00 ml) was slowly added. The mixture was heated under reflux for 3 hours. The solvent was distilled off under a reduced pressure. After the volume of the mixture was Ethyl 4-amino-3-methylbenzoate (12.6 g, 70.0 mmol) prepared in the Step 4-1-1 and potassium acetate (7.20 g, 73.5 mmol) were suspended in chloroform (70 ml). Acetic anhydride (14.3 g, 140 mmol) was added to the suspension, and the mixture was stirred for one hour. To the mixture, 18-crown-6 (3.70 g, 14.0 mmol) and isoamyl nitrite (18.9 g, 161 mmol) were added, and the resulting mixture was heated under reflux for 21 hours. After being allowed to cool, under an ice cooling the mixture was rendered faintly alkaline with a saturated sodium bicarbonate solution and a 25% ammonia water. The faintly alkalified mixture was subjected to extraction with chloroform, and the extract was dried over anhydrous magnesium sulfate and then concentrated. The concentrate was purified by silica gel column chromatography (n-hexane:ethyl acetate=1:1) to give the title compound (4.06 g, 31%) as a light-brown powder and ethyl 1-acetyl-1H-indazole-5-carboxylate.

The resulting ethyl 1-acetyl-1H-indazole-5-carboxylate was stirred in a mixture of concentrated hydrochloric acid (15 ml), water (15 ml) and ethanol (30 ml) for 15 hours at a room temperature. The resulting mixture was rendered faintly alkaline with a 25% ammonia water. The faintly alkalified mixture was subjected to extraction with chloroform. The extract was crystallized from n-hexane, and then the resulting crystal was separated by filtration and dried to give the title compound (6.45 g, 48%) as a light-brown powder.

$^1$H-NMR (DMSO-$d_6$) δ: 13.38 (s, 1H), 8.49 (s, 1H), 7.92 (dd, J=1.5, 8.9 Hz, 1H), 7.62 (d, J=8.9 Hz, 1H), 4.33 (q, J=7.3 Hz, 2H), 1.35 (t, J=7.3 Hz, 3H)

Mass, m/z: 190 (M$^+$), 145 (base)

Step 4-1-3

Ethyl 1-methyl-1H-indazole-5-carboxylate and ethyl 2-methyl-2H-indazole-5-carboxylate

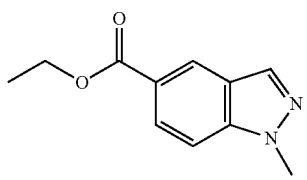

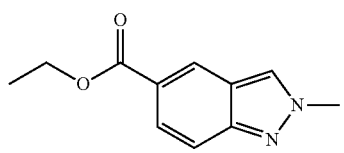

Ethyl 1H-indazole-5-carboxylate (1.62 g, 10.0 mmol) obtained in the Step 4-1-2 was dissolved in tetrahydrofuran (20 ml). To the solution, 60% sodium hydride suspension in oil (420 mg, 10.5 mmol) was added, and the mixture was stirred for 10 minutes. Methyl iodide (1.49 g, 10.5 mmol) was added dropwise to the mixture. The resulting mixture was stirred at a room temperature overnight. Ethyl acetate was added thereto, and the resulting mixture was washed with a saturated sodium bicarbonate solution and then dried over anhydrous magnesium sulfate and concentrated. The concentrate was purified by silica gel column chromatography (n-hexane:ethyl acetate=3:1) to firstly give ethyl 1-methyl-1H-indazole-5-carboxylate (light-brown solid, 0.80 g, 39%) and to secondly give ethyl 2-methyl-2H-indazole-5-carboxylate (light-brown solid, 0.60 g, 29%).

4-1-3-A: Ethyl 1-methyl-1H-indazole-5-carboxylate $^1$H-NMR (CDCl$_3$) δ: 8.51 (d, J=1.5 Hz, 1H), 8.08 (d, J=1.2 Hz, 1H), 8.07 (dd, J=1.5, 8.9 Hz, 1H), 7.39 (dd, J=0.8, 8.9 Hz, 1H), 4.40 (q, J=6.9 Hz, 2H), 4.10 (s, 3H), 1.42 (t, J=6.9 Hz, 3H)

Mass, m/z: 204 (M$^+$), 159 (base)

4-1-3-B: Ethyl 2-methyl-2H-indazole-5-carboxylate $^1$H-NMR (CDCl$_3$) δ: 8.48 (s, 1H), 8.03 (s, 1H), 7.90 (dd, J=1.5, 9.2 Hz, 1H), 7.68 (d, J=8.9 Hz, 1H), 4.38 (q, J=7.3 Hz, 2H), 4.24 (s, 3H), 1.40 (t, J=7.3 Hz, 3H)

Mass, m/z: 204 (M$^+$), 159 (base)

Step 4-1-4

(1-Methyl-1H-indazol-5-yl)methanol

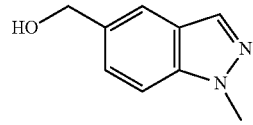

Lithium aluminum hydride (300 mg, 7.83 mmol) was suspended in tetrahydrofuran (20 ml); and under an ice cooling, a solution (10 ml) of ethyl 1-methyl-1H-indazole-5-carboxylate (800 mg, 3.92 mmol) prepared in the Step 4-1-3-A in tetrahydrofuran was slowly added thereto. After the mixture was stirred under an ice cooling for 30 minutes, 5 drops of a saturated sodium bicarbonate solution were slowly added to the mixture. Ethyl acetate was added to the mixture, and 5 drops of a saturated sodium bicarbonate solution was further added thereto. The precipitate was removed by filtration, and the filtrate was concentrated. The concentrate was purified by silica gel column chromatography (n-hexane:ethyl acetate=1:1) to give the title compound (420 mg, 66%) as a light-brown powder.

$^1$H-NMR (CDCl$_3$) δ: 7.95 (s, 1H), 7.69 (s, 1H), 7.43-7.37 (m, 2H), 4.78 (d, J=5.8 Hz, H), 4.07 (s, 3H)

Mass, m/z: 162 (M$^+$, base)

Example 4-2

Step 4-1-5

(2-Methyl-2H-indazol-5-yl)methanol

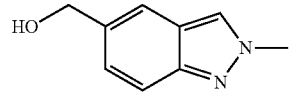

Ethyl 2-methyl-2H-indazole-5-carboxylate prepared in the Step 4-1-3-B was used and subjected to the same procedure as in the Step 4-1-4 to give the title compound.

$^1$H-NMR (DMSO-$d_6$) δ: 8.25 (s, 1H), 7.57 (d, J=1.5 Hz, 1H), 7.53 (d, J=8.9 Hz, 1H), 7.18 (dd, J=1.5, 8.9 Hz, 1H), 5.10 (t, J=5.8 Hz, 1H), 4.52 (d, J=5.8 Hz, 2H), 4.14 (s, 3H)

Mass, m/z: 162 (M$^+$, base)

Examples 4-3 to 4-7

According to the production processes shown in the following table, compounds shown in the following table were used instead of methyl iodide as an alkylating component or 4-amino-3-methylbenzoic acid as a monocyclic compound to give the objective bicyclic compounds.

TABLE 12

| Alkylating component | Mono-cyclic compound | Production process | Example | ¹H-NMR | Mass, m/z |
|---|---|---|---|---|---|
| Ethyl iodide | — | Example 4-1 | Example 4-3 | (DMSO-$d_6$) δ: 8.00 (d, J = 1.8 Hz, 1H), 7.65 (d, J = 0.8 Hz, 1H), 7.60 (d, J = 8.5 Hz, 1H), 7.35 (dd, J = 1.5, 8.9 Hz, 1H), 4.58 (s, 2H), 4.42 (q, J = 7.3 Hz, 2H), 1.38 (t, J = 7.3 Hz, 3H) | 176 ($M^+$, base), 161 |
| Ethyl iodide | — | Example 4-2 | Example 4-4 | (DMSO-$d_6$) δ: 8.30 (d, J = 0.8 Hz, 1H), 7.57 (d, J = 1.5 Hz, 1H), 7.54 (d, J = 8.9 Hz, 1H), 7.18 (dd, J = 1.5, 8.9 Hz, 1H), 5.10 (t, J = 5.4 Hz, 1H), 4.53 (d, J = 5.4 Hz, 2H), 4.43 (q, J = 7.3 Hz, 2H), 1.50 (t, J = 7.3 Hz, 3H) | 176 ($M^+$, base), 147 |
| — | 3-Amino-4-methyl benzoic acid | Example 4-1 Example 4-2 | Example 4-5 | (DMSO-$d_6$) δ: 8.25 (s, 1H), 7.61 (d, J = 8.9 Hz, 1H), 7.48 (d, J = 1.2 Hz, 1H), 6.98 (dd, J = 1.2, 8.9 Hz, 1H), 5.16 (t, J = 5.8 Hz, 1H), 4.56 (d, J = 5.8 Hz, 2H), 4.14 (s, 2H) | 162 ($M^+$, base) |
| Ethyl iodide | 3-Amino-4-methyl benzoic acid | Example 4-1 Example 4-2 | Example 4-6 | (DMSO-$d_6$) δ: 8.30 (d, J = 0.8 Hz, 1H), 7.61 (d, J = 8.5 Hz, 1H), 7.48 (d, J = 0.8 Hz, 1H), 6.98 (dd, J = 1.2, 8.5 Hz, 1H), 5.16 (t, J = 5.8 Hz, 1H), 4.55 (d, J = 5.8 Hz, 2H), 4.43 (q, J = 7.3 Hz, 2H), 1.50 (t, J = 7.3 Hz, 3H) | 176 ($M^+$, base) |
| Ethyl iodide | 3-Amino-4-methyl benzoic acid | Example 4-1 | Example 4-7 | (DMSO-$d_6$) δ: 7.98 (s, 1H), 7.68 (d, J = 8.5 Hz, 1H), 7.56 (s, 1H), 7.08 (d, J = 8.1 Hz, 1H), 5.27 (t, J = 5.8 Hz, 1H), 4.64 (d, J = 5.8 Hz, 2H), 4.41 (q, J = 7.3 Hz, 2H), 1.39 (t, J = 7.3 Hz, 3H) | 176 ($M^+$) (base), 161, 147, 131 |

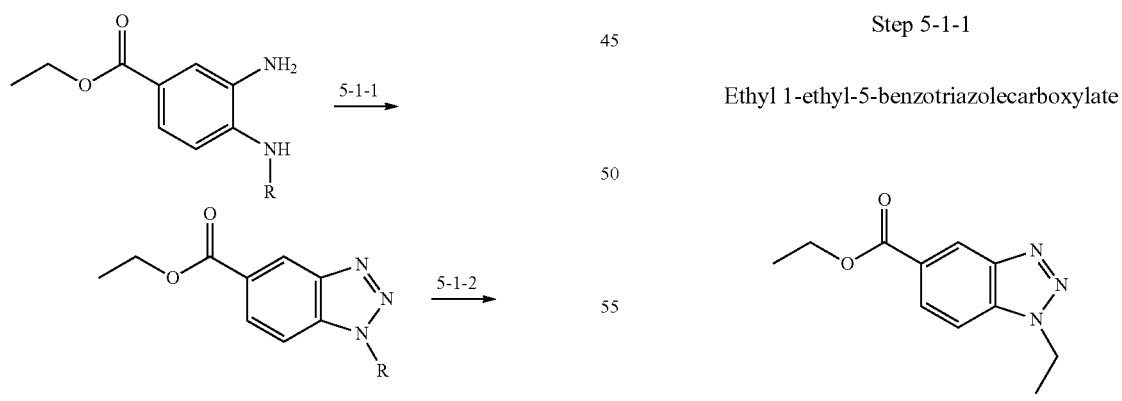

In the formulae, R represents an alkyl group.

Example 5-1

Step 5-1-1

Ethyl 1-ethyl-5-benzotriazolecarboxylate

Ethyl 3-amino-4-ethylaminobenzoate (1.80 g, 9.27 mmol) prepared in the same manner as in the Step 1-1-3 was dissolved in acetic acid (5 ml), and under an ice cooling sodium nitrite (1.28 g, 18.5 mmol) was added to the solution little by little. The mixture was stirred for 10 minutes under a water cooling. The mixture was cooled by ice again and neutralized with a 25% ammonia water. Thereafter, ethyl acetate was added to the mixture, and the resulting mixture was washed with a saturated saline solution and water in order. The washed mixture was dried over anhydrous magnesium sulfate and then concentrated. The residue was purified by silica gel column chromatography (n-hexane:ethyl acetate=3:1 to 1:1) to give the title compound (1.40 g, 69%) as a brown powder.

$^1$H-NMR (CDCl$_3$) δ: 8.63 (s, 1H), 8.10 (dd, J=1.5, 8.9 Hz, 1H), 8.02 (d, J=8.6 Hz, 1H), 4.49 (q, J=7.3 Hz, 2H), 4.38 (q, J=6.9 Hz, 2H), 1.54 (t, J=7.3 Hz, 3H), 1.37 (t, J=6.9 Hz, 3H)

Mass, m/z: 219 (M$^+$), 118 (base)

Step 5-1-2

(1-Ethyl-1H-benzotriazol-5-yl)methanol

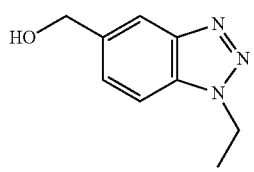

Ethyl 1-ethyl-5-benzotriazolecarboxylate prepared in the Step 5-1-1 was used and subjected to the same procedure as in the Step 1-1-5 to give the title compound.

$^1$H-NMR (CDCl$_3$) δ: 8.00 (d, J=1.2 Hz, 1H), 7.52 (t, J=1.2 Hz, 2H), 4.85 (d, J=3.1 Hz, 1H), 4.68 (q, J=7.3 Hz, 2H), 1.62 (t, J=7.3 Hz, 3H)

Mass, m/z: 177 (M$^+$), 104 (base)

Synthesis scheme 6

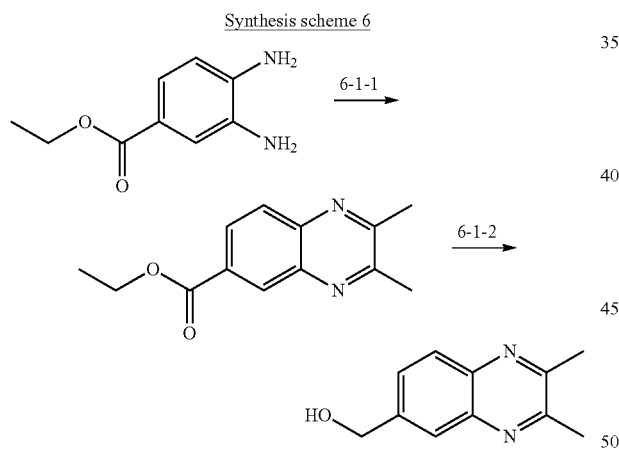

Example 6-1

Step 6-1-1

Ethyl 2,3-dimethylquinoxaline-6-carboxylate

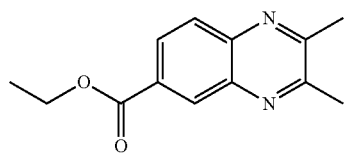 [SMILES: CCOC(=O)c1ccc2nc(C)c(C)nc2c1]

Ethyl 3,4-diaminobenzoate (500 mg, 2.77 mmol) and diacetyl (238 mg, 2.77 mmol) were dissolved in ethanol (20 ml), and the mixture was heated under reflux. One hour after, diacetyl (30 mg) was added thereto, and the mixture was heated under reflux. After the mixture was heated under reflux for 2.5 hours in total, the reaction solution was poured into water, and the precipitate was separated by filtration and washed with water. By through circulation drying for 15 hours, the title compound (650 mg, quantitative) as a light-brown powder was obtained.

$^1$H-NMR (DMSO-d$_6$) δ: 8.52 (d, J=1.5 Hz, 1H), 8.19 (dd, J=1.9, 8.5 Hz, 1H), 8.07 (d, J=8.5 Hz, 1H), 4.40 (q, J=6.9 Hz, 2H), 2.72 (s, 3H), 2.72 (s, 3H)

Mass, m/z: 230 (M$^+$), 185 (base)

Step 6-1-2

(2,3-Dimethylquinoxalin-6-yl)methanol

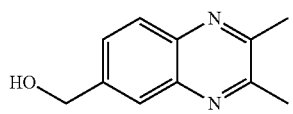

Ethyl 2,3-dimethylquinoxaline-6-carboxylate prepared in the Step 6-1-1 used and subjected to the same procedure as in the Step 1-1-5 to give the title compound.

$^1$H-NMR (DMSO-d$_6$) δ: 8.31 (s, 1H), 7.91 (d, J=8.5 Hz, 1H), 7.86 (d, J=1.2 Hz, 1H), 7.66 (dd, J=1.9, 8.5 Hz, 1H), 6.29 (brs, 1H), 4.71 (d, J=5.8 Hz, 1H), 2.67 (s, 3H), 2.67 (s, 3H)

Mass, m/z: 188 (M$^+$), 159 (base)

Synthesis scheme 7

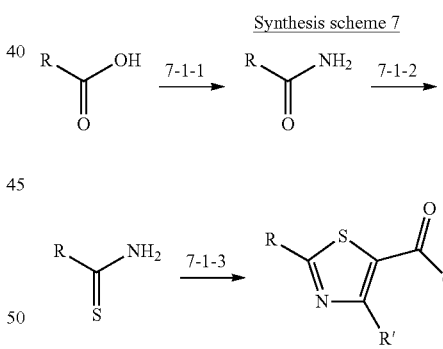

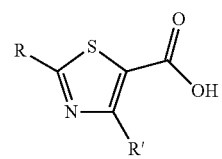

In the formulae, R represents a carbocyclic (homocyclic) or heterocyclic group which may have a substituent (such as a halogen atom, an alkyl group, or an alkoxy group); and R' represents a hydrogen atom, an alkyl group, a haloalkyl group or a cycloalkyl group.

Example 7-1

Step 7-1-1

4-Chloro-2-methoxybenzamide

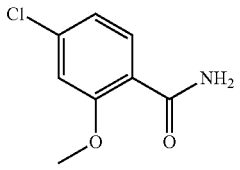

Thionyl chloride (262 g, 2.20 mol) was added to 4-chloro-2-methoxybenzoic acid (155 g, 0.831 mmol), and the mixture was heated under reflux for 2 hours. After thionyl chloride was distilled off under a reduced pressure, tetrahydrofuran was added thereto and the residue was dissolved. Under an ice cooling, a 25% ammonia water (1.0 L) was slowly added thereto. The resulting mixture was stirred at a room temperature for 18 hours. The precipitate was separated by filtration, washed with water and then subjected to through circulation drying to give the title compound (147 g, 95%) as a white powder.

$^1$H-NMR (DMSO-d$_6$) δ: 7.79 (d, J=8.1 Hz, 1H), 7.58 (d, J=12.3 Hz, 1H), 7.22 (d, J=1.9 Hz, 1H), 3.91 (s, 3H)

Mass, m/z: 187&185 (M$^+$), 165 (base)

Step 7-1-2

4-Chloro-2-methoxythiobenzamide

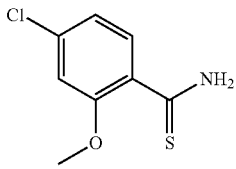

In tetrahydrofuran (100 ml), 4-chloro-2-methoxybenzamide (9.40 g, 50.6 mmol) prepared in the Step 7-1-1 and Lawesson's reagent (10.2 g, 25.3 mmol) were suspended, and the suspension was heated under reflux for 2 hours. After the suspension was allowed to cool, a saturated sodium bicarbonate solution was added to the suspension to stop the reaction. Then the reaction mixture was subjected to extraction with ethyl acetate, and the extract was dried over anhydrous magnesium sulfate and then concentrated. The concentrate was purified by silica gel column chromatography (n-hexane: ethyl acetate=1:1) to give the title compound (6.63 g, 65%) as a yellow powder.

$^1$H-NMR (CDCl$_3$) δ: 8.89 (brs, 1H), 8.60 (d, J=8.5 Hz, 1H), 7.96 (brs, 1H), 7.04 (dd, J=1.9, 8.5 Hz, 1H), 6.95 (d, J=1.9 Hz, 1H), 3.97 (s, 3H)

Mass, m/z: 201&203 (M$^+$), 168 (base)

Step 7-1-3

Ethyl 2-(4-chloro-2-methoxyphenyl)-4-methylthiazole-5-carboxylate

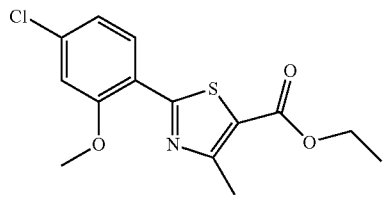 [SMILES: CCOC(=O)c1sc(-c2ccc(Cl)cc2OC)nc1C]

In ethanol (50 ml), 4-chloro-2-methoxythiobenzamide (4.00 g, 20.0 mmol) prepared in the Step 7-1-2 was suspended, and ethyl 2-chloroacetoacetate (3.62 g, 22.0 mmol) was added to the suspension. The mixture was heated under reflux overnight. After the mixture was allowed to cool, the solvent was distilled off under a reduced pressure, and ethyl acetate and a saturated sodium bicarbonate solution were added to the mixture. The resulting mixture was subjected to extraction with ethyl acetate. The extract was dried over anhydrous magnesium sulfate and then concentrated. The residue was suspended in ethyl acetate-n-hexane (ethyl acetate:n-hexane=1:1) and separated by filtration. The separated product was washed with the same solvent and dried under a reduced pressure to give the title compound (4.84 g, 78%) as a light-yellow powder.

$^1$H-NMR (DMSO-d$_6$) δ: 8.31 (d, J=8.9 Hz, 1H), 7.41 (d, J=1.9 Hz, 1H), 7.20 (dd, J=1.9, 8.5 Hz, 1H), 4.31 (q, J=7.3 Hz, 2H), 4.09 (s, 3H), 2.70 (s, 3H), 1.32 (t, J=7.3 Hz, 3H)

Mass, m/z: 311 (M$^+$), 71 (base)

Step 7-1-4

2-(4-Chloro-2-methoxyphenyl)-4-methylthiazole-5-carboxylic acid

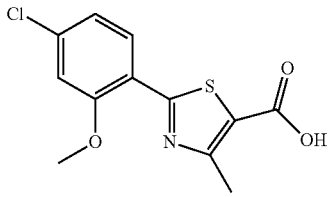 [SMILES: COc1cc(Cl)ccc1-c1nc(C)c(C(=O)O)s1]

Ethyl 2-(4-chloro-2-methoxyphenyl)-4-methylthiazole-5-carboxylate (4.83 g, 15.5 mmol) prepared in the Step 7-1-3 was suspended in ethanol (30 ml), 1 mol/l of sodium hydroxide (30 ml) was added thereto, and the mixture was heated under reflux for 1.5 hours. After being allowed to cool, the mixture was neutralized with hydrobromic acid, then separated by filtration and washed with water. The washed product was subjected to through circulation drying to give the title compound (4.28 g, 97%) as a white powder.

$^1$H-NMR (DMSO-d$_6$) δ: 8.29 (d, J=8.5 Hz, 1H), 7.38 (d, J=1.9 Hz, 1H), 7.19 (dd, J=1.9, 8.5 Hz, 1H), 4.08 (s, 3H), 2.67 (s, 3H)

Mass, m/z: 283&285 (M$^+$), 144 (base)

Examples 7-2 to 7-25 and 7-27 to 7-41

The objective compounds were obtained according to the same procedure as in Example 7-1 except that compounds shown in the following table were used instead of 4-chloro-2-methoxybenzoic acid as a carboxylic acid component or ethyl 2-chloroacetoacetate as a ring-forming component.

TABLE 13

| Carboxylic acid component | Ring-forming component | Example | ¹H-NMR | Mass, m/z |
|---|---|---|---|---|
| 2-Fluoro benzoic acid | — | Example 7-2 | (DMSO-$d_6$) δ: 13.44 (br s, 1H), 8.26 (dt, J = 1.5, 7.7 Hz, 1H), 7.64-7.58 (m, 1H), 7.49-7.38 (m, 2H), 2.71 (s, 3H) | 237 (M⁺), 71 (base) |
| 3-Fluoro benzoic acid | — | Example 7-3 | (DMSO-$d_6$) δ: 13.45 (br s, 1H), 7.84 (dd, J = 0.8, 1.5 Hz, 1H), 7.82-7.79 (m, 1H), 7.77-7.55 (m, 1H), 7.42-7.37 (m, 1H), 2.68 (s, 3H) | 237 (M⁺), base |
| 4-Fluoro benzoic acid | — | Example 7-4 | (DMSO-$d_6$) δ: 13.38 (br s, 1H), 8.07-8.01 (m, 2H), 7.39-7.33 (m, 2H), 2.67 (s, 3H) | 237 (M⁺), base |
| 2-Chloro-4-fluoro benzoic acid | — | Example 7-5 | (DMSO-$d_6$) δ: 13.46 (br s, 1H), 8.33 (dd, J = 6.6, 8.9 Hz, 1H), 7.71 (dd, J = 2.7, 8.9 Hz, 1H), 7.46-7.41 (m, 1H), 2.70 (s, 3H) | 271 (M⁺), base |
| 4-Fluoro-2-methyl benzoic acid | — | Example 7-6 | (DMSO-$d_6$) δ: 7.88 (dd, J = 5.8, 8.5 Hz, 1H), 7.29 (dd, J = 2.7, 10.0 Hz, 1H), 7.19 (dt, J = 2.7, 8.5 Hz, 1H), 2.68 (s, 3H), 2.57 (s, 3H) | 251 (M⁺), base |
| 4-Chloro-2-methyl benzoic acid | — | Example 7-7 | (DMSO-$d_6$) δ: 7.86 (d, J = 8.1 Hz, 1H), 7.52 (d, J = 1.9 Hz, 1H), 7.41 (dd, J = 2.3, 8.5 Hz, 1H), 2.69 (s, 3H), 2.57 (s, 3H) | 267 (M⁺), base |

TABLE 13-continued

| Carboxylic acid component | Ring-forming component | Example | ¹H-NMR | Mass, m/z |
|---|---|---|---|---|
| 2-Methoxy benzoic acid | — | Example 7-8 | (DMSO-d$_6$) δ: 8.32 (dd, J = 1.9, 8.1 Hz, 1H), 7.56-7.51 (m, 1H), 7.28 (d, J = 8.1 Hz, 1H), 7.15-7.11 (m, 1H), 4.05 (s, 3H), 2.68 (s, 3H) | 249 (M⁺), 144, 71 (base) |

TABLE 14

| Carboxylic acid component | Ring-forming component | Example | ¹H-NMR | Mass, m/z |
|---|---|---|---|---|
| 2-Methyl benzoic acid | — | Example 7-9 | (DMSO-d$_6$) δ: 7.81 (d, J = 7.7 Hz, 1H), 7.45-7.33 (m, 3H), 2.70 (s, 3H), 2.56 (s, 3H) | 233 (M⁺, base) |
| 3-Methyl benzoic acid | — | Example 7-10 | (DMSO-d$_6$) δ: 7.80 (s, 1H), 7.76 (d, J = 7.7 Hz, 1H), 7.42-7.34 (m, 2H), 2.67 (s, 3H), 2.39 (s, 3H) | 233 (M⁺), 118 (base) |
| 4-Methyl benzoic acid | — | Example 7-11 | (DMSO-d$_6$) δ: 7.87 (d, J = 8.1 Hz, 2H), 7.33 (d, J = 8.1 Hz, 2H), 2.67 (s, 3H), 2.37 (s, 3H) | 233 (M⁺), 118 (base) |
| 2-Ethyl benzoic acid | — | Example 7-12 | (DMSO-d$_6$) δ: 7.66 (d, J = 7.7 Hz, 1H), 7.47 (dt, J = 1.2, 7.7 Hz, 1H), 7.41 (dd, J = 1.2, 7.7 Hz, 1H), 7.35-7.31 (m, 1H), 2.93 (q, J = 7.7 Hz, 2H), 2.69 (s, 3H), 1.15 (t, J = 7.7 Hz, 3H) | 247 (M⁺, base), 201 |

TABLE 14-continued

| Carboxylic acid component | Ring-forming component | Example | ¹H-NMR | Mass, m/z |
|---|---|---|---|---|
| 4-Fluoro-2-methoxy benzoic acid | — | Example 7-13 | (DMSO-d₆) δ: 13.17 (br s, 1H), 8.34 (dd, J = 6.9, 9.0 Hz, 1H), 7.22 (dd, J = 2.7, 11.2 Hz, 1H), 6.98 (dt, J = 2.7, 8.9 Hz, 1H), 4.06 (s, 3H), 2.67 (s, 3H) | 267 (M⁺, base) |
| 2-Methoxy-4-methyl benzoic acid | — | Example 7-14 | (DMSO-d₆) δ: 8.18 (d, J = 8.5 Hz, 1H), 7.09 (s, 1H), 6.94 (d, J = 8.5 Hz, 1H), 4.02 (s, 3H), 2.66 (s, 3H), 2.50 (s, 3H) | 263 (M⁺), 71 (base) |
| 2,4-Dimethoxy benzoic acid | — | Example 7-15 | (DMSO-d₆) δ: 8.23 (d, J = 8.5 Hz, 1H), 6.78 (d, J = 2.3 Hz, 1H), 6.71 (dd, J = 2.3, 8.8 Hz, 1H), 4.04 (s, 3H), 3.87 (s, 3H), 2.65 (s, 3H) | 279 (M⁺, base), 233 |

TABLE 15

| Carboxylic acid component | Ring-forming component | Example | ¹H-NMR | Mass, m/z |
|---|---|---|---|---|
| 2,4-Dimethyl benzoic acid | — | Example 7-16 | (DMSO-d₆) δ: 7.73 (d, J = 8.1 Hz, 1H), 7.21 (s, 1H), 7.16 (d, J = 8.1 Hz, 1H), 2.68 (s, 3H), 2.54 (s, 3H), 2.50 (s, 3H) | 247 (M⁺, base) |
| 2,3-Dihydro benzofuran-7-carboxylic acid | — | Example 7-17 | (DMSO-d₆) δ: 13.18 (br s, 1H), 7.95 (dd, J = 1.2, 8.1 Hz, 1H), 7.40 (dd, J = 1.2, 7.3 Hz, 1H), 6.99 (dd, J = 7.3, 8.1 Hz, 1H), 4.81 (t, J = 8.9 Hz, 2H), 3.30 (t, J = 8.9 Hz, 2H), 2.68 (s, 3H) | 261 (M⁺, base) |

TABLE 15-continued

| Carboxylic acid component | Ring-forming component | Example | 1H-NMR | Mass, m/z |
|---|---|---|---|---|
| 2,3-Dihydro benzofuran-5-carboxylic acid | — | Example 7-18 | (DMSO-d6) δ: 13.19 (br s, 1H), 7.86 (d, J = 1.5 Hz, 1H), 7.76 (dd, J = 1.9, 8.5 Hz, 1H), 6.88 (dd, J = 8.5 Hz, 1H), 4.63 (t, J = 8.9 Hz, 2H), 3.28-3.24 (m, 2H), 2.64 (s, 3H) | 261 (M+, base) |
| 2-Methyl cyclohexyl carboxylic acid | — | Example 7-19 | (DMSO-d6) δ: 13.11 (br s, 1H), 2.58 (s, 3H), 1.90-1.86 (m, 1H), 1.80-1.60 (m, 4H), 1.52-1.28 (m, 4H), 1.12-1.06 (m, 1H), 0.75-0.73 (m, 3H) | 239 (M+), 157 (base) |
| Adamantane-1-carboxylic acid | — | Example 7-20 | (DMSO-d6) δ: 2.58 (s, 3H), 2.06 (s, 3H), 1.96 (d, J = 3.1 Hz, 6H), 1.80-1.65 (m, 6H) | 277 (M+, base) |
| 2-Furan carboxylic acid | — | Example 7-21 | (CDCl3) δ: 7.57 (d, J = 1.2 Hz, 1H), 7.15 (dd, J = 3.5 Hz, 1H), 6.56 (dd, J = 1.5, 3.5 Hz, 1H), 2.78 (s, 3H) | 209 (M+, base) |
| 3-Furan carboxylic acid | — | Example 7-22 | (DMSO-d6) δ: 13.30 (br s, 1H), 8.48 (s, 1H), 7.86-7.85 (m, 1H), 6.97-6.97 (m, 1H), 2.64 (s, 3H) | 209 (M+, base) |

TABLE 16

| Carboxylic acid component | Ring-forming component | Example | ¹H-NMR | Mass, m/z |
|---|---|---|---|---|
| 2-Thiophene carboxylic acid | — | Example 7-23 | (DMSO-d$_6$) δ: 13.41 (br s, 1H), 7.81 (dd, J = 0.8, 5.4 Hz, 1H), 7.78 (dd, J = 1.2, 3.9 Hz, 1H), 7.20 (dd, J = 3.9, 5.0 Hz, 1H), 2.62 (s, 3H) | 225 (M⁺, base) |
| 3-Chloro thiophene-2-carboxylic acid | — | Example 7-24 | (DMSO-d$_6$) δ: 13.46 (br s, 1H), 7.93 (d, J = 5.4 Hz, 1H), 7.30 (d, J = 5.4 Hz, 1H), 2.65 (s, 3H) | 259 (M⁺), 71 (base) |
| 5-Chloro thiophene-2-carboxylic acid | — | Example 7-25 | (DMSO-d$_6$) δ: 13.43 (br s, 1H), 7.70 (d, J = 4.2 Hz, 1H), 7.25 (d, J = 3.9 Hz, 1H) | 259 (M⁺), 71 (base) |
| 2-Methoxy benzoic acid | 2-Chloro-3-oxo pentanoic acid | Example 7-27 | (DMSO-d$_6$) δ: 13.15 (br s, 1H), 8.34 (dd, J = 1.9, 8.1 Hz, 1H), 7.55-7.51 (m, 1H), 7.28 (d, J = 8.5 Hz, 1H), 7.15-7.11 (m, 1H), 4.05 (s, 3H), 3.12 (q, J = 7.7 Hz, 2H), 1.27 (t, J = 7.7 Hz, 3H) | 263 (M⁺, base) |
| — | 2-Chloro-3-oxo pentanoic acid | Example 7-28 | (DMSO-d$_6$) δ: 13.21 (br s, 1H), 8.32 (d, J = 8.5 Hz, 1H), 7.39 (d, J = 2.3 Hz, 1H), 7.20 (dd, J = 1.9, 8.5 Hz, 1H), 4.08 (s, 3H), 3.11 (q, J = 7.7 Hz, 2H), 1.26 (t, J = 7.7 Hz, 3H) | 297 (M⁺, base) |
| 2,4-Dimethyl benzoic acid | 2-Chloro-3-oxo pentanoic acid | Example 7-29 | (DMSO-d$_6$) δ: 7.73 (d, J = 7.7 Hz, 1H), 7.21 (s, 1H), 7.16 (d, J = 7.7 Hz, 1H), 3.12 (q, J = 7.7 Hz, 2H), 2.54 (s, 3H), 2.33 (s, 3H), 1.26 (t, J = 7.7 Hz, 3H) | 261 (M⁺, base) |

TABLE 16-continued

| Carboxylic acid component | Ring-forming component | Example | $^1$H-NMR | Mass, m/z |
|---|---|---|---|---|
| 4-Fluoro-2-methyl benzoic acid | 2-Chloro-3-oxo pentanoic acid | Example 7-30 | (DMSO-d$_6$) δ: 13.38 (br s, 1H), 7.88 (dd, J = 5.8, 8.9 Hz, 1H), 7.29 (dd, J = 2.7, 10.0 Hz, 1H), 7.19 (dt, J = 2.7, 8.5 Hz, 1H), 3.12 (q, J = 7.3 Hz, 2H), 2.57 (s, 3H), 1.27 (t, J = 7.3 Hz, 3H) | 265 (M$^+$, base) |

TABLE 17

| Carboxylic acid component | Ring-forming component | Example | $^1$H-NMR | Mass, m/z |
|---|---|---|---|---|
| 2-Methoxy-4-methyl benzoic acid | 2-Chloro-3-oxo pentanoic acid | Example 7-31 | (DMSO-d$_6$) δ: 13.08 (br s, 1H), 8.21 (dd, J = 7.7 Hz, 1H), 7.11 (s, 1H), 6.95 (d, J = 7.7 Hz, 1H), 4.03 (s, 3H), 3.10 (q, J = 7.7 Hz, 2H), 2.39 (s, 3H), 1.26 (t, J = 7.7 Hz, 3H) | 277 (M$^+$, base) |
| — | Methyl 2-chloro-3-oxo propionate | Example 7-32 | (DMSO-d$_6$) δ: 13.45 (br s, 1H), 8.45 (s, 1H), 8.33 (d, J = 8.5 Hz, 1H), 7.43 (d, J = 1.9 Hz, 1H), 7.22 (dd, J = 1.9, 8.5 Hz, 1H), 4.10 (s, 3H) | 269 (M$^+$), 169 (base) |
| 2-Methoxy benzoic acid | Methyl 2-chloro-3-oxopropionate | Example 7-33 | (DMSO-d$_6$) δ: 13.37 (br s, 1H), 8.43 (s, 1H), 8.34 (dd, J = 1.9, 8.1 Hz, 1H), 7.57-7.53 (m, 1H), 7.30 (d, J = 8.1 Hz, 1H), 7.17-7.12 (m, 1H), 4.07 (s, 3H) | 235 (M$^+$), 189 (base) |
| — | Ethyl 2-chloro-3-oxohexanoate | Example 7-34 | (CDCl$_3$) δ: 8.41 (d, J = 8.5 Hz, 1H), 7.08 (dd, J = 1.9, 8.5 Hz, 1H), 7.03 (d, J = 1.9 Hz, 1H), 4.05 (s, 3H), 3.18 (t, J = 7.7 Hz, 2H), 1.87-1.78 (m, 2H), 1.02 (t, J = 7.7 Hz, 3H) | 311 (M$^+$), 283 (base) |

TABLE 17-continued

| Carboxylic acid component | Ring-forming component | Example | ¹H-NMR | Mass, m/z |
|---|---|---|---|---|
| 2,4-Dimethyl benzoic acid | Ethyl 2-chloro-3-oxohexanoate | Example 7-35 | (CDCl₃) δ: 7.70 (d, J = 7.7 Hz, 1H), 7.12-7.04 (m, 2H), 3.19 (t, J = 7.3 Hz, 2H), 2.58 (s, 3H), 2.36 (s, 3H), 1.88-1.76 (m, 2H), 1.02 (t, J = 7.3 Hz, 3H). | 275 (M⁺), 247 (base) |
| 2,4-Dimethyl benzoic acid | Methyl 2-chloro-3-cyclopropyl-3-oxo propionate | Example 7-36 | (CDCl₃) δ: 7.67-7.62 (m, 1H), 7.10-6.85 (m, 2H), 3.10-3.03 (m, 1H), 2.35 (s, 3H), 2.34 (s, 3H), 1.25-1.18 (m, 2H), 1.14-1.07 (m, 2H) | 273 (M⁺, base) |
| 4-Chloro-2-methyl benzoic acid | Ethyl 2-chloro-4,4,4-trifluoro-3-oxobutyrate | Example 7-37 | (CDCl₃) δ: 7.80 (d, J = 8.1 Hz, 1H), 7.35 (d, J = 1.9 Hz, 1H), 7.31 (dd, J = 1.9, 8.1 Hz, 1H), 2.63 (s, 3H) | 273 (M⁺, base) |

TABLE 18

| Carboxylic acid component | Ring-forming component | Example | ¹H-NMR | Mass, m/z |
|---|---|---|---|---|
| 2,4-Difluoro benzoic acid | — | Example 7-38 | (DMSO-d₆) δ: 13.44 (br s, 1H), 8.30 (dt, J = 6.6, 8.9 Hz, 1H), 7.54 (ddd, J = 2.3, 8.9, 11.9 Hz, 1H), 7.30 (dt, J = 2.7, 8.5 Hz, 1H), 2.70 (s, 3H) | 255 (M⁺) (base), 140, 116 |
| 3-Methyl picolinic acid | — | Example 7-39 | (DMSO-d₆) δ: 8.51 (dd, J = 1.5, 4.6 Hz, 1H), 7.81 (d, J = 8.1 Hz, 1H), 7.42 (dd, J = 4.6, 7.7 Hz, 1H), 2.74 (s, 3H), 2.69 (s, 3H) | 234 (M⁺, base) |

TABLE 18-continued

| Carboxylic acid component | Ring-forming component | Example | | ¹H-NMR | Mass, m/z |
|---|---|---|---|---|---|
| 4-Fluoro-2-methoxy benzoic acid | 2-Chloro-3-oxo pentanoic acid | Example 7-40 | 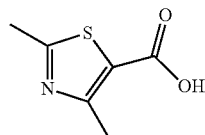 | (DMSO-d₆) δ: 8.36 (dd, J = 6.9, 8.9 Hz, 1H), 7.21 (dd, J = 2.3, 11.2 Hz, 1H), 6.98 (dt, J = 2.3, 8.5 Hz, 1H), 4.06 (s, 3 H), 3.11 (q, J = 7.7 Hz, 2H), 1.28 (t, J = 7.7 Hz, 3H) | 281 (M⁺, base) |
| 4-Chloro-2-methyl benzoic acid | 2-Chloro-3-oxo pentanoic acid | Example 7-41 | | (DMSO-d₆) δ: 13.40 (br s, 1 H), 7.86 (d, J = 8.5 Hz, 1H), 7.51 (d, J = 1.9 Hz, 1H), 7.41 (dd, J = 1.9, 8.5 Hz, 1H), 3.12 (q, J = 7.7 Hz, 2H), 2.57 (s, 3 H), 1.26 (t, J = 7.7 Hz, 3H) | 281 (M⁺, base) |

Example 7-26

2,4-Dimethylthiazole-5-carboxylic acid

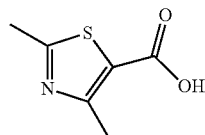

The title compound was obtained according to the same procedure as in Example 7-1 except that thioacetamide was used instead of 4-chloro-2-methoxythiobenzamide.

¹H-NMR (DMSO-d₆) δ: 13.13 (brs, 1H), 2.62 (s, 3H), 2.56 (s, 3H)

Mass, m/z: 157 (M⁺, base)

Synthesis scheme 8

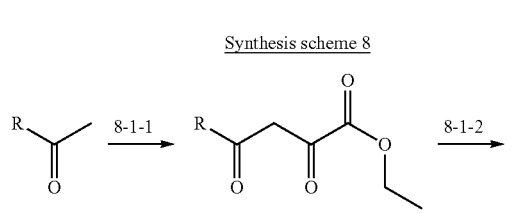

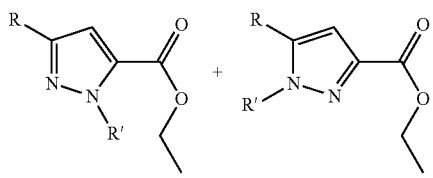

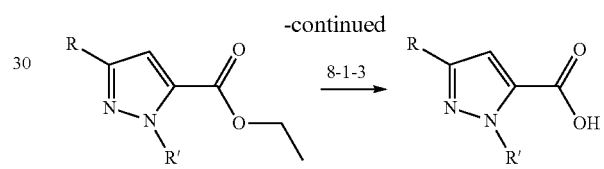

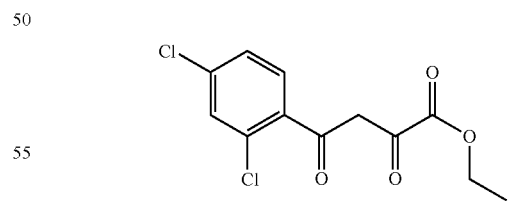

In the formulae, R represents a carbocyclic (homocyclic) or heterocyclic group which may have a substituent (such as a halogen atom, an alkyl group, a haloalkyl group, an alkoxy group, an amino group, or an N-alkyl-substituted amino group); and R' represents a hydrogen atom, an alkyl group or an aralkyl group.

Example 8-1

Step 8-1-1

Ethyl 4-(2,4-dichlorophenyl)-2,4-dioxobutyrate

A 20% sodium ethoxide-ethanol solution (17 g) was added to tetrahydrofuran (100 ml), and the mixture was cooled to 0° C. It took 60 minutes to dropwise add a solution of 2',4'-dichloroacetophenone (9.45 g) and diethyl oxalate (7.30 g) in tetrahydrofuran (100 ml) to the mixture. After the completion of the dropping, the mixture was allowed to warm to a room temperature and stirred for 2 hours. To the mixture, 2-N hydrochloric acid (200 ml) and chloroform (200 ml) were added. The organic layer was collected by separation and dried over anhydrous magnesium sulfate, and the solvent was distilled off. Thus, the title compound (11.3 g, 78%) as a light-brown oily substance was obtained.

¹H-NMR (DMSO-d₆) δ: 7.85-7.74 (m, 1H), 7.70-7.62 (m, 1H), 7.58-7.55 (m, 2H), 6.53 (brs, 1H), 4.29-4.21 (m, 2H), 1.29-1.25 (m, 3H)

Mass, m/z: 288 (M⁺), 215 (base)

Step 8-1-2

Ethyl 5-(2,4-dichlorophenyl)-2-methyl-2H-pyrazole-3-carboxylate and ethyl 5-(2,4-dichlorophenyl)-1-methyl-1H-pyrazole-3-carboxylate

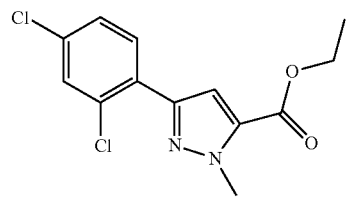

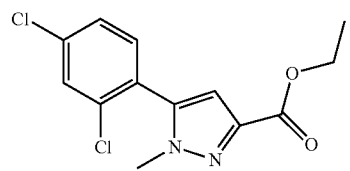

Ethyl 4-(2,4-dichlorophenyl)-2,4-dioxobutyrate (11 g, 38 mmol) was added to ethanol (50 ml), and methylhydrazine (1.84 g, 40 mmol) was added thereto at a room temperature under stirring. After the mixture was stirred for 60 minutes, ethanol was distilled off. To the residue, chloroform (300 ml) and water (200 ml) were added. The organic layer was collected by separation, dried over anhydrous magnesium sulfate, and the solvent was distilled off. Thus, 13 g of the residue was obtained. The residue was separated by silica gel column (ethyl acetate:n-hexane=5:1) to give ethyl 5-(2,4-dichlorophenyl)-2-methyl-2H-pyrazole-3-carboxylate (5.01 g, 45%) as a first eluate and ethyl 5-(2,4-dichlorophenyl)-1-methyl-1H-pyrazole-3-carboxylate (1.92 g, 17%) as a second eluate.

8-1-2-A: Ethyl 5-(2,4-dichlorophenyl)-2-methyl-2H-pyrazole-3-carboxylate

¹H-NMR (DMSO-d₆) δ: 7.83 (d, J=8.5 Hz, 1H), 7.73 (d, J=1.9 Hz, 1H), 7.51 (dd, J=1.9, 8.5 Hz, 1H), 7.31 (s, 1H), 4.34 (q, J=7.3 Hz, 2H), 4.17 (s, 3H), 1.33 (t, J=7.3 Hz, 3H)

Mass, m/z: 298 (M⁺), 55 (base)

8-1-2-B: Ethyl 5-(2,4-dichlorophenyl)-1-methyl-1H-pyrazole-3-carboxylate

¹H-NMR (DMSO-d₆) δ: 7.87 (d, J=1.9 Hz, 1H), 7.62-7.56 (m, 2H), 6.86 (s, 1H), 4.29 (q, J=6.9 Hz, 2H), 3.72 (s, 3H), 1.30 (t, J=6.9 Hz, 3H)

Mass, m/z: 298 (M⁺), 226 (base)

Step 8-1-3

5-(2,4-Dichlorophenyl)-2-methyl-2H-pyrazole-3-carboxylic acid

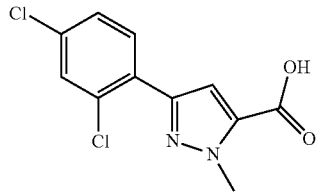 [SMILES: Cn1nc(-c2ccc(Cl)cc2Cl)cc1C(=O)O]

Ethyl 5-(2,4-dichlorophenyl)-2-methyl-2H-pyrazole-3-carboxylate (2.98 g) was added to ethanol (50 ml), and sodium hydroxide (5.0 g) was added thereto at a room temperature under stirring, and subsequently the mixture was heated and stirred for 60 minutes. The mixture was adjusted to pH 5 by addition of 2-N hydrochloric acid, and the precipitated crystal was separated by filtration and subjected to through circulation drying to give the title compound (1.90 g, 70%) as a white powder.

¹H-NMR (DMSO-d₆) δ: 13.54 (brs, 1H), 7.83 (d, J=8.5 Hz, 1H), 7.72 (d, J=2.3 Hz, 1H), 7.51 (dd, J=2.3, 8.5 Hz, 1H), 7.27 (s, 1H), 4.16 (s, 3H)

Mass, m/z: 270 (M⁺, base)

Example 8-2

5-(2,4-Dichlorophenyl)-1-methyl-1H-pyrazole-3-carboxylic acid

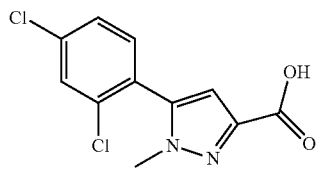 [SMILES: Cn1nc(C(=O)O)cc1-c1ccc(Cl)cc1Cl]

The compound 8-1-2-B was used and subjected to the same procedure as in the Step 8-1-3 to give the title compound.

¹H-NMR (DMSO-d₆) δ: 12.75 (brs, 1H), 7.86 (d, J=1.9 Hz, 1H), 7.61-7.55 (m, 2H), 6.80 (s, 1H), 3.71 (s, 3H)

Mass, m/z: 270 (M⁺, base)

Examples 8-3 to 8-29 and 8-31 to 8-35

According to the production processes shown in the following table, compounds shown in the following table were used instead of 2',4'-dichloroacetophenone as a carbonyl compound or methylhydrazine as a ring-forming component to give the objective compounds.

TABLE 19

| Carbonyl compound | Ring-forming component | Production process | Example | 1H-NMR | Mass, m/z |
|---|---|---|---|---|---|
| Acetophenone | — | Example 8-1 | Example 8-3 | (DMSO-d6) δ: 13.41 (br s, 1H), 7.85-7.83 (m, 2H), 7.43-7.40 (m, 2H), 7.34-7.31 (m, 1H), 7.28(s, 1H), 4.13 (s, 3H) | 202 (M+, base) |
| 2'-Methyl acetophenone | — | Example 8-1 | Example 8-4 | (DMSO-d6) δ: 13.39 (br s, 1H), 7.56-7.53 (m, 1H), 7.29-7.21 (m, 3H), 7.05 (s, 1H), 4.13 (s, 3H), 2.44 (s, 3H) | 216 (M+, base) |
| — | Ethyl hydrazine | Example 8-1 | Example 8-5 | (DMSO-d6) δ: 13.54 (br s, 1H), 7.85(d, J = 8.5 Hz, 1H), 7.72 (d, J = 2.3 Hz, 1H), 7.51 (dd, J = 2.3, 8.5 Hz, 1H), 7.28 (s, 1H), 4.58 (q, J = 7.3 Hz, 2H), 1.40 (t, J = 7.3 Hz, 3H) | 284 (M+, base), 256 |
| 3',4'-Dichloro acetophenone | Ethyl hydrazine | Example 8-1 | Example 8-6 | (DMSO-d6) δ: 13.51 (br s, 1H), 8.09 (d, J = 1.9 Hz, 1H), 7.85 (dd, J = 2.3, 8.5 Hz, 1H), 7.67 (d, J = 8.5 Hz, 1H), 7.43 (s, 1H), 4.55 (q, J = 7.3 Hz, 2H), 1.39 (t, J = 7.3 Hz, 3H) | 284 (M+, base) |
| 2'-Methoxy acetophenone | — | Example 8-1 | Example 8-7 | (DMSO-d6) δ: 13.34 (br s, 1H), 7.88 (dd, J = 1.5, 7.7 Hz, 1H), 7.34 (ddd, J = 1.5, 7.3, 8.9 Hz, 1H), 7.23 (s, 1H), 7.11 (d, J = 8.5 Hz, 1H), 7.00 (dt, J = 0.8, 7.3 Hz, 1H), 4.13 (s, 3H), 3.88 (s, 3H) | 232 (M+, base) |
| 4'-Fluoro-2'-methoxy acetophenone | Ethyl hydrazine | Example 8-1 | Example 8-8 | (DMSO-d6) δ: 13.35 (br s, 1H), 7.90 (dd, J = 6.9, 8.5 Hz, 1H), 7.18 (s, 1H), 7.03 (dd, J = 2.3, 11.6 Hz, 1H), 6.84 (dt, J = 2.7, 8.5 Hz, 1H), 4.55 (q, J = 7.3 Hz, 2H), 3.90 (s, 3H), 1.37 (t, J = 7.3 Hz, 3H) | 264 (M+, base) |

TABLE 19-continued

| Carbonyl compound | Ring-forming component | Production process | Example | ¹H-NMR | Mass, m/z |
|---|---|---|---|---|---|
| 4'-Chloro-2'-methoxy acetophenone | — | Example 8-1 | Example 8-9 | (DMSO-d₆) δ: 13.39 (br s, 1H), 7.90 (d, J = 8.1 Hz, 1H), 7.22 (s, 1H), 7.20 (d, J = 1.9 Hz, 1H), 7.07 (dd, J = 1.9, 8.1 Hz, 1H), 4.13 (s, 3H), 3.92 (s, 3H) | 266 (M⁺, base) |

TABLE 20

| Carbonyl compound | Ring-forming component | Production process | Example | ¹H-NMR | Mass, m/z |
|---|---|---|---|---|---|
| 4'-Chloro-2'-methoxy acetophenone | Ethyl hydrazine | Example 8-1 | Example 8-10 | (DMSO-d₆) δ: 13.41 (br s, 1H), 7.91 (d, J = 8.5 Hz, 1H), 7.22 (s, 1H), 7.20 (d, J = 1.9 Hz, 1H), 7.07 (dd, J = 1.9, 8.5 Hz, 1H), 4.56 (q, J = 7.3 Hz, 2H), 3.92 (s, 3H), 1.37 (t, J = 7.3 Hz, 3H) | 280 (M⁺, base) |
| 4'-Chloro-2'-methoxy acetophenone | Isopropyl hydrazine | Example 8-1 | Example 8-11 | (DMSO-d₆) δ: 12.64 (br s, 1H), 7.30 (d, J = 8.1 Hz, 1H), 7.28 (d, J = 1.9 Hz, 1H), 7.14 (dd, J = 1.9, 8.1 Hz, 1H), 6.61 (s, 1H), 4.20-4.14 (m, 1H), 3.82 (s, 3H), 1.32 (d, J = 6.9 Hz, 6H) | 294 (M⁺, base) |
| 2'-Methoxy-4'-methyl acetophenone | Ethyl hydrazine | Example 8-1 | Example 8-12 | (DMSO-d₆) δ: 13.29 (br s, 1H), 7.78 (d, J = 7.7 Hz, 1H), 7.18 (s, 1H), 6.93 (s, 1H), 6.82 (d, J = 7.7 Hz, 1H), 4.55 (q, J = 6.9 Hz, 2H), 3.86 (s, 3H), 1.37 (t, J = 6.9 Hz, 3H) | 260 (M⁺, base) |
| 2',4'-Dimethoxy acetophenone | — | Example 8-1 | Example 8-13 | (DMSO-d₆) δ: 13.28 (br s, 1H), 7.79 (d, J = 8.9 Hz, 1H), 7.13 (s, 1H), 6.65 (d, J = 2.3 Hz, 1H), 6.60 (dd, J = 2.3, 8.5 Hz, 1H), 4.11 (s, 3H), 3.87 (s, 3H), 3.80 (s, 3H) | 262 (M⁺, base) |

TABLE 20-continued

| Carbonyl compound | Ring-forming component | Production process | Example | 1H-NMR | Mass, m/z |
|---|---|---|---|---|---|
| 3',4'-Dimethoxy acetophenone | — | Example 8-1 | Example 8-14 | (DMSO-$d_6$) δ: 13.36 (br s, 1H), 7.39-7.36 (m, 2H), 7.25 (s, 1H), 6.98 (d, J = 8.1 Hz, 1H), 4.11 (s, 3H), 3.82 (s, 3H), 3.78 (s, 3H) | 262 (M+, base) |
| 2',6'-Dimethoxy acetophenone | — | Example 8-1 | Example 8-15 | (CDCl$_3$) δ: 7.30 (t, J = 8.1 Hz, 1H), 7.05 (s, 1H), 6.64 (s, 1H), 6.62 (s, 1H), 4.26 (s, 3H), 3.78 (s, 6H) | 262 (M+, base) |
| 2',4'-Dimethyl acetophenone | — | Example 8-1 | Example 8-16 | (DMSO-$d_6$) δ: 13.38 (br s, 1H), 7.45 (d, J = 7.7 Hz, 1H), 7.09 (s, 1H) 7.05 (d, J = 7.7 Hz, 1H), 7.01 (s, 1H), 4.12 (s, 3H), 2.40 (s, 3H), 2.29 (s, 3H) | 230 (M+, base) |

TABLE 21

| Carbonyl compound | Ring-forming component | Production process | Example | 1H-NMR | Mass, M/Z |
|---|---|---|---|---|---|
| 2',4'-Dimethyl acetophenone | Ethyl hydrazine | Example 8-1 | Example 8-17 | (DMSO-$d_6$) δ: 13.38 (br s, 1H), 7.46 (d, J = 7.7 Hz, 1H), 7.09 (s, 1H), 7.05 (d, J = 8.5 Hz, 1H), 7.00 (s, 1H), 4.55 (q, J = 7.3 Hz, 2H), 2.41 (s, 3H), 2.29 (s, 3H), 1.38 (t, J = 7.3 Hz, 3H) | 244 (M+, base) |
| 2',4'-Dimethyl acetophenone | Benzyl hydrazine | Example 8-1 | Example 8-18 | (DMSO-$d_6$) δ: 12.73 (br s, 1H), 7.29-7.21 m, 3H), 7.14 (s, 1H), 7.11-7.07 (m, 2H), 6.90 (dd, J = 1.9, 7.7 Hz, 2H), 6.71 (s, 1H), 5.16 (s, 2H), 2.32 (s, 3H), 1.95 (s, 3H) | 306 (M+, base) |

TABLE 21-continued

| Carbonyl compound | Ring-forming component | Production process | Example | ¹H-NMR | Mass, M/Z |
|---|---|---|---|---|---|
| 2'-Trifluoro methyl acetophenone | — | Example 8-1 | Example 8-19 | (DMSO-d₆) δ: 13.51 (br s, 1 H), 7.84 (d, J = 8.1 Hz, 1H), 7.75-7.72 (m, 1H), 7.68 (d, J = 6.9 Hz, 1H), 7.64-7.60 (m, 1H), 6.96 (s, 1H), 4.14 (s, 3H) | 270 (M⁺, base) |
| 4'-Dimethyl amino acetophenone | — | Example 8-1 | Example 8-20 | (DMSO-d₆) δ: 13.29 (br s, 1H), 7.64 (d, J = 8.9 Hz, 1H), 7.09 (s, 1H), 6.74 (d, J = 8.9 Hz, 1H), 4.09 (s, 3H), 2.92 (s, 6H) | 245 (M⁺, base) |
| 4-Chromanone | — | Example 8-1 | Example 8-21 | (DMSO-d₆) δ: 13.71 (br s, 1H), 7.24-7.20 (m, 1H), 7.02-6.98 (m, 1H), 6.96-6.92 (m, 1H), 5.44 (s, 2H), 4.12 (s, 3H) | 230 (M⁺), 229 (base) |
| 4-Chromanone | Ethyl hydrazine | Example 8-1 | Example 8-22 | (DMSO-d₆) δ: 13.71 (br s, 1H), 7.62 (dd, J = 1.5, 7.7 Hz, 1H), 7.22 (dt, J = 1.5, 7.7 Hz, 1H), 7.00 (t, J = 7.7 Hz, 1H), 6.93 (d, J = 7.7 Hz, 1H), 5.41 (s, 2H), 4.55 (q, J = 7.3 Hz, 2H), 1.37 (t, J = 7.3 Hz, 3H) | 244 (M⁺), 215 (base) |
| 2-Acetylfuran | — | Example 8-1 | Example 8-23 | (DMSO-d₆) δ: 13.49 (br s, 1H), 7.71 (dd, J = 0.8, 1.9 Hz, 1H), 7.03 (s, 1H), 6.78 (d, J = 3.1 Hz, 1H), 6.57 (dd, J = 1.5, 3.1 Hz, 1H), 4.11 (s, 3H) | 192 (M⁺, base) |

TABLE 22

| Carbonyl compound | Ring-forming component | Production process | Example | ¹H-NMR | Mass, m/z |
|---|---|---|---|---|---|
| 1-(4-Chloro-2-methoxy phenyl) propan-1-one | — | Example 8-1 | Example 8-24 | (DMSO-d$_6$) δ: 13.34 (br s, 1H), 7.24 (d, J = 8.1 Hz, 1H), 7.18 (d, J = 1.9 Hz, 1H), 7.07 (dd, J = 1.9, 8.1 Hz, 1H), 4.05 (s, 3H), 3.79 (s, 3H) | 280 (M⁺, base) |
| Acetophenone | — | Example 8-2 | Example 8-25 | (DMSO-d$_6$) δ: 12.66 (br s, 1H), 7.59-7.46 (m, 5H), 6.83 (s, 1H), 3.91 (s, 3H) | 202 (M⁺, base) |
| 4'-Fluoro-2'-methoxy acetophenone | — | Example 8-2 | Example 8-26 | (DMSO-d$_6$) δ: 12.60 (br s, 1H), 7.35 (dd, J = 6.9, 8.5 Hz, 1H), 7.11 (dd, J = 2.3, 11.6 Hz, 1H), 6.90 (dt, J = 2.3, 8.5 Hz, 1H), 3.83 (s, 3H), 3.67 (s, 3H) | 250 (M⁺, base) |
| 4'-Chloro-2'-methoxy acetophenone | — | Example 8-2 | Example 8-27 | (DMSO-d$_6$) δ: 12.65 (br s, 1H), 7.34 (d, J = 8.1 Hz, 1H), 7.28 (d, J = 1.9 Hz, 1H), 7.14 (dd, J = 1.9, 8.1 Hz, 1H), 6.69 (s, 1H), 3.84 (s, 3H), 3.68 (s, 3H) | 266 (M⁺, base) |
| 2',4'-Dimethyl acetophenone | Hydrazine monohydrate | Example 8-1 | Example 8-28 | (DMSO-d$_6$) δ: 7.39 (d, J = 7.7 Hz, 1H), 7.13 (s, 1H), 7.08 (d, J = 8.1 Hz, 1H), 6.86 (s, 1H), 2.36 (s, 3H), 2.31 (s, 3H) | 256 (M⁺, base) |
| 4'-Chloro-2'-methoxy acetophenone | Hydrazine monohydrate | Example 8-1 | Example 8-29 | (DMSO-d$_6$) δ: 7.87 (d, J = 8.5 Hz, 1H), 7.18 (d, J = 1.9 Hz, 1H), 7.07 (dd, J = 2.3, 8.5 Hz, 1H), 7.00 (s, 1H), 3.92 (s, 3H) | 252 (M⁺, base) |

TABLE 22-continued

| Carbonyl compound | Ring-forming component | Production process | Example | ¹H-NMR | Mass, m/z |
|---|---|---|---|---|---|
| 4'-Fluoro-2'-methyl acetophenone | — | Example 8-1 | Example 8-31 | (DMSO-d$_6$) δ: 13.41 (br s, 1H), 7.58 (dd, J = 6.2, 8.5 Hz, 1H), 7.15 (dd, J = 2.7, 10.4 Hz, 1H), 7.09-7.05 (m, 1H), 7.04 (s, 1H), 4.13 (s, 3H), 2.45 (s, 3H) | 234 (M⁺) (base), 189, 148 |
| 2'-methoxy acetophenone | Ethyl hydrazine | Example 8-1 | Example 8-32 | (DMSO-d$_6$) δ: 13.27 (br s, 1H), 7.90 (dd, J = 1.5, 7.7 Hz, 1H), 7.33 (ddd, J = 1.9, 7.3, 8.5 Hz, 1H), 7.23 (s, 1H), 7.12 (d, J = 8.1 Hz, 1H), 7.00 (t, 1H), 4.56 (q, J = 7.3 Hz, 2H), 3.88 (s, 3H), 1.38 (t, J = 7.3 Hz, 3H) | 246 (M⁺) (base), 217, 201, 171 |

TABLE 23

| Carbonyl compound | Ring-forming component | Production process | Example | ¹H-NMR | Mass, m/z |
|---|---|---|---|---|---|
| 4'-Fluoro-2'-methoxy acetophenone | — | Example 8-1 | Example 8-33 | (DMSO-d$_6$) δ: 13.36 (br s, 1H), 7.89 (dd, J = 6.9, 8.5 Hz, 1H), 7.18 (s, 1H), 7.02 (dd, J = 2.3, 11.6 Hz, 1H), 6.83 (dt, J = 2.7, 8.5 Hz, 1H), 4.12 (s, 3H), 3.90 (s, 3H) | 250 (M⁺) (base), 220, 205, 175 |
| 2'-Methoxy-4'-methyl acetophenone | — | Example 8-1 | Example 8-34 | (DMSO-d$_6$) δ: 13.30 (br s, 1H), 7.77 (d, J = 7.7 Hz, 1H) 7.19 (s, 1H) 6.94 (s, 1H), 6.81 (d, J = 8.1 Hz, 1H), 4.11 (s, 3H), 3.87 (s, 3H), 2.34 (s, 3H) | 246 (M⁺) (base), 217, 201, 173 |
| 1-Indanone | — | Example 8-1 | Example 8-35 | (DMSO-d$_6$) δ: 12.66 (br s, 1H), 7.77 (d, J = 7.7 Hz, 1H), 7.58 (d, J = 7.3 Hz, 1H), 7.40 (t, J = 7.7 Hz, 1H), 7.32 (t, J = 7.7 Hz, 1H) 4.16 (s, 3H), 3.68 (s, 2H) | 214 (M⁺) (base), 169, 140, 115 |

Example 8-30

2,5-Dimethyl-2H-pyrazole-3-carboxylic acid

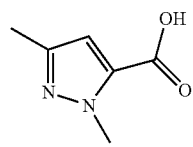

The title compound was obtained according to the same procedure as in Example 8-1 except that ethyl 2,4-dioxopentanoate was used instead of ethyl 4-(2,4-dichlorophenyl)-2,4-dioxobutyrate.

$^1$H-NMR (DMSO-d$_6$) δ: 13.16 (brs, 1H), 6.58 (s, 1H), 3.98 (s, 3H), 2.16 (s, 3H)

Mass, m/z: 140 (M$^+$, base)

Synthesis scheme 9

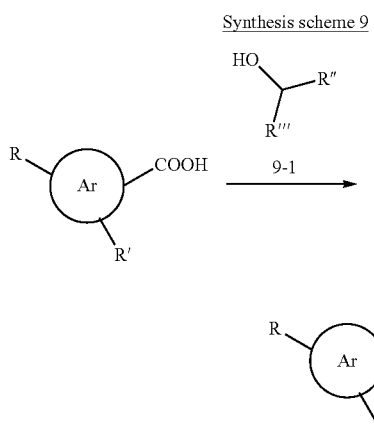

In the formulae, Ar represents a thiazole or pyrazole ring which may have a carbocyclic (homocyclic) or heterocyclic group as a substituent; R and R' are the same or different and each represent a hydrogen atom, a halogen atom, an alkyl group, a haloalkyl group, an alkoxy group, an amino group or an N-alkyl-substituted amino group; R" represents a carbocyclic (homocyclic) or heterocyclic group which may have a substituent (such as an alkyl group, a hydroxyl group, an alkoxy group, an alkoxyalkyl group, or an alkylthio group); and R''' represents an alkyl group.

Example 9-1

Step 9-1

[2-(4-Chloro-2-methoxyphenyl)-4-methylthiazol-5-yl]carbamic acid 1,2,3,4-tetrahydrobenzo[4,5]imidazo[1,2-a]pyridin-7-ylmethyl ester

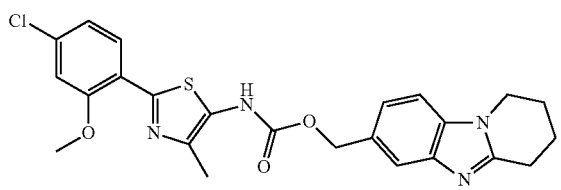 [SMILES: COc1cc(Cl)ccc1-c1nc(C)c(NC(=O)OCc2ccc3c(c2)nc2n3CCCC2)s1]

In toluene (50 ml), 2-(4-chloro-2-methoxyphenyl)-4-methylthiazole-5-carboxylic acid (1.11 g, 3.91 mmol) prepared in Example 7-1 and (1,2,3,4-tetrahydrobenzo[4,5]imidazo[1,2-a]pyridin-7-yl)methanol (870 mg, 4.30 mmol) prepared in Example 3-1 were suspended. Triethylamine (475 mg, 4.69 mmol) and then diphenylphosphoryl azide (1.18 g, 4.30 mmol) were added to the suspension, and the mixture was heated under reflux for 2 hours. Chloroform was added to the mixture, and the resulting mixture was washed with a saturated sodium bicarbonate solution. The washed mixture was dried over anhydrous magnesium sulfate and then concentrated. The concentrate was purified by silica gel column chromatography (chloroform:methanol=10:1) to give the title compound (1.34 g, 71%) as a white powder.

$^1$H-NMR (DMSO-d$_6$) δ: 10.08 (brs, 1H), 8.16 (d, J=8.5 Hz, 1H), 7.62 (s, 1H), 7.47 (d, J=8.1 Hz, 1H), 7.30 (d, J=1.9 Hz, 1H), 7.27 (d, J=7.7 Hz, 1H), 7.12 (dd, J=1.9, 8.5 Hz, 1H), 5.29 (s, 2H), 4.11-4.08 (m, 2H), 4.02 (s, 3H), 2.98-2.95 (m, 2H), 2.31 (s, 3H), 2.07-2.04 (m, 2H), 1.97-1.92 (m, 2H)

Mass, m/z: 482 (M$^+$), 438, 280, 202 (base)

Examples 9-2 to 9-377

The objective compounds were obtained according to the same procedure as in Example 9-1 except that any one of carboxylic acids or any one of hydroxy compounds shown in the following table were used instead of 2-(4-chloro-2-methoxyphenyl)-4-methylthiazole-5-carboxylic acid or (1,2,3,4-tetrahydrobenzo[4,5]imidazo[1,2-a]pyridin-7-yl)methanol.

TABLE 24

| Carboxylic acid | Hydroxy compound | Example | $^1$H-NMR | Mass, m/z |
|---|---|---|---|---|
| Example 7-8 | 4-Methoxy benzyl alcohol | Example 9-2 | (DMSO-d$_6$) δ: 10.00 (br s, 1H), 7.41-7.37 (m, 2H), 7.25-7.19 (m, 2H), 6.99-6.96 (m, 2H), 6.90-6.86 (m, 2H), 5.13 (s, 2H), 3.99 (s, 3H), 3.74 (s, 3H), 2.30 (s, 3H) | 384 (M$^+$), 121 (base) |

TABLE 24-continued

| Carboxylic acid | Hydroxy compound | Example | ¹H-NMR | Mass, m/z |
|---|---|---|---|---|
| Example 7-1 | 4-Methoxy benzyl alcohol | Example 9-3 | (DMSO-d$_6$) δ: 10.08 (br s, 1H), 8.16 (d, J = 8.5 Hz, 1H), 7.39 (d, J = 8.9 Hz, 2H), 7.30 (d, J = 1.9 Hz, 1H), 7.12 (dd, J = 1.9, 8.5 Hz, 1H), 6.96 (d, J = 8.9 Hz, 2H), 5.12 (s, 2H), 4.02 (s, 3H), 3.77 (s, 3H), 2.31 (s, 3H) | 418 (M$^+$), 374, 121 (base) |
| Example 7-20 | 4-Methoxy benzyl alcohol | Example 9-4 | (DMSO-d$_6$) δ: 9.69 (br s, 1H), 7.36-7.32 (m, 2H), 6.95 (d, J = 8.9 Hz, 2H), 5.07 (s, 2H), 3.76 (s, 3H), 2.16 (s, 3H), 2.03 (s, 3H), 1.91 (d, J = 2.7 Hz, 6H), 1.80-1.68 (m, 6H) | 412 (M$^+$), 368, 121 (base) |
| Example 7-8 | 4-Methylthio benzyl alcohol | Example 9-5 | (DMSO-d$_6$) δ: 10.03 (br s, 1H), 8.18 (dd, J = 1.5, 7.7 Hz, 1H), 7.42-7.37 (m, 3H), 7.30 (d, J = 8.5 Hz, 2H), 7.20 (d, J = 7.7 Hz, 1H), 7.08-7.04 (m, 1H), 5.16 (s, 2H), 3.98 (s, 3H), 2.49 (s, 3H), 2.31 (s, 3H) | 400 (M$^+$), 137 (base) |
| Example 7-8 | 2,3-Dihydro-1-benzofuran-5-ylmethanol | Example 9-6 | (DMSO-d$_6$) δ: 9.97 (br s, 1H), 8.17 (dd, J = 1.5, 8.1 Hz, 1H), 7.41-7.37 (m, 1H), 7.31 (s, 1H), 7.20 (d, J = 7.7 Hz, 1H), 7.18 (d, J = 8.1 Hz, 1H), 7.08-7.04 (m, 1H), 6.77 (d, J = 8.1 Hz, 1H), 5.10 (s, 2H), 4.53 (t, J = 8.9 Hz, 2H), 3.98 (s, 3H), 3.18 (t, J = 8.5 Hz, 2H), 2.30 (s, 3H) | 396 (M$^+$), 133 (base) |

TABLE 25

| Carboxylic acid | Hydroxy compound | Example | ¹H-NMR | Mass, m/z |
|---|---|---|---|---|
| — | 2,3-Dihydro-1-benzofuran-5-ylmethanol | Example 9-7 | (DMSO-d$_6$) δ: 10.04 (br s, 1H), 8.16 (d, J = 8.5 Hz, 1H), 7.32 (s, 1H), 7.30 (d, J = 2.3 Hz, 1H), 7.18 (d, J = 8.5 Hz, 1H), 7.12 (dd, J = 1.9, 8.5 Hz, 1H), 6.77 (d, J = 8.9, Hz 1H), 5.10 (s, 2H), 4.54 (t, J = 8.9 Hz, 2H), 4.02 (s, 3H), 3.19 (t, J = 8.9 Hz, 2H), 2.31 (s, 3H) | 386 (M$^+$ − 44), 133 (base) |
| Example 7-16 | 2,3-Dihydro-1-benzofuran-5-ylmethanol | Example 9-8 | (DMSO-d$_6$) δ: 10.07 (br s, 1H), 7.55 (d, J = 8.1 Hz, 1H), 7.31 (s, 1H), 7.17 (d, J = 7.7 Hz, 1H), 7.13 (s, 1H), 7.10 (d, J = 8.1 Hz, 1H), 6.77 (d, J = 8.1 Hz, 1H), 5.10 (s, 2H), 4.54 (t, J = 8.9 Hz, 2H), 3.18 (t, J = 8.9 Hz, 2H), 2.50 (s, 3H), 2.31 (s, 3H), 2.30 (s, 3H) | 394 (M$^+$), 133 (base) |

TABLE 25-continued

| Carboxylic acid | Hydroxy compound | Example | 1H-NMR | Mass, m/z |
|---|---|---|---|---|
| Example 7-8 | 3,4-Methylenedioxy benzyl alcohol | Example 9-9 | (DMSO-d$_6$) δ: 10.03 (br s, 1H), 8.17 (dd, J = 1.5, 7.7 Hz, 1H), 7.42-7.37 (m, 1H), 7.20 (d, J = 7.7 Hz, 1H), 7.08-7.02 (m, 1H), 6.94 (s, 1H), 6.86-6.83 (m, 2H), 5.98 (s, 2H), 5.09 (s, 2H), 3.99 (s, 3H), 2.31 (s, 3H) | 398 (M$^+$), 135 (base) |
| Example 7-8 | 3-Dimethylamino benzyl alcohol | Example 9-10 | (DMSO-d$_6$) δ: 10.02 (br s, 1H), 8.18 (dd, J = 1.5, 7.7 Hz, 1H), 7.41-7.37 (m, 1H), 7.22-7.17 (m, 2H), 7.08-7.04 (m, 1H), 6.78 (s, 1H), 6.72-6.70 (m, 2H), 5.13 (s, 2H), 3.98 (s, 3H), 2.90 (s, 6H), 2.31 (s, 3H) | 397 (M$^+$), 134 (base) |
| — | 3-Dimethylamino benzyl alcohol | Example 9-11 | (DMSO-d$_6$) δ: 10.01 (br s, 1H), 8.17 (d, J = 8.4 Hz, 1H), 7.51-7.43 (m, 1H), 7.36-7.32 (m, 2H), 7.22-7.18 (m, 1H), 6.72-6.70 (m, 2H), 5.13 (s, 2H), 4.01 (s, 3H), 2.90 (s, 6H), 2.32 (s, 3H) | 431 (M$^+$), 253, 134 (base) |

TABLE 26

| Carboxylic acid | Hydroxy compound | Example | 1H-NMR | Mass, m/z |
|---|---|---|---|---|
| Example 7-9 | 1-Methyl-1H-benzotriazole-5-methanol | Example 9-12 | (DMSO-d$_6$) δ: 10.23 (br s, 1H), 8.12 (s, 1H), 7.89 (d, J = 8.5 Hz, 1H), 7.67-7.63 (m, 2H), 7.38-7.28 (m, 3H), 5.38 (s, 2H), 4.32 (s, 3H), 2.52 (s, 3H), 2.33 (s, 3H) | 393 (M$^+$), 349, 118 (base) |
| Example 7-8 | 1-Methyl-1H-benzotriazole-5-methanol | Example 9-13 | (DMSO-d$_6$) δ: 10.08 (br s, 1H), 8.18 (dd, J = 1.5, 7.7 Hz, 1H), 8.12 (s, 1H), 7.89 (d, J = 8.5 Hz, 1H), 7.65 (d, J = 8.5 Hz, 1H), 7.41-7.37 (m, 1H), 7.20 (d, J = 7.7 Hz, 1H), 7.08-7.04 (m, 1H), 5.37 (s, 2H), 4.32 (s, 3H), 3.90 (s, 3H), 2.32 (s, 3H) | 409 (M$^+$), 365, 118 (base) |
| Example 7-13 | 1-Methyl-1H-benzotriazole-5-methanol | Example 9-14 | (DMSO-d$_6$) δ: 10.08 (br s, 1H), 8.19 (dd, J = 6.9, 8.5 Hz, 1H), 8.12 (s, 1H), 7.89 (d, J = 8.5 Hz, 1H), 7.64 (d, J = 8.5 Hz, 1H), 7.13 (dd, J = 2.3, 11.2 Hz, 1H), 6.90 (dt, J = 2.3, 8.5 Hz, 1H), 5.37 (s, 2H), 4.32 (s, 3H), 4.00 (s, 3H), 2.31 (s, 3H) | 427 (M$^+$), 383, 118 (base) |

TABLE 26-continued

| Carboxylic acid | Hydroxy compound | Example | ¹H-NMR | Mass, m/z |
|---|---|---|---|---|
| — | 1-Methyl-1H-benzotriazole-5-methanol | Example 9-15 | (DMSO-d$_6$) δ:10.16 (br s, 1H), 8.17 (d, J = 8.5 Hz, 1H), 8.12 (s, 1H), 7.89 (d, J = 8.9 Hz, 1H), 7.64 (d, J = 8.5 Hz, 1H), 7.30 (d, J =1.9 Hz, 1H), 7.12 (dd, J = 1.9, 8.5 Hz, 1H), 5.37 (s, 2H), 4.32 (s, 3H), 4.01 (s, 3H), 2.32 (s, 3H) | 443 (M⁺), 399, 280, 118 (base) |
| Example 7-14 | 1-Methyl-1H-benzotriazole-5-methanol | Example 9-16 | (DMSO-d$_6$) δ: 10.01 (br s, 1H), 8.12 (s, 1H), 8.05 (d, J = 7.7 Hz, 1H), 7.89 (d, J = 8.5 Hz, 1H), 7.64 (d, J = 8.1 Hz, 1H), 7.02 (s, 1H), 6.88 (d, J = 7.3 Hz, 1H), 5.36 (s, 2H), 4.32 (s, 3H), 3.96 (s, 3H), 2.36 (s, 3H), 2.30 (s, 3H) | 423 (M⁺), 379, 118 (base) |

TABLE 27

| Carboxylic acid | Hydroxy compound | Example | ¹H-NMR | Mass, m/z |
|---|---|---|---|---|
| Example 7-16 | 1-Methyl-1H-benzotriazole-5-methanol | Example 9-17 | (DMSO-d$_6$) δ: 10.17 (br s, 1H), 8.12 (s, 1H), 7.89 (d, J = 8.9 Hz, 1H), 7.64 (d, J = 8.5 Hz, 1H), 7.55 (d, J = 7.7 Hz, 1H), 7.14 (3, 1H), 7.10 (d, J = 8.1 Hz, 1H), 5.37 (s, 2H), 4.32 (s, 3H), 2.50 (s, 3H), 2.31 (s, 6H) | 407 (M⁺), 363, 118 (base) |
| Example 7-5 | 1-Methyl-1H-benzotriazole-5-methanol | Example 9-18 | (DMSO-d$_6$) δ: 10.38 (br s, 1H), 8.19-8.17 (m, 1H), 8.14 (d, J = 8.9 Hz, 1H), 7.89 (d, J = 8.5 Hz, 1H), 7.65 (d, J = 8.9 Hz, 1H), 7.60 (dd, J = 2.7, 8.9 Hz, 1H), 7.35 (dt, J = 2.7, 8.9 Hz, 1H), 5.38 (s, 2H), 4.32 (s, 3H), 2.35 (s, 3H) | 431 (M⁺), 387, 118 (base) |
| Example 7-6 | 1-Methyl-1H-benzotriazole-5-methanol | Example 9-19 | (DMSO-d$_6$) δ: 10.24 (br s, 1H), 8.12 (s, 1H), 7.89 (d, J = 8.5 Hz, 1H), 7.70 (dd, J = 6.2, 8.5 Hz, 1H), 7.64 (d, J = 8.5 Hz, 1H), 7.21 (dd, J = 2.7, 10.2 Hz, 1H), 7.12 (dt, J = 2.7, 8.5 Hz, 1H), 5.38 (s, 2H), 4.32 (s, 3H), 2.53 (s, 3H), 2.32 (s, 3H) | 411 (M⁺), 367, 248 (base) |
| Example 7-7 | 1-Methyl-1H-benzotriazole-5-methanol | Example 9-20 | (DMSO-d$_6$) δ: 10.30 (br s, 1H), 8.12 (s, 1H), 7.89 (d, J = 8.5 Hz, 1H), 7.70 (d, J = 8.5 Hz, 1H), 7.64 (d, J = 8.5 Hz, 1H), 7.44 (d, J = 1.9 Hz, 1H), 7.35 (dd, J = 2.3, 8.5 Hz, 1H), 5.38 (s, 2H), 4.32 (s, 3H), 2.53 (s, 3H), 2.34 (s, 3H) | 427 (M⁺), 383, 118 (base) |

TABLE 27-continued

| Carboxylic acid | Hydroxy compound | Example | ¹H-NMR | Mass, m/z |
|---|---|---|---|---|
| Example 7-17 | 1-Methyl-1H-benzotriazole-5-methanol | Example 9-21 | (DMSO-d$_6$) δ: 10.16 (br s, 1H), 8.12 (s, 1H), 7.89 (d, J = 8.1 Hz, 1H), 7.84 (d, J = 8.1 Hz, 1H), 7.65 (d, J = 8.9 Hz, 1H), 7.27 (d, J = 5.8 Hz, 1H), 6.94-6.91 (m, 1H), 5.37 (s, 2H), 4.74 (t, J = 8.5 Hz, 2H), 4.32 (s, 3H), 3.28 (t, J = 8.5 Hz, 2H), 2.32 (s, 3H) | 421 (M⁺), 377, 258 (base) |

TABLE 28

| Carboxylic acid | Hydroxy compound | Example | ¹H-NMR | Mass, m/z |
|---|---|---|---|---|
| Example 7-8 | Example 5-1 | Example 9-22 | (DMSO-d$_6$) δ: 10.07 (br s, 1H), 8.18 (dd, J = 1.5, 7.7 Hz, 1H), 8.13 (s, 1H), 7.94 (d, J = 8.5 Hz, 1H), 7.64 (d, J = 8.9 Hz, 1H), 7.41-7.37 (m, 1H), 7.20 (d, J = 8.5 Hz, 1H), 7.08-7.04 (m, 1H), 5.37 (s, 2H), 4.75 (q, J = 7.3 Hz, 2H), 3.98 (s, 3H), 2.32 (s, 3H), 1.52 (t, J = 7.3 Hz, 3H) | 423 (M⁺), 379, 104 (base) |
| Example 7-13 | Example 5-1 | Example 9-23 | (DMSO-d$_6$) δ: 10.08 (br s, 1H), 8.19 (dd, J = 6.9, 8.5 Hz, 1H), 8.13 (s, 1H), 7.94 (d, J = 8.5 Hz, 1H), 7.63 (d, J = 8.1 Hz, 1H), 7.13 (dd, J = 2.3, 11.2 Hz, 1H), 6.90 (dt, J = 2.3, 8.5 Hz, 1H), 5.37 (s, 2H), 4.65 (q, J = 7.3 Hz, 2H), 4.00 (s, 3H), 2.31 (s, 3H), 1.52 (t, J = 7.3 Hz, 3H) | 441 (M⁺), 397, 104 (base) |
| — | Example 5-1 | Example 9-24 | (DMSO-d$_6$) δ: 10.15 (br s, 1H), 8.17 (d, J = 8.5 Hz, 1H), 8.13 (s, 1H), 7.94 (d, J = 8.5 Hz, 1H), 7.63 (d, J = 8.5 Hz, 1H), 7.30 (d, J = 1.9 Hz, 1H), 7.12 (dd, J = 1.9, 8.5 Hz, 1H), 5.37 (s, 2H), 4.75 (q, J = 7.3 Hz, 2H), 4.01 (s, 3H), 2.32 (s, 3H), 1.52 (t, J = 7.3 Hz, 3H) | 457 (M⁺), 413, 104 (base) |
| Example 7-14 | Example 5-1 | Example 9-25 | (DMSO-d$_6$) δ: 10.01 (br s, 1H), 8.12 (s, 1H), 8.05 (d, J = 7.7 Hz, 1H), 7.94 (d, J = 8.5 Hz, 1H), 7.63 (d, J = 8.5 Hz, 1H), 7.02 (s, 1H), 6.88 (d, J = 8.5 Hz, 1H), 5.36 (s, 2H), 4.75 (q, J = 7.3 Hz, 2H), 3.96 (s, 3H), 2.35 (s, 3H), 2.30 (s, 3H), 1.52 (t, J = 7.3 Hz, 3H) | 437 (M⁺), 393, 104 (base) |
| Example 7-16 | Example 5-1 | Example 9-26 | (DMSO-d$_6$) δ: 10.16 (br s, 1H), 8.12 (s, 1H), 7.94 (d, J = 8.9 Hz, 1H), 7.63 (d, J = 8.5 Hz, 1H), 7.56 (d, J = 8.1 Hz, 1H), 7.14 (s, 1H), 7.10 (d, J = 8.1 Hz, 1H), 5.37 (s, 2H), 4.75 (q, J = 7.3 Hz, 2H), 2.50 (s, 3H), 2.31 (s, 3H), 2.31 (s, 3H), 1.52 (t, J = 7.3 Hz, 3H) | 421 (M⁺), 377, 104 (base) |

TABLE 29

| Carboxylic acid | Hydroxy compound | Example | ¹H-NMR | Mass, m/z |
|---|---|---|---|---|
| Example 7-6 | Example 5-1 | Example 9-27 | (DMSO-d$_6$) δ: 10.24 (br s, 1H), 8.13 (s, 1H), 7.94 (d, J = 8.5 Hz, 1H), 7.72-7.68 (m, 1H), 7.63 (d, J = 8.5 Hz, 1H), 7.23-7.20 (m, 1H), 7.12 (dt, J = 2.7, 8.5 Hz, 1H), 5.37 (s, 2H), 4.75 (q, J = 7.3 Hz, 2H), 4.32 (s, 3H), 2.52 (s, 3H), 2.33 (s, 3H), 1.52 (t, J = 7.3 Hz, 3H) | 425 (M⁺), 381, 104 (base) |
| Example 7-7 | Example 5-1 | Example 9-28 | (DMSO-d$_6$) δ: 10.30 (br s, 1H), 8.13 (s, 1H), 7.94 (d, J = 8.9 Hz, 1H), 7.70 (d, J = 8.5 Hz, 1H), 7.64 (d, J = 8.5 Hz, 1H), 7.44 (d, J = 1.9 Hz, 1H), 7.35 (dd, J = 1.9, 8.5 Hz, 1H), 5.38 (s, 2H), 4.75 (q, J = 7.3 Hz, 2H), 2.53 (s, 3H), 2.34 (s, 3H), 1.52 (t, J = 7.3 Hz, 3H) | 441 (M⁺), 397, 104 (base) |
| Example 7-8 | (1-Methyl-1H-indol-5-yl)methanol | Example 9-29 | (DMSO-d$_6$) δ: 9.98 (br s, 1H), 8.17 (dd, J = 1.5, 8.1 Hz, 1H), 7.64 (s, 1H), 7.46 (d, J = 8.5 Hz, 1H), 7.41-7.35 (m, 2H), 7.24 (d, J = 8.5 Hz, 1H), 7.19 (d, J = 8.1 Hz, 1H), 7.07-7.04 (m, 1H), 6.45 (d, J = 2.7 Hz, 1H), 5.27 (s, 2H), 3.98 (s, 3H), 3.80 (s, 3H), 2.30 (s, 3H) | 407 (M⁺), 363, 144 (base) |
| — | (1-Methyl-1H-indol-5-yl)methanol | Example 9-30 | (DMSO-d$_6$) δ: 10.08 (br s, 1H), 8.16 (d, J = 8.5 Hz, 1H), 7.63 (s, 1H), 7.46 (d, J = 8.1 Hz, 1H), 7.35 (d, J = 3.1 Hz, 2H), 7.30 (d, J = 1.9 Hz, 1H), 7.24 (d, J = 8.5 Hz, 1H), 7.12 (dd, J = 1.9, 8.5 Hz, 1H), 6.45 (d, J = 2.7 Hz, 1H), 5.27 (s, 2H), 4.02 (s, 3H), 3.80 (s, 3H), 2.30 (s, 3H) | 397 (M⁺ − 44), 254, 144 (base) |
| Example 7-7 | (1-Methyl-1H-indol-5-yl)methanol | Example 9-31 | (DMSO-d$_6$) δ: 10.21 (br s, 1H), 7.70 (d, J = 8.1 Hz, 1H), 7.64 (s, 1H), 7.46 (d, J = 8.5 Hz, 1H), 7.44 (d, J = 2.3 Hz, 1H), 7.37-7.33 (m, 2H), 7.24 (dd, J = 1.5, 8.5 Hz, 1H), 6.45 (d, J = 3.1 Hz, 1H), 5.28 (s, 2H), 3.80 (s, 3H), 2.53 (s, 3H), 2.32 (s, 3H) | 381 (M⁺ − 44), 144 (base) |

TABLE 30

| Carboxylic acid | Hydroxy compound | Example | ¹H-NMR | Mass, m/z |
|---|---|---|---|---|
| 4-Methyl-2-phenyl-1,3-thiazole-5-carboxylic acid | Example 1-1 | Example 9-32 | (DMSO-d$_6$) δ: 10.20 (br s, 1H), 8.21 (s, 1H), 7.84 (d, J = 1.5 Hz, 1H), 7.82 (d, J = 1.2 Hz, 1H), 7.75 (s, 1H), 7.59 (d, J = 8.5 Hz, 1H), 7.78-7.36 (m, 4H), 5.32 (s, 2H), 3.85 (s, 3H), 2.31 (s, 3H) | 334 (M⁺ − 44), 145 (base) |

TABLE 30-continued

| Carboxylic acid | Hydroxy compound | Example | 1H-NMR | Mass, m/z |
|---|---|---|---|---|
| Example 7-9 | Example 1-1 | Example 9-33 | (DMSO-d$_6$) δ: 10.16 (br s, 1H), 8.21 (s, 1H), 7.75 (s, 1H), 7.66 (d, J = 6.9 Hz, 1H), 7.59 (d, J = 8.5 Hz, 1H), 7.37 (d, J = 7.7 Hz, 1H), 7.33-7.26 (m, 3H), 5.32 (s, 2H), 3.85 (s, 3H), 2.52 (s, 3H), 2.32 (s, 3H) | 392 (M$^+$), 348, 145 (base) |
| Example 7-10 | Example 1-1 | Example 9-34 | (DMSO-d$_6$) δ: 10.18 (br s, 1H), 8.21 (s, 1H), 7.75 (s, 1H), 7.66 (s, 1H), 7.62-7.58 (m, 1H), 7.37 (d, J = 8.5 Hz, 1H), 7.32 (d, J = 7.7 Hz, 1H), 7.23 (d, J = 7.3 Hz, 1H), 5.32 (s, 2H), 3.85 (s, 3H), 2.36 (s, 3H), 2.30 (s, 3H) | 392 (M$^+$), 145 (base) |
| Example 7-11 | Example 1-1 | Example 9-35 | (DMSO-d$_6$) δ: 10.14 (br s, 1H), 8.22 (s, 1H), 7.75 (s, 1H), 7.71 (d, J = 7.1 Hz, 2H), 7.60 (d, J = 8.1 Hz, 1H), 7.37 (d, J = 8.1 Hz, 1H), 7.26 (d, J = 8.1 Hz, 2H), 5.31 (s, 2H), 3.85 (s, 3H), 2.34 (s, 3H), 2.29 (s, 3H) | 392 (M$^+$), 348, 145 (base) |
| Example 7-12 | Example 1-1 | Example 9-36 | (DMSO-d$_6$) δ: 10.16 (br s, 1H), 8.21 (s, 1H), 7.75 (s, 1H), 7.59 (d, J = 8.5 Hz, 1H), 7.53 (d, J = 7.3 Hz, 1H), 7.39-7.34 (m, 3H), 7.30-7.26 (m, 1H), 5.32 (s, 2H), 3.85 (s, 3H), 2.91 (q, J = 7.3 Hz, 2H), 2.31 (s, 3H), 1.13 (t, J = 7.3 Hz, 3H) | 406 (M$^+$), 362, 145 (base) |

TABLE 31

| Carboxylic acid | Hydroxy compound | Example | 1H-NMR | Mass, m/z |
|---|---|---|---|---|
| Example 7-8 | Example 1-1 | Example 9-37 | (DMSO-d$_6$) δ: 10.02 (br s, 1H), 8.21 (d, J = 2.3 Hz, 1H), 8.18 (dd, J = 1.5, 7.7 Hz, 1H), 7.77 (d, J = 8.1 Hz, 1H), 7.60 (d, J = 8.5 Hz, 1H), 7.41-7.36 (m, 2H), 7.20 (d, J = 8.1 Hz, 1H), 7.08-7.04 (m, 1H), 5.31 (s, 2H), 3 98 (s, 3H), 3.85 (s, 3H), 2.31 (s, 3H) | 408 (M$^+$), 364, 246, 145 (base) |
| Example 7-13 | Example 1-1 | Example 9-38 | (DMSO-d$_6$) δ: 10.03 (br s, 1H), 8.21 (s, 1H), 8.17 (d, J = 8.9 Hz, 1H), 7.75 (s, 1H), 7.59 (d, J = 8.1 Hz, 1H), 7.37 (d, J = 8.5 Hz, 1H), 7.13 (dd, J = 2.3, 11.2 Hz, 1H), 6.90 (dt, J = 2.3, 8.5 Hz, 1H), 5.31 (s, 2H), 4.00 (s, 3H), 3.85 (s, 3H), 2.30 (s, 3H) | 426 (M$^+$), 382, 145 (base) |

TABLE 31-continued

| Carboxylic acid | Hydroxy compound | Example | ¹H-NMR | Mass, m/z |
|---|---|---|---|---|
| — | Example 1-1 | Example 9-39 | (DMSO-d$_6$) δ: 10.10 (br s, 1H), 8.21 (s, 1H), 8.16 (d, J = 8.5 Hz, 1H), 7.75 (s, 1H), 7.59 (d, J = 8.1 Hz, 1H), 7.40-7.35 (m, 1H), 7.30 (d, J = 1.9 Hz, 1H), 7.12 (dd, J = 1.9, 8.5 Hz, 1H), 5.31 (s, 2H), 4.02 (s, 3H), 3.85 (s, 3H), 2.31 (s, 3H) | 442 (M⁺), 398, 280, 133 (base) |
| Example 7-14 | Example 1-1 | Example 9-40 | (DMSO-d$_6$) δ: 9.94 (br s, 1H), 8.21 (s, 1H), 8.05 (d, J = 8.1 Hz, 1H), 7.74 (s, 1H), 7.59 (d, J = 8.5 Hz, 1H), 7.36 (d, J = 8.5 Hz, 1H), 7.02 (s, 1H), 6.87 (dd, J = 0.8, 8.1 Hz, 1H), 5.30 (s, 2H), 3.96 (s, 3H), 3.85 (s, 3H), 2.35 (s, 3H), 2.29 (s, 3H) | 422 (M⁺) 378, 145 (base) |

TABLE 32

| Carboxylic acid | Hydroxy compound | Example | ¹H-NMR | Mass, m/z |
|---|---|---|---|---|
| Example 7-15 | Example 1-1 | Example 9-41 | (DMSO-d$_6$) δ: 9.87 (br s, 1H), 8.21 (s, 1H), 8.08 (d, J = 8.5 Hz, 1H), 7.74 (s, 1H), 7.59 (d, J = 8.5 Hz, 1H), 7.36 (d, J = 8.1 Hz, 1H), 6.73 (d, J = 2.3 Hz, 1H), 6.66 (dd, J = 2.3, 8.9 Hz, 1H), 5.29 (s, 2H), 3.97 (s, 3H), 3.85 (s, 3H), 3.83 (s, 3H), 2.27 (s, 3H) | 438 (M⁺) 394, 133 (base) |
| Example 7-16 | Example 1-1 | Example 9-42 | (DMSO-d$_6$) δ: 10.11 (br s, 1H), 8.21 (s, 1H), 7.74 (s, 1H), 7.59 (d, J = 8.1 Hz, 1H), 7.56 (d, J = 8.1 Hz, 1H), 7.36 (d, J = 8.5 Hz, 1H), 7.14 (s, 1H), 7.09 (d, J = 8.5 Hz, 1H), 5.31 (s, 2H), 3.85 (s, 3H), 2.31 (s, 9H) | 406 (M⁺) 362, 244, 145 (base) |
| Example 7-2 | Example 1-1 | Example 9-43 | (DMSO-d$_6$) δ: 10.33 (br s, 1H), 8.21 (s, 1H), 8.14 (dt, J = 1.6, 7.8 Hz, 1H), 7.76 (s, 1H), 7.60 (d, J = 8.1 Hz, 1H), 7.49-7.43 (m, 1H), 7.40-7.30 (m, 2H), 5.33 (s, 2H), 3.85 (s, 3H), 2.35 (s, 3H) | 396 (M⁺), 352, 234, 145 (base) |
| Example 7-3 | Example 1-1 | Example 9-44 | (DMSO-d$_6$) δ: 10.32 (br s, 1H), 8.21 (s, 1H), 7.75 (s, 1H), 7.67-7.63 (m, 1H), 7.62-7.59 (m, 2H), 7.53-7.49 (m, 1H), 7.38-7.36 (m, 1H), 7.25 (dt, J = 2.3, 8.5 Hz, 1H), 5.33 (s, 2H), 3.85 (s, 3H), 2.32 (s, 3H) | 396 (M⁺) 352, 234, 145 (base) |

TABLE 32-continued

| Carboxylic acid | Hydroxy compound | Example | ¹H-NMR | Mass, m/z |
|---|---|---|---|---|
| Example 7-4 | Example 1-1 | Example 9-45 | (DMSO-d₆) δ: 10.22 (br s, 1H), 8.22 (s, 1H), 7.89 (dd, J = 3.1, 5.4 Hz, 1H), 7.86 (dd, J = 3.1, 5.4 Hz, 1H), 7.75 (s, 1H), 7.59 (d, J = 8.1 Hz, 1H), 7.37 (d, J = 8.5 Hz, 1H), 7.32-7.20 (m, 2H), 5.32 (s, 2H), 3.84 (s, 3H), 2.30 (s, 3H) | 396 (M⁺), 352, 234, 145 (base) |

TABLE 33

| Carboxylic acid | Hydroxy compound | Example | ¹H-NMR | Mass, m/z |
|---|---|---|---|---|
| Example 7-38 | Example 1-1 | Example 9-46 | (DMSO-d₆) δ: 10.34 (br s, 1H), 8.21 (s, 1H), 8.20-8.14 (m, 1H), 7.75 (s, 1H), 7.59 (d, J = 8.1 Hz, 1H), 7.48-7.42 (m, 1H), 7.37 (d, J = 8.1 Hz, 1H), 7.25-7.20 (m, 1H), 5.33 (s, 2H), 3.85 (s, 3H), 2.35 (s, 3H) | 414 (M⁺), 370, 145 (base) |
| Example 7-5 | Example 1-1 | Example 9-47 | (DMSO-d₆) δ: 10.33 (br s, 1H), 8.22 (s, 1H), 8.17 (dd, J = 6.2, 8.9 Hz, 1H), 7.75 (s, 1H), 7.62-7.59 (m, 2H), 7.39-7.33 (m, 2H), 5.33 (s, 2H), 3.85 (s, 3H), 2.34 (s, 3H) | 386 (M⁺ − 44), 145 (base) |
| Example 7-6 | Example 1-1 | Example 9-48 | (DMSO-d₆) δ: 10.19 (br s, 1H), 8.22 (s, 1H), 7.75 (s, 1H), 7.71-7.68 (m, 1H), 7.60 (d, J = 8.1 Hz, 1H), 7.37 (d, J = 8.1 Hz, 1H), 7.21 (dd, J = 2.7, 10.0 Hz, 1H), 7.12 (dt, J = 2.7, 8.5 Hz, 1H), 5.32 (s, 2H), 3.85 (s, 3H), 2.52 (s, 3H), 2.31 (s, 3H) | 410 (M⁺), 366, 145 (base) |
| Example 7-7 | Example 1-1 | Example 9-49 | (DMSO-d₆) δ: 10.25 (br s, 1H), 8.21 (s, 1H), 7.75 (s, 1H), 7.70 (d, J = 8.1 Hz, 1H), 7.59 (d, J = 8.5 Hz, 1H), 7.44 (d, J = 1.9 Hz, 1H), 7.38-7.34 (m, 2H), 5.32 (s, 2H), 3.85 (s, 3H), 2.53 (s, 3H), 2.32 (s, 3H) | 382 (M⁺ − 44), 145, 133 (base) |
| Example 7-18 | Example 1-1 | Example 9-50 | (DMSO-d₆) δ: 8.22 (s, 1H), 7.74-7.73 (m, 1H), 7.71-7.66 (m, 1H), 7.61-7.56 (m, 2H), 7.37 (d, J = 8.5 Hz, 1H), 6.82 (dd, J = 3.5, 8.5 Hz, 1H), 5.30 (s, 2H), 4.58 (t, J = 8.5 Hz, 2H), 3.85 (s, 3H), 3.23 (t, J = 8.5 Hz, 2H), 2.26 (s, 3H) | 420 (M⁺), 376, 258 (base) |

TABLE 34

| Carboxylic acid | Hydroxy compound | Example | ¹H-NMR | Mass, m/z |
|---|---|---|---|---|
| 4-Methyl-2-[4-(trifluoromethyl)phenyl]thiazole-5-carboxylic acid | Example 1-1 | Example 9-51 | (DMSO-$d_6$) δ: 10.42 (br s, 1H), 8.21 (s, 1H), 8.04 (d, J = 8.5 Hz, 2H), 7.80 (d, J = 8.5 Hz, 2H), 7.76 (s, 1H), 7.60 (d, J = 8.5 Hz, 1H), 7.38 (dd, J = 1.5, 8.5 Hz, 1H), 5.34 (s, 2H), 3.85 (s, 3H), 2.35 (s, 3H) | 446 (M⁺) 402, 145 (base) |
| Example 7-20 | Example 1-1 | Example 9-52 | (DMSO-$d_6$) δ: 9.71 (br s, 1H), 8.21 (s, 1H), 7.71 (s, 1H), 7.58 (d, J = 8.5 Hz, 1H), 7.33 (d, J = 7.7 Hz, 1H), 5.26 (s, 2H), 3.84 (s, 3H), 2.17 (s, 3H), 2.04 (s, 3H), 1.92 (d, J = 2.7 Hz, 6H), 1.78-1.65 (m, 6H) | 436 (M+), 392, 145 (base) |
| Example 7-9 | Example 1-2 | Example 9-53 | (DMSO-$d_6$) δ: 10.16 (br s, 1H), 8.28 (s, 1H), 7.75 (s, 1H), 7.68-7.63 (m, 2H), 7.36-7.27 (m, 4H), 5.31 (s, 2H), 4.29 (q, J = 7.3 Hz, 2H), 2.52 (s, 3H), 2.32 (s, 3H), 1.42 (t, J = 7.3 Hz, 3H) | 406 (M+), 362, 159 (base) |
| Example 7-10 | Example 1-2 | Example 9-54 | (DMSO-$d_6$) δ: 10.18 (br s, 1H), 8.28 (s, 1H), 7.75 (s, 1H), 7.66-7.60 (m, 3H), 7.36-7.31 (m, 2H), 7.23 (d, J = 7.3 Hz, 1H), 5.31 (s, 2H), 4.29 (q, J = 7.3 Hz, 2H), 2.36 (s, 3H), 2.30 (s, 3H), 1.42 (t, J = 7.3 Hz, 3H) | 406 (M⁺) 362, 159 (base) |
| Example 7-11 | Example 1-2 | Example 9-55 | (DMSO-$d_6$) δ: 10.14 (br s, 1H), 8.28 (s, 1H), 7.75 (s, 1H), 7.71 (d, J = 8.1 Hz, 2H), 7.64 (d, J = 8.1 Hz, 1H), 7.35 (d, J = 8.1 Hz, 1H), 7.26 (d, J = 7.7 Hz, 2H), 5.31 (s, 2H), 4.29 (q, J = 7.3 Hz, 3H), 2.34 (s, 3H), 2.29 (s, 3H), 1.42 (t, J = 7.3 Hz, 3H) | 406 (M+), 362, 159 (base) |

TABLE 35

| Carboxylic acid | Hydroxy compound | Example | ¹H-NMR | Mass, m/z |
|---|---|---|---|---|
| Example 7-12 | Example 1-2 | Example 9-56 | (DMSO-d6) δ: 10.16 (br s, 1H), 8.27 (s, 1H), 7.75 (s, 1H), 7.63 (d, J = 8.5 Hz, 1H), 7.53 (d, J = 7.3 Hz, 1H), 7.39-7.34 (m, 3H), 7.30-7.26 (m, 1H), 5.31 (s, 2H), 4.29 (q, J = 7.3 Hz, 2H), 2.91 (q, J = 7.3 Hz, 2H), 2.32 (s, 3H), 1.42 (t, J = 7.3 Hz, 3H), 1.13 (t, J = 7.3 Hz, 3H) | 420 (M⁺), 376, 159 (base) |

TABLE 35-continued

| Carboxylic acid | Hydroxy compound | Example | 1H-NMR | Mass, m/z |
|---|---|---|---|---|
| Example 7-8 | Example 1-2 | Example 9-57 | (DMSO-d6) δ: 10.01 (br s, 1H), 8.28 (s, 1H), 8.18 (dd, J = 1.5, 7.7 Hz, 1H), 7.75 (s, 1H), 7.64 (d, J = 8.5 Hz, 1H), 7.41-7.35 (m, 2H), 7.0 (d, J = 7.7 Hz, 1H), 7.06 (dt, J = 0.8, 7.7 Hz, 1H), 5.31 (s, 2H), 4.29 (q, J = 7.3 Hz, 2H), 4.03 (s, 3H), 2.31 (s, 3H), 1.42 (t, J = 7.3 Hz, 3H) | 422 (M+), 378, 246, 159 (base) |
| Example 7-13 | Example 1-2 | Example 9-58 | (DMSO-d6) δ: 10.05 (br s, 1H), 8.28 (s, 1H), 8.18 (dd, J = 6.9, 8.9 Hz, 1H), 7.75 (s, 1H), 7.64 (d, J = 8.5 Hz, 1H), 7.35 (d, J = 8.5 Hz, 1H), 7.13 (dd, J = 2.3, 11.2 Hz, 1H), 6.90 (dt, J = 2.3, 8.5 Hz, 1H), 5.30 (s, 2H), 4.29 (q, J = 7.3 Hz, 2H), 4.00 (s, 3H), 2.30 (s, 3H), 1.41 (t, J = 7.3 Hz, 3H) | 440 (M+), 396, 264 (base) |
| — | Example 1-2 | Example 9-59 | (DMSO-d6) δ: 10.10 (br s, 1H), 8.33 (s, 1H), 8.16 (d, J = 8.5 Hz, 1H), 7.76 (s, 1H), 7.66 (d, J = 8.1 Hz, 1H), 7.37 (d, J = 8.5 Hz, 1H), 7.30 (d, J = 2.3 Hz, 1H), 7.12 (dd, J = 1.9, 8.5 Hz, 1H), 5.31 (s, 2H), 4.30 (q, J = 7.3 Hz, 2H), 4.02 (s, 3H), 2.31 (s, 3H), 1.42 (dt, J = 2.7, 7.3 Hz, 3H) | 456 (M+), 412, 147 (base) |
| Example 7-14 | Example 1-2 | Example 9-60 | (DMSO-d6) δ: 9.94 (br s, 1H), 8.27 (s, 1H), 8.04 (d, J = 8.1 Hz, 1H), 7.74 (s, 1H), 7.63 (d, J = 8.5 Hz, 1H), 7.35 (d, J = 8.5 Hz, 1H), 7.02 (s, 1H), 6.87 (d, J = 8.1 Hz, 1H), 5.30 (s, 2H), 4.29 (q, J = 7.3 Hz, 2H), 3.96 (s, 3H), 2.35 (s, 3H), 2.29 (s, 3H), 1.42 (t, J = 7.3 Hz, 3H) | 436 (M+), 392, 131 (base) |

TABLE 36

| Carboxylic acid | Hydroxy compound | Example | 1H-NMR | Mass, m/z |
|---|---|---|---|---|
| Example 7-15 | Example 1-2 | Example 9-61 | (DMSO-d6) δ: 9.87 (br s, 1H), 8.28 (s, 1H), 8.08 (d, J = 8.9 Hz, 1H), 7.74 (s, 1H), 7.64 (d, J = 8.5 Hz, 1H), 7.35 (d, J = 8.1 Hz, 1H), 6.72 (d, J = 2.3 Hz, 1H), 6.66 (dd, J = 2.3, 8.5 Hz, 1H), 5.29 (s, 2H), 4.28 (q, J = 7.3 Hz, 2H), 3.97 (s, 3H), 3.83 (s, 3H), 2.27 (s, 3H), 1.42 (t, J = 7.3 Hz, 3H) | 408 (M+ − 44), 147 (base) |
| Example 7-16 | Example 1-2 | Example 9-62 | (DMSO-d6) δ: 10.10 (br s, 1H), 8.28 (s, 1H), 7.74 (s, 1H), 7.63 (d, J = 8.5 Hz, 1H), 7.56 (d, J = 8.1 Hz, 1H), 7.35 (d, J = 8.5 Hz, 1H), 7.14 (s, 1H), 7.10 (d, J = 8.1 Hz, 1H), 5.31 (s, 2H), 4.29 (q, J = 7.3 Hz, 2H), 2.31 (s, 9H), 1.42 (t, J = 7.3 Hz, 3H) | 376 (M+ − 44), 244 (base) |

TABLE 36-continued

| Carboxylic acid | Hydroxy compound | Example | 1H-NMR | Mass, m/z |
|---|---|---|---|---|
| Example 7-6 | Example 1-2 | Example 9-63 | (DMSO-$d_6$) δ: 10.21 (br s, 1H), 8.28 (s, 1H), 7.75 (s, 1H), 7.70 (dd, J = 5.8, 8.5 Hz, 1H), 7.64 (d, J = 8.1 Hz, 1H), 7.35 (d, J = 8.5 Hz, 1H), 7.21 (dd, J = 2.7, 10.0 Hz, 1H), 7.13 (dt, J = 2.7, 8.5 Hz, 1H), 5.31 (s, 2H), 4.29 (q, J = 7.3 Hz, 2H), 2.52 (s, 3H), 2.32 (s, 3H), 1.41 (t, J = 7.3 Hz, 3H) | 380 ($M^+$ − 44), 248, 159 (base) |
| Example 7-7 | Example 1-2 | Example 9-64 | (DMSO-$d_6$) δ: 10.23 (br s, 1H), 8.27 (s, 1H), 7.75 (s, 1H), 7.70 (d, J = 8.1 Hz, 1H), 7.63 (d, J = 8.1 Hz, 1H), 7.44 (d, J = 2.3 Hz, 1H), 7.36 (d, J = 1.9 Hz, 1H), 7.34 (d, J = 1.9 Hz, 1H), 5.31 (s, 2H), 4.29 (q, J = 7.3 Hz, 2H), 2.52 (s, 3H), 2.32 (s, 3H), 1.41 (t, J = 7.3 Hz, 3H) | 382 ($M^+$ − 44), 145, 133 (base) |
| 4-Methyl-2-[4-(trifluoro-methyl)phenyl]thiazole-5-carboxylic acid | Example 1-2 | Example 9-65 | (DMSO-$d_6$) δ: 10.42 (br s, 1H), 8.28 (s, 1H), 8.04 (d, J = 8.1 Hz, 2H), 7.80 (d, J = 8.5 Hz, 2H), 7.76 (s, 1H), 7.64 (d, J = 8.1 Hz, 1H), 7.36 (dd, J = 1.2, 8.1 Hz, 1H), 5.34 (s, 2H), 4.29 (q, J = 7.3 Hz, H), 2.35 (s, 3H), 1.42 (t, J = 7.3 Hz, 3H) | 460 ($M^+$) 416, 159 (base) |

TABLE 37

| Carboxylic acid | Hydroxy compound | Example | 1H-NMR | Mass, m/z |
|---|---|---|---|---|
| Example 7-8 | Example 1-3 | Example 9-66 | (DMSO-$d_6$) δ: 10.01 (br s, 1H), 8.17 (dd, J = 1.5, 7.7 Hz, 1H), 7.75 (s, 1H), 7.64 (d, J = 8.1 Hz, 1H), 7.41-7.34 (m, 2H), 7.20 (d, J = 8.1 Hz, 1H), 7.08-7.04 (m, 1H), 5.31 (s, 2H), 4.22 (t, J = 6.9 Hz, 2H), 3.98 (s, 3H), 2.31 (s, 3H), 1.86-1.77 (m, 2H), 0.84 (t, J = 7.3 Hz, 3H) | 436 ($M^+$) 392, 246, 161 (base) |
| — | Example 1-3 | Example 9-67 | (DMSO-$d_6$) δ: 10.09 (br s, 1H), 8.26 (s, 1H), 8.16 (d, J = 8.5 Hz, 1H), 7.75 (s, 1H), 7.64 (d, J = 8.5 Hz, 1H), 7.35 (d, J = 8.5 Hz, 1H), 7.30 (d, J = 1.9 Hz, 1H), 7.12 (dd, J = 1.9, 8.5 Hz, 1H), 5.31 (s, 2H), 4.22 (t, J = 7.3 Hz, 2H), 4.02 (s, 3H), 2.31 (s, 3H), 1.84-1.79 (m, 2H), 0.84 (t, J = 7.3 Hz, 3H) | 470 ($M^+$) 426, 280 (base) |
| Example 7-14 | Example 1-3 | Example 9-68 | (DMSO-$d_6$) δ: 9.94 (br s, 1H), 8.26 (s, 1H), 8.05 (d, J = 8.1 Hz, 1H), 7.74 (s, 1H), 7.64 (d, J = 8.5 Hz, 1H), 7.34 (d, J = 8.5 Hz, 1H), 7.02 (s, 1H), 6.87 (dd, J = 0.8, 8.1 Hz, 1H), 5.30 (s, 2H), 4.22 (t, J = 6.9 Hz, 2H), 3.96 (s, 3H), 2.35 (s, 3H), 2.29 (s, 3H), 1.86-1.77 (m, 2H), 1.84 (t, J = 7.3 Hz, 3H) | 450 ($M^+$), 406, 260 (base) |

TABLE 37-continued

| Carboxylic acid | Hydroxy compound | Example | ¹H-NMR | Mass, m/z |
|---|---|---|---|---|
| Example 7-16 | Example 1-3 | Example 9-69 | (DMSO-d₆) δ: 10.11 (br s, 1H), 8.26 (s, 1H), 7.74 (s, 1H), 7.64 (d, J = 8.1 Hz, 1H), 7.55 (d, J = 7.7 Hz, 1H), 7.34 (d, J = 8.5 Hz, 1H), 7.14 (s, 1H), 7.09 (d, J = 8.5 Hz, 1H), 5.30 (s, 2H), 4.22 (t, J = 6.9 Hz, 2H), 2.50 (s, 3H), 2.31 (s, 6H), 1.86-1.77 (m, 2H), 0.84 (t, J = 7.3 Hz, 3H) | 434 (M⁺) 390, 173 (base) |
| Example 7-13 | Example 1-4 | Example 9-37 | (DMSO-d₆) δ: 10.02 (br s, 1H), 8.36 (s, 1H), 8.18 (dd, J = 6.9, 8.9 Hz, 1H), 7.74 (s, 1H), 7.67 (d, J = 8.1 Hz, 1H), 7.34 (d, J = 8.5 Hz, 1H), 7.13 (dd, J = 2.3, 11.2 Hz, 1H), 6.95-6.88 (m, 1H), 5.30 (s, 2H), 4.80-4.73 (m, 1H), 4.00 (s, 3H), 2.30 (s, 3H), 1.54 (d, J = 6.9 Hz, 6H) | 454 (M⁺) 410, 118 (base) |

TABLE 38

| Carboxylic acid | Hydroxy compound | Example | ¹H-NMR | Mass, m/z |
|---|---|---|---|---|
| — | Example 1-4 | Example 9-71 | (DMSO-d₆) δ: 10.08 (br s, 1H), 8.35 (s, 1H), 8.16 (d, J = 8.5 Hz, 1H), 7.75 (s, 1H), 7.70 (d, J = 8.1 Hz, 1H), 7.34 (d, J = 8.1 Hz, 1H), 7.29 (d, J = 1.9 Hz, 1H), 7.12 (dd, J = 1.9, 8.5 Hz, 1H), 5.31 (s, 2H), 4.80-4.52 (m, 1H), 4.01 (s, 3H), 2.31 (s, 3H), 1.54 (d, J = 6.6 Hz, 6H) | 470 (M⁺) 280 (base) |
| Example 7-15 | Example 1-4 | Example 9-72 | (DMSO-d₆) δ: 9.87 (br s, 1H), 8.35 (s, 1H), 8.08 (d, J = 8.5 Hz, 1H), 7.74 (s, 1H), 7.66 (d, J = 8.5 Hz, 1H), 7.33 (d, J = 8.1 Hz, 1H), 6.72 (d, J = 2.3 Hz, 1H), 6.66 (dd, J = 2.3, 8.9 Hz, 1H), 5.29 (s, 2H), 4.80-4.73 (m, 1H), 3.96 (s, 3H), 3.83 (s, 3H), 2.27 (s, 3H), 1.54 (d, J = 6.6 Hz, 6H) | 466 (M⁺), 422, 276 (base) |
| Example 7-16 | Example 1-4 | Example 9-73 | (DMSO-d₆) δ: 10.12 (br s, 1H), 8.36 (s, 1H), 7.74 (s, 1H), 7.66 (d, J = 8.5 Hz, 1H), 7.55 (d, J = 7.7 Hz, 1H), 7.34 (d, J = 8.1 Hz, 1H), 7.14 (s, 1H), 7.09 (d, J = 8.5 Hz, 1H), 5.30 (s, 2H), 4.80-4.73 (m, 1H), 2.50 (s, 3H), 2.31 (s, 6H), 1.84 (d, J = 6.3 Hz, 6H) | 390 (M⁺ − 44), 244 (base) |
| Example 7-8 | Example 2-1 | Example 9-74 | (DMSO-d₆) δ: 10.00 (br s, 1H), 8.17 (dd, J = 1.9, 8.1 Hz, 1H), 7.61 (s, 1H), 7.49 (d, J = 8.1 Hz, 1H), 7.39 (ddd, J = 1.5, 7.3, 8.5 Hz, 1H), 7.28 (d, J = 8.1 Hz, 1H), 7.20 (d, J = 7.7 Hz, 1H), 7.06 (dt, J = 1.2, 8.1 Hz, 1H), 5.28 (s, 2H), 4.03 (s, 3H), 3.74 (s, 3H), 2.53 (s, 3H), 2.30 (s, 3H) | 442 (M⁺), 378, 147 (base) |

TABLE 38-continued

| Carboxylic acid | Hydroxy compound | Example | ¹H-NMR | Mass, m/z |
|---|---|---|---|---|
| Example 7-13 | Example 2-1 | Example 9-75 | (DMSO-$d_6$) δ: 10.02 (br s, 1H), 8.18 (dd, J = 6.9, 8.9 Hz, 1H), 7.61 (s, 1H), 7.50 (d, J = 8.1 Hz, 1H), 7.29 (d, J = 8.1 Hz, 1H), 7.13 (dd, J = 2.3, 11.2 Hz, 1H), 6.90 (dt, J = 2.3, 8.5 Hz, 1H), 5.28 (s, 2H), 4.00 (s, 3H), 3.74 (s, 3H), 2.54 (s, 3H), 2.30 (s, 3H) | 440 ($M^+$), 396, 159 (base) |

TABLE 39

| Carboxylic acid | Hydroxy compound | Example | ¹H-NMR | Mass, m/z |
|---|---|---|---|---|
| — | Example 2-1 | Example 9-76 | (DMSO-$d_6$) δ: 10.08 (br s, 1H), 8.17 (d, J = 8.5 Hz, 1H), 7.61 (s, 1H), 7.49 (d, J = 8.5 Hz, 1H), 7.30 (d, J = 1.9 Hz, 1H), 7.28 (d, J = 8.9 Hz, 1H), 7.12 (dd, J = 1.9, 8.5 Hz, 1H), 5.28 (s, 2H), 4.02 (s, 3H), 3.73 (s, 3H), 2.53 (s, 3H), 2.31 (s, 3H) | 412 ($M^+$ − 44) 159 (base) |
| Example 7-14 | Example 2-1 | Example 9-77 | (DMSO-$d_6$) δ: 9.93 (br s, 1H), 8.04 (d, J = 8.1 Hz, 1H), 7.60 (s, 1H), 7.49 (d, J = 8.5 Hz, 1H), 7.28 (d, J = 8.5 Hz, 1H), 7.02 (s, 1H), 6.87 (d, J = 8.1 Hz, 1H), 5.27 (s, 2H), 3.96 (s, 3H), 3.74 (s, 3H), 2.53 (s, 3H), 2.35 (s, 3H), 2.28 (s, 3H) | 436 ($M^+$), 392, 159 (base) |
| Example 7-16 | Example 2-1 | Example 9-78 | (DMSO-$d_6$) δ: 10.10 (br s, 1H), 7.60 (s, 1H), 7.55 (d, J = 8.1 Hz, 1H), 7.49 (d, J = 8.1 Hz, 1H), 7.28 (d, J = 8.5 Hz, 1H), 7.14 (s, 1H), 7.09 (d, J = 8.5 Hz, 1H), 5.28 (s, 2H), 3.73 (s, 3H), 2.53 (s, 3H), 2.50 (s, 3H), 2.31 (s, 3H), 2.30 (s, 3H) | 420 ($M^+$), 376, 159 (base) |
| Example 7-5 | Example 2-1 | Example 9-79 | (DMSO-$d_6$) δ: 10.31 (br s, 1H), 8.17 (dd, J = 6.2, 8.9 Hz, 1H), 7.61 (d, J = 2.3 Hz, 1H), 7.59 (d, J = 2.7 Hz, 1H), 7.35 (ddd, J = 2.7, 8.1, 8.9 Hz, 1H), 7.28 (dd, J = 1.2, 8.5 Hz, 1H), 5.30 (s, 2H), 3.73 (s, 3H), 2.53 (s, 3H), 2.33 (s, 3H) | 400 ($M^+$ − 44), 159 (base) |
| Example 7-6 | Example 2-1 | Example 9-80 | (DMSO-$d_6$) δ: 10.17 (br s, 1H), 7.69 (dd, J = 6.2, 8.5 Hz, 1H), 7.61 (s, 1H), 7.49 (d, J = 8.1 Hz, 1H), 7.28 (d, J = 8.9 Hz, 1H), 7.21 (dd, J = 2.7, 10.0 Hz, 1H), 7.12 (dt, J = 2.7, 8.5 Hz, 1H), 5.29 (s, 2H), 3.74 (s, 3H), 2.53 (s, 3H), 2.50 (s, 3H), 2.31 (s, 3H) | 380 ($M^+$ − 44), 159 (base) |

TABLE 40

| Carboxylic acid | Hydroxy compound | Example | ¹H-NMR | Mass, m/z |
|---|---|---|---|---|
| Example 7-7 | Example 2-1 | Example 9-81 | (DMSO-d₆) δ: 10.23 (br s, 1H), 7.71 (d, J = 8.5 Hz, 1H), 7.61 (s, 1H), 7.50 (d, J = 8.1 Hz, 1H), 7.44 (d, J = 1.9 Hz, 1H), 7.35 (dd, J = 2.3, 8.5 Hz, 1H), 7.28 (dd, J = 1.9, 8.5 Hz, 1H), 5.29 (s, 2H), 3.74 (s, 3H), 2.53 (s, 3H), 2.50 (s, 3H), 2.32 (s, 3H) | 396 (M⁺ − 44), 159 (base) |
| — | Example 2-2 | Example 9-82 | (DMSO-d₆) δ: 10.08 (br s, 1H), 8.16 (d, J = 8.5 Hz, 1H), 7.64 (s, 1H), 7.50 (d, J = 8.1 Hz, 1H), 7.30 (d, J = 1.9 Hz, 1H), 7.27 (d, J = 1.2 Hz, 1H), 7.12 (dd, J = 1.9, 8.5 Hz, 1H), 5.29 (s, 2H), 4.02 (s, 3H), 3.74 (s, 3H), 2.89 (q, J = 7.7 Hz, 2H), 2.31 (s, 3H), 1.33 (t, J = 7.7 Hz, 3H) | 426 (M⁺ − 44), 173 (base) |
| Example 7-16 | Example 2-2 | Example 9-83 | (DMSO-d₆) δ: 10.09 (br s, 1H), 7.63 (s, 1H), 7.55 (d, J = 7.7 Hz, 1H), 7.50 (d, J = 8.1 Hz, 1H), 7.28 (d, J = 8.1 Hz, 1H), 7.14 (s, 1H), 7.09 (d, J = 8.5 Hz, 1H), 5.28 (s, 2H), 3.73 (s, 3H), 2.88 (q, J = 7.3 Hz, 2H), 2.50 (s, 3H), 2.31 (s, 3H), 2.30 (s, 3H), 1.33 (t, J = 7.3 Hz, 3H) | 390 (M⁺ − 44), 244 (base) |
| Example 7-12 | Example 2-3 | Example 9-84 | (DMSO-d₆) δ: 10.15 (br s, 1H), 7.61 (s, 1H), 7.54-7.51 (m, 2H), 7.39-7.33 (m, 2H), 7.30-7.26 (m, 2H), 5.28 (s, 2H), 4.22 (q, J = 7.2 Hz, 2H), 2.90 (q, J = 7.2 Hz, 2H), 2.54 (s, 3H), 2.31 (s, 3H), 1.29 (t, J = 7.2 Hz, 3H), 1.13 (t, J = 7.2 Hz, 3H) | 434 (M⁺), 390, 173 (base) |
| Example 7-8 | Example 2-3 | Example 9-85 | (DMSO-d₆) δ: 9.99 (br s, 1H), 8.17 (dd, J = 1.5, 7.7 Hz, 1H), 7.61 (s, 1H), 7.52 (d, J = 8.5 Hz, 1H), 7.41-7.37 (m, 1H), 7.27 (d, J = 8.5 Hz, 1H), 7.20 (d, J = 8.1 Hz, 1H), 7.07-7.03 (m, 1H), 5.28 (s, 2H), 4.22 (q, J = 7.3 Hz, 2H), 3.98 (s, 3H), 2.54 (s, 3H), 2.30 (s, 3H), 1.29 (t, J = 7.3 Hz, 3H) | 392 (M⁺ − 44), 85 (base) |

TABLE 41

| Carboxylic acid | Hydroxy compound | Example | ¹H-NMR | Mass, m/z |
|---|---|---|---|---|
| — | Example 2-3 | Example 9-86 | (DMSO-d₆) δ: 10.07 (br s, 1H), 8.16 (d, J = 8.5 Hz, 1H), 7.61 (s, 1H) 7.52 (d, J = 8.5 Hz, 1H), 7.30-7.26 (m, 2H), 7.12 (dd, J = 1.9, 8.5 Hz, 1H), 5.28 (s, 2H), 4.22 (q, J = 7.3 Hz, 2H), 4.02 (s, 3H), 2.54 (s, 3H), 2.31 (s, 3H), 1.29 (t, J = 7.3 Hz, 3H) | 426 (M⁺ − 44), 280 (base) |

TABLE 41-continued

| Carboxylic acid | Hydroxy compound | Example | 1H-NMR | Mass, m/z |
|---|---|---|---|---|
| Example 7-14 | Example 2-3 | Example 9-87 | (DMSO-$d_6$) δ: 9.92 (br s, 1H), 8.04 (d, J = 8.1 Hz, 1H), 7.60 (s, 1H) 7.52 (d, J = 8.1 Hz, 1H), 7.27 (d, J = 7.7 Hz, 1H), 7.02 (s, 1H) 6.87 (d, J = 8.1 Hz, 1H), 5.27 (s, 2H), 4.22 (q, J = 7.3 Hz, 2H), 3.96 (s, 3H), 2.54 (s, 3H), 2.35 (s, 3H), 2.28 (s, 3H), 1.29 (t, J = 7.3 Hz, 3H) | 466 ($M^+$ − 44), 260, 161 (base) |
| Example 7-16 | Example 2-3 | Example 9-88 | (DMSO-$d_6$) δ: 10.09 (br s, 1H), 7.61 (s, 1H), 7.55 (d, J = 7.7 Hz, 1H), 7.52 (d, J = 8.1 Hz, 1H), 7.27 (d, J = 8.5 Hz, 1H), 7.14 (s, 1H), 7.09 (d, J = 8.1 Hz, 1H), 5.28 (s, 2H), 4.22 (q, J = 7.3 Hz, 2H), 2.54 (s, 3H), 2.50 (s, 3H), 2.31 (s, 3H), 2.30 (s, 3H), 1.29 (t, J = 7.3 Hz, 3H) | 390 ($M^+$ − 44), 173 (base) |
| Example 7-7 | Example 2-3 | Example 9-89 | (DMSO-$d_6$) δ: 10.22 (br s, 1H), 7.70 (d, J = 8.5 Hz, 1H), 7.61 (s, 1H), 7.52 (d, J = 8.1 Hz, 1H), 7.44 (d, J = 2.3 Hz, 1H), 7.35 (dd, J = 2.3, 8.5 Hz, 1H), 7.28 (d, J = 8.1 Hz, 1H), 5.29 (s, 2H), 4.22 (q, J = 6.9 Hz, 2H), 2.54 (s, 3H), 2.31 (s, 3H), 1.29 (t, J = 6.9 Hz, 3H) | 410 ($M^+$ − 44), 173 (base) |
| Example 7-12 | Example 3-6 | Example 9-90 | (DMSO-$d_6$) δ: 10.17 (br s, 1H), 7.69 (s, 1H), 7.57-7.52 (m, 2H), 7.39-7.29 (m, 3H), 7.28-7.25 (m, 1H), 5.31 (s, 2H), 4.96 (s, 2H), 4.22-4.20 (m, 2H), 4.18-4.15 (m, 2H), 2.90 (q, J = 7.3 Hz, 2H), 2.31 (s, 3H), 1.18 (t, J = 7.3 Hz, 3H) | 448 ($M^+$), 404, 287 (base) |

TABLE 42

| Carboxylic acid | Hydroxy compound | Example | 1H-NMR | Mass, m/z |
|---|---|---|---|---|
| Example 7-8 | Example 3-6 | Example 9-91 | (DMSO-$d_6$) δ: 10.02 (br s, 1H), 8.18 (dd, J = 1.9, 8.1 Hz, 1H), 7.69 (s, 1H), 7.55 (d, J = 8.1 Hz, 1H), 7.41-7.37 (m, 1H), 7.34 (d, J = 7.7 Hz, 1H), 7.20 (d, J = 8.1 Hz, 1H), 7.08-7.04 (m, 1H), 5.31 (s, 2H), 4.96 (s, 2H), 4.22-4.15 (m, 4H), 3.98 (s, 3H), 2.31 (s, 3H) | 450 ($M^+$), 406, 175 (base) |
| Example 7-13 | Example 3-6 | Example 9-92 | (DMSO-$d_6$) δ: 10.03 (br s, 1H), 8.18 (dd, J = 6.9, 8.5 Hz, 1H), 7.69 (s, 1H), 7.55 (d, J = 8.1 Hz, 1H), 7.33 (d, J = 8.1 Hz, 1H), 7.13 (dd, J = 2.3, 11.2 Hz, 1H), 6.90 (dt, J = 2.7, 8.5 Hz, 1H), 5.30 (s, 2H), 4.96 (s, 2H), 4.21-4.17 (m, 4H), 4.00 (s, 3H), 2.3 (s, 3H) | 264, 204, 85 (base) |

TABLE 42-continued

| Carboxylic acid | Hydroxy compound | Example | ¹H-NMR | Mass, m/z |
|---|---|---|---|---|
| — | Example 3-6 | Example 9-93 | (DMSO-d₆) δ: 10.10 (br s, 1H), 8.16 (d, J = 8.5 Hz, 1H), 7.69 (s, 1H), 7.55 (d, J = 8.1 Hz, 1H), 7.33 (d, J = 8.9 Hz, H), 7.30 (d, J = 1.9 Hz, 1H), 7.12 (dd, J = 2.3, 8.5 Hz, 1H), 5.31 (s, 2H), 4.96 (s, 2H), 4.22-4.16 (m, 4H), 4.02 (s, 3H), 2.31 (s, 3H) | 440 (M⁺ − 44), 85 (base) |
| Example 7-14 | Example 3-6 | Example 9-94 | (DMSO-d₆) δ: 9.95 (br s, 1H), 8.04 (d, J = 8.1 Hz, 1H), 7.69 (s, 1H), 7.55 (d, J = 8.1 Hz, 1H), 7.33 (d, J = 7.3 Hz, 1H), 7.02 (s, 1H), 6.87 (dd, J = 0.8, 8.1 Hz, 1H), 5.30 (s, 2H), 4.96 (s, 2H), 4.21-4.17 (m, 4H), 3.96 (s, 3H), 2.35 (s, 3H), 2.29 (s, 3H) | 464 (M⁺), 260 (base) |
| Example 7-15 | Example 3-6 | Example 9-95 | (DMSO-d₆) δ: 9.88 (br s, 1H), 8.08 (d, J = 8.9 Hz, 1H), 7.68 (s, 1H), 7.55 (d, J = 8.1 Hz, 1H), 7.33 (d, J = 7.7 Hz, 1H), 6.72 (d, J = 2.3 Hz, 1H), 6.66 (dd, J = 2.3, 8.9 Hz, 1H), 5.29 (s, 2H), 4.96 (s, 2H), 4.22-4.16 (m, 4H), 3.97 (s, 3H), 3.83 (s, 3H), 2.2 (s, 3H) | 480 (M⁺), 436, 276 (base) |

TABLE 43

| Carboxylic acid | Hydroxy compound | Example | ¹H-NMR | Mass, m/z |
|---|---|---|---|---|
| Example 7-16 | Example 3-6 | Example 9-96 | (DMSO-d₆) δ: 10.11 (br s, 1H), 7.69 (s, 1H), 7.55 (d, J = 8.1 Hz, 1H), 7.55 (d, J = 7.7 Hz, 1H), 7.33 (d, J = 8.1 Hz, 1H), 7.14 (s, 1H), 7.09 (d, J = 7.7 Hz, 1H), 5.30 (s, 2H), 4.96 (s, 2H), 4.22-4.15 (m, 4H), 2.50 (s, 3H), 2.31 (s, 6H) | 448 (M⁺) 404, 187 (base) |
| Example 7-6 | Example 3-6 | Example 9-97 | (DMSO-d₆) δ: 10.19 (br s, 1H), 7.71-7.68 (m, 2H), 7.55 (d, J = 8.5 Hz, 1H), 7.33 (d, J = 7.7 Hz, 1H), 7.21 (dd, J = 2.3, 10.0 Hz, 1H), 7.12 (dt, J = 2.7, 8.5 Hz, 1H), 5.31 (s, 2H), 4.96 (s, 2H), 4.22-4.15 (m, 4H), 2.52 (s, 3H), 2.31 (s, 3H) | 452 (M⁺) 406, 187 (base) |
| Example 7-7 | Example 3-6 | Example 9-98 | (DMSO-d₆) δ: 10.25 (br s, 1H), 7.71-7.69 (m, 2H), 7.56 (d, J = 8.1 Hz, 1H), 7.44 (d, J = 1.9 Hz, 1H), 7.36 (d, J = 1.9 Hz, 1H), 7.34 (d, J = 1.9 Hz, 1H), 5.32 (s, 2H), 4.97 (s, 2H), 4.18-4.16 (m, 4H), 2.53 (s, 3H), 2.32 (s, 3H) | 424 (M⁺ − 44), 175 (base) |

TABLE 43-continued

| Carboxylic acid | Hydroxy compound | Example | ¹H-NMR | Mass, m/z |
|---|---|---|---|---|
| Example 7-9 | Example 3-2 | Example 9-99 | (DMSO-d₆) δ: 10.15 (br s, 1H), 7.67-7.64 (m, 2H), 7.45 (d, J = 8.1 Hz, 1H), 7.33-7.24 (m, 4H), 5.29 (s, 2H), 4.12 (t, J = 6.9 Hz, 2H), 2.98-2.94 (m, 2H), 2.68-2.60 (m, 2H), 2.52 (m, 3H), 2.32 (s, 3H) | 418 (M⁺) 374, 171 (base) |
| Example 7-12 | Example 3-2 | Example 9-100 | (DMSO-d₆) δ: 10.16 (br s, 1H), 7.64 (s, 1H), 7.53 (d, J = 7.3 Hz, 1H), 7.45 (d, J = 8.1 Hz, 1H), 7.39-7.34 (m, 2H), 7.29-7.24 (m, 2H), 5.29 (s, 2H), 4.13-4.10 (m, 2H), 2.98-2.4 (m, 2H), 2.90 (q, J = 7.3 Hz, 2H), 2.68-2.60 (m, 2H), 2.31 (s, 3H), 1.13 (t, J = 7.3 Hz, 3H) | 388 (M⁺ − 44) 159 (base) |

TABLE 44

| Carboxylic acid | Hydroxy compound | Example | ¹H-NMR | Mass, m/z |
|---|---|---|---|---|
| Example 7-8 | Example 3-2 | Example 9-101 | (DMSO-d₆) δ: 10.01 (br s, 1H), 8.17 (dd, J = 1.9, 8.1 Hz, 1H), 7.64 (s, 1H), 7.46 (d, J = 8.1 Hz, 1H), 7.41- 7.37 (m, 1H), 7.26 (d, J = 8.5 Hz, 1H), 7.20 (d, J = 8.1 Hz, 1H), 7.08-7.04 (m, 1H), 5.28 (s, 2H), 4.14-4.10 (m, 2H), 3.98 (s, 3H), 2.98-2.95 (m, 2H), 2.68-2.60 (m, 2H), 2.31 (s, 3H) | 390 (M⁺ − 44), 159 (base) |
| Example 7-13 | Example 3-2 | Example 9-102 | (DMSO-d₆) δ: 10.01 (br s, 1H), 8.18 (dd, J = 6.9, 8.9 Hz, 1H), 7.64 (s, 1H), 7.45 (d, J = 8.1 Hz, 1H), 7.25 (d, J = 8.5 Hz, 1H), 7.13 (dd, J = 2.7, 11.2 Hz, 1H), 6.90 (dt, J = 2.7, 8.5 Hz, 1H), 5.28 (s, 2H), 4.12 (t, J = 6.9 Hz, 2H), 4.00 (s, 3H), 2.98-2.95 (m, 2H), 2.66-2.62 (m, 2H), 2.30 (s, 3H) | 408 (M⁺ − 44), 159 (base) |

TABLE 44-continued

| Carboxylic acid | Hydroxy compound | Example | ¹H-NMR | Mass, m/z |
|---|---|---|---|---|
| — | Example 3-2 | Example 9-103 | (DMSO-$d_6$) δ: 10.08 (br s, 1H), 8.16 (d, J = 8.5 Hz, 1H), 7.64 (s, 1H), 7.45 (d, J = 8.5 Hz, 1H), 7.30 (d, J = 1.9 Hz, 1H), 7.25 (d, J = 8.1 Hz, 1H), 7.12 (dd, J = 1.9, 8.5 Hz, 1H), 5.29 (s, 2H), 4.12 (t, J = 6.9 Hz, 2H), 4.02 (s, 3H), 2.98-2.95 (m, 2H), 2.66-2.62 (m, 2H), 2.31 (s, 3H) | 424 ($M^+$ − 44), 159 (base) |
| Example 7-14 | Example 3-2 | Example 9-104 | (DMSO-$d_6$) δ: 9.94 (br s, 1H), 8.04 (d, J = 8.1 Hz, 1H), 7.63 (s, 1H), 7.45 (d, J = 8.1 Hz, 1H), 7.26 (d, J = 8.1 Hz, 1H), 7.02 (s, 1H), 6.87 (d, J = 8.1 Hz, 1H), 5.27 (s, 2H), 4.12 (t, J = 7.3 Hz, 2H), 3.96 (s, 3H), 2.96 (t, J = 7.3 Hz, 2H), 2.68-2.60 (m, 2H), 2.35 (s, 3H), 2.28 (s, 3H) | 448 ($M^+$), 404, 159 (base) |

TABLE 45

| Carboxylic acid | Hydroxy compound | Example | ¹H-NMR | Mass, m/z |
|---|---|---|---|---|
| Example 7-15 | Example 3-2 | Example 9-105 | (DMSO-$d_6$) δ: 9.87 (br s, 1H), 8.08 (d, J = 8.9 Hz, 1H), 7.63 (s, 1H), 7.45 (d, J = 8.1 Hz, 1H), 7.25 (d, J = 8.1 Hz, 1H), 7.26 (d, J = 2.3 Hz, 1H), 6.65 (dd, J = 2.3, 8.9 Hz, 1H), 5.27 (s, 2H), 4.11 (t, J = 6.9 Hz, 2H), 3.97 (s, 3H), 3.83 (s, 3H), 2.98-2.94 (m, 2H), 2.67-2.60 (m, 2H), 2.26 (s, 2H) | 276, 188, 159 (base) |
| Example 7-6 | Example 3-2 | Example 9-106 | (DMSO-$d_6$) δ: 10.17 (br s, 1H), 7.71-7.68 (m, 1H), 7.64 (s, 1H), 7.45 (dd, J = 3.1, 8.1 Hz, 1H), 7.26-7.17 (m, 2H), 7.12 (dt, J = 2.7, 8.5 Hz, 1H), 5.29 (s, 2H), 4.13-4.10 (m, 2H), 2.98-2.94 (m, 2H), 2.68-2.60 (m, 2H), 2.52 (s, 3H), 2.31 (s, 3H) | 436 ($M^+$), 392, 171 (base) |
| Example 7-7 | Example 3-2 | Example 9-107 | (DMSO-$d_6$) δ: 10.23 (br s, 1H), 7.70 (d, J = 8.5 Hz, 1H), 7.64 (s, 1H), 7.47-7.44 (m, 1H), 7.35 (dd, J = 2.3, 8.5 Hz, 1H), 7.25 (dd, J = 2.3, 8.5 Hz, 1H), 5.29 (s, 2H), 4.12 (t, J = 7.3 Hz, 2H), 2.96 (t, J = 7.3 Hz, 2H), 2.68-2.60 (m, 2H), 2.53 (s, 3H), 2.32 (s, 3H) | 452 ($M^+$), 408, 159 (base) |

TABLE 45-continued

| Carboxylic acid | Hydroxy compound | Example | ¹H-NMR | Mass, m/z |
|---|---|---|---|---|
| Example 7-16 | Example 3-2 | Example 9-108 | (DMSO-d$_6$) δ: 10.11 (br s, 1H), 7.64 (s, 1H), 7.55 (d, J = 7.7 Hz, 1H), 7.45 (d, J = 8.1 Hz, 1H), 7.25 (d, J = 7.7 Hz, 1H), 7.14 (s, 1H), 7.09 (d, J = 8.1 Hz, 1H), 5.28 (s, 2H), 4.11 (t, J = 6.9 Hz, 2H), 2.96 (t, J = 7.3 Hz, 2H), 2.64 (t, J = 6.9 Hz, 2H), 2.50 (s, 3H), 2.31 (s, 6H) | 388 (M⁺ − 44), 159 (base) |

TABLE 46

| Carboxylic acid | Hydroxy compound | Example | ¹H-NMR | Mass, m/z |
|---|---|---|---|---|
| Example 7-12 | — | Example 9-109 | (DMSO-d$_6$) δ: 10.15 (brs, 1H), 7.61 (s, 1H), 7.53 (d, J = 7.3 Hz, 1H), 7.47 (d, J = 8.5 Hz, 1H), 7.39-7.34 (m, 2H), 7.30-7.26 (m, 2H), 5.29 (s, 2H), 4.12-4.09 (m, 2H), 2.97 (t, J = 6.2 Hz, 2H), 2.90 (q, J = 7.3 Hz, 2H), 2.31 (s, 3H), 2.07-2.04 (m, 2H), 1.95-1.91 (m, 2H), 1.13 (t, J = 7.3 Hz, 3H) | 446 (M⁺), 402, 202 (base) |
| Example 7-8 | — | Example 9-110 | (DMSO-d$_6$) δ: 10.01 (brs, 1H), 8.17 (dd, J = 1.9, 8.1 Hz, 1H), 7.62 (s, 1H), 7.47 (d, J = 8.5 Hz, 1H), 7.41-7.37 (m, 1H), 7.29 (d, J = 7.7 Hz, 1H), 7.20 (d, J = 8.1 Hz, 1H), 7.08-7.04 (m, 1H), 5.29 (s, 2H), 4.11-4.08 (m, 2H), 4.03 (s, 3H), 2.98-2.95 (m, 2H), 2.31 (s, 3H), 2.06-2.02 (m, 2H), 1.97-1.92 (m, 2H) | 448 (M⁺), 404, 185 (base) |
| Example 7-13 | — | Example 9-111 | (DMSO-d$_6$) δ: 10.02 (brs, 1H), 8.18 (dd, J = 6.9, 8.9 Hz, 1H), 7.61 (s, 1H), 7.47 (d, J = 8.1 Hz, 1H), 7.27 (d, J = 7.7 Hz, 1H), 7.13 (dd, J = 2.3, 11.2 Hz, 1H), 6.90 (dt, J = 2.3, 8.5 Hz, 1H), 5.29 (s, 2H), 4.10 (t, J = 6.2 Hz, 2H), 4.00 (s, 3H), 2.98-2.95 (m, 2H), 2.30 (s, 3H), 2.07-2.02 (m, 2H), 1.96-1.90 (m, 2H) | 422 (M⁺ − 44), 173 (base) |

TABLE 46-continued

| Carboxylic acid | Hydroxy compound | Example | ¹H-NMR | Mass, m/z |
|---|---|---|---|---|
| Example 7-14 | — | Example 9-112 | (DMSO-d₆) δ: 9.93 (brs, 1H), 8.04 (d, J = 7.7 Hz, 1H), 7.61 (s, 1H), 7.47 (d, J = 8.1 Hz, 1H), 7.27 (d, J = 8.1 Hz, 1H), 7.02 (s, 1H), 6.87 (dd, J = 0.8, 8.1 Hz, 1H), 5.28 (s, 2H), 4.10 (t, J = 6.2 Hz, 2H), 3.96 (s, 3H), 2.96 (t, J = 6.2 Hz, 2H), 2.35 (s, 3H), 2.28 (s, 3H), 2.08-2.02 (m, 2H), 1.97-1.91 (m, 2H) | 462 (M⁺), 418, 173 (base) |

TABLE 47

| Carboxylic acid | Hydroxy compound | Example | ¹H-NMR | Mass, m/z |
|---|---|---|---|---|
| Example 7-16 | — | Example 9-113 | (DMSO-d₆) δ: 10.10 (brs, 1H), 7.61 (s, 1H), 7.55 (d, J = 7.7 Hz, 1H), 7.46 (d, J = 8.1 Hz, 1H), 7.27 (d, J = 7.7 Hz, 1H), 7.14 (s, 1H), 7.10 (d, J = 8.5 Hz, 1H), 5.29 (s, 2H), 4.10 (t, J = 5.8 Hz, 2H), 2.96 (t, J = 6.1 Hz, 2H), 2.50 (s, 3H), 2.31 (s, 3H), 2.30 (s, 3H), 2.10-1.99 (m, 2H), 1.97-1.92 (m, 2H) | 446 (M⁺), 402, 244 (base) |
| Example 7-6 | — | Example 9-114 | (DMSO-d₆) δ: 10.18 (brs, 1H), 7.69 (dd, J = 6.2, 8.9 Hz, 1H), 7.61 (s, 1H), 7.46 (d, J = 8.5 Hz, 1H), 7.27 (d, J = 7.7 Hz, 1H), 7.21 (dd, J = 2.7, 10.0 Hz, 1H), 7.12 (dt, J = 2.7, 8.5 Hz, 1H), 5.29 (s, 2H), 4.11-4.08 (m, 2H), 2.98-2.95 (m, 2H), 2.52 (s, 3H), 2.31 (s, 3H), 2.08-2.02 (m, 2H), 1.96-1.90 (m, 2H) | 406 (M⁺ − 44), 173 (base) |
| Example 7-7 | — | Example 9-115 | (DMSO-d₆) δ: 10.23 (brs, 1H), 7.70 (d, J = 8.5 Hz, 1H), 7.62 (s, 1H), 7.46 (d, J = 8.5 Hz, 1H), 7.44 (d, J = 2.3 Hz, 1H), 7.35 (dd, J = 2.3, 8.5 Hz, 1H), 7.27 (d, J = 8.1 Hz, 1H), 5.30 (s, 2H), 4.11-4.08 (m, 2H), 3.00-2.95 (m, 2H), 2.53 (s, 3H), 2.32 (s, 3H), 2.08-2.02 (m, 2H), 1.96-1.91 (m, 2H) | 422 (M⁺ − 44), 185 (base) |

TABLE 47-continued

| Carboxylic acid | Hydroxy compound | Example | ¹H-NMR | Mass, m/z |
|---|---|---|---|---|
| Example 7-13 | Example 3-4 | 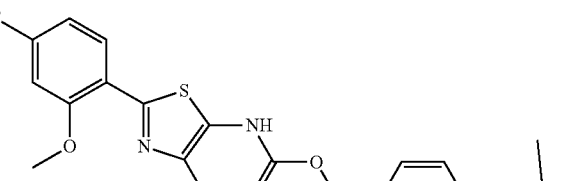Example 9-116 | (DMSO-d₆) δ: 10.01 (brs, 1H), 8.18 (dd, J = 6.9, 8.9 Hz, 1H), 7.61 (s, 1H), 7.53 (d, J = 8.5 Hz, 1H), 7.26 (d, J = 8.1 Hz, 1H), 7.13 (dd, J = 2.3, 11.2 Hz, 1H), 6.90 (dt, J = 2.3, 8.5 Hz, 1H), 5.28 (s, 2H), 4.69-4.65 (m, 1H), 4.00 (s, 3H), 3.02-2.97 (m, 1H), 2.93-2.89 (m, 1H), 2.30 (s, 3H), 2.15-2.11 (m, 1H), 2.04-2.01 (m, 1H), 1.91-1.89 (m, 2H), 1.43 (d, J = 6.2 Hz, 3H) | 436 (M⁺ − 44), 264 (base) |

TABLE 48

| Carboxylic acid | Hydroxy compound | Example | ¹H-NMR | Mass, m/z |
|---|---|---|---|---|
| — | Example 3-4 | 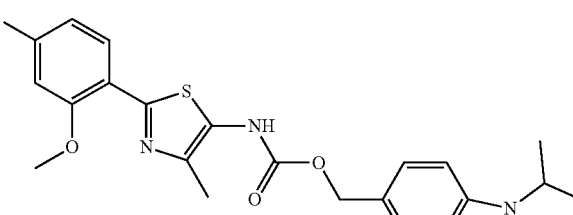Example 9-117 | (DMSO-d₆) δ: 10.08 (brs, 1H), 8.16 (d, J = 8.5 Hz, 1H), 7.61 (s, 1H), 7.53 (d, J = 8.5 Hz, 1H), 7.30 (d, J = 1.9 Hz, 1H), 7.26 (d, J = 8.5 Hz, 1H), 7.12 (dd, J = 2.3, 8.5 Hz, 1H), 5.28 (s, 2H), 4.68-4.65 (m, 1H), 4.02 (s, 3H), 3.02-2.97 (m, 1H), 2.93-2.89 (m, 1H), 2.31 (s, 3H), 2.15-2.11 (m, 1H), 2.04-2.02 (m, 1H), 1.91-1.89 (m, 2H), 1.43 (d, J = 6.6 Hz, 3H) | 280, 216 (base) |
| Example 7-16 | Example 3-4 | Example 9-118 | (DMSO-d₆) δ: 10.10 (brs, 1H), 7.61 (s, 1H), 7.55 (d, J = 8.1 Hz, 1H), 7.53 (d, J = 8.5 Hz, 1H), 7.26 (d, J = 8.1 Hz, 1H), 7.14 (s, 1H), 7.09 (d, J = 8.1 Hz, 1H), 5.28 (s, 2H), 4.69-4.65 (m, 1H), 3.03-2.97 (m, 1H), 2.93-2.85 (m, 1H), 2.50 (s, 3H), 2.31 (s, 6H), 2.18-2.10 (m, 1H), 2.06-1.98 (m, 1H), 1.91-1.89 (m, 2H), 1.43 (d, J = 6.6 Hz, 3H) | 416 (M⁺ − 44), 244 (base) |

TABLE 48-continued

| Carboxylic acid | Hydroxy compound | Example | ¹H-NMR | Mass, m/z |
|---|---|---|---|---|
| Example 7-7 | Example 3-4 | 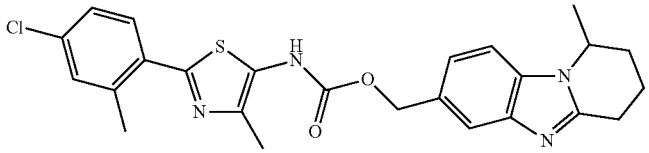<br>Example 9-119 | (DMSO-d$_6$) δ: 10.23 (brs, 1H), 7.70 (d, J = 8.5 Hz, 1H), 7.61 (s, 1H), 7.53 (d, J = 8.1 Hz, 1H), 7.44 (d, J = 2.3 Hz, 1H), 7.35 (dd, J = 2.3, 8.5 Hz, 1H), 7.26 (d, J = 7.3 Hz, 1H), 5.29 (s, 2H), 4.69-4.65 (m, 1H), 3.01-2.96 (m, 1H), 2.93-2.85 (m, 1H), 2.53 (s, 3H), 2.32 (s, 3H), 2.18-2.10 (m, 1H), 2.06-1.98 (m, 1H), 1.91-1.89 (m, 2H), 1.43 (d, J = 6.6 Hz, 3H) | 264 (base), 216 |
| — | Example 3-5 | 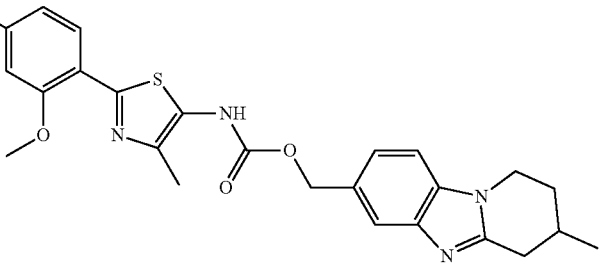<br>Example 9-120 | (DMSO-d$_6$) δ: 10.08 (brs, 1H), 8.16 (d, J = 8.5 Hz, 1H), 7.62 (s, 1H), 7.47 (d, J = 8.1 Hz, 1H), 7.41 (d, J = 1.9 Hz, 1H), 7.27 (d, J = 8.5 Hz, 1H), 7.11 (dd, J = 1.9, 8.5 Hz, 1H), 5.29 (s, 2H), 4.29-4.23 (m, 1H), 4.01 (s, 3H), 3.99-3.93 (m, 1H), 3.10-3.04 (m, 1H), 2.59-2.56 (m, 1H), 2.31 (s, 3H), 2.15-2.10 (m, 2H), 1.79-1.69 (m, 1H), 1.12 (d, J = 6.6 Hz, 3H) | 496 (M⁺), 452, 199 (base) |

TABLE 49

| Carboxylic acid | Hydroxy compound | Example | ¹H-NMR | Mass, m/z |
|---|---|---|---|---|
| Example 7-14 | Example 3-5 | 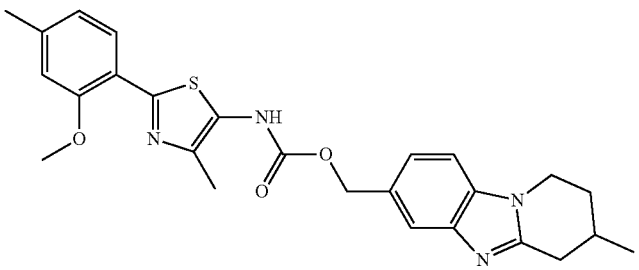<br>Example 9-121 | (DMSO-d$_6$) δ: 9.93 (brs, 1H), 8.04 (d, J = 8.1 Hz, 1H), 7.61 (s, 1H), 7.47 (d, J = 8.1 Hz, 1H), 7.27 (d, J = 8.1 Hz, 1H), 7.02 (s, 1H), 6.87 (d, J = 8.1 Hz, 1H), 5.28 (s, 2H), 4.28-4.24 (m, 1H), 4.00-3.95 (m, 1H), 3.96 (s, 3H), 3.10-3.04 (m, 1H), 2.70-2.56 (m, 1H), 2.35 (s, 3H), 2.28 (s, 3H), 2.15-2.05 (m, 2H), 1.77-1.72 (m, 1H), 1.12 (d, J = 6.6 Hz, 3H) | 476 (M⁺), 432, 216 (base) |

TABLE 49-continued

| Carboxylic acid | Hydroxy compound | Example | ¹H-NMR | Mass, m/z |
|---|---|---|---|---|
| Example 7-16 | Example 3-5 | Example 9-122 | (DMSO-d₆) δ: 10.10 (brs, 1H), 7.61 (s, 1H), 7.55 (d, J = 7.7 Hz, 1H), 7.46 (d, J = 8.1 Hz, 1H), 7.27 (d, J = 8.1 Hz, 1H), 7.14 (s, 1H), 7.09 (d, J = 8.1 Hz, 1H), 5.29 (s, 2H), 4.29-4.23 (m, 1H), 4.00-3.93 (m, 1H), 3.10-3.04 (m, 1H), 2.70-2.55 (m, 1H), 2.35 (s, 3H), 2.49 (s, 3H), 2.31 (s, 3H), 2.30 (s, 3H), 2.20-2.10 (m, 2H), 1.79-1.69 (m, 1H), 1.12 (d, J = 6.6 Hz, 3H) | 416 (M⁺ − 44), 244 (base) |
| — | Example 3-3 | Example 9-123 | (DMSO-d₆) δ: 10.07 (brs, 1H), 8.16 (d, J = 8.5 Hz, 1H), 7.61 (s, 1H), 7.53 (d, J = 8.1 Hz, 1H), 7.30 (d, J = 1.9 Hz, 1H), 7.27 (d, J = 9.2 Hz, 1H), 7.12 (dd, J = 1.9, 8.5 Hz, 1H), 5.28 (s, 2H), 4.27-4.24 (m, 2H), 4.01 (s, 3H), 3.04-3.02 (m, 2H), 2.31 (s, 3H), 1.88-1.85 (m, 2H), 1.75-1.71 (m, 2H), 1.70-1.65 (m, 2H) | 496 (M⁺), 452, 280, 216 (base) |
| Example 7-16 | Example 3-3 | Example 9-124 | (DMSO-d₆) δ: 10.09 (brs, 1H), 7.60 (s, 1H), 7.55 (d, J = 8.1 Hz, 1H), 7.52 (d, J = 8.5 Hz, 1H), 7.27 (d, J = 8.1 Hz, 1H), 7.14 (s, 1H), 7.09 (d, J = 8.1 Hz, 1H), 5.28 (s, 2H), 4.26-4.24 (m, 2H), 3.04-3.02 (m, 2H), 2.50 (s, 3H), 2.31 (s, 3H), 2.30 (s, 3H), 1.91-1.85 (m, 2H), 1.75-1.71 (m, 2H), 1.70-1.66 (m, 2H) | 416 (M⁺ − 44), 244 (base) |

TABLE 50

| Carboxylic acid | Hydroxy compound | Example | ¹H-NMR | Mass, m/z |
|---|---|---|---|---|
| Example 7-12 | Example 4-1 | Example 9-125 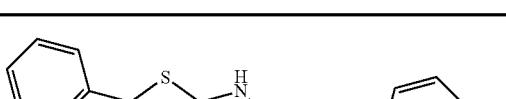 | (DMSO-d₆) δ: 10.17 (brs, 1H), 8.08 (s, 1H), 7.85 (s, 1H), 7.67 (d, J = 8.9 Hz, 1H), 7.53 (d, J = 7.3 Hz, 1H), 7.48 (d, J = 7.7 Hz, 1H), 7.42-7.38 (m, 2H), 7.30-7.26 (m, 1H), 5.31 (s, 2H), 4.06 (s, 3H), 2.90 (q, J = 7.3 Hz, 2H), 2.31 (s, 3H), 1.13 (t, J = 7.3 Hz, 3H) | 406 (M⁺), 362, 145 (base) |

TABLE 50-continued

| Carboxylic acid | Hydroxy compound | Example | ¹H-NMR | Mass, m/z |
|---|---|---|---|---|
| Example 7-8 | Example 4-1 | Example 9-126 | (DMSO-d₆) δ: 10.02 (brs, 1H), 8.18 (dd, J = 1.9, 8.1 Hz, 1H), 8.08 (s, 1H), 7.85 (s, 1H), 7.68 (d, J = 8.5 Hz, 1H), 7.49 (d, J = 8.1 Hz, 1H), 7.41-7.37 (m, 1H), 7.20 (d, J = 7.7 Hz, 1H), 7.06 (dt, J = 1.2, 8.1 Hz, 1H), 5.30 (s, 2H), 4.06 (s, 3H), 3.98 (s, 3H), 2.31 (s, 3H) | 408 (M⁺), 364, 145 (base) |
| Example 7-13 | Example 4-1 | Example 9-127 | (DMSO-d₆) δ: 10.04 (brs, 1H), 8.18 (dd, J = 6.9, 8.9 Hz, 1H), 8.08 (d, J = 0.8 Hz, 1H), 7.84 (s, 1H), 7.67 (d, J = 8.9 Hz, 1H), 7.48 (d, J = 8.9 Hz, 1H), 7.13 (dd, J = 2.7, 11.2 Hz, 1H), 6.90 (dt, J = 2.3, 8.5 Hz, 1H), 5.30 (s, 2H), 4.06 (s, 3H), 4.00 (s, 3H), 2.30 (s, 3H) | 426 (M⁺), 382, 145 (base) |
| — | Example 4-1 | Example 9-128 | (DMSO-d₆) δ: 10.10 (brs, 1H), 8.16 (d, J = 8.5 Hz, 1H), 8.08 (s, 1H), 7.85 (s, 1H), 7.68 (d, J = 8.9 Hz, 1H), 7.48 (d, J = 8.9 Hz, 1H), 7.30 (d, J = 1.9 Hz, 1H), 7.12 (dd, J = 1.9, 8.5 Hz, 1H), 5.30 (s, 2H), 4.06 (s, 3H), 4.02 (s, 3H), 2.31 (s, 3H) | 442 (M⁺), 398, 145 (base) |

TABLE 51

| Carboxylic acid | Hydroxy compound | Example | ¹H-NMR | Mass, m/z |
|---|---|---|---|---|
| Example 7-14 | Example 4-1 | Example 9-129 | (DMSO-d₆) δ: 9.96 (brs, 1H), 8.07 (d, J = 2.7 Hz, 1H), 8.05 (d, J = 8.1 Hz, 1H), 7.84 (s, 1H), 7.67 (d, J = 8.5 Hz, 1H), 7.48 (d, J = 8.5 Hz, 1H), 7.02 (s, 1H), 6.87 (d, J = 8.5 Hz, 1H), 5.29 (s, 2H), 4.06 (s, 3H), 3.96 (s, 3H), 2.35 (s, 3H), 2.29 (s, 3H) | 422 (M⁺), 378, 145 (base) |
| Example 7-16 | Example 4-1 | Example 9-130 | (DMSO-d₆) δ: 10.12 (brs, 1H), 8.08 (s, 1H), 7.84 (s, 1H), 7.67 (d, J = 8.5 Hz, 1H), 7.55 (d, J = 8.1 Hz, 1H), 7.48 (d, J = 8.1 Hz, 1H), 7.37-7.32 (m, 1H), 7.14 (s, 1H), 5.30 (s, 2H), 4.06 (s, 3H), 2.50 (s, 3H), 2.31 (s, 6H) | 406 (M⁺), 362, 145 (base) |
| Example 7-5 | Example 4-1 | Example 9-131 | (DMSO-d₆) δ: 10.34 (brs, 1H), 8.19-8.15 (m, 1H), 8.08 (s, 1H), 7.85 (s, 1H), 7.61 (dd, J = 2.7, 8.9 Hz, 1H), 7.49 (dd, J = 1.2, 8.5 Hz, 1H), 7.35 (ddd, J = 2.7, 8.1, 8.9 Hz, 1H), 5.32 (s, 2H), 4.06 (s, 3H), 2.34 (s, 3H) | 386 (M⁺ − 44), 145 (base) |

TABLE 51-continued

| Carboxylic acid | Hydroxy compound | Example | ¹H-NMR | Mass, m/z |
|---|---|---|---|---|
| Example 7-19 | Example 4-1 | Example 9-132 | (DMSO-$d_6$) δ: 9.79 (brs, 1H), 8.07 (s, 1H), 7.81 (s, 1H), 7.52-7.44 (m, 1H), 7.36-7.34 (m, 1H), 5.25 (s, 2H), 4.05 (s, 3H), 2.45-2.38 (m, 1H), 2.17 (s, 3H), 1.87-1.84 (m, 1H), 1.77-1.68 (m, 4H), 1.59-1.57 (m, 1H), 1.48-1.39 (m, 1H), 1.38-1.26 (m, 1H), 1.14-1.03 (m, 1H), 0.74 (d, J = 6.2 Hz, 3H) | 398 (M⁺), 354, 145 (base) |
| Example 7-12 | Example 4-3 | Example 9-133 | (DMSO-$d_6$) δ: 10.17 (brs, 1H), 8.09 (s, 1H), 7.84 (s, 1H), 7.70 (d, J = 8.9 Hz, 1H), 7.53 (d, J = 7.3 Hz, 1H), 7.47 (d, J = 8.5 Hz, 1H), 7.37-7.34 (m, 2H), 7.30-7.26 (m, 1H), 5.30 (s, 2H), 4.45 (q, J = 7.3 Hz, 2H), 2.90 (q, J = 7.3 Hz, 2H), 2.31 (s, 3H), 1.39 (t, J = 7.3 Hz, 3H), 1.12 (t, J = 7.3 Hz, 3H) | 420 (M⁺), 376, 159 (base) |

TABLE 52

| Carboxylic acid | Hydroxy compound | Example | ¹H-NMR | Mass, m/z |
|---|---|---|---|---|
| Example 7-8 | Example 4-3 | Example 9-134 | (DMSO-$d_6$) δ: 10.01 (brs, 1H), 8.17 (dd, J = 1.9, 8.1 Hz, 1H), 8.09 (s, 1H), 7.85 (s, 1H), 7.70 (d, J = 8.5 Hz, 1H), 7.47 (d, J = 8.5 Hz, 1H), 7.41-7.37 (m, 1H), 7.20 (d, J = 7.7 Hz, 1H), 7.08-7.04 (m, 1H), 5.30 (s, 2H), 4.45 (q, J = 7.3 Hz, 2H), 3.98 (s, 3H), 2.31 (s, 3H), 1.40 (t, J = 7.3 Hz, 3H) | 422 (M⁺), 378, 159 (base) |
| Example 7-13 | Example 4-3 | Example 9-135 | (DMSO-$d_6$) δ: 10.01 (brs, 1H), 8.18 (dd, J = 7.3, 8.9 Hz, 1H), 8.09 (s, 1H), 7.84 (s, 1H), 7.71 (d, J = 8.5 Hz, 1H), 7.47 (d, J = 8.1 Hz, 1H), 7.13 (dd, J = 2.3, 11.2 Hz, 1H), 6.90 (dt, J = 2.3, 8.5 Hz, 1H), 5.29 (s, 2H), 4.45 (q, J = 7.3 Hz, 2H), 4.00 (s, 3H), 2.30 (s, 3H), 1.39 (t, J = 7.3 Hz, 3H) | 440 (M⁺), 396, 159 (base) |
| — | Example 4-3 | Example 9-136 | (DMSO-$d_6$) δ: 10.10 (brs, 1H), 8.16 (d, J = 8.5 Hz, 1H), 8.09 (s, 1H), 7.84 (s, 1H), 7.71 (d, J = 8.9 Hz, 1H), 7.47 (d, J = 8.1 Hz, 1H), 7.30 (d, J = 1.9 Hz, 1H), 7.12 (dd, J = 2.3 Hz, 8.5 Hz, 1H), 5.30 (s, 2H), 4.45 (q, J = 7.3 Hz, 2H), 4.01 (s, 3H), 2.31 (s, 3H), 1.39 (t, J = 7.3 Hz, 3H) | 456 (M⁺), 412, 159 (base) |

TABLE 52-continued

| Carboxylic acid | Hydroxy compound | Example | ¹H-NMR | Mass, m/z |
|---|---|---|---|---|
| Example 7-14 | Example 4-3 | 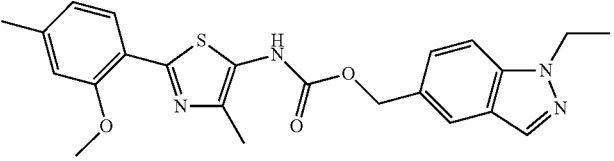<br>Example 9-137 | (DMSO-d₆) δ: 9.95 (brs, 1H), 8.09 (s, 1H), 8.04 (d, J = 8.1 Hz, 1H), 7.84 (s, 1H), 7.71 (d, J = 8.9 Hz, 1H), 7.47 (d, J = 8.1 Hz, 1H), 7.02 (s, 1H), 6.87 (d, J = 8.1 Hz, 1H), 5.29 (s, 2H), 4.46 (q, J = 7.3 Hz, 2H), 3.96 (s, 3H), 2.35 (s, 3H), 2.29 (s, 3H), 1.39 (t, J = 7.3 Hz, 3H) | 436 (M⁺), 396, 159 (base) |
| Example 7-15 | Example 4-3 | 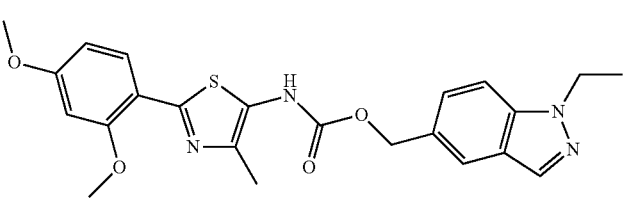<br>Example 9-138 | (DMSO-d₆): 9.88 (brs, 1H), 8.09 (s, 1H), 8.07 (s, 1H), 7.84 (s, 1H), 7.70 (d, J = 8.9 Hz, 1H), 7.46 (d, J = 8.5 Hz, 1H), 6.73 (d, J = 2.3 Hz, 1H), 6.66 (dd, J = 2.3, 8.5 Hz, 1H), 5.28 (s, 2H), 4.45 (q, J = 7.3 Hz, 2H), 3.97 (s, 3H), 3.83 (s, 3H), 2.27 (s, 3H), 1.39 (t, J = 7.3 Hz, 3H) | 452 (M⁺), 408, 159 (base) |

TABLE 53

| Carboxylic acid | Hydroxy compound | Example | ¹H-NMR | Mass, m/z |
|---|---|---|---|---|
| Example 7-16 | Example 4-3 | 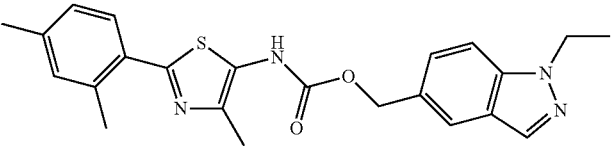<br>Example 9-139 | (DMSO-d₆) δ: 10.12 (brs, 1H), 8.09 (s, 1H), 7.84 (s, 1H), 7.70 (d, J = 8.9 Hz, 1H), 7.55 (d, J = 8.1 Hz, 1H), 7.47 (d, J = 8.5 Hz, 1H), 7.14 (s, 1H), 7.10 (d, J = 8.1 Hz, 1H), 5.30 (s, 2H), 4.45 (q, J = 7.3 Hz, 2H), 4.06 (s, 3H), 2.50 (s, 3H), 2.31 (s, 3H), 2.30 (s, 3H), 1.39 (t, J = 7.3 Hz, 3H) | 420 (M⁺), 376, 159 (base) |
| Example 7-6 | Example 4-3 | 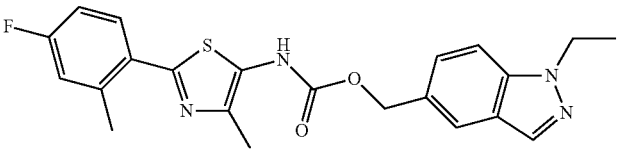<br>Example 9-140 | (DMSO-d₆) δ: 10.19 (brs, 1H), 8.09 (s, 1H), 7.84 (s, 1H), 7.70 (d, J = 8.5 Hz, 1H), 7.69 (d, J = 8.1 Hz, 1H), 7.51-7.45 (m, 1H), 7.21 (dd, J = 2.7, 10.0 Hz, 1H), 7.12 (dt, J = 2.7, 8.5 Hz, 1H), 5.30 (s, 2H), 4.45 (q, J = 7.3 Hz, 2H), 2.52 (s, 3H), 2.31 (s, 3H), 1.39 (t, J = 7.3 Hz, 3H) | 424 (M⁺), 380, 159 (base) |
| Example 7-7 | Example 4-3 | 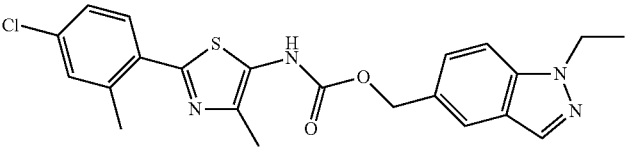<br>Example 9-141 | (DMSO-d₆) δ: 10.24 (brs, 1H), 8.09 (s, 1H), 7.71 (s, 1H), 7.69 (s, 1H), 7.71 (d, J = 8.9 Hz, 1H), 7.51-7.44 (m, 2H), 7.36-7.32 (m, 1H), 5.31 (s, 2H), 4.45 (q, J = 7.3 Hz, 2H), 2.51 (s, 3H), 2.32 (s, 3H), 1.39 (t, J = 7.3 Hz, 3H) | 440 (M⁺), 396, 159 (base) |

TABLE 53-continued

| Carboxylic acid | Hydroxy compound | Example | ¹H-NMR | Mass, m/z |
|---|---|---|---|---|
| Example 7-12 | Example 4-2 | Example 9-142 | (DMSO-d₆) δ: 10.18 (brs, 1H), 8.37 (s, 1H), 7.78 (s, 1H), 7.62 (d, J = 8.9 Hz, 1H), 7.53 (d, J = 7.3 Hz, 1H), 7.40-7.34 (m, 2H), 7.30-7.26 (m, 2H), 5.25 (s, 2H), 4.17 (s, 3H), 2.91 (q, J = 7.3 Hz, 2H), 2.32 (s, 3H), 1.13 (t, J = 7.3 Hz, 3H) | 406 (M⁺), 362, 145 (base) |
| Example 7-13 | Example 4-2 | Example 9-143 | (DMSO-d₆) δ: 10.04 (brs, 1H), 8.37 (s, 1H), 8.18 (dd, J = 7.3, 8.9 Hz, 1H), 7.77 (s, 1H), 7.62 (d, J = 8.9 Hz, 1H), 7.29 (d, J = 8.9 Hz, 1H), 7.13 (dd, J = 2.3, 11.2 Hz, 1H), 6.90 (dt, J = 2.7, 8.5 Hz, 1H), 5.24 (s, 2H), 4.17 (s, 3H), 4.00 (s, 3H), 2.30 (s, 3H) | 426 (M⁺), 382, 145 (base) |

TABLE 54

| Carboxylic acid | Hydroxy compound | Example | ¹H-NMR | Mass, m/z |
|---|---|---|---|---|
| — | Example 4-2 | Example 9-144 | (DMSO-d₆) δ: 10.11 (brs, 1H), 8.37 (s, 1H), 8.17 (d, J = 8.9 Hz, 1H), 7.78 (s, 1H), 7.62 (d, J = 8.9 Hz, 1H), 7.34-7.28 (m, 2H), 7.12 (dd, J = 1.9, 8.5 Hz, 1H), 5.25 (s, 2H), 4.17 (s, 3H), 4.02 (s, 3H), 2.31 (s, 3H) | 442 (M⁺), 398, 145 (base) |
| Example 7-14 | Example 4-2 | Example 9-145 | (DMSO-d₆) δ: 9.96 (brs, 1H), 8.37 (s, 1H), 8.05 (d, J = 7.7 Hz, 1H), 7.77 (s, 1H), 7.62 (d, J = 8.9 Hz, 1H), 7.29 (d, J = 8.5 Hz, 1H), 7.02 (s, 1H), 6.87 (d, J = 8.1 Hz, 1H), 5.23 (s, 2H), 4.17 (s, 3H), 3.96 (s, 3H), 2.35 (s, 3H), 2.29 (s, 3H) | 422 (M⁺), 378, 145 (base) |
| Example 7-15 | Example 4-2 | Example 9-146 | (DMSO-d₆) δ: 9.89 (brs, 1H), 8.36 (s, 1H), 8.08 (d, J = 8.9 Hz, 1H), 7.77 (s, 1H), 7.62 (d, J = 8.9 Hz, 1H), 7.29 (d, J = 8.9 Hz, 1H), 6.73 (d, J = 2.3 Hz, 1H), 6.66 (dd, J = 2.3, 8.9 Hz, 1H), 5.23 (s, 2H), 4.17 (s, 3H), 3.97 (s, 3H), 3.83 (s, 3H), 2.27 (s, 3H) | 438 (M⁺), 394, 145 (base) |
| Example 7-16 | Example 4-2 | Example 9-147 | (DMSO-d₆) δ: 10.13 (brs, 1H), 8.37 (s, 1H), 7.77 (s, 1H), 7.62 (d, J = 8.9 Hz, 1H), 7.55 (d, J = 7.7 Hz, 1H), 7.29 (dd, J = 1.2, 8.9 Hz, 1H), 7.14 (s, 1H), 7.10 (d, J = 8.5 Hz, 1H), 5.24 (s, 2H), 4.17 (s, 3H), 2.50 (s, 3H), 2.31 (s, 6H) | 406 (M⁺), 362, 145 (base) |

TABLE 54-continued

| Carboxylic acid | Hydroxy compound | Example | ¹H-NMR | Mass, m/z |
|---|---|---|---|---|
| Example 7-5 | Example 4-2 | 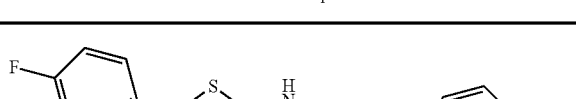<br>Example 9-148 | (DMSO-d₆) δ: 10.34 (brs, 1H), 8.37 (s, 1H), 8.17 (dd, J = 6.2, 8.9 Hz, 1H), 7.78 (s, 1H), 7.63-7.59 (m, 1H), 7.35 (dt, J = 2.7, 8.9 Hz, 1H), 7.30 (d, J = 8.9 Hz, 1H), 5.24 (s, 2H), 4.17 (s, 3H), 2.34 (s, 3H) | 386 (M⁺ − 44), 145 (base) |

TABLE 55

| Carboxylic acid | Hydroxy compound | Example | ¹H-NMR | Mass, m/z |
|---|---|---|---|---|
| Example 7-6 | Example 4-2 | 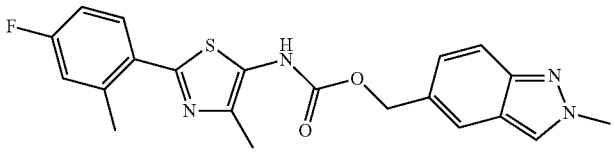<br>Example 9-149 | (DMSO-d₆) δ: 10.20 (brs, 1H), 8.36 (s, 1H), 7.77 (s, 1H), 7.69 (dd, J = 6.3, 8.7 Hz, 1H), 7.62 (d, J = 9.2 Hz, 1H), 7.29 (d, J = 9.2 Hz, 1H), 7.21 (dd, J = 2.4, 10.1 Hz, 1H), 7.12 (dt, J = 2.9, 8.7 Hz, 1H), 5.25 (s, 2H), 4.17 (s, 3H), 2.52 (s, 3H), 2.32 (s, 3H) | 410 (M⁺), 366, 145 (base) |
| Example 7-7 | Example 4-2 | 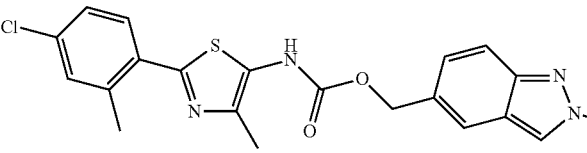<br>Example 9-150 | (DMSO-d₆) δ: 10.25 (brs, 1H), 8.37 (s, 1H), 7.78 (s, 1H), 7.70 (d, J = 8.2 Hz, 1H), 7.63 (d, J = 8.7 Hz, 1H), 7.44 (d, J = 2.4 Hz, 1H), 7.35 (dd, J = 2.4, 8.7 Hz, 1H), 7.30 (dd, J = 2.0, 8.7 Hz, 1H), 5.25 (s, 2H), 4.17 (s, 3H), 2.53 (s, 3H), 2.32 (s, 3H) | 426 (M⁺), 382, 145 (base) |
| Example 7-12 | Example 4-4 | 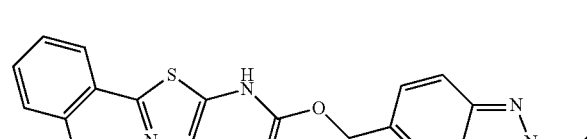<br>Example 9-151 | (DMSO-d₆) δ: 10.17 (brs, 1H), 8.41 (s, 1H), 7.78 (s, 1H), 7.63 (d, J = 8.9 Hz, 1H), 7.53 (d, J = 7.3 Hz, 1H), 7.40-7.34 (m, 2H), 7.30-7.26 (m, 2H), 5.25 (s, 2H), 4.46 (q, J = 7.3 Hz, 2H), 2.91 (q, J = 7.3 Hz, 2H), 2.32 (s, 3H), 1.51 (t, J = 7.3 Hz, 3H), 1.13 (t, J = 7.3 Hz, 3H) | 420 (M⁺), 376, 159 (base) |
| Example 7-8 | Example 4-4 | <br>Example 9-152 | (DMSO-d₆) δ: 10.03 (brs, 1H), 8.41 (s, 1H), 8.18 (dd, J = 1.9, 8.1 Hz, 1H), 7.78 (s, 1H), 7.64 (d, J = 8.9 Hz, 1H), 7.41-7.37 (m, 1H), 7.31-7.29 (m, 1H), 7.20 (d, J = 8.1 Hz, 1H), 7.08-7.04 (m, 1H), 5.25 (s, 2H), 4.46 (q, J = 7.3 Hz, 2H), 3.98 (s, 3H), 2.31 (s, 3H), 1.51 (t, J = 7.3 Hz, 3H) | 422 (M⁺), 378, 159 (base) |

TABLE 55-continued

| Carboxylic acid | Hydroxy compound | Example | $^1$H-NMR | Mass, m/z |
|---|---|---|---|---|
| Example 7-13 | Example 4-4 | Example 9-153 | (DMSO-$d_6$) δ: 10.03 (brs, 1H), 8.41 (s, 1H), 8.18 (dd, J = 6.9, 8.9 Hz, 1H), 7.77 (s, 1H), 7.63 (d, J = 8.9 Hz, 1H), 7.30 (dd, J = 1.5, 8.9 Hz, 1H), 7.13 (dd, J = 2.3, 11.2 Hz, 1H), 6.90 (dt, J = 2.7, 8.5 Hz, 1H), 5.24 (s, 2H), 4.46 (q, J = 7.3 Hz, 2H), 4.00 (s, 3H), 2.30 (s, 3H), 1.51 (t, J = 7.3 Hz, 3H) | 440 (M+), 396, 159 (base) |

TABLE 56

| Carboxylic acid | Hydroxy compound | Example | $^1$H-NMR | Mass, m/z |
|---|---|---|---|---|
| — | Example 4-4 | Example 9-154 | (DMSO-$d_6$) δ: 10.10 (brs, 1H), 8.41 (s, 1H), 8.17 (d, J = 8.5 Hz, 1H), 7.78 (s, 1H), 7.63 (d, J = 8.9 Hz, 1H), 7.30-7.28 (m, 2H), 7.12 (dd, J = 2.3, 8.5 Hz, 1H), 5.25 (s, 2H), 4.46 (q, J = 7.3 Hz, 2H), 4.02 (s, 3H), 2.31 (s, 3H), 1.51 (t, J = 7.3 Hz, 3H) | 456 (M+), 412, 159 (base) |
| Example 7-14 | Example 4-4 | Example 9-155 | (DMSO-$d_6$) δ: 9.96 (brs, 1H), 8.41 (s, 1H), 8.05 (d, J = 8.1 Hz, 1H), 7.77 (s, 1H), 7.63 (d, J = 8.9 Hz, 1H), 7.30 (dd, J = 1.2, 8.9 Hz, 1H), 7.02 (s, 1H), 6.87 (d, J = 7.3 Hz, 1H), 5.24 (s, 2H), 4.46 (q, J = 7.3 Hz, 2H), 3.96 (s, 3H), 2.35 (s, 3H), 2.29 (s, 3H), 1.51 (t, J = 7.3 Hz, 3H) | 436 (M+), 392, 159 (base) |
| Example 7-15 | Example 4-4 | Example 9-156 | (DMSO-$d_6$) δ: 9.89 (brs, 1H), 8.41 (s, 1H), 8.08 (d, J = 8.9 Hz, 1H), 7.77 (s, 1H), 7.62 (d, J = 8.9 Hz, 1H), 7.29 (d, J = 8.5 Hz, 1H), 6.73 (d, J = 2.3 Hz, 1H), 6.66 (dd, J = 2.3, 8.9 Hz, 1H), 5.23 (s, 2H), 4.46 (q, J = 7.3 Hz, 2H), 3.97 (s, 3H), 3.83 (s, 3H), 2.27 (s, 3H), 1.51 (t, J = 7.3 Hz, 3H) | 452 (M+), 408, 159 (base) |
| Example 7-16 | Example 4-4 | Example 9-157 | (DMSO-$d_6$) δ: 10.12 (brs, 1H), 8.41 (s, 1H), 7.77 (s, 1H), 7.63 (d, J = 8.9 Hz, 1H), 7.55 (d, J = 8.1 Hz, 1H), 7.29 (dd, J = 1.2, 8.9 Hz, 1H), 7.14 (s, 1H), 7.10 (d, J = 8.9 Hz, 1H), 5.24 (s, 2H), 4.46 (q, J = 7.3 Hz, 2H), 2.50 (s, 3H), 2.31 (s, 6H), 1.51 (t, J = 7.3 Hz, 3H) | 420 (M+), 376, 159 (base) |

TABLE 56-continued

| Carboxylic acid | Hydroxy compound | Example | ¹H-NMR | Mass, m/z |
|---|---|---|---|---|
| Example 7-6 | Example 4-4 | 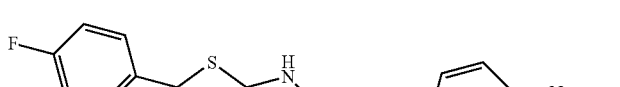<br>Example 9-158 | (DMSO-d$_6$) δ: 10.20 (brs, 1H), 8.41 (s, 1H), 7.77 (s, 1H), 7.69 (dd, J = 6.2, 8.5 Hz, 1H), 7.63 (d, J = 8.9 Hz, 1H), 7.29 (dd, J = 0.8, 8.9 Hz, 1H), 7.21 (dd, J = 2.7, 10.0 Hz, 1H), 7.12 (dt, J = 2.7, 8.5 Hz, 1H), 5.25 (s, 2H), 4.46 (q, J = 7.3 Hz, 2H), 2.52 (s, 3H), 2.32 (s, 3H), 1.51 (t, J = 7.3 Hz, 3H) | 424 (M⁺), 380, 159 (base) |

TABLE 57

| Carboxylic acid | Hydroxy compound | Example | ¹H-NMR | Mass, m/z |
|---|---|---|---|---|
| Example 7-7 | Example 4-4 | Example 9-159 | (DMSO-d$_6$) δ: 10.25 (brs, 1H), 8.41 (s, 1H), 7.77 (s, 1H), 7.70 (d, J = 8.5 Hz, 1H), 7.63 (d, J = 8.9 Hz, 1H), 7.44 (d, J = 1.9 Hz, 1H), 7.35 (dd, J = 1.9, 8.9 Hz, 1H), 7.29 (d, J = 8.5 Hz, 1H), 5.25 (s, 2H), 4.46 (q, J = 7.3 Hz, 2H), 2.52 (s, 3H), 2.32 (s, 3H), 1.51 (t, J = 7.3 Hz, 3H) | 396 (M⁺ − 44), 159 (base) |
| Example 7-28 | Example 5-1 | Example 9-160 | (DMSO-d$_6$) δ: 10.11 (brs, 1H), 8.19 (d, J = 8.5 Hz, 1H), 8.13 (s, 1H), 7.94 (d, J = 8.5 Hz, 1H), 7.63 (d, J = 8.5 Hz, 1H), 7.30 (d, J = 1.9 Hz, 1H), 7.13 (dd, J = 1.9, 8.5 Hz, 1H), 5.37 (s, 2H), 4.75 (q, J = 7.3 Hz, 2H), 4.01 (s, 3H), 2.75-2.70 (m, 2H), 1.52 (t, J = 7.3 Hz, 3H), 1.81 (t, J = 7.3 Hz, 3H) | 471 (M⁺), 427, 104 (base) |
| Example 7-27 | Example 1-1 | <br>Example 9-161 | (DMSO-d$_6$) δ: 9.98 (brs, 1H), 8.21 (s, 1H), 8.19 (d, J = 1.9 Hz, 1H), 7.75 (s, 1H), 7.59 (d, J = 8.5 Hz, 1H), 7.40 (dd, J = 1.9, 7.3 Hz, 1H), 7.36 (dd, J = 1.5, 8.1 Hz, 1H), 7.20 (d, J = 8.1 Hz, 1H), 7.09-7.04 (m, 1H), 5.31 (s, 2H), 3.98 (s, 3H), 3.85 (s, 3H), 2.68 (q, J = 7.3 Hz, 2H), 1.18 (t, J = 7.3 Hz, 3H) | 422 (M⁺), 378, 260, 145 (base) |

TABLE 57-continued

| Carboxylic acid | Hydroxy compound | Example | ¹H-NMR | Mass, m/z |
|---|---|---|---|---|
| Example 7-27 | Example 1-2 | 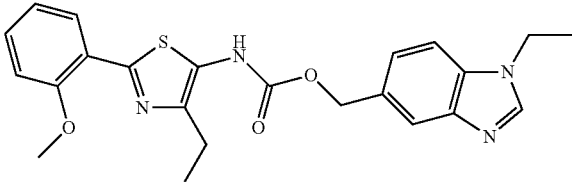 Example 9-162 | (DMSO-d$_6$) δ: 9.97 (brs, 1H), 8.28 (d, J = 2.7 Hz, 1H), 8.19 (dd, J = 1.9, 8.1 Hz, 1H), 7.75 (s, 1H), 7.64 (d, J = 8.1 Hz, 1H), 7.41-7.34 (m, 2H), 7.20 (d, J = 8.5 Hz, 1H), 7.08-7.04 (m, 1H), 5.30 (s, 2H), 4.29 (q, J = 7.3 Hz, 2H), 3.98 (s, 3H), 2.75-2.65 (m, 2H), 1.42 (t, J = 7.3 Hz, 3H), 1.18 (t, J = 7.3 Hz, 3H) | 436 (M⁺), 392, 260 (base) |
| Example 7-30 | Example 1-1 | 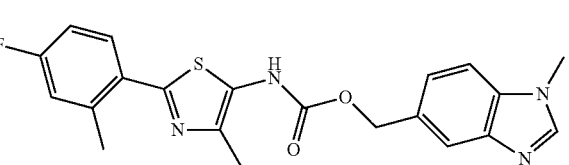 Example 9-163 | (DMSO-d$_6$) δ: 10.15 (brs, 1H), 8.21 (s, 1H), 7.74 (s, 1H), 7.69 (dd, J = 6.2, 8.5 Hz, 1H), 7.59 (d, J = 8.5 Hz, 1H), 7.36 (d, J = 8.5 Hz, 1H), 7.21 (dd, J = 2.7, 10.0 Hz, 1H), 7.12 (dt, J = 2.7, 8.9 Hz, 1H), 5.31 (s, 2H), 3.85 (s, 3H), 2.69 (q, J = 7.3 Hz, 2H), 2.53 (s, 3H), 1.18 (t, J = 7.3 Hz, 3H) | 424 (M⁺), 380, 145 (base) |

TABLE 58

| Carboxylic acid | Hydroxy compound | Example | ¹H-NMR | Mass, m/z |
|---|---|---|---|---|
| Example 7-28 | Example 1-2 | 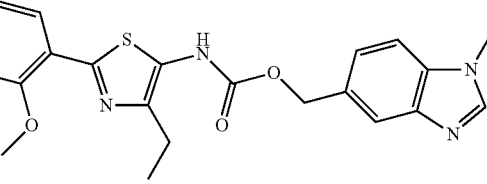 Example 9-164 | (DMSO-d$_6$) δ: 10.06 (brs, 1H), 8.27 (s, 1H), 8.19 (d, J = 8.5 Hz, 1H), 7.75 (s, 1H), 7.63 (d, J = 8.5 Hz, 1H), 7.35 (d, J = 8.1 Hz, 1H), 7.30 (d, J = 2.3 Hz, 1H), 7.13 (dd, J = 1.9, 8.5 Hz, 1H), 5.30 (s, 2H), 4.29 (q, J = 7.3 Hz, 2H), 4.01 (s, 3H), 2.72-2.66 (m, 2H), 1.42 (t, J = 7.3 Hz, 3H), 1.17 (t, J = 7.3 Hz, 3H) | 470 (M⁺), 426, 294 (base) |
| Example 7-31 | Example 1-2 | 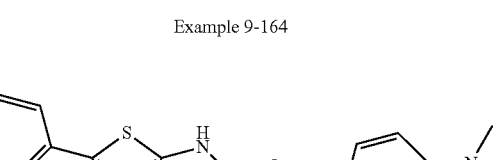 Example 9-165 | (DMSO-d$_6$) δ: 9.90 (brs, 1H), 8.27 (s, 1H), 8.07 (d, J = 8.1 Hz, 1H), 7.74 (s, 1H), 7.63 (d, J = 8.5 Hz, 1H), 7.35 (d, J = 8.1 Hz, 1H), 7.02 (s, 1H), 6.88 (d, J = 7.7 Hz, 1H), 5.29 (s, 2H), 4.29 (q, J = 7.3 Hz, 2H), 3.96 (s, 3H), 2.69-2.64 (m, 2H), 2.36 (s, 3H), 1.42 (t, J = 7.3 Hz, 3H), 1.17 (t, J = 7.3 Hz, 3H) | 450 (M⁺), 406, 147 (base) |
| Example 7-29 | Example 1-2 | 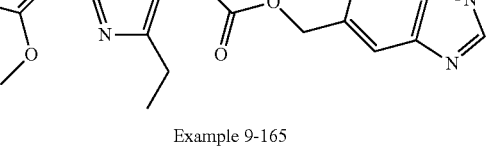 Example 9-166 | (DMSO-d$_6$) δ: 10.07 (brs, 1H), 8.27 (s, 1H), 7.74 (s, 1H), 7.63 (d, J = 8.5 Hz, 1H), 7.55 (d, J = 8.1 Hz, 1H), 7.35 (d, J = 8.1 Hz, 1H), 7.14 (s, 1H), 7.10 (d, J = 8.5 Hz, 1H), 5.30 (s, 2H), 4.29 (q, J = 7.3 Hz, 2H), 2.67 (q, J = 7.3 Hz, 2H), 2.50 (s, 3H), 2.31 (s, 3H), 1.41 (t, J = 7.3 Hz, 3H), 1.18 (t, J = 7.3 Hz, 3H) | 434 (M⁺), 258 (base) |

TABLE 58-continued

| Carboxylic acid | Hydroxy compound | Example | $^1$H-NMR | Mass, m/z |
|---|---|---|---|---|
| Example 7-30 | Example 1-2 | 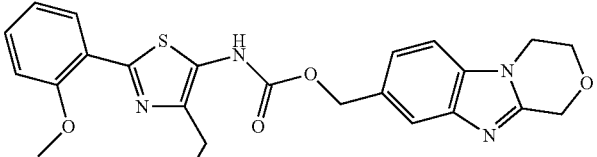<br>Example 9-167 | (DMSO-$d_6$) δ: 10.15 (brs, 1H), 8.27 (s, 1H), 7.74 (s, 1H), 7.69 (dd, J = 5.8, 8.5 Hz, 1H), 7.63 (d, J = 8.1 Hz, 1H), 7.35 (d, J = 8.5 Hz, 1H), 7.21 (dd, J = 2.7, 10.0 Hz, 1H), 7.13 (dt, J = 2.7, 8.5 Hz, 1H), 5.31 (s, 2H), 4.29 (q, J = 7.3 Hz, 2H), 2.75-2.65 (m, 2H), 2.53 (s, 3H), 1.42 (t, J = 7.3 Hz, 3H), 1.18 (t, J = 7.3 Hz, 3H) | 438 (M$^+$), 394, 159 (base) |

TABLE 59

| Carboxylic acid | Hydroxy compound | Example | $^1$H-NMR | Mass, m/z |
|---|---|---|---|---|
| Example 7-27 | Example 3-6 | 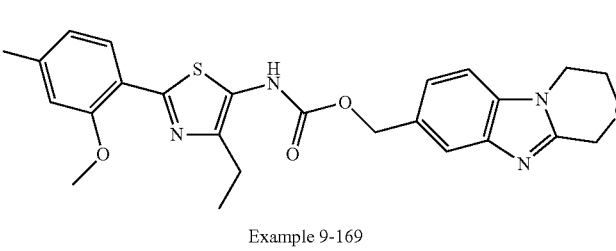<br>Example 9-168 | (DMSO-$d_6$) δ: 9.96 (brs, 1H), 8.20 (dd, J = 1.9, 8.1 Hz, 1H), 7.69 (s, 1H), 7.55 (d, J = 8.1 Hz, 1H), 7.41-7.37 (m, 1H), 7.33 (d, J = 8.1 Hz, 1H), 7.20 (d, J = 7.7 Hz, 1H), 7.08-7.04 (m, 1H), 5.30 (s, 2H), 4.96 (s, 2H), 4.21-4.17 (m, 4H), 3.98 (s, 3H), 2.68 (q, J = 7.3 Hz, 2H), 1.20-1.16 (m, 3H) | 464 (M$^+$), 420, 187 (base) |
| Example 7-28 | Example 3-6 | <br>Example 9-169 | (DMSO-$d_6$) δ: 10.07 (brs, 1H), 8.19 (d, J = 8.5 Hz, 1H), 7.69 (s, 1H), 7.55 (d, J = 8.1 Hz, 1H), 7.33 (d, J = 8.1 Hz, 1H), 7.30 (d, J = 1.9 Hz, 1H), 7.12 (dd, J = 1.9, 8.5 Hz, 1H), 5.30 (s, 2H), 4.96 (s, 2H), 4.22-7.15 (m, 4H), 4.01 (s, 3H), 2.75-2.65 (m, 2H), 1.17 (t, J = 7.3 Hz, 3H) | 498 (M$^+$), 454, 204 (base) |
| Example 7-28 | Example 3-2 | Example 9-170 | (DMSO-$d_6$) δ: 10.06 (brs, 1H), 8.18 (d, J = 8.5 Hz, 1H), 7.64 (s, 1H), 7.45 (d, J = 8.1 Hz, 1H), 7.30 (d, J = 1.9 Hz, 1H), 7.25 (d, J = 8.5 Hz, 1H), 7.13 (dd, J = 1.9, 8.5 Hz, 1H), 5.28 (s, 2H), 4.12 (t, J = 6.9 Hz, 2H), 4.02 (s, 3H), 2.98-2.94 (m, 2H), 2.72-2.60 (m, 4H), 1.71 (t, J = 7.3 Hz, 3H) | 482 (M$^+$), 436, 159 (base) |

TABLE 59-continued

| Carboxylic acid | Hydroxy compound | Example | ¹H-NMR | Mass, m/z |
|---|---|---|---|---|
| Example 7-31 | Example 3-2 | Example 9-171 | (DMSO-d₆) δ: 9.90 (brs, 1H), 8.07 (d, J = 8.1 Hz, 1H), 7.63 (s, 1H), 7.45 (d, J = 8.1 Hz, 1H), 7.25 (d, J = 7.7 Hz, 1H), 7.02 (s, 1H), 6.88 (d, J = 8.1 Hz, 1H), 5.27 (s, 2H), 4.12 (t, J = 7.3 Hz, 2H), 3.96 (s, 3H), 2.96 (t, J = 7.3 Hz, 2H), 2.68-2.60 (m, 4H), 2.35 (s, 3H), 1.20-1.15 (m, 6H) | 462 (M⁺), 418, 171 (base) |

TABLE 60

| Carboxylic acid | Hydroxy compound | Example | ¹H-NMR | Mass, m/z |
|---|---|---|---|---|
| Example 7-28 | — | Example 9-172 | (DMSO-d₆) δ: 10.05 (brs, 1H), 8.18 (d, J = 8.5 Hz, 1H), 7.61 (s, 1H), 7.47 (d, J = 8.1 Hz, 1H), 7.30 (d, J = 1.9 Hz, 1H), 7.27 (d, J = 7.7 Hz, 1H), 7.13 (dd, J = 1.9, 8.5 Hz, 1H), 5.29 (s, 2H), 4.10 (t, J = 6.2 Hz, 2H), 4.01 (s, 3H), 2.98-2.95 (m, 2H), 2.69 (q, J = 7.3 Hz, 2H), 2.08-2.02 (m, 2H), 1.97-1.91 (m, 2H), 1.17 (t, J = 7.3 Hz, 3H) | 496 (M⁺), 452, 202 (base) |
| Example 7-28 | Example 4-3 | Example 9-173 | (DMSO-d₆) δ: 10.06 (brs, 1H), 8.18 (d, J = 8.5 Hz, 1H), 8.09 (s, 1H), 7.84 (s, 1H), 7.71 (d, J = 8.5 Hz, 1H), 7.47 (d, J = 8.5 Hz, 1H), 7.30 (d, J = 2.3 Hz, 1H), 7.13 (dd, J = 1.9, 8.5 Hz, 1H), 5.29 (s, 2H), 4.45 (q, J = 7.3 Hz, 2H), 4.01 (s, 3H), 2.75-2.65 (m, 2H), 1.39 (t, J = 7.3 Hz, 3H), 1.17 (t, J = 7.3 Hz, 3H) | 470 (M⁺), 426, 159 (base) |
| Example 7-31 | Example 4-3 | Example 9-174 | (DMSO-d₆) δ: 9.91 (brs, 1H), 8.09 (s, 1H), 8.07 (d, J = 8.1 Hz, 1H), 7.84 (s, 1H), 7.71 (d, J = 8.5 Hz, 1H), 7.47 (d, J = 8.5 Hz, 1H), 7.02 (s, 1H), 6.88 (d, J = 8.5 Hz, 1H), 5.28 (s, 2H), 4.45 (q, J = 7.3 Hz, 2H), 3.96 (s, 3H), 2.75-2.65 (m, 2H), 2.36 (s, 3H), 1.39 (t, J = 7.3 Hz, 3H), 1.17 (t, J = 7.3 Hz, 3H) | 450 (M⁺), 406, 159 (base) |
| Example 7-29 | Example 4-3 | Example 9-175 | (DMSO-d₆) δ: 10.08 (brs, 1H), 8.08 (s, 1H), 7.84 (s, 1H), 7.70 (d, J = 8.9 Hz, 1H), 7.55 (d, J = 7.7 Hz, 1H), 7.46 (d, J = 8.9 Hz, 1H), 7.14 (s, 1H), 7.10 (d, J = 8.1 Hz, 1H), 5.29 (s, 2H), 4.45 (q, J = 7.3 Hz, 2H), 2.67 (q, J = 7.3 Hz, 2H), 2.50 (s, 3H), 2.31 (s, 3H), 1.39 (t, J = 7.3 Hz, 3H), 1.71 (t, J = 7.3 Hz, 3H) | 434 (M⁺), 390, 159 (base) |

TABLE 61

| Carboxylic acid | Hydroxy compound | Example | ¹H-NMR | Mass, m/z |
|---|---|---|---|---|
| | | Example 9-176 | | |
| Example 7-28 | Example 4-4 | 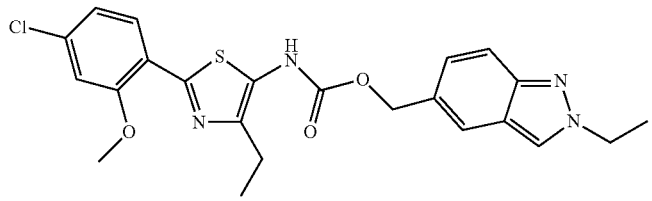 [SMILES: CCc1nc(-c2ccc(Cl)cc2OC)sc1NC(=O)OCc1ccc2nn(CC)cc2c1] | (DMSO-d6) δ :10.07 (brs, 1H), 8.41 (s, 1H), 8.19 (d, J = 8.5Hz, 1H), 7.77 (s, 1H), 7.63 (d, J = 8.9Hz, 1H), 7.30-7.28 (m, 2H), 7.13 (dd, J = 1.9, 8.5Hz, 1H), 5.24 (s, 2H), 4.46 (q, J = 7.3Hz, 2H), 4.01 (s, 3H), 2.75-2.65 (m, 2H), 1.51 (t, J = 7.3Hz, 3H), 1.17 (t, J = 7.3Hz, 3H) | 470 (M⁺), 426, 159 (base) |
| | | Example 9-177 | | |
| Example 7-32 | Example 1-2 | 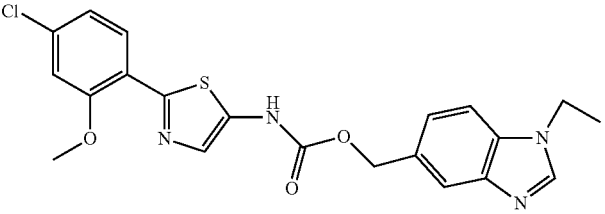 [SMILES: CCn1cnc2cc(COC(=O)Nc3cnc(-c4ccc(Cl)cc4OC)s3)ccc21] | (DMSO-d₆) δ :10.91 (brs, 1H), 8.27 (s, 1H), 8.17 (d, J = 8.5Hz, 1H), 7.74 (s, 1H), 7.64 (d, J = 8.1Hz, 1H), 7.48 (s, 1H), 7.35 (dd, J = 1.5, 8.5Hz, 1H), 7.31 (d, J = 1.9Hz, 1H), 7.13 (dd, J = 1.9, 8.5Hz, 1H), 5.32 (s, 2H), 4.29 (q, J = 7.3Hz, 2H), 4.03 (s, 3H), 1.41 (t, J = 7.3Hz, 3H) | 398 (M⁺ − 44), 147 (base) |
| | | Example 9-178 | | |
| Example 7-33 | Example 1-1 | 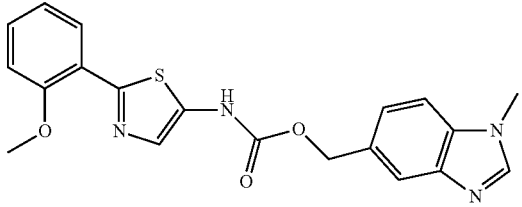 [SMILES: COc1ccccc1-c1ncc(NC(=O)OCc2ccc3c(c2)ncn3C)s1] | (DMSO-d₆) δ :10.84 (brs, 1H), 8.21 (s, 1H), 8.18 (dd, J = 1.5, 8.1Hz, 1H), 7.74 (s, 1H), 7.60 (d, J = 8.5Hz, 1H), 7.47 (s, 1H), 7.41-7.36 (m, 2H), 7.21 (d, J = 8.1Hz, 1H), 7.08-7.04 (m, 1H), 5.32 (s, 2H), 4.00 (s, 3H), 3.85 (s, 3H) | 394 (M⁺), 350, 133 (base) |
| | | Example 9-179 | | |
| Example 7-33 | Example 4-3 | 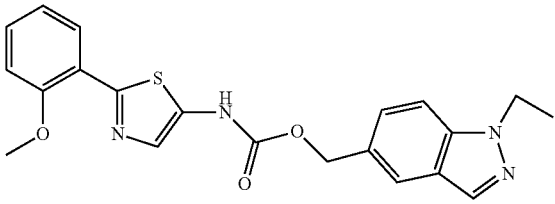 [SMILES: CCn1ncc2cc(COC(=O)Nc3cnc(-c4ccccc4OC)s3)ccc21] | (CDCl₃) δ :8.29 (dd, J = 1.5, 7.7Hz, 1H), 7.98 (s, 1H), 7.77 (s, 1H), 7.49 (s, 1H), 7.43 (s, 1H), 7.42 (s, 1H), 7.37-7.32 (m, 1H), 7.07-7.03 (m, 1H), 7.00 (d, J = 8.1Hz, 1H), 5.35 (s, 2H), 4.44 (q, J = 7.3Hz, 2H), 4.01 (s, 3H), 1.50 (t, J = 7.3Hz, 3H) | 408 (M⁺), 364, 159 (base) |

TABLE 62

| Carboxylic acid | Hydroxy compound | Example | ¹H-NMR | Mass, m/z |
|---|---|---|---|---|
| Example 7-33 | Example 4-4 | Example 9-180 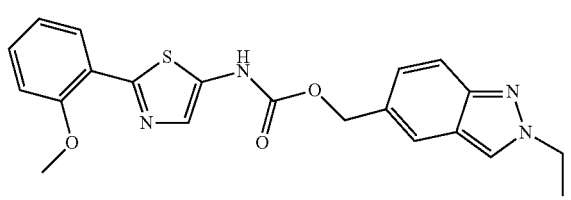 | (CDCl₃) δ: 8.29 (dd, J = 1.5, 7.7 Hz, 1H), 7.93 (s, 1H), 7.71 (d, J = 9.6 Hz, 1H), 7.70 (s, 1H), 7.49 (s, 1H), 7.37-7.32 (m, 1H), 7.29 (dd, J = 1.5, 8.9 Hz, 1H), 7.07-7.03 (m, 1H), 7.00 (d, J = 8.1 Hz, 1H), 5.30 (d, J = 5.0 Hz, 2H), 4.48 (q, J = 7.3 Hz, 2H), 4.01 (s, 3H), 1.63 (t, J = 7.3 Hz, 3H) | 364 (M⁺ − 44), 159 (base) |

TABLE 62-continued

| Carboxylic acid | Hydroxy compound | Example | ¹H-NMR | Mass, m/z |
|---|---|---|---|---|
| Example 7-28 | Example 1-1 | Example 9-181 | (DMSO-d₆) δ: 10.06 (brs, 1H), 8.21 (s, 1H), 8.19 (d, J = 8.5 Hz, 1H), 7.75 (s, 1H), 7.59 (d, J = 8.5 Hz, 1H), 7.36 (d, J = 8.9 Hz, 1H), 7.30 (d, J = 1.9 Hz, 1H), 7.13 (dd, J = 1.9, 8.5 Hz, 1H), 5.31 (s, 2H), 4.01 (s, 3H), 3.85 (s, 3H), 2.69 (q, J = 7.3 Hz, 2H), 1.17 (t, J = 7.3 Hz, 3H) | 4.12 (M⁺ − 44), 133 (base) |
| Example 7-29 | Example 1-1 | Example 9-182 | (CDCl₃) δ: 7.90 (s, 1H), 7.85 (s, 1H), 7.55 (d, J = 8.1 Hz, 1H), 7.40 (brs, 2H), 7.07 (s, 1H), 7.03 (d, J = 8.5 Hz, 1H), 6.75 (brs, 1H), 5.36 (s, 2H), 3.85 (s, 3H), 2.66 (q, J = 7.3 Hz, 2H), 2.53 (s, 3H), 2.33 (s, 3H), 1.28 (t, J = 7.3 Hz, 3H) | 4.20 (M⁺), 376, 145 (base) |
| Example 7-34 | Example 1-1 | Example 9-183 | (DMSO-d₆) δ: 10.07 (brs, 1H), 8.21 (s, 1H), 8.17 (d, J = 8.5 Hz, 1H), 7.75 (s, 1H), 7.59 (d, J = 8.1 Hz, 1H), 7.36 (d, J = 7.7 Hz, 1H), 7.30 (d, J = 2.3 Hz, 1H), 7.12 (dd, J = 1.9, 8.5 Hz, 1H), 5.31 (s, 2H), 4.01 (s, 3H), 3.85 (s, 3H), 2.66 (t, J = 7.3 Hz, 2H), 1.62 (sextet, J = 7.3 Hz, 2H), 0.89 (t, J = 7.3 Hz, 3H) | 426 (M⁺ − 44), 133 (base) |

TABLE 63

| Carboxylic acid | Hydroxy compound | Example | ¹H-NMR | Mass, m/z |
|---|---|---|---|---|
| Example 7-35 | Example 1-1 | Example 9-184 | (CDCl₃) δ: 7.90 (s, 1H), 7.86 (s, 1H), 7.55 (d, J = 7.7 Hz, 1H), 7.40 (brs, 2H), 7.06 (s, 1H), 7.03 (d, J = 8.1 Hz, 1H), 6.73 (brs, 1H), 5.36 (s, 2H), 3.86 (s, 3H), 2.60 (t, J = 7.7 Hz, 2H), 2.52 (s, 3H), 2.33 (s, 3H), 1.76-1.71 (m, 2H), 0.95 (t, J = 7.3 Hz 3H) | 434 (M⁺), 390, 145 (base) |

TABLE 63-continued

| Carboxylic acid | Hydroxy compound | Example | $^1$H-NMR | Mass, m/z |
|---|---|---|---|---|
| Example 7-36 | Example 1-1 | Example 9-185 | (CDCl$_3$) δ: 7.91 (s, 1H), 7.87 (s, 1H), 7.52 (d, J = 7.7 Hz, 1H), 7.41 (brs, 2H), 7.05 (s, 1H), 7.02 (d, J = 8.1 Hz, 1H), 6.93 (brs, 1H), 5.38 (s, 2H), 3.86 (s, 3H), 2.50 (s, 3H), 2.32 (s, 3H), 1.85-1.68 (m, 1H), 1.00-0.97 (m, 2H), 0.95-0.91 (m, 2H) | 432 (M$^+$), 388, 270 (base) |
| Example 7-37 | Example 1-1 | Example 9-186 | (DMSO-d$_6$) δ: 10.83 (brs, 1H), 8.21 (s, 1H), 7.77 (s, 1H), 7.74 (d, J = 8.5 Hz, 1H), 7.60 (d, J = 8.5 Hz, 1H), 7.50 (d, J = 1.9 Hz, 1H), 7.42-7.39 (m, 1H), 5.37 (s, 2H), 3.85 (s, 3H), 2.53 (s, 3H) | 318, 162, 145 (base) |
| Example 7-21 | Example 1-1 | Example 9-187 | (CDCl$_3$) δ: 7.89 (s, 1H), 7.84 (s, 1H), 7.45 (d, J = 1.5 Hz, 1H), 7.39 (brs, 1H), 6.97 (brs, 1H), 6.86 (d, J = 3.5 Hz, 1H), 6.48 (dd, J = 1.5, 3.5 Hz, 1H), 5.36 (s, 2H), 3.85 (s, 3H), 2.32 (s, 3H) | 368 (M$^+$), 145 (base) |

TABLE 64

| Carboxylic acid | Hydroxy compound | Example | $^1$H-NMR | Mass, m/z |
|---|---|---|---|---|
| Example 7-22 | Example 1-1 | Example 9-188 | (CDCl$_3$) δ: 7.88 (s, 2H), 7.84 (s, 1H), 7.44-7.44 (m, 1H), 7.39 (s, 2H), 6.89 (brs, 1H), 6.76 (d, J = 1.2 Hz, 1H), 5.36 (s, 2H), 3.85 (s, 3H), 2.31 (s, 3H) | 368 (M$^+$ − 44), 145 (base) |
| Example 7-21 | Example 4-1 | Example 9-189 | (CDCl$_3$) δ: 7.98 (s, 1H), 7.77 (s, 1H), 7.46-7.36 (m, 3H), 6.86 (d, J = 3.5 Hz, 1H), 6.68 (brs, 1H), 6.48 (dd, J = 1.5, 3.5 Hz, 1H), 5.34 (s, 2H), 4.08 (s, 3H), 2.31 (s, 3H) | 368 (M$^+$), 145 (base) |

TABLE 64-continued

| Carboxylic acid | Hydroxy compound | Example | ¹H-NMR | Mass, m/z |
|---|---|---|---|---|
| Example 7-22 | Example 4-1 | Example 9-190 | (CDCl$_3$) δ: 7.98 (s, 1H), 7.90 (dd, J = 0.8, 1.5 Hz, 1H), 7.78 (s, 1H), 46-7.40 (m, 3H), 6.76 (d, J = 1.2 Hz, 1H), 6.64 (brs, 1H), 5.33 (s, 2H), 4.08 (s, 3H), 2.30 (s, 3H) | 368 (M$^+$), 324, 145 (base) |
| Example 7-23 | Example 1-1 | Example 9-191 | (CDCl$_3$) δ: 7.89 (s, 1H), 7.85 (s, 1H), 7.40-7.38 (m, 3H), 7.32 (dd, J = 0.8, 5.4 Hz, 1H), 7.03 (dd, J = 3.9, 5.0 Hz, 1H), 5.36 (s, 2H), 3.85 (s, 3H), 2.31 (s, 3H) | 340 (M$^+$ − 44), 222 (base) |
| Example 7-24 | Example 1-1 | Example 9-192 | (DMSO-d$_6$) δ: 10.37 (brs, 1H), 8.21 (s, 1H), 7.75 (s, 1H), 7.71 (d, J = 5.4 Hz, 1H), 7.60 (d, J = 8.1 Hz, 1H), 7.38 (d, J = 8.1 Hz, 1H), 7.18 (d, J = 5.4 Hz, 1H), 5.33 (s, 2H), 3.85 (s, 3H), 2.30 (s, 3H) | 374 (M$^+$ − 44), 145 (base) |

TABLE 65

| Carboxylic acid | Hydroxy compound | Example | ¹H-NMR | Mass, m/z |
|---|---|---|---|---|
| Example 7-25 | Example 1-1 | Example 9-193 | (DMSO-d$_6$) δ: 10.36 (brs, 1H), 8.21 (s, 1H), 7.74 (s, 1H), 7.59 (d, J = 8.5 Hz, 1H), 7.38 (d, J = 3.9 Hz, 1H), 7.35 (d, J = 1.9 Hz, 1H), 7.14 (d, J = 3.9 Hz, 1H), 5.32 (s, 2H), 3.85 (s, 3H), 2.26 (s, 3H) | 374 (M$^+$ − 44), 145 (base) |
| Example 7-23 | Example 4-1 | Example 9-194 | (CDCl$_3$) δ: 7.98 (s, 1H), 7.77 (s, 1H), 7.46-7.38 (m, 2H), 7.33-7.32 (m, 1H), 7.03 (dd, J = 3.9, 5.0 Hz, 1H), 6.74 (brs, 1H), 5.33 (s, 2H), 4.08 (s, 3H), 2.30 (s, 3H) | 384 (M$^+$), 340, 145 (base) |
| Example 7-39 | Example 1-1 | Example 9-195 | (DMSO-d$_6$) δ: 10.21 (brs, 1H), 8.43-8.41 (m, 1H), 8.21 (s, 1H), 7.76 (s, 1H), 7.72 (dd, J = 0.8, 7.7 Hz, 1H), 7.69 (d, J = 8.1 Hz, 1H), 7.38 (d, J = 7.7 Hz, 1H), 7.29 (dd, J = 4.6, 7.7 Hz, 1H), 5.33 (s, 2H), 3.85 (s, 3H), 2.69 (s, 3H), 2.34 (s, 3H) | 393 (M$^+$), 349, 231 (base) |

TABLE 65-continued

| Carboxylic acid | Hydroxy compound | Example | ¹H-NMR | Mass, m/z |
|---|---|---|---|---|
| Example 7-39 | Example 1-2 | Example 9-196 | (DMSO-d$_6$) δ: 10.20 (brs, 1H), 8.42 (dd, J = 1.2, 4.6 Hz, 1H), 8.27 (s, 1H), 7.76 (s, 1H), 7.72 (d, J = 6.9 Hz, 1H), 7.64 (d, J = 8.1 Hz, 1H), 7.37 (d, J = 7.3 Hz, 1H), 7.30 (dd, J = 4.6, 7.7 Hz, 1H), 5.33 (s, 2H), 4.29 (q, J = 7.3 Hz, 2H), 2.69 (s, 3H), 2.34 (s, 3H), 1.42 (t, J = 7.3 Hz, 3H) | 407 (M⁺), 363, 231 (base) |
| Example 7-26 | Example 1-1 | Example 9-197 | (DMSO-d$_6$) δ: 9.80 (brs, 1H), 8.21 (s, 1H), 7.76 (s, 1H), 7.71 (s, 1H), 7.58 (d, J = 8.1 Hz, 1H), 7.34 (d, J = 8.1 Hz, 1H), 5.26 (s, 2H), 3.85 (s, 3H), 2.49 (s, 3H), 2.16 (s, 3H) | 316 (M⁺), 272, 145 (base) |

TABLE 66

| Carboxylic acid | Hydroxy compound | Example | ¹H-NMR | Mass, m/z |
|---|---|---|---|---|
| Example 7-26 | — | Example 9-198 | (DMSO-d$_6$) δ: 9.79 (brs, 1H), 7.59 (s, 1H), 7.47 (d, J = 8.1 Hz, 1H), 7.47 (d, J = 8.1 Hz, 1H), 7.25 (d, J = 8.5 Hz, 1H), 5.24 (s, 2H), 4.10 (t, J = 6.2 Hz, 2H), 2.96 (t, J = 6.2 Hz, 2H), 2.49 (s, 3H), 2.15 (s, 3H), 2.08-2.02 (m, 2H), 1.97-1.91 (m, 2H) | 312 (M⁺ − 44), 185 (base) |
| Example 7-26 | Example 3-6 | Example 9-199 | (DMSO-d$_6$) δ: 9.80 (brs, 1H), 7.66 (s, 1H), 7.54 (d, J = 8.1 Hz, 1H), 7.30 (d, J = 8.1 Hz, 1H), 5.26 (s, 2H), 4.96 (s, 2H), 4.22-4.15 (m, 4H), 2.49 (s, 3H), 2.16 (s, 6H) | 358 (M⁺), 314, 187 (base) |
| — | Example 6-1 | Example 9-200 | (DMSO-d$_6$) δ: 10.23 (brs, 1H), 8.17 (d, J = 8.5 Hz, 1H), 8.03 (s, 1H), 8.00 (d, J = 8.5 Hz, 1H), 7.77 (d, J = 8.1 Hz, 1H), 7.30 (d, J = 1.9 Hz, 1H), 7.12 (dd, J = 2.3, 8.5 Hz, 1H), 5.43 (s, 2H), 4.01 (s, 3H), 2.69 (s, 6H), 2.34 (s, 3H) | 468 (M⁺), 171 (base) |

TABLE 66-continued

| Carboxylic acid | Hydroxy compound | Example | ¹H-NMR | Mass, m/z |
|---|---|---|---|---|
| Example 7-16 | Example 6-1 | Example 9-201 | (DMSO-d₆) δ: 10.25 (brs, 1H), 8.03 (s, 1H), 7.99 (d, J = 8.5 Hz, 1H), 7.77 (d, J = 8.5 Hz, 1H), 7.56 (d, J = 8.1 Hz, 1H), 7.14 (s, 1H), 7.10 (d, J = 8.5 Hz, 1H), 5.43 (s, 2H), 2.69 (s, 6H), 2.50 (s, 3H), 2.33 (s, 3H), 2.31 (s, 3H) | 432 (M⁺), 171 (base) |
| Example 8-4 | 4-Methoxy benzyl alcohol | Example 9-202 | (DMSO-d₆) δ: 9.72 (brs, 1H), 7.52-7.48 (m, 1H), 7.38 (d, J = 8.5 Hz, 2H), 7.25-7.18 (m, 3H), 6.96 (d, J = 8.5 Hz, 2H), 6.37 (s, 1H), 5.11 (s, 2H), 3.77 (s, 3H), 3.70 (s, 3H), 2.43 (s, 3H) | 351 (M⁺), 307, 121 (base) |

TABLE 67

| Carboxylic acid | Hydroxy compound | Example | ¹H-NMR | Mass, m/z |
|---|---|---|---|---|
| Example 8-33 | 4-Methoxy benzyl alcohol | Example 9-203 | (DMSO-d₆) δ: 9.64 (brs, 1H), 7.82 (dd, J = 7.3, 8.9 Hz, 1H), 7.37 (d, J = 8.5 Hz, 2H), 6.97 (dd, J = 2.3, 11.2 Hz, 1H), 6.96 (d, J = 8.9 Hz, 2H), 6.79 (dt, J = 2.3, 8.5 Hz, 1H), 6.53 (s, 1H), 5.10 (s, 2H), 3.85 (s, 3H), 3.77 (s, 3H), 3.67 (s, 3H) | 385 (M⁺), 341, 247, 138, 121 (base) |
| Example 8-3 | Example 1-1 | Example 9-204 | (DMSO-d₆) δ: 9.74 (brs, 1H), 8.21 (s, 1H), 7.75-7.73 (m, 3H), 7.59 (d, J = 8.1 Hz, 1H), 7.40-7.35 (m, 3H), 7.30-7.26 (m, 1H), 6.57 (s, 1H), 5.29 (s, 2H), 3.85 (s, 3H), 3.69 (s, 3H) | 361 (M⁺), 317, 199 (base), 145 |
| Example 8-4 | Example 1-1 | Example 9-205 | (DMSO-d₆) δ: 9.72 (brs, 1H), 8.21 (s, 1H), 7.74 (s, 1H), 7.59 (d, J = 8.5 Hz, 1H), 7.51-7.48 (m, 1H), 7.36 (dd, J = 1.2, 8.5 Hz, 1H), 7.25-7.19 (m, 3H), 6.38 (s, 1H), 5.29 (s, 2H), 3.85 (s, 3H), 3.70 (s, 3H), 2.43 (s, 3H) | 375 (M⁺), 311, 213 (base) |

TABLE 67-continued

| Carboxylic acid | Hydroxy compound | Example | ¹H-NMR | Mass, m/z |
|---|---|---|---|---|
| Example 8-20 | Example 1-1 | Example 9-206 | (DMSO-$d_6$) δ: 9.64 (brs, 1H), 8.20 (s, 1H), 7.59 (d, J = 8.5 Hz, 1H), 7.55 (d, J = 8.9 Hz, 2H), 7.36 (dd, J = 1.2, 8.5 Hz, 1H), 6.72 (d, J = 8.9 Hz, 1H), 6.39 (s, 1H), 5.28 (s, 2H), 3.85 (s, 3H), 3.64 (s, 3H), 2.91 (s, 6H) | 404 ($M^+$), 242 (base) |
| Example 8-1 | Example 1-1 | Example 9-207 | (DMSO-$d_6$) δ: 9.85 (brs, 1H), 8.26 (s, 1H), 7.80 (d, J = 8.9 Hz, 1H), 7.74 (s, 1H), 7.66 (d, J = 2.3 Hz, 1H), 7.61 (d, J = 8.1 Hz, 1H), 7.46 (dd, J = 2.3, 8.5 Hz, 1H), 7.38 (d, J = 8.1 Hz, 1H), 6.67 (s, 1H), 5.30 (s, 2H), 3.86 (s, 3H), 3.73 (s, 3H) | 267, 162, 145, 133 (base) |

TABLE 68

| Carboxylic acid | Hydroxy compound | Example | ¹H-NMR | Mass, m/z |
|---|---|---|---|---|
| Example 8-5 | Example 1-1 | Example 9-208 | (DMSO-$d_6$) δ: 9.78 (brs, 1H), 8.20 (s, 1H), 7.82 (d, J = 8.5 Hz, 1H), 7.73 (s, 1H), 7.66 (d, J = 2.3 Hz, 1H), 7.59 (d, J = 8.5 Hz, 1H), 7.46 (dd, J = 2.3, 8.5 Hz, 1H), 7.36 (dd, J = 1.2, 8.5 Hz, 1H), 6.67 (s, 1H), 5.29 (s, 2H), 4.07 (q, J = 7.3 Hz, 2H), 3.85 (s, 3H), 1.31 (t, J = 7.3 Hz, 3H) | 399 ($M^+$ − 44), 281, 253 (base), 161, 145 |
| Example 8-1 | Example 1-2 | Example 9-209 | (DMSO-$d_6$) δ: 9.83 (brs, 1H), 8.27 (s, 1H), 7.80 (d, J = 8.9 Hz, 1H), 7.74 (s, 1H), 7.66 (d, J = 2.3 Hz, 1H), 7.63 (d, J = 8.5 Hz, 1H), 7.46 (dd, J = 2.3, 8.5 Hz, 1H), 7.35 (dd, J = 1.2, 8.5 Hz, 1H), 6.66 (s, 1H), 5.29 (s, 2H), 4.29 (q, J = 7.3 Hz, 2H), 3.73 (s, 3H), 1.42 (t, J = 7.3 Hz, 3H) | 267, 176, 147 (base), 119 |
| Example 8-5 | Example 1-2 | Example 9-210 | (DMSO-$d_6$) δ: 9.77 (brs, 1H), 8.27 (s, 1H), 7.82 (d, J = 8.5 Hz, 1H), 7.73 (s, 1H), 7.64 (d, J = 1.9 Hz, 1H), 7.63 (d, J = 8.1 Hz, 1H), 7.46 (dd, J = 1.9, 8.5 Hz, 1H), 7.34 (dd, J = 1.2, 8.5 Hz, 1H), 6.67 (s, 1H), 5.29 (s, 2H), 4.29 (q, J = 7.3 Hz, 2H), 4.03 (q, J = 7.3 Hz, 2H), 1.42 (t, J = 7.3 Hz, 3H), 1.31 (t, J = 7.3 Hz, 3H) | 413 ($M^+$ − 44), 281, 253 (base), 176, 147 |

TABLE 68-continued

| Carboxylic acid | Hydroxy compound | Example | ¹H-NMR | Mass, m/z |
|---|---|---|---|---|
| Example 8-6 | Example 1-1 | Example 9-211 | (DMSO-$d_6$) δ: 8.20 (s, 1H), 7.97 (d, J = 1.9 Hz, 1H), 7.75 (dd, J = 2.4, 8.7 Hz, 1H), 7.74 (s, 1H), 7.63 (d, J = 8.2 Hz, 1H), 7.59 (d, J = 8.7 Hz, 1H), 7.36 (d, J = 8.2 Hz, 1H), 6.70 (s, 1H), 5.29 (s, 2H), 4.04 (q, J = 7.2 Hz, 2H), 3.85 (s, 3H), 1.30 (t, J = 7.2 Hz, 3H) | 281, 253, 161, 145, 133 (base) |
| Example 8-19 | Example 1-2 | Example 9-212 | (DMSO-$d_6$) δ: 9.79 (brs, 1H), 8.27 (s, 1H), 7.80 (d, J = 8.1 Hz, 1H), 7.73 (s, 1H), 7.71-7.65 (m, 2H), 7.63 (d, J = 8.1 Hz, 1H), 7.59-7.55 (m, 1H), 7.34 (dd, J = 1.2, 8.1 Hz, 1H), 6.35 (s, 1H), 5.29 (s, 2H), 4.29 (q, J = 7.3 Hz, 2H), 3.72 (s, 3H), 1.42 (t, J = 7.3 Hz, 3H) | 399 (M$^+$ − 44), 267, 176, 159 (base) |

TABLE 69

| Carboxylic acid | Hydroxy compound | Example | ¹H-NMR | Mass, m/z |
|---|---|---|---|---|
| Example 8-7 | Example 1-1 | Example 9-213 | (DMSO-$d_6$) δ: 9.66 (brs, 1H), 8.21 (s, 1H), 7.83 (dd, J = 1.9, 7.7 Hz, 1H), 7.73 (s, 1H), 7.59 (d, J = 8.1 Hz, 1H), 7.36 (d, J = 8.1 Hz, 1H), 7.29-7.25 (m, 1H), 7.07 (d, J = 8.1 Hz, 1H), 6.98-6.94 (m, 1H), 6.59 (s, 1H), 5.29 (s, 2H), 3.85 (s, 3H), 3.82 (s, 3H), 3.68 (s, 3H) | 391 (M$^+$), 347, 229 (base), 162 |
| Example 8-32 | Example 1-1 | Example 9-214 | (DMSO-$d_6$) δ: 9.58 (brs, 1H), 8.20 (s, 1H), 7.84 (dd, J = 1.5, 7.7 Hz, 1H), 7.73 (s, 1H), 7.59 (d, J = 8.5 Hz, 1H), 7.35 (dd, J = 0.8, 8.9 Hz, 1H), 7.30-7.25 (m, 1H), 7.07 (d, J = 7.7 Hz, 1H), 6.96 (dt, J = 0.8, 7.3 Hz, 1H), 6.58 (s, 1H), 5.28 (s, 2H), 4.03 (q, J = 7.3 Hz, 2H), 3.85 (s, 3H), 3.83 (s, 3H), 1.30 (t, J = 7.3 Hz, 3H) | 405 (M$^+$), 361, 133 (base) |
| Example 8-7 | Example 1-2 | Example 9-215 | (DMSO-$d_6$) δ: 9.65 (brs, 1H), 8.27 (s, 1H), 7.83 (dd, J = 1.5, 7.7 Hz, 1H), 7.74 (s, 1H), 7.63 (d, J = 8.5 Hz, 1H), 7.34 (d, J = 8.1 Hz, 1H), 7.29-7.25 (m, 1H), 7.07 (d, J = 8.1 Hz, 1H), 6.98-6.94 (m, 1H), 6.59 (s, 1H), 5.28 (s, 2H), 4.29 (q, J = 7.3 Hz, 2H), 3.82 (s, 3H), 3.69 (s, 3H), 1.42 (t, J = 7.3 Hz, 3H) | 405 (M$^+$), 361, 229, 176, 147 (base) |

TABLE 69-continued

| Carboxylic acid | Hydroxy compound | Example | ¹H-NMR | Mass, m/z |
|---|---|---|---|---|
| Example 8-32 | Example 1-2 | Example 9-216 | (DMSO-d$_6$) δ: 9.59 (brs, 1H), 8.27 (s, 1H), 7.85 (dd, J = 1.9, 7.7 Hz, 1H), 7.73 (s, 1H), 7.63 (d, J = 8.5 Hz, 1H), 7.34 (d, J = 7.7 Hz, 1H), 7.27 (ddd, J = 1.5, 7.3, 8.5 Hz, 1H), 7.07 (d, J = 7.7 Hz, 1H), 6.96 (dt, J = 1.2, 7.3 Hz, 1H), 6.58 (s, 1H), 5.28 (s, 2H), 4.29 (q, J = 7.3 Hz, 2H), 4.03 (q, J = 7.3 Hz, 2H), 3.83 (s, 3H), 1.42 (t, J = 7.3 Hz, 3H), 1.30 (t, J = 7.3 Hz, 3H) | 419 (M$^+$), 375, 243, 147 (base) |

TABLE 70

| Carboxylic acid | Hydroxy compound | Example | ¹H-NMR | Mass, m/z |
|---|---|---|---|---|
| Example 8-33 | Example 1-1 | Example 9-217 | (DMSO-d$_6$) δ: 9.66 (brs, 1H), 8.20 (s, 1H), 7.82 (dd, J = 6.9, 8.5 Hz, 1H), 7.73 (s, 1H), 7.59 (d, J = 8.1 Hz, 1H), 7.36 (d, J = 8.1 Hz, 1H), 6.97 (dd, J = 2.3, 11.6 Hz, 1H), 6.79 (dt, J = 2.3, 8.5 Hz, 1H), 6.54 (s, 1H), 5.28 (s, 2H), 3.85 (s, 6 H), 3.68 (s, 3H) | 409 (M$^+$), 365, 247, 162, 145 (base) |
| Example 8-8 | Example 1-1 | Example 9-218 | (DMSO-d$_6$) δ: 9.60 (brs, 1H), 8.20 (s, 1H), 7.84 (dd, J = 7.3, 8.5 Hz, 1H), 7.73 (s, 1H), 7.59 (d, J = 8.5 Hz, 1H), 7.35 (d, J = 8.1 Hz, 1H), 6.97 (dd, J = 2.3, 11.6 Hz, 1H), 6.79 (dt, J = 2.3, 8.5 Hz, 1H), 6.54 (s, 1H), 5.28 (s, 2H), 4.02 (q, J = 7.3 Hz, 2H), 3.85 (s, 6H), 1.29 (t, J = 7.3 Hz, 3H) | 423 (M$^+$), 379, 261, 162, 133 (base) |
| Example 8-33 | Example 1-2 | Example 9-219 | (DMSO-d$_6$) δ: 9.66 (brs, 1H), 8.27 (s, 1H), 7.82 (dd, J = 7.3, 8.5 Hz, 1H), 7.73 (s, 1H), 7.63 (d, J = 8.1 Hz, 1H), 7.34 (dd, J = 1.2, 8.1 Hz, 1H), 6.97 (dd, J = 2.3, 11.6 Hz, 1H), 6.79 (dt, J = 2.3, 8.5 Hz, 1H), 6.54 (s, 1H), 5.28 (s, 2H), 4.29 (q, J = 7.3 Hz, 2H), 3.84 (s, 3H), 3.68 (s, 3H), 1.42 (t, J = 7.3 Hz, 3H) | 423 (M$^+$), 247, 176, 147 (base) |
| Example 8-8 | Example 1-2 | Example 9-220 | (DMSO-d$_6$) δ: 9.59 (brs, 1H), 8.27 (s, 1H), 7.84 (dd, J = 6.9, 8.5 Hz, 1H), 7.73 (s, 1H), 7.63 (d, J = 8.5 Hz, 1H), 7.34 (d, J = 7.7 Hz, 1H), 6.97 (dd, J = 2.7, 11.6 Hz, 1H), 6.79 (dt, J = 2.7, 8.5 Hz, 1H), 6.54 (s, 1H), 5.27 (s, 2H), 4.29 (q, J = 7.3 Hz, 2H), 4.02 (q, J = 7.3 Hz, 2H), 3.84 (s, 3H), 1.42 (t, J = 7.3 Hz, 3H), 1.29 (t, J = 7.3 Hz, 3H) | 437 (M$^+$), 393, 261 (base), 176 |

TABLE 71

| Carboxylic acid | Hydroxy compound | Example | ¹H-NMR | Mass, m/z |
|---|---|---|---|---|
| Example 8-9 | Example 1-1 | Example 9-221 | (DMSO-d$_6$) δ: 8.21 (s, 1H), 7.84 (d, J = 8.1 Hz, 1H), 7.73 (s, 1H), 7.59 (d, J = 8.1 Hz, 1H), 7.36 (dd, J = 1.2, 8.5 Hz, 1H), 7.15 (d, J = 1.9 Hz, 1H), 7.02 (dd, J = 1.9, 8.5 Hz, 1H), 6.59 (s, 1H), 5.28 (s, 2H), 3.86 (s, 3H), 3.85 (s, 3H), 3.69 (s, 3H) | 425 (M⁺), 381, 263, 162, 133 (base) |
| Example 8-10 | Example 1-1 | Example 9-222 | (DMSO-d$_6$) δ: 9.67 (brs, 1H), 8.21 (s, 1H), 7.86 (d, J = 8.5 Hz, 1H), 7.73 (s, 1H), 7.59 (d, J = 8.1 Hz, 1H), 7.36 (d, J = 8.5 Hz, 1H), 7.15 (d, J = 1.9 Hz, 1H), 7.03 (dd, J = 1.9, 8.5 Hz, 1H), 6.59 (s, 1H), 5.28 (s, 2H), 4.03 (q, J = 7.3 Hz, 2H), 3.87 (s, 3H), 3.85 (s, 3H), 1.29 (t, J = 7.3 Hz, 3H) | 439 (M⁺), 395, 277, 162, 145 (base) |
| Example 8-9 | Example 1-2 | Example 9-223 | (DMSO-d$_6$) δ: 9.67 (brs, 1H), 8.27 (s, 1H), 7.84 (d, J = 8.5 Hz, 1H), 7.73 (s, 1H), 7.63 (d, J = 8.5 Hz, 1H), 7.34 (d, J = 6.9 Hz, 1H), 7.14 (d, J = 1.9 Hz, 1H), 7.02 (dd, J = 1.9, 8.1 Hz, 1H), 6.58 (s, 1H), 5.28 (s, 2H), 4.29 (q, J = 7.3 Hz, 2H), 3.86 (s, 3H), 3.69 (s, 3H), 1.42 (t, J = 7.3 Hz, 3H) | 263, 176, 147, 119, 98 (base) |
| Example 8-10 | Example 1-2 | Example 9-224 | (DMSO-d$_6$) δ: 9.61 (brs, 1H), 8.27 (s, 1H), 7.86 (d, J = 8.1 Hz, 1H), 7.73 (s, 1H), 7.63 (d, J = 8.1 Hz, 1H), 7.34 (d, J = 7.3 Hz, 1H), 7.15 (d, J = 1.9 Hz, 1H), 7.03 (dd, J = 1.9, 8.5 Hz, 1H), 6.58 (s, 1H), 5.28 (s, 2H), 4.29 (q, J = 7.3 Hz, 2H), 4.03 (q, J = 7.3 Hz, 2H), 3.86 (s, 3H), 1.42 (t, J = 7.3 Hz, 3H), 1.29 (t, J = 7.3 Hz, 3H) | 453 (M⁺), 277, 219, 176, 147 (base) |

TABLE 72

| Carboxylic acid | Hydroxy compound | Example | ¹H-NMR | Mass, m/z |
|---|---|---|---|---|
| Example 8-11 | Example 1-1 | Example 9-225 | (DMSO-d$_6$) δ: 10.05 (brs, 1H), 8.19 (s, 1H), 7.68 (d, J = 0.8 Hz, 1H), 7.56 (d, J = 8.1 Hz, 1H), 7.31 (dd, J = 1.5, 8.1 Hz, 1H), 7.26 (d, J = 8.1 Hz, 1H), 7.24 (d, J = 1.9 Hz, 1H), 7.11 (dd, J = 1.9, 8.1 Hz, 1H), 6.21 (s, 1H), 5.23 (s, 2H), 4.04-3.97 (m, 1H), 3.84 (s, 3H), 3.81 (s, 3H) 1.26 (d, J = 6.5 Hz, 6H) | 453 (M⁺), 409, 276, 145 (base) |
| Example 8-34 | Example 1-1 | Example 9-226 | (DMSO-d$_6$) δ: 9.61 (brs, 1H), 8.20 (s, 1H), 7.73 (s, 1H), 7.71 (d, J = 7.7 Hz, 1H), 7.59 (d, J = 8.5 Hz, 1H), 7.36 (d, J = 8.1 Hz, 1H), 6.88 (s, 1H), 6.77 (d, J = 7.3 Hz, 1H), 6.54 (s, 1H), 5.28 (s, 2H), 3.85 (s, 3H), 3.81 (s, 3H), 3.67 (s, 3H), 2.32 (s, 3H) | 405 (M⁺), 361, 243 (base) |
| Example 8-12 | Example 1-1 | Example 9-227 | (DMSO-d$_6$) δ: 9.57 (brs, 1H), 8.20 (s, 1H), 7.73 (s, 1H), 7.72 (d, J = 7.7 Hz, 1H), 7.59 (d, J = 8.1 Hz, 1H), 7.35 (d, J = 8.1 Hz, 1H), 6.89 (s, 1H), 6.78 (d, J = 8.1 Hz, 1H), 6.53 (s, 1H), 5.28 (s, 2H), 4.01 (q, J = 7.3 Hz, 2H), 3.85 (s, 3H), 3.81 (s, 3H), 2.32 (s, 3H), 1.29 (t, J = 7.3 Hz, 3H) | 257, 228, 199, 162, 133 (base) |
| Example 8-34 | Example 1-2 | Example 9-228 | (DMSO-d$_6$) δ: 9.62 (brs, 1H), 8.27 (s, 1H), 7.73 (s, 1H), 7.70 (d, J = 8.1 Hz, 1H), 7.63 (d, J = 8.5 Hz, 1H), 7.34 (dd, J = 0.8, 8.1 Hz, 1H), 6.89 (s, 1H), 6.54 (s, 1H), 5.27 (s, 2H), 4.29 (q, J = 7.3 Hz, 2H), 3.81 (s, 3H), 3.67 (s, 3H), 2.32 (s, 3H), 1.41 (t, J = 7.3 Hz) | 419 (M⁺), 375, 243 (base) |

TABLE 73

| Carboxylic acid | Hydroxy compound | Example | ¹H-NMR | Mass, m/z |
|---|---|---|---|---|
| Example 8-12 | Example 1-2 | Example 9-229 | (DMSO-d₆) δ: 9.56 (brs, 1H), 8.27 (s, 1H), 7.73 (s, 1H), 7.72 (d, J = 7.7 Hz, 1H), 7.63 (d, J = 8.1 Hz, 1H), 7.34 (d, J = 8.5 Hz, 1H), 6.89 (s, 1H), 6.78 (d, J = 7.7 Hz, 1H), 6.53 (s, 1H), 5.27 (s, 2H), 4.29 (q, J = 7.3 Hz, 2H), 4.03 (q, J = 7.3 Hz, 2H), 3.81 (s, 3H), 2.32 (s, 3H), 1.42 (t, J = 7.3 Hz, 3H), 1.29 (t, J = 7.3 Hz, 3H) | 433 (M⁺), 389, 257 (base), 176 |
| Example 8-13 | Example 1-1 | Example 9-230 | (DMSO-d₆) δ: 9.61 (brs, 1H), 8.20 (s, 1H), 7.73 (d, J = 8.5 Hz, 1H), 7.73 (s, 1H), 7.59 (d, J = 8.5 Hz, 1H), 7.36 (d, J = 8.5 Hz, 1H), 6.61 (d, J = 2.3 Hz, 1H), 6.56 (dd, J = 2.3, 8.5 Hz, 1H), 6.49 (s, 1H), 5.28 (s, 2H), 3.85 (s, 3H), 3.82 (s, 3H), 3.79 (s, 3H), 3.66 (s, 3H) | 421 (M⁺), 377, 259 (base), 162 |
| Example 8-14 | Example 1-1 | Example 9-231 | (DMSO-d₆) δ: 8.21 (s, 1H), 7.73 (s, 1H), 7.59 (d, J = 8.1 Hz, 1H), 7.36 (dd, J = 0.8, 8.1 Hz, 1H), 7.30 (d, J = 1.5 Hz, 1H), 7.25 (dd, J = 1.5, 8.1 Hz, 1H), 6.95 (d, J = 8.5 Hz, 1H), 6.51 (s, 1H), 5.29 (s, 2H), 3.85 (s, 3H), 3.80 (s, 3H), 3.77 (s, 3H), 3.67 (s, 3H) | 421 (M⁺), 259 (base) |
| Example 8-15 | Example 1-1 | Example 9-232 | (DMSO-d₆) δ: 9.57 (brs, 1H), 8.20 (s, 1H), 7.72 (s, 1H), 7.59 (d, J = 8.1 Hz, 1H), 7.35 (dd, J = 1.2, 8.5 Hz, 1H), 7.28 (t, J = 8.1 Hz, 1H), 6.67 (d, J = 8.5 Hz, 1H), 5.98 (s, 1H), 5.28 (s, 2H), 3.85 (s, 3H), 3.65 (s, 6H), 3.64 (s, 3H) | 421 (M⁺), 259, 133 (base) |
| Example 8-16 | Example 1-1 | Example 9-233 | (DMSO-d₆) δ: 9.71 (brs, 1H), 8.20 (s, 1H), 7.73 (s, 1H), 7.59 (d, J = 8.1 Hz, 1H), 7.39 (d, J = 7.7 Hz, 1H), 7.36 (dd, J = 0.8, 8.5 Hz, 1H), 7.04 (s, 1H), 7.01 (d, J = 7.7 Hz, 1H), 6.33 (s, 1H), 5.29 (s, 2H), 3.85 (s, 3H), 3.69 (s, 3H), 2.39 (s, 3H), 2.28 (s, 3H) | 389 (M⁺), 345, 227 (base) |

TABLE 74

| Carboxylic acid | Hydroxy compound | Example | ¹H-NMR | Mass, m/z |
|---|---|---|---|---|
| Example 8-17 | Example 1-1 | Example 9-234 | (DMSO-d₆) δ: 9.65 (brs, 1H), 8.20 (s, 1H), 7.73 (s, 1H), 7.59 (d, J = 8.5 Hz, 1H), 7.41 (d, J = 7.7 Hz, 1H), 7.36 (d, J = 8.1 Hz, 1H), 7.05 (s, 1H), 7.01 (d, J = 8.1 Hz, 1H), 6.34 (s, 1H), 5.28 (s, 2H), 4.03 (q, J = 7.3 Hz, 2H), 3.85 (s, 3H), 2.40 (s, 3H), 2.28 (s, 3H), 1.30 (t, J = 7.3 Hz, 3H) | 403 (M⁺), 359, 241 (base) |
| Example 8-16 | Example 1-2 | Example 9-235 | (DMSO-d₆) δ: 9.71 (brs, 1H), 8.27 (s, 1H), 7.73 (s, 1H), 7.63 (d, J = 8.5 Hz, 1H), 7.39 (d, J = 7.7 Hz, 1H), 7.34 (dd, J = 1.2, 8.5 Hz, 1H), 7.04 (s, 1H), 7.01 (d, J = 7.7 Hz, 1H), 6.33 (s, 1H), 5.28 (s, 2H), 4.29 (q, J = 7.3 Hz, 2H), 3.69 (s, 3H), 2.39 (s, 3H), 2.28 (s, 3H), 1.42 (t, J = 7.3 Hz, 3H) | 227, 176 147 (base), 119 |
| Example 8-17 | Example 1-2 | Example 9-236 | (DMSO-d₆) δ: 9.65 (brs, 1H), 8.27 (s, 1H), 7.73 (s, 1H), 7.63 (d, J = 8.5 Hz, 1H), 7.41 (d, J = 7.7 Hz, 1H), 7.34 (d, J = 8.9 Hz, 1H), 7.05 (s, 1H), 7.01 (d, J = 8.1 Hz, 1H), 6.34 (s, 1H), 5.28 (s, 2H), 4.29 (q, J = 7.3 Hz, 2H), 4.02 (q, J = 7.3 Hz, 2H), 2.40 (s, 3H), 2.28 (s, 3H), 1.42 (t, J = 7.3 Hz, 3H), 1.30 (t, J = 7.3 Hz, 3H) | 417 (M⁺), 373, 241 (base), 176 |
| Example 8-6 | Example 2-1 | Example 9-237 | (DMSO-d₆) δ: 9.73 (brs, 1H), 7.97 (d, J = 1.9 Hz, 1H), 7.75 (dd, J = 2.3, 8.5 Hz, 1H), 7.63 (d, J = 8.5 Hz, 1H), 7.59 (s, 1H), 7.48 (d, J = 8.1 Hz, 1H), 7.27 (dd, J = 1.2, 8.1 Hz, 1H), 6.70 (s, 1H), 5.26 (s, 2H), 4.04 (q, J = 6.9 Hz, 2H), 3.73 (s, 3H), 2.53 (s, 3H), 1.30 (t, J = 6.9 Hz, 3H) | none |

TABLE 74-continued

| Carboxylic acid | Hydroxy compound | Example | ¹H-NMR | Mass, m/z |
|---|---|---|---|---|
| Example 8-4 | Example 2-1 | Example 9-238 | (DMSO-d$_6$) δ: 9.72 (brs, 1H), 7.60 (s, 1H), 7.51-7.49 (m, 1H), 7.49 (d, J = 8.5 Hz, 1H), 7.27 (dd, J = 1.2, 8.5 Hz, 1H), 7.25-7.18 (m, 3H), 6.37 (s, 1H), 5.26 (s, 3H), 3.74 (s, 3H), 3.70 (s, 3H), 2.53 (s, 3H), 2.43 (s, 3H) | 389 (M$^+$), 345, 213 (base) |

TABLE 75

| Carboxylic acid | Hydroxy compound | Example | ¹H-NMR | Mass, m/z |
|---|---|---|---|---|
| Example 8-9 | Example 2-1 | Example 9-239 | (DMSO-d$_6$) δ: 9.68 (brs, 1H), 7.84 (d, J = 8.5 Hz, 1H), 7.59 (s, 1H), 7.49 (d, J = 8.1 Hz, 1H), 7.27 (dd, J = 1.2, 8.5 Hz, 1H), 7.14 (d, J = 1.9 Hz, 1H), 7.02 (dd, J = 1.9, 8.1 Hz, 1H), 6.58 (s, 1H), 5.25 (s, 2H), 3.87 (s, 3H), 3.73 (s, 3H), 3.68 (s, 3H), 2.53 (s, 3H) | 263, 233, 176 (base), 147 |
| Example 8-17 | Example 2-1 | Example 9-240 | (DMSO-d$_6$) δ: 9.64 (brs, 1H), 7.59 (s, 1H), 7.48 (d, J = 8.5 Hz, 1H), 7.40 (d, J = 7.7 Hz, 1H), 7.26 (d, J = 8.9 Hz, 1H), 7.05 (s, 1H), 7.01 (d, J = 8.1 Hz, 1H), 6.33 (s, 1H), 5.25 (s, 2H), 4.04 (q, J = 7.3 Hz, 2H), 3.73 (s, 3H), 2.53 (s, 3H), 2.40 (s, 3H), 2.28 (s, 3H), 1.30 (t, J = 7.3 Hz, 3H) | 417 (M$^+$), 373, 241 (base), 176, 147 |
| Example 8-1 | Example 2-2 | Example 9-241 | (DMSO-d$_6$) δ: 9.82 (brs, 1H), 7.80 (d, J = 8.5 Hz, 1H), 7.66 (d, J = 2.3 Hz, 1H), 7.63 (s, 1H), 7.51 (s, 1H), 7.48 (d, J = 8.1 Hz, 1H), 7.46 (dd, J = 2.3, 8.5 Hz, 1H), 6.66 (s, 1H), 5.27 (s, 2H), 3.74 (s, 3H), 3.72 (s, 3H), 2.88 (q, J = 7.7 Hz, 2H), 1.32 (t, J = 7.7 Hz, 3H) | 267 (base), 190, 173, 161 |
| Example 8-9 | Example 2-2 | Example 9-242 | (DMSO-d$_6$) δ: 9.65 (brs, 1H), 7.84 (d, J = 8.5 Hz, 1H), 7.62 (s, 1H), 7.50 (d, J = 8.1 Hz, 1H), 7.27 (dd, J = 1.2, 8.5 Hz, 1H), 7.14 (d, J = 2.3 Hz, 1H), 7.02 (dd, J = 2.3, 8.5 Hz, 1H), 6.58 (s, 1H), 5.26 (s, 2H), 3.86 (s, 3H), 3.74 (s, 3H), 3.68 (s, 3H), 2.89 (q, J = 7.7 Hz, 2H), 1.33 (t, J = 7.7 Hz, 3H) | 263, 234, 189 (base), 173, 161 |

TABLE 75-continued

| Carboxylic acid | Hydroxy compound | Example | ¹H-NMR | Mass, m/z |
|---|---|---|---|---|
| Example 8-7 | Example 3-6 | Example 9-243 | (DMSO-d₆) δ: 9.66 (brs, 1H), 7.83 (dd, J = 1.9, 7.7 Hz, 1H), 7.68 (s, 1H), 7.55 (d, J = 8.1 Hz, 1H), 7.32 (d, J = 8.1 Hz, 1H), 7.25-7.29 (m, 1H), 7.07 (d, J = 7.7 Hz, 1H), 6.96 (dt, J = 1.2, 7.7 Hz, 1H), 6.58 (s, 1H), 5.28 (s, 2H), 4.96 (s, 2H), 4.22-4.15 (m, 4H), 3.83 (s, 3H), 3.68 (s, 3H) | 229, 204, 187, 175 (base) |

TABLE 76

| Carboxylic acid | Hydroxy compound | Example | ¹H-NMR | Mass, m/z |
|---|---|---|---|---|
| Example 8-32 | Example 3-6 | Example 9-244 | (DMSO-d₆) δ: 9.59 (brs, 1H), 7.85 (dd, J = 1.5, 7.7 Hz, 1H), 7.68 (s, 1H), 7.55 (d, J = 8.5 Hz, 1H), 7.33-7.28 (m, 1H) 7.27-7.25 (m, 1H), 7.07 (d, J = 8.1 Hz, 1H), 6.96 (dt, J = 1.2, 7.7 Hz, 1H), 6.58 (s, 1H), 5.28 (s, 2H), 4.96 (s, 2H), 4.21-4.15 (m, 4H), 4.03 (q, J = 7.3 Hz, 2H), 3.83 (s, 3H), 1.30 (t, J = 7.3 Hz, 3H) | 447 (M⁺), 403, 243 (base) |
| Example 8-33 | Example 3-6 | Example 9-245 | (DMSO-d₆) δ: 9.66 (brs, 1H), 7.82 (dd, J = 7.3, 8.5 Hz, 1H), 7.68 (s, 1H), 7.55 (d, J = 8.1 Hz, 1H), 7.32 (dd, J = 0.8, 8.1 Hz, 1H) 6.97 (dd J = 2.3, 11.6 Hz, 1H), 6.78 (dt, J = 2.3, 8.5 Hz, 1H), 6.54 (s, 1H), 5.28 (s, 2H), 4.96 (s, 2H), 4.22-4.15 (m, 4H), 3.84 (s, 3H), 3.67 (s, 3H) | 451 (M⁺), 407, 247, 204 (base) |
| Example 8-8 | Example 3-6 | Example 9-246 | (DMSO-d₆) δ: 9.62 (brs, 1H), 7.84 (dd, J = 6.9, 8.5 Hz, 1H), 7.68 (s, 1H), 7.55 (d, J = 8.1 Hz, 1H), 7.33 (d, J = 8.5 Hz, 1H), 6.97 (dd, J = 2.3, 11.7 Hz, 1H), 6.79 (dt, J = 2.7, 8.5 Hz, 1H), 6.54 (s, 1H), 5.28 (s, 2H), 4.97 (s, 2H), 4.23-4.16 (m, 4H), 4.02 (q, J = 7.3 Hz, 2H), 3.85 (s, 3H), 1.29 (t, J = 7.3 Hz, 3H) | 465 (M⁺), 421, 261 (base) |
| Example 8-9 | Example 3-6 | Example 9-247 | (DMSO-d₆) δ: 9.68 (brs, 1H), 7.83 (d, J = 8.1 Hz, 1H), 7.68 (s, 1H), 7.55 (d, J = 8.1 Hz, 1H), 7.32 (d, J = 8.5 Hz, 1H), 7.14 (d, J = 1.9 Hz, 1H), 7.02 (dd, J = 1.9, 8.1 Hz, 1H), 6.58 (s, 1H), 5.28 (s, 2H), 4.96 (s, 2H), 4.22-4.15 (m, 4H), 3.86 (s, 3H), 3.68 (s, 3H) | 467 (M⁺), 449, 263, 234, 204 (base), 175 |

TABLE 76-continued

| Carboxylic acid | Hydroxy compound | Example | ¹H-NMR | Mass, m/z |
|---|---|---|---|---|
| Example 8-10 | Example 3-6 | Example 9-248 | (DMSO-d$_6$) δ: 9.62 (brs, 1H), 7.86 (d, J = 8.5 Hz, 1H), 7.67 (s, 1H), 7.55 (d, J = 8.1 Hz, 1H), 7.32 (d, J = 8.5 Hz, 1H), 7.14 (d, J = 1.9 Hz, 1H), 7.03 (dd, J = 1.9, 8.1 Hz, 1H), 6.58 (s, 1H), 5.28 (s, 2H), 4.96 (s, 2H), 4.21-4.17 (m, 4H), 4.03 (q, J = 7.3 Hz, 2H), 3.87 (s, 3H), 1.29 (t, J = 7.3 Hz, 3H) | 481 (M⁺), 437, 277, 204, 187 (base) |

TABLE 77

| Carboxylic acid | Hydroxy compound | Example | ¹H-NMR | Mass, m/z |
|---|---|---|---|---|
| Example 8-34 | Example 3-6 | Example 9-249 | (DMSO-d$_6$) δ: 9.63 (br s, 1H), 7.71 (d, J = 7.7 Hz, 1H), 7.69 (d, J = 7.7 Hz, 1H), 7.55 (d, J = 8.5 Hz, 1H), 7.32 (d, J = 8.5 Hz, 1H), 6.88 (s, 1H), 6.77 (d, J = 7.7 Hz, 1H), 6.54 (s, 1H), 5.28 (s, 2H), 4.96 (s, 2H), 4.22-4.15 (m, 4H), 3.81 (s, 3H), 3.66 (s, 3H), 2.32 (s, 3H) | 447 (M⁺), 403, 243 (base), 204 |
| Example 8-12 | Example 3-6 | Example 9-250 | (DMSO-d$_6$) δ: 9.58 (br s, 1H), 7.72 (d, J = 8.1 Hz, 1H), 7.67 (s, 1H), 7.54 (d, J = 8.1Hz, 1H), 7.32 (d, J = 8.1 Hz, 1H), 6.89 (s, 1H), 6.78 (dd, J = 0.8, 7.7 Hz, 1H), 6.53 (s, 1H), 5.27 (s, 2H), 4.96 (s, 2H), 4.22-4.15 (m, 4H), 4.01 (q, J = 7.3 Hz, 2H), 3.82 (s, 3H), 2.32 (s, 3H), 1.29 (t, J = 7.3 Hz, 3H) | 461 (M⁺), 417, 257 (base) |
| Example 8-16 | Example 3-6 | Example 9-251 | (DMSO-d$_6$) δ: 9.71 (br s, 1H), 7.68 (s, 1H), 7.54 (d, J = 8.1 Hz, 1H), 7.39 (d, J = 8.1 Hz, 1H), 7.32 (dd, J = 1.2, 8.1 Hz, 1H), 7.04 (s, 1H), 7.01 (d, J = 7.7 Hz, 1H), 6.33 (s, 1H), 5.28 (s, 2H), 4.96 (s, 2H), 4.21-4.16 (m, 4H), 3.68 (s, 3H), 2.39 (s, 3H), 2.28 (s, 3H) | 227 (base), 204, 187, 175 |

TABLE 77-continued

| Carboxylic acid | Hydroxy compound | Example | ¹H-NMR | Mass, m/z |
|---|---|---|---|---|
| Example 8-17 | Example 3-6 | Example 9-252 | (DMSO-d₆) δ: 9.65 (br s, 1H), 7.67 (s, 1H), 7.54 (d, J = 8.5 Hz, 1H), 7.41 (d, J = 7.7 Hz, 1H), 7.32 (d, J = 7.7 Hz, 1H), 7.05 (s, 1H), 7.01 (d, J = 8.1 Hz, 1H), 6.33 (s, 1H), 5.28 (s, 2H), 4.96 (s, 2H), 4.22-4.15 (m, 4H), 4.02 (q, J = 7.3 Hz, 2H), 2.40 (s, 3H), 2.28 (s, 3H), 1.30 (t, J = 7.3 Hz, 3H) | 241 (base) |
| Example 8-31 | Example 3-6 | Example 9-253 | (DMSO-d₆) δ: 9.74 (br s, 1H), 7.67 (s, 1H), 7.55-7.50 (m, 2H), 7.32 (d, J = 8.5 Hz, 1H), 7.09 (dd, J = 2.7, 10.0 Hz, 1H), 7.05-7.00 (m, 1H), 6.36 (s, 1H), 5.29 (s, 2H), 4.96 (s, 2H), 4.20-4.15 (m, 4H), 3.69 (s, 3H), 2.43 (s, 3H) | 435 (M⁺), 231, 204, 175 (base) |

TABLE 78

| Carboxylic acid | Hydroxy compound | Example | ¹H-NMR | Mass, m/z |
|---|---|---|---|---|
| Example 8-7 | Example 3-2 | Example 9-254 | (DMSO-d₆) δ: 9.65 (br s, 1H), 7.84-7.82 (m, 1H), 7.63 (s, 1H), 7.45 (d, J = 8.5 Hz, 1H), 7.29-7.23 (m, 2H), 7.06 (d, J = 8.1 Hz, 1H), 6.98-6.94 (m, 1H), 6.58 (s, 1H), 5.26 (s, 2H), 4.12 (t, J = 7.3 Hz, 2H), 3.83 (s, 3H), 3.68 (s, 3H), 2.96 (t, J = 7.3 Hz, 2H), 2.64 (quint, J = 7.3 Hz, 2H) | 417 (M⁺), 373, 229, 188, 171 (base) |
| Example 8-32 | Example 3-2 | Example 9-255 | (DMSO-d₆) δ: 9.61 (br s, 1H), 7.86 (dd, J = 1.9, 7.7 Hz, 1H), 7.62 (s, 1H), 7.45 (d, J = 8.1 Hz, 1H), 7.28-7.23 (m, 2H), 7.07 (d, J = 7.7 Hz, 1H), 6.98-6.94 (m, 1H), 6.58 (s, 1H), 5.25 (s, 2H), 4.12 (t, J = 6.9 Hz, 2H), 4.03 (q, J = 7.3 Hz, 2H), 3.83 (s, 3H), 2.96 (t, J = 7.3 Hz, 2H), 2.64 (t, J = 6.9 Hz, 2H), 1.30 (t, J = 7.3 Hz, 3H) | 431 (M⁺), 387, 243, 217, 188, 171 (base) |

TABLE 78-continued

| Carboxylic acid | Hydroxy compound | Example | 1H-NMR | Mass, m/z |
|---|---|---|---|---|
| Example 8-33 | Example 3-2 | Example 9-256 | (DMSO-d$_6$) δ: 9.64 (br s, 1H), 7.82 (dd, J = 7.3, 8.5 Hz, 1H), 7.62 (s, 1H), 7.45 (d, J = 8.5 Hz, 1H), 7.24 (dd, J = 1.2, 8.1 Hz, 1H), 6.97 (dd, J = 2.7, 11.6 Hz, 1H), 6.79 (dt, J = 2.3, 8.5 Hz, 1H), 6.54 (s, 1H), 5.25 (s, 2H), 4.12 (t, J = 7.3 Hz, 2H), 3.84 (s, 3H), 3.67 (s, 3H), 2.96 (t, J = 7.3 Hz, 2H), 2.68-2.60 (m, 2H) | 435 (M$^+$), 391, 247, 171 (base) |
| Example 8-8 | Example 3-2 | Example 9-257 | (DMSO-d$_6$) δ: 9.59 (br s, 1H), 7.84 (dd, J = 7.3, 8.5 Hz, 1H), 7.61 (s, 1H), 7.45 (d, J = 8.1 Hz, 1H), 7.24 (d, J = 8.1 Hz, 1H), 6.96 (dd, J = 2.3, 11.5 Hz, 1H), 6.81-6.76 (m, 1H), 6.54 (s, 1H), 5.24 (s, 2H), 4.12 (t, J = 6.9 Hz, 2H), 4.03 (t, J = 7.3 Hz, 2H), 3.85 (s, 3H), 2.97 (t, J = 7.3 Hz, 2H), 2.65 (quint, J = 7.3 Hz, 2H), 1.29 (t, J = 7.3 Hz, 3H) | 449 (M$^+$), 405, 261, 188, 171 (base) |
| Example 8-9 | Example 3-2 | Example 9-258 | (DMSO-d$_6$) δ: 9.68 (br s, 1H), 7.84 (d, J = 8.5 Hz, 1H), 7.63 (s, 1H), 7.45 (d, J = 8.1 Hz, 1H), 7.25 (dd, J = 0.8, 8.1 Hz, 1H), 7.14 (d, J = 1.9 Hz, 1H), 7.02 (dd, J = 1.9, 8.1 Hz, 1H), 6.58 (s, 1H), 5.26 (s, 2H), 4.12 (t, J = 6.9 Hz, 2H), 3.87 (s, 3H), 3.68 (s, 3H), 2.96 (t, J = 6.9 Hz, 2H), 2.68-2.60 (m, 2H) | 451 (M$^+$), 407, 263, 188, 93 (base) |

TABLE 79

| Carboxylic acid | Hydroxy compound | Example | ¹H-NMR | Mass, m/z |
|---|---|---|---|---|
| Example 8-10 | Example 3-2 | Example 9-259 | (DMSO-d$_6$) δ: 9.62 (br s, 1H), 7.86 (d, J = 8.5 Hz, 1H), 7.62 (s, 1H), 7.45 (d, J = 8.5 Hz, 1H), 7.23 (d, J = 8.1 Hz, 1H), 7.14 (d, J = 1.9 Hz, 1H), 7.02 (dd, J = 1.9, 8.1 Hz, 1H), 6.58 (s, 1H), 5.25 (s, 2H), 4.12 (t, J = 6.9 Hz, 2H), 4.03 (q, J = 7.3 Hz, 2H), 3.87 (s, 3H), 2.97 (dt, J = 7.3, 8.1 Hz, 2H), 2.64 (quint, J = 7.3 Hz, 2H), 1.30 (t, J = 7.3 Hz, 3H) | 465 (M⁺), 421, 277, 188, 171 (base) |
| Example 8-16 | Example 3-2 | Example 9-260 | (DMSO-d$_6$) δ: 9.71 (br s, 1H), 7.62 (s, 1H), 7.45 (d, J = 8.1 Hz, 1H), 7.39 (d, J = 7.7 Hz, 1H), 7.24 (dd, J = 0.8, 8.1 Hz, 1H), 7.04 (s, 1H), 7.00 (d, J = 8.1 Hz, 1H), 6.32 (s, 1H), 5.26 (s, 2H), 4.11 (t, J = 7.3 Hz, 2H), 3.68 (s, 3H), 2.96 (t, J = 7.3 Hz, 2H), 2.64 (quint, J = 7.3 Hz, 2H), 2.39 (s, 3H), 2.28 (s, 3H) | 415 (M⁺), 371, 227, 188, 171 (base) |
| Example 8-34 | Example 3-2 | Example 9-261 | (DMSO-d$_6$) δ: 7.70 (d, J = 8.1 Hz, 1H), 7.62 (s, 1H), 7.45 (d, J = 8.1 Hz, 1H), 7.24 (dd, J = 1.2, 8.1 Hz, 1H), 6.89 (s, 1H), 6.77 (d, J = 7.3 Hz, 1H), 6.53 (s, 1H), 5.25 (s, 2H), 4.12 (t, J = 7.3 Hz, 2H), 3.81 (s, 3H), 3.86 (s, 3H), 2.96 (t, J = 7.3 Hz, 2H), 2.68-2.62 (m, 2H), 2.32 (s, 3H) | 387 (M⁺ − 44), 159 (base) |
| Example 8-12 | Example 3-2 | Example 9-262 | (DMSO-d$_6$) δ: 9.56 (br s, 1H), 7.72 (d, J = 7.7 Hz, 1H), 7.61 (s, 1H), 7.45 (d, J = 8.5 Hz, 1H), 7.24 (d, J = 7.3 Hz, 1H), 6.89 (s, 1H), 6.78 (d, J = 7.3 Hz, 1H), 6.53 (s, 1H), 5.25 (s, 2H), 4.12 (t, J = 6.9 Hz, 2H), 4.01 (q, J = 7.3 Hz, 2H), 3.82 (s, 3H), 2.96 (t, J = 7.3 Hz, 2H), 2.68-2.60 (m, 2H), 2.32 (s, 3H), 1.29 (t, J = 7.3 Hz, 3H) | 445 (M⁺), 401, 257, 188, 171 (base) |

TABLE 79-continued

| Carboxylic acid | Hydroxy compound | Example | ¹H-NMR | Mass, m/z |
|---|---|---|---|---|
| Example 8-7 | — | Example 9-263 | (DMSO-d$_6$) δ: 9.63 (br s, 1H), 7.83 (dd, J = 1.5, 7.7 Hz, 1H), 7.60 (s, 1H), 7.46 (d, J = 8.5 Hz, 1H), 7.29-7.25 (m, 2H), 7.07 (d, J = 7.7 Hz, 1H), 6.96 (dt, J = 0.8, 7.7 Hz, 1H), 6.58 (s, 1H), 5.26 (s, 2H), 4.10 (t, J = 6.2 Hz, 2H), 3.83 (s, 3H), 3.68 (s, 3H), 2.96 (t, J = 6.6 Hz, 2H), 2.08-2.02 (m, 2H), 1.96-1.91 (m, 2H) | 431 (M⁺), 387, 229, 202, 173 (base) |

TABLE 80

| Carboxylic acid | Hydroxy compound | Example | ¹H-NMR | Mass, m/z |
|---|---|---|---|---|
| Example 8-32 | — | Example 9-264 | (DMSO-d$_6$) δ: 9.60 (br s, 1H), 7.85 (dd, J = 1.9, 7.7 Hz, 1H), 7.60 (s, 1H), 7.46 (d, J = 8.1 Hz, 1H), 7.30-7.23 (m, 2H), 7.07 (d, J = 8.5 Hz, 1H), 6.98-6.94 (m, 1H), 6.58 (s, 1H), 5.26 (s, 2H), 4.10 (t, J = 6.2 Hz, 2H), 4.02 (q, J = 7.3 Hz, 2H), 3.83 (s, 3H), 2.98-2.95 (m, 2H), 2.08-1.99 (m, 2H), 1.97-1.91 (m, 2H), 1.30 (t, J = 7.3 Hz, 3H) | 243, 202 173 (base) |
| Example 8-33 | — | Example 9-265 | (DMSO-d$_6$) δ: 9.64 (br s, 1H), 7.82 (dd, J = 7.3, 8.9 Hz, 1H), 7.60 (s, 1H), 7.46 (d, J = 8.1 Hz, 1H), 7.26 (dd, J = 1.2, 8.5 Hz, 1H), 6.97 (dd, J = 2.3, 11.2 Hz, 1H), 6.79 (dt, J = 2.7, 8.5 Hz, 1H), 6.54 (s, 1H), 5.26 (s, 2H), 4.10 (t, J = 6.2 Hz, 2H), 3.85 (s, 3H), 3.67 (s, 3H), 2.94 (t, J = 6.6 Hz, 2H), 2.08-2.02 (m, 2H), 1.96-1.91 (m, 2H) | 247 (base), 202, 173 |

TABLE 80-continued

| Carboxylic acid | Hydroxy compound | Example | ¹H-NMR | Mass, m/z |
|---|---|---|---|---|
| Example 8-8 | — | Example 9-266 | (DMSO-d$_6$) δ: 9.58 (br s, 1H), 7.84 (dd, J = 7.3, 8.9 Hz, 1H), 7.60 (s, 1H), 7.46 (d, J = 8.5 Hz, 1H), 7.25 (d, J = 8.5 Hz, 1H), 6.97 (dd, J = 2.3, 11.6 Hz, 1H), 6.79 (dt, J = 2.7, 8.5 Hz, 1H), 6.53 (s, 1H), 5.26 (s, 2H), 4.10 (t, J = 6.2 Hz, 2H), 4.02 (q, J = 7.3 Hz, 2H), 3.85 (s, 3H), 2.98-2.95 (m, 2H), 2.08-1.99 (m, 2H), 1.97-1.91 (m, 2H), 1.29 (t, J = 7.3 Hz, 3H) | 463 (M⁺), 419, 261 (base) |
| Example 8-9 | — | Example 9-267 | (DMSO-d$_6$) δ: 9.65 (br s, 1H), 7.84 (d, J = 8.5 Hz, 1H), 7.60 (s, 1H), 7.46 (d, J = 8.1 Hz, 1H), 7.25 (dd, J = 1.2, 8.1 Hz, 1H), 7.14 (d, J = 1.9 Hz, 1H), 7.02 (dd, J = 1.9, 8.1 Hz, 1H), 6.58 (s, 1H), 5.26 (s, 2H), 4.10 (t, J = 6.2 Hz, 2H), 3.86 (s, 3H), 3.68 (s, 3H), 2.96 (t, J = 6.6 Hz, 2H), 2.08-2.02 (m, 2H), 1.96-1.91 (m, 2H) | 263, 173 (base) |
| Example 8-10 | — | Example 9-268 | (DMSO-d$_6$) δ: 9.62 (br s, 1H), 7.86 (d, J = 8.5 Hz, 1H), 7.60 (s, 1H), 7.46 (d, J = 8.1 Hz, 1H), 7.25 (d, J = 8.1 Hz, 1H), 7.14 (d, J = 1.9 Hz, 1H), 7.03 (dd, J = 1.9, 8.1 Hz, 1H), 6.58 (s, 1H), 5.26 (s, 2H), 4.10 (t, J = 6.2 Hz, 2H), 4.03 (q, J = 7.3 Hz, 2H), 3.87 (s, 3H), 2.96 (t, J = 6.6 Hz, 2H), 2.08-2.00 (m, 2H), 1.97-1.90 (m, 2H), 1.29 (t, J = 7.3 Hz, 3H) | 479 (M⁺), 435, 277, 202 (base) |

TABLE 81

| Carboxylic acid | Hydroxy compound | Example | ¹H-NMR | Mass, m/z |
|---|---|---|---|---|
| Example 8-34 | — | Example 9-269 | (DMSO-d₆) δ: 9.60 (br s, 1H), 7.70 (d, J = 7.7 Hz, 1H), 7.60 (s, 1H), 7.46 (d, J = 8.2 Hz, 1H), 7.26 (d, J = 7.2 Hz, 1H), 7.24-7.17 (m, 1H), 6.89 (s, 1H), 6.77 (d, J = 7.7 Hz, 1H), 5.26 (s, 2H), 4.10 (t, J = 5.8 Hz, 2H), 3.81 (s, 3H), 3.66 (s, 3H), 2.97 (t, J = 6.3 Hz, 2H), 2.32 (s, 3H), 2.07-2.04 (m, 2H), 1.97-1.92 (m, 2H) | 401 (M⁺ − 44), 173 (base) |
| Example 8-12 | — | Example 9-270 | (DMSO-d₆) δ: 9.57 (br s, 1H), 7.72 (d, J = 7.7 Hz, 1H), 7.62 (s, 1H), 7.51 (d, J = 8.5 Hz, 1H), 7.29 (d, J = 7.7 Hz, 1H), 6.89 (s, 1H), 6.78 (d, J = 8.5 Hz, 1H), 6.53 (s, 1H), 5.26 (s, 2H), 4.12 (t, J = 6.2 Hz, 2H), 4.01 (q, J = 7.3 Hz, 2H), 3.81 (s, 3H), 2.99 (t, J = 6.6 Hz, 2H), 2.32 (s, 3H), 2.09-1.99 (m, 2H), 1.97-1.91 (m, 2H), 1.29 (t, J = 7.3 Hz, 3H) | 459 (M⁺), 415, 257 (base) |
| Example 8-16 | — | Example 9-271 | (DMSO-d₆) δ: 9.70 (br s, 1H), 7.60 (s, 1H), 7.46 (d, J = 8.1 Hz, 1H), 7.49 (d, J = 7.7 Hz, 1H), 7.26 (dd, J = 0.8, 8.1 Hz, 1H), 7.05 (s, 1H), 7.01 (d, J = 8.1 Hz, 1H), 6.33 (s, 1H), 5.27 (s, 2H), 4.10 (t, J = 6.2 Hz, 2H), 3.68 (s, 3H), 2.96 (t, J = 6.6 Hz, 2H), 2.39 (s, 3H), 2.28 (s, 3H), 2.08-2.02 (m, 2H), 1.97-1.91 (m, 2H) | 229, 173 (base) |
| Example 8-17 | — | Example 9-272 | (DMSO-d₆) δ: 9.64 (br s, 1H), 7.60 (s, 1H), 7.46 (d, J = 8.5 Hz, 1H), 7.40 (d, J = 7.7 Hz, 1H), 7.27-7.24 (m, 1H), 7.05 (s, 1H), 7.01 (d, J = 8.1 Hz, 1H), 6.33 (s, 1H), 5.26 (s, 2H), 4.10 (t, J = 6.2 Hz, 2H), 4.02 (q, J = 7.3 Hz, 2H), 2.98-2.95 (m, 2H), 2.40 (s, 3H), 2.28 (s, 3H), 2.08-1.99 (m, 2H), 1.96-1.90 (m, 2H), 1.30 (t, J = 7.3 Hz, 3H) | 241 (base) |

TABLE 81-continued

| Carboxylic acid | Hydroxy compound | Example | ¹H-NMR | Mass, m/z |
|---|---|---|---|---|
| Example 8-9 | Example 1-6 | Example 9-273 | (DMSO-$d_6$) δ: 9.68 (br s, 1H), 8.20 (s, 1H), 7.84 (d, J = 8.5 Hz, 1H), 7.73 (s, 1H), 7.64 (d, J = 8.5 Hz, 1H), 7.33 (dd, J = 0.8, 8.5 Hz, 1H), 7.14 (d, J = 1.9 Hz, 1H), 7.02 (dd, J = 1.9, 8.1 Hz, 1H), 6.58 (s, 1H), 5.28 (s, 2H) 4.42 (t, J = 5.4 Hz, 2H), 3.82 (s, 3H), 3.69 (m, 5H), 3.22 (s, 3H) | 469 (M⁺), 425, 263, 206, 161 (base) |

TABLE 82

| Carboxylic acid | Hydroxy compound | Example | ¹H-NMR | Mass, m/z |
|---|---|---|---|---|
| Example 8-9 | Example 2-4 | Example 9-274 | (DMSO-$d_6$) δ: 9.69 (br s, 1H), 7.84 (d, J = 8.1 Hz, 1H), 7.70 (s, 1H), 7.58 (d, J = 8.5 Hz, 1H), 7.36 (dd, J = 1.5, 8.5 Hz, 1H), 7.14 (d, J = 1.9 Hz, 1H), 7.02 (dd, J = 1.9, 8.5 Hz, 1H), 6.58 (s, 1H), 5.28 (s, 2H), 4.70 (s, 2H), 3.86 (s, 3H), 3.82 (s, 3H), 3.69 (s, 3H), 3.33 (s, 3H) | 425 (M⁺ − 44), 263, 176 (base) |
| Example 8-1 | Example 4-1 | Example 9-275 | (DMSO-$d_6$) δ: 9.84 (br s, 1H), 8.07 (d, J = 0.8 Hz, 1H), 7.84 (s, 1H), 7.80 (d, J = 8.5 Hz, 1H), 7.67 (d, J = 8.1 Hz, 1H), 7.66 (d, J = 2.3 Hz, 1H), 7.48 (dd, J = 1.5, 7.7 Hz, 1H), 7.46 (dd, J = 2.3, 8.5 Hz, 1H), 6.66 (s, 1H), 5.28 (s, 2H), 4.03 (s, 3H), 3.72 (s, 3H) | 385 (M⁺ − 44), 267, 162, 145 (base) |
| Example 8-5 | Example 4-1 | Example 9-276 | (DMSO-$d_6$) δ: 9.80 (br s, 1H), 8.07 (s, 1H), 7.83 (s, 1H), 7.82 (d, J = 8.5 Hz, 1H), 7.67 (d, J = 8.1 Hz, 1H), 7.66 (s, 1H), 7.47 (dd, J = 1.2, 8.5 Hz, 1H), 7.46 (dd, J = 2.3, 8.5 Hz, 1H), 6.67 (s, 1H), 5.28 (s, 2H), 4.07 (q, J = 7.3 Hz, 2H), 4.05 (s, 3H), 1.31 (t, J = 7.3 Hz, 3H) | 443 (M⁺), 399, 281, 253, 145 (base) |

TABLE 82-continued

| Carboxylic acid | Hydroxy compound | Example | ¹H-NMR | Mass, m/z |
|---|---|---|---|---|
| Example 8-4 | Example 4-1 | Example 9-277 | (DMSO-d₆) δ: 9.73 (br s, 1H), 8.07 (s, 1H), 7.84 (s, 1H), 7.67 (d, J = 8.5 Hz, 1H), 7.51-7.47 (m, 2H), 7.25-7.18 (m, 3H), 6.38 (s, 1H), 5.28 (s, 2H), 4.06 (s, 3H), 3.70 (s, 3H), 2.43 (s, 3H) | 375 (M⁺), 331, 145 (base) |
| Example 8-19 | Example 4-1 | Example 9-278 | (DMSO-d₆) δ: 9.81 (br s, 1H), 8.20 (s, 1H), 7.80 (d, J = 7.7 Hz, 1H), 7.73 (s, 1H), 7.71-7.65 (m, 2H), 7.60-7.55 (m, 2H), 7.36 (d, J = 7.3 Hz, 1H), 6.35 (s, 1H), 5.29 (s, 2H), 3.85 (s, 3H), 3.72 (s, 3H) | 385 (M⁺ − 44), 267 (base), 162, 145 |

TABLE 83

| Carboxylic acid | Hydroxy compound | Example | ¹H-NMR | Mass, m/z |
|---|---|---|---|---|
| Example 8-8 | Example 4-1 | Example 9-279 | (DMSO-d₆) δ: 9.60 (br s, 1H), 8.07 (s, 1H), 7.86-7.82 (m, 2H), 7.67 (d, J = 8.9 Hz, 1H), 7.47 (d, J = 8.5 Hz, 1H), 6.97 (dd, J = 2.3, 11.6 Hz, 1H), 6.79 (dt, J = 2.3, 8.5 Hz, 1H), 6.54 (s, 1H), 5.27 (s, 2H), 4.06 (s, 3H), 4.02 (q, J = 7.3 Hz, 2H), 3.84 (s, 3H), 1.29 (t, J = 7.3 Hz, 3H) | 423 (M⁺), 379, 261, 162, 145 (base) |
| Example 8-9 | Example 4-1 | Example 9-280 | (DMSO-d₆) δ: 8.07 (s, 1H), 7.84 (d, J = 8.5 Hz, 1H), 7.83 (s, 1H), 7.67 (d, J = 8.5 Hz, 1H), 7.48 (dd, J = 1.2, 8.9 Hz, 1H), 7.15 (d, J = 1.9 Hz, 1H), 7.02 (dd, J = 1.9, 8.5 Hz, 1H), 6.58 (s, 1H), 5.27 (s, 2H), 4.06 (s, 3H), 3.86 (s, 3H), 3.69 (s, 3H) | 425 (M⁺), 381, 263, 145 (base) |

TABLE 83-continued

| Carboxylic acid | Hydroxy compound | Example | ¹H-NMR | Mass, m/z |
|---|---|---|---|---|
| Example 8-10 | Example 4-1 | Example 9-281 | (DMSO-d₆) δ: 9.67 (br s, 1H), 8.08 (s, 1H), 7.86 (d, J = 8.1 Hz, 1H), 7.83 (s, 1H), 7.67 (d, J = 8.5 Hz, 1H), 7.47 (d, J = 8.5 Hz, 1H), 7.15 (d, J = 1.9 Hz, 1H), 7.03 (dd, J = 1.9, 8.5 Hz, 1H), 6.58 (s, 1H), 5.27 (s, 2H), 4.06 (s, 3H), 4.03 (q, J = 7.3 Hz, 2H), 3.86 (s, 3H), 1.29 (t, J = 7.3 Hz, 3H) | 439 (M⁺), 395, 277, 162, 145 (base) |
| Example 8-11 | Example 4-1 | Example 9-282 | (DMSO-d₆) δ: 10.05 (br s, 1H), 8.05 (d, J = 0.8 Hz, 1H), 7.78 (s, 1H), 7.65 (d, J = 8.9 Hz, 1H), 7.43 (dd, J = 1.5, 8.5 Hz, 1H), 7.25 (d, J = 8.5 Hz, 1H), 7.24 (d, J = 2.3 Hz, 1H), 7.11 (dd, J = 1.9, 8.1 Hz, 1H), 6.21 (s, 1H), 5.22 (s, 2H), 4.04 (s, 3H), 4.04-3.97 (m, 1H), 3.81 (s, 3H) 1.26 (d, J = 6.5 Hz, 6H) | 453 (M⁺), 409, 276, 145 (base) |

TABLE 84

| Carboxylic acid | Hydroxy compound | Example | ¹H-NMR | Mass, m/z |
|---|---|---|---|---|
| Example 8-34 | Example 4-1 | Example 9-283 | (DMSO-d₆) δ: 9.62 (br s, 1H), 8.07 (s, 1H), 7.83 (s, 1H), 7.70 (d, J = 8.1 Hz, 1H), 7.67 (d, J = 8.9 Hz, 1H), 7.47 (d, J = 8.5 Hz, 1H), 6.89 (s, 1H), 6.77 (d, J = 7.7 Hz, 1H), 6.54 (s, 1H), 5.27 (s, 2H), 4.05 (s, 3H), 3.81 (s, 3H), 3.67 (s, 3H), 2.32 (s, 3H) | 405 (M⁺), 387, 361, 243, 162, 145 (base) |
| Example 8-12 | Example 4-1 | Example 9-284 | (DMSO-d₆) δ: 9.57 (br s, 1H), 8.07 (s, 1H), 7.83 (s, 1H), 7.72 (d, J = 7.7 Hz, 1H), 7.67 (d, J = 8.5 Hz, 1H), 7.47 (d, J = 8.9 Hz, 1H), 6.89 (s, 1H), 6.78 (d, J = 8.5 Hz, 1H), 6.53 (s, 1H), 5.27 (s, 2H), 4.05 (s, 3H), 4.01 (q, J = 7.3 Hz, 2H), 3.81 (s, 3H), 2.32 (s, 3H), 1.28 (t, J = 7.3 Hz, 3H) | 419 (M⁺), 375, 257, 145 (base) |

TABLE 84-continued

| Carboxylic acid | Hydroxy compound | Example | ¹H-NMR | Mass, m/z |
|---|---|---|---|---|
| Example 8-16 | Example 4-1 | Example 9-285 | (DMSO-d₆) δ: 9.72 (br s, 1H), 8.07 (d, J = 0.8 Hz, 1H), 7.83 (s, 1H), 7.67 (d, J = 8.5 Hz, 1H), 7.48 (dd, J = 1.2, 8.9 Hz, 1H), 7.39 (d, J = 7.7 Hz, 1H), 7.05 (s, 1H), 7.01 (d, J = 8.1 Hz, 1H), 6.33 (s, 1H), 5.28 (s, 2H), 4.06 (s, 3H), 3.69 (s, 3H), 2.39 (s, 3H), 2.30 (s, 3H) | 389 (M⁺), 345, 227, 145 (base) |
| Example 8-17 | Example 4-1 | Example 9-286 | (DMSO-d₆) δ: 9.65 (br s, 1H), 8.07 (d, J = 0.8 Hz, 1H), 7.83 (s, 1H), 7.67 (d, J = 8.9 Hz, 1H), 7.47 (dd, J = 1.2, 8.5 Hz, 1H), 7.40 (d, J = 7.7 Hz, 1H), 7.05 (s, 1H), 7.02 (d, J = 8.1 Hz, 1H), 6.34 (s, 1H), 5.27 (s, 2H), 4.06 (s, 3H), 4.02 (q, J = 7.3 Hz, 2H), 2.40 (s, 3H), 2.28 (s, 3H), 1.30 (t, J = 7.3 Hz, 3H) | 403 (M⁺), 359, 241, 145 (base) |

TABLE 85

| Carboxylic acid | Hydroxy compound | Example | ¹H-NMR | Mass, m/z |
|---|---|---|---|---|
| Example 8-18 | Example 4-1 | Example 9-287 | (DMSO-d₆) δ: 10.07 (br s, 1H), 8.05 (d, J = 0.8 Hz, 1H), 7.79 (s, 1H), 7.64 (d, J = 8.5 Hz, 1H), 7.43 (dd, J = 1.5, 8.9 Hz, 1H), 7.27-7.18 (m, 3H), 7.14 (s, 1H), 7.09-7.05 (m, 2H), 6.91 (d, J = 8.5 Hz, 1H), 6.91 (s, 1H), 6.33 (s, 1H), 5.23 (s, 2H), 4.94 (s, 2H), 4.04 (s, 3H), 2.31 (s, 3H), 2.04 (s, 3H) | 465 (M⁺), 421, 330, 145 (base) |
| Example 8-7 | Example 4-2 | Example 9-288 | (DMSO-d₆) δ: 9.67 (br s, 1H), 8.36 (s, 1H), 7.82 (dd, J = 1.5, 7.7 Hz, 1H), 7.76 (s, 1H), 7.62 (d, J = 8.9 Hz, 1H), 7.30-7.25 (m, 2H), 7.07 (d, J = 8.5 Hz, 1H), 6.96 (t, J = 7.3 Hz, 1H), 6.59 (s, 1H), 5.22 (s, 2H), 4.17 (s, 3H), 3.83 (s, 3H), 3.69 (s, 3H) | 391 (M⁺), 373, 347, 229, 162, 145 (base) |

TABLE 85-continued

| Carboxylic acid | Hydroxy compound | Example | ¹H-NMR | Mass, m/z |
|---|---|---|---|---|
| Example 8-32 | Example 4-2 | Example 9-289 | (DMSO-d₆) δ: 9.62 (br s, 1H), 8.36 (s, 1H), 7.85 (dd, J = 1.9, 7.7 Hz, 1H), 7.76 (s, 1H), 7.62 (d, J = 8.9 Hz, 1H), 7.30-7.25 (m, 2H), 7.07 (d, J = 7.7 Hz, 1H), 6.97 (dt, J = 0.8, 7.7 Hz, 1H), 6.59 (s, 1H), 5.21 (s, 2H), 4.17 (s, 3H), 4.03 (q, J = 7.3 Hz, 2H), 3.83 (s, 3H), 1.30 (t, J = 7.3 Hz, 3H) | 405 (M⁺), 361, 243, 162, 145 (base) |
| Example 8-33 | Example 4-2 | Example 9-290 | (DMSO-d₆) δ: 9.69 (br s, 1H), 8.36 (s, 1H), 7.82 (dd, J = 7.3, 8.5 Hz, 1H), 7.76 (s, 1H), 7.62 (d, J = 8.9 Hz, 1H), 7.29 (d, J = 8.9 Hz, 1H), 6.97 (dd, J = 2.3, 11.6 Hz, 1H), 6.79 (dt, J = 2.3, 8.5 Hz, 1H), 6.55 (s, 1H), 5.21 (s, 2H), 4.17 (s, 3H), 3.84 (s, 3H), 3.68 (s, 3H) | 247, 162, 145 (base) |

TABLE 86

| Carboxylic acid | Hydroxy compound | Example | ¹H-NMR | Mass, m/z |
|---|---|---|---|---|
| Example 8-9 | Example 4-2 | Example 9-291 | (DMSO-d₆) δ: 9.70 (br s, 1H), 8.36 (s, 1H), 7.84 (d, J = 8.1 Hz, 1H), 7.76 (s, 1H), 7.62 (d, J = 8.9 Hz, 1H), 7.29 (dd, J = 1.2, 8.9 Hz, 1H), 7.14 (d, J = 1.9 Hz, 1H), 7.02 (dd, J = 1.9, 8.1 Hz, 1H), 6.59 (s, 1H), 5.21 (s, 2H), 4.17 (s, 3H), 3.86 (s, 3H), 3.69 (s, 3H) | 425 (M⁺), 381, 263, 162, 145 (base) |
| Example 8-10 | Example 4-2 | Example 9-292 | (DMSO-d₆) δ: 9.64 (br s, 1H), 8.36 (s, 1H), 7.86 (d, J = 8.1 Hz, 1H), 7.75 (s, 1H), 7.62 (d, J = 8.9 Hz, 1H), 7.29 (dd, J = 1.2, 8.9 Hz, 1H), 7.14 (d, J = 1.9 Hz, 1H), 7.03 (dd, J = 1.9, 8.1 Hz, 1H), 6.59 (s, 1H), 5.21 (s, 2H), 4.30 (q, J = 7.3 Hz, 2H), 4.17 (s, 3H), 3.86 (s, 3H), 1.29 (t, J = 7.3 Hz, 3H) | 439 (M⁺), 395, 277, 162, 145 (base) |

TABLE 86-continued

| Carboxylic acid | Hydroxy compound | Example | ¹H-NMR | Mass, m/z |
|---|---|---|---|---|
| Example 8-34 | Example 4-2 | Example 9-293 | (DMSO-d$_6$) δ: 9.64 (br s, 1H), 8.36 (s, 1H), 7.76 (s, 1H), 7.71 (d, J = 7.7 Hz, 1H), 7.62 (d, J = 8.9 Hz, 1H), 7.29 (dd, J = 1.2, 8.9 Hz, 1H), 6.89 (s, 1H), 6.54 (s, 1H), 5.21 (s, 2H), 4.17 (s, 3H), 3.81 (s, 3H), 3.67 (s, 3H), 2.31 (s, 3H) | 406 (M⁺), 361, 243, 162, 145 (base) |
| Example 8-13 | Example 4-2 | Example 9-294 | (DMSO-d$_6$) δ: 9.61 (br s, 1H), 8.36 (s, 1H), 7.76 (s, 1H), 7.73 (d, J = 8.5 Hz, 1H), 7.62 (d, J = 8.9 Hz, 1H), 7.29 (dd, J = 1.5, 8.9 Hz, 1H), 6.61 (d, J = 2.3 Hz, 1H), 6.56 (dd, J = 2.3, 8.5 Hz, 1H), 6.49 (s, 1H), 5.21 (s, 2H), 4.17 (s, 3H), 3.82 (s, 3H), 3.79 (s, 3H), 3.66 (s, 3H) | 421 (M⁺), 377, 145 (base) |
| Example 8-16 | Example 4-2 | Example 9-295 | (DMSO-d$_6$) δ: 9.73 (br s, 1H), 8.36 (s, 1H), 7.76 (s, 1H), 7.61 (d, J = 8.9 Hz, 1H), 7.39 (d, J = 7.7 Hz, 1H), 7.29 (dd, J = 1.5, 8.9 Hz, 1H), 7.01 (d, J = 8.1 Hz, 1H), 6.34 (s, 1H), 5.22 (s, 2H), 4.17 (s, 3H), 3.69 (s, 3H), 1.39 (s, 3H), 2.29 (s, 3H) | 389 (M⁺), 345, 145 (base) |

TABLE 87

| Carboxylic acid | Hydroxy compound | Example | ¹H-NMR | Mass, m/z |
|---|---|---|---|---|
| Example 8-17 | Example 4-2 | Example 9-296 | (DMSO-d$_6$) δ: 9.67 (br s, 1H), 8.36 (s, 1H), 7.76 (s, 1H), 7.61 (d, J = 8.9 Hz, 1H), 7.40 (d, J = 7.7 Hz, 1H), 7.29 (dd, J = 1.2, 8.9 Hz, 1H), 7.05 (s, 1H), 7.01 (d, J = 8.1 Hz, 1H), 6.34 (s, 1H), 5.21 (s, 2H), 4.17 (s, 3H), 4.02 (q, J = 7.3 Hz, 2H), 2.40 (s, 3H), 2.28 (s, 3H), 1.30 (t, J = 7.3 Hz, 3H) | 403 (M⁺), 385, 359, 241, 162, 145 (base) |

TABLE 87-continued

| Carboxylic acid | Hydroxy compound | Example | ¹H-NMR | Mass, m/z |
|---|---|---|---|---|
| Example 8-9 | (1-Methyl-1H-indazol-6-yl)methanol | Example 9-297 | (DMSO-d$_6$) δ: 9.75 (br s, 1H), 8.05 (d, J = 0.8 Hz, 1H), 7.84 (d, J = 8.1 Hz, 1H), 7.79 (d, J = 8.1 Hz, 1H), 7.70 (s, 1H), 7.21 (d, J = 8.5 Hz, 1H), 7.15 (d, J = 1.9 Hz, 1H), 7.03 (dd, J = 1.9, 8.5 Hz, 1H), 6.60 (s, 1H), 5.32 (s, 2H), 4.05 (s, 3H), 3.86 (s, 3H), 3.71 (s, 3H) | 425 (M⁺), 381, 263, 162, 145 (base) |
| Example 8-9 | Example 4-7 | Example 9-298 | (CDCl$_3$) δ: 7.99 (s, 1H), 7.83 (d, J = 8.5 Hz, 1H), 7.73 (d, J = 8.1 Hz, 1H), 7.42 (br s, 1H), 7.18-7.15 (m, 2H), 6.98 (dd, J = 1.9, 8.5 Hz, 1H), 6.92 (d, J = 1.9 Hz, 1H), 6.83 (s, 1H), 5.36 (s, 2H), 4.43 (br s, 2H), 3.85 (s, 3H), 3.77 (s, 3H), 1.49 (br s, 3H) | 439 (M⁺), 395, 263, 176, 159 (base) |
| Example 8-17 | (1-Methyl-1H-indazol-6-yl)methanol | Example 9-299 | (DMSO-d$_6$) δ: 9.71 (br s, 1H), 8.05 (d, J = 0.8 Hz, 1H), 7.78 (d, J = 8.1 Hz, 1H), 7.69 (s, 1H), 7.41 (d, J = 8.1 Hz, 1H), 7.21 (d, J = 8.1 Hz, 1H), 7.05 (s, 1H), 7.02 (d, J = 8.1 Hz, 1H), 6.35 (s, 1H), 5.25 (s, 2H), 4.05 (s, 3H), 4.03 (q, J = 6.9 Hz, 2H), 2.40 (s, 3H), 2.28 (s, 3H), 1.31 (t, J = 7.3 Hz, 3H) | 403 (M⁺), 359, 241, 145 (base) |

TABLE 88

| Carboxylic acid | Hydroxy compound | Example | ¹H-NMR | Mass, m/z |
|---|---|---|---|---|
| Example 8-9 | Example 4-5 | Example 9-300 | (DMSO-d$_6$) δ: 9.74 (br s, 1H), 8.33 (s, 1H), 7.84 (d, J = 8.1 Hz, 1H), 7.72 (d, J = 8.9 Hz, 1H), 7.64 (s, 1H), 7.15 (d, J = 2.3 Hz, 1H), 7.08 (dd, J = 0.8, 8.5 Hz, 1H), 7.02 (dd, J = 1.9, 8.1 Hz, 1H), 6.60 (s, 1H), 5.25 (s, 2H), 4.17 (s, 3H), 3.86 (s, 3H), 3.70 (s, 3H) | 425 (M⁺), 381, 263, 162, 145 (base) |

TABLE 88-continued

| Carboxylic acid | Hydroxy compound | Example | ¹H-NMR | Mass, m/z |
|---|---|---|---|---|
| Example 8-9 | Example 4-6 | Example 9-301 | (DMSO-d₆) δ: 9.74 (br s, 1H), 8.38 (s, 1H), 7.84 (d, J = 8.5 Hz, 1H), 7.72 (d, J = 8.9 Hz, 1H), 7.65 (s, 1H), 7.15 (d, J = 1.9 Hz, 1H), 7.08 (dd, J = 0.8, 8.5 Hz, 1H), 7.02 (dd, J = 1.9, 8.1 Hz, 1H), 6.60 (s, 1H), 5.25 (s, 2H), 4.46 (q, J = 7.3 Hz, 2H), 3.86 (s, 3H) 3.70 (s, 3H), 1.51 (t, J = 7.3 Hz, 3H) | 439 (M⁺), 395, 263, 176, 159 (base) |
| Example 8-10 | Example 4-6 | Example 9-302 | (DMSO-d₆) δ: 9.66 (br s, 1H), 8.38 (s, 1H), 7.86 (d, J = 8.5 Hz, 1H), 7.72 (d, J = 8.9 Hz, 1H), 7.65 (s, 1H), 7.15 (d, J = 1.9 Hz, 1H), 7.07 (d, J = 8.5 Hz, 1H), 7.03 (dd, J = 1.9, 8.5 Hz, 1H), 6.59 (s, 1H), 5.25 (s, 2H), 4.46 (q, J = 7.3 Hz, 2H), 4.04 (q, J = 7.3 Hz, 2H), 3.87 (s, 3H) 1.51 (t, J = 7.3 Hz, 3H), 1.30 (t, J = 7.3 Hz, 3H) | 453 (M⁺), 409, 277, 176, 159 (base) |
| Example 8-17 | Example 4-5 | Example 9-303 | (DMSO-d₆) δ: 9.70 (br s, 1H), 8.33 (s, 1H), 7.72 (d, J = 8.9 Hz, 1H), 7.64 (s, 1H), 7.41 (d, J = 8.1 Hz, 1H), 7.07 (d, J = 9.2 Hz, 1H), 7.05 (s, 1H), 7.02 (d, J = 8.1 Hz, 1H), 6.35 (s, 1H), 5.25 (s, 2H), 4.17 (s, 3H), 4.04 (q, J = 7.3 Hz, 2H), 2.40 (s, 3H), 2.28 (s, 3H), 1.31 (t, J = 7.3 Hz, 3H) | 403 (M⁺), 359, 241, 145 (base) |
| Example 8-16 | Example 4-6 | Example 9-304 | (CDCl₃) δ: 7.92 (s, 1H), 7.69 (s, 1H), 7.66 (d, J = 8.5 Hz, 1H), 7.42 (d, J = 7.7 Hz, 1H), 7.09 (d, J = 8.1 Hz, 1H), 7.03 (s, 1H), 7.01 (d, J = 7.7 Hz, 1H), 6.73 (br s, 1H), 6.31 (s, 1H), 5.31 (s, 2H), 4.48 (q, J = 7.3 Hz, 2H), 3.76 (s, 3H), 2.41 (s, 3H), 2.32 (s, 3H), 1.63 (t, J = 7.3 Hz, 3H) | 403 (M⁺), 359, 227, 176, 159 (base) |

TABLE 89

| Carboxylic acid | Hydroxy compound | Example | ¹H-NMR | Mass, m/z |
|---|---|---|---|---|
| Example 8-17 | Example 4-6 | Example 9-305 | (CDCl₃) δ: 7.93 (s, 1H), 7.70 (s, 1H), 7.66 (d, J = 8.5 Hz, 1H), 7.43 (d, J = 7.7 Hz, 1H), 7.09 (d, J = 8.5 Hz, 1H), 7.03 (s, 1H), 7.01 (d, J = 8.1 Hz, 1H), 6.55 (br s, 1H), 6.32 (s, 1H), 5.31 (s, 2H), 4.48 (q, J = 7.3 Hz, 2H), 4.07 (q, J = 7.3 Hz, 2H), 2.42 (s, 3H), 2.31 (s, 3H), 1.63 (t, J = 7.3 Hz, 3H), 1.43 (t, J = 7.3 Hz, 3H) | 417 (M⁺), 373, 241, 176, 159 (base) |
| Example 8-25 | Example 1-1 | Example 9-306 | (DMSO-d₆) δ: 9.99 (br s, 1H), 8.19 (s, 1H), 7.70 (s, 1H), 7.57 (d, J = 8.5 Hz, 1H), 7.53-7.43 (m, 5H), 7.33 (dd, J = 1.2, 8.5 Hz, 1H), 6.43 (s, 1H), 5.25 (s, 2H), 3.84 (s, 3H), 3.72 (s, 3H) | 361 (M⁺), 317, 199, 145 (base) |
| Example 8-2 | Example 1-1 | Example 9-307 | (DMSO-d₆) δ: 10.08 (br s, 1H), 8.06 (s, 1H), 7.83 (d, J = 0.8 Hz, 1H), 7.80 (s, 1H), 7.65 (d, J = 8.9 Hz, 1H), 7.56 (dd, J = 1.9, 8.1 Hz, 1H), 7.51 (d, J = 8.1 Hz, 1H), 7.44 (dd, J = 1.5, 8.9 Hz, 1H), 6.39 (s, 1H), 5.23 (s, 2H), 4.05 (s, 3H), 3.52 (s, 3H) | 417 (M⁺), 385, 267, 241, 145 (base) |
| Example 8-26 | Example 1-1 | Example 9-308 | (DMSO-d₆) δ: 9.92 (br s, 1H), 8.19 (s, 1H), 7.69 (s, 1H), 7.57 (d, J = 8.1 Hz, 1H), 7.32 (dd, J = 1.5, 8.1 Hz, 1H), 7.31 (dd, J = 6.6, 8.5 Hz, 1H), 7.08 (dd, J = 2.3, 11.6 Hz, 1H), 6.87 (dt, J = 2.3, 8.5 Hz, 1H), 6.26 (s, 1H), 5.24 (s, 2H), 3.84 (s, 3H), 3.82 (s, 3H), 3.47 (s, 3H) | 409 (M⁺), 365, 247, 162, 147 (base) |
| Example 8-27 | Example 1-1 | Example 9-309 | (DMSO-d₆) δ: 8.20 (s, 1H), 7.69 (s, 1H), 7.58 (d, J = 8.5 Hz, 1H), 7.32 (d, J = 8.1 Hz, 1H), 7.29 (d, J = 8.1 Hz, 1H), 7.25 (d, J = 1.9 Hz, 1H), 7.11 (dd, J = 1.9, 8.1 Hz, 1H), 6.29 (s, 1H), 5.23 (s, 2H), 3.84 (s, 3H), 3.83 (s, 3H), 3.49 (s, 3H) | 425 (M⁺), 381, 263, 145 (base) |

TABLE 90

| Carboxylic acid | Hydroxy compound | Example | ¹H-NMR | Mass, m/z |
|---|---|---|---|---|
| Example 8-27 | Example 4-1 | Example 9-310 | (DMSO-d$_6$) δ: 9.98 (br s, 1H), 8.06 (s, 1H), 7.79 (s, 1H), 7.65 (d, J = 8.9 Hz, 1H), 7.44 (d, J = 8.9 Hz, 1H), 7.29 (d, J = 8.1 Hz, 1H), 7.25 (d, J = 1.9 Hz, 1H), 7.11 (dd, J = 1.9, 8.1 Hz, 1H), 6.28 (s, 1H), 5.23 (s, 2H), 4.05 (s, 3H), 3.83 (s, 3H), 3.48 (s, 3H) | 425 (M⁺), 381, 263, 145 (base) |
| Example 8-24 | Example 1-1 | Example 9-311 | (DMSO-d$_6$) δ: 9.30 (br s, 1H), 8.20 (s, 1H), 7.72 (s, 1H), 7.59 (d, J = 8.5 Hz, 1H), 7.35 (d, J = 5.4 Hz, 1H), 7.26 (d, J = 8.1 Hz, 1H), 7.15 (d, J = 1.5 Hz, 1H), 7.03 (dd, J = 1.5, 8.1 Hz, 1H), 5.27 (s, 3H), 3.85 (s, 3H), 3.78 (s, 3H), 3.61 (s, 3H), 1.72 (s, 3H) | 277, 144 (base) |
| Example 8-24 | Example 2-1 | Example 9-312 | (DMSO-d$_6$) δ: 9.28 (br s, 1H), 7.58 (s, 1H), 7.49 (d, J = 8.5 Hz, 1H), 7.27 (s, 1H), 7.25 (s, 1H), 7.15 (d, J = 1.9 Hz, 1H), 7.03 (dd, J = 1.9, 8.1 Hz, 1H), 5.24 (s, 3H), 3.78 (s, 3H), 3.74 (s, 3H), 3.61 (s, 3H), 2.53 (s, 3H), 1.71 (s, 3H) | 453 (M⁺), 409, 159 (base) |
| Example 8-24 | Example 1-2 | Example 9-313 | (DMSO-d$_6$) δ: 9.30 (br s, 1H), 8.28 (s, 1H), 7.72 (s, 1H), 7.63 (d, J = 8.1 Hz, 1H), 7.33 (d, J = 7.7 Hz, 1H), 7.26 (d, J = 8.1 Hz, 1H), 7.14 (d, J = 1.5 Hz, 1H), 7.03 (dd, J = 1.5, 8.1 Hz, 1H), 5.27 (s, 3H), 4.29 (q, J = 7.3 Hz, 2H), 3.78 (s, 3H), 3.62 (s, 3H), 1.72 (s, 3H), 1.42 (t, J = 7.3 Hz, 3H) | 453 (M⁺), 159 (base) |

TABLE 91

| Carboxylic acid | Hydroxy compound | Example | ¹H-NMR | Mass, m/z |
|---|---|---|---|---|
| Example 8-24 | Example 4-1 | Example 9-314 | (DMSO-d$_6$) δ: 9.29 (br s, 1H), 8.07(s, 1H), 7.83 (s, 1H), 7.67 (d, J = 8.5 Hz, 1H), 7.48 (s, 1H), 7.26 (d, J = 8.1 Hz, 1H), 7.14 (d, J = 2.9 Hz, 1H), 7.03 (dd, J = 1.9, 8.1 Hz, 1H), 5.26 (s, 3H), 4.05 (s, 3H), 3.78 (s, 3H), 3.61 (s, 3H), 1.71 (s, 3H) | 439 (M⁺), 395, 145 (base) |
| Example 8-28 | 4-Methoxy benzyl alcohol | Example 9-315 | (DMSO-d$_6$) δ: 12.34 (br s, 1H), 9.88 (br s, 1H), 7.35 (d, J = 8.9 Hz, 2H), 7.30 (d, J = 7.7 Hz, 1H), 7.13 (s, 1H), 7.08 (d, J = 7.7 Hz, 1H), 6.94 (d, J = 8.9 Hz, 1H), 6.41 (s, 1H), 5.06 (s, 2H), 3.76 (s, 3H), 2.32 (s, 3H), 2.30 (s, 3H) | 351 (M⁺), 121 (base) |
| Example 8-29 | Example 1-1 | Example 9-316 | (DMSO-d$_6$) δ: 12.41 (br s, 1H), 9.92 (br s, 1H), 8.19 (s, 1H), 7.71 (s, 1H), 7.65 (d, J = 6.9 Hz, 1H), 7.57 (d, J = 8.5 Hz, 1H), 7.33 (dd, J = 1.5, 8.5 Hz, 1H), 7.20 (s, 1H), 7.08 (dd, J = 1.9, 8.1 Hz, 1H), 6.73 (s, 1H), 5.25 (s, 2H), 3.90 (s, 3H), 3.84 (s, 3H) | 411 (M⁺), 267, 133 (base) |
| Example 8-28 | Example 1-1 | Example 9-317 | (DMSO-d$_6$) δ: 12.34 (br s, 1H), 9.92 (br s, 1H), 8.19 (s, 1H), 7.71 (s, 1H), 7.57 (d, J = 8.5 Hz, 1H), 7.33 (dd, J = 1.5, 8.5 Hz, 1H), 7.30 (d, J = 7.7 Hz, 1H), 7.12 (s, 1H), 7.08 (d, J = 7.7 Hz, 1H), 6.43 (s, 1H), 5.25 (s, 2H), 3.84 (s, 3H), 2.32 (s, 3H), 2.30 (s, 3H) | 375 (M⁺), 331, 145 (base) |
| Example 8-23 | Example 1-1 | Example 9-318 | (DMSO-d$_6$) δ: 9.80 (br s, 1H), 8.20 (s, 1H), 7.73 (s, 1H), 7.65 (dd, J = 0.8, 1.9 Hz, 1H), 7.59 (d, J = 8.1 Hz, 1H), 7.36 (d, J = 8.5 Hz, 1H), 6.64 (d, J = 2.7 Hz, 1H), 6.53 (dd, J = 1.5, 3.1 Hz, 1H), 6.39 (s, 1H), 5.29 (s, 2H), 3.85 (s, 3H), 3.67 (s, 3H) | 351 (M⁺), 307, 189 (base), 162 |

TABLE 92

| Carboxylic acid | Hydroxy compound | Example | ¹H-NMR | Mass, m/z |
|---|---|---|---|---|
| | | Example 9-319 | | |
| Example 8-22 | 4-Methoxy benzyl alcohol | | (DMSO-$d_6$) δ :9.70 (brs, 1H), 7.58 (dd, J = 1.5, 7.3Hz, 1H), 7.37 (d, J = 8.1Hz, 2H), 7.18 (dt, J = 1.9, 8.1Hz, 1H), 7.00-6.95 (m, 3H), 6.92(d, J = 8.1Hz, 1H), 5.09 (s, 4H), 4.01 (q, J = 6.9Hz, 2H), 3.77 (s, 3H), 2.32 (s, 3H), 1.30 (t, J = 6.9Hz, 3H) | 379 (M⁺), 335, 121 (base) |
| | | Example 9-320 | | |
| Example 8-21 | Example 1-1 | | (DMSO-$d_6$) δ :9.76 (brs, 1H), 8.21 (s, 1H), 7.73 (s, 1H), 7.59 (d, J = 8.5 Hz, 1H), 7.56 (dd, J = 1.2, 7.7Hz, 1H), 7.36 (d, J = 8.1Hz, 1H), 7.18 (dt, J = 1.5, 7.7Hz, 1H), 6.97 (dt, J = 0.8, 7.3Hz, 1H), 6.91 (d, J = 8.1 Hz, 1H), 5.28 (s, 2H), 5.11 (brs, 2H), 3.85 (s, 3H), 3.69 (s, 3H) | 389 (M⁺), 345, 226 (base) |
| | | Example 9-321 | | |
| Example 8-22 | Example 1-1 | | (DMSO-$d_6$) δ :9.70 (brs, 1H), 8.21 (s, 1H), 7.73 (s, 1H), 7.59 (d, J = 8.1Hz, 1H), 7.58 (dd, J = 1.5, 7.3Hz, 1H), 7.35 (d, J = 8.1Hz, 1H), 7.27-7.24 (m, 1H), 7.00-6.96(m, 1H), 6.92 (d, J = 7.7Hz, 1H), 5.28 (s, 2H), 5.09 (brs, 2H), 4.02 (q, J = 7.3 Hz, 2H), 3.85 (s, 3H), 2.31 (s, 3H), 1.30 (t, J = 7.3Hz, 3H) | 403 (M⁺), 240 (base) |
| | | Example 9-322 | | |
| Example 8-21 | Example 2-1 | | (DMSO-$d_6$) δ :9.74 (brs, 1H), 7.60 (s, 1H), 7.56 (d, J = 7.3Hz, 1H), 7.49 (d, J = 8.1Hz, 1H), 7.27 (d, J = 8.1Hz, 1H), 7.18 (t, J = 7.3Hz, 1H), 6.97 (t, J = 7.3 Hz, 1H), 6.91 (d, J = 8.1Hz, 1H), 5.25 (s, 2H), 5.10 (brs, 2H), 3.74 (s, 3H), 3.68 (s, 3H), 2.53 (s, 3H) | 403 (M⁺), 226 (base) |

TABLE 93

| Carboxylic acid | Hydroxy compound | Example | ¹H-NMR | Mass, m/z |
|---|---|---|---|---|
| | | Example 9-323 | | |
| Example 8-22 | Example 2-1 | | (DMSO-$d_6$) δ :9.71 (brs, 1H), 7.59 (s, 1H), 7.58 (d, J = 8.1Hz, 1H), 7.49 (d, J = 8.1Hz, 1H), 7.26 (d, J = 8.5Hz, 1H), 7.18 (dt, J = 1.5, 7.7Hz, 1H), 6.97 (dt, J = 0.8, 7.3hZ, 1H), 6.91 (d, J = 8.1Hz, 1H), 5.25 (s, 2H), 5.09 (brs, 2H), 4.02 (q, J = 7.3Hz, 2H), 3.74 (s, 3H), 1.30 (t, J = 7.3z, 3H) | 417 (M⁺), 240 (base) |

TABLE 93-continued

| Carboxylic acid | Hydroxy compound | Example | ¹H-NMR | Mass, m/z |
|---|---|---|---|---|
| | | Example 9-324 | | |
| Example 8-21 | Example 4-1 | | (DMSO-d$_6$) δ :9.80 (brs, 1H), 8.08 (s, 1H), 7.84 (s, 1H), 7.67 (d, J = 8.9Hz, 1H), 7.56 (dd, J = 1.5, 7.7Hz, 1H), 7.48 (d, J = 8.5Hz, 1H), 7.18 (dt, J = 1.5, 8.1Hz, 1H), 6.97 (dt, J = 0.8, 7.3Hz, 1H), 6.91 (d, J = 7.7Hz, 1H), 5.27 (s, 2H), 5.11 (brs, 2H), 4.06 (s, 3H), 3.69 (s, 3H) | 389 (M⁺), 345, 145 (base) |
| | | Example 9-325 | | |
| Example 8-22 | Example 4-1 | | (DMSO-d$_6$) δ :9.71 (brs, 1H), 8.07 (s, 1H), 7.83 (s, 1H), 7.67 (d, J = 8.5Hz, 1H), 7.58 (dd, J = 1.5, 7.7Hz, 1H), 7.47 (d, J = 8.5Hz, 1H), 7.18 (dt, J = 1.5, 7.7Hz, 1H), 6.99-6.96 (m, 1H), 6.92 (d, J = 8.1Hz, 1H), 5.27 (s, 2H), 5.10 (brs, 2H), 4.06 (s, 3H), 4.01 (q, J = 7.3Hz, 2H), 1.30 (t, J = 7.3Hz, 3H) | 403 (M⁺), 359, 145 (base) |
| | | Example 9-326 | | |
| Example 8-35 | Example 1-1 | | (DMSO-d$_6$) δ :9.91 (brs, 1H), 8.20 (s, 1H), 7.72 (s, 1H), 7.70 (d, J = 7.7Hz, 1H), 7.58 (d, J = 8.1Hz, 1H), 7.50 (s, 1H), 7.37-7.34 (m, 2H), 7.27 (dd, J = 6.9, 7.7Hz, 1H), 5.27 (s, 2H), 3.95 (s, 3H), 3.84 (s, 3H), 3.63 (brs, 3H) | 373 (M⁺), 329, 211 (base) |

TABLE 94

| Carboxylic acid | Hydroxy compound | Example | ¹H-NMR | Mass, m/z |
|---|---|---|---|---|
| | | Example 9-327 | | |
| Example 8-35 | Example 2-1 | | (DMSO-d$_6$) δ :9.89 (brs, 1H), 7.70 (d, J = 7.7Hz, 1H), 7.58 (s, 1H), 7.51 (s, 1H), 7.48 (d, J = 8.5Hz, 1H), 7.38-7.34 (m, 1H), 7.29-7.25 (m, 2H), 5.24 (s, 2H), 3.95 (s, 3H), 3.73 (s, 3H), 3.63 (brs, 2H), 2.52 (s, 3H) | 387 (M⁺), 343, 159 (base) |
| | | Example 9-328 | | |
| Example 8-35 | Example 4-1 | | (DMSO-d$_6$) δ :9.92 (brs, 1H), 8.07 (d, J = 0.8Hz, 1H), 7.82 (s, 1H), 7.70 (d, J = 7.3 Hz, 1H), 7.66 (d, J = 8.5Hz, 1H), 7.50 (s, 1H), 7.47 (dd, J = 1.2, 8.5Hz, 1H), 7.37-7.34 (m, 1H), 7.29-7.25 (m, 1H), 5.26 (s, 2H), 4.05 (s, 3H), 3.95 (s, 3H), 3.63 (brs, 3H) | 373 (M⁺), 329, 145 (base) |

TABLE 94-continued

| Carboxylic acid | Hydroxy compound | Example | ¹H-NMR | Mass, m/z |
|---|---|---|---|---|
| | | Example 9-329 | | |
| Example 8-9 | 4-Fluoro benzyl alcohol | | (DMSO-d$_6$) δ :9.73 (brs, 1H), 7.84 (d, J = 8.1Hz, 1H), 7.51-7.48 (m, 2H), 7.26-7.22 (m, 2H), 7.15 (d, J = 1.9Hz, 1H), 7.02 (dd, J = 1.9, 8.1Hz, 1H), 6.58 (s, 1H), 5.16 (s, 2H), 3.87 (s, 3H), 3.69 (s, 3H) | 389 (M⁺), 263, 236, 126, 109 (base) |
| | | Example 9-330 | | |
| 5-(4-Chloro phenyl)furan-2-carboxylic acid | Example 1-2 | | (DMSO-d$_6$) δ :10.47 (brs, 1H), 8.27 (s, 1H), 7.72 (s, 1H), 7.62 (d, J = 8.5Hz, 1H), 7.58 (d, J = 8.9Hz, 2H), 7.44 (d, J = 8.9Hz, 2H), 7.33 (dd, J = 1.5, 8.5Hz, 1H), 6.94 (d, J = 3.5Hz, 1H), 6.12 (d, J = 3.1Hz, 1H), 5.27 (s, 2H), 4.28 (q, J = 7.3 Hz, 2H), 1.41 (t, J = 7.3 Hz, 3H) | 395 (M⁺), 351, 159 (base) |
| | | Example 9-331 | | |
| 3-(4-Chloro phenyl)-2-methylfuran-3-carboxylic acid | Example 1-2 | | (DMSO-d$_6$) δ :9.14 (brs, 1H), 8.26 (s, 1H), 7.72 (s, 1H), 7.63 (d, J = 8.1Hz, 1H), 7.62 (d, J = 8.1Hz, 2H), 7.43 (d, J = 8.5 Hz, 2H), 7.33 (dd, J = 0.8, 8.1Hz, 1H), 7.08 (brs, 1H), 5.24 (s, 2H), 4.28 (q, J = 7.3Hz, 2H), 2.27 (s, 3H), 1.41 (t, J = 7.3Hz, 3H) | 409 (M⁺), 365, 159 (base) |

TABLE 95

| Carboxylic acid | Hydroxy compound | Example | ¹H-NMR | Mass, m/z |
|---|---|---|---|---|
| | | Example 9-332 | | |
| 4-(4-Chloro phenyl) thiophene-2-carboxylic acid | Example 1-2 | | (DMSO-d$_6$) δ :10.82 (brs, 1H), 8.27 (s, 1H), 7.73 (s, 1H), 7.63 (d, J = 8.1Hz, 1H), 7.61 (d, J = 8.1Hz, 2H), 7.43 (d, J = 8.1Hz, 2H), 7.35(dd, J = 1.2, 8.5Hz, 1H), 7.30 (d, J = 1.5Hz, 1H), 6.90 (d, J = 1.5Hz, 1H), 5.30 (s, 2H), 4.28 (q, J = 7.3 Hz, 2H), 1.41 (t, J = 7.3Hz, 3H) | 411 (M⁺), 367, 235 (base) |
| | | Example 9-333 | | |
| 4-(4-Chloro phenyl) thiophene-2-carboxylic acid | — | | (DMSO-d$_6$) δ :10.82 (brs, 1H), 7.62-7.60 (m, 3H), 7.43 (d, J = 8.5Hz, 2H), 7.31 (d, J = 1.5Hz, 1H), 7.26 (dd, J = 1.5, 8.5Hz, 1H), 6.89 (d, J = 1.5Hz, 1H), 5.28 (s, 2H), 4.09 (t, J = 6.2Hz, 2H), 2.96 (t, J = 6.2Hz, 2H), 2.08-2.02 (m, 2H), 1.96-1.90 (m, 2H) | 437 (M⁺), 393, 235 (base) |
| | | Example 9-334 | | |
| 5-(2,4-Dichloro phenyl)thia diazole-2-carboxylic acid | Example 1-1 | | (DMSO-d$_6$) δ :12.47 (brs, 1H), 8.22 (s, 1H), 8.13 (d, J = 8.5 Hz, 1H), 7.88 (d, J = 2.3Hz, 1H), 7.76 (s, 1H), 7.61 (dd, J = 2.3, 8.5Hz, 1H), 7.60 (d, J = 8.1Hz, 1H), 7.38 (dd, J = 1.5, 8.5Hz, 1H), 5.40 (s, 2H), 3.85 (s, 3H) | 389 (M⁺ − 44), 133 (base) |

TABLE 95-continued

| Carboxylic acid | Hydroxy compound | Example | ¹H-NMR | Mass, m/z |
|---|---|---|---|---|
| | | Example 9-335 | | |
| 5-(2,4-Dichlorophenyl)thiadiazole-2-carboxylic acid | Example 4-1 | 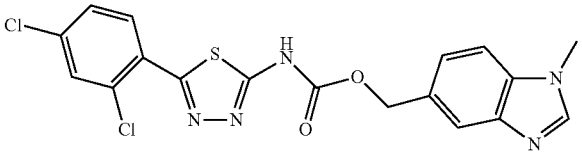 [SMILES: Cn1cnc2cc(COC(=O)Nc3nnc(-c4ccc(Cl)cc4Cl)s3)ccc21] | (DMSO-d$_6$) δ :12.47 (brs, 1H), 8.13 (d, J = 8.5Hz, 1H), 8.09 (d, J = 8.5Hz, 1H), 7.89 (d, J = 2.3Hz, 1H), 7.86 (s, 1H), 7.68 (d, J = 8.9Hz, 1H), 7.62 (dd, J = 2.3, 8.5Hz, 1H), 7.49 (dd, J = 1.5, 8.5Hz. 1H), 5.39 (s, 2H), 4.06 (s, 3H) | 433 (M⁺), 389, 145 (base) |
| | | Example 9-336 | | |
| Example 7-8 | 4-Methoxy phenethyl alcohol | 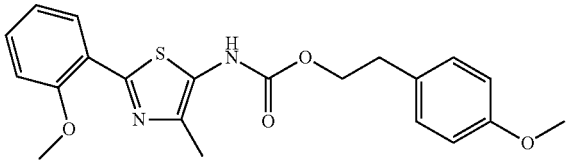 [SMILES: COc1ccc(CCOC(=O)Nc2sc(-c3ccccc3OC)nc2C)cc1] | (DMSO-d$_6$) δ :9.90 (brs, 1H), 8.18 (dd, J = 1.5, 7.7Hz, 1H), 7.42-7.37 (m, 1H), 7.23-7.19 (m, 2H), 7.12 (dd, J = 1.9, 6.6 Hz, 1H), 7.08-7.04 (m, 1H), 6.89 (d, J = 8.1Hz, 1H), 6.85-6.81 (m, H), 4.30 (t, J = 6.9Hz, 2H), 3.98 (s, 3H), 3.72 (s, 3 H), 2.90 (t, J = 6.9Hz, 2H), 2.30 (s, 3H) | 398 (M⁺), 135 (base) |

TABLE 96

| Carboxylic acid | Hydroxy compound | Example | ¹H-NMR | Mass, m/z |
|---|---|---|---|---|
| | | Example 9-337 | | |
| Example 8-5 | Example 1-5 | 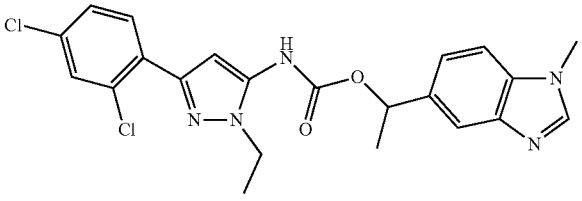 [SMILES: CCn1nc(-c2ccc(Cl)cc2Cl)cc1NC(=O)OC(C)c1ccc2c(c1)ncn2C] | (DMSO-d$_6$) δ :9.76 (brs, 1H), 8.19 (s, 1H), 7.81 (d, J = 8.5Hz, 1H), 7.70 (s, 1H), 7.65 (d, J = 2.3Hz, 1H), 7.57 (d, J = 8.1 Hz, 1H), 7.46 (dd, J = 2.3, 8.5Hz, 1H), 7.34 (d, J = 8.1Hz, 1 H), 6.64 (s, 1H), 5.95 (q, J = 6.6Hz, 1H), 4.06 (q, J = 7.3Hz, 2H), 3.84 (s, 3H), 1.61 (d, J = 6.6Hz, 3H), 1.30 (t, J = 7.3Hz, 3H) | 457 (M⁺), 158 (base) |
| | | Example 9-338 | | |
| Example 8-9 | Example 1-5 | 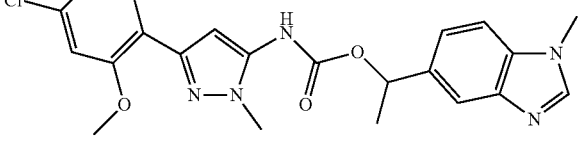 | (DMSO-d$_6$) δ :9.66 (brs, 1H), 8.19 (s, 1H), 7.83 (d, J = 8.5Hz, 1H), 7.70 (s, 1H), 7.57 (d, J = 8.5Hz, 1H), 7.34 (d, J = 8.1 Hz, 1H), 7.14 (d, J = 1.9Hz, 1H), 7.02 (dd, J = 1.9, 8.1Hz, 1 H), 6.56 (s, 1H), 5.95 (q, J = 6.6Hz, 1H), 3.85 (s, 3H), 3.84 (s, 3H), 3.68 (s, 3H), 1.61 (d, J = 6.6Hz, 3H) | 395 (M⁺ − 44), 133 (base) |
| | | Example 9-339 | | |
| Example 8-16 | Example 1-5 | 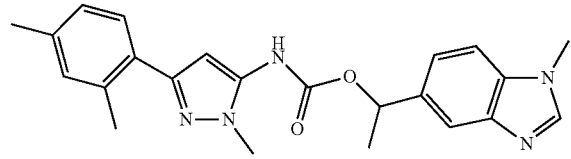 | (DMSO-d$_6$) δ :9.69 (brs, 1H), 8.19 (s, 1H), 7.70 (s, 1H), 7.57 (d, J = 8.1Hz, 1H), 7.38 (d, J = 7.7Hz, 1H), 7.34 (d, J = 8.5 Hz, 1H), 7.04 (s, 1H), 7.00 (d, J = 8.1 Hz, 1H), 6.30 (s, 1H), 5.95 (q, J = 6.6Hz, 1H), 3.84 (s, 3H), 3.68 (s, 3H), 2.38 (s, 3H), 2.27 (s, 3H), 1.61 (d, J = 6.6Hz, 3H) | 403 (M⁺), 359, 158 (base) |

TABLE 96-continued

| Carboxylic acid | Hydroxy compound | Example | ¹H-NMR | Mass, m/z |
|---|---|---|---|---|
| | | Example 9-340 | | |
| — | Example 3-7 | 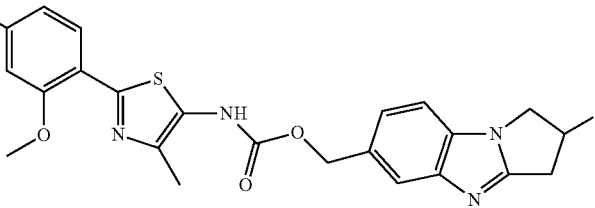 | (DMSO-d$_6$) δ :10.09 (brs, 1H), 8.17 (d, J = 8.5Hz, 1H), 7.65 (s, 1H), 7.47 (d, J = 8.1Hz, 1H), 7.30 (d, J = 1.9Hz, 1H), 7.26 (d, J = 8.1Hz, 1H), 7.12 (dd, J = 1.9, 8.5Hz, 1H), 5.64 (d, J = 4.2Hz, 1H), 5.29 (s, 2H), 5.01-4.97 (m, 1H), 4.30 (dd, J = 5.8Hz, 11.2Hz, 1H), 4.02 (s, 3H), 3.93 (dd, J = 2.3, 11.3Hz, 1H), 3.29-3.24 (m, 1H), 2.79 (dd, J = 2.7, 17.0Hz, 1H), 2.31 (s, 3H) | 440 (M$^+$ − 44), 254 (base) |
| | | Example 9-341 | | |
| Example 7-14 | Example 3-7 | 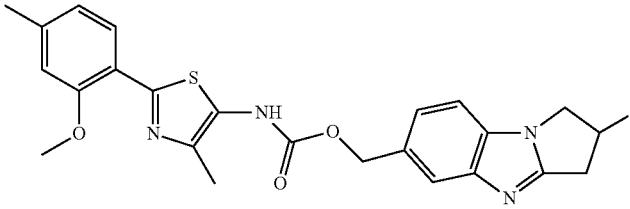 | (DMSO-d$_6$) δ :9.94 (brs, 1H), 8.04 (d, J = 8.1Hz, 1H), 7.64 (s, 1H), 7.47 (d, J = 8.5Hz, 1H), 7.26 (d, J = 8.5Hz, 1H), 7.02 (s, 1H), 6.87 (d, J = 8.1Hz, 1H), 5.64 (d, J = 4.2Hz, 1H), 5.28 (s, 2H), 5.01-4.97 (m, 1H), 4.30 (dd, J = 5.8, 11.2Hz, 1 H), 3.96 (s, 3H), 3.93 (dd, J = 2.7, 11.3Hz, 1H), 3.34-3.24 (m, 1H), 2.79 (dd, J = 2.7, 17.0Hz, 1H), 2.35 (s, 3H), 2.28 (s, 3H) | 420 (M$^+$ − 44), 234 (base) |

TABLE 97

| Carboxylic acid | Hydroxy compound | Example | ¹H-NMR | Mass, m/z |
|---|---|---|---|---|
| | | Example 9-342 | | |
| Example 7-14 | Example 3-8 | 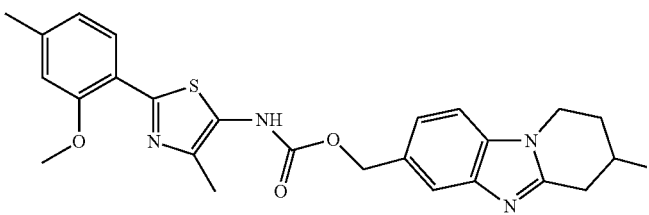 | (DMSO-d$_6$) δ :9. 94 (brs, 1H), 8.04 (d, J = 7.7Hz, 1H), 7.61 (s, 1H), 7.48 (d, J = 8.5Hz, 1H), 7.27 (d, J = 8.1Hz, 1H), 7.02 (s, 1H), 6.87 (d, J = 8.1Hz, 1H), 5.28 (s, 2H), 5.17 (d, J = 3.5Hz, 1H), 4.28-4.27 (m, 1H), 4.13 (t, J = 6.6Hz, 1H), 3.96 (s, 3H), 3.15 (dd, J = 3.9, 17.0Hz, 1H), 2.90 (dd, J = 5.4, 17.0 Hz, 1H), 2.35 (s, 3H), 2.28 (s, 3H), 2.19-2.11 (m, 2H) | 478 (M$^+$), 434, 201 (base) |
| | | Example 9-343 | | |
| — | Example 3-8 | 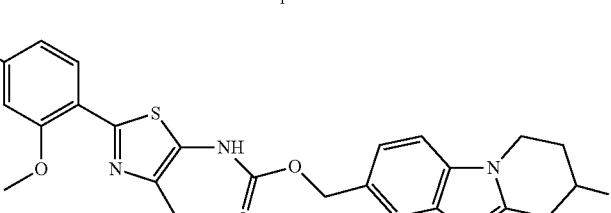 | (DMSO-d$_6$) δ :10.08 (brs, 1H), 7.16 (d, J = 8.5Hz, 1H), 7.62 (s, 1H), 7.48 (d, J = 8.1Hz, 1H), 7.30 (d, J = 1.9Hz, 1H), 7.28 (d, J = 8.5Hz, 1H), 7.12 (dd, J = 1.9, 8.5Hz, 1H), 5.29 (s, 2 H), 5.18 (d, J = 3.5Hz, 1H), 4.29-4.26 (m, 1H), 4.13 (t, J = 6.6Hz, 1H), 4.02 (s, 3H), 3.15 (dd, J = 4.2, 17.0Hz, 1H), 2.90 (dd, J = 5.4, 17.3Hz, 1H), 2.31 (s, 3H), 2.19-1.91 (m, 2H) | 454 (M$^+$ − 44), 254 (base) |

TABLE 97-continued

| Carboxylic acid | Hydroxy compound | Example | ¹H-NMR | Mass, m/z |
|---|---|---|---|---|
| | | Example 9-344 | | |
| Example 7-31 | Example 1-1 | 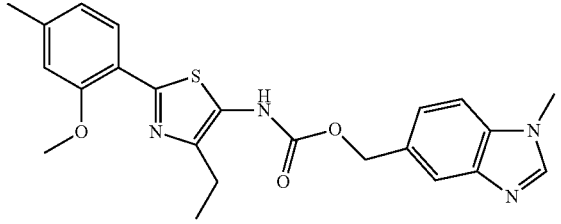 | (DMSO-d₆) δ :9.91 (brs, 1H), 8.20 (s, 1H), 8.07 (d, J = 7.7Hz, 1H), 7.74 (s, 1H), 7.59 (d, J = 8.1Hz, 1H), 7.36 (d, J = 8.1 Hz, 1H), 7.02 (s, 1H), 6.88 (d, J = 8.1Hz, 1H), 5.30 (s, 2H), 3.96 (s, 3H), 3.85 (s, 3H), 2.66 (q, J = 7.7Hz, 2H), 2.36 (s, 3H), 1.17 (t, J = 7.7Hz, 3H) | 436 (M⁺), 392, 274 (base) |
| | | Example 9-345 | | |
| Example 7-41 | Example 1-2 | 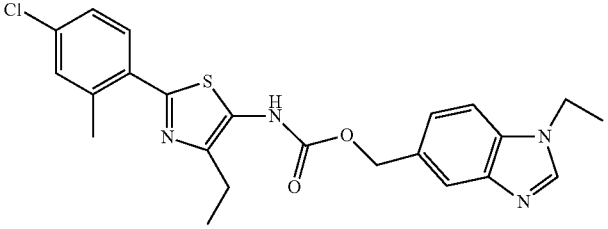 [SMILES: CCc1nc(-c2ccc(Cl)cc2C)sc1NC(=O)OCc1ccc2c(c1)ncn2CC] | (DMSO-d₆) δ :10.20 (brs, 1H), 8.27 (s, 1H), 7.75 (s, 1H), 7.70 (d, J = 8.5Hz, 1H), 7.63 (d, J = 8.1Hz, 1H), 7.44 (d, J = 2.3Hz, 1H), 7.36 (d, J = 1.9Hz, 1H), 7.34 (d, J = 1.9Hz, 1H), 5.31 (s, 2H), 4.29 (q, J = 7.3Hz, 2H), 2.69 (q, J = 7.3Hz, 2H), 2.53 (s, 3H), 1.41 (t, J = 7.3Hz, 3H), 1.17 (t, J = 7.3Hz, 3H) | 454 (M⁺), 410, 278 (base) |

TABLE 98

| Carboxylic acid | Hydroxy compound | Example | ¹H-NMR | Mass, m/z |
|---|---|---|---|---|
| | | Example 9-346 | | |
| Example 7-40 | Example 1-2 | 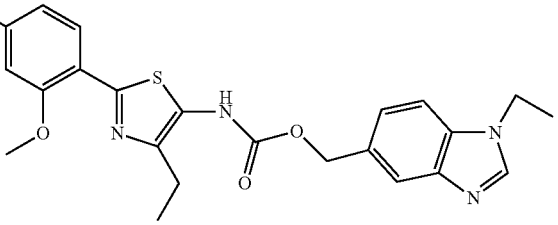 | (DMSO-d₆) δ :9.99 (brs, 1H), 8.27 (s, 1H), 8.20 (dd, J = 6.9, 8.9Hz, 1H), 7.74 (s, 1H), 7.63 (d, J = 8.5Hz, 1H), 7.35 (d, J = 8.5Hz, 1H), 7.13 (dd, J = 2.3, 11.2Hz, 1H), 6.91 (dt, J = 2.7, 8.5Hz, 1H), 5.30 (s, 2H), 4.29 (q, J = 7.3Hz, 2H), 4.00 (s, 3H), 2.67 (q, J = 7.3Hz, 2H), 1.41 (t, J = 7.3Hz, 3H), 1.17 (t, J = 7.7Hz, 3H) | 454 (M⁺), 410 |
| | | Example 9-347 | | |
| Example 7-27 | Example 3-2 | 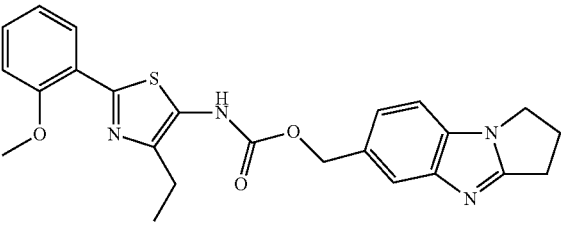 [SMILES: CCc1nc(-c2ccccc2OC)sc1NC(=O)OCc1ccc2c(c1)nc1n2CCC1] | (DMSO-d₆) δ :9.97 (brs, 1H), 8.19 (dd, J = 1.9, 8.1Hz, 1H), 7.64 (s, 1H), 7.45 (d, J = 8.1Hz, 1H), 7.41-7.37 (m, 1H), 7.25 (d, J = 8.5Hz, 1H), 7.20 (d, J = 8.1Hz, 1H), 7.08-7.04 (m, 1H), 5.28 (s, 2H), 4.12 (t, J = 6.9Hz, 2H), 3.98 (s, 3H), 2.96 (t, J = 7.3Hz, 2H), 2.71-2.60 (m, 4H), 1.18 (t, J = 7.3Hz, 3H) | 448 (M⁺), 404 |
| | | Example 9-348 | | |
| Example 7-30 | Example 3-2 | 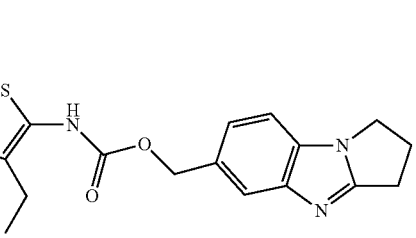 | (DMSO-d₆) δ :10.15 (brs, 1H), 7.70 (dd, J = 6.9, 8.9Hz, 1H), 7.63 (s, 1H), 7.45 (d, J = 8.1Hz, 1H), 7.25 (d, J = 8.1Hz, 1H), 7.21 (dd, J = 2.7, 10.0Hz, 1H), 7.12 (dt, J = 2.7, 8.5Hz, 1H), 5.28 (s, 2H), 4.11 (t, J = 6.9Hz, 2H), 2.96 (t, J = 7.3 Hz, 2H), 2.71-2.60 (m, 4H), 2.53 (s, 3H), 1.18 (t, J = 7.3Hz, 3H) | 450 (M⁺), 406, 262 (base) |

TABLE 98-continued

| Carboxylic acid | Hydroxy compound | Example | ¹H-NMR | Mass, m/z |
|---|---|---|---|---|
| | | Example 9-349 | | |
| Example 7-41 | Example 3-2 | 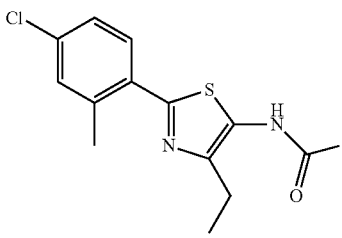 | (DMSO-d₆) δ :10.21 (brs, 1H), 7.70 (d, J = 8.1Hz, 1H), 7.64 (s, 1H), 7.45 (d, J = 8.1Hz, 1H), 7.44 (s, 1H), 7.35 (dd, J = 1.9, 8.1Hz, 1H), 7.25 (d, J = 8.5Hz, 1H), 5.29 (s, 2H), 4.11 (t, J = 6.9Hz, 2H), 2.96 (t, J = 7.3Hz, 2H), 2.72-2.60 (m, 4 H), 2.54 (s, 3H), 1.18 (t, J = 7.3Hz, 3H) | 466 (M⁺), 422 (base) |

TABLE 99

| Carboxylic acid | Hydroxy compound | Example | ¹H-NMR | Mass, m/z |
|---|---|---|---|---|
| | | Example 9-350 | | |
| Example 7-29 | Example 3-2 | | (DMSO-d₆) δ :10.10 (brs, 1H), 7.63 (s, 1H), 7.55 (d, J = 7.7 Hz, 1H), 7.45 (d, J = 8.1Hz, 1H), 7.25 (d, J = 8.1Hz, 1H), 7.14 (s, 1H), 7.10 (d, J = 8.1Hz, 1H), 5.28 (s, 2H), 4.11 (t, J = 6.9Hz, 2H), 2.96 (t, J = 7.7Hz, 2H), 2.68-2.62 (m, 4H), 2.50 (s, 3H), 2.31 (s, 3H), 1.17 (t, J = 7.7Hz, 3H) | 446 (M⁺), 402, 258 |
| | | Example 9-351 | | |
| Example 7-27 | — | | (DMSO-d₆) δ :9.97 (brs, 1H), 8.19 (dd, J = 1.5, 8.1Hz, 1H), 7.61 (s, 1H), 7.47 (d, J = 8.1Hz, 1H), 7.39 (dt, J = 1.5, 8.5Hz, 1H), 7.27 (d, J = 8.1Hz, 1H), 7.20 (d, J = 8.5Hz, 1H), 7.06 (t, J = 8.1 Hz, 1H), 5.28 (s, 2H), 4.10 (t, J = 6.1Hz, 2H), 3.98 (s, 3H), 2.96 (t, J = 6.1 Hz, 2H), 2.68 (q, J = 7.3Hz, 2H), 2.10-2.01 (m, 2H), 1.98-1.89 (m, 2H), 1.18 (t, J = 7.3Hz, 3H) | 462 (M⁺), 185 (base) |
| | | Example 9-352 | | |
| Example 7-40 | — | 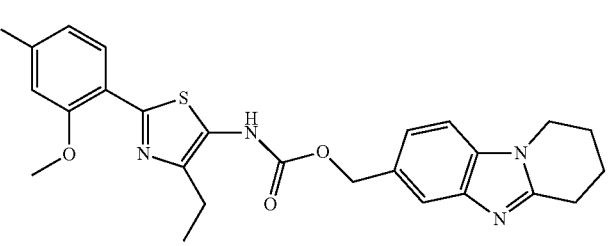 | (DMSO-d₆) δ :9.98 (brs, 1H), 8.20 (dd, J = 6.9, 8.9Hz, 1H), 7.61 (s, 1H), 7.46 (d, J = 8.1Hz, 1H), 7.26 (d, J = 8.5Hz, 1 H), 7.13 (dd, J = 2.3, 11.2Hz, 1H), 6.91 (dt, J = 2.3, 8.5Hz, 1H), 5.28 (s, 2H), 4.10 (t, J = 6.2Hz, 2H), 4.00 (s, 3H), 2.96 (t, J = 6.2Hz, 2H), 2.67 (q, J = 7.3Hz, 2H), 2.08-2.02 (m, 2 H), 1.96-1.90 (m, 2H), 1.17 (t, J = 7.3Hz, 3H) | 480 (M⁺), 436, 278 |

TABLE 99-continued

| Carboxylic acid | Hydroxy compound | Example | ¹H-NMR | Mass, m/z |
|---|---|---|---|---|
| | | Example 9-353 | | |
| Example 7-31 | — | 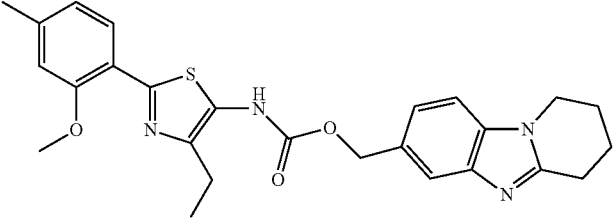 [SMILES: CCc1nc(-c2ccc(C)cc2OC)sc1NC(=O)OCc1ccc2c(c1)nc1n2CCCC1] | (DMSO-d₆) δ :9.90 (brs, 1H), 8.06 (d, J = 8.1Hz, 1H), 7.61 (s, 1H), 7.46 (d, J = 8.5Hz, 1H), 7.26 (d, J = 8.1Hz, 1H), 7.02 (s, 1H), 6.88 (d, J = 8.1Hz, 1H), 5.27 (s, 2H), 4.10 (t, J = 5.1Hz, 2H), 3.96 (s, 3H), 2.96 (t, J = 7.2Hz, 2H), 2.64 (q, J = 7.7Hz, 2H), 2.36 (s, 3H), 2.08-2.02 (m, 2H), 1.96-1.90 (m, 2H), 1.17 (t, J = 7.7Hz, 3H) | 476 (M⁺), 432, 274 (base) |

TABLE 100

| Carboxylic acid | Hydroxy compound | Example | ¹H-NMR | Mass, m/z |
|---|---|---|---|---|
| | | Example 9-354 | | |
| Example 7-29 | — | | (DMSO-d₆) δ :10.06 (brs, 1H), 7.61 (s, 1H), 7.55 (d, J = 7.7 Hz, 1H), 7.46 (d, J = 8.1Hz, 1H), 7.26 (d, J = 8.1Hz, 1H), 7.14 (s, 1H), 7.10 (d, J = 7.7Hz, 1H), 5.28 (s, 2H), 4.10 (t, J = 5.8Hz, 2H), 2.96 (t, J = 6.2Hz, 2H), 2.67 (q, J = 7.7Hz, 2H), 2.50 (s, 3H), 2.31 (s, 3H), 2.08-2.02 (m, 2H), 1.96-1.90 (m, 2H), 1.17 (t, J = 7.7Hz, 3H) | 460 (M⁺), 416, 185 (base) |
| | | Example 9-355 | | |
| Example 7-30 | — | | (DMSO-d₆) δ :10.15(brs, 1H), 7.70 (dd, J = 6.2, 8.9Hz, 1 H), 6.15 (s, 1H), 7.46 (d, J = 8.1Hz, 1H), 7.26 (d, J = 7.3Hz, 1H), 7.21 (dd, J = 2.7, 10.4Hz, 1H), 7.12 (dt, J = 2.7, 8.5Hz, 1H), 5.29 (s, 2H), 4.10 (t, J = 5.8Hz, 2H), 2.96 (t, J = 6.2 Hz, 2H), 2.68 (q, J = 7.3Hz, 2H), 2.53 (s, 3H), 2.08-2.02 (m, 2H), 1.96-1.90 (m, 2H), 1.17 (t, J = 7.7Hz, 3H) | 420 (M⁺ − 44), 185 (base) |
| | | Example 9-356 | | |
| Example 7-41 | — | 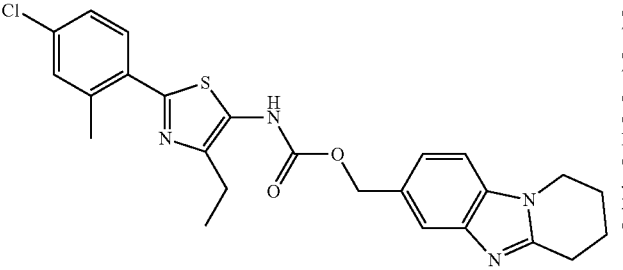 | (DMSO-d₆) δ :10.20 (brs, 1H), 7.70 (d, J = 8.5Hz, 1H), 7.61 (s, 1H), 7.46 (d, J = 8.1Hz, 1H), 7.44 (d, J = 1.9Hz, 1H), 7.35 (dd, J = 1.9, 8.5Hz, 1H), 7.27 (d, J = 7.3Hz, 1H), 5.29 (s, 2 H), 4.10 (t, J = 6.2Hz, 2H), 2.96 (t, J = 6.2Hz, 2H), 2.69 (q, J = 7.3Hz, 2H), 2.54 (s, 3H), 2.09-2.00 (m, 2H), 1.98-1.89 (m, 2H), 1.18 (t, J = 7.3Hz, 3H) | 480 (M⁺), 278 (base) |

TABLE 100-continued

| Carboxylic acid | Hydroxy compound | Example | $^1$H-NMR | Mass, m/z |
|---|---|---|---|---|
| | | Example 9-357 | | |
| Example 7-40 | Example 3-6 |  | (DMSO-$d_6$) δ :9.99 (brs, 1H), 8.20 (dd, J = 6.9, 8.9Hz, 1H), 7.69 (s, 1H), 7.55 (d, J = 8.1Hz, 1H), 7.33 (d, J = 8.1Hz, 1H), 7.13 (dd, J = 2.7, 11.2Hz, 1H), 6.91 (dt, J = 2.7, 8.5Hz, 1H), 5.30 (s, 2H), 4.96 (s, 2H), 4.22-4.15 (m, 4H), 4.00 (s, 3H), 2.67 (q, J = 7.3Hz, 2H), 1.17 (t, J = 7.3Hz, 3H) | 482 (M$^+$), 438, 278, 187 (base) |

TABLE 101

| Carboxylic acid | Hydroxy compound | Example | $^1$H-NMR | Mass, m/z |
|---|---|---|---|---|
| | | Example 9-358 | | |
| Example 7-31 | Example 3-6 | | (DMSO-$d_6$) δ :9.91 (brs, 1H), 8.07 (d, J = 8.1Hz, 1H), 7.68 (s, 1H), 7.55 (d, J = 8.5Hz, 1H), 7.33 (d, J = 7.7 Hz, 1H), 7.02 (s, 1H), 6.88 (d, J = 7.3Hz, 1H), 5.29 (s, 2H), 4.96 (s, 2H), 4.22-4.19 (m, 2H), 4.18-4.15 (m, 2H), 3.96 (s, 3H), 2.66 (q, J = 7.3Hz, 2H), 2.36 (s, 3H), 1.17 (t, J = 7.3Hz, 3H) | 478 (M$^+$), 434, 274, 187 (base) |
| | | Example 9-359 | | |
| Example 7-41 | Example 1-1 | | (DMSO-$d_6$) δ :10.21 (brs, 1H), 8.21 (s, 1H), 7.74 (s, 1H), 7.70 (d, J = 8.5Hz, 1H), 7.59 (d, J = 8.1Hz, 1H), 7.44 (d, J = 1.9Hz, 1H), 7.39-7.32 (m, 2H), 5.31 (s, 2H), 3.85 (s, 3H), 2.70 (q, J = 7.3Hz, 2H), 2.54 (s, 3H), 1.18 (t, J = 7.3Hz, 3H) | 440 (M$^+$), 145 (base) |
| | | Example 9-360 | | |
| Example 7-40 | Example 4-3 |  | (DMSO-$d_6$) δ :10.00 (brs, 1H), 8.20 (dd, J = 6.4, 8.9Hz, 1H), 8.09 (s, 1H), 7.84 (s, 1H), 7.71 (d, J = 8.5Hz, 1H), 7.47 (dd, J = 0.8, 8.5Hz, 1H), 7.13 (dd, J = 2.3, 11.2Hz, 1H), 6.90 (dt, J = 2.7, 8.5Hz, 1H), 5.29 (s, 2H), 4.45 (q, J = 7.3Hz, 2H), 3.99 (s, 3H), 3.70-3.64 (m, 2H), 1.39 (t, J = 7.3Hz, 3H), 1.17 (t, J = 7.7Hz, 3H) | 454 (M$^+$), 410, 159 (base) |

TABLE 101-continued

| Carboxylic acid | Hydroxy compound | Example | ¹H-NMR | Mass, m/z |
|---|---|---|---|---|
| | | Example 9-361 | | |
| Example 7-30 | Example 4-3 | 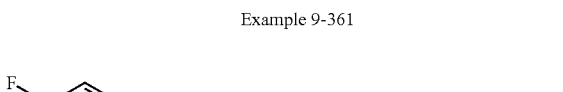 | (DMSO-d₆) δ :10.15 (brs, 1H), 8.08 (s, 1H), 7.84 (s, 1H), 7.73-7.66 (m, 2H), 7.46 (d, J = 8.5Hz, 1H), 7.21 (dd, J = 2.7, 10.0Hz, 1H), 7.12 (dt, J = 2.7, 8.5Hz, 1H), 5.29 (s, 2H), 4.45 (q, J = 7.3Hz, 2H), 2.68 (q, J = 7.3Hz, 2H), 2.53 (s, 3H), 1.39 (t, J = 7.3Hz, 3H), 1.17 (t, J = 7.3Hz, 3H) | 438 (M⁺), 159 (base) |

TABLE 102

| Carboxylic acid | Hydroxy compound | Example | ¹H-NMR | Mass, m/z |
|---|---|---|---|---|
| | | Example 9-362 | | |
| Example 7-41 | Example 4-3 | 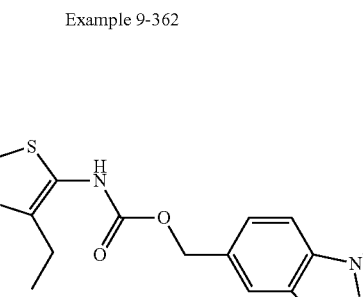 | (DMSO-d₆) δ :10.21 (brs, 1H), 8.09 (s, 1H), 7.84 (s, 1H), 7.70 (d, J = 8.5Hz, 2H), 7.47 (d, J = 8.9Hz, 1H), 7.44 (d, J = 1.9Hz, 1H), 7.35 (dd, J = 2.3, 8.5Hz, 1H), 5.30 (s, 2H), 4.45 (q, J = 7.3Hz, 2H), 2.69 (q, J = 7.3Hz, 2H), 2.54 (s, 3H), 1.39 (t, 3H), 1.18 (t, J = 7.3Hz, 3H) | 454 (M⁺), 159 (base) |
| | | Example 9-363 | | |
| Example 7-30 | Example 4-2 | 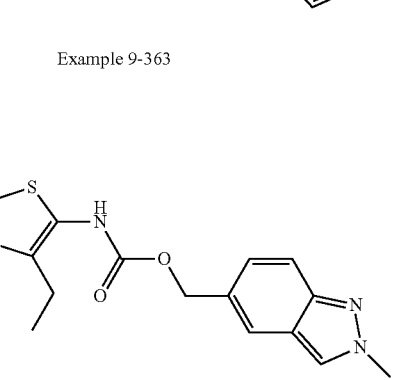 | (DMSO-d₆) δ :10.17 (brs, 1H), 8.36 (s, 1H), 7.77 (s, 1H), 7.69 (dd, J = 6.2, 8.5Hz, 1H), 7.62 (d, J = 8.9Hz, 1H), 7.29 (d, J = 8.9Hz, 1H), 7.21 (dd, J = 2.7, 10.0Hz, 1H), 7.12 (dt, J = 2.7, 8.5Hz, 1H), 5.24 (s, 2H), 4.17 (s, 3H), 2.69 (q, J = 7.3Hz, 2H), 2.53 (s, 3H), 1.18 (t, J = 7.3Hz, 3H) | 424 (M⁺), 145 (base) |
| | | Example 9-364 | | |
| Example 7-28 | Example 4-2 | | (DMSO-d₆) δ :10.07 (brs, 1H), 8.36 (s, 1H), 8.18 (d, J = 8.5 Hz, 1H), 7.77 (s, 1H), 7.62 (d, J = 8.9Hz, 1H), 7.30-7.28 (m, 2H), 7.13 (dd, J = 1.9, 8.5Hz, 1H), 5.24 (s, 2H), 4.17 (s, 3H), 4.01 (s, 3H), 2.70 (q, J = 7.7Hz, 2H), 1.17 (t, J = 7.7 Hz, 3H) | 456 (M⁺), 412 |

TABLE 102-continued

| Carboxylic acid | Hydroxy compound | Example | ¹H-NMR | Mass, m/z |
|---|---|---|---|---|
| | | Example 9-365 | | |
| Example 7-31 | Example 4-2 | | (DMSO-d$_6$) δ :9.92 (brs, 1H), 8.36 (s, 1H), 8.07 (d, J = 7.7Hz, 1H), 7.77 (s, 1H), 7.62 (d, J = 8.9Hz, 1H), 7.29 (d, J = 8.9 Hz, 1H), 7.02 (s, 1H), 6.88 (d, J = 8.1Hz, 1H), 5.23 (s, 2H), 4.17 (s, 3H), 3.96 (s, 3H), 2.66 (q, J = 7.7Hz, 2H), 2.36 (s, 3H), 1.17 (t, J = 7.7Hz, 3H) | 436 (M⁺), 145 (base) |

TABLE 103

| Carboxylic acid | Hydroxy compound | Example | ¹H-NMR | Mass, m/z |
|---|---|---|---|---|
| | | Example 9-366 | | |
| Example 7-29 | Example 4-2 | | (DMSO-d$_6$) δ :10.09 (brs, 1H), 8.36 (s, 1H), 7.77 (s, 1H), 7.61 (d, J = 8.9Hz, 1H), 7.55 (d, J = 8.1Hz, 1H), 7.29 (d, J = 8.9Hz, 1H), 7.14 (s, 1H), 7.10 (d, J = 7.7Hz, 1H), 5.23 (s, 2H), 4.17 (s, 3H), 2.67 (q, J = 7.3Hz, 2H), 2.50 (s, 3H), 2.31 (s, 3H), 1.18 (t, J = 7.3Hz, 3H) | 420 (M⁺), 145 (base) |
| | | Example 9-367 | | |
| Example 7-27 | Example 4-4 | | (DMSO-d$_6$) δ :9.99 (brs, 1H), 8.41 (s, 1H), 8.19 (dd, J = 1.5, 7.7Hz, 1H), 7.77 (s, 1H), 7.63 (d, J = 8.9Hz, 1H), 7.39 (dt, J = 1.5, 7.3Hz, 1H), 7.30 (d, J = 8.9Hz, 1H), 7.20 (d, J = 8.1 Hz, 1H), 7.06 (t, J = 7.3Hz, 1H), 5.24 (s, 2H), 4.46 (q, J = 7.3Hz, 2H), 3.98 (s, 3H), 2.68 (q, J = 6.9Hz, 2H), 1.51 (t, J = 6.9Hz, 3H), 1.18 (t, J = 7.3Hz, 3H) | 436 (M⁺), 159 (base) |
| | | Example 9-368 | | |
| Example 7-31 | Example 4-4 | | (DMSO-d$_6$) δ :9.92 (brs, 1H), 8.41 (s, 1H), 8.07 (d, J = 8.1Hz, 1H), 7.77 (s, 1H), 7.63 (d, J = 8.9Hz, 1H), 7.29 (d, J = 8.5 Hz, 1H), 7.02 (s, 1H), 6.88 (d, J = 8.1Hz, 1H), 5.23 (s, 2H), 4.46 (q, J = 7.3Hz, 2H), 3.96 (s, 3H), 2.66 (q, J = 7.3Hz, 2H), 2.36 (s, 3H), 1.51 (t, J = 7.3Hz, 3H), 1.17 (t, J = 7.3Hz, 3H) | 450 (M⁺), 406, 274 |

TABLE 103-continued

| Carboxylic acid | Hydroxy compound | Example | ¹H-NMR | Mass, m/z |
|---|---|---|---|---|
| | | Example 9-369 | | |
| Example 7-30 | Example 4-4 | 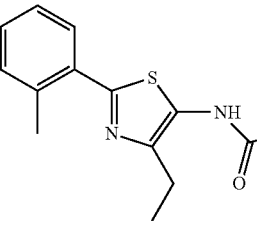 | (DMSO-d₆) δ :10.16 (brs, 1H), 8.41 (s, 1H), 7.77 (s, 1H), 7.69 (dd, J = 6.2, 8.9Hz, 1H), 7.63 (d, J = 8.9Hz, 1H), 7.29 (d, J = 8.9Hz, 1H), 7.21 (dd, J = 2.7, 10.0Hz, 1H), 7.13 (dt, J = 2.7, 8.5Hz, 1H), 5.24 (s, 2H), 4.46 (q, J = 7.3Hz, 2H), 2.69 (q, J = 7.3Hz, 2H), 2.53 (s, 3H), 1.51 (t, J = 7.3Hz, 3H), 1.18 (t, J = 7.3Hz, 3H) | 438 (M⁺), 394 |

TABLE 104

| Carboxylic acid | Hydroxy compound | Example | ¹H-NMR | Mass, m/z |
|---|---|---|---|---|
| | | Example 9-370 | | |
| Example 7-41 | Example 4-4 | 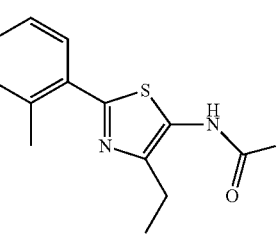 | (DMSO-d₆) δ :10.22 (brs, 1H), 8.41 (s, 1H), 7.77 (s, 1H), 7.70 (d, J = 8.5Hz, 1H), 7.63 (d, J = 9.2Hz, 1H), 7.44 (d, J = 1.9Hz, 1H), 7.35 (dd, J = 2.3, 8.5Hz, 1H), 7.30-7.28 (m, 1H), 5.25 (s, 2H), 4.46 (q, J = 7.3Hz, 2H), 2.70 (q, J = 7.3Hz, 2H), 2.54 (s, 3H), 1.51 (t, J = 7.3Hz, 3H), 1.18 (t, J = 7.3Hz, 3H) | 454 (M⁺), 410 |
| | | Example 9-371 | | |
| Example 7-29 | Example 4-4 | 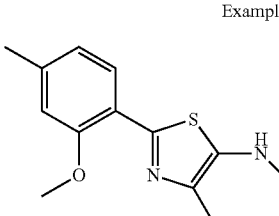 | (DMSO-d₆) δ : 10.09 (brs, 1H), 8.41 (s, 1H), 7.77 (s, 1H), 7.63 (d, J = 9.2Hz, 1H), 7.55 (d, J = 7.7Hz, 1H), 7.29 (d, J = 8.9Hz, 1H), 7.14 (s, 1H), 7.10 (d, J = 8.1Hz, 1H), 5.24 (s, 2H), 4.46 (q, J = 7.3Hz, 2H), 2.67 (q, J = 7.3Hz, 2H), 2.50 (s, 3H), 2.31 (s, 3H), 1.51 (t, J = 7.3Hz, 3H), 1.18 (t, J = 7.3Hz, 3H) | 434 (M⁺), 390 |
| | | Example 9-372 | | |
| Example 7-31 | 1-Methyl-1H-benzo-thiazole-5-methanol | | (DMSO-d₆) δ :9.97 (brs, 1H), 8.11 (s, 1H), 8.07 (d, J = 8.1Hz, 1H), 7.89 (d, J = 8.5Hz, 1H), 7.64 (d, J = 8.5Hz, 1H), 7.02 (s, 1H), 6.88 (d, J = 8.1Hz, 1H), 5.36 (s, 2H), 4.32 (s, 3H), 3.96 (s, 3H), 2.67 (q, J = 7.7Hz, 2H), 2.36 (s, 3H), 1.18 (t, J = 7.7Hz, 3H) | 437 (M⁺), 393 |
| | | Example 9-373 | | |
| Example 7-28 | Example 2-1 | 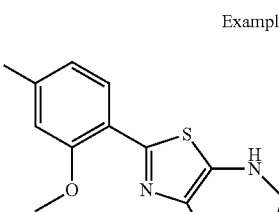 | (DMSO-d₆) δ : 10.05 (brs, 1H), 8.18 (d, J = 8.5Hz, 1H), 7.61 (s, 1H), 7.49 (d, J = 8.1Hz, 1H), 7.30 (s, 1H), 7.29 (d, J = 3.5, 1H), 7.13 (dd, J = 1.9, 8.5Hz, 1H), 5.28 (s, 2H), 4.01 (s, 3H), 3.73 (s, 3H), 2.69 (q, J = 7.5Hz, 2H), 2.53 (s, 3H), 1.17 (t, J = 7.5Hz, 3H) | 470 (M⁺), 159 (base) |

TABLE 105

| Carboxylic acid | Hydroxy compound | Example | 1H-NMR | Mass, m/z |
|---|---|---|---|---|
| | | Example 9-374 | | |
| Example 7-31 | Example 2-1 | | (DMSO-d₆) δ :9.90 (brs, 1H), 8.06 (d, J = 8.1Hz, 1H), 7.60 (s, 1H), 7.49 (d, J = 8.1Hz, 1H), 7.27 (d, J = 8.1Hz, 1H), 7.02 (s, 1H), 6.88 (d, J = 7.6Hz, 1H), 5.27 (s, 2H), 3.96 (s, 3 H), 3.73 (s, 3H), 2.66 (q, J = 7.6Hz, 2H), 2.53 (s, 3H), 2.36 (s, 3H), 1.17 (t, J = 7.6Hz, 3H) | 450 (M⁺), 159 (base) |
| | | Example 9-375 | | |
| Example 7-29 | Example 2-1 | | (DMSO-d₆) δ :10.07 (brs, 1H), 7.60 (s, 1H), 7.55 (d, J = 7.7 Hz, 1H), 7.48 (d, J = 8.1Hz, 1H), 7.27 (d, J = 7.7Hz, 1H), 7.14 (s, 1H), 7.10 (d, J = 8.1Hz, 1H), 5.28 (s, 2H), 3.73 (s, 3 H), 2.67 (q, J = 7.3Hz, 2H), 2.53 (s, 3H), 2.31 (s, 3H), 1.17 (t, J = 7.3Hz, 3H) | 434 (M⁺), 159 (base) |
| | | Example 9-376 | | |
| Example 7-41 | Example 2-1 | | (DMSO-d₆) δ :10.20 (brs, 1H), 7.70 (d, J = 8.5Hz, 1H), 7.61 (s, 1H), 7.49 (d, J = 8.1Hz, 1H), 7.44 (d, J = 1.9Hz, 1H), 7.35 (dd, J = 2.1, 6.2Hz, 1H), 7.27 (d, J = 8.1Hz, 1H), 5.28 (s, 2 H), 3.73 (s, 3H), 3.28 (s, 3H), 2.69 (q, J = 7.3Hz, 2H), 2.54 (s, 3H), 2.53 (s, 3H), 1.18 (t, J = 7.3Hz, 3H) | 454 (M⁺), 278 (base) |
| | | Example 9-377 | | |
| Example 7-41 | Example 3-6 | | (DMSO-d₆) δ :10.22 (brs, 1H), 7.70 (d, J = 8.5Hz, 1H), 7.55 (d, J = 8.1Hz, 1H), 7.44 (s, 1H), 7.35 (dd, 2.3, 6.6Hz, 1H), 7.63 (d, J = 7.3Hz, 1H), 5.31 (s, 2H), 4.96 (s, 2H), 4.21-4.16 (m, 4H), 2.70 (q, J = 7.3Hz, 2H), 2.54 (s, 3H), 1.18 (t, J = 7.3Hz, 3H) | 482 (M⁺), 278 (base) |

Synthesis scheme 10

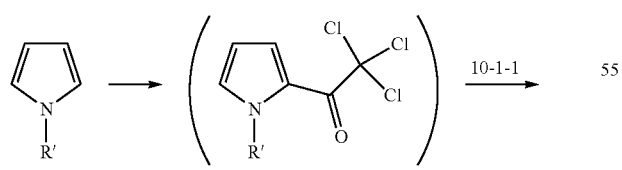
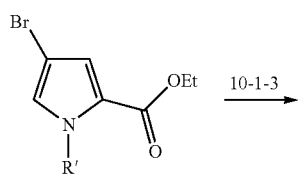
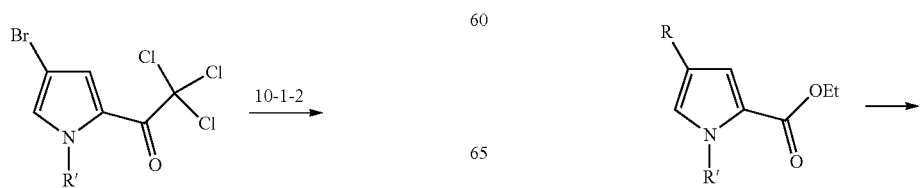

-continued

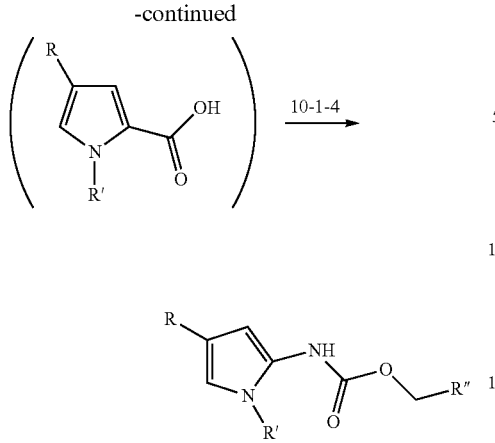

In the formulae, R represents an aryl group which may have a substituent (such as a halogen atom or an alkoxy group); R' represents an alkyl group; and R" represents an aryl or heterocyclic group which may have a substituent (such as an alkyl group or an alkoxy group).

Example 10-1

Step 10-1-1

1-(4-Bromo-1-methyl-1H-pyrrol-2-yl)-2,2,2-trichloroethanone

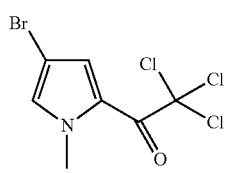

Under an ice cooling, N-methylpyrrole (8.10 g, 100 mmol) was dissolved in methylene chloride (100 ml), and trichloroacetyl chloride (20.00 g, 115 mmol) was added thereto. Thereafter, the mixture was stirred at a room temperature for 16 hours. A saturated sodium hydrogen carbonate aqueous solution was added to the mixture. The organic phase was collected by separation, washed with water, and dried over anhydrous magnesium sulfate. The solvent was distilled off. Thus, 2,2,2-trichloro-1-(methyl-1H-pyrrol-2-yl)ethanone (16.3 g, 72%) was obtained. The resulting 2,2,2-trichloro-1-(methyl-1H-pyrrol-2-yl)ethanone (15.0 g, 66.7 mmol) was dissolved in chloroform (150 ml), and N-bromosuccinimide (12.5 g, 70.2 mmol) was added thereto at a room temperature. The mixture was heated under reflux for 16 hours. After the mixture was allowed to cool, a saturated sodium hydrogen carbonate aqueous solution was added to the mixture. The organic phase was collected by separation, washed with water, and dried over anhydrous magnesium sulfate. The solvent was distilled off. The resulting residue was purified by silica gel column chromatography (ethyl acetate:n-hexane=1:9) to give the title compound (14.0 g, 69%).

$^1$H-NMR (DMSO-$d_6$) δ: 7.66 (d, J=1.5 Hz, 1H), 7.43 (d, J=1.5 Hz, 1H), 3.91 (s, 3H)

Step 10-1-2

Ethyl 4-bromo-1-methyl-1H-pyrrole-2-carboxylate

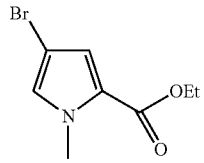

In ethanol (100 ml), 1-(4-bromo-1-methyl-1H-pyrrol-2-yl)-2,2,2-trichloroethanone (12.1 g, 40 mmol) prepared in the Step 10-1-1 was dissolved, and under an ice cooling a 20% sodium ethoxide-ethanol solution was added thereto. Thereafter, the mixture was heated under reflux for 3 hours. After the mixture was allowed to cool, the solvent was distilled off, and 3.5% hydrochloric acid (100 ml) and chloroform (150 ml) was added to the mixture. The organic phase was collected by separation, washed with a saturated sodium hydrogen carbonate aqueous solution and water in order, and dried over anhydrous magnesium sulfate. The solvent was distilled off, and the resulting residue was purified by silica gel column chromatography (ethyl acetate:n-hexane=1:5) to give the title compound (7.39 g, 80%).

$^1$H-NMR (DMSO-$d_6$) δ: 7.28 (d, J=2.3 Hz, 1H), 6.85 (d, J=1.9 Hz, 1H), 4.21 (q, J=7.3 Hz, 2H), 3.84 (s, 3H), 1.27 (t, J=7.3 Hz, 3H)

Mass, m/z: 231 (M$^+$)

Step 10-1-3

Ethyl 4-(4-chloro-2-methoxyphenyl)-1-methyl-1H-pyrrole-2-carboxylate

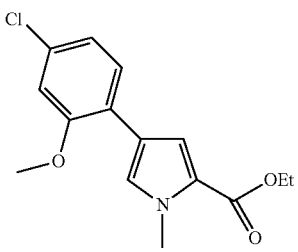 [SMILES: CCOC(=O)c1cc(-c2ccc(Cl)cc2OC)cn1C]

Ethyl 4-bromo-1-methyl-1H-pyrrole-2-carboxylate (5.00 g, 21.6 mmol) prepared in the Step 10-1-2 was dissolved in N,N-dimethylformamide (20 ml)/water (5 ml), and sodium carbonate (6.87 g, 64.8 mmol), tetrakis(triphenylphosphine)palladium (120 mg, 0.1 mmol) and 4-chloro-2-methoxyphenylboronic acid (8.04 g, 4.32 mmol) was added to the solution. The mixture was heated under reflux for 5 hours. After the mixture was allowed to cool, water and chloroform was added to the mixture. The organic phase was collected by separation and dried over anhydrous magnesium sulfate. The solvent was distilled off, and the resulting residue was purified by silica gel column chromatography (ethyl acetate:n-hexane=1:3) to give the title compound (3.23 g, 51%).

¹H-NMR (DMSO-d₆) δ: 7.59-7.56 (m, 2H), 7.25 (d, J=2.3 Hz, 1H), 7.11 (d, J=1.9 Hz, 1H), 6.98 (dd, J=1.9, 8.1 Hz, 1H), 4.24 (q, J=7.3 Hz, 2H), 3.89 (s, 3H), 3.89 (s, 3H), 1.30 (t, J=7.3 Hz, 3H)

Mass, m/z: 293 (M⁺. base)

Step 10-1-4

[4-(4-Chloro-2-methoxyphenyl)-1-methyl-1H-pyrrol-2-yl]carbamic acid 4-methoxybenzyl ester

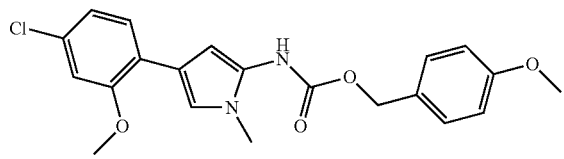 [SMILES: COc1ccc(COC(=O)Nc2cc(-c3ccc(Cl)cc3OC)cn2C)cc1]

Ethyl 4-(4-chloro-2-methoxyphenyl)-1-methyl-1H-pyrrole-2-carboxylate prepared in the Step 10-1-3 was hydrolyzed according to the same procedure as in the Step 7-1-4 to give a carboxylic acid. The title compound was obtained according to the same procedure as in Example 9-1 except that the resulting carboxylic acid and 4-methoxybenzyl alcohol were used instead of 2-(4-chloro-2-methoxyphenyl)-4-methylthiazole-5-carboxylic acid and (1,2,3,4-tetrahydrobenzo[4,5]imidazo[1,2-a]pyridin-7-yl)methanol, respectively.

¹H-NMR (DMSO-d₆) δ: 9.00 (brs, 1H), 7.45 (d, J=8.1 Hz, 1H), 7.35 (d, J=6.6 Hz, 2H), 7.12 (d, J=1.9 Hz, 1H), 6.95-6.93 (m, 3H), 6.25 (s, 1H), 5.05 (s, 2H), 3.86 (s, 3H), 3.76 (s, 3H), 3.41 (s, 3H)

Mass, m/z: 400 (M⁺), 356, 235, 121 (base)

Example 10-2

[4-(4-Chloro-2-methoxyphenyl)-1-methyl-1H-pyrrol-2-yl]carbamic acid 1-methyl-1H-benzimidazol-5-ylmethyl ester

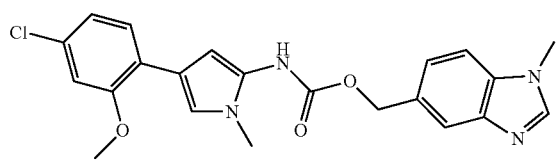 [SMILES: COc1cc(Cl)ccc1-c1cc(NC(=O)OCc2ccc3c(c2)ncn3C)n(C)c1]

The title compound was obtained according to the same procedure as in Example 10-1 except that the compound of Example 1-1 was used instead of 4-methoxybenzyl alcohol.

¹H-NMR (DMSO-d₆) δ: 9.04 (brs, 1H), 8.20 (s, 1H), 7.75-7.65 (m, 1H), 7.58 (d, J=8.1 Hz, 1H), 7.45 (d, J=8.5 Hz, 1H), 7.33 (d, J=6.6 Hz, 1H), 7.13 (d, J=1.9 Hz, 1H), 7.04 (d, J=1.9 Hz, 1H), 6.94 (dd, J=1.9, 8.5 Hz, 1H), 6.26 (s, 1H), 5.23 (s, 3H), 3.86 (s, 3H), 3.84 (s, 3H), 3.42 (s, 3H)

Mass, m/z: 424 (M⁺), 380, 262, 145 (base)

Synthesis scheme 11

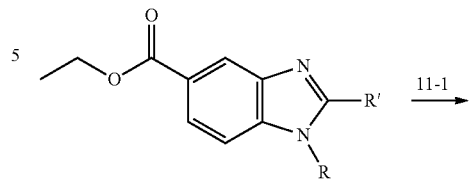

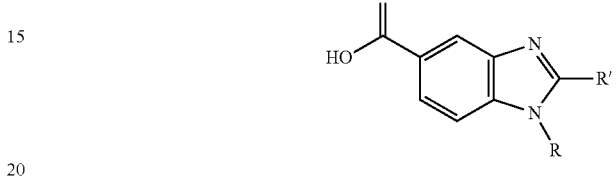

In the formulae, R and R' are the same or different and each represent a hydrogen atom, an alkyl group or an alkoxyalkyl group, and R and R' may bond together to form a 5- to 7-membered ring containing the nitrogen atom and the carbon atom adjacent to R and R', respectively, as constituent atoms thereof.

Example 11-1

Step 11-1

1-Methyl-1H-benzimidazole-5-carboxylic acid

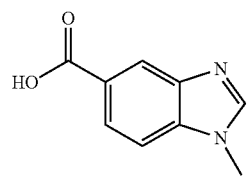

Ethyl 1-methyl-1H-benzimidazole-5-carboxylate (800 mg, 3.92 mmol) prepared in the Step 1-1-4 was suspended in 2-propanol (10 ml), and a 1 mol/L sodium hydroxide aqueous solution (10 ml) was added thereto. The mixture was heated under reflux for one hour. After being allowed to cool, the mixture was neutralized with 1 mol/L hydrochloric acid. The resulting mixture was then acidified with citric acid, separated by filtration, and washed with a small quantity of water. Then, the resulting product was subjected to through circulation drying overnight to give the title compound (595 mg, 86%) as a gray powder.

¹H-NMR (DMSO-d₆) δ: 12.74 (brs, 1H), 8.33 (s, 1H), 8.29 (s, 1H), 7.90 (dd, J=1.5, 8.5 Hz, 1H), 7.65 (d, J=8.5 Hz, 1H), 3.88 (s, 3H)

Mass, m/z: 176 (M⁺, base), 159

Examples 11-2 to 11-15

The objective compounds were obtained according to the same procedure as in Example 11-1 except that any one of ester compounds obtained based on the production process A shown in the following tables was used instead of ethyl 1-methyl-1H-benzimidazole-5-carboxylate.

TABLE 106

| Production process A | Ester compound | Example | ¹H-NMR | Mass, m/z |
|---|---|---|---|---|
| Step 1-1-4 of Example 1-2 | Ethyl 1-ethyl-1H-benzimidazole-5-carboxylate | 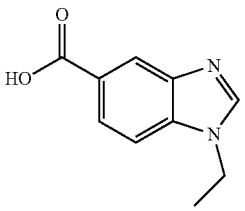<br>Example 11-2 | (DMSO-$d_6$)<br>δ: 12.60 (brs, 1H), 8.39 (s, 1H), 8.24 (s, 1H), 7.89 (d, J = 8.5 Hz, 1H), 7.70 (d, J = 8.5 Hz, 1H), 4.32 (q, J = 7.3 Hz, 2H), 1.43 (t, J = 7.3 Hz, 3H) | 190 (M⁺), 175 (base) |
| Step 1-1-4 of Example 1-3 | Ethyl 1-propyl-1H-benzimidazole-5-carboxylate | 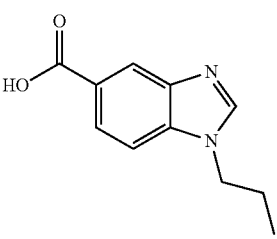<br>Example 11-3 | (DMSO-$d_6$)<br>δ: 12.70 (brs, 1H), 8.41 (s, 1H), 8.24 (d, J = 1.2 Hz, 1H), 7.88 (dd, J = 1.5, 8.5 Hz, 1H), 7.72 (d, J = 8.9 Hz, 1H), 4.26 (t, J = 7.3 Hz, 2H), 1.88-1.79 (m, 2H), 0.85 (t, J = 7.3 Hz, 3H) | 204 (M⁺), 175 (base) |
| Step 2-1-1 of Example 2-3 | Ethyl 1-ethyl-2-methyl-1H-benzimidazole-5-carboxylate | 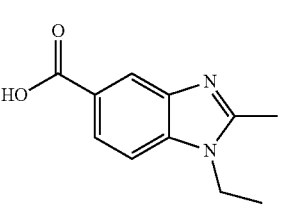<br>Example 11-4 | (DMSO-$d_6$)<br>δ: 12.61 (brs, 1H), 8.11 (s, 1H), 7.82 (dd, J = 1.5, 8.5 Hz, 1H), 7.58 (d, J = 8.5 Hz, 1H), 4.25 (t, J = 7.3 Hz, 2H), 2.57 (s, 3H), 1.31 (t, J = 7.3 Hz, 3H) | 204 (M⁺, base), 189 |
| Step 3-1-3 of Example 3-6 | Ethyl 3,4-dihydro-1H-2-oxa-4a,9-diazafluorene-7-carboxylate | 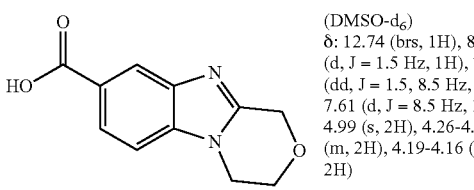<br>Example 11-5 | (DMSO-$d_6$)<br>δ: 12.74 (brs, 1H), 8.17 (d, J = 1.5 Hz, 1H), 7.87 (dd, J = 1.5, 8.5 Hz, 1H), 7.61 (d, J = 8.5 Hz, 1H), 4.99 (s, 2H), 4.26-4.24 (m, 2H), 4.19-4.16 (m, 2H) | 218 (M⁺, base) |
| Step 3-1-3 of Example 3-2 | Ethyl 2,3-dihydro-1H-2-benzo[d]pyrrolo[1,2-a]imidazole-6-carboxylate | 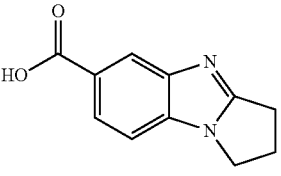<br>Example 11-6 | (DMSO-$d_6$)<br>δ: 8.16 (d, J = 1.5 Hz, 1H), 7.88 (dd, J = 1.5, 8.5 Hz, 1H), 7.60 (d, J = 8.5 Hz, 1H), 4.21 (t, J = 7.3 Hz, 2H), 3.08 (t, J = 7.3 Hz, 2H), 2.72-2.64 (m, 2H) | 202 (M⁺, base) |
| Step 3-1-3 of Example 3-1 | Ethyl 1,2,3,4-tetrahydrobenzo[4,5]imidazo[1,2-a]pyridine-7-carboxylate | 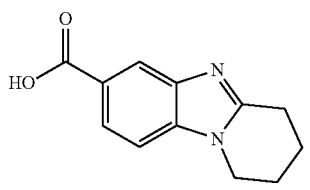<br>Example 11-7 | (DMSO-$d_6$)<br>δ: 12.62 (brs, 1H), 8.11 (d, J = 1.5 Hz, 1H), 7.82 (dd, J = 1.5, 8.5 Hz, 1H), 7.52 (d, J = 8.5 Hz, 1H), 4.15-4.12 (m, 2H), 3.01-2.98 (m, 2H), 2.09-2.03 (m, 2H), 1.98-1.92 (m, 2H) | 216 (M⁺, base) |

TABLE 106-continued

| Production process A | Ester compound | Example | ¹H-NMR | Mass, m/z |
|---|---|---|---|---|
| Step 3-1-3 of Example 3-3 | Ethyl 7,8,9,10-tetrahydro-6H-benzo[4,5]imidazo[1,2-a]azepine-3-carboxylate | Example 11-8 | (DMSO-d₆) δ: 12.63 (brs, 1H), 8.11 (d, J = 1.5 Hz, 1H), 7.83 (dd, J = 1.5, 8.5 Hz, 1H), 7.61 (d, J = 8.9 Hz, 1H), 4.30 (t, J = 5.0 Hz, 2H), 3.08-3.05 (m, 2H), 1.91-1.86 (m, 2H), 1.77-1.74 (m, 2H), 1.72-1.68 (m, 2H) | 230 (M⁺, base) |

TABLE 107

| Production process A | Ester compound | Example | ¹H-NMR | Mass, m/z |
|---|---|---|---|---|
| Step 3-1-3 of Example 3-4 | Ethyl 1-methyl-1,2,3,4-tetrahydrobenzo[4,5]imidazo[1,2-a]pyridine-7-carboxylate | Example 11-9 | (DMSO-d₆) δ: 12.60 (brs, 1H), 8.11 (d, J = 1.2 Hz, 1H), 7.82 (dd, J = 1.5, 8.5 Hz, 1H), 7.60 (d, J = 8.5 Hz, 1H), 4.74-4.70 (m, 1H), 3.06-3.00 (m, 1H), 2.97-2.88 (m, 1H), 2.19-2.11 (m, 1H), 2.07-1.99 (m, 1H), 1.95-1.85 (m, 2H), 1.45 (d, J = 6.6 Hz, 3H) | 230 (M⁺), 215 (base) |
| Step 4-1-3 of Example 4-1 | Ethyl 1-methyl-1H-indazole-5-carboxylate | Example 11-10 | (DMSO-d₆) δ: 12.75 (brs, 1H), 8.44 (dd, J = 0.8, 1.5 Hz, 1H), 8.22 (d, J = 0.8 Hz, 1H), 7.95 (dd, J = 1.5, 8.9 Hz, 1H), 7.70 (d, J = 8.9 Hz, 1H), 4.08 (s, 3H) | 176 (M⁺, base) |
| Step 4-1-3 of Example 4-3 | Ethyl 1-ethyl-1H-indazole-5-carboxylate | Example 11-11 | (DMSO-d₆) δ: 12.68 (brs, 1H), 8.44 (dd, J = 0.8, 1.5 Hz, 1H), 8.23 (d, J = 1.2 Hz, 1H), 7.94 (dd, J = 1.5, 8.9 Hz, 1H), 7.74 (d, J = 8.9 Hz, 1H), 4.46 (q, J = 7.3 Hz, 2H), 1.41 (t, J = 7.3 Hz, 3H) | 190 (M⁺, base), 175 |
| Step 4-1-3 of Example 4-2 | Ethyl 2-methyl-2H-indazole-5-carboxylate | Example 11-12 | (DMSO-d₆) δ: 12.64 (brs, 1H), 8.55 (s, 1H), 8.45 (d, J = 0.8 Hz, 1H), 7.74 (dd, J = 1.5, 8.9 Hz, 1H), 7.62 (d, J = 8.9 Hz, 1H), 4.20 (s, 3H) | 176 (M⁺, base) |
| Step 4-1-3 of Example 4-4 | Ethyl 2-ethyl-2H-indazole-5-carboxylate | Example 11-13 | (DMSO-d₆) δ: 12.60 (brs, 1H), 8.59 (s, 1H), 8.45 (dd, J = 0.8, 1.5 Hz, 1H) 7.75 (dd, J = 1.5, 9.3 Hz, 1H), 7.64 (d, J = 8.9 Hz, 1H), 4.49 (q, J = 7.3 Hz, 2H), 1.52 (t, J = 7.3 Hz, 3H) | 190 (M⁺), 162 (base) |

TABLE 107-continued

| Production process A | Ester compound | Example | $^1$H-NMR | Mass, m/z |
|---|---|---|---|---|
| Step 1-1-4 of Example 1-6 | Ethyl 1-(2-methoxyethyl)-1H-benzimidazole-5-carboxylate | 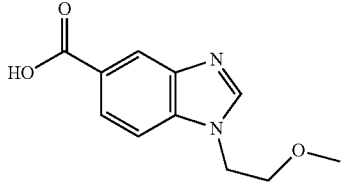<br>Example 11-14 | (DMSO-$d_6$) δ: 12.68 (brs, 1H), 8.31 (s, 1H), 8.23 (d, J = 0.8 Hz, 1H), 7.88 (dd, J = 1.5, 8.5 Hz, 1H), 7.71 (d, J = 8.5 Hz, 1H), 4.46 (t, J = 5.4 Hz, 2H), 3.79 (t, J = 5.4 Hz, 2H), 3.23 (s, 3H) | 220 (M$^+$), 175 (base) |
| Step 2-1-1 of Example 2-4 | Ethyl 2-methoxyethyl-1-methyl-1H-benzimidazole-5-carboxylate | 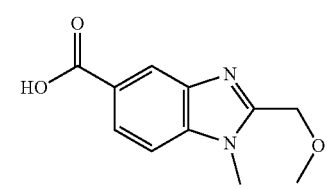<br>Example 11-15 | (DMSO-$d_6$) δ: 8.21 (d, J = 1.5 Hz, 1H), 7.90 (dd, J = 1.5, 8.5 Hz, 1H), 7.65 (d, J = 8.5 Hz, 1H), 4.73 (s, 2H), 3.85 (s, 3H), 3.34 (s, 3H) | 220 (M$^+$), 190 (base) |

Synthesis scheme 12

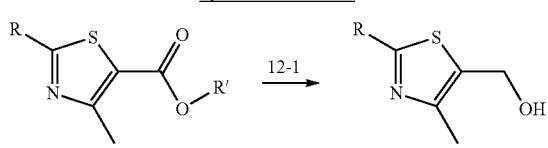

In the formulae, R represents a carbocyclic (homocyclic) or heterocyclic group which may have a substituent (such as a halogen atom, an alkyl group, or an alkoxy group), and R' represents a hydrogen atom or an alkyl group.

Example 12-1

Step 12-1

[2-(4-Chloro-2-methoxyphenyl)-4-methylthiazol-5-yl]methanol

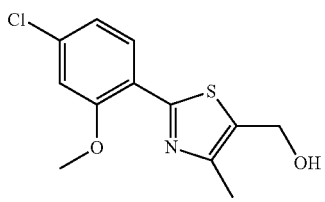 [SMILES: COc1cc(Cl)ccc1-c1nc(C)c(CO)s1]

Lithium aluminum hydride (380 mg, 10.0 mmol) was suspended in tetrahydrofuran (10 ml), and a suspension (10 ml) of 2-(4-chloro-2-methoxyphenyl)-4-methylthiazole-5-carboxylic acid (1.42 g, 5.00 mmol) prepared in Example 7-1 in tetrahydrofuran was added thereto at a room temperature. The mixture was stirred for 3 hours at a room temperature. Under an ice cooling, 5 drops of a saturated sodium bicarbonate solution were slowly added to the mixture. Ethyl acetate was added to the mixture, and another 5 drops of a saturated sodium bicarbonate solution were added thereto. The precipitate was removed by filtration, and the removed solid was washed with chloroform. The washings and the filtrate were concentrated together. The concentrate was purified by silica gel column chromatography (chloroform:methanol=20:1) to give the title compound (580 mg, 43%) as a light-brown powder.

$^1$H-NMR (DMSO-$d_6$) δ: 8.21 (d, J=8.5 Hz, 1H), 7.32 (d, J=1.2 Hz, 1H), 7.14 (dd, J=1.5, 8.5 Hz, 1H), 5.44 (t, J=5.4 Hz, 1H), 4.65 (d, J=5.4 Hz, 1H), 4.03 (s, 3H), 2.35 (s, 3H)

Mass, m/z: 269 (M$^+$, base), 130

Examples 12-2 to 12-17, 12-19 to 12-25, 12-30, and 12-32 to 12-34

The objective compounds were obtained according to the same procedure as in Example 12-1 except that any one of carboxylic acids of Examples shown in the following tables was used instead of 2-(4-chloro-2-methoxyphenyl)-4-methylthiazole-5-carboxylic acid.

TABLE 108

| Carboxylic acid | Example | $^1$H-NMR | Mass, m/z |
|---|---|---|---|
| Example 7-9 | 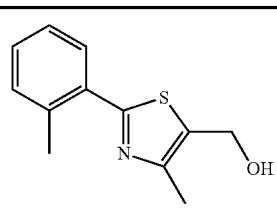<br>Example 12-2 | (DMSO-$d_6$) δ: 7.69 (d, J = 7.3 Hz, 1H), 7.38-7.34 (m, 2H), 7.32-7.28 (m, 1H), 5.51 (t, J = 5.8 Hz, 1H), 4.66 (d, J = 5.8 Hz, 2H), 2.53 (s, 3H), 2.36 (s, 3H) | 219 (M$^+$, base) |

TABLE 108-continued

| Carboxylic acid | Example | ¹H-NMR | Mass, m/z |
|---|---|---|---|
| Example 7-8 | Example 12-3 | (DMSO-d$_6$) δ: 8.22 (dd, J = 1.5, 7.7 Hz, 1H), 7.45-7.40 (m, 1H), 7.20 (d, J = 8.5 Hz, 1H), 7.09-7.05 (m, 1H), 5.40 (t, J = 5.4 Hz, 1H), 4.65 (d, J = 5.4 Hz, 2H), 3.99 (s, 3H), 2.35 (s, 3H) | 235 (M⁺), 130 (base) |
| Example 7-14 | Example 12-4 | (DMSO-d$_6$) δ: 8.09 (d, J = 7.7 Hz, 1H), 7.04 (s, 1H), 6.89 (dd, J = 0.8, 7.7 Hz, 1H), 5.37 (t, J = 5.4 Hz, 1H), 4.63 (d, J = 5.4 Hz, 2H), 3.97 (s, 3H), 2.36 (s, 3H), 2.34 (s, 3H) | 249 (M⁺, base) |
| Example 7-15 | Example 12-5 | (DMSO-d$_6$) δ: 8.13 (d, J = 8.5 Hz, 1H), 6.74 (d, J = 2.3 Hz, 1H), 6.67 (dd, J = 2.3, 8.5 Hz, 1H), 5.33 (t, J = 5.4 Hz, 1H), 4.62 (d, J = 5.4 Hz, 2H), 3.98 (s, 3H), 3.84 (s, 3H), 2.33 (s, 3H) | 265 (M⁺, base) |
| Example 7-16 | Example 12-6 | (DMSO-d$_6$) δ: 7.59 (d, J = 8.1 Hz, 1H), 7.16 (s, 1H), 7.11 (d, J = 8.1 Hz, 1H), 5.48 (t, J = 5.4 Hz, 1H), 4.64 (d, J = 5.4 Hz, 1H), 2.50 (s, 3H), 2.35 (s, 3H), 2.31 (s, 3H) | 233 (M⁺, base) |
| Example 7-6 | Example 12-7 | (DMSO-d$_6$) δ: 7.72 (dd, J = 6.2, 8.9 Hz, 1H), 7.22 (dd, J = 2.7, 10.0 Hz, 1H), 7.13 (dt, J = 2.7, 8.5 Hz, 1H), 5.52 (t, J = 5.8 Hz, 1H), 4.66 (d, J = 5.8 Hz, 1H), 2.53 (s, 3H), 2.36 (s, 3H) | 237 (M⁺, base) |
| Example 7-7 | Example 12-8 | (DMSO-d$_6$) δ: 7.73 (d, J = 8.5 Hz, 1H), 7.46 (d, J = 2.3 Hz, 1H), 7.37 (dd, J = 2.3, 8.5 Hz, 1H), 5.54 (t, J = 5.4 Hz, 1H), 4.66 (d, J = 5.4 Hz, 1H), 2.54 (s, 3H), 2.36 (s, 3H) | 253 (M⁺, base) |

TABLE 109

| Carboxylic acid | Example | ¹H-NMR | Mass, m/z |
|---|---|---|---|
| Example 7-5 | Example 12-9 (4-fluoro-2-chlorophenyl thiazole methanol) | (DMSO-$d_6$) δ: 8.18 (dd, J = 6.2, 8.9 Hz, 1H), 7.63 (dd, J = 2.3, 8.5 Hz, 1H), 7.37 (ddd, J = 2.7, 8.1, 8.9 Hz, 1H), 5.57 (t, J = 5.4 Hz, 1H), 4.67 (d, J = 5.4 Hz, 1H), 2.37 (s, 3H) | 257 (M⁺), 71 (base) |
| Example 7-21 | Example 12-10 (furan-2-yl thiazole methanol) | (DMSO-$d_6$) δ: 7.83 (dd, J = 0.8, 1.9 Hz, 1H), 7.00 (d, J = 3.6 Hz, 1H), 6.66 (dd, J = 1.9, 3.6 Hz, 1H), 5.53 (t, J = 5.8 Hz, 1H), 4.63 (d, J = 5.8 Hz, 2H), 2.31 (s, 3H) | 195 (M⁺, base) |
| Example 7-23 | Example 12-11 (thiophen-2-yl thiazole methanol) | (DMSO-$d_6$) δ: 7.65 (dd, J = 1.2, 5.4 Hz, 1H), 7.55 (dd, J = 0.8, 5.4 Hz, 1H), 7.14 (dd, J = 3.9, 5.0 Hz, 1H), 5.51 (t, J = 5.4 Hz, 1H), 4.63 (d, J = 5.4 Hz, 2H), 2.29 (s, 3H) | 211 (M⁺, base) |
| Example 7-24 | Example 12-12 (3-chlorothiophen-2-yl thiazole methanol) | (DMSO-$d_6$) δ: 7.76 (d, J = 5.4 Hz, 1H), 7.21 (d, J = 5.4 Hz, 1H), 5.58 (t, J = 5.8 Hz, 1H), 4.67 (d, J = 5.8 Hz, 2H), 2.33 (s, 3H) | 245 (M⁺, base) |
| Example 7-39 | Example 12-13 (3-methylpyridin-2-yl thiazole methanol) | (DMSO-$d_6$) δ: 8.45 (dd, J = 1.2, 4.6 Hz, 1H), 7.75 (d, J = 7.7 Hz, 1H), 7.33 (dd, J = 4.6, 7.7 Hz, 1H), 5.48 (t, J = 5.8 Hz, 1H), 4.65 (d, J = 5.8 Hz, 2H), 2.72 (s, 3H), 2.37 (s, 3H) | 211 (M⁺, base) |
| Example 7-33 | Example 12-14 (2-methoxyphenyl thiazole methanol) | (CDCl₃) δ: 8.34 (dd, J = 1.9, 8.1 Hz, 1H), 7.75 (s, 1H), 7.39 (dt, J = 1.5, 7.3 Hz, 1H), 7.07 (dt, J = 0.8, 7.3 Hz, 1H), 7.03 (d, J = 8.1 Hz, 1H), 4.92 (s, 2H), 4.02 (s, 3H) | 211 (M⁺), 116 (base) |

TABLE 109-continued

| Carboxylic acid | Example | ¹H-NMR | Mass, m/z |
| --- | --- | --- | --- |
| Example 7-28 | Example 12-15 | (CDCl₃) δ: 8.30 (d, J = 8.5 Hz, 1H), 7.04 (dd, J = 1.9, 8.5 Hz, 1H), 6.99 (d, J = 1.9 Hz, 1H), 4.85 (d, J = 5.4 Hz, 2H), 4.00 (s, 3H), 3.72-3.68 (m, 1H), 2.79 (q, J = 7.3 Hz, 2H), 1.31 (t, J = 7.3 Hz, 3H) | 283 (M⁺), 144 (base) |

TABLE 110

| Carboxylic acid | Example | ¹H-NMR | Mass, m/z |
| --- | --- | --- | --- |
| Example 7-34 | Example 12-16 | (CDCl₃) δ: 8.30 (d, J = 8.5 Hz, 1H), 7.04 (dd, J = 1.9, 8.5 Hz, 1H), 6.99 (d, J = 1.9 Hz, 1H), 4.84 (d, J = 5.8 Hz, 2H), 4.00 (s, 3H), 3.69 (t, J = 5.8 Hz, 1H), 2.74 (t, J = 7.3 Hz, 2H), 1.76 (sextet, J = 7.3 Hz, 2H), 0.96 (t, J = 7.3 Hz, 3H) | 297 (M⁺, base) |
| Example 8-34 | Example 12-17 | (DMSO-d₆) δ: 7.72 (dd, J = 2.3, 7.7 Hz, 1H), 6.89 (s, 1H), 6.65 (d, J = 7.7 Hz, 1H), 6.59 (s, 1H), 5.22 (t, J = 5.4 Hz, 1H), 4.51 (d, J = 5.8 Hz, 2H), 3.83 (s, 3H), 3.81 (s, 3H), 2.32 (s, 3H) | 232 (M⁺) |
| Example 8-33 | Example 12-19 | (DMSO-d₆) δ: 7.83 (dd, J = 6.9, 8.5 Hz, 1H), 6.97 (dd, J = 2.7, 11.6 Hz, 1H), 6.81-6.76 (m, 1H), 6.59 (s, 1H), 5.24 (t, J = 5.8 Hz, 1H), 4.51 (d, J = 5.8 Hz, 2H), 3.86 (s, 3H), 3.82 (s, 3H) | 236 (M⁺, base) |
| Example 8-9 | Example 12-20 | (DMSO-d₆) δ: 7.85 (d, J = 8.1 Hz, 1H), 7.15 (d, J = 1.9 Hz, 1H), 7.02 (dd, J = 1.9, 8.1 Hz, 1H), 6.63 (s, 1H), 5.25 (t, J = 5.8 Hz, 1H), 4.52 (d, J = 5.8 Hz, 2H), 3.88 (s, 3H), 3.83 (s, 3H) | 252 (M⁺), 56 (base) |

TABLE 110-continued

| Carboxylic acid | Example | ¹H-NMR | Mass, m/z |
|---|---|---|---|
| Example 8-7 | 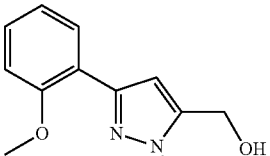<br>Example 12-21 | (DMSO-d₆) δ: 7.84 (dd, J = 1.5, 7.7 Hz, 1H), 7.26 (ddd, J = 1.5, 7.3, 8.9 Hz, 1H), 7.07 (d, J = 8.1 Hz, 1H), 6.96 (dt, 0.8, 7.3 Hz, 1H), 6.63 (s, 1H), 5.24 (t, J = 5.4 Hz, 1H), 4.52 (d, J = 5.4 Hz, 2H), 3.84 (s, 3H), 3.83 (s, 3H) | 218 (M⁺, base) |
| Example 8-32 | 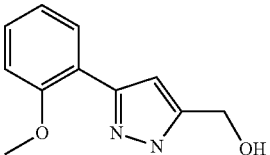<br>Example 12-22 | (DMSO-d₆) δ: 7.85 (dd, J = 1.5, 7.7 Hz, 1H), 7.26 (ddd, J = 1.5, 7.3, 8.5 Hz, 1H), 7.07 (d, J = 8.1 Hz, 1H), 6.96 (dt, 0.8, 7.7 Hz, 1H), 6.62 (s, 1H), 5.26 (t, J = 5.4 Hz, 1H), 4.53 (d, J = 5.4 Hz, 2H), 4.16 (q, J = 7.3 Hz, 2H), 3.85 (s, 3H), 1.37 (t, J = 7.3 Hz, 3H) | 232 (M⁺, base) |

TABLE 111

| Carboxylic acid | Example | ¹H-NMR | Mass, m/z |
|---|---|---|---|
| Example 8-12 | 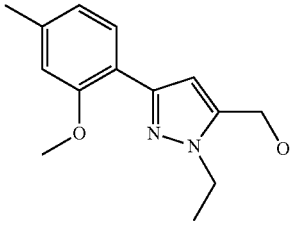<br>Example 12-23 | (DMSO-d₆) δ: 7.73 (d, J = 7.7 Hz, 1H), 6.89 (s, 1H), 6.77 (d, J = 7.7 Hz, 1H), 6.57 (s, 1H), 5.24 (t, J = 5.8 Hz, 1H), 4.51 (d, J = 5.8 Hz, 2H), 4.14 (q, J = 7.3 Hz, 2H), 3.83 (s, 3H), 2.32 (s, 3H), 1.36 (t, J = 7.3 Hz, 3H) | 246 (M⁺, base) |
| Example 8-8 | 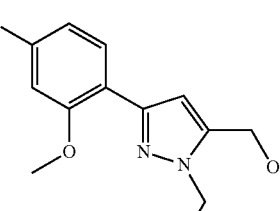<br>Example 12-24 | (DMSO-d₆) δ: 7.85 (dd, J = 6.9, 8.5 Hz, 1H), 6.97 (dd, J = 2.3, 11.2 Hz, 1H), 6.79 (dt, J = 2.3, 8.5 Hz, 1H), 6.57 (s, 1H), 5.26 (t, J = 5.4 Hz, 1H), 4.52 (d, J = 5.4 Hz, 2H), 4.15 (q, J = 7.3 Hz, 2H), 3.86 (s, 3H), 1.36 (t, J = 7.3 Hz, 3H) | 250 (M⁺, base) |
| Example 8-17 | 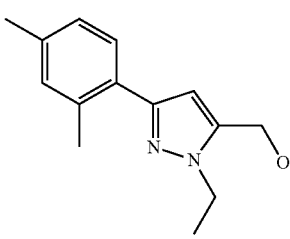<br>Example 12-25 | (DMSO-d₆) δ: 7.41 (d, J = 8.1 Hz, 1H), 7.05 (s, 1H), 7.01 (d, J = 7.7 Hz, 1H), 6.35 (s, 1H), 5.28 (t, J = 5.4 Hz, 1H), 4.54 (d, J = 5.4 Hz, 2H), 4.15 (q, J = 7.3 Hz, 2H), 2.41 (s, 3H), 2.28 (s, 3H), 1.38 (t, J = 7.3 Hz, 3H) | 230 (M⁺, base) |

TABLE 111-continued

| Carboxylic acid | Example | ¹H-NMR | Mass, m/z |
|---|---|---|---|
| Example 8-27 | Example 12-30 | (DMSO-d₆) δ: 7.27-7.24 (m, 2H), 7.12-7.10 (m, 1H), 6.18 (s, 1H), 4.97 (t, J = 5.4 Hz, 1H), 4.39 (d, J = 5.8 Hz, 2H), 3.83 (s, 3H), 3.55 (s, 3H) | 252 (M⁺, base) |
| Example 8-26 | Example 12-32 | (DMSO-d₆) δ: 7.27 (dd, J = 6.9, 8.1 Hz, 1H), 7.09-7.04 (m, 1H), 6.87 (dt, J = 2.3, 8.5 Hz, 1H), 4.95 (t, J = 5.8 Hz, 1H), 4.39 (d, J = 5.8 Hz, 2H), 3.81 (s, 3H), 3.54 (s, 3H) | 236 (M⁺) |
| Example 8-10 | Example 12-33 | (DMSO-d₆) δ: 7.85 (dd, J = 1.5, 7.7 Hz, 1H), 7.07 (d, J = 8.5 Hz, 1H), 6.96 (dt, J = 0.8, 7.3 Hz, 1H), 6.61 (s, 1H), 5.25 (t, J = 5.4 Hz, 1H), 4.53 (d, J = 5.4 Hz, 2H), 4.15 (q, J = 7.3 Hz, 2H), 3.84 (s, 3H), 1.37 (t, J = 7.3 Hz, 3H) | 266 (M⁺) |

TABLE 112

| Carboxylic acid | Example | ¹H-NMR | Mass, m/z |
|---|---|---|---|
| Example 7-30 | Example 12-34 | (DMSO-d₆) δ: 7.73 (dd, J = 6.2, 8.9 Hz, 1H), 7.22 (dd, J = 2.7, 10.1 Hz, 1H), 7.13 (dt, J = 2.7, 8.5 Hz, 1H), 5.52 (t, J = 5.4 Hz, 1H), 4.67 (d, J = 5.4 Hz, 2H), 2.70 (q, J = 7.3 Hz, 2H), 2.54 (s, 3H), 1.23 (t, J = 7.3 Hz, 1H) | 251 (M⁺, base) |

Example 12-18

[5-(2-Methoxy-4-methylphenyl)-1-methyl-1H-pyrazol-3-yl]methanol

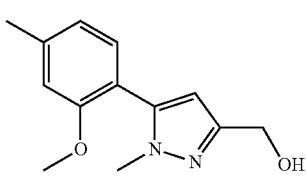 [SMILES: COc1cc(C)ccc1-c1cc(CO)nn1C]

Ethyl 5-(2-methoxy-4-methylphenyl)-1-methyl-1H-pyrazole-3-carboxylate obtained in the Step 8-1-2 of Example 8-34 was subjected to the same procedure as in the Step 8-1-3 to give a carboxylic acid. The title compound was obtained according to the same procedure as in Example 12-1 except that the resulting carboxylic acid was used instead of 2-(4-chloro-2-methoxyphenyl)-4-methylthiazole-5-carboxylic acid.

¹H-NMR (DMSO-d₆) δ: 7.11 (d, J=7.7 Hz, 1H), 6.98 (s, 1H), 6.85 (d, J=7.3 Hz, 1H), 6.12 (s, 1H), 4.94 (t, J=5.8 Hz, 1H), 4.39 (d, J=5.8 Hz, 2H), 3.78 (s, 3H), 3.54 (s, 3H), 2.37 (s, 3H)

Mass, m/z: 232 (M⁺, base)

Example 12-26

1-Ethyl-[5-(4-fluoro-2-methoxyphenyl)-1H-pyrazol-3-yl]methanol

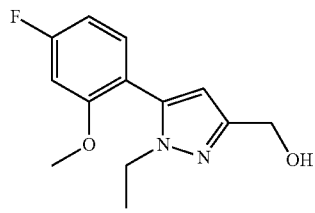 [SMILES: CCn1nc(CO)cc1-c1ccc(F)cc1OC]

Ethyl 1-ethyl-5-(4-fluoro-2-methoxyphenyl)-1H-pyrazole-3-carboxylate obtained in the Step 8-1-2 of Example 8-8 was subjected to the same procedure as in the Step 8-1-3 to give a carboxylic acid. The title compound was obtained in the same procedure as in Example 12-1 except that the resulting carboxylic acid was used instead of 2-(4-chloro-2-methoxyphenyl)-4-methylthiazole-5-carboxylic acid.

$^1$H-NMR (DMSO-$d_6$) δ: 7.25 (dd, J=6.9, 8.5 Hz, 1H), 7.07 (dd, J=2.3, 11.2 Hz, 1H), 6.87 (dt, J=2.3, 8.5 Hz, 1H), 6.11 (s, 1H), 5.00 (brs, 1H), 4.41 (d, J=4.2 Hz, 2H), 3.79 (s, 3H), 3.78 (q, J=7.3 Hz, 2H), 1.22 (t, J=7.3 Hz, 3H)

Mass, m/z: 250 (M$^+$, base)

Example 12-27

1-Ethyl-[5-(2-methoxyphenyl)-1H-pyrazol-3-yl]methanol

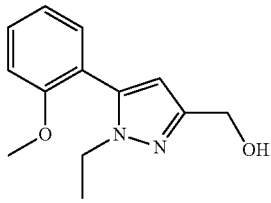 [SMILES: CCn1nc(CO)cc1-c1ccccc1OC]

Ethyl 1-ethyl-5-(2-methoxyphenyl)-1H-pyrazole-3-carboxylate obtained in the Step 8-1-2 of Example 8-32 was subjected to the same procedure as in the Step 8-1-3 to give a carboxylic acid. The title compound was obtained according to the same procedure as in Example 12-1 except that the resulting carboxylic acid was used instead of 2-(4-chloro-2-methoxyphenyl)-4-methylthiazole-5-carboxylic acid.

$^1$H-NMR (DMSO-$d_6$) δ: 7.45 (dt, J=1.9, 7.7 Hz, 1H), 7.22 (dd, J=1.9, 7.7 Hz, 1H), 7.15 (d, J=8.1 Hz, 1H), 7.06-7.02 (m, 1H), 6.12 (s, 1H), 4.97 (t, J=5.8 Hz, 1H), 4.42 (d, J=5.4 Hz, 2H), 3.80 (q, J=7.3 Hz, 2H), 3.78 (s, 3H), 1.22 (t, J=7.3 Hz, 3H)

Mass, m/z: 232 (M$^+$, base)

Example 12-28

[5-(4-Chloro-2-methoxyphenyl)-1-ethyl-1H-pyrazol-3-yl]methanol

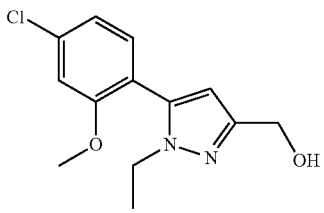 [SMILES: CCn1nc(CO)cc1-c1ccc(Cl)cc1OC]

Ethyl 5-(4-chloro-2-methoxyphenyl)-1-ethyl-1H-pyrazole-3-carboxylate obtained in the Step 8-1-2 of Example 8-10 was subjected to the same procedure as in the Step 8-1-3 to give a carboxylic acid. The title compound was obtained according to the same procedure as in Example 12-1 except that the resulting carboxylic acid was used instead of 2-(4-chloro-2-methoxyphenyl)-4-methylthiazole-5-carboxylic acid.

$^1$H-NMR (DMSO-$d_6$) δ: 7.25-7.23 (m, 2H), 7.11 (dd, J=1.9, 8.1 Hz, 1H), 6.13 (s, 1H), 4.98 (t, J=5.8 Hz, 1H), 4.41 (d, J=5.8 Hz, 2H), 3.82-3.77 (m, 5H), 1.22 (t, J=7.3 Hz, 3H)

Mass, m/z: 266 (M$^+$, base)

Example 12-29

1-Ethyl-[5-(2-methoxy-4-methylphenyl)-1H-pyrazol-3-yl]methanol

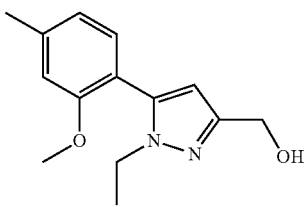 [SMILES: CCn1nc(CO)cc1-c1ccc(C)cc1OC]

Ethyl 1-ethyl-5-(2-methoxy-4-methylphenyl)-1H-pyrazole-3-carboxylate obtained in the Step 8-1-2 of Example 8-12 was subjected to the same procedure as in the Step 8-1-3 to give a carboxylic acid. The title compound was obtained according to the same procedure as in Example 12-1 except that the resulting carboxylic acid was used instead of 2-(4-chloro-2-methoxyphenyl)-4-methylthiazole-5-carboxylic acid.

$^1$H-NMR (DMSO-$d_6$) δ: 7.08 (d, J=7.7 Hz, 1H), 6.97 (s, 1H), 6.85 (dd, J=0.8, 7.3 Hz, 1H), 6.08 (s, 1H), 4.95 (t, J=5.8 Hz, 1H), 4.40 (d, J=5.8 Hz, 2H), 3.82-3.76 (m, 2H), 3.76 (s, 3H), 2.37 (s, 3H), 1.21 (t, J=7.3 Hz, 3H)

Mass, m/z: 246 (M$^+$, base)

Example 12-31

[5-(2,4-Dimethylphenyl)-1-methyl-1H-pyrazol-3-yl]methanol

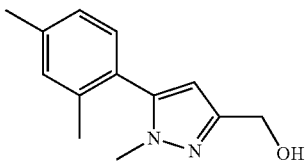 [SMILES: Cc1ccc(-c2cc(CO)nn2C)c(C)c1]

Ethyl 5-(2,4-dimethylphenyl)-1-methyl-1H-pyrazole-3-carboxylate obtained in the Step 8-1-2 of Example 8-16 was subjected to the same procedure as in the Step 8-1-3 to give a carboxylic acid. The title compound was obtained according to the same procedure as in Example 12-1 except that the resulting carboxylic acid was used instead of 2-(4-chloro-2-methoxyphenyl)-4-methylthiazole-5-carboxylic acid.

$^1$H-NMR (DMSO-$d_6$) δ: 7.17 (s, 1H), 7.11 (s, 2H), 6.14 (s, 1H), 4.97 (t, J=5.8 Hz, 1H), 4.41 (d, J=5.8 Hz, 2H), 3.51 (s, 3H), 2.33 (s, 3H), 2.10 (s, 3H)

Mass, m/z: 216 (M$^+$, base)

Synthesis scheme 13

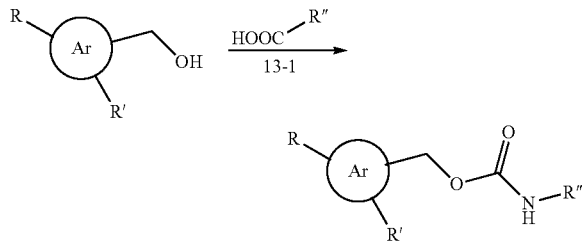

In the formulae, Ar represents a thiazole or pyrazole ring which may have a carbocyclic (homocyclic) or heterocyclic group as a substituent; R and R' are the same or different and each represent a hydrogen atom, a halogen atom, an alkyl group or an alkoxy group; and R" represents a carbocyclic (homocyclic) or heterocyclic group which may have a substituent (such as a halogen atom, an alkyl group, an alkoxy group, or an alkoxyalkyl group).

Example 13-1

Step 13-1

(1-Methyl-1H-benzimidazol-5-yl)carbamic acid 4-methyl-2-(2-methylphenyl)thiazol-5-ylmethyl ester

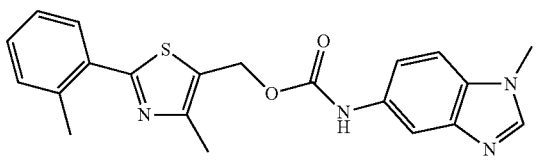 [SMILES: Cc1ccccc1-c1nc(C)c(COC(=O)Nc2ccc3c(c2)ncn3C)s1]

In toluene (3 ml), [2-(2-methylphenyl)-4-methylthiazol-5-yl]methanol (80 mg, 0.37 mmol) prepared in Example 12-2 and 1-methyl-1H-benzimidazole-5-carboxylic acid (77 mg, 0.44 mmol) prepared in Example 11-1 were suspended, and triethylamine (48 mg, 0.47=1) and then diphenylphosphoryl azide (0.12 g, 0.44 mmol) were added thereto. The mixture was heated under reflux for one hour. After being allowed to cool, the mixture was purified by silica gel column chromatography (ethyl acetate:methanol=20:1) to give the title compound (0.11 g, 75%) as a light-brown powder.
$^1$H-NMR (DMSO-$d_6$) δ: 9.71 (brs, 1H), 8.11 (s, 1H), 7.81 (s, 1H), 7.72 (d, J=7.3 Hz, 1H), 7.46 (d, J=8.5 Hz, 1H), 7.40-7.35 (m, 2H), 7.33-7.29 (m, 2H), 5.34 (s, 2H), 3.80 (s, 3H), 2.54 (s, 3H), 2.50 (s, 3H)
Mass, m/z: 348 (M$^+$-44), 173 (base)

Examples 13-2 to 13-150

The objective compounds were obtained according to the same procedure as in Example 13-1 except that hydroxy compounds or carboxylic acids known or obtained in Examples as shown in the following tables were used instead of [2-(2-methylphenyl)-4-methylthiazol-5-yl]methanol or 1-methyl-1H-benzimidazole-5-carboxylic acid.

TABLE 113

| Hydroxy compound | Carboxylic acid | Example | $^1$H-NMR | Mass, m/z |
|---|---|---|---|---|
| Example 12-6 | 4-Methoxy benzoic acid | Example 13-2 | (DMSO-$d_6$) δ: 9.57 (brs, 1H), 7.61 (d, J = 8.1 Hz, 1H), 7.37-7.32 (m, 2H), 7.17 (s, 1H), 7.12 (d, J = 7.7 Hz, 1H), 6.89-6.84 (m, 2H), 5.34 (s, 2H), 3.71 (s, 3H), 2.50 (s, 3H), 2.47 (s, 3H), 2.32 (s, 3H) | 338 (M$^+$ − 44), 216 (base) |
| Example 12-8 | 1-Methyl-1H-benzotriazole-5-carboxylic acid | Example 13-3 | (DMSO-$d_6$) δ: 10.03 (brs, 1H), 8.16 (s, 1H), 7.78 (s, 1H), 7.76 (s, 1H), 7.55 (dd, J = 1.9, 9.2 Hz, 1H), 7.48 (d, J = 1.9 Hz, 1H), 7.38 (dd, J = 1.9, 8.1 Hz, 1H), 5.43 (s, 2H), 4.26 (s, 3H), 2.55 (s, 3H), 2.50 (s, 3H) | 427 (M$^+$), 383, 236 (base) |
| Example 12-3 | — | Example 13-4 | (DMSO-$d_6$) δ: 9.67 (brs, 1H), 8.25 (dd, J = 1.9, 8.1 Hz, 1H), 8.11 (s, 1H), 7.81 (s, 1H), 7.48-7.44 (m, 2H), 7.32 (d, J = 8.1 Hz, 1H), 7.24 (d, J = 8.5 Hz, 1H), 7.11-7.07 (m, 1H), 5.37 (s, 2H), 4.00 (s, 3H), 3.80 (s, 3H), 2.49 (s, 3H) | 364 (M$^+$ − 44), 218 (base) |
| Example 12-1 | — | Example 13-5 | (DMSO-$d_6$) δ: 9.67 (brs, 1H), 8.25 (d, J = 8.5 Hz, 1H), 8.11 (s, 1H), 7.80 (s, 1H), 7.46 (d, J = 8.9 Hz, 1H), 7.35 (d, J = 1.9 Hz, 1H), 7.32 (dd, J = 0.8, 8.5 Hz, 1H), 7.16 (dd, J = 1.9, 8.5 Hz, 1H), 5.37 (s, 2H), 4.04 (s, 3H), 3.80 (s, 3H), 2.49 (s, 3H) | 398 (M$^+$ − 44), 173 (base) |

TABLE 113-continued

| Hydroxy compound | Carboxylic acid | Example | ¹H-NMR | Mass, m/z |
|---|---|---|---|---|
| Example 12-4 | — | 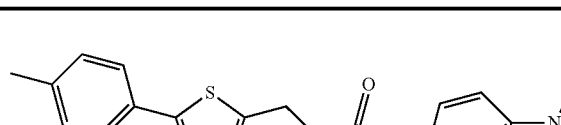<br>Example 13-6 | (DMSO-$d_6$) δ: 9.66 (brs, 1H), 8.13 (d, J = 8.1 Hz, 1H), 8.10 (s, 1H), 7.80 (s, 1H), 7.45 (d, J = 8.5 Hz, 1H), 7.32 (d, J = 8.1 Hz, 1H), 7.06 (s, 1H), 6.91 (d, J = 7.3 Hz, 1H), 5.35 (s, 2H), 3.99 (s, 3H), 3.80 (s, 3H), 2.47 (s, 3H), 2.37 (s, 3H) | 378 (M$^+$ − 44), 232 (base) |

TABLE 114

| Hydroxy compound | Carboxylic acid | Example | ¹H-NMR | Mass, m/z |
|---|---|---|---|---|
| Example 12-5 | — | 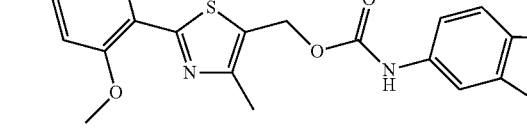<br>Example 13-7 | (DMSO-$d_6$) δ: 9.65 (brs, 1H), 8.17 (d, J = 8.9 Hz, 1H), 8.11 (s, 1H), 7.80 (s, H), 7.45 (d, J = 8.9 Hz, 1H), 7.32 (dd, J = 1.2, 8.5 Hz, 1H), 6.76 (d, J = 2.3 Hz, 1H), 6.68 (dd, J = 2.3, 8.5 Hz, 1H), 5.37 (s, 2H), 4.03 (s, 3H), 4.00 (s, 3H), 3.84 (s, 3H), 2.46 (s, 3H) | 394 (M$^+$ − 44), 248 (base) |
| Example 12-6 | — | 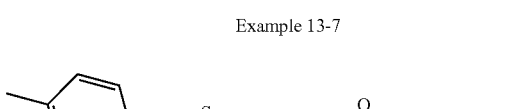<br>Example 13-8 | (DMSO-$d_6$) δ: 9.71 (brs, 1H), 8.13 (s, 1H), 7.81 (s, 1H), 7.62 (d, J = 8.1 Hz, 1H), 7.47 (d, J = 8.9 Hz, 1H), 7.33 (dd, J = 1.2, 8.1 Hz, 1H), 7.17 (s, 1H), 7.12 (dd, J = 1.2, 7.7 Hz, 1H), 5.37 (s, 2H), 3.80 (s, 3H), 2.50 (s, 3H), 2.48 (s, 3H), 2.32 (s, 3H) | 362 (M$^+$ − 44), 216 (base) |
| Example 12-7 | — | 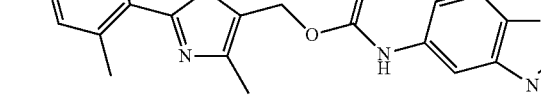<br>Example 13-9 | (DMSO-$d_6$) δ: 9.72 (brs, 1H), 8.15 (s, 1H), 7.82 (s, 1H), 7.76 (dd, J = 6.2, 8.9 Hz, 1H), 7.47 (d, J = 8.5 Hz, 1H), 7.33 (dd, J = 0.8, 8.9 Hz, 1H), 7.25 (dd, J = 2.7, 10.0 Hz, 1H), 7.15 (dt, J = 2.7, 8.5 Hz, 1H), 5.39 (s, 2H), 3.81 (s, 3H), 2.55 (s, 3H), 2.50 (s, 3H) | 410 (M$^+$), 366, 220 (base) |
| Example 12-8 | — | 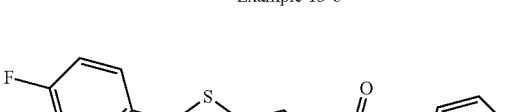<br>Example 13-10 | (DMSO-$d_6$) δ: 9.71 (brs, 1H), 8.11 (s, 1H), 7.80 (s, 1H), 7.76 (d, J = 8.5 Hz, 1H), 7.50-7.45 (m, 2H), 7.38 (dd, J = 1.9, 8.1 Hz, 1H), 7.32 (d, J = 8.5 Hz, 1H), 5.39 (s, 2H), 3.80 (s, 3H), 2.54 (s, 3H), 2.50 (s, 3H) | 382 (M$^+$ − 44), 173 (base) |
| Example 12-9 | — | 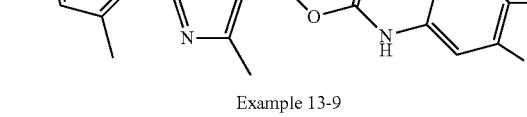<br>Example 13-11 | (DMSO-$d_6$) δ: 9.71 (brs, 1H), 8.23 (dd, J = 6.2, 8.9 Hz, 1H), 8.11 (s, 1H), 7.80 (s, 1H), 7.66 (dd, J = 2.7, 8.9 Hz, 1H), 7.46 (d, J = 8.9 Hz, 1H), 7.39 (dt, J = 2.7, 8.1 Hz, 1H), 7.34-7.30 (m, 1H), 5.40 (s, 2H), 3.80 (s, 3H), 2.50 (s, 3H) | 430 (M$^+$), 386, 240 (base) |

TABLE 115

| Hydroxy compound | Carboxylic acid | Example | ¹H-NMR | Mass, m/z |
|---|---|---|---|---|
| — | Example 11-2 | Example 13-12 | (DMSO-d$_6$) δ: 9.71 (brs, 1H), 8.18 (s, 1H), 7.81 (s, 1H), 7.72 (d, J = 7.3 Hz, 1H), 7.51 (d, J = 8.9 Hz, 1H), 7.38-7.36 (m, 2H), 7.35-7.29 (m, 2H), 5.39 (s, 2H), 4.23 (q, J = 7.3 Hz, 2H), 2.54 (s, 3H), 2.49 (s, 3H), 1.40 (t, J = 7.3 Hz, 3H) | 406 (M⁺), 362, 202 (base) |
| Example 12-1 | Example 11-2 | Example 13-13 | (DMSO-d$_6$) δ: 9.67 (brs, 1H), 8.25 (d, J = 8.9 Hz, 1H), 8.18 (s, 1H), 7.80 (s, 1H), 7.50 (d, J = 8.9 Hz, 1H), 7.34 (d, J = 1.9 Hz, 1H), 7.31 (d, J = 8.5 Hz, 1H), 7.16 (dd, J = 1.9, 8.5 Hz, 1H), 5.37 (s, 2H), 4.23 (q, J = 7.3 Hz, 2H), 4.04 (s, 3H), 2.49 (s, 3H), 1.40 (t, J = 7.3 Hz, 3H) | 456 (M⁺), 412, 252 (base) |
| Example 12-4 | Example 11-2 | Example 13-14 | (DMSO-d$_6$) δ: 9.65 (brs, 1H), 8.17 (s, 1H), 8.13 (d, J = 8.1 Hz, 1H), 7.80 (s, 1H), 7.49 (d, J = 8.5 Hz, 1H), 7.31 (d, J = 8.5 Hz, 1H), 7.06 (s, 1H), 6.91 (dd, J = 0.8, 8.1 Hz, 1H), 5.35 (s, 2H), 4.23 (q, J = 7.3 Hz, 2H), 3.99 (s, 3H), 2.47 (s, 3H), 2.37 (s, 3H), 1.40 (t, J = 7.3 Hz, 3H) | 392 (M⁺ − 44), 187 (base) |
| Example 12-6 | Example 11-2 | Example 13-15 | (DMSO-d$_6$) δ: 9.70 (brs, 1H), 8.17 (s, 1H), 7.81 (s, 1H), 7.62 (d, J = 7.7 Hz, 1H), 7.49 (d, J = 8.9 Hz, 1H), 7.31 (d, J = 8.9 Hz, 1H), 7.17 (s, 1H), 7.12 (d, J = 8.1 Hz, 1H), 5.37 (s, 2H), 4.23 (q, J = 7.3 Hz, 2H), 2.50 (s, 3H), 2.49 (s, 3H), 2.32 (s, 3H), 1.40 (t, J = 7.3 Hz, 3H) | 420 (M⁺), 376, 233 (base) |
| Example 12-7 | Example 11-2 | Example 13-16 | (DMSO-d$_6$) δ: 9.70 (brs, 1H), 8.17 (s, 1H), 7.81 (s, 1H), 7.77 (dd, J = 6.2, 8.9 Hz, 1H), 7.50 (d, J = 8.5 Hz, 1H), 7.31 (d, J = 8.5 Hz, 1H), 7.25 (dd, J = 2.7, 10.0 Hz, 1H), 7.14 (dt, J = 2.7, 8.5 Hz, 1H), 5.38 (s, 2H), 4.23 (q, J = 7.3 Hz, 2H), 2.54 (s, 3H), 2.49 (s, 3H), 1.40 (t, J = 7.3 Hz, 3H) | 424 (M⁺), 380, 220 (base) |

TABLE 116

| Hydroxy compound | Carboxylic acid | Example | 1H-NMR | Mass, m/z |
|---|---|---|---|---|
| Example 12-8 | Example 11-2 | 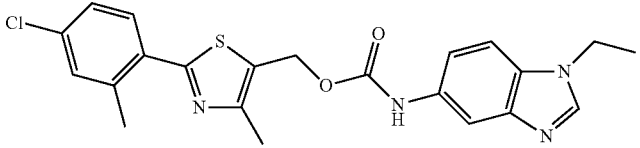<br>Example 13-17 | (DMSO-d$_6$)<br>δ: 9.70 (brs, 1H), 8.17 (s, 1H), 7.80 (s, 1H), 7.76 (d, J = 8.5 Hz, 1H), 7.50 (d, J = 9.2 Hz, 1H), 7.48 (s, 1H), 7.38 (dd, J = 2.3, 8.5 Hz, 1H), 7.31 (d, J = 8.9 Hz, 1H), 5.39 (s, 2H), 4.23 (q, J = 7.3 Hz, 2H), 2.55 (s, 3H), 2.50 (s, 3H), 1.40 (t, J = 7.3 Hz, 3H) | 396 (M$^+$ − 44), 187 (base) |
| Example 12-9 | Example 11-2 | 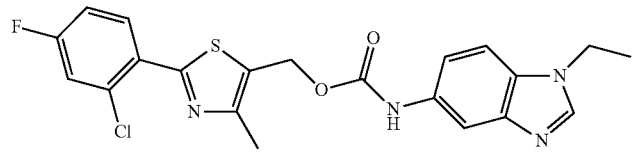<br>Example 13-18 | (DMSO-d$_6$)<br>δ: 9.72 (brs, 1H), 8.23 (dd, J = 6.2, 8.9 Hz, 1H), 8.20 (s, 1H), 7.81 (s, 1H), 7.66 (dd, J = 2.7, 8.9 Hz, 1H), 7.51 (d, J = 8.9 Hz, 1H), 7.39 (ddd, J = 2.7, 8.1, 8.9 Hz, 1H), 7.31 (dd, J = 1.9, 8.5 Hz, 1H), 5.40 (s, 2H), 4.23 (q, J = 7.3 Hz, 2H), 2.49 (s, 3H), 1.40 (t, J = 7.3 Hz, 3H) | 444 (M$^+$), 400, 240 (base) |
| Example 12-6 | Example 11-3 | 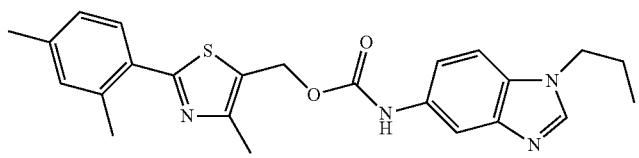<br>Example 13-19 | (DMSO-d$_6$)<br>δ: 9.69 (brs, 1H), 8.15 (s, 1H), 7.80 (s, 1H), 7.62 (d, J = 7.7 Hz, 1H), 7.50 (d, J = 8.9 Hz, 1H), 7.30 (d, J = 9.2 Hz, 1H), 7.17 (s, 1H), 7.12 (dd, J = 0.8, 8.1 Hz, 1H), 5.37 (s, 2H), 4.16 (t, J = 6.9 Hz, 2H), 2.50 (s, 3H), 2.49 (s, 3H), 2.32 (s, 3H), 1.82-1.75 (m, 2H), 0.83 (t, J = 7.3 Hz, 3H) | 434 (M$^+$), 390, 172 (base) |
| Example 12-6 | Example 11-4 | 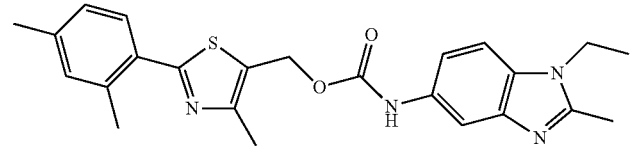<br>Example 13-20 | (DMSO-d$_6$)<br>δ: 9.85 (brs, 1H), 7.81 (s, 1H), 7.62 (d, J = 8.1 Hz, 1H), 7.57 (d, J = 8.9 Hz, 1H), 7.34 (dd, J = 1.2, 8.9 Hz, 1H), 7.21 (s, 1H), 7.13 (d, J = 8.5 Hz, 1H), 5.38 (s, 2H), 4.25 (q, J = 7.3 Hz, 2H), 2.62 (s, 3H), 2.50 (s, 3H), 2.49 (s, 3H), 2.32 (s, 3H), 1.32 (t, J = 7.3 Hz, 3H) | 434 (M$^+$), 390, 216 (base) |
| Example 12-8 | Example 11-4 | 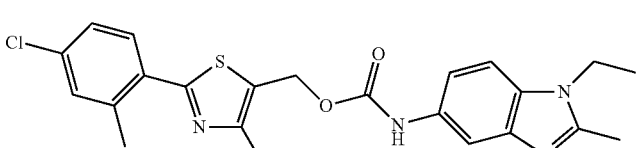<br>Example 13-21 | (DMSO-d$_6$)<br>δ: 9.68 (brs, 1H), 7.76 (d, J = 8.1 Hz, 1H), 7.70 (s, 1H), 7.48 (d, J = 2.3 Hz, 1H), 7.41 (d, J = 8.5 Hz, 1H), 7.39-7.36 (m, 1H), 7.25 (d, J = 8.1 Hz, 1H), 5.38 (s, 2H), 4.18 (q, J = 7.3 Hz, 2H), 2.55 (s, 3H), 2.52 (s, 3H), 2.50 (s, 3H), 1.28 (t, J = 7.3 Hz, 3H) | 454 (M$^+$), 410, 236 (base) |

TABLE 117

| Hydroxy compound | Carboxylic acid | Example | ¹H-NMR | Mass, m/z |
|---|---|---|---|---|
| Example 12-3 | Example 11-5 | Example 13-22 | (DMSO-d$_6$) δ: 9.68 (brs, 1H), 8.25 (dd, J = 1.9, 8.1 Hz, 1H), 7.77 (s, 1H), 7.48-7.40 (m, 2H), 7.30-7.28 (m, 1H), 7.24 (d, J = 8.5 Hz, 1H), 7.11-7.07 (m, 1H), 5.37 (s, 2H), 4.92 (s, 2H), 4.19-1.14 (m, 4H), 4.01 (s, 3H), 2.49 (s, 3H) | 406 (M$^+$ − 44), 218 (base) |
| Example 12-1 | Example 11-5 | Example 13-23 | none | 440 (M$^+$ − 44), 252 (base) |
| Example 12-6 | Example 11-5 | Example 13-24 | (DMSO-d$_6$) δ: 9.71 (brs, 1H), 7.77 (s, 1H), 7.62 (d, J = 7.7 Hz, 1H), 7.42 (d, J = 8.5 Hz, 1H), 7.29 (d, J = 8.1 Hz, 1H), 7.17 (s, 1H), 7.12 (d, J = 8.1 Hz, 1H), 5.37 (s, 2H), 4.92 (s, 2H), 4.15 (brs, 4H), 2.50 (s, 3H), 2.49 (s, 3H), 2.32 (s, 3H) | 404 (M$^+$ − 44), 216 (base) |
| Example 12-7 | Example 11-5 | Example 13-25 | (DMSO-d$_6$) δ: 9.71 (brs, 1H), 7.77 (d, J = 8.5 Hz, 1H), 7.76 (d, J = 8.5 Hz, 1H), 7.42 (d, J = 8.9 Hz, 1H), 7.30-7.23 (m, 2H), 7.25 (dd, J = 2.7, 10.0 Hz, 1H), 7.15 (dt, J = 3.1, 8.9 Hz, 1H), 5.38 (s, 2H), 4.92 (s, 2H), 4.15 (brs, 4H), 2.54 (s, 3H) | 452 (M$^+$), 408, 220 (base) |
| Example 12-8 | Example 11-5 | Example 13-26 | (DMSO-d$_6$) δ: 9.72 (brs, 1H), 7.78-7.75 (m, 2H), 7.48 (d, J = 2.3 Hz, 1H), 7.42 (d, J = 8.5 Hz, 1H), 7.38 (dd, J = 2.3, 8.1 Hz, 1H), 7.29 (dd, J = 1.2, 8.5 Hz, 1H), 5.38 (s, 2H), 4.92 (s, 2H), 4.14 (brs, 4H), 2.55 (s, 3H), 2.50 (s, 3H) | 424 (M$^+$ − 44), 215 (base) |

TABLE 118

| Hydroxy compound | Carboxylic acid | Example | ¹H-NMR | Mass, m/z |
|---|---|---|---|---|
| Example 12-1 | Example 11-6 | Example 13-27 | (DMSO-$d_6$) δ: 9.61 (brs, 1H), 8.24 (d, J = 8.5 Hz, 1H), 7.71 (s, 1H), 7.34 (d, J = 1.9 Hz, 1H), 7.32 (d, J = 8.5 Hz, 1H), 7.21 (d, J = 8.1 Hz, 1H), 7.16 (dd, J = 1.9, 8.5 Hz, 1H), 5.36 (s, 2H), 4.08-4.03 (m, 2H), 4.04 (s, 3H), 2.94-2.90 (m, 2H), 2.65-2.58 (m, 2H), 2.48 (s, 3H) | 468 (M⁺), 424, 269, 199 (base) |
| Example 12-6 | Example 11-6 | Example 13-28 | (DMSO-$d_6$) δ: 9.64 (brs, 1H), 7.71 (s, 1H), 7.62 (d, J = 7.7 Hz, 1H), 7.32 (d, J = 8.9 Hz, 1H), 7.22 (d, J = 7.3 Hz, 1H), 7.17 (s, 1H), 7.12 (d, J = 7.7 Hz, 1H), 5.36 (s, 2H), 4.10-4.03 (m, 2H), 2.95-2.90 (m, 2H), 2.65-2.59 (m, 2H), 2.50 (s, 3H), 2.48 (s, 3H), 2.32 (s, 3H) | 388 (M⁺ − 44), 199 (base) |
| Example 12-8 | Example 11-6 | Example 13-29 | (DMSO-$d_6$) δ: 9.66 (brs, 1H), 7.76 (d, J = 8.5 Hz, 1H), 7.71 (s, 1H), 7.48 (d, J = 1.9 Hz, 1H), 7.38 (dd, J = 1.9, 8.1 Hz, 1H), 7.32 (d, J = 8.1 Hz, 1H), 7.25-7.20 (m, 1H), 5.38 (s, 2H), 4.08-4.05 (m, 2H), 2.94-2.91 (m, 2H), 2.65-2.59 (m, 2H), 2.55 (s, 3H), 2.50 (s, 3H) | 452 (M⁺), 408, 199 (base) |
| Example 12-9 | Example 11-6 | Example 13-30 | (DMSO-$d_6$) δ: 9.66 (brs, 1H), 8.22 (dd, J = 6.6, 8.9 Hz, 1H), 7.71 (s, 1H), 7.66 (dd, J = 2.7, 8.9 Hz, 1H), 7.41-7.30 (m, 2H), 7.27-7.17 (m, 1H), 5.39 (s, 2H), 4.07 (t, J = 6.9 Hz, 2H), 2.94-2.91 (m, 2H), 2.65-2.59 (m, 2H), 2.48 (s, 3H) | 412 (M⁺ − 44), 199 (base) |
| Example 12-1 | Example 11-7 | Example 13-31 | (DMSO-$d_6$) δ: 9.62 (brs, 1H), 8.24 (d, J = 8.5 Hz, 1H), 7.69 (s, 1H), 7.41-7.32 (m, 2H), 7.24-7.19 (m, 1H), 7.15 (dd, J = 1.9, 8.5 Hz, 1H), 5.36 (s, 2H), 4.06-4.01 (m, 2H), 4.04 (s, 3H), 2.94-2.91 (m, 2H), 2.48 (s, 3H), 2.05-1.99 (m, 2H), 1.94-1.88 (m, 2H) | 269, 213 (base) |

TABLE 119

| Hydroxy compound | Carboxylic acid | Example | 1H-NMR | Mass, m/z |
|---|---|---|---|---|
| Example 12-5 | Example 11-7 | 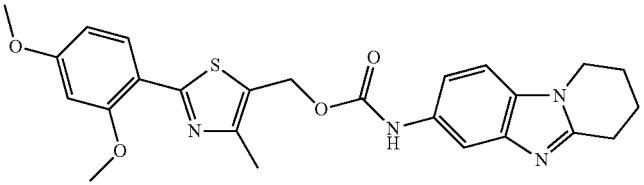<br>Example 13-32 | (DMSO-d$_6$) δ: 9.59 (brs, 1H), 8.18 (d, J = 8.9 Hz, 1H), 7.69 (s, 1H), 7.33 (d, J = 8.9 Hz, 1H), 7.24-7.12 (m, 1H), 6.75 (d, J = 2.7 Hz, 1H), 6.68 (dd, J = 2.3, 8.9 Hz, 1H), 5.33 (s, 2H), 4.06-4.03 (m, 2H), 4.00 (s, 3H), 3.84 (s, 3H), 2.94-2.91 (m, 2H), 2.45 (s, 3H), 2.06-2.00 (m, 2H), 1.94-1.88 (m, 2H) | 434 (M$^+$ − 44), 248 (base) |
| Example 12-6 | Example 11-7 | 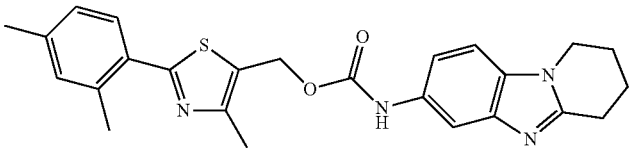<br>Example 13-33 | (DMSO-d$_6$) δ: 9.64 (brs, 1H), 7.69 (s, 1H), 7.62 (d, J = 8.1 Hz, 1H), 7.32 (d, J = 8.5 Hz, 1H), 7.23 (d, J = 8.5 Hz, 1H), 7.17 (s, 1H), 7.12 (d, J = 8.1 Hz, 1H), 5.36 (s, 2H), 4.06-4.03 (m, 2H), 2.94-2.91 (m, 2H), 2.50 (s, 3H), 2.48 (s, 3H), 2.32 (s, 3H), 2.06-1.99 (m, 2H), 1.94-1.88 (m, 2H) | 446 (M$^+$), 402, 216 (base) |
| Example 12-7 | Example 11-7 | 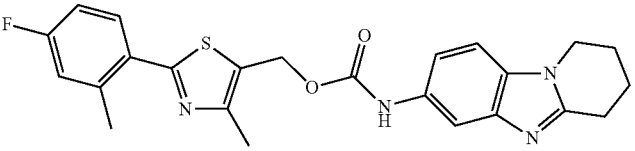<br>Example 13-34 | (DMSO-d$_6$) δ: 9.69 (brs, 1H), 7.77 (dd, J = 6.2, 8.9 Hz, 1H), 7.71 (s, 1H), 7.36 (d, J = 8.5 Hz, 1H), 7.27-7.22 (m, 2H), 7.20-7.11 (m, 1H), 5.38 (s, 2H), 4.07-4.04 (m, 2H), 2.96-2.93 (m, 2H), 2.54 (s, 3H), 2.50 (s, 3H), 2.06-1.99 (m, 2H), 1.95-1.88 (m, 2H) | 450 (M$^+$), 406, 220 (base) |
| Example 12-8 | Example 11-7 | 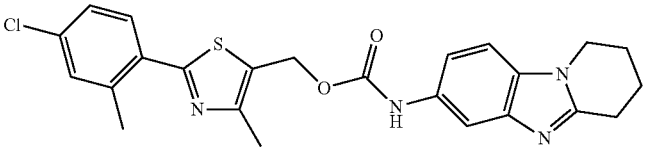<br>Example 13-35 | (DMSO-d$_6$) δ: 9.65 (brs, 1H), 7.76 (d, J = 8.1 Hz, 1H), 7.69 (s, 1H), 7.48 (d, J = 1.9 Hz, 1H), 7.38 (dd, J = 1.9, 8.1 Hz, 1H), 7.33 (d, J = 8.5 Hz, 1H), 7.23 (d, J = 8.5 Hz, 1H), 5.38 (s, 2H), 4.06-4.03 (m, 2H), 2.94-2.91 (m, 2H), 2.55 (s, 3H), 2.50 (s, 3H), 2.05-1.99 (m, 2H), 1.94-1.88 (m, 2H) | 422 (M$^+$ − 44), 213 (base) |

TABLE 119-continued

| Hydroxy compound | Carboxylic acid | Example | ¹H-NMR | Mass, m/z |
|---|---|---|---|---|
| Example 12-1 | Example 11-9 | Example 13-36 | (DMSO-d$_6$) δ: 9.61 (brs, 1H), 8.24 (d, J = 8.5 Hz, 1H), 7.68 (s, 1H), 7.39 (d, J = 8.9 Hz, 1H), 7.34 (d, J = 1.9 Hz, 1H), 7.27-7.20 (m, 1H), 7.16 (dd, J = 1.9, 8.5 Hz, 1H), 5.36 (s, 2H), 4.60-4.58 (m, 1H), 4.04 (s, 3H), 3.00-2.90 (m, 1H), 2.89-2.80 (m, 1H), 2.48 (s, 3H), 2.20-2.07 (m, 1H), 2.07-1.95 (m, 1H), 1.95-1.82 (m, 2H), 1.42 (d, J = 6.6 Hz, 3H) | 452 (M$^+$ − 44), 212 (base) |

TABLE 120

| Hydroxy compound | Carboxylic acid | Example | ¹H-NMR | Mass, m/z |
|---|---|---|---|---|
| Example 12-8 | Example 11-9 | Example 13-37 | (DMSO-d$_6$) δ: 9.65 (brs, 1H), 7.76 (d, J = 8.5 Hz, 1H), 7.68 (s, 1H), 7.48 (d, J = 2.3 Hz, 1H), 7.41-7.37 (m, 2H), 7.22 (d, J = 8.5 Hz, 1H), 5.38 (s, 2H), 4.61-4.57 (m, 1H), 2.98-2.92 (m, 1H), 2.89-2.81 (m, 1H), 2.55 (s, 3H), 2.50 (s, 3H), 2.16-2.08 (m, 1H), 2.03-1.95 (m, 1H), 1.88-1.86 (m, 2H), 1.42 (d, J = 6.6 Hz, 3H) | 480 (M$^+$), 436, 236 (base) |
| Example 12-9 | Example 11-9 | Example 13-38 | (DMSO-d$_6$) δ: 9.65 (brs, 1H), 8.22 (dd, J = 6.2, 8.9 Hz, 1H), 7.68-7.64 (m, 2H), 7.42-7.37 (m, 2H), 7.22 (d, J = 8.1 Hz, 1H), 5.39 (s, 2H), 4.61-4.57 (m, 1H), 2.98-2.92 (m, 1H), 2.89-2.81 (m, 1H), 2.49 (s, 3H), 2.16-2.07 (m, 1H), 2.03-1.93 (m, 1H), 1.91-1.83 (m, 2H), 1.41 (d, J = 6.6 Hz, 3H) | 484 (M$^+$), 440, 200 (base) |

TABLE 120-continued

| Hydroxy compound | Carboxylic acid | Example | ¹H-NMR | Mass, m/z |
|---|---|---|---|---|
| Example 12-8 | Example 11-8 | 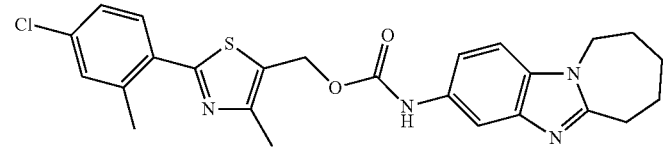Example 13-39 | (DMSO-d₆) δ: 9.63 (brs, 1H), 7.76 (d, J = 8.5 Hz, 1H), 7.68 (s, 1H), 7.48 (d, J = 1.9 Hz, 1H), 7.40-7.37 (m, 2H), 7.22 (d, J = 8.1 Hz, 1H), 5.38 (s, 2H), 4.20-4.18 (m, 2H), 3.00-2.97 (m, 2H), 2.55 (s, 3H), 2.50 (s, 3H), 1.88-1.84 (m, 2H), 1.72-1.65 (m, 2H) | 480 (M⁺), 436, 227 (base) |
| Example 12-9 | Example 11-8 | 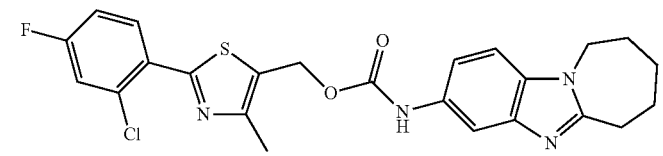Example 13-40 | (DMSO-d₆) δ: 9.64 (brs, 1H), 8.22 (dd, J = 6.6, 9.2 Hz, 1H), 7.67 (d, J = 2.7 Hz, 1H), 7.65 (d, J = 2.7 Hz, 1H), 7.42-7.37 (m, 2H), 7.22 (d, J = 8.5 Hz, 1H), 5.39 (s, 2H), 4.19 (t, J = 5.0 Hz, 2H), 3.00-2.98 (m, 2H), 2.48 (s, 3H), 1.87-1.84 (m, 2H), 1.73-1.65 (m, 2H) | 484 (M⁺), 440, 200 (base) |
| Example 12-1 | Example 11-10 | 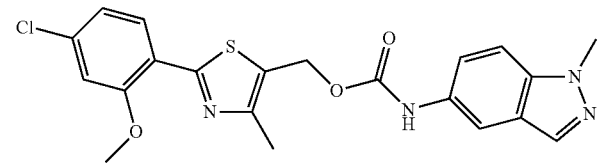Example 13-41 | (DMSO-d₆) δ: 9.73 (brs, 1H), 8.24 (d, J = 8.5 Hz, 1H), 7.96 (dd, J = 0.8, 6.6 Hz, 1H), 7.90 (d, J = 8.1 Hz, 1H), 7.55 (dd, J = 2.7, 8.9 Hz, 1H), 7.41-7.37 (m, 1H), 7.35 (d, J = 1.9 Hz, 1H), 7.16 (dd, J = 1.9, 8.5 Hz, 1H), 5.37 (s, 2H), 4.04 (s, 3H), 4.00 (s, 3H), 2.49 (s, 3H) | 398 (M⁺ − 44), 252 (base) |

TABLE 121

| Hydroxy compound | Carboxylic acid | Example | ¹H-NMR | Mass, m/z |
|---|---|---|---|---|
| Example 12-6 | Example 11-10 | 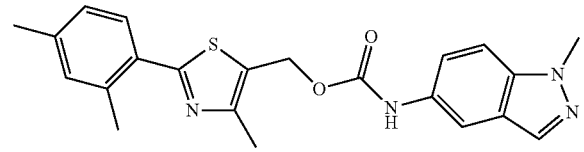Example 13-42 | (DMSO-d₆) δ: 9.76 (brs, 1H), 7.97 (d, J = 0.8 Hz, 1H), 7.89 (s, 1H), 7.62 (d, J = 8.1 Hz, 1H), 7.55 (d, J = 8.9 Hz, 1H), 7.41 (dd, J = 1.5, 8.9 Hz, 1H), 7.17 (s, 1H), 7.12 (d, J = 8.1 Hz, 1H), 5.38 (s, 2H), 4.00 (s, 3H), 2.50 (s, 3H), 2.49 (s, 3H), 2.32 (s, 3H) | 362 (M⁺ − 44), 216 (base) |

TABLE 121-continued

| Hydroxy compound | Carboxylic acid | Example | ¹H-NMR | Mass, m/z |
|---|---|---|---|---|
| Example 12-7 | Example 11-10 | Example 13-43 | (DMSO-d₆) δ: 9.76 (brs, 1H), 7.96 (d, J = 0.8 Hz, 1H), 7.89 (s, 1H), 7.76 (dd, J = 6.2, 8.9 Hz, 1H), 7.55 (d, J = 9.2 Hz, 1H), 7.41 (dd, J = 1.9, 9.2 Hz, 1H), 7.25 (dd, J = 2.7, 10.0 Hz, 1H), 7.15 (dt, J = 2.7, 8.5 Hz, 1H), 5.38 (s, 2H), 4.00 (s, 3H), 2.54 (s, 3H), 2.50 (s, 3H) | 410 (M⁺), 366, 220 (base) |
| Example 12-7 | Example 11-11 | Example 13-44 | (DMSO-d₆) δ: 9.76 (brs, 1H), 7.98 (d, J = 0.8 Hz, 1H), 7.89 (s, 1H), 7.77 (dd, J = 6.2, 8.9 Hz, 1H), 7.59 (d, J = 9.2 Hz, 1H), 7.40 (dd, J = 1.9, 8.9 Hz, 1H), 7.25 (dd, J = 2.7, 10.0 Hz, 1H), 7.15 (dt, J = 2.7, 8.5 Hz, 1H), 5.39 (s, 2H), 4.39 (q, J = 7.3 Hz, 2H), 2.54 (s, 3H), 2.50 (s, 3H), 1.38 (t, J = 7.3 Hz, 3H) | 424 (M⁺), 380, 220 (base) |
| Example 12-6 | Example 11-11 | Example 13-45 | (DMSO-d₆) δ: 9.74 (brs, 1H), 7.98 (d, J = 0.8 Hz, 1H), 7.89 (s, 1H), 7.62 (d, J = 7.7 Hz, 1H), 7.59 (d, J = 8.6 Hz, 1H), 7.39 (dd, J = 1.5, 8.9 Hz, 1H), 7.17 (s, 1H), 7.12 (d, J = 8.5 Hz, 1H), 5.38 (s, 2H), 4.39 (q, J = 7.3 Hz, 2H), 2.50 (s, 3H), 2.49 (s, 3H), 2.32 (s, 3H), 1.40-1.35 (m, 3H) | 420 (M⁺), 376, 216 (base) |
| Example 12-1 | Example 11-12 | Example 13-46 | (DMSO-d₆) δ: 9.64 (brs, 1H), 8.24 (d, J = 8.5 Hz, 1H), 8.21 (s, 1H), 7.84 (s, 1H), 7.50 (d, J = 9.2 Hz, 1H), 7.35 (d, J = 1.9 Hz, 1H), 7.21 (dd, 1.9, 9.2 Hz, 1H), 7.16 (dd, J = 1.9, 8.5 Hz, 1H), 5.36 (s, 2H), 4.12 (s, 3H), 4.04 (s, 3H), 2.48 (s, 3H) | 442 (M⁺), 398, 252 (base) |

TABLE 122

| Hydroxy compound | Carboxylic acid | Example | ¹H-NMR | Mass, m/z |
|---|---|---|---|---|
| Example 12-4 | Example 11-12 | 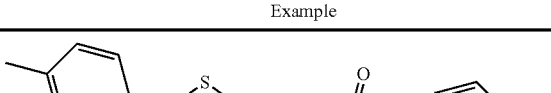 Example 13-47 | (DMSO-d₆) δ: 9.63 (brs, 1H), 8.21 (s, 1H), 8.12 (d, J = 8.1 Hz, 1H), 7.84 (s, 1H), 7.50 (d, J = 9.2 Hz, 1H), 7.21 (d, J = 1.9, 9.2 Hz, 1H), 7.06 (s, 1H), 6.91 (d, J = 8.1 Hz, 1H), 5.35 (s, 2H), 4.12 (s, 3H), 3.99 (s, 3H), 2.47 (s, 3H), 2.37 (s, 3H) | 378 (M⁺ − 44), 232 (base) |

TABLE 122-continued

| Hydroxy compound | Carboxylic acid | Example | ¹H-NMR | Mass, m/z |
|---|---|---|---|---|
| Example 12-6 | Example 11-12 | 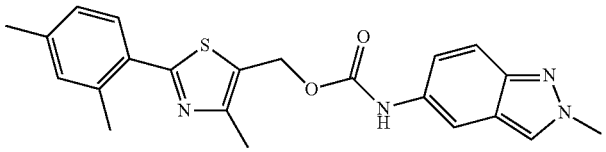 Example 13-48 | (DMSO-d₆) δ: 9.67 (brs, 1H), 8.21 (s, 1H), 7.85 (s, 1H), 7.62 (d, J = 8.1 Hz, 1H), 7.51 (d, J = 8.9 Hz, 1H), 7.22 (dd, J = 1.9, 8.9 Hz, 1H), 7.17 (s, 1H), 7.12 (d, J = 8.1 Hz, 1H), 5.37 (s, 2H), 4.12 (s, 3H), 2.50 (s, 3H), 2.48 (s, 3H), 2.32 (s, 3H) | 362 (M⁺ − 44), 216 (base) |
| Example 12-7 | Example 11-12 | 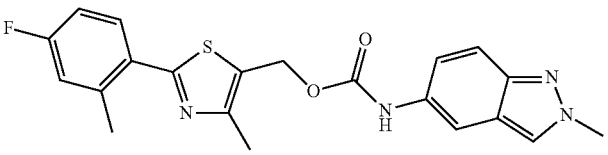 Example 13-49 | (DMSO-d₆) δ: 9.68 (brs, 1H), 8.21 (s, 1H), 7.85 (s, 1H), 7.76 (dd, J = 6.3, 8.7 Hz, 1H), 7.51 (d, J = 8.2 Hz, 1H), 7.25 (dd, J = 2.9, 10.2 Hz, 1H), 7.22 (dd, J = 1.9, 9.2 Hz, 1H), 7.17-7.12 (m, 1H), 5.38 (s, 2H), 4.12 (s, 3H), 2.54 (s, 3H), 2.49 (s, 3H) | 410 (M⁺), 366, 220 (base) |
| Example 12-8 | Example 11-12 | 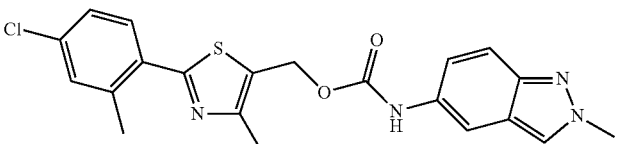 Example 13-50 | (DMSO-d₆) δ: 9.68 (brs, 1H), 8.21 (s, 1H), 7.84 (s, 1H), 7.76 (d, J = 8.5 Hz, 1H), 7.51 (d, J = 9.2 Hz, 1H), 7.48 (d, J = 1.9 Hz, 1H), 7.38 (dd, J = 2.3, 8.5 Hz, 1H), 7.21 (dd, J = 1.9, 9.2 Hz, 1H), 5.38 (s, 2H), 4.12 (s, 3H), 2.55 (s, 3H), 2.50 (s, 3H) | 426 (M⁺), 382, 236 (base) |
| Example 12-3 | Example 11-13 | 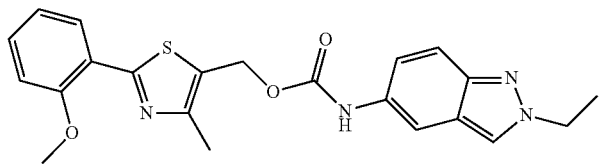 Example 13-51 | (DMSO-d₆) δ: 9.67 (brs, 1H), 8.26 (d, J = 2.3 Hz, 1H), 8.24 (d, J = 1.5 Hz, 1H), 7.86 (s, 1H), 7.52 (d, J = 9.2 Hz, 1H), 7.46 (dt, J = 1.5, 8.5 Hz, 1H), 7.27-7.20 (m, 2H), 7.11-7.07 (m, 1H), 5.37 (s, 2H), 4.40 (q, J = 7.3 Hz, 2H), 4.01 (s, 3H), 2.49 (s, 3H), 1.49 (t, J = 7.3 Hz, 3H) | 422 (M⁺), 378, 218 (base) |

TABLE 123

| Hydroxy compound | Carboxylic acid | Example | ¹H-NMR | Mass, m/z |
|---|---|---|---|---|
| Example 12-4 | Example 11-13 | 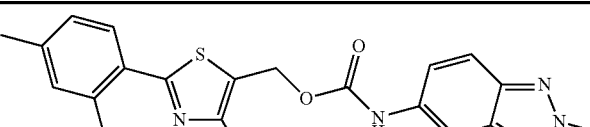 Example 13-52 | (DMSO-d₆) δ: 9.63 (brs, 1H), 8.25 (s, 1H), 8.12 (d, J = 8.1 Hz, 1H), 7.85 (s, 1H), 7.52 (d, J = 9.2 Hz, 1H), 7.22 (d, J = 1.9, 9.2 Hz, 1H), 7.06 (s, 1H), 6.90 (d, J = 7.7 Hz, 1H), 5.35 (s, 2H), 4.40 (q, J = 7.3 Hz, 2H), 3.99 (s, 3H), 2.47 (s, 3H), 2.37 (s, 3H), 1.49 (t, J = 7.3 Hz, 3H) | 392 (M⁺ − 44), 232 (base) |

TABLE 123-continued

| Hydroxy compound | Carboxylic acid | Example | ¹H-NMR | Mass, m/z |
|---|---|---|---|---|
| Example 12-6 | Example 11-13 | Example 13-53 | (DMSO-d$_6$) δ: 9.67 (brs, 1H), 8.26 (d, J = 0.8 Hz, 1H), 7.85 (s, 1H), 7.62 (d, J = 8.1 Hz, 1H), 7.52 (d, J = 8.9 Hz, 1H), 7.27-7.11 (m, 3H), 5.37 (s, 2H), 4.40 (q, J = 7.3 Hz, 2H), 2.50 (s, 3H), 2.49 (s, 3H), 2.32 (s, 3H), 1.49 (t, J = 7.3 Hz, 3H) | 420 (M⁺), 376, 216 (base) |
| Example 12-7 | Example 11-13 | Example 13-54 | (DMSO-d$_6$) δ: 9.68 (brs, 1H), 8.26 (d, J = 0.8 Hz, 1H), 7.85 (s, 1H), 7.76 (dd, J = 6.2, 8.9 Hz, 1H), 7.52 (d, J = 8.1 Hz, 1H), 7.27-7.21 (m, 2H), 7.15 (dt, J = 2.7, 8.5 Hz, 1H), 5.38 (s, 2H), 4.40 (q, J = 7.3 Hz, 2H), 2.54 (s, 3H), 2.49 (s, 3H), 1.49 (t, J = 7.3 Hz, 3H) | 424 (M⁺), 380, 220 (base) |
| Example 12-8 | Example 11-13 | Example 13-55 | (DMSO-d$_6$) δ: 9.68 (brs, 1H), 8.26 (s, 1H), 7.85 (s, 1H), 7.76 (d, J = 8.5 Hz, 1H), 7.52 (d, J = 9.2 Hz, 1H), 7.49 (s, 1H), 7.38 (dd, J = 2.3, 8.5 Hz, 1H), 7.22 (dd, J = 1.9, 9.2 Hz, 1H), 5.38 (s, 2H), 4.40 (q, J = 7.3 Hz, 2H), 2.55 (s, 3H), 2.50 (s, 3H) 1.49 (t, J = 7.3 Hz, 3H) | 440 (M⁺), 396, 236 (base) |
| Example 12-9 | Example 11-13 | Example 13-56 | (DMSO-d$_6$) δ: 9.68 (brs, 1H), 8.26 (s, 1H), 8.22 (dd, J = 6.3, 9.2 Hz, 1H), 7.85 (s, 1H), 7.65 (dd, J = 2.4, 8.7 Hz, 1H), 7.52 (d, J = 9.2 Hz, 1H), 7.42-7.37 (m, 1H), 7.22 (dd, J = 1.9, 9.2 Hz, 1H), 5.40 (s, 2H), 4.40 (q, J = 7.2 Hz, 2H), 2.48 (s, 3H), 1.49 (t, J = 7.2 Hz, 3H) | 444 (M⁺), 400, 240 (base) |

TABLE 124

| Hydroxy compound | Carboxylic acid | Example | ¹H-NMR | Mass, m/z |
|---|---|---|---|---|
| Example 12-10 | Example 11-2 | Example 13-57 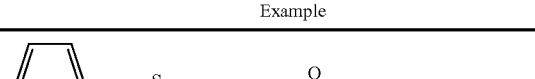 | (DMSO-d$_6$) δ: 9.70 (brs, 1H), 8.17 (s, 1H), 7.87-7.86 (m, 1H), 7.80 (s, 1H), 7.50 (d, J = 8.9 Hz, 1H), 7.30 (d, J = 8.1 Hz, 1H), 7.08 (d, J = 3.1 Hz, 1H), 6.68 (dd, J = 1.9, 3.5 Hz, 1H), 5.35 (s, 2H), 4.23 (q, J = 7.3 Hz, 2H), 2.45 (s, 3H), 1.40 (t, J = 7.3 Hz, 3H) | 382 (M⁺), 338, 178 (base) |

TABLE 124-continued

| Hydroxy compound | Carboxylic acid | Example | ¹H-NMR | Mass, m/z |
|---|---|---|---|---|
| Example 12-11 | Example 11-2 | Example 13-58 | (DMSO-d₆) δ: 9.70 (brs, 1H), 8.17 (s, 1H), 7.80 (s, 1H), 7.71 (dd, d = 1.2, 5.0 Hz, 1H), 7.64 (dd, J = 1.2, 3.9 Hz, 1H), 7.50 (d, J = 8.5 Hz, 1H), 7.31 (d, J = 8.5 Hz, 1H), 7.15 (dd, J = 3.9, 5.0 Hz, 1H), 5.34 (s, 2H), 4.23 (q, J = 7.3 Hz, 2H), 2.43 (s, 3H), 1.40 (t, J = 7.3 Hz, 3H) | 398 (M⁺), 354, 194 (base) |
| Example 12-12 | Example 11-2 | Example 13-59 | (DMSO-d₆) δ: 9.71 (brs, 1H), 8.17 (s, 1H), 7.82 (d, J = 5.4 Hz, 1H), 7.80 (s, 1H), 7.71 (dd, d = 1.2, 5.0 Hz, 1H), 7.64 (dd, J = 1.2, 3.9 Hz, 1H), 7.50 (d, J = 8.9 Hz, 1H), 7.31 (d, J = 8.1 Hz, 1H), 7.24 (d, J = 5.4 Hz, 1H), 5.39 (s, 2H), 4.23 (q, J = 7.3 Hz, 2H), 2.47 (s, 3H), 1.40 (t, J = 7.3 Hz, 3H) | 432 (M⁺), 388, 228 (base) |
| Example 12-10 | Example 11-5 | Example 13-60 | (DMSO-d₆) δ: 9.71 (brs, 1H), 7.87-7.86 (m, 1H), 7.76 (s, 1H), 7.42 (d, J = 8.9 Hz, 1H), 7.28 (d, J = 9.2 Hz, 1H), 7.08 (dd, J = 0.8, 3.5 Hz, 1H), 6.69 (dd, J = 1.5, 3.5 Hz, 1H), 5.35 (s, 2H), 4.92 (s, 2H), 4.15 (s, 4H), 2.45 (s, 3H) | 407 (M⁺), 363, 203 (base) |
| Example 12-12 | Example 11-5 | Example 13-61 | (DMSO-d₆) δ: 9.72 (brs, 1H), 7.82 (d, J = 5.4 Hz, 1H), 7.76 (s, 1H), 7.42 (d, J = 8.9 Hz, 1H), 7.29 (d, J = 6.9 Hz, 1H), 7.24 (d, J = 5.4 Hz, 1H), 5.39 (s, 2H), 4.92 (s, 2H), 4.14 (s, 4H), 2.46 (s, 3H) | 460 (M⁺), 416, 215 (base) |

TABLE 125

| Hydroxy compound | Carboxylic acid | Example | ¹H-NMR | Mass, m/z |
|---|---|---|---|---|
| Example 12-10 | Example 11-7 | Example 13-62 | (DMSO-d₆) δ: 9.65 (brs, 1H), 7.87-7.86 (m, 1H), 7.69 (s, 1H), 7.33 (d, J = 8.9 Hz, 1H), 7.22 (d, J = 8.9 Hz, 1H), 7.08 (dd, J = 0.8, 3.5 Hz, 1H), 6.69 (dd, J = 1.9, 3.5 Hz, 1H), 5.34 (s, 2H), 4.06-4.03 (m, 2H), 2.94-2.91 (m, 2H), 2.45 (s, 3H), 2.04-1.99 (m, 2H), 1.94-1.90 (m, 2H) | 408 (M⁺), 364, 178 (base) |
| Example 12-11 | Example 11-7 | Example 13-63 | (DMSO-d₆) δ: 9.65 (brs, 1H), 7.71-7.00 (m, 2H), 7.64 (dd, J = 0.8, 3.5 Hz, 1H), 7.33 (d, J = 8.5 Hz, 1H), 7.23 (d, J = 8.9 Hz, 1H), 7.15 (dd, J = 3.5, 5.0 Hz, 1H), 5.33 (s, 2H), 4.04 (t, J = 6.2 Hz, 2H), 2.94-2.91 (m, 2H), 2.43 (s, 3H), 2.04-1.99 (m, 2H), 1.94-1.90 (m, 2H) | 380 (M⁺ − 44), 194 (base) |

TABLE 125-continued

| Hydroxy compound | Carboxylic acid | Example | ¹H-NMR | Mass, m/z |
|---|---|---|---|---|
| Example 12-13 | Example 11-2 | 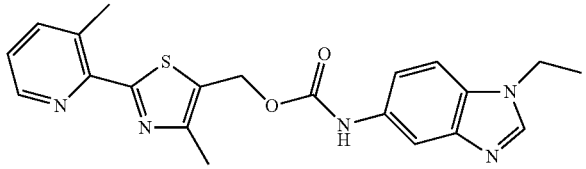 Example 13-64 | (DMSO-d$_6$) δ: 9.70 (brs, 1H), 8.46 (dd, J = 1.2, 4.6 Hz, 1H), 8.17 (s, 1H), 7.80-7.77 (m, 2H), 7.50 (d, J = 8.9 Hz, 1H), 7.37 (dd, J = 4.6, 7.7 Hz, 1H), 7.31 (d, J = 8.5 Hz, 1H), 5.37 (s, 2H), 4.23 (q, J = 7.3 Hz, 2H), 2.73 (s, 3H), 2.50 (s, 3H), 1.40 (t, J = 7.3 Hz, 3H) | 407 (M⁺), 363, 203 (base) |
| Example 12-13 | Example 11-5 | 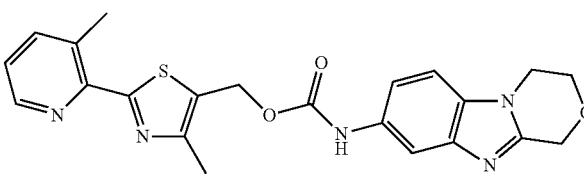 Example 13-65 | (DMSO-d$_6$) δ: 9.71 (brs, 1H), 8.47-8.46 (m, 1H), 7.79-7.77 (m, 2H), 7.42 (d, J = 8.5 Hz, 1H), 7.37 (dd, J = 5.0, 7.7 Hz, 1H), 7.29 (d, J = 8.5 Hz, 1H), 5.37 (s, 2H), 4.92 (s, 2H), 4.14 (s, 4H), 2.73 (s, 3H), 2.50 (s, 3H) | 435 (M⁺), 391, 203 (base) |
| Example 12-14 | — | 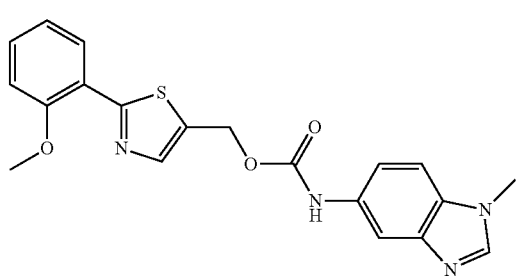 Example 13-66 | (DMSO-d$_6$) δ: 9.69 (brs, 1H), 8.28 (dd, J = 1.9, 8.1 Hz, 1H), 8.11 (s, 1H), 7.99 (s, 1H), 7.81 (s, 1H), 7.50-7.45 (m, 2H), 7.33 (d, J = 8.1 Hz, 1H), 7.26 (d, J = 8.5 Hz, 1H), 7.13-7.09 (m, 1H), 5.43 (s, 2H), 4.02 (s, 3H), 3.80 (s, 3H), 1.41 (t, J = 7.3 Hz, 3H) | 350 (M⁺ − 44), 173 (base) |

TABLE 126

| Hydroxy compound | Carboxylic acid | Example | ¹H-NMR | Mass, m/z |
|---|---|---|---|---|
| Example 12-15 | — | 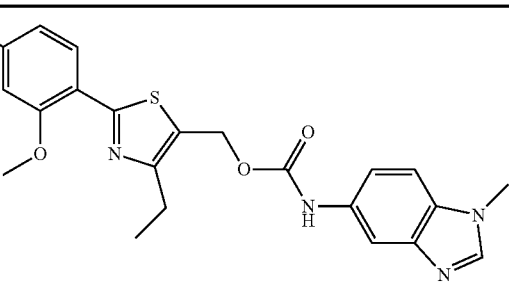 Example 13-67 | (DMSO-d$_6$) δ: 9.66 (brs, 1H), 8.27 (d, J = 8.5 Hz, 1H), 8.10 (s, 1H), 7.80 (s, 1H), 7.45 (d, J = 8.9 Hz, 1H), 7.35 (d, J = 1.5 Hz, 1H), 7.32 (d, J = 8.5 Hz, 1H), 7.17 (dd, J = 1.5, 8.5 Hz, 1H), 5.38 (s, 2H), 4.04 (s, 3H), 3.80 (s, 3H), 2.84 (q, J = 7.3 Hz, 2H), 1.28 (t, J = 7.3 Hz, 3H) | 412 (M⁺ − 44), 283, 173 (base) |
| Example 12-16 | — | 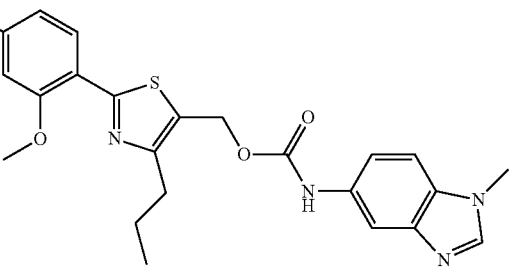 Example 13-68 | (DMSO-d$_6$) δ: 9.65 (brs, 1H), 8.25 (d, J = 8.5 Hz, 1H), 8.10 (s, 1H), 7.80 (s, 1H), 7.45 (d, J = 8.9 Hz, 1H), 7.35 (d, J = 1.9 Hz, 1H), 7.34-7.30 (m, 1H), 7.16 (dd, J = 1.9, 8.5 Hz, 1H), 5.38 (s, 2H), 4.04 (s, 3H), 3.80 (s, 3H), 2.80 (q, J = 7.3 Hz, 2H), 1.73 (sextet, J = 7.3 Hz, 2H), 0.95 (t, J = 7.3 Hz, 3H) | 426 (M⁺ − 44), 297, 173 (base) |

TABLE 126-continued

| Hydroxy compound | Carboxylic acid | Example | ¹H-NMR | Mass, m/z |
|---|---|---|---|---|
| Example 12-20 | 4-Fluoro benzoic acid | Example 13-69 | (DMSO-d₆) δ: 9.81 (brs, 1H), 7.86 (d, J = 8.5 Hz, 1H), 7.51-7.44 (m, 2H), 7.34-7.32 (m, 1H), 7.20-7.11 (m, 2H), 7.04 (dd, J = 1.9, 8.5 Hz, 1H), 6.82 (s, 1H), 5.24 (s, 2H), 3.91 (s, 3H), 3.89 (s, 3H) | 389 (M⁺), 343, 248, 235, 111 (base) |
| Example 12-19 | 4-Methoxy benzoic acid | Example 13-70 | (DMSO-d₆) δ: 9.57 (brs, 1H), 7.84 (dd, J = 7.38, 5 Hz, 1H), 7.36 (d, J = 8.5 Hz, 2H), 6.99 (dd, J = 2.3, 11.6 Hz, 1H), 6.87 (d, J = 9.2 Hz, 2H), 6.80 (dt, J = 2.3, 8.5 Hz, 1H), 6.77 (s, 1H), 5.21 (s, 2H), 3.90 (s, 3H), 3.87 (s, 3H), 3.71 (s, 3H) | 385 (M⁺), 341, 236, 219 (base), 178 |

TABLE 127

| Hydroxy compound | Carboxylic acid | Example | ¹H-NMR | Mass, m/z |
|---|---|---|---|---|
| Example 12-20 | 3-Fluoro-4-methoxy-benzoic acid | Example 13-71 | (DMSO-d₆) δ: 9.78 (br s, 1H), 7.86 (d, J = 8.1 Hz, 1H), 7.37 (d, J = 13.7 Hz, 1H), 7.15 (dd, J = 1.5, 8.1 Hz, 1H), 7.12-7.08 (m, 1H), 7.04 (dd, J = 1.9, 8.5 Hz, 1H), 6.82 (s, 1H), 5.24 (s, 2H), 3.91 (s, 3H), 3.89 (s, 3H), 3.79 (s, 3H) | 419 (M⁺), 375, 235 (base) |
| Example 12-17 | 3-Fluoro-4-methoxy-benzoic acid | Example 13-72 | (DMSO-d₆) δ: 9.77 (br s, 1H), 7.73 (d, J = 7.7 Hz, 1H), 7.37 (d, J = 13.1 Hz, 1H), 7.19-7.08 (m, 2H), 6.91 (s, 1H), 6.80-6.78 (m, 2H), 5.23 (s, 2H), 3.89 (s, 3H), 3.84 (s, 3H), 3.79 (s, 3H) | 399 (M⁺), 355, 248, 215 (base) |
| Example 12-20 | 2,3-Dihydro-1-benzofuran-5-carboxylic acid | Example 13-73 | (DMSO-d₆) δ: 9.50 (br s, 1H), 7.86 (d, J = 8.5 Hz, 1H), 7.33 (s, 1H), 7.16 (d, J = 1.9 Hz, 1H), 7.11 (d, J = 8.1 Hz, 1H), 7.03 (dd, J = 2.3, 8.5 Hz, 1H), 6.81 (s, 1H), 6.67 (d, J = 8.5 Hz, 1H), 5.21 (s, 2H), 4.48 (t, J = 8.5 Hz, 2H), 3.91 (s, 3H), 3.89 (s, 3H), 3.14 (t, J = 8.5 Hz, 3H) | 413 (M⁺), 399, 235 (base) |
| Example 12-17 | 2,3-Dihydro-1-benzofuran-5-carboxylic acid | Example 13-74 | (DMSO-d₆) δ: 9.50 (br s, 1H), 7.73 (d, J = 8.1 Hz, 1H), 7.34 (s, 1H), 7.11 (d, J = 8.5 Hz, 1H), 6.90 (s, 1H), 6.78 (dd, J = 0.8, 8.5 Hz, 1H), 6.77 (s, 1H), 6.67 (d, J = 8.9 Hz, 1H), 5.20 (s, 2H), 4.48 (t, J = 8.5 Hz, 2H), 3.89 (s, 3H), 3.84 (s, 3H), 3.14 (t, J = 8.5 Hz, 3H), 2.32 (s, 3H) | 393 (M⁺), 349, 215 (base) |

TABLE 128

| Hydroxy compound | Carboxylic acid | Example | ¹H-NMR | Mass, m/z |
|---|---|---|---|---|
| Example 12-20 | Benzoxazole-6-carboxylic acid | Example 13-75 | (DMSO-d$_6$) δ: 10.08 (br s, 1H), 8.63 (s, 1H), 7.99 (d, J = 0.8 Hz, 1H), 7.86 (d, J = 8.1 Hz, 1H), 7.70 (d, J = 8.5 Hz, 1H), 7.37 (dd, J = 1.9, 8.5 Hz, 1H), 7.17 (d, J = 1.9 Hz, 1H), 7.03 (dd, J = 1.9, 8.1 Hz, 1H), 6.85 (s, 1H), 5.28 (s, 2H), 3.93 (s, 3H), 3.89 (s, 3H) | 412 (M⁺), 368, 235, 160 (base) |
| Example 12-21 | — | Example 13-76 | (DMSO-d$_6$) δ: 9.70 (br s, 1H), 8.11 (s, 1H), 7.86 (dd, J = 1.9, 7.7 Hz, 1H), 7.81 (s, 1H), 7.46 (d, J = 8.5 Hz, 1H), 7.33-7.30 (m, 1H), 7.28 (dd, J = 1.9, 7.3 Hz, 1H), 7.09 (dd, J = 0.8, 8.5 Hz, 1H), 6.97 (dt, J = 1.2, 7.3 Hz, 1H), 6.84 (s, 1H), 5.26 (s, 2H), 3.93 (s, 3H), 3.85 (s, 3H), 3.80 (s, 3H) | 391 (M⁺), 347, 173 (base) |
| Example 12-22 | — | Example 13-77 | (DMSO-d$_6$) δ: 9.68 (s, 1H), 8.11 (s, 1H), 7.87 (dd, J = 1.9, 7.7 Hz, 1H), 7.81 (s, 1H), 7.46 (d, J = 8.5 Hz, 1H), 7.33-7.27 (m, 2H), 7.09 (d, J = 7.7 Hz, 1H), 7.00-6.96 (m, 1H), 6.83 (s, 1H), 5.27 (s, 2H), 4.24 (q, J = 7.3 Hz, 2H), 3.86 (s, 3H), 3.80 (s, 3H), 1.42 (t, J = 7.3 Hz, 3H) | 405 (M⁺), 232, 215, 173 (base) |
| Example 12-21 | Example 11-2 | Example 13-78 | (DMSO-d$_6$) δ: 9.69 (br s, 1H), 8.17 (s, 1H), 7.86 (dd, J = 1.5, 7.7 Hz, 1H), 7.81 (s, 1H), 7.50 (d, J = 8.9 Hz, 1H), 7.32-7.26 (m, 2H), 7.09 (d, J = 7.7 Hz, 1H), 6.99-6.95 (m, 1H), 6.83 (s, 1H), 5.26 (s, 2H), 4.23 (q, J = 7.3 Hz, 2H), 3.93 (s, 3H), 3.85 (s, 3H), 1.40 (t, J = 7.3 Hz, 3H) | 405 (M⁺), 361, 201 (base), 187 |

TABLE 129

| Hydroxy compound | Carboxylic acid | Example | ¹H-NMR | Mass, m/z |
|---|---|---|---|---|
| Example 12-22 | Example 11-2 | Example 13-79 | (DMSO-d$_6$) δ: 9.68 (br s, 1H), 8.18 (s, 1H), 7.87 (dd, J = 1.9, 7.7 Hz, 1H), 7.81 (s, 1H), 7.51 (d, J = 8.9 Hz, 1H), 7.32-7.27 (m, 2H), 7.09 (d, J = 7.7 Hz, 1H), 6.98 (dt, J = 0.8, 7.7 Hz, 1H), 6.83 (s, 1H), 5.27 (s, 2H), 4.24 (q, J = 7.3 Hz, 2H), 4.23 (q, J = 7.3 Hz, 2H), 3.86 (s, 3H), 1.44-1.38 (m, 6H) | 419 (M⁺), 375, 232, 187 (base) |

TABLE 129-continued

| Hydroxy compound | Carboxylic acid | Example | ¹H-NMR | Mass, m/z |
|---|---|---|---|---|
| Example 12-19 | — | Example 13-80 | (DMSO-d$_6$) δ: 9.70 (s, 1H), 8.11 (s, 1H), 7.87-7.81 (m, 2H), 7.47 (d, J = 8.9 Hz, 1H), 7.32 (d, J = 7.7 Hz, 1H), 6.99 (dd, J = 2.7, 11.6 Hz, 1H), 6.83-6.78 (m, 2H), 5.25 (s, 2H), 3.92 (s, 3H), 3.87 (s, 3H), 3.80 (s, 3H) | 409 (M⁺), 365, 236, 219 (base) |
| Example 12-24 | — | Example 13-81 | (DMSO-d$_6$) δ: 9.68 (br s, 1H), 8.11 (s, 1H), 7.86 (dd, J = 7.3, 8.5 Hz, 1H), 7.81 (s, 1H), 7.46 (dd, J = 2.3, 11.6 Hz, 1H), 6.82 (dd, J = 2.7, 8.5 Hz, 1H), 6.78 (s, 1H), 5.26 (s, 2H), 4.24 (q, J = 7.3 Hz, 2H), 3.87 (s, 3H), 3.80 (s, 3H), 1.41 (t, J = 7.3 Hz, 3H) | 423 (M⁺), 379, 250, 233 (base) |
| Example 12-19 | Example 11-2 | Example 13-82 | (DMSO-d$_6$) δ: 9.69 (br s, 1H), 8.17 (s, 1H), 7.85 (dd, J = 6.9, 8.5 Hz, 1H), 7.81 (s, 1H), 7.50 (d, J = 8.9 Hz, 1H), 7.31 (dd, J = 0.8, 8.5 Hz, 1H), 6.99 (dd, J = 2.3, 11.6 Hz, 1H), 6.80 (dt, J = 2.3, 8.5 Hz, 1H), 6.79 (s, 1H), 5.25 (s, 2H), 4.23 (q, J = 7.3 Hz, 2H), 3.92 (s, 3H), 3.87 (s, 3H), 1.40 (t, J = 7.3 Hz, 3H) | 423 (M⁺), 379, 236, 187 (base), 172 |

TABLE 130

| Hydroxy compound | Carboxylic acid | Example | ¹H-NMR | Mass, m/z |
|---|---|---|---|---|
| Example 12-24 | Example 11-2 | Example 13-83 | (DMSO-d$_6$) δ: 9.67 (br s, 1H), 8.17 (s, 1H), 7.86 (dd, J = 6.9, 8.5 Hz, 1H), 7.81 (s, 1H), 7.50 (d, J = 8.5 Hz, 1H), 7.31 (d, J = 8.5 Hz, 1H), 6.99 (dd, J = 2.3, 11.6 Hz, 1H), 6.81 (dd, J = 2.7, 8.5 Hz, 1H), 6.78 (s, 1H), 5.26 (s, 2H), 4.26-4.20 (m, 4H), 3.87 (s, 3H), 1.43-1.20 (m, 6H) | 437 (M⁺), 393, 250, 233, 187 (base) |
| Example 12-20 | — | Example 13-84 | (DMSO-d$_6$) δ: 9.71 (br s, 1H), 8.12 (s, 1H), 7.86 (d, J = 8.1 Hz, 1H), 7.81 (s, 1H), 7.47 (d, J = 8.5 Hz, 1H), 7.32 (d, J = 8.5 Hz, 1H), 7.17 (d, J = 1.9 Hz, 1H), 7.04 (dd, J = 1.9, 8.5 Hz, 1H), 6.84 (s, 1H), 5.25 (s, 2H), 3.93 (s, 3H), 3.90 (s, 3H), 3.80 (s, 3H) | 381 (M⁺ − 44), 173 (base) |

TABLE 130-continued

| Hydroxy compound | Carboxylic acid | Example | ¹H-NMR | Mass, m/z |
|---|---|---|---|---|
| Example 12-33 | — | Example 13-85 | (DMSO-d₆) δ: 9.68 (s, 1H), 8.11 (s, 1H), 7.88 (d, J = 8.5 Hz, 1H), 7.80 (s, 1H), 7.46 (d, J = 8.5 Hz, 1H), 7.32 (d, J = 8.1 Hz, 1H), 7.16 (d, J = 1.9 Hz, 1H), 7.04 (dd, J = 1.9, 8.5 Hz, 1H), 6.82 (s, 1H), 5.26 (s, 2H), 4.24 (q, J = 7.3 Hz, 2H), 3.90 (s, 3H), 3.80 (s, 3H), 1.42 (t, J = 7.3 Hz, 3H) | 439 (M⁺), 395, 266, 249, 173 (base) |
| Example 12-20 | Example 11-2 | Example 13-86 | (DMSO-d₆) δ: 9.69 (s, 1H), 8.17 (s, 1H), 7.86 (d, J = 8.5 Hz, 1H), 7.80 (s, 1H), 7.50 (d, J = 8.5 Hz, 1H), 7.31 (d, J = 8.5 Hz, 1H), 7.16 (d, J = 5.3 Hz, 1H), 7.04 (d, J = 8.5 Hz, 1H), 6.83 (s, 1H), 5.25 (s, 2H), 4.23 (q, J = 7.3 Hz, 2H), 3.93 (s, 3H), 3.89 (s, 3H), 1.40 (t, J = 7.3 Hz, 3H) | 439 (M⁺), 395, 252, 187 (base) |

TABLE 131

| Hydroxy compound | Carboxylic acid | Example | ¹H-NMR | Mass, m/z |
|---|---|---|---|---|
| Example 12-33 | Example 11-2 | Example 13-87 | (DMSO-d₆) δ: 9.67 (br s, 1H), 8.17 (s, 1H), 7.88 (d, J = 8.5 Hz, 1H), 7.81 (s, 1H), 7.50 (d, J = 8.5 Hz, 1H), 7.31 (d, J = 8.1 Hz, 1H), 7.16 (d, J = 1.9 Hz, 1H), 7.04 (dd, J = 1.9, 8.5 Hz, 1H), 6.82 (s, 1H), 5.27 (s, 2H), 4.27-4.20 (m, 4H), 3.89 (s, 3H), 1.44-1.38 (m, 6H) | 453 (M⁺), 409, 266, 187 (base), 172 |
| Example 12-17 | — | Example 13-88 | (DMSO-d₆) δ: 9.68 (br s, 1H), 8.11 (s, 1H), 7.81 (s, 1H), 7.73 (d, J = 7.7 Hz, 1H), 7.46 (d, J = 8.5 Hz, 1H), 7.32 (d, J = 8.5 Hz, 1H), 6.79 (s, 1H), 6.79-6.78 (m, 1H), 5.24 (s, 2H), 3.91 (s, 3H), 3.84 (s, 3H), 3.80 (s, 3H), 2.32 (s, 3H) | 405 (M⁺), 361, 173 (base) |
| Example 12-23 | — | Example 13-89 | (DMSO-d₆) δ: 9.67 (s, 1H), 8.11 (s, 1H), 7.81 (s, 1H), 7.75 (d, J = 7.7 Hz, 1H), 7.46 (d, J = 8.5 Hz, 1H), 7.32 (d, J = 8.5 Hz, 1H), 6.91 (s, 1H), 6.79 (d, J = 8.5 Hz, 1H), 6.79 (s, 1H), 5.25 (s, 2H), 4.23 (q, J = 7.3 Hz, 2H), 3.84 (s, 3H), 3.80 (s, 3H), 2.33 (s, 3H), 1.41 (t, J = 7.3 Hz, 3H) | 419 (M⁺), 375, 246, 229, 173 (base) |

TABLE 131-continued

| Hydroxy compound | Carboxylic acid | Example | | ¹H-NMR | Mass, m/z |
|---|---|---|---|---|---|
| Example 12-17 | Example 11-2 | Example 13-90 | | (DMSO-d₆) δ: 9.64 (br s, 1H), 8.17 (s, 1H), 7.81 (s, 1H), 7.73 (d, J = 8.1 Hz, 1H), 7.50 (d, J = 8.9 Hz, 1H), 7.31 (dd, J = 0.8, 8.1 Hz, 1H), 6.91 (s, 1H), 6.79-6.77 (m, 2H), 5.24 (s, 2H), 4.22 (q, J = 7.3 Hz, 2H), 3.91 (s, 3H), 3.84 (s, 3H), 2.32 (s, 3H), 1.40 (t, J = 7.3 Hz, 3H) | 419 (M⁺), 375, 232, 215, 187 (base) |

TABLE 132

| Hydroxy compound | Carboxylic acid | Example | | ¹H-NMR | Mass, m/z |
|---|---|---|---|---|---|
| Example 12-23 | Example 11-2 | Example 13-91 | | (DMSO-d₆) δ: 9.66 (br s, 1H), 8.17 (s, 1H), 7.81 (s, 1H), 7.75 (d, J = 8.1 Hz, 1H), 7.50 (d, J = 8.5 Hz, 1H), 7.31 (d, J = 7.7 Hz, 1H), 6.91 (s, 1H), 6.79 (d, J = 8.9 Hz, 1H), 6.78 (s, 1H), 5.25 (s, 2H), 4.23 (q, J = 7.3 Hz, 4H), 3.84 (s, 3H), 2.33 (s, 3H), 1.43-1.38 (m, 6H) | 433 (M⁺), 389, 246, 187, 172 (base) |
| Example 12-34 | Example 11-2 | Example 13-92 | | (DMSO-d₆) δ: 9.71 (br s, 1H), 8.71 (s, 1H), 7.81 (s, 1H), 7.51 (d, J = 8.9 Hz, 1H), 7.41 (d, J = 7.7 Hz, 1H), 7.32-7.30 (m, 1H), 7.07 (s, 1H), 7.03 (d, J = 8.1 Hz, 1H), 6.59 (s, 1H), 5.26 (s, 2H), 4.23 (q, J = 7.3 Hz, 2H), 3.93 (s, 3H), 2.40 (s, 3H), 2.28 (s, 3H), 1.40 (t, J = 7.3 Hz, 3H) | 403 (M⁺), 359, 216, 187 (base) |
| Example 12-17 | Example 11-15 | Example 13-93 | | (DMSO-d₆) δ: 9.70 (br s, 1H), 8.76 (d, J = 8.5 Hz, 1H), 7.79 (s, 1H), 7.46 (d, J = 8.5 Hz, 1H), 7.31 (d, J = 8.5 Hz, 1H), 7.16 (d, J = 1.9 Hz, 1H), 7.04 (dd, J = 1.9, 8.5 Hz, 1H), 6.83 (m, 1H), 6.23 (s, 1H), 5.25 (s, 2H), 4.66 (s, 2H), 3.93 (s, 3H), 3.89 (s, 3H), 3.77 (s, 3H), 3.32 (s, 3H) | 469 (M⁺), 325, 172 (base) |
| Example 12-20 | Example 11-14 | Example 13-94 | | (DMSO-d₆) δ: 9.69 (br s, 1H), 8.11 (s, 1H), 7.86 (d, J = 8.5 Hz, 1H), 7.80 (s, 1H), 7.51 (d, J = 8.9 Hz, 1H), 7.29 (d, J = 7.3 Hz, 1H), 7.16 (d, J = 1.9 Hz, 1H), 7.04 (dd, J = 1.9, 8.5 Hz, 1H), 6.84 (s, 1H), 5.27 (s, 2H), 4.36 (t, J = 5.1 Hz, 2H), 3.93 (s, 3H), 3.89 (s, 3H), 3.66 (t, J = 5.1 Hz, 2H), 3.22 (s, 3H) | 469 (M⁺), 425, 252, 217, 172 (base) |

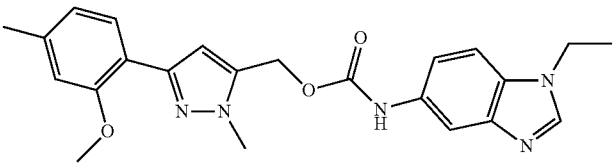

TABLE 132-continued

| Hydroxy compound | Carboxylic acid | Example | $^1$H-NMR | Mass, m/z |
|---|---|---|---|---|
| Example 12-21 | Example 11-5 | Example 13-95 | (DMSO-d$_6$) δ: 9.70 (s, 1H), 7.85 (dd, J = 1.9, 7.7 Hz, 1H), 7.77 (s, 1H), 7.42 (d, J = 8.5 Hz, 1H), 7.31-7.26 (m, 2H), 7.09 (d, J = 7.7 Hz, 1H), 6.99-6.95 (m, 1H), 6.84 (s, 1H), 5.25 (s, 2H), 4.92 (s, 2H), 4.15 (s, 4H), 3.92 (s, 3H), 3.85 (s, 3H) | 433 (M$^+$), 389, 215, 201 (base) |

TABLE 133

| Hydroxy compound | Carboxylic acid | Example | $^1$H-NMR | Mass, m/z |
|---|---|---|---|---|
| Example 12-22 | Example 11-5 | Example 13-96 | (DMSO-d$_6$) δ: 9.68 (br s, 1H), 7.87 (dd, J = 1.5, 7.7 Hz, 1H), 7.77 (s, 1H), 7.42 (d, J = 8.9 Hz, 1H), 7.31-7.27 (m, 2H), 7.09 (d, J = 8.1 Hz, 1H), 6.97 (t, J = 7.3 Hz, 1H), 6.82 (s, 1H), 5.26 (s, 2H), 4.92 (s, 2H), 4.24 (q, J = 7.3 Hz, 2H), 4.15 (s, 4H), 3.86 (s, 3H), 1.42 (t, J = 7.3 Hz, 3H) | 403 (M$^+$ − 44), 232, 215 (base) |
| Example 12-19 | Example 11-5 | Example 13-97 | (DMSO-d$_6$) δ: 9.70 (s, 1H), 7.85 (dd, J = 7.3, 8.5 Hz, 1H), 7.76 (s, 1H), 7.42 (d, J = 8.5 Hz, 1H), 7.28 (d, J = 7.7 Hz, 1H), 6.99 (dd, J = 2.3, 11.6 Hz, 1H), 6.81-6.78 (m, 1H), 6.79 (s, 1H), 5.24 (s, 2H), 4.91 (s, 2H), 4.15 (s, 4H), 3.92 (s, 3H), 3.87 (s, 3H) | 451 (M$^+$), 407, 236, 215 (base) |
| Example 12-24 | Example 11-5 | Example 13-98 | (DMSO-d$_6$) δ: 9.68 (s, 1H), 7.88-7.84 (m, 1H), 7.77 (s, 1H), 7.42 (d, J = 8.5 Hz, 1H), 7.29 (d, J = 7.7 Hz, 1H), 6.99 (dd, J = 2.7, 11.6 Hz, 1H), 6.81-6.79 (m, 1H), 6.78 (s, 1H), 5.26 (s, 2H), 4.92 (s, 2H), 4.23 (q, J = 7.3 Hz, 2H), 4.15 (s, 4H), 3.87 (s, 3H), 1.42 (t, J = 7.3 Hz, 3H) | 465 (M$^+$), 421, 250, 215 (base) |
| Example 12-20 | Example 11-5 | Example 13-99 | (DMSO-d$_6$) δ: 9.70 (br s, 1H), 7.86 (d, J = 8.1 Hz, 1H), 7.77 (s, 1H), 7.42 (d, J = 8.9 Hz, 1H), 7.28 (d, J = 8.9 Hz, 1H), 7.16 (d, J = 2.3 Hz, 1H), 7.04 (dd, J = 1.9, 8.5 Hz, 1H), 6.82 (s, 1H), 5.25 (s, 2H), 4.92 (s, 2H), 4.15 (s, 4H), 3.93 (s, 3H), 3.89 (s, 3H) | 467 (M$^+$), 424, 252, 215 (base) |

TABLE 134

| Hydroxy compound | Carboxylic acid | Example | ¹H-NMR | Mass, m/z |
|---|---|---|---|---|
| Example 12-33 | Example 11-5 | Example 13-100 | (DMSO-d$_6$) δ: 9.68 (br s, 1H), 7.88 (d, J = 8.5 Hz, 1H), 7.77 (s, 1H), 7.42 (d, J = 8.5 Hz, 1H), 7.28 (d, J = 8.1 Hz, 1H), 7.16, (d, J = 2.3 Hz, 1H), 7.04 (dd, J = 1.9, 8.5 Hz, 1H), 6.82 (s, 1H), 5.26 (s, 2H), 4.92 (s, 2H), 4.24 (q, J = 7.3 Hz, 2H), 4.15 (s, 4H), 3.89 (s, 3H), 1.42 (t, 7.3 Hz, 3H) | 481 (M⁺), 437, 266, 249 (base) |
| Example 12-17 | Example 11-5 | Example 13-101 | (DMSO-d$_6$) δ: 9.70 (br s, 1H), 7.77 (s, 1H), 7.73 (d, J = 7.7 Hz, 1H), 7.42 (d, J = 8.9 Hz, 1H), 7.28 (d, J = 8.9 Hz, 1H), 6.90 (s, 1H), 6.79 (s, 1H), 6.78 (d, J = 5.4 Hz, 1H), 5.24 (s, 2H), 4.92 (s, 2H), 4.15 (s, 4H), 3.91 (s, 3H), 3.84 (s, 3H), 2.32 (s, 3H) | 447 (M⁺), 403, 232, 215 (base) |
| Example 12-23 | Example 11-5 | Example 13-102 | (DMSO-d$_6$) δ: 9.67 (br s, 1H), 7.77-7.74 (m, 2H), 7.42 (d, J = 8.5 Hz, 1H), 7.29 (d, J = 9.2 Hz, 1H), 6.91 (s, 1H), 6.79 (d, J = 9.6 Hz, 1H), 6.78 (s, 1H), 5.25 (s, 2H), 4.92 (s, 2H), 4.23 (q, J = 7.3 Hz, 2H), 4.15 (s, 4H), 3.84 (s, 3H), 2.33 (s, 3H), 1.41 (t, J = 7.3 Hz, 3H) | none |
| Example 12-34 | Example 11-5 | Example 13-103 | (DMSO-d$_6$) δ: 9.72 (br s, 1H), 7.80 (br s, 1H), 7.44-7.40 (m, 2H), 7.30-7.27 (m, 1H), 7.06 (s, 1H), 7.02 (d, J = 7.7 Hz, 1H), 6.59 (s, 1H), 5.26 (s, 2H), 4.92 (s, 2H), 4.15 (s, 4H), 3.92 (s, 3H), 2.41 (s, 3H), 2.28 (s, 3H) | 431 (M⁺), 387, 215 (base), 185 |
| Example 12-25 | Example 11-5 | Example 13-104 | (DMSO-d$_6$) δ: 9.72 (s, 1H), 7.79 (s, 1H), 7.45-7.41 (m, 2H), 7.29 (dd, J = 1.2, 8.5 Hz, 1H), 7.07 (s, 1H), 7.02 (d, J = 8.1 Hz, 1H), 6.58 (s, 1H), 5.27 (s, 2H), 4.22 (q, J = 7.3 Hz, 2H), 4.93 (s, 2H), 4.15 (s, 4H), 2.42 (s, 3H), 2.29 (s, 3H), 1.43 (t, J = 7.3 Hz, 3H) | 445 (M⁺), 401, 230, 215 (base) |

TABLE 135

| Hydroxy compound | Carboxylic acid | Example | ¹H-NMR | Mass, m/z |
|---|---|---|---|---|
| Example 12-21 | Example 11-6 | Example 13-105 | (DMSO-d$_6$) δ: 9.64 (br s, 1H), 7.85 (dd, J = 1.9, 7.7 Hz, 1H), 7.71 (br s, 1H), 7.32 (d, J = 8.9 Hz, 1H), 7.29 (dd, J = 1.9, 7.3 Hz, 1H), 7.28-7.26 (m, 1H), 7.08 (d, J = 7.3 Hz, 1H), 6.99-6.95 (m, 1H), 6.83 (s, 1H), 5.24 (s, 2H), 4.07 (t, J = 6.9 Hz, 2H), 3.92 (s, 3H), 3.85 (s, 3H), 2.92 (t, J = 7.3 Hz, 2H), 2.61 (quint, J = 7.3 Hz, 2H) | 417 (M⁺), 373, 218, 199 (base) |
| Example 12-19 | Example 11-6 | Example 13-106 | (DMSO-d$_6$) δ: 9.63 (br s, 1H), 7.85 (dd, J = 7.3, 8.5 Hz, 1H), 7.71 (s, 1H), 7.31 (d, J = 8.5 Hz, 1H), 7.21 (d, J = 8.5 Hz, 1H), 6.98 (dd, J = 2.7, 11.6 Hz, 1H), 6.79 (s, 1H), 6.82-6.77 (m, 1H), 5.24 (s, 2H), 4.07 (t, J = 6.9 Hz, 2H), 3.92 (s, 3H), 3.87 (s, 3H), 2.93 (t, J = 7.3 Hz, 2H), 2.62 (quint, J = 7.3 Hz, 2H) | 435 (M⁺), 391, 236, 199 (base) |
| Example 12-24 | Example 11-6 | Example 13-107 | (DMSO-d$_6$) δ: 9.62 (br s, 1H), 7.86 (dd, J = 7.3, 8.5 Hz, 1H), 7.71 (s, 1H), 7.32 (d, J = 8.9 Hz, 1H), 7.21 (d, J = 8.5 Hz, 1H), 6.99 (dd, J = 2.3, 11.6 Hz, 1H), 6.81 (dt, J = 2.3, J = 8.5 Hz, 1H), 6.78 (s, 1H), 5.25 (s, 2H), 4.23 (q, J = 7.3 Hz, 2H), 4.06 (t, J = 6.9 Hz, 2H), 3.87 (s, 3H), 2.92 (t, J = 7.3 Hz, 2H), 2.61 (quint, J = 7.3 Hz, 2H), 1.42 (t, J = 7.3 Hz, 3H) | 449 (M⁺), 405, 233, 199 (base) |
| Example 12-20 | Example 11-6 | Example 13-108 | (DMSO-d$_6$) δ: 9.64 (br s, 1H), 7.86 (d, J = 8.5 Hz, 1H), 7.71 (s, 1H), 7.32 (d, J = 8.5 Hz, 1H), 7.21 (d, J = 9.3 Hz, 1H), 7.16 (d, J = 1.9 Hz, 1H), 7.04 (dd, J = 1.9, 8.5 Hz, 1H), 6.83 (s, 1H), 5.24 (s, 2H), 4.07 (t, J = 7.3 Hz, 2H), 3.92 (s, 3H), 3.89 (s, 3H), 2.92 (t, J = 7.3 Hz, 2H), 2.61 (quint, J = 7.3 Hz, 2H) | 451 (M⁺), 407, 252, 199 (base) |

TABLE 136

| Hydroxy compound | Carboxylic acid | Example | ¹H-NMR | Mass, m/z |
|---|---|---|---|---|
| Example 12-33 | Example 11-6 | Example 13-109 | (DMSO-d$_6$) δ: 9.62 (br s, 1H), 7.88 (d, J = 8.5 Hz, 1H), 7.71 (s, 1H), 7.32 (d, J = 8.9 Hz, 1H), 7.22-7.20 (m, 2H), 7.16 (d, J = 1.9 Hz, 1H), 6.81 (s, 1H), 5.25 (s, 2H), 4.24 (q, J = 7.3 Hz, 2H), 4.06 (t, J = 6.9 Hz, 2H), 3.89 (s, 3H), 2.92 (t, J = 7.3 Hz, 2H), 2.61 (quint, J = 7.3 Hz, 2H), 1.42 (t, J = 7.3 Hz, 3H) | 465 (M⁺), 421, 266, 199 (base) |

TABLE 136-continued

| Hydroxy compound | Carboxylic acid | Example | ¹H-NMR | Mass, m/z |
|---|---|---|---|---|
| Example 12-34 | Example 11-6 | Example 13-110 | (DMSO-d₆) δ: 9.65 (br s, 1H), 7.71 (s, 1H), 7.41 (d, J = 7.7 Hz, 1H), 7.32 (d, J = 8.5 Hz, 1H), 7.21 (d, J = 8.5 Hz, 1H), 7.06-7.01 (m, 2H), 6.59 (s, 1H), 5.25 (s, 2H), 4.07 (t, J = 6.9 Hz, 2H), 3.92 (s, 3H), 2.93 (t, J = 7.3 Hz, 2H), 2.64-2.60 (m, 2H), 2.41 (s, 3H), 2.28 (s, 3H) | 415 (M⁺), 371, 216, 199 (base) |
| Example 12-25 | Example 11-6 | Example 13-111 | (DMSO-d₆) δ: 9.63 (br s, 1H), 7.72 (s, 1H), 7.42 (d, J = 7.7 Hz, 1H), 7.32 (d, J = 8.5 Hz, 1H), 7.23-7.21 (m, 1H), 7.07-7.02 (m, 2H), 6.58 (s, 1H), 5.26 (s, 2H), 4.23 (q, J = 7.3 Hz, 2H), 4.07 (t, J = 7.3 Hz, 2H), 2.93 (t, J = 7.3 Hz, 2H), 2.63-2.60 (m, 2H), 2.42 (s, 3H), 2.29 (s, 3H), 1.43 (t, J = 7.3 Hz, 3H) | 429 (M⁺), 385, 230, 199 (base) |
| Example 12-17 | Example 11-6 | Example 13-112 | (DMSO-d₆) δ: 9.63 (s, 1H), 7.73 (d, J = 7.7 Hz, 1H), 7.71 (s, 1H), 7.32 (d, J = 8.5 Hz, 1H), 7.21 (d, J = 8.9 Hz, 1H), 6.91 (s, 1H), 6.79 (d, J = 7.3 Hz, 1H), 6.79 (s, 1H), 5.23 (s, 2H), 4.07 (t, J = 6.9 Hz, 2H), 3.91 (s, 3H), 3.84 (s, 3H), 2.92 (t, J = 7.3 Hz, 2H), 2.61 (quint, J = 7.3 Hz, 2H), 2.32 (s, 3H) | 431 (M⁺), 387, 232, 215, 199 (base) |
| Example 12-23 | Example 11-6 | Example 13-113 | (DMSO-d₆) δ: 9.61 (br s, 1H), 7.74 (d, J = 7.7 Hz, 1H), 7.71 (s, 1H), 7.32 (d, J = 8.5 Hz, 1H), 7.21 (d, J = 8.1 Hz, 1H), 6.90 (s, 1H), 6.79 (dd, J = 0.8, 7.7 Hz, 1H), 6.77 (s, 1H), 5.24 (s, 2H), 4.23 (q, J = 7.3 Hz, 2H), 4.07 (t, J = 7.3 Hz, 2H), 3.84 (s, 3H), 2.92 (t, J = 7.3 Hz, 2H), 2.62 (t, J = 7.7 Hz, 2H), 2.32 (s, 3H), 1.41 (t, J = 7.3 Hz, 3H) | 445 (M⁺), 401, 246, 199 (base) |

TABLE 137

| Hydroxy compound | Carboxylic acid | Example | ¹H-NMR | Mass, m/z |
|---|---|---|---|---|
| Example 12-21 | Example 11-7 | Example 13-114 | (DMSO-d$_6$) δ: 9.64 (br s, 1H), 7.85 (dd, J = 1.9, 7.7 Hz, 1H), 7.70 (s, 1H), 7.34 (d, J = 8.5 Hz, 1H), 7.31-7.26 (m, 1H), 7.23 (d, J = 8.9 Hz, 1H), 7.09 (d, J = 7.7 Hz, 1H), 6.97 (dt, J = 1.2, 7.7 Hz, 1H), 6.83 (s, 1H), 5.24 (s, 2H), 4.06-4.03 (m, 2H), 3.93 (s, 3H), 3.86 (s, 3H), 2.92 (t, J = 6.2 Hz, 2H), 2.06-1.99 (m, 2H), 1.94-1.88 (m, 2H) | 431 (M⁺), 387, 213 (base) |
| Example 12-22 | Example 11-7 | Example 13-115 | (DMSO-d$_6$) δ: 9.62 (br s, 1H), 7.87 (dd, J = 1.9, 7.7 Hz, 1H), 7.70 (s, 1H), 7.34 (d, J = 8.5 Hz, 1H), 7.31-7.26 (m, 1H), 7.23 (d, J = 8.1 Hz, 1H), 7.09 (d, J = 8.5 Hz, 1H), 6.98 (dt, J = 1.2, 7.7 Hz, 1H), 6.82 (s, 1H), 5.25 (s, 2H), 4.24 (q, J = 7.3 Hz, 2H), 4.06-4.01 (m, 2H), 3.86 (s, 3H), 2.94-2.91 (m, 2H), 2.06-1.99 (m, 2H), 1.94-1.88 (m, 2H), 1.42 (t, J = 7.3 Hz, 3H) | 445 (M⁺), 401, 213 (base) |
| Example 12-19 | Example 11-7 | Example 13-116 | (DMSO-d$_6$) δ: 9.64 (br s, 1H), 7.85 (dd, J = 7.3, 8.5 Hz, 1H), 7.70 (s, 1H), 7.34 (d, J = 8.9 Hz, 1H), 7.22 (d, J = 8.5 Hz, 1H), 6.99 (dd, J = 2.3 Hz, 11.2 Hz, 1H), 6.80 (dt, J = 2.3, 8.5 Hz, 1H), 6.79 (s, 1H), 5.24 (s, 2H), 4.06-4.03 (m, 2H), 3.92 (s, 3H), 3.87 (s, 3H), 2.94-2.91 (m, 2H), 2.06-1.99 (m, 2H), 1.94-1.88 (m, 2H) | 449 (M⁺), 405, 213 (base) |
| Example 12-24 | Example 11-7 | Example 13-117 | (DMSO-d$_6$) δ: 9.62 (br s, 1H), 7.86 (dd, J = 6.9, 8.5 Hz, 1H), 7.70 (s, 1H), 7.34 (d, J = 8.5 Hz, 1H), 7.23 (d, J = 8.1 Hz, 1H), 6.99 (dd, J = 2.3 Hz, 11.2 Hz, 1H), 6.81 (dt, J = 2.3, 8.5 Hz, 1H), 6.78 (s, 1H), 5.25 (s, 2H), 4.23 (q, J = 7.3 Hz, 2H), 4.04 (t, J = 6.2 Hz, 2H), 3.87 (s, 3H), 2.92 (t, J = 6.2 Hz, 2H), 2.04-1.99 (m, 2H), 1.94-1.90 (m, 2H), 1.42 (t, J = 7.3 Hz, 3 H) | 463 (M⁺), 419, 213 (base) |

TABLE 138

| Hydroxy compound | Carboxylic acid | Example | ¹H-NMR | Mass, m/z |
|---|---|---|---|---|
| Example 12-20 | Example 11-7 | Example 13-118 | (DMSO-d$_6$) δ: 9.64 (s, 1H), 7.86 (d, J = 8.1 Hz, 1H), 7.70 (s, 1H), 7.34 (d, J = 8.5 Hz, 1H), 7.23 (d, J = 8.1 Hz, 1H), 7.16 (d, J = 1.9 Hz, 1H), 7.04 (dd, J = 1.9, 8.5 Hz, 1H), 6.83 (s, 1H), 5.24 (s, 2H), 4.04 (t, J = 6.2 Hz, 2H), 3.93 (s, 3H), 3.89 (s, 3H), 2.92 (t, J = 6.2 Hz, 2H), 2.04-2.01 (m, 2H), 1.93-1.90 (m, 2H) | 421 (M$^+$), 252, 213 (base) |
| Example 12-33 | Example 11-7 | Example 13-119 | (DMSO-d$_6$) δ: 9.61 (s, 1H), 7.88 (d, J = 8.5 Hz, 1H), 7.70 (s, 1H), 7.34 (d, J = 8.5 Hz, 1H), 7.23 (d, J = 8.1 Hz, 1H), 7.17 (d, J = 2.3 Hz, 1H), 7.04 (dd, J = 2.3, 8.5 Hz, 1H), 6.82 (s, 1H), 5.25 (s, 2H), 4.24 (q, J = 7.3 Hz, 2H), 4.04 (t, J = 6.2 Hz, 2H), 3.89 (s, 3H), 2.93 (t, J = 6.2 Hz, 2H), 2.04-2.01 (m, 2H), 2.00-1.90 (m, 2H), 1.42 (t, J = 6.9 Hz, 3H) | 479 (M$^+$), 435, 266, 213 (base), 185 |
| Example 12-17 | Example 11-7 | Example 13-120 | (DMSO-d$_6$) δ: 9.63 (s, 1H), 7.73 (d, J = 7.7 Hz, 1H), 7.70 (s, 1H), 7.34 (d, J = 8.9 Hz, 1H), 7.23 (d, J = 8.5 Hz, 1H), 6.91 (s, 1H), 6.80-6.78 (m, 2H), 5.23 (s, 2H), 4.04 (t, J = 6.2 Hz, 2H), 3.91 (s, 3H), 3.84 (s, 3H), 2.92 (t, J = 6.2 Hz, 2H), 2.32 (s, 3H), 2.04-2.00 (m, 2H), 1.93-1.90 (m, 2H) | 401 (M$^+$ − 44), 232, 213 (base) |
| Example 12-23 | Example 11-7 | Example 13-121 | (DMSO-d$_6$) δ: 9.61 (br s, 1H), 7.74 (d, J = 7.7 Hz, 1H), 7.70 (s, 1H), 7.33 (d, J = 8.9 Hz, 1H), 7.23 (d, J = 8.1 Hz, 1H), 6.91 (s, 1 H), 6.80 (s, 1H), 6.77 (s, 1H), 5.24 (s, 2H), 4.22 (q, J = 7.3 Hz, 2H), 4.04 (t, J = 7.3 Hz, 2H), 3.84 (s, 3H), 2.94-2.91 (m, 2H), 2.33 (s, 3H), 2.04-1.99 (m, 2H), 1.94-1.90 (m, 2H), 1.41 (t, J = 7.3 Hz, 3H) | 459 (M$^+$), 415, 213 (base) |

TABLE 139

| Hydroxy compound | Carboxylic acid | Example | ¹H-NMR | Mass, m/z |
|---|---|---|---|---|
| Example 12-34 | Example 11-7 | Example 13-122 | (DMSO-$d_6$) δ: 9.66 (s, 1H), 7.71 (s, 1H), 7.41 (d, J = 7.7 Hz, 1H), 7.34 (d, J = 8.5 Hz, 1H), 7.23 (d, J = 7.3 Hz, 1H), 7.06 (s, 1H), 7.02 (d, J = 7.7 Hz, 1H), 6.59 (s, 1H), 5.24 (s, 2H), 4.05 (t, J = 6.2 Hz, 2H), 3.93 (s, 3H), 2.93 (t, J = 6.2 Hz, 2H), 2.41 (s, 3H), 2.28 (s, 3H), 2.04-2.00 (m, 2H), 1.93-1.89 (m, 2H) | 429 (M⁺), 385, 213 (base), 185 |
| Example 12-25 | Example 11-7 | Example 13-123 | (DMSO-$d_6$) δ: 9.64 (s, 1H), 7.71 (s, 1H), 7.42 (d, J = 7.7 Hz, 1H), 7.34 (d, J = 8.5 Hz, 1H), 7.23 (d, J = 8.1 Hz, 1H), 7.07 (s, 1H), 7.03 (d, J = 7.7 Hz, 1H), 6.58 (s, 1H), 5.26 (s, 2H), 4.23 (q, J = 6.9 Hz, 2H), 4.05 (t, J = 6.2 Hz, 2H), 2.93 (t, J = 6.2 Hz, 2H), 2.41 (s, 3H), 2.28 (s, 3H), 2.06-2.00 (m, 2H), 1.94-1.89 (m, 2H), 1.43 (t, J = 6.9 Hz, 3H) | 443 (M⁺), 399, 230, 213 (base) |
| Example 12-22 | Example 11-10 | Example 13-124 | (DMSO-$d_6$) δ: 9.73 (br s, 1H), 7.97 (d, J = 0.8 Hz, 1H), 7.89 (s, 1H), 7.87 (dd, J = 1.9, 7.7 Hz, 1H), 7.56 (d, J = 8.9 Hz, 1H), 7.41 (dd, J = 1.5, 8.9 Hz, 1H), 7.31-7.27 (m, 1H), 7.09 (d, J = 7.7 Hz, 1H), 6.98 (dt, J = 0.8, 7.7 Hz, 1H), 6.82 (s, 1H), 5.27 (s, 2H), 4.24 (q, J = 7.3 Hz, 2H), 4.04 (s, 3H), 3.86 (s, 3H), 1.42 (t, J = 7.3 Hz, 3H) | 405 (M⁺), 361, 215 (base), 173 |
| Example 12-19 | Example 11-10 | Example 13-125 | (DMSO-$d_6$) δ: 9.75 (br s, 1H), 7.97 (d, J = 0.8 Hz, 1H), 7.89 (s, 1H), 7.85 (dd, J = 6.9, 8.9 Hz, 1H), 7.56 (d, J = 9.3 Hz, 1H), 7.41 (dd, J = 1.9, 8.9 Hz, 1H), 6.99 (dd, J = 2.3, 11.6 Hz, 1H), 6.80 (dt, J = 2.3, 8.5 Hz, 1H), 6.79 (s, 1H), 5.25 (s, 2H), 4.00 (s, 3H), 3.92 (s, 3H), 3.87 (s, 3H) | 409 (M⁺), 365, 236, 219 (base), 173 |

TABLE 140

| Hydroxy compound | Carboxylic acid | Example | ¹H-NMR | Mass, m/z |
|---|---|---|---|---|
| Example 12-24 | Example 11-10 | Example 13-126 | (DMSO-$d_6$) δ: 9.73 (br s, 1H), 7.97 (s, 1H), 7.88-7.84 (m, 2H), 7.56 (d, J = 9.3 Hz, 1H), 7.41 (dd, J = 1.5, 9.3 Hz, 1H), 6.99 (dd, J = 2.7, 11.6 Hz, 1H), 6.81 (dt, J = 2.7, 8.5 Hz, 1H), 6.78 (s, 1H), 5.26 (s, 2H), 4.23 (q, J = 7.3 Hz, 2H), 4.00 (s, 3H), 3.87 (s, 3H), 1.42 (t, J = 7.3 Hz, 3H) | 423 (M⁺), 379, 233 (base), 178 |
| Example 12-20 | Example 11-10 | Example 13-127 | (DMSO-$d_6$) δ: 9.74 (br s, 1H), 7.97 (d, J = 0.8 Hz, 1H), 7.89 (d, J = 1.2 Hz, 1H), 7.86 (d, J = 8.5 Hz, 1H), 7.56 (d, J = 8.9 Hz, 1H), 7.41 (dd, J = 1.5, 8.9 Hz, 1H), 7.16 (d, J = 2.3 Hz, 1H), 7.04 (dd, J = 1.9, 8.5 Hz, 1H), 6.83 (s, 1H), 5.25 (s, 2H), 4.00 (s, 3H), 3.93 (s, 3H), 3.89 (s, 3H) | 425 (M⁺), 381, 235, 173 (base) |
| Example 12-33 | Example 11-10 | Example 13-128 | (DMSO-$d_6$) δ: 9.73 (br s, 1H), 7.97 (d, J = 0.8 Hz, 1H), 7.88 (d, J = 8.5 Hz, 1H), 7.56 (d, J = 8.9 Hz, 1H), 7.41 (dd, J = 1.5, 8.9 Hz, 1H), 7.17 (d, J = 1.9 Hz, 1H), 7.04 (dd, J = 1.9, 8.5 Hz, 1H), 6.82 (s, 1H), 5.27 (s, 2H), 4.24 (q, J = 7.3 Hz, 2H), 4.00 (s, 3H), 3.89 (s, 3H), 1.42 (t, J = 7.3 Hz, 3H) | 425 (M⁺), 381, 235, 173 (base) |
| Example 12-20 | Example 11-11 | Example 13-129 | (DMSO-$d_6$) δ: 9.74 (br s, 1H), 7.98 (d, J = 0.8 Hz, 1H), 7.89 (s, 1H), 7.86 (d, J = 8.5 Hz, 1H), 7.59 (d, J = 8.9 Hz, 1H), 7.39 (dd, J = 1.5, 8.9 Hz, 1H), 7.17 (d, J = 1.9 Hz, 1H), 7.04 (dd, J = 1.9, 8.5 Hz, 1H), 6.84 (s, 1H), 5.26 (s, 2H), 4.39 (q, J = 7.3 Hz, 2H), 3.93 (s, 3H), 3.89 (s, 3H), 1.38 (t, J = 7.3 Hz, 3H) | 439 (M⁺), 395, 172 (base) |

TABLE 141

| Hydroxy compound | Carboxylic acid | Example | ¹H-NMR | Mass, m/z |
|---|---|---|---|---|
| Example 12-23 | Example 11-10 | Example 13-130 | (DMSO-$d_6$) δ: 9.72 (br s, 1H), 7.97 (d, J = 0.8 Hz, 1H), 7.89 (s, 1H), 7.74 (d, J = 7.7 Hz, 1H), 7.56 (d, J = 8.9 Hz, 1H), 7.41 (dd, J = 1.5, 8.9 Hz, 1H), 6.91 (s, 1H), 6.79 (d, J = 7.9 Hz, 1H), 6.78 (s, 1H), 5.25 (s, 2H), 4.23 (q, J = 7.3 Hz, 2H), 4.00 (s, 3H), 3.84 (s, 3H), 2.33 (s, 3H), 1.41 (t, J = 7.3 Hz, 3H) | 419 (M⁺), 375, 229 (base), 174 |

TABLE 141-continued

| Hydroxy compound | Carboxylic acid | Example | ¹H-NMR | Mass, m/z |
|---|---|---|---|---|
| Example 12-34 | Example 11-10 | Example 13-131 | (DMSO-d₆) δ: 9.77 (s, 1H), 7.97 (d, J = 0.8 Hz, 1H), 7.89 (s, 1H), 7.56 (d, J = 8.9 Hz, 1H), 7.42-7.40 (m, 2H), 7.06 (s, 1H), 7.02 (d, J = 8.1 Hz, 1H), 6.59 (s, 1H), 5.26 (s, 2H), 4.01 (s, 3H), 3.92 (s, 3H), 2.40 (s, 3H), 2.28 (s, 3H) | 389 (M⁺), 345, 199, 173, 158 (base) |
| Example 12-25 | Example 11-10 | Example 13-132 | (DMSO-d₆) δ: 9.75 (s, 1H), 7.96 (s, 1H), 7.89 (s, 1H), 7.56 (d, J = 9.3 Hz, 1H), 7.43-7.40 (m, 2H), 7.07 (s, 1H), 7.03 (d, J = 7.7 Hz, 1H), 6.58 (s, 1H), 5.27 (s, 2H), 4.23 (q, J = 7.3 Hz, 2H), 4.01 (s, 3H), 2.42 (s, 3H), 2.28 (s, 3H), 1.43 (t, J = 7.3 Hz, 3H) | 403 (M⁺), 359, 213 (base) |
| Example 12-20 | Example 11-13 | Example 13-133 | (DMSO-d₆) δ: 9.66 (br s, 1H), 8.27 (s, 1H), 7.86 (d, J = 8.5 Hz, 1H), 7.85 (s, 1H), 7.53 (d, J = 9.2 Hz, 1H), 7.22 (dd, J = 1.2, 9.2 Hz, 1H), 7.17 (d, J = 1.9 Hz, 1H), 7.03 (dd, J = 1.9, 8.1 Hz, 1H), 6.83 (s, 1H), 5.25 (s, 2H), 4.40 (q, J = 7.3 Hz, 2H), 3.93 (s, 3H), 3.89 (s, 3H), 1.49 (t, J = 7.3 Hz, 3H) | 439 (M⁺), 395, 159 (base) |
| Example 12-27 | — | Example 13-134 | (DMSO-d₆) δ: 9.65 (br s, 1H), 8.10 (s, 1H), 7.82 (s, 1H), 7.49-7.44 (m, 2H), 7.33 (dd, J = 1.9, 8.9 Hz, 1H), 7.24 (dd, J = 1.9, 7.3 Hz, 1H), 7.16 (d, J = 8.5 Hz, 1H), 7.05 (dt, J = 0.8, 7.3 Hz, 1H), 6.28 (s, 1H), 5.10 (s, 2H), 3.86 (q, J = 7.3 Hz, 2H), 3.80 (s, 3H), 3.79 (s, 3H), 1.25 (t, J = 7.3 Hz, 3H) | 405 (M⁺), 361, 215 (base) |

TABLE 142

| Hydroxy compound | Carboxylic acid | Example | ¹H-NMR | Mass, m/z |
|---|---|---|---|---|
| Example 12-32 | — | Example 13-135 | (DMSO-d₆) δ: 9.63 (s, 1H), 8.10 (s, 1H), 7.81 (ds, 1H), 7.45 (d, J = 8.9 Hz, 1H), 7.34-7.28 (m, 2H), 7.09 (dd, J = 2.3, 11.6 Hz, 1H), 6.88 (dt, J = 2.3, 8.5 Hz, 1H), 6.31 (s, 1H), 5.08 (s, 2H), 3.82 (s, 3H), 3.80 (s, 3H), 3.60 (s, 3H) | 409 (M⁺), 365, 236, 219 (base), 173 |

TABLE 142-continued

| Hydroxy compound | Carboxylic acid | Example | ¹H-NMR | Mass, m/z |
|---|---|---|---|---|
| Example 12-26 | — | Example 13-136 | (DMSO-d₆) δ: 9.65 (brs, 1H), 8.10 (s, 1H), 7.81 (s, 1H), 7.45 (d, J = 8.5 Hz, 1H), 7.33 (dd, J = 1.9, 8.9 Hz, 1H), 7.30-7.23 (m, 2H), 7.09 (dd, J = 2.3, 11.6 Hz, 1H), 6.88 (dd, J = 2.3, 8.5 Hz, 1H), 6.28 (s, 1H), 5.09 (s, 2H), 4.03 (q, J = 6.9 Hz, 2H), 3.85 (s, 3H), 3.83 (s, 3H), 1.25 (t, J = 6.9 Hz, 3H) | 423 (M⁺), 379, 173 (base) |
| Example 12-30 | — | Example 13-137 | (DMSO-d₆) δ: 9.63 (s, 1H), 8.10 (s, 1H), 7.81 (s, 1H), 7.44-7.45 (m, 1H), 7.33-7.24 (m, 3H), 7.18-7.03 (m, 1H), 6.33 (s, 1H), 5.09 (s, 2H), 3.83 (s, 3H), 3.79 (s, 3H), 3.60 (s, 3H) | 425 (M⁺), 381, 252, 173 (base) |
| Example 12-28 | — | Example 13-138 | (DMSO-d₆) δ: 9.65 (brs, 1H), 8.45 (d, J = 8.9 Hz, 1H), 8.10 (s, 1H), 7.81 (s, 1H), 7.33 (dd, J = 1.9, 8.9 Hz, 1H), 7.26 (d, J = 6.2 Hz, 1H), 7.25 (s, 1H), 7.11 (dd, J = 1.9, 8.1 Hz, 1H), 6.30 (s, 1H), 5.09 (s, 2H), 3.88-3.82 (m, 2H), 3.82 (s, 3H), 3.80 (s, 3H), 1.25 (t, J = 7.3 Hz) | 439 (M⁺), 395, 266, 249, 173 (base) |

TABLE 143

| Hydroxy compound | Carboxylic acid | Example | ¹H-NMR | Mass, m/z |
|---|---|---|---|---|
| Example 12-18 | — | Example 13-139 | (DMSO-d₆) δ: 9.62 (s, 1H), 8.10 (s, 1H), 7.81 (s, 1H), 7.45 (d, J = 8.9 Hz, 1H), 7.34 (d, J = 1.5 Hz, 1H), 7.12 (d, J = 7.7 Hz, 1H), 6.99 (s, 1H), 6.87 (d, J = 7.7 Hz, 1H), 6.27 (s, 1H), 5.08 (s, 2H), 3.80 (s, 3H), 3.79 (s, 3H), 3.59 (s, 3H), 2.38 (s, 3H) | 405 (M⁺), 316, 232, 215 (base), 173 |
| Example 12-29 | — | Example 13-140 | (DMSO-d₆) δ: 9.65 (brs, 1H), 8.10 (s, 1H), 7.81 (s, 1H), 7.45 (d, J = 8.9 Hz, 1H), 7.33 (dd, J = 1.9 Hz, 8.9 Hz, 1H), 7.10 (d, J = 7.7 Hz, 1H), 6.99 (s, 1H), 6.87-6.85 (m, 1H), 6.23 (s, 1H), 5.09 (s, 2H), 4.03 (q, J = 7.3 Hz, 2H), 3.87 (s, 3H), 3.85 (s, 3H), 2.38 (s, 3H), 1.24 (t, J = 7.3 Hz, 3H) | 419 (M⁺), 375, 246, 173 (base) |

TABLE 143-continued

| Hydroxy compound | Carboxylic acid | Example | $^1$H-NMR | Mass, m/z |
|---|---|---|---|---|
| Example 12-31 | — | Example 13-141 | (DMSO-$d_6$) δ: 9.64 (s, 1H), 8.10 (s, 1H), 7.81 (s, 1H), 7.45 (d, J = 8.5 Hz, 1H), 7.34 (d, J = 8.9 Hz, 1H), 7.18 (s, 1H), 7.15-7.09 (m, 2H), 6.31 (s, 1H), 5.10 (s, 2H), 3.80 (s, 3H), 3.57 (s, 3H), 2.33 (s, 3H), 2.11 (s, 3H) | 389 (M$^+$), 345, 216, 199 (base) |
| Example 12-27 | Example 11-5 | Example 13-142 | (DMSO-$d_6$) δ: 9.66 (brs, 1H), 7.78 (s, 1H), 7.47 (ddd, J = 1.5, 7.7, 8.5 Hz, 1H), 7.41 (d, J = 8.9 Hz, 1H), 7.29 (dd, J = 1.9, 8.5 Hz, 1H), 7.24 (dd, J = 1.9, 7.7 Hz, 1H), 7.16 (d, J = 8.1 Hz, 1H), 7.05 (dt, J = 1.2, 7.7 Hz, 1H), 6.28 (s, 1H), 5.10 (s, 2H), 4.92 (s, 2H), 4.14 (s, 4H), 3.86 (q, J = 7.3 Hz, 2H), 3.78 (s, 3H), 1.25 (t, 7.3 Hz, 3H) | 447 (M$^+$), 403, 215 (base) |
| Example 12-26 | Example 11-5 | Example 13-143 | (DMSO-$d_6$) δ: 9.65 (brs, 1H), 7.78 (s, 1H), 7.41 (d, J = 8.5 Hz, 1H), 7.30-7.26 (m, 2H), 7.09 (dd, J = 2.3, 11.2 Hz, 1H), 6.88 (dt, J = 2.3, 8.5 Hz, 1H), 6.27 (s, 1H), 5.09 (s, 2H), 4.92 (s, 2H), 4.14 (s, 4H), 3.84 (q, J = 7.3 Hz, 2H), 3.80 (s, 3H), 1.25 (t, J = 7.3 Hz, 3H) | 465 (M$^+$), 421, 215 (base) |

TABLE 144

| Hydroxy compound | Carboxylic acid | Example | $^1$H-NMR | Mass, m/z |
|---|---|---|---|---|
| Example 12-30 | Example 11-5 | Example 13-144 | (DMSO-$d_6$) δ: 9.64 (s, 1H), 7.77 (s, 1H), 7.41 (d, J = 8.5 Hz, 1H), 7.29-7.25 (m, 3H), 7.13-7.05 (m, 1H), 6.33 (s, 1H), 5.08 (s, 2H), 4.92 (s, 2H), 4.14 (s, 4H), 3.83 (s, 3H), 3.60 (s, 3H) | 467 (M$^+$), 423, 252, 215 (base) |

TABLE 144-continued

| Hydroxy compound | Carboxylic acid | Example | ¹H-NMR | Mass, m/z |
|---|---|---|---|---|
| Example 12-28 | Example 11-5 | Example 13-145 | (DMSO-d₆) δ: 9.65 (brs, 1H), 7.77 (s, 1H), 7.41 (d, J = 8.5 Hz, 1H), 7.30-7.25 (m, 3H), 7.11 (dd, J = 1.9, 8.1 Hz, 1H), 6.29 (s, 1H), 5.09 (s, 2H), 4.91 (s, 2H), 4.15 (s, 4H), 3.87-3.84 (m, 2H), 3.81 (s, 3H), 1.25 (t, J = 7.3 Hz, 3H) | 437 (M⁺ − 44), 266, 215 (base) |
| Example 12-18 | Example 11-5 | Example 13-146 | (DMSO-d₆) δ: 9.63 (s, 1H), 7.77 (s, 1H), 7.71 (s, 1H), 7.41 (d, J = 8.9 Hz, 1H), 7.29 (dd, J = 1.5, 8.9 Hz, 1H), 6.99 (s, 1H), 6.86 (d, J = 7.7 Hz, 1H), 6.27 (s, 1H), 5.07 (s, 2H), 4.92 (s, 2H), 4.14 (s, 4H), 3.79 (s, 3H), 3.59 (s, 3H), 2.38 (s, 3H) | 447 (M⁺), 403, 232, 215 (base) |
| Example 12-29 | Example 11-5 | Example 13-147 | (DMSO-d₆) δ: 9.65 (brs, 1H), 7.78 (s, 1H), 7.41 (d, J = 8.5 Hz, 1H), 7.29 (dd, J = 1.9, 8.9 Hz, 1H), 7.10 (d, J = 7.3 Hz, 1H), 6.99 (s, 1H), 6.86 (d, J = 6.9 Hz, 1H), 6.23 (s, 1H), 5.08 (s, 2H), 4.92 (s, 2H), 4.14 (s, 4H), 3.84 (q, J = 7.3 Hz, 2H), 3.77 (s, 3H), 2.37 (s, 3H), 1.24 (t, 7.3 Hz, 3H) | 461 (M⁺), 417, 246, 215 (base) |
| Example 12-31 | Example 11-5 | Example 13-148 | (DMSO-d₆) δ: 9.65 (s, 1H), 7.78 (s, 1H), 7.41 (d, J = 8.5 Hz, 1H), 7.29 (dd, J = 1.2, 8.1 Hz, 1H), 7.18 (s, 1H), 7.14-7.11 (m, 2H), 6.31 (s, 1H), 5.10 (s, 2H), 4.92 (s, 2H), 4.14 (s, 4H), 3.57 (s, 3H), 2.33 (s, 3H), 2.11 (s, 3H) | 431 (M⁺), 387, 215 (base), 199 |

TABLE 145

| Hydroxy compound | Carboxylic acid | Example | ¹H-NMR | Mass, m/z |
|---|---|---|---|---|
| Example 12-34 | — | 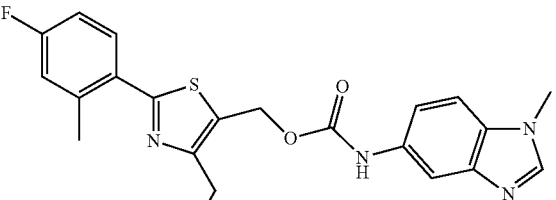 | (DMSO-d₆) δ: 9.70 (brs, 1H), 8.10 (s, 1H), 7.81 (s, 1H), 7.77 (dd, J = 6.1, 8.9 Hz, 1H), 7.46 (d, J = 8.5 Hz, 1H), 7.32 (dd, J = 1.2, 8.5 Hz, 1H), 7.25 (dd, J = 2.7, 10.0 Hz, 1H), 7.15 (dt, J = 3.1, 8.5 Hz, 1H), 5.39 (s, 2H), 3.80 (s, 3H), 2.85 (q, J = 7.7 Hz, 2H), 2.56 (s, 3H), 1.28 (t, J = 7.3 Hz, 3H) | 424 (M⁺), 409, 380 |
| Example 12-34 | Example 11-5 | 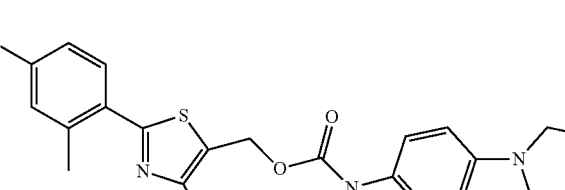 | (DMSO-d₆) δ: 9.71 (brs, 1H), 7.79-7.75 (m, 2H), 7.42 (d, J = 8.5 Hz, 1H), 7.29 (d, J = 8.9 Hz, 1H), 7.25 (dd, J = 2.7, 10.0 Hz, 1H), 7.15 (dt, J = 2.7, 8.5 Hz, 1H), 5.39 (s, 2H), 4.92 (s, 2H), 4.41 (brs, 4H), 2.85 (q, J = 7.3 Hz, 2H), 2.55 (s, 3H), 1.28 (t, J = 7.3 Hz, 3H) | 466 (M⁺), 422, 234 (base) |

Synthesis scheme 14

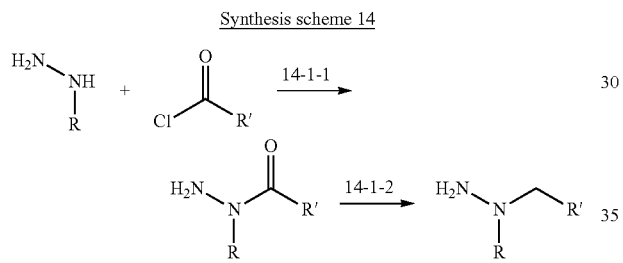

In the formulae, R represents an alkyl group, and R' represents an aryl or heterocyclic group which may have a substituent (such as a halogen atom, an alkoxy group, or an alkylthio group).

Example 14-1

Step 14-1-1

4-Methoxybenzoic acid N-methyl hydrazide

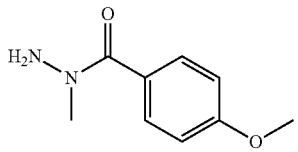

Methylhydrazine (2.76 g) was dissolved in dichloromethane (60 ml), and a solution of 4-methoxybenzoyl chloride (5.12 g) in dichloromethane (10 ml) was added thereto under an ice cooling and stirring. The mixture was further stirred at a room temperature for 1.5 hours, and then the reaction solution washed with water and a saturated saline solution in order. The washed product was dried over anhydrous sodium sulfate, concentrated under a reduced pressure, and dried to give the title compound (4.81 g, 89%).

¹H-NMR (CDCl₃) δ: 7.54 (d, J=8.9 Hz, 2H), 7.45 (d, J=8.1 Hz, 2H), 3.83 (s, 3H), 3.24 (s, 3H)

Mass, m/z: 180 (M⁺), 135 (base)

Step 14-1-2

N-(4-Methoxybenzyl)-N-methylhydrazine

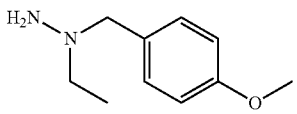

Tetrahydrofuran (40 ml) was added to lithium aluminumhydride (1.94 g), the mixture was heated and stirred gently under an argon atmosphere, and a solution (10 ml) of 4-methoxybenzoic acid N-methyl hydrazide (4.78 g) prepared in the Step 14-1-1 in THF was added thereto. The resulting mixture was further stirred for 15 hours under heat reflux. The mixture was allowed to cool to a room temperature, and then water (2 ml) and a 1-N sodium hydroxide aqueous solution (7.5 ml) were added dropwise to the mixture. The reaction solution was filtered through a celite, and the filtrate was concentrated under a reduced pressure. The concentrate was purified by silica gel column chromatography (dichloromethane:methanol=50:1) to give the title compound (2.27 g, 45%).

¹H-NMR (CDCl₃) δ: 7.70 (d, J=8.5 Hz, 2H), 7.23 (d, J=8.5 Hz, 2H), 3.80 (s, 3H), 3.56 (s, 2H), 2.49 (s, 3H)

Mass, m/z: 166 (M⁺), 121 (base)

Example 14-2

N-Ethyl-N-(4-methoxybenzyl)hydrazine

The title compound was obtained according to the same procedure as in Example 14-1 except that ethylhydrazine was used instead of methylhydrazine.

$^1$H-NMR (CDCl$_3$) δ: 7.24 (d, J=8.1 Hz, 2H), 6.87 (d, J=8.9 Hz, 2H), 3.80 (s, 3H), 3.61 (s, 2H), 2.59 (q, J=7.3 Hz, 2H), 1.15 (t, J=7.3 Hz, 3H)

Mass, m/z: 180 (M$^+$), 121 (base)

Examples 14-3 to 14-7

The objective compounds were obtained according to the same procedure as in Example 14-1 except that any one of acid chloride components shown in the following table was used instead of 4-methoxybenzoyl chloride.

TABLE 146

| Acid chloride component | Example | $^1$H-NMR | Mass, m/z |
|---|---|---|---|
| 3,4-Dimethoxybenzoyl chloride | Example 14-3 | (CDCl$_3$) δ: 6.90 (brs, 1H), 6.82 (s, 1H), 6.82 (s, 1H), 3.89 (s, 3H), 3.87 (s, 3H), 3.56 (s, 2H), 2.50 (s, 3H) | 196 (M$^+$), 151 (base) |
| 2,3-Dihydro-1-benzofuran-5-carbonyl chlorlide | Example 14-4 | (CDCl$_3$) δ: 7.17 (brs, 1H), 7.02 (dd, J = 0.8 Hz, 8.1 Hz, 1H), 6.73 (d, J = 8.1 Hz, 1H), 4.56 (t, J = 8.9 Hz, 2H), 3.53 (s, 2H), 3.19 (t, J = 8.9 Hz, 2H), 2.49 (s, 3H) | 178 (M$^+$), 133 (base) |
| 4-Ethoxybenzoyl chloride | Example 14-5 | (CDCl$_3$) δ: 7.22 (d, J = 8.5 Hz, 2H), 6.86 (d, J = 8.5 Hz, 2H), 4.02 (q, J = 7.0 Hz, 2H), 3.55 (s, 2H), H), 2.49 (s, 3H), 1.40 (t, J = 7.0 Hz, 3H) | 180 (M$^+$), 107 (base) |
| 3-Fluoro-4-methoxybenzoyl chloride | Example 14-6 | (CDCl$_3$) δ: 7.08 (dd, J = 1.9, 12.0 Hz, 1H), 7.01 (brd, J = 8.1 Hz, 1H), 6.91 (dd, J = 8.1 Hz, 8.5 Hz, 1H), 3.88 (s, 3H), 3.54 (s, 2H), 2.49 (s, 3H) | 184 (M$^+$), 139 (base) |
| 4-Methylthiobenzoyl chloride | Example 14-7 | (CDCl$_3$) δ: 7.24 (brs, 4H), 3.58 (s, 2H), 2.50 (s, 3H), 2.48 (s, 3H) | 182 (M$^+$), 137 (base) |

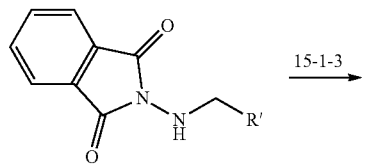

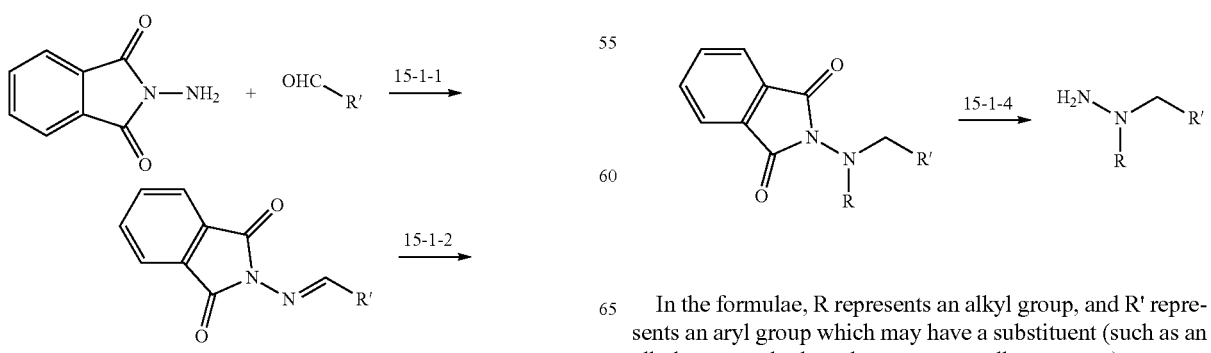

In the formulae, R represents an alkyl group, and R' represents an aryl group which may have a substituent (such as an alkyl group, a hydroxyl group, or an alkoxy group).

Example 15-1

Step 15-1-1

2-{[1-(4-Methoxy-3-methylphenyl)-methylidene]amino}isoindole-1,3-dione

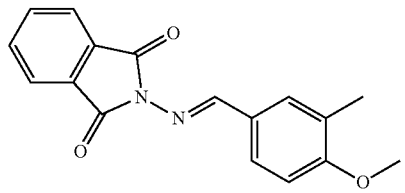 [SMILES: COc1ccc(/C=N/N2C(=O)c3ccccc3C2=O)cc1C]

N-aminophthalimide (1.62 g) and 4-methoxy-3-methylbenzaldehyde (1.50 g) were added to ethanol (20 ml), the mixture was stirred under heat reflux overnight. The mixture was allowed to cool to a room temperature, and then the precipitate was separated by filtration, washed with ethanol, and dried under a reduced pressure to give the title compound (2.50 g, 84%).

$^1$H-NMR (CDCl$_3$) δ: 9.19 (s, 1H), 7.90 (dd, J=3.1 Hz, 5.4 Hz, 2H), 7.77 (brs, 1H), 7.76 (dd, J=3.1 Hz, 5.4 Hz, 2H), 7.64 (dd, J=2.3 Hz, 8.5 Hz, 1H), 6.87 (d, J=8.5 Hz, 1H), 3.89 (s, 3H), 2.26 (s, 3H)

Mass, m/z: 294 (M$^+$), 147 (base)

Step 15-1-2

2-(4-Methoxy-3-methylbenzylamino)isoindole-1,3-dione

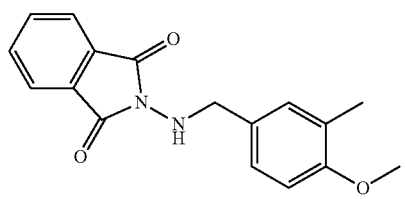 [SMILES: COc1ccc(CNN2C(=O)c3ccccc3C2=O)cc1C]

Acetic acid (40 ml) and pyridine-borane (4.3 ml) were added to 2-{[1-(4-methoxy-3-methylphenyl)-methylidene]amino}isoindole-1,3-dione (2.50 g) prepared in the Step 15-1-1, and the mixture was stirred under a room temperature for 0.5 hours. The mixture was concentrated under a reduced pressure, and under an ice cooling 10% hydrochloric acid (10 ml) was added to the resulting residue. Sodium hydroxide (1.1 g) was added thereto, and the resulting mixture was subjected to extraction with ethyl acetate. The organic layer was washed with a saturated saline solution, and then dried over sodium sulfate and concentrated under a reduced pressure. To the resulting residue, ethanol (10 ml) was added, and the mixture was stirred at a room temperature. The precipitate was separated by filtration, washed with ethanol, and concentrated under a reduced pressure to give the title compound (1.71 g, 68%).

$^1$H-NMR (CDCl$_3$) δ: 7.83 (dd, J=3.1 Hz, 5.4 Hz, 2H), 7.72 (dd, J=3.1 Hz, 5.4 Hz, 2H), 7.23 to 7.20 (m, 2H), 6.76 (d, J=8.9 Hz, 1H), 4.68 (brd, J=5.0 Hz, 1H), 4.10 (d, J=5.0 Hz, 2H), 3.80 (s, 3H), 2.19 (s, 3H)

Mass, m/z: 296 (M$^+$), 135 (base)

Step 15-1-3

2-[(4-Methoxy-3-methylbenzyl)methylamino]isoindole-1,3-dione

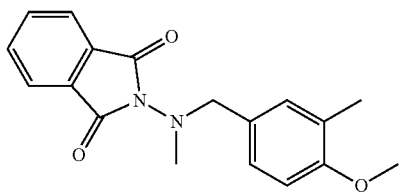 [SMILES: COc1ccc(CN(C)N2C(=O)c3ccccc3C2=O)cc1C]

N,N-dimethylformamide (20 ml), methyl iodide (0.7 ml) and potassium carbonate (3.12 g) were added to 2-(4-methoxy-3-methylbenzylamino)isoindole-1,3-dione (1.67 g) prepared in the Step 15-1-2, and the mixture was stirred overnight. Methyl iodide (0.35 ml) was added thereto, and the resulting mixture was stirred for another 5 hours. Thereafter, an ethyl acetate-toluene (3:1) solution was added thereto. The resulting mixture was washed with water and a saturated saline solution in order, and then dried over sodium sulfate and concentrated under a reduced pressure. To the resulting residue, diethyl ether was added, and the mixture was stirred at a room temperature. The precipitate was separated by filtration, washed with diethyl ether, and dried under a reduced pressure to give the title compound (1.15 g, 65%).

$^1$H-NMR (CDCl$_3$) δ: 7.74 (dd, J=3.1 Hz, 5.4 Hz, 2H), 7.66 (dd, J=3.1 Hz, 5.4 Hz, 2H), 7.16 to 7.12 (m, 2H), 6.66 (d, J=8.8 Hz, 1H), 4.31 (s, 2H), 3.74 (s, 3H), 3.06 (s, 3H), 2.11 (s, 3H)

Mass, m/z: 310 (M$^+$), 135 (base)

Step 15-1-4

N-(4-Methoxy-3-methylbenzyl)-N-methylhydrazine

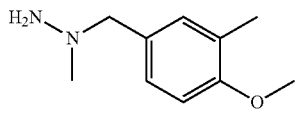

Tetrahydrofuran (30 ml) and methylhydrazine (138 mg) were added to 2-[(4-methoxy-3-methylbenzyl)methylamino]isoindole-1,3-dione (621 mg) prepared in the Step 15-1-3, and the mixture was stirred at a room temperature for one hour. Another methylhydrazine (138 mg) was added thereto, the resulting mixture was stirred for 12 hours. The solvent was distilled off under a reduced pressure. Dichloromethane was added to the residue, and the insoluble matter was removed by filtration. The filtrate was concentrated under a reduced pressure and then purified by silica gel column chromatography (dichloromethane:methanol=20:1) to give the title compound (115 mg, 31%).

$^1$H-NMR (CDCl$_3$) δ: 7.12 to 7.08 (m, 2H), 6.78 (d, J=8.5 Hz, 1H), 3.82 (s, 3H), 3.57 (s, 2H), 3.27 (brs, 2H), 2.52 (s, 3H), 2.20 (s, 3H)

Mass, m/z: 180 (M$^+$), 135 (base)

Example 15-2

2-Methoxy-5-(N-methylhydrazinomethyl)phenol

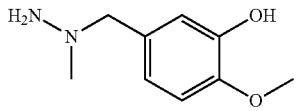

The title compound was obtained according to the same procedure as in Example 15-1 except that 3-hydroxy-4-methoxybenzaldehyde was used instead of 4-methoxy-3-methylbenzaldehyde.

$^1$H-NMR (CDCl$_3$) δ: 6.91 (d, J=1.5 Hz, 1H), 6.81 to 6.79 (m, 2H), 3.88 (s, 3H), 3.53 (s, 2H), 2.49 (s, 3H)

Mass, m/z: 182 (M$^+$), 137 (base)

Synthesis scheme 16

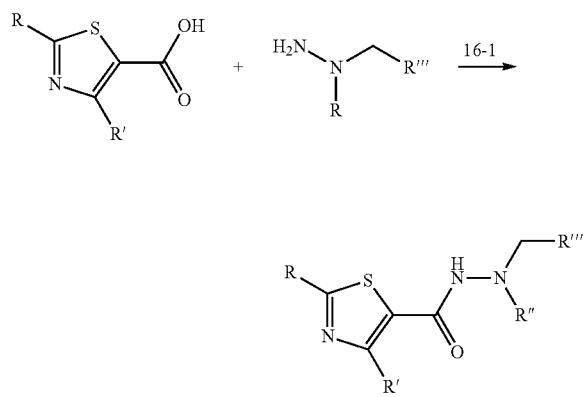

In the formulae, R and R''' are the same or different and each represent an aryl group which may have a substituent (such as a halogen atom, an alkyl group, or an alkoxy group), and R' and R'' are the same or different and each represent a hydrogen atom or an alkyl group.

Example 16-1

2-(4-Chloro-2-methoxyphenyl)-4-methylthiazole-5-carboxylic acid N'-(4-methoxybenzyl)-N'-methyl hydrazide To N,N-dimethylformamide (12 ml), 2-(4-chloro-2-methoxyphenyl)-4-methylthiazole-5-carboxylic acid (1.02 g) prepared in Example 7-1, N-(4-methoxybenzyl)-N-methylhydrazine (718 mg) prepared in Example 14-1, 1-ethyl-3-(3-dimethylaminopropyl)carbodiimide hydrochloride (828 mg), 1-hydroxy-1H-benzotriazole monohydrate (662 mg) and N,N-diisopropylethylamine (558 mg), and the mixture was stirred at a room temperature for 22 hours. An ethyl acetate-toluene (3:1) solution was added thereto. The resulting mixture was washed with water, a 5% potassium bisulfate aqueous solution, a saturated sodium bicarbonate solution and a saturated saline solution in order, and then dried over sodium sulfate and concentrated under a reduced pressure. The concentrate was purified by silica gel column chromatography (chloroform:methanol=100:1) to give the title compound (1.05 g, 67%).

$^1$H-NMR (DMSO-d$_6$) δ: 9.17, 8.81 (two s, 1H), 8.29, 8.25 (two d, J=8.1 Hz, 1H), 7.37 (brs, 1H), 7.29 (d, J=8.5 Hz, 2H), 7.18 (dd, J=2.0 Hz, 8.5 Hz, 1H), 6.86 (d, J=8.5 Hz, 2H), 4.07 (s, 3H), 3.91 to 3.79 (m, 2H), 3.72 (s, 3H), 2.63, 2.60 (two s, 3H), 2.53, 2.41 (two s, 3H)

Mass, m/z: 431 (M$^+$), 121 (base)

Examples 16-2 to 16-25

The objective compounds were obtained according to the same procedure as in Example 16-1 except that carboxylic acids or hydrazine compounds shown in the following tables were used instead of 2-(4-chloro-2-methoxyphenyl)-4-methylthiazole-5-carboxylic acid or N-(4-methoxybenzyl)-N-methylhydrazine.

TABLE 147

| Carboxylic acid | Hydrazine compound | Example | $^1$H-NMR | Mass, m/z |
|---|---|---|---|---|
| 2-(4-Chloro phenyl)-4-methyl-thiazole-5-carboxylic acid | — | Example 16-2 | (DMSO-d$_6$) δ: 9.24, 8.83 (two s, 1H), 7.96 (d, J = 8.5 Hz, 2H), 7.59 (d, J = 8.5 Hz, 2H), 7.28, 7.24 (two d, J = 8.1 Hz, 2H), 6.88, 6.82 (two d, J = 8.1 Hz, 2H), 3.91-3.71 (m, 2H), 3.70 (s, 3H), 2.64, 2.60 (two s, 3H), 2.56, 2.40 (two s, 3H) | 401 (M$^+$), 121 base) |

TABLE 147-continued

| Carboxylic acid | Hydrazine compound | Example | ¹H-NMR | Mass, m/z |
|---|---|---|---|---|
| Example 7-9 | — | Example 16-3 | (DMSO-d₆) δ: 9.22, 8.82 (two s, 1H), 7.76 (d, J = 7.7 Hz, 1H), 7.43-7.32 (m, 3H), 7.29, 7.23 (two d, J = 8.1 Hz, 2H), 6.88, 6.81 (two d, J = 8.5 Hz, 2H), 3.92-3.72 (m, 2H), 3.71 (s, 3H), 2.64, 2.57 (two s, 6H), 2.54, 2.42 (two s, 3H) | 381 (M⁺), 121 base) |
| Example 7-8 | — | Example 16-4 | (DMSO-d₆) δ: 9.14, 8.77 (two s, 1H), 8.30, 8.26 (two d, J = 7.7 Hz, 1H), 7.49 (ddd, J = 1.6 Hz, 7.3 Hz, 8.5 Hz, 1H), 7.30 (d, J = 8.9 Hz, 2H), 7.26 (brd, J = 8.5 Hz, 1H), 7.11 (dd, J = 7.3 Hz, 7.7 Hz, 1H), 6.86 (d, J = 7.7 Hz, 2H), 4.04 (s, 3H), 3.92-3.76 (m, 2H), 3.72 (s, 3H), 2.64, 2.60 (two s, 3H), 2.53, 2.42 (two s, 3H) | 397 (M⁺), 121 base) |
| 2-(2,3-Dimethylphenyl)-4-methyl-thiazole-5-carboxylic acid | — | Example 16-5 | (DMSO-d₆) δ: 9.21, 8.79 (two s, 1H), 7.39 (d, J = 7.3 Hz, 1H), 7.32 (d, J = 7.3 Hz, 1H), 7.25-7.19 (m, 3H), 6.81 (d, J = 8.5 Hz, 2H), 3.92-3.72 (m, 2H), 3.71 (s, 3H), 2.64, 2.57 (two s, 3H), 2.56, 2.41 (two s, 3H), 2.36 (s, 3H), 2.34 (s, 3H) | 395 (M⁺), 121 base) |

TABLE 148

| Carboxylic acid | Hydrazine compound | Example | ¹H-NMR | Mass, m/z |
|---|---|---|---|---|
| Example 7-7 | — | Example 16-6 | (DMSO-d₆) δ: 9.24, 8.85 (two s, 1H), 7.79 (d, J = 8.1 Hz, 1H), 7.50 (d, J = 2.3 Hz, 1H), 7.42 (brd, J = 8.1 Hz, 1H), 7.23 (d, J = 8.1 Hz, 2H), 6.81 (d, J = 8.5 Hz, 2H), 3.92-3.72 (m, 2H), 3.71 (s, 3H), 2.64, 2.57 (two s, 6H), 2.56, 2.42 (two s, 3H) | 415 (M⁺), 121 (base) |
| Example 7-38 | — | Example 16-7 | (DMSO-d₆) δ: 9.26, 8.89 (two s, 1H), 8.32-8.23 (m, 1H), 7.53 (ddd, J = 2.3 Hz, 9.3 Hz, 11.6 Hz, 1H), 7.28 (ddd, J = 2.3 Hz, 8.1 Hz, 8.5 Hz, 1H), 7.24 (d, J = 8.5 Hz, 2H), 6.81 (d, J = 8.1 Hz, 2H), 3.92-3.76 (m, 2H), 3.71 (s, 3H), 2.64, 2.60 (two s, 3H), 2.56, 2.45 (two s, 3H) | 403 (M⁺), 121 (base) |

TABLE 148-continued

| Carboxylic acid | Hydrazine compound | Example | ¹H-NMR | Mass, m/z |
|---|---|---|---|---|
| Example 7-13 | — | Example 16-8 | (DMSO-d₆) δ: 9.14, 8.77 (two s, 1H), 8.35-8.26 (m, 1H), 7.29 (d, J = 8.9 Hz, 2H), 7.19 (dd, J = 2.3 Hz, 11.2 Hz, 1H), 6.95 (ddd, J = 2.3 Hz, 8.5 Hz, 8.9 Hz, 1H), 6.86 (d, J = 8.1 Hz, 2H), 4.05 (s, 3H), 3.92-3.78 (m, 2H), 3.72 (s, 3H), 2.63, 2.59 (two s, 3H), 2.52, 2.41 (two s, 3H) | 415 (M⁺), 121 (base) |
| 2-(2-Chloro-4-methoxy-phenyl)-4-methyl thiazole-5-carboxylic acid | — | Example 16-9 | (DMSO-d₆) δ: 9.21, 8.86 (two s, 1H), 8.16 (d, J = 8.9 Hz, 1H), 7.27 (d, J = 8.5 Hz, 2H), 7.23 (d, J = 2.3 Hz, 1H), 7.09 (dd, J = 2.3 Hz, 8.9 Hz, 1H), 6.81 (d, J = 8.5 Hz, 2H), 3.91-3.78 (m, 2H), 3.87 (s, 3H), 3.71 (s, 3H), 2.64, 2.60 (two s, 3H), 2.53, 2.42 (two s, 3H) | 431 (M⁺), 121 (base) |

TABLE 149

| Carboxylic acid | Hydrazine compound | Example | ¹H-NMR | Mass, m/z |
|---|---|---|---|---|
| 2-(2,4-Dichloro phenyl)-4-methyl-thiazole-5-carboxylic acid | — | Example 16-10 | (CDCl₃) δ: 8.26 (d, J = 8.5 Hz, 1H), 7.53 (s, 1H), 7.36 (dd, J = 1.9 Hz, 8.5 Hz, 1H), 7.25 (d, J = 8.1 Hz, 2H), 6.85 (d, J = 8.1 Hz, 2H), 6.17 (s, 1H), 4.07-3.74 (m, 2H), 3.80 (s, 3H), 2.79 (s, 3H), 2.57 (s, 3H) | 435 (M⁺), 121 (base) |
| Example 7-16 | — | Example 16-11 | (CDCl₃) δ: 7.65 (d, J = 7.7 Hz, 1H), 7.27-7.18 (m, 2H), 7.12 (s, 1H), 7.08 (d, J = 7.7 Hz, 1H), 6.85 (d, J = 7.7 Hz, 2H), 6.11 (s, 1H), 4.08-3.74 (m, 2H), 3.79 (s, 3H), 2.78 (s, 3H), 2.56 (s, 6H), 2.36 (s, 3H) | 395 (M⁺), 121 (base) |
| Example 7-8 | Example 14-2 | Example 16-12 | (CDCl₃) δ: 8.46-8.35 (m, 1H), 7.44-7.39 (m, 1H), 7.28 (d, J = 8.8 Hz, 2H), 7.12-7.01 (m, 2H), 6.84 (d, J = 8.5 Hz, 2H), 6.43, 5.97 (two s, 1H), 4.04 (s, 3H), 4.03 から 3.81 (m, 2H), 3.79 (s, 3H), 3.02-2.92, 2.60-2.53 (two m, 2H), 2.79, 2.62 (two s, 3H), 1.21-1.14 (m, 3H) | 411 (M⁺), 121 (base) |

TABLE 149-continued

| Carboxylic acid | Hydrazine compound | Example | ¹H-NMR | Mass, m/z |
|---|---|---|---|---|
| — | Example 14-2 | Example 16-13 | (CDCl₃) δ: 8.39, 8.31 (two d, J = 8.5 Hz, 1H), 7.27 (d, J = 8.9 Hz, 2H), 7.10-7.01 (m, 2H), 6.84 (d, J = 8.5 Hz, 2H), 6.41, 5.97 (two s, 1H), 4.14-3.81 (m, 2H), 4.04 (s, 3H), 3.79 (s, 3H), 3.01-2.91, 2.60-2.54 (two m, 2H), 2.78, 2.59 (two s, 3H), 1.20-1.14 (m, 3H) | 445 (M⁺), 121 (base) |

TABLE 150

| Carboxylic acid | Hydrazine compound | Example | ¹H-NMR | Mass, m/z |
|---|---|---|---|---|
| 2-(2,3-Dimethylphenyl)-4-methyl-thiazole-5-carboxylic acid | Example 14-2 | Example 16-14 | (DMSO-d₆) δ: 9.01, 8.59 (two s, 1H), 7.37 (d, J = 7.4 Hz, 1H), 7.33-7.28, 7.25-7.19 (m, 2H), 7.21 (d, J = 8.8 Hz, 2H), 6.87, 6.78 (two d, J = 8.5 Hz, 2H), 3.94-3.64 (m, 2H), 3.73, 3.70 (two s, 3H), 2.95-2.86, 2.74-2.67 (two m, 2H), 2.53, 2.40 (two s, 3H), 2.35, 2.34 (two s, 6H), 1.07 (t, J = 7.0 Hz, 3H) | 409 (M⁺), 121 (base) |
| Example 7-7 | Example 14-2 | Example 16-15 | (DMSO-d₆) δ: 9.04, 8.66 (two s, 1H), 7.78 (d, J = 8.5 Hz, 1H), 7.50 (d, J = 1.9 Hz, 1H), 7.42 (dd, J = 1.9 Hz, 8.1 Hz, 1H), 7.30, 7.23 (two d, J = 8.5 Hz, 2H), 6.87, 6.79 (two d, J = 8.5 Hz, 2H), 3.93-3.67 (m, 2H), 3.73, 3.69 (two s, 3H), 2.94-2.86, 2.74-2.68 (two m, 2H), 2.55, 2.40 (two s, 6H), 1.06 (t, J = 7.3 Hz, 3H) | 429 (M⁺), 121 (base) |
| — | Example 14-3 | Example 16-16 | (DMSO-d₆) δ: 9.16, 8.79 (two s, 1H), 8.29, 8.25 (two d, J = 8.5 Hz, 1H), 7.37 (s, 1H), 7.18 (dd, J = 1.9 Hz, 8.5 Hz, 1H), 7.04, 6.87 (two brs, 1H), 6.85 (s, 2H), 4.06, 4.03 (two s, 3H), 3.93-3.73 (m, 2H), 3.71, 3.51 (two s, 6H), 2.67, 2.60 (two s, 3H), 2.55, 2.41 (two s, 3H) | 461 (M⁺), 151 (base) |

TABLE 150-continued

| Carboxylic acid | Hydrazine compound | Example | ¹H-NMR | Mass, m/z |
|---|---|---|---|---|
| Example 7-7 | Example 14-3 | Example 16-17 | (DMSO-d₆) δ: 9.21, 8.85 (two s, 1H), 7.77 (d, J = 8.5 Hz, 1H), 7.50 (d, J = 1.9 Hz, 1H), 7.41 (dd, J = 2.0 Hz, 8.5 Hz, 1H), 7.06-7.02, 6.88-6.78 (m, 3H), 3.93-3.71 (m, 2H), 3.70, 3.52 (two s, 6H), 2.67, 2.60 (two s, 3H), 2.56, 2.41 (two s, 3H), 2.54 (s, 3H) | 445 (M⁺), 151 (base) |

TABLE 151

| Carboxylic acid | Hydrazine compound | Example | ¹H-NMR | Mass, m/z |
|---|---|---|---|---|
| — | Example 14-4 | Example 16-18 | (DMSO-d₆) δ: 9.18, 8.76 (two s, 1H), 8.29, 8.26 (two d, J = 8.5 Hz, 1H), 7.37 (s, 1H), 7.24, 7.14 (two s, 1H), 7.18 (dd, J = 1.9 Hz, 8.5 Hz, 1H), 7.07 (brd, J = 7.7 Hz, 1H), 6.67 (d, J = 8.1 Hz, 1H), 4.52-4.45 (m, 2H), 4.07 (s, 3H), 3.87, 3.77 (two s, 2H), 3.17-3.02 (m, 2H), 2.62, 2.57 (two s, 3H), 2.54, 2.44 (two s, 3H) | 443 (M⁺), 133 (base) |
| — | Example 14-5 | Example 16-19 | (DMSO-d₆) δ: 9.16, 8.80 (two s, 1H), 8.29, 8.25 (two d, J = 8.5 Hz, 1H), 7.37 (brs, 1H), 7.27 (d, J = 8.5 Hz, 2H), 7.18 (dd, J = 1.9 Hz, 8.5 Hz, 1H), 6.84 (d, J = 8.5 Hz, 2H), 4.07 (s, 3H), 3.99 (q, J = 6.9 Hz, 2H), 3.90-3.77 (m, 2H), 2.63, 2.60 (two s, 3H), 2.52, 2.41 (two s, 3H), 1.30 (t, J = 6.9 Hz, 3H) | 445 (M⁺), 135 (base) |
| — | Example 14-6 | Example 16-20 | (DMSO-d₆) δ: 9.21, 8.83 (two s, 1H), 8.29, 8.25 (two d, J = 8.1 Hz, 1H), 7.38 (d, J = 1.9 Hz, 1H), 7.30-7.15 (m, 2H), 7.12-7.05 (m, 2H), 4.07 (s, 3H), 3.92, 3.72 (two s, 3H), 3.80 (s, 3H), 2.66, 2.59 (two s, 3H), 2.56, 2.42 (two s, 3H) | 449 (M⁺), 266 (base) |

TABLE 151-continued

| Carboxylic acid | Hydrazine compound | Example | ¹H-NMR | Mass, m/z |
|---|---|---|---|---|
| 2-(2,4-Difluoro phenyl)-4-methyl-thiazole-5-carboxylic acid | Example 14-6 | Example 16-21 | (DMSO-d$_6$) δ: 9.31, 8.91 (two s, 1H), 8.31-8.24 (m, 1H), 7.53 (ddd, J = 2.3 Hz, 9.2 Hz, 11.6 Hz, 1H), 7.29 (ddd, J = 2.3 Hz, 8.5 Hz, 8.8 Hz, 1H), 7.24-7.02 (m, 3H), 3.93-3.71 (m, 2H), 3.79 (s, 3H), 2.67, 2.59 (two s, 3H), 2.58, 2.45 (two s, 3H) | 421 (M$^+$), 139 (base) |

TABLE 152

| Carboxylic acid | Hydrazine compound | Example | ¹H-NMR | Mass, m/z |
|---|---|---|---|---|
| — | Example 14-7 | Example 16-22 | (DMSO-d$_6$) δ: 9.20, 8.84 (two s, 1H), 8.32-8.23 (m, 1H), 7.37 (d, J = 1.9 Hz, 1H), 7.30 (d, J = 8.5 Hz, 2H), 7.24-7.16 (m, 3H), 4.07 (s, 3H), 3.94, 3.84 (two s, 2H), 2.66, 2.59 (two s, 3H), 2.55, 2.41 (two s, 3H), 2.44 (s, 3H) | 447 (M$^+$), 137 (base) |
| — | Example 15-1 | Example 16-23 | (DMSO-d$_6$) δ: 9.17, 8.77 (two s, 1H), 8.29, 8.25 (two d, J = 8.5, 1H), 7.37 (s, 1H), 7.18 (dd, J = 1.6 Hz, 8.5 Hz, 1H), 7.15, 7.05 (two brs, 1H), 7.14 (d, J = 7.0 Hz, 1H), 6.83 (d, J = 8.5 Hz, 1H), 4.06 (s, 3H), 3.87, 3.76 (two s, 2H), 3.74 (s, 3H), 2.62, 2.56 (two s, 3H), 2.55, 2.43 (two s, 3H), 2.14, 2.03 (two s, 3H) | 445 (M$^+$), 135 (base) |
| — | Example 15-2 | Example 16-24 | (DMSO-d$_6$) δ: 9.15, 8.83 (two s, 1H), 8.80, 8.77 (two s, 1H), 8.30, 8.25 (two d, J = 8.5, 1H), 7.37 (brs, 1H), 7.18 (dd, J = 1.9 Hz, 8.5 Hz, 1H), 6.86-6.74 (m, 3H), 4.06 (s, 3H), 3.84-3.69 (two s, 2H), 3.74 (s, 3H), 2.74, 2.62 (two s, 3H), 2.61, 2.44 (two s, 3H) | 447 (M$^+$), 137 (base) |

TABLE 152-continued

| Carboxylic acid | Hydrazine compound | Example | ¹H-NMR | Mass, m/z |
|---|---|---|---|---|
| Example 7-7 | Example 15-1 | Example 16-25 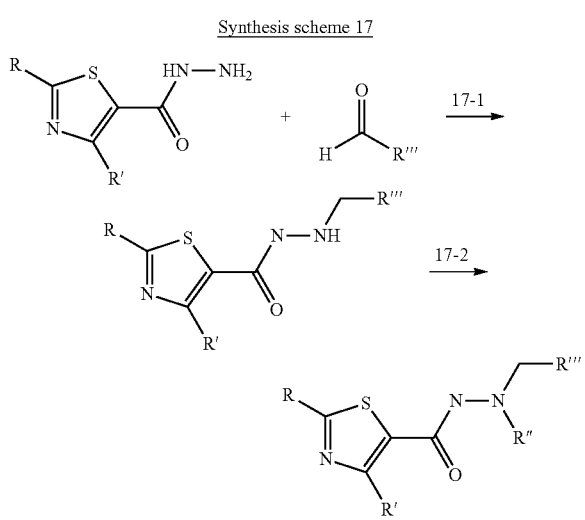 | (DMSO-d₆) δ: 9.23, 8.83 (two s, 1H), 8.83, 8.80 (two s, 1H), 7.82, 7.78 (two d, J = 8.5, 1H), 7.50 (d, J = 2.3 Hz, 1H), 7.41 (dd, J = 1.6 Hz, 8.5 Hz, 1H), 6.84-6.68 (m, 3H), 3.83, 3.71 (two s, 2H), 3.72 (s, 3H), 2.74, 2.61 (two s, 3H), 2.56 (s, 3H), 2.54, 2.44 (two s, 3H) | 431 (M⁺), 137 (base) |

Synthesis scheme 17

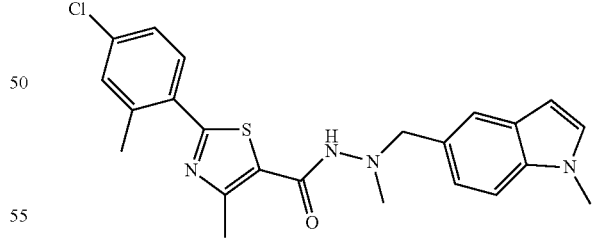

In the formulae, R and R''' are the same or different and each represent an aryl or heterocyclic group which may have a substituent (such as a halogen atom, an alkyl group, a hydroxyl group, or an alkoxy group), and R' and R'' are the same or different and each represent a hydrogen atom or an alkyl group.

Example 17-1

Step 17-1

2-(4-Chloro-2-methoxyphenyl)-4-methylthiazole-5-carboxylic acid N'-(1-methyl-1H-indol-5-ylmethyl) hydrazide

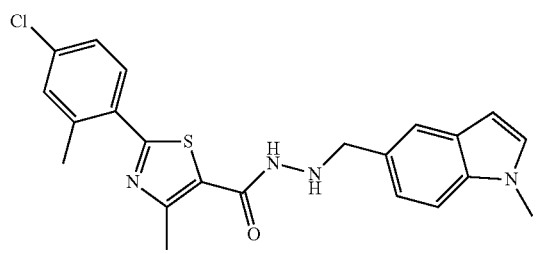 [SMILES: Cc1cc(Cl)ccc1-c1nc(C)c(C(=O)NNCc2ccc3c(ccn3C)c2)s1]

A mixture of 2-(4-chloro-2-methylphenyl)-4-methylthiazole-5-carboxylic acid hydrazide (150 mg) prepared in the same manner as in the after-mentioned Step 23-1-2, 1-methyl-1H-indolecarboaldehyde (85 mg), pyridine borane (0.11 ml), acetic acid (1 ml) and methanol (10 ml) was stirred under a room temperature for 48 hours. To the reaction solution, 10% hydrochloric acid (1 ml) was added, and the resulting mixture was stirred for one hour. Thereafter, the resulting mixture was neutralized with a 1-N sodium hydroxide aqueous solution. The neutralized mixture was concentrated under a reduced pressure, and then the precipitate was separated by filtration, washed with water and ethanol in order and dried under a reduced pressure to give the title compound (140 mg, 61%).

¹H-NMR (DMSO-d₆) δ: 7.78 (d, J=8.5 Hz, 1H), 7.53 (s, 1H), 7.50 (s, 1H), 7.42 to 7.34 (m, 2H), 7.30 (d, J=3.1 Hz, 1H), 7.19 (brd, J=8.5 Hz, 1H), 6.39 (d, J=2.7 Hz, 1H), 4.04, 3.90 (two d, J=5.8 Hz, 2H), 3.78, 3.76 (two s, 3H), 2.64, 2.55 (two s, 6H)

Mass, m/z: 424 (M⁺), 144 (base)

Example 17-2

Step 17-2

2-(4-Chloro-2-methoxyphenyl)-4-methylthiazole-5-carboxylic acid N'-methyl-N'-(1-methyl-1H-indol-5-ylmethyl)hydrazide A mixture of 2-(4-chloro-2-methoxyphenyl)-4-methylthiazole-5-carboxylic acid N'-(1-methyl-1H-indol-5-ylmethyl) hydrazide (100 mg) prepared in the Step 17-1, a 37% formaldehyde solution (23 mg), pyridine borane (0.07 ml), acetic acid (2 ml) and methanol (4 ml) was stirred at a room temperature for 41 hours. To the reaction solution, 10% hydrochloric acid (0.5 ml) was added, and the resulting mixture was stirred for 20 minutes. Thereafter, the resulting mixture was neutralized with a 1-N sodium hydroxide aqueous solution. The neutralized mixture was concentrated under a reduced pressure. Then, water was added thereto, and the mixture was subjected to extraction twice with ethyl acetate. The organic layer was washed with a saturated sodium bicarbonate solution and a saturated saline solution in order, dried over sodium sulfate, and concentrated under a reduced pressure. The concentrate was purified by a first thin-layer chromatography (chloroform:methanol=20:1) and then a second thin-layer chromatography (hexane:ethyl acetate=1:1) to give the title compound (22 mg, 21%).

$^1$H-NMR (DMSO-$d_6$) δ: 9.21, 8.89 (two s, 1H), 7.80 (d, J=8.5 Hz, 1H), 7.50 (brs, 2H), 7.42 (dd, J=1.6 Hz, 8.5 Hz, 1H), 7.31 (d, J=8.5 Hz, 1H), 7.28 (d, J=3.1 Hz, 1H), 7.15 (brd, J=8.5 Hz, 1H), 6.35 (d, J=2.7 Hz, 1H), 4.03, 3.92 (two s, 2H), 3.75 (s, 3H), 2.64, 2.57 (two s, 3H), 2.56, 2.42 (two s, 3H), 2.53 (s, 3H)

Mass, m/z: 438 (M$^+$), 144 (base)

Example 17-3

2-(4-Chloro-2-methoxyphenyl)-4-methylthiazole-5-carboxylic acid N'-(4-hydroxy-3,5-dimethylbenzyl)hydrazide

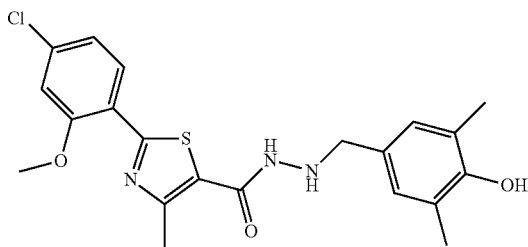 [SMILES: COc1cc(Cl)ccc1-c1nc(C)c(C(=O)NNCc2cc(C)c(O)c(C)c2)s1]

The title compound was obtained according to the same procedure as in Example 17-1 except that 4-hydroxy-3,5-dimethylbenzaldehyde was used instead of 1-methyl-1H-indolecarboaldehyde.

$^1$H-NMR (DMSO-$d_6$) δ: 8.27 (d, J=8.5 Hz, 1H), 8.09 (s, 1H), 7.38 (brs, 1H), 7.18 (dd, J=1.6 Hz, 8.5 Hz, 1H), 6.91 (s, 2H), 4.07, 3.97 (two s, 3H), 3.79 (d, J=3.8 Hz, 2H), 2.60, 2.54 (two s, 3H), 2.16, 2.12 (two s, 6H)

Mass, m/z: 431 (M$^+$), 135 (base)

Example 17-4

2-(4-Chloro-2-methoxyphenyl)-4-methylthiazole-5-carboxylic acid N'-(4-hydroxy-3,5-dimethylbenzyl)-N'-methyl hydrazide

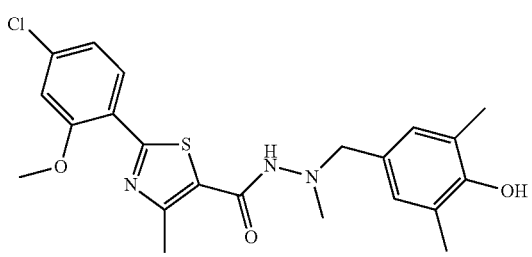 [SMILES: COc1cc(Cl)ccc1-c1nc(C)c(C(=O)NN(C)Cc2cc(C)c(O)c(C)c2)s1]

The title compound was obtained according to the same procedure as in Example 17-2 except that the compound of Example 17-3 was used instead of 2-(4-chloro-2-methoxyphenyl)-4-methylthiazole-5-carboxylic acid N'-(1-methyl-1H-indol-5-ylmethyl)hydrazide.

$^1$H-NMR (DMSO-$d_6$) δ: 9.14, 8.71 (two s, 1H), 8.29, 8.26 (two d, J=8.5 Hz, 1H), 8.09, 8.07 (two s, 1H), 7.38 (d, J=1.5 Hz, 1H), 7.18 (dd, J=1.9 Hz, 8.5 Hz, 1H), 6.91, 6.82 (two s, 2H), 4.07, 4.03 (two s, 3H), 3.79, 3.68 (two s, 2H), 2.59, 2.55 (two s, 3H), 2.55, 2.46 (two s, 3H), 2.14, 2.05 (two s, 6H)

Mass, m/z: 445 (M$^+$), 135 (base)

Synthesis scheme 18

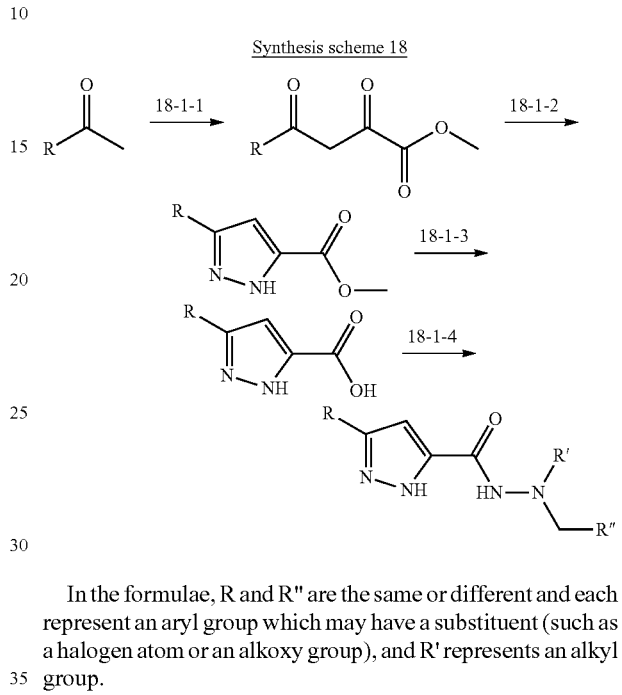

In the formulae, R and R" are the same or different and each represent an aryl group which may have a substituent (such as a halogen atom or an alkoxy group), and R' represents an alkyl group.

Example 18-1

Step 18-1-1

Methyl 4-(4-chloro-2-methoxyphenyl)-2,4-dioxobutyrate

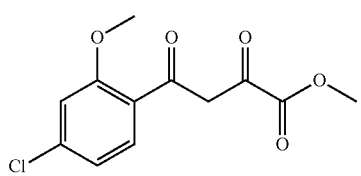 [SMILES: COC(=O)C(=O)CC(=O)c1ccc(Cl)cc1OC]

To dimethylformamide (13 ml), 1-(4-chloro-2-methoxyphenyl)ethanone (3.13 g) and dimethyl oxalate (2.4 g) were added, and 60% sodium hydride suspension in oil (811 mg) was added thereto at 0° C. The mixture was stirred at a room temperature for one hour, and then heated to 50° C. and stirred for 19 hours. The mixture was allowed to cool to a room temperature, 3-N hydrochloric acid was added to the mixture. The resulting mixture was subjected to extraction with ethyl acetate. The organic layer was washed with water and a saturated saline solution in order, then dried over anhydrous magnesium sulfate, and concentrated under a reduced pressure. In the process of the concentration, the precipitated crystal was separated by filtration to give the title compound (2.47 g, 54%).

¹H-NMR (CDCl₃) δ: 15.21 (s, 1H), 7.85 (d, J=8.7 Hz, 1H), 7.04 (dd, J=1.9, 8.2 Hz, 1H), 6.99 (d, J=1.9 Hz, 1H), 3.95 (s, 3H), 3.92 (s, 3H)

Mass, m/z: 270 (M⁺), 211, 169 (base)

Step 18-1-2

Methyl 5-(4-chloro-2-methoxyphenyl)-2H-pyrazole-3-carboxylate

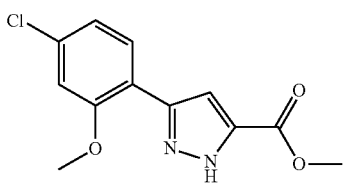 [SMILES: COC(=O)c1cc(-c2ccc(Cl)cc2OC)n[nH]1]

Methyl 4-(4-chloro-2-methoxyphenyl)-2,4-dioxobutyrate (2.47 g) obtained in the Step 18-1-1 was dissolved in ethanol (15 ml), and hydrazine monohydrate (457 mg) was added thereto. The mixture was heated under reflux. After 19 hours, the mixture was allowed to cool to a room temperature, the crystal was separated by filtration to give the title compound (1.8 g, 74%).

¹H-NMR (DMSO-d₆) δ: 14.14 and 13.64 (two s, 1H), 7.94 and 7.76 (two d, J=8.5 Hz, 1H), 7.26 and 7.23 (two d, J=1.9 Hz, 1H), 7.21 and 7.16 (two d, J=2.3 Hz, 1H), 7.13 and 7.08 (two dd, J=1.9, 8.5 Hz, 1H), 3.95 and 3.93 (twos, 3H), 3.87 and 3.83 (two s, 3H)

Mass, m/z: 266 (M⁺) (base), 235, 178, 148, 115

Step 18-1-3

5-(4-Chloro-2-methoxyphenyl)-2H-pyrazole-3-carboxylic acid

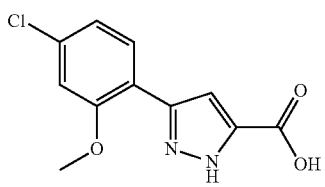 [SMILES: COc1cc(Cl)ccc1-c1cc(C(=O)O)[nH]n1]

Ethanol (1 ml) and a 20% sodium hydroxide aqueous solution were mixed with methyl 5-(4-chloro-2-methoxyphenyl)-2H-pyrazole-3-carboxylate (100 mg) obtained in the Step 18-1-2, and the mixture was heated under reflux. After one hour, the mixture was allowed to cool to a room temperature and acidified with 2-N hydrochloric acid. The precipitated crystal was separated by filtration to give the title compound (90 mg, 95%).

¹H-NMR (DMSO-d₆) δ: 7.83 (d, J=6.9 Hz, 1H), 7.22 (d, J=1.5 Hz, 1H), 7.10 (dd, J=1.9, 7.5 Hz, 1H), 3.93 (s, 3H)

Mass, m/z: 252 (M⁺) (base)

Step 18-1-4

5-(4-Chloro-2-methoxyphenyl)-2H-pyrazole-3-carboxylic acid N'-(4-methoxybenzyl)-N'-methyl hydrazide

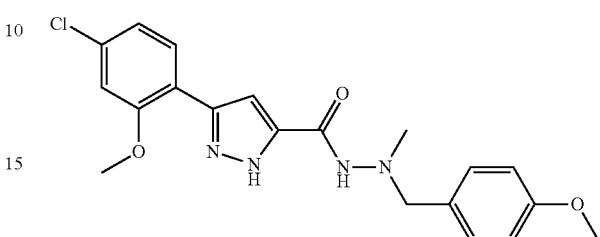

5-(4-Chloro-2-methoxyphenyl)-2H-pyrazole-3-carboxylic acid obtained in the Step 18-1-3 was used and subjected to the same procedure as in Example 16-1 to give the title compound.

¹H-NMR (DMSO-d₆) δ: 13.58 and 13.27 (two brs, 1H), 9.44 and 8.90 (two brs, 1H), 7.89 and 7.69 (two d, J=8.5 Hz, 1H), 7.29 (d, J=8.5 Hz, 2H), 7.24 (s, 1H), 7.19 and 6.97 (two s, 1H), 7.12 and 7.05 (two d, J=8.5 Hz, 1H), 6.85 (d, J=8.5 Hz, 2H), 3.92 (s, 5H), 3.72 (s, 3H), 2.65 and 2.61 (two s, 3H)

Mass, m/z: 400 (M⁺), 385, 235, 150, 121 (base)

Example 18-2

5-(4-Chloro-2-methoxyphenyl)-2H-pyrazole-3-carboxylic acid N'-ethyl-N'-(4-methoxybenzyl)hydrazide

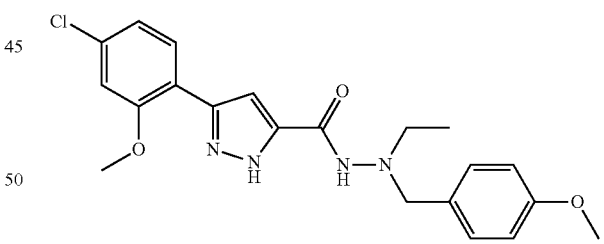

The title compound was obtained according to the same procedure as in Example 18-1 except that the compound of Example 14-5 was used instead of N-(4-methoxybenzyl)-N-methylhydrazine.

¹H-NMR (DMSO-d₆) δ: 13.55 and 13.26 (two brs, 1H), 9.20 and 8.63 (two brs, 1H), 7.89 and 7.69 (two d, J=8.1 Hz, 1H), 7.30 (d, J=8.5 Hz, 2H), 7.24 (s, 1H), 7.19 and 6.96 (two s, 1H), 7.12 and 7.06 (two d, J=8.5 Hz, 1H), 6.84 (d, J=8.5 Hz, 2H), 3.94 (s, 2H), 3.92 (s, 3H), 3.71 (s, 3H), 2.96-2.81 (m, 2H), 1.02 (brt, J=6.9 Hz, 3H)

Mass, m/z: 414 (M⁺), 399, 235, 164, 121 (base)

Synthesis scheme 19

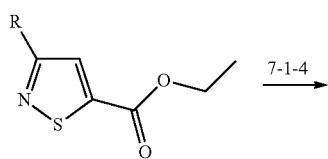

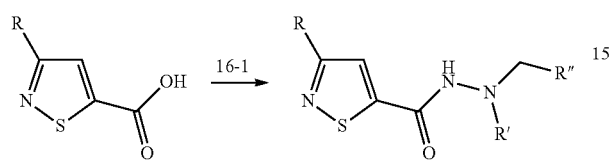

In the formulae, R and R″ are the same or different and each represent an aryl group which may have a substituent (such as a halogen atom or an alkoxy group), and R′ represents an alkyl group.

Example 19-1

3-(4-Chloro-2-methoxyphenyl)isothiazole-5-carboxylic acid N′-(4-methoxybenzyl)-N′-methyl hydrazide

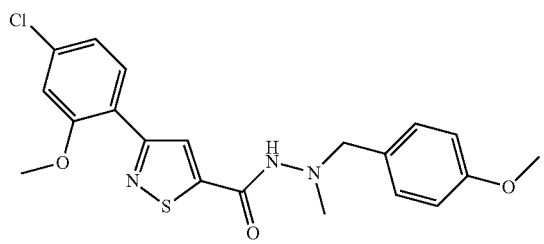

Ethyl 3-(4-chloro-2-methoxyphenyl)isothiazole-5-carboxylate was obtained according to the same procedure as in the after-mentioned Step 27-1-4 and then subjected to the same procedure as in the Step 7-1-4 to give 3-(4-chloro-2-methoxyphenyl)isothiazole-5-carboxylic acid. The carboxylic acid was used and subjected to the same procedure as in Example 16-1 to give the title compound.

$^1$H-NMR (CDCl$_3$) δ: 8.47 (s, 1H), 7.96 (d, J=8.1 Hz, 1H), 7.28 (d, J=8.5 Hz, 2H), 7.04 (dd, J=1.9, 8.1 Hz, 1H), 6.99 (d, J=1.9 Hz, 1H), 6.89 (d, J=8.9 Hz, 2H), 6.49 (s, 1H), 3.96 (d, J=13.1 Hz, 1H), 3.91 (s, 3H), 3.88 (d, J=12.7 Hz, 1H), 3.80 (s, 3H), 2.63 (s, 3H)

Mass, m/z: 417 (M$^+$), 149, 121 (base)

Example 19-2

3-(4-Chloro-2-methoxyphenyl)isothiazole-5-carboxylic acid N′-(4-methoxybenzyl)-N′-ethyl hydrazide

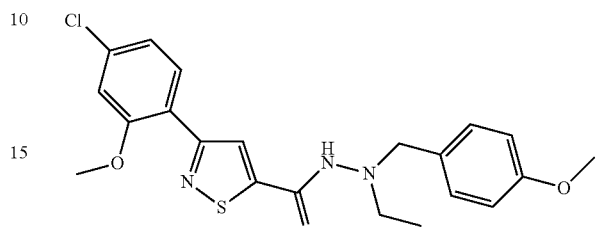

The title compound was obtained according to the same procedure as in Example 19-1 except that the compound of Example 14-5 was used instead of N-(4-methoxybenzyl)-N-methylhydrazine.

$^1$H-NMR (CDCl$_3$) δ: 8.48 (s, 1H), 7.97 (d, J=8.5 Hz, 1H), 7.26 (d, J=8.5 Hz, 2H), 7.04 (dd, J=1.9, 8.5 Hz, 1H), 6.99 (d, J=1.9 Hz, 1H), 6.88 (d, J=8.9 Hz, 2H), 6.32 (s, 1H), 3.99 (d, J=13.1 Hz, 1H), 3.93 (d, J=12.7 Hz, 1H), 3.92 (s, 3H), 3.79 (s, 3H), 3.05-2.96 (m, 1H), 2.68-2.59 (m, 1H), 1.17 (t, J=7.3 Hz, 3H)

Mass, m/z: 431 (M$^+$), 163, 121 (base)

Synthesis scheme 20

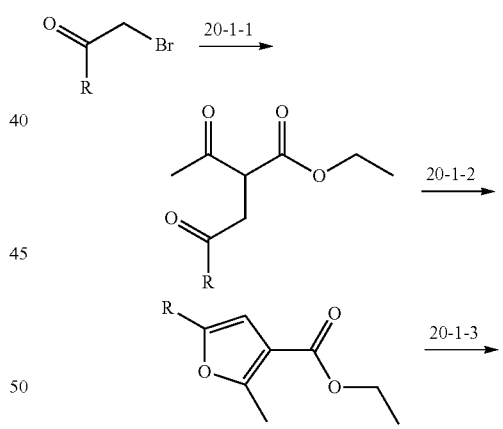

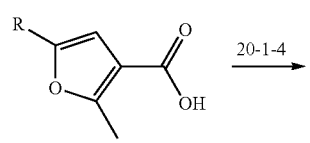

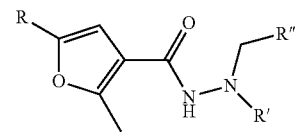

In the formulae, R and R" are the same or different and each represent an aryl group which may have a substituent (such as a halogen atom, an alkyl group, or an alkoxy group), and R' represents an alkyl group.

Example 20-1

Step 20-1-1

Ethyl 2-[2-(2-methoxyphenyl)-2-oxoethyl-3-oxobutyrate

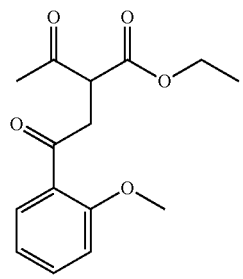 [SMILES: CCOC(=O)C(CC(=O)c1ccccc1OC)C(C)=O]

In tetrahydrofuran (20 ml), 60% sodium hydride suspension in oil (400 mg, 10.0 mmol) was suspended, and a solution (5 ml) of ethyl acetoacetate (1.30 g, 10.0 mmol) in tetrahydrofuran was added dropwise to the suspension. After the mixture was stirred for about 30 minutes, a solution (5 ml) of 2-bromo-2'-methoxyacetophenone (2.30 g, 10.0=1) in tetrahydrofuran was added dropwise to the mixture. After the mixture was stirred for about 30 minutes, ethyl acetate was added thereto, and the resulting mixture was washed with water. The organic layer was dried over anhydrous magnesium sulfate and then concentrated. The concentrate was purified by silica gel column chromatography (n-hexane:ethyl acetate=5:1) to give the title compound (2.30 g, 83%) as a colorless oily substance.

$^1$H-NMR (CDCl$_3$) δ: 7.75 (dd, J=1.5, 7.7 Hz, 1H), 7.47 (ddd, J=1.5, 7.3, 9.2 Hz, 1H), 7.01 to 6.96 (m, 2H), 4.21 (q, J=7.3 Hz, 2H), 4.17 (dd, J=5.8, 8.1 Hz, 1H), 3.70 (dd, J=8.1, 9.3 Hz, 1H), 3.55 (dd, J=5.8, 8.5 Hz, 1H), 2.40 (s, 3H), 1.28 (t, J=7.3 Hz, 3H)

Mass, m/z: 278 (m$^+$), 135 (base)

Step 20-1-2

Ethyl 5-(2-methoxyphenyl)-2-methylfuran-3-carboxylate

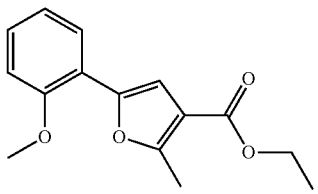 [SMILES: CCOC(=O)c1cc(-c2ccccc2OC)oc1C]

Ethyl 2-[2-(2-methoxyphenyl)-2-oxoethyl-3-oxobutyrate (2.10 g, 7.55 mmol) prepared in the Step 20-1-1 was dissolved in ethanol (20 ml), and concentrated hydrochloric acid (10 ml) was added thereto. The mixture was heated under reflux for about 16 hours. Water was added to the mixture, and the resulting mixture was subjected to extraction with ethyl acetate. The organic layer was washed with water, and then dried over anhydrous magnesium sulfate and concentrated. The concentrate was purified by silica gel column chromatography (n-hexane:ethyl acetate=10:1 to 5:1) to give the title compound (1.59 g, 81%) as a colorless oily substance.

$^1$H-NMR (CDCl$_3$) δ: 7.80 (dd, J=1.9, 7.7 Hz, 1H), 7.27 to 7.22 (m, 1H), 7.13 (s, 1H), 7.03 to 6.95 (m, 2H), 4.32 (q, J=6.9 Hz, 2H), 3.95 (s, 3H), 2.64 (s, 3H), 1.37 (t, J=6.9 Hz, 3H)

Mass, m/z: 260 (m$^+$), 231 (base)

Step 20-1-3

5-(2-Methoxyphenyl)-2-methylfuran-3-carboxylic acid

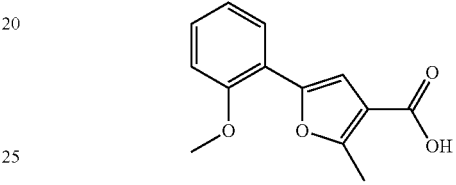

Ethyl 5-(2-methoxyphenyl)-2-methylfuran-3-carboxylate (1.00 g, 3.84 mmol) prepared in the Step 20-1-2 was dissolved in ethanol (8 ml), and a 1 mol/ml sodium hydroxide aqueous solution (8 ml) was added thereto. The mixture was heated under reflux for about 40 minutes. After being allowed to cool, the mixture was adjusted to weak acidity with 2 mol/ml hydrochloric acid, and the precipitate was filtered. The residue was washed with water and dried to give the title compound (0.95 g, quantitative) as a white powder.

$^1$H-NMR (CDCl$_3$) δ: 7.81 (dd, J=1.5, 7.7 Hz, 1H), 7.28 to 7.24 (m, 1H), 7.18 (s, 1H), 7.01 (dt, J=1.2, 7.7 Hz, 1H), 6.97 (d, J=8.5 Hz, 1H), 3.95 (s, 3H), 2.68 (s, 3H)

Mass, m/z: 232 (m$^+$, base)

Step 20-1-4

5-(2-Methoxyphenyl)-2-methylfuran-3-carboxylic acid N'-(4-methoxybenzyl)-N'-methyl hydrazide

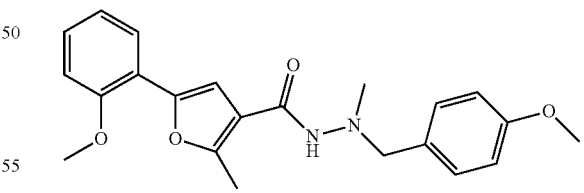

5-(2-Methoxyphenyl)-2-methylfuran-3-carboxylic acid prepared in the Step 20-1-3 and N-(4-methoxybenzyl)-N-methylhydrazine prepared in the Step 14-1-2 were used and subjected to the same procedure as in Example 16-1 to give the title compound.

$^1$H-NMR (CDCl$_3$) δ: 7.79 (d, J=5.8 Hz, 1H), 7.29 to 7.21 (m, 2H), 7.19 (d, J=8.9 Hz, 2H), 7.03 to 6.85 (m, 2H), 6.85 (d, J=8.9 Hz, 2H), 3.94 (s, 2H), 3.81 (s, 3H), 3.79 (s, 3H), 2.99, 2.76 (two s, 3H), 2.60 (s, 3H)

Mass, m/z: 380 (m$^+$), 121 (base)

Example 20-2

5-(2,4-Dichlorophenyl)-2-methylfuran-3-carboxylic acid N'-(4-methoxybenzyl)-N'-methyl hydrazide

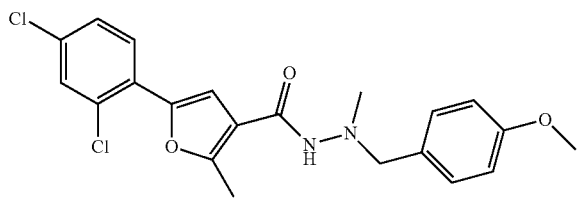 [SMILES: COc1ccc(CN(C)NC(=O)c2cc(-c3ccc(Cl)cc3Cl)oc2C)cc1]

The title compound was obtained according to the same procedure as in Example 20-1 except that 5-(2,4-dichlorophenyl)-2-methylfuran-3-carboxylic acid was used instead of 5-(2-methoxyphenyl)-2-methylfuran-3-carboxylic acid.

$^1$H-NMR (CDCl$_3$) δ: 7.75 (d, J=8.5 Hz, 1H), 7.44 (s, 1H), 7.29 (d, J=8.5 Hz, 2H), 7.25 to 7.18 (m, 1H), 6.87 (d, J=8.5 Hz, 2H), 4.03 (s, 2H), 3.81 (s, 3H), 3.79 (s, 3H), 2.95, 2.87 (twos, 3H), 2.58 (s, 3H)

Mass, m/z: 418 (m$^+$), 121 (base)

Example 20-3

5-(2,4-Dichlorophenyl)-2-methylfuran-3-carboxylic acid N'-(4-methoxy-3,5-dimethylbenzyl)-N'-methyl hydrazide

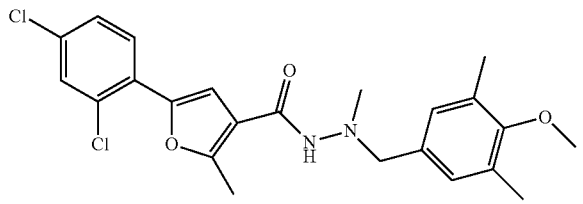 [SMILES: COc1c(C)cc(CN(C)NC(=O)c2cc(-c3ccc(Cl)cc3Cl)oc2C)cc1C]

The title compound was obtained according to the same procedure as in Example 20-1 except that 5-(2,4-dichlorophenyl)-2-methylfuran-3-carboxylic acid and N-(4-methoxy-3,5-dimethylbenzyl)-N-methylhydrazine were used instead of 5-(2-methoxyphenyl)-2-methylfuran-3-carboxylic acid and N-(4-methoxybenzyl)-N-methylhydrazine, respectively.

$^1$H-NMR (CDCl$_3$) δ: 7.76 (d, J=8.5 Hz, 1H), 7.45 (s, 1H), 7.35 to 7.23 (m, 1H), 6.99 (s, 2H), 3.97 (s, 2H), 3.71 (s, 3H), 2.74, 2.59 (two s, 3H), 2.50 (s, 3H), 2.69 (s, 6H)

Mass, m/z: 446 (m$^+$), 149 (base)

Synthesis scheme 21

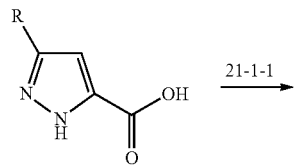

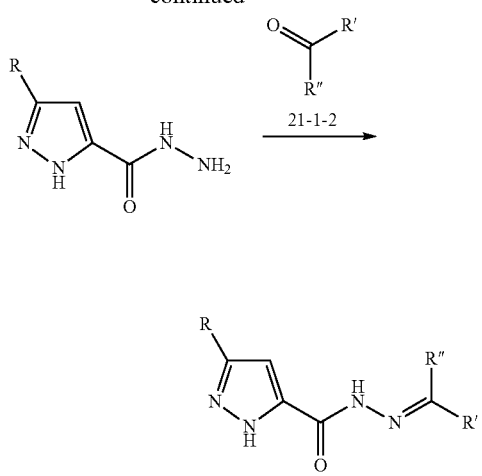

In the formulae, R represents an aryl group which may have a substituent (such as a halogen atom or an alkoxy group); R' represents an aryl or heterocyclic group which may have a substituent (such as a halogen atom, an alkyl group, a hydroxyl group, an alkoxy group, or a nitro group); and R" represents a hydrogen atom or an alkyl group.

Example 21-1

Step 21-1-1

5-(2,4-Dichlorophenyl)-2H-pyrazole-3-carboxylic acid hydrazide

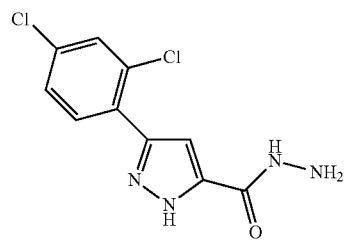 [SMILES: NNC(=O)c1cc(-c2ccc(Cl)cc2Cl)n[nH]1]

In methanol (20 ml), 5-(2,4-dichlorophenyl)-2H-pyrazole-3-carboxylic acid (1.00 g) was dissolved, and 6 drops of concentrated sulfuric acid was added thereto. The mixture was heated under reflux for 19 hours. After the mixture was allowed to cool, hydrazine monohydrate (0.97 g) was added to the mixture, and the resulting mixture was heated under reflux for 16 hours. The mixture was concentrated under a reduced pressure, and water was added thereto. The precipitated crystal was separated by filtration, washed with water, and dried to give the title compound (912 mg, 87%) as a white powder.

$^1$H-NMR (DMSO-d$_6$) δ: 13.88 (brs, 1H), 9.85 and 9.44 (two brs, 1H), 7.90-7.60 (m, 2H), 7.52 (s, 1H), 7.38 (s, 1H), 4.50 (brs, 2H)

Mass, m/z: 270 (M$^+$), 239 (base)

Step 21-1-2

5-(2,4-Dichlorophenyl)-2H-pyrazole-3-carboxylic acid[1-(2,4-dihydroxyphenyl)methylidene]hydrazide

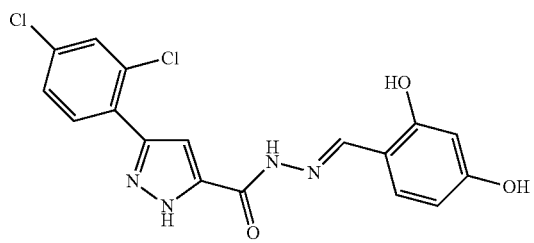 [SMILES: O=C(N/N=C/c1ccc(O)cc1O)c1cc(-c2ccc(Cl)cc2Cl)n[nH]1]

In ethanol (30 ml), 5-(2,4-dichlorophenyl)-2H-pyrazole-3-carboxylic acid hydrazide (136 mg) prepared in the Step 21-1-1 and 2,4-dihydroxybenzaldehyde (69 mg) was heated under reflux for 29 hours. Crystal appeared as the mixture was concentrated under a reduced pressure, the resulting crystal was separated by filtration, washed with ethanol, washed with ethyl acetate, and dried to give the title compound (129 mg, 66%).

$^1$H-NMR (DMSO-$d_6$) δ: 14.15 and 13.84 (two brs, 1H), 11.92 (brs, 1H), 11.57 and 11.14 (two brs, 1H), 9.93 (s, 1H), 8.58 and 8.53 (s, 1H), 7.98-7.07 (m, 5H), 6.37 (dd, J=1.6, 8.5 Hz, 1H), 6.32 (s, 1H)

Mass, m/z: 390 (M$^+$), 239 (base)

Examples 21-2 to 21-25

The objective compounds were obtained according to the same procedure as in Example 21-1 except that carbonyl compounds or carboxylic acids shown in the following tables were used instead of 2,4-dihydroxybenzaldehyde or 5-(2,4-dichlorophenyl)-2H-pyrazole-3-carboxylic acid.

TABLE 153

| Carbonyl compound | Carboxylic acid | Example | $^1$H-NMR | Mass, m/z |
|---|---|---|---|---|
| 3,4-Dihydroxy benzaldehyde | — | Example 21-2 | (DMSO-$d_6$) δ: 11.65 (brs, s, 1H), 9.32 (brs, s, 1H), 8.30 (s, 1H), 7.90-7.66 (m, 3H), 7.60-7.48 (m, 1H), 7.25 (s, 1H), 6.94 (d, J = 8.1 Hz, 1H), 6.79 (d, J = 8.1 Hz, 1H) | 390 (M$^+$), 239 (base) |
| 2,5-Dihydroxy benzaldehyde | — | Example 21-3 | (DMSO-$d_6$) δ: 14.19 and 13.88 (two brs, 1H), 12.01 (brs, s, 1H), 10.49 and 10.09 (two brs, 1H), 8.97 (s, 1H), 8.63 and 8.61 (two s, 1H), 7.96-7.47 (m, 3H), 7.20-6.68 (m, 3H), 6.75 (s, 1H) | 390 (M$^+$), 239 (base) |
| 2,3-Dihydroxy benzaldehyde | — | Example 21-4 | (DMSO-$d_6$) δ: 14.22 and 13.89 (two brs, 1H), 12.14 (brs, 1H), 11.33 and 10.73 (two brs, 1H), 9.28 and 9.13 (two s, 1H), 8.68 and 8.62 (two s, 1H), 7.97-7.46 (m, 3H), 7.20-6.68 (m, 4H) | 390 (M$^+$), 239 (base) |

TABLE 154

| Carbonyl compound | Carboxylic acid | Example | | ¹H-NMR | Mass, m/z |
|---|---|---|---|---|---|
| 3,5-Dihydroxy benzaldehyde | — | Example 21-5 | (structure) | (DMSO-d₆) δ: 14.16 and 13.83 (two brs, 1H), 11.79 and 11.65 (two brs, 1H), 9.44 (s, 2H), 8.33 and 8.25 (two s, 1H), 8.01-7.42 (m, 4H), 6.69-6.51 (m, 2H), 6.33-6.22 (m, 1H) | 390 (M⁺), 239 (base) |
| 4-Hydroxy-3-methoxy benzaldehyde | — | Example 21-6 | (structure) | (DMSO-d₆) δ: 13.99 (brs, 1H), 11.64 (brs, 1H), 9.53 (brs, 1H), 8.38 (s, 1H), 7.92-7.68 (m, 2H), 7.56 (d, J = 7.7 Hz, 1H), 7.31 (s, 1H), 7.09 (d, J = 8.1 Hz, 1H), 6.85 (d, J = 8.1 Hz, 1H), 3.85 (s, 3H) | 404 (M⁺), 149 (base) |
| 4-Hydroxy-3-methyl benzaldehyde | — | Example 21-7 | (structure) | (DMSO-d₆) δ: 14.30-13.6 (brs, 1H), 11.69 and 11.53 (two brs, 1H), 9.83 (s, 1H), 8.34 (s, 1H), 8.06-7.28 (m, 5H), 6.85 (d, J = 8.5 Hz, 1H), 2.17 (s, 3H) | 388 (M⁺), 150 (base) |
| 2-Chloro-4-hydroxy benzaldehyde | — | Example 21-8 | (structure) | (DMSO-d₆) δ: 13.98 (brs, 1H), 11.91 (s, 1H), 10.40 (s, 1H), 8.78 (s, 1H), 8.01-7.61 (m, 3H), 7.56 (d, J = 8.1 Hz, 1H), 6.91-6.80 (m, 2H) | 408 (M⁺), 239 (base) |

TABLE 155

| Carbonyl compound | Carboxylic acid | Example | ¹H-NMR | Mass, m/z |
|---|---|---|---|---|
| 3-Hydroxy-4-methoxy benzaldehyde | — | Example 21-9 | (DMSO-d$_6$) δ: 14.01 (brs, 1H), 11.67 (s, 1H), 9.29 (s, 1H), 8.34 (s, 1H), 7.97-7.64 (m, 2H), 7.56 (d, J = 7.3 Hz, 1H), 7.28 (s, 1H), 7.06 (d, J = 8.5 Hz, 1H), 6.98 (d, J = 8.5 Hz, 1H), 3.82 (s, 3H) | 404 (M⁺), 239 (base) |
| 4-Hydroxy-2-methoxy benzaldehyde | — | Example 21-10 | (DMSO-d$_6$) δ: 13.96 (brs, 1H), 11.68 (s, 1H), 9.99 (s, 1H), 8.69 (s, 1H), 7.97-7.47 (m, 3H), 6.52-6.41 (m, 2H), 3.81 (s, 3H) | 404 (M⁺), 135 (base) |
| 4-Hydroxy-3,5-dimethyl benzaldehyde | — | Example 21-11 | (DMSO-d$_6$) δ: 13.95 (brs, 1H), 11.62 (s, 1H), 8.75 (brs, 1H), 8.31 (s, 1H), 7.89-7.70 (m, 2H), 7.56 (d, J = 7.7 Hz, 1H), 7.31 (s, 2H), 2.21 (s, 6H) | 402 (M⁺), 147 (base) |

TABLE 156

| Carbonyl compound | Carboxylic acid | Example | ¹H-NMR | Mass, m/z |
|---|---|---|---|---|
| 4-Hydroxy-3,5-dimethoxy benzaldehyde | — | Example 21-12 | (DMSO-d$_6$) δ: 14.12 and 13.80 (two s, 1H), 11.77 and 11.59 (two s, 1H), 8.93 and 8.86 (two s, 1H), 8.41 and 8.34 (two s, 1H), 7.98-7.48 (m, 3H), 7.00 and 6.96 (two s, 2H), 3.83 (s, 6H) | 434 (M⁺), 179 (base) |

TABLE 156-continued

| Carbonyl compound | Carboxylic acid | Example | ¹H-NMR | Mass, m/z |
|---|---|---|---|---|
| 3-Chloro-4-hydroxy benzaldehyde | — | Example 21-13 | (DMSO-d$_6$) δ: 14.14 and 13.81 (two s, 1H), 11.84 and 11.67 (two s, 1H), 10.73 and 10.67 (two s, 1H), 8.41 and 8.32 (two s, 1H), 8.08-7.44 (m, 5H), 7.05 (d, J = 7.3 Hz, 1H) | 408 (M⁺), 239 (base) |
| 5-Hydroxy-2-nitro benzaldehyde | — | Example 21-14 | (DMSO-d$_6$) δ: 14.08 (brs, 1H), 12.23 (s, 1H), 11.10 (brs, 1H), 9.01 (s, 1H), 8.07 (d, J = 8.9 Hz, 1H), 7.89-7.70 (m, 2H), 7.57 (d, J = 8.1 Hz, 1H), 7.49 (d, J = 2.3 Hz, 1H), 6.98 (dd, J = 2.7, 8.9 Hz, 1H) | 419 (M⁺), 239 (base) |

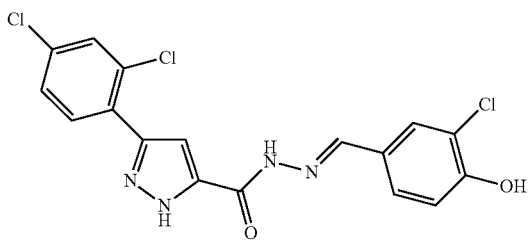

TABLE 157

| Carbonyl compound | Carboxylic acid | Example | ¹H-NMR | Mass, m/z |
|---|---|---|---|---|
| 3-Hydroxy-4-nitro benzaldehyde | — | Example 21-15 | (DMSO-d$_6$) δ: 14.24 and 13.89 (two s, 1H), 12.13 and 12.02 (two s, 1H), 11.16 (s, 1H), 8.52 and 8.42 (two s, 1H), 7.99 (d, J = 8.5Hz, 1H), 7.93-7.08 (m, 5H) | 419 (M⁺), 239 (base) |
| 4-Hydroxy-3-nitro benzaldehyde | — | Example 21-16 | (DMSO-d$_6$) δ: 14.17 and 13.83 (two s, 1H),, 11.97 and 11.82 (two s, 1H), 11.47 (s, 1H), 8.50 and 8.41 (two s, 1H), 8.22 and 8.16 (two s, 1H), 7.99-7.48 (m, 4H), 7.22 (d, J = 8.5Hz, 1H) | 419 (M⁺), 239 (base) |

TABLE 157-continued

| Carbonyl compound | Carboxylic acid | Example | ¹H-NMR | Mass, m/z |
|---|---|---|---|---|
| | | Example 21-17 | | |
| 3,5-Di-tert-butyl-4-hydroxy benzaldehyde | — | (structure) | (DMSO-d$_6$) δ: 14.10 and 13.79 (two s, 1H), 11.67 and 11.46 (two s, 1H), 8.45 and 8.39 (two s, 1H), 8.10-7.36 (m, 7H), 1.42 (s, 18H) | 486 (M$^+$), 216 (base) |

TABLE 158

| Carbonyl compound | Carboxylic acid | Example | ¹H-NMR | Mass, m/z |
|---|---|---|---|---|
| | | Example 21-18 | | |
| 3-Fluoro-4-hydroxy benzaldehyde | — | (structure) | (DMSO-d$_6$) δ: 14.14 and 13.81 (two s, 1H), 11.82 and 11.65 (two s, 1H), 10.40 and 10.34 (two s, 1H), 8.42 and 8.33 (two s, 1H), 8.07-6.97 (m, 6H) | 392 (M$^+$), 239 (base) |
| | | Example 21-19 | | |
| 4-Methoxy benzaldehyde | — | (structure) | (DMSO-d$_6$) δ: 14.14 and 13.81 (two brs, 1H), 11.79 and 11.61 (two s, 1H), 8.48 and 8.39 (two s, 1H), 7.98-7.10 (m, 6H), 7.03 (dd, J = 6.9, 6.2Hz, 2H), 3.82 (s, 3H) | 388 (M$^+$), 150 (base) |
| | | Example 21-20 | | |
| 3-Hydroxy-4-methoxy benzaldehyde | 5-(4-Chloro phenyl)-2H-pyrazole-3-carboxylic acid | (structure) | (DMSO-d$_6$) δ: 13.92 and 13.80 (two s, 1H), 11.71 and 11.51 (two s, 1H), 9.30 and 9.26 (two s, 1H), 8.38 and 8.28 (two s, 1H), 7.87 (d, J = 8.5Hz, 1H), 7.82 and 7.52 (two d, J = 8.5Hz, 1H), 7.57 (d, J = 8.5Hz, 1H), 7.46-7.27 (m, 1H), 7.25 (dd, J = 1.5, 8.1Hz, 1H), 7.10 and 7.03 (two dd, J = 1.6, 8.5Hz, 1H), 6.98 (t, J = 7.7, 8.1Hz. 1H), 3.82 and 3.81 (two s, 3H) | 370 (M$^+$), 205 (base) |

TABLE 158-continued

| Carbonyl compound | Carboxylic acid | Example | $^1$H-NMR | Mass, m/z |
|---|---|---|---|---|
| | | Example 21-21 | | |
| 4-Hydroxy-3,5-dimethyl benzaldehyde | 5-(4-Chloro phenyl)-2H-pyrazole-3-carboxylic acid | | (DMSO-$d_6$) δ : 13.89 and 13.80 (two brs, 1H), 11.67 and 11.47 (two brs, 1H), 8.70 and 8.35 (two s, 1H), 7.85 (s, 2H), 7.55 (s, 2H), 7.40-7.19 (m, 3H), 2.21 (s, 6H) | 368 (M$^+$), 148 (base) |

TABLE 159

| Carbonyl compound | Carboxylic acid | Example | $^1$H-NMR | Mass, m/z |
|---|---|---|---|---|
| | | Example 21-22 | | |
| 3-Hydroxy-4-methoxy benzaldehyde | 2-Methyl-5-phenyl-2H-pyrazole-3-carboxylic acid | | (DMS0-$d_6$) δ : 11.73 (s, 1H), 9.30 (s, 1H), 8.28 (s, 1H), 7.80 (d, J = 7.7Hz, 2H), 7.45 (dd, J = 7.3, 8.1Hz, 2H). 7.34 (dd, J = 5.8, 8.9Hz, 2H), 7.28 (d, J = 1.5Hz, 1H), 7.08 (dd, J = 1.5, 8.5Hz, 1H), 6.99 (d, J = 8.1Hz, 1H), 4.13 (s, 3H), 3.82 (s, 3H) | 350 (M$^+$), 185 (base) |
| | | Example 21-23 | | |
| 4-Hydroxy-3,5-dimethyl benzaldehyde | 2-Methyl-5-phenyl-2H-pyrazole-3-carboxylic acid | | (DMSO-$d_6$) δ : 11.70 (s, 1H), 8.76 (s, 1H), 8.25 (s, 1H), 7.80 (d, J = 7.3Hz, 2H), 7.45 (dd, J = 7.3, 8.1Hz, 2H), 7.37-7.31 (m, 4H), 4.13 (s, 3H), 2.22 (s, 6H) | 348 (M$^+$), 201 (base) |
| | | Example 21-24 | | |
| 4'-Hydroxy aceto-phenone | — | | (DMSO-$d_6$) δ : 14.00 (brs, 1H), 10.91 and 10.48 (two brs, 1 H), 9.79 (s, 1H), 8.04-7.45 (m, 5H), 6.82 (d, J = 7.7Hz, 1H), 2.31 (s, 3H) | 388 (M$^+$), 150 (base) |

TABLE 159-continued

Example 21-25

| Carbonyl compound | Carboxylic acid | Example | $^1$H-NMR | Mass, m/z |
|---|---|---|---|---|
| 1-Methyl-1H-benzimidazole-5-carboxyaldehyde | Example 3-2 | 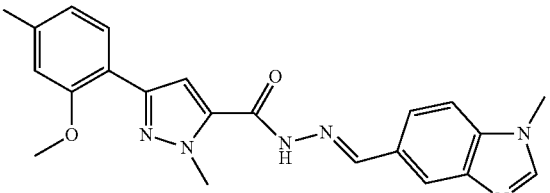 | (DMSO-$d_6$) δ : 11.86 (s, 1H), 8.57 (s, 1H), 8.26 (s, 1H), 7.96-7.92 (m, 1H), 7.79 (d, J = 8.5Hz, 1H), 7.67 (d, J = 8.1Hz, 1H), 7.46 (s, 1H), 7.23 (d, J = 1.5Hz, 1H), 7.09 (dd, J = 1.9, J = 8.5Hz, 1H), 4.16 (s, 3H), 3.97 (s, 3H), 3.88 (s, 3H) | 422 (M$^+$), 249 (base) |

Synthesis scheme 22

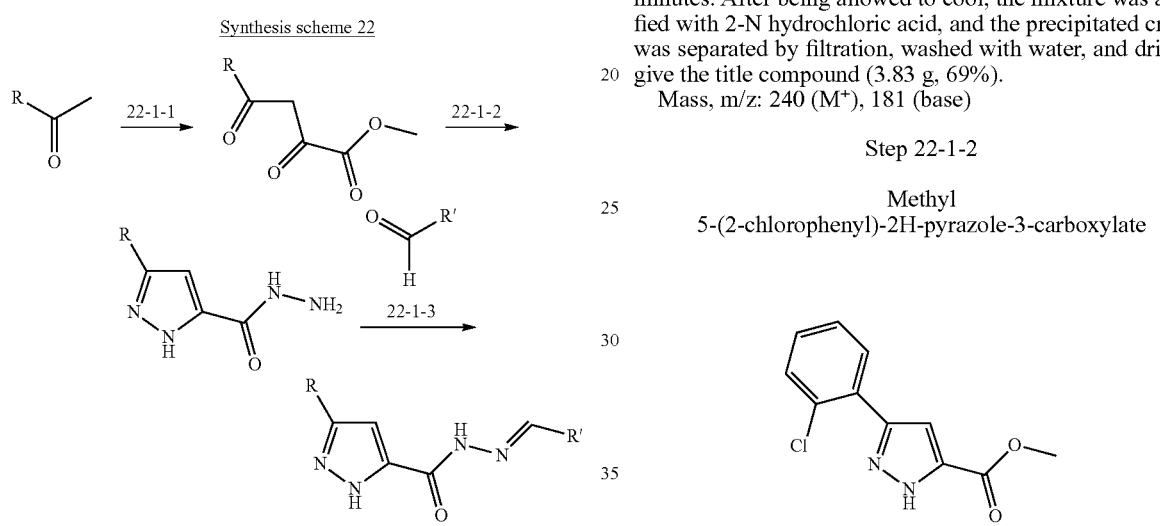

In the formulae, R represents an aryl group which may have a substituent (such as a halogen atom, an alkyl group, or an alkoxy group), and R' represents an aryl or heterocyclic group which may have a substituent (such as an alkyl group, a hydroxyl group, or an alkoxy group).

Example 22-1

Step 22-1-1

Methyl 4-(2-chlorophenyl)-2,4-dioxobutyrate

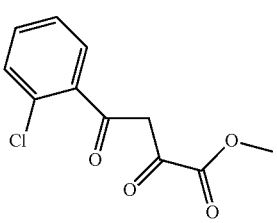 [SMILES: COC(=O)C(=O)CC(=O)c1ccccc1Cl]

In dimethylformamide (22 ml), 1-(2-chlorophenyl)ethanone (3.56 g) and dimethyl oxalate (3.26 g) were dissolved, and 60% sodium hydride suspension in oil (1.1 g) was added thereto while stirring at 5° C. The mixture was heated at a room temperature for one hour and then at 50° C. for 30 minutes. After being allowed to cool, the mixture was acidified with 2-N hydrochloric acid, and the precipitated crystal was separated by filtration, washed with water, and dried to give the title compound (3.83 g, 69%).

Mass, m/z: 240 (M$^+$), 181 (base)

Step 22-1-2

Methyl 5-(2-chlorophenyl)-2H-pyrazole-3-carboxylate

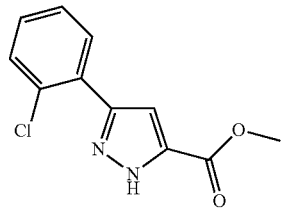 [SMILES: COC(=O)c1cc(-c2ccccc2Cl)n[nH]1]

In ethanol (8 ml), methyl 4-(2-chlorophenyl)-2,4-dioxobutyrate (1.2 g) obtained in the Step 22-1-1 and hydrazine monohydrate (0.25 g) were heated under reflux for 11 hours while stirring. After the mixture was allowed to cool, the precipitated crystal was separated by filtration and dried to give the title compound (617 mg, 52%).

Mass, m/z: 236 (M$^+$), 148 (base)

Step 22-1-3

5-(2-Chlorophenyl)-2H-pyrazole-3-carboxylic acid hydrazide

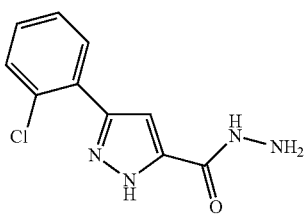 [SMILES: NNC(=O)c1cc(-c2ccccc2Cl)n[nH]1]

In ethanol (10 ml), methyl 5-(2-chlorophenyl)-2H-pyrazole-3-carboxylate (135 mg) obtained in the Step 22-1-2 and hydrazine monohydrate (429 mg) were heated under reflux for 9 hours. The mixture was concentrated under a reduced pressure, and water was added thereto. The precipitated crystal was separated by filtration and dried to give the title compound (116 mg, 86%).

¹H-NMR (DMSO-d₆) δ: 13.67 (brs, 1H), 9.79 (brs, 1H), 7.74 (s, 1H), 7.60 (d, J=6.2 Hz, 1H), 7.50-7.00 (m, 3H), 4.47 (brs, 2H)

Mass, m/z: 236 (M⁺), 205 (base)

Step 22-1-4

5-(2-Chlorophenyl)-2H-pyrazole-3-carboxylic acid [1-(3-hydroxy-4-methoxyphenyl)methylidene]hydrazide

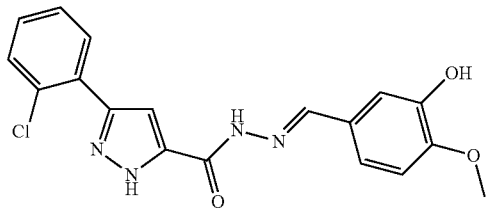 [SMILES: COc1ccc(/C=N/NC(=O)c2cc(-c3ccccc3Cl)n[nH]2)cc1O]

In ethanol (3 ml), 5-(2-chlorophenyl)-2H-pyrazole-3-carboxylic acid hydrazide (30 mg) prepared in the Step 22-1-3 and 3-hydroxy-4-methoxybenzaldehyde (25 mg) was heated under reflux for 24 hours. After the mixture was allowed to cool, the precipitated crystal was separated by filtration and dried to give the title compound (32 mg, 68%).

¹H-NMR (DMSO-d₆) δ: 14.04 (and 13.74 (two s, 1H), 11.73 and 11.55 (two s, 1H), 9.30 and 9.27 (two s, 1H), 8.39 and 8.30 (two s, 1H), 7.73-7.60 (m, 1H), 7.60-7.36 (m, 3H), 7.32-7.24 (m, 1H), 7.14-6.95 (m, 3H), 3.82 and 3.81 (two s, 3H)

Mass, m/z: 370 (M⁺), 205 (base)

Examples 22-2 to 22-10

The objective compounds were obtained according to the same procedure as in Example 22-1 except that any one of aldehyde compounds or any one of ketone compounds shown in the following tables were used instead of 3-hydroxy-4-methoxybenzaldehyde or 1-(2-chlorophenyl)ethanone.

TABLE 160

| Aldehyde compound | Ketone compound | Example | | ¹H-NMR | Mass, m/z |
|---|---|---|---|---|---|
| | | Example 22-2 | | | |
| 4-Hydroxy-3-methyl benzaldehyde | — | 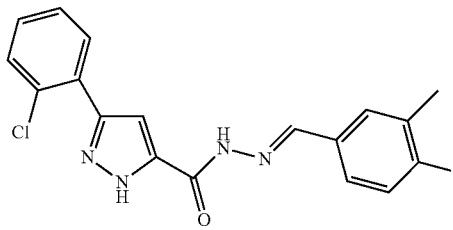 | | (DMSO-d₆) δ: 14.02 and 13.72 (two s, 1H), 11.68 and 11.49 (two s, 1H), 9.86 and 9.79 (two s, 1H), 8.39 and 8.31 (two s, 1H), 8.06-7.00 (m, 7H), 6.85 (d, J = 7.3Hz, 1H), 2.17 (s, 3H) | 354 (M⁺), 205 (base) |
| | | Example 22-3 | | | |
| — | 1-(2-Methyl phenyl) ethanone | 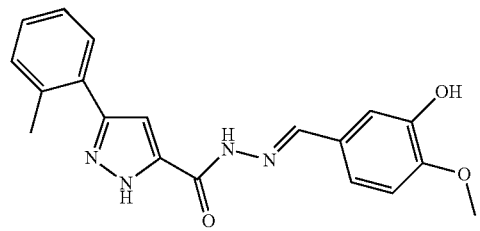 | | (DMSO-d₆) δ: 13.52 (s, 1H), 11.50 (s, 1H), 9.27 (s, 1H), 8.38 (s, 1H), 7.64-6.88 (m, 8H), 3.81 (s, 3H), 2.39 (s, 3H) | 350 (M⁺), 185 (base) |
| | | Example 22-4 | | | |
| 4-Hydroxy-3-methyl benzaldehyde | 1-(2-Methyl phenyl) ethanone | 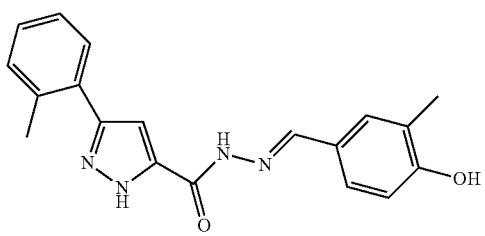 [SMILES: Cc1cc(/C=N/NC(=O)c2cc(-c3ccccc3Cl)n[nH]2)ccc1O] | | (DMSO-d₆) δ: 13.50 (s, 1H), 11.45 (s, 1H), 9.78 (s, 1H), 8.38 (s, 1H), 7.70-6.88 (m, 7H), 6.85 (d, J = 8.1 Hz, 1H), 2.39 (s, 1.8H), 2.17 (s, 3H) | 334 (M⁺), 185 (base) |

TABLE 160-continued

| Aldehyde compound | Ketone compound | Example | ¹H-NMR | Mass, m/z |
|---|---|---|---|---|
| | | Example 22-5 | | |
| 4-Hydroxy-benzaldehyde | 1-(2-Methyl phenyl) ethanone | | (DMSO-$d_6$) δ : 13.51 (s, 1H), 11.47 (s, 1H), 9.87 (s, 1H), 8.42 (s, 1H), 7.66-6.88 (m, 7H), 6.84 (d, J = 8.1 Hz, 2H), 2.39 (s, 3H) | 320 (M⁺), 185 (base) |

TABLE 161

| Aldehyde compound | Ketone compound | Example | ¹H-NMR | Mass, m/z |
|---|---|---|---|---|
| | | Example 22-6 | | |
| 4-Hydroxy-3,5-dimethyl benzaldehyde | 1-(2-Methoxy phenyl) ethanone | | (DMSO-$d_6$) δ : 13.40 (s, 1H), 11.38 (s, 1H), 8.69 (s, 1H), 8.35 (s, 1H), 7.75 (dd, J = 1.5Hz, J = 7.7Hz, 1H), 7.40 (dt, J = 1.5Hz, J = 7.7Hz, 1H), 7.33 and 7.29 (two s, 2H), 7.19 (d, J = 7.7Hz, 1H), 7.14 and 7.13 (two s, 1H), 7.07 (dt, J = 0.8Hz, J = 7.7Hz, 1H), 3.93 (s, 3H), 2.22 (two s, 6H) | 364 (M⁺), 201 (base) |
| | | Example 22-7 | | |
| — | 1-(2-Methoxy phenyl) ethanone | | (DMSO-$d_6$) δ : 13.47 (s, 1H), 11.43 (s, 1H), 9.27 (s, 1H), 8.38 (s, 1H), 7.75 (dd, J = 1.5Hz, J = 7.7Hz, 1H), 7.40 (t, J = 7.7Hz, 1H), 7.27 (s, 1H), 7.19 (d, J = 7.7Hz, 1H), 7.14 (s, 1H), 7.07 (t, J = 7.7Hz. 1H), 7.04 (d, J = 8.5Hz, 1H), 6.98 (d, J = 8.1Hz, 1H), 3.93 (s, 3H), 3.82 (s, 3H) | 366 (M⁺), 201 (base) |
| | | Example 22-8 | | |
| — | 1-(4-Chloro-2-methoxy phenyl) ethanone | | (DMSO-$d_6$) δ : 13.48 (s, 1H), 11.45 (s, 1H), 9.27 (s, 1H), 8.38 (s, 1H), 7.77 (d, J = 8.1Hz, 1H), 7.31-7.11 (m, 2H), 7.18-7.00 (m, 2H), 7.09 (d, J = 8.9Hz, 1H), 7.03 (d, J = 8.9Hz, 1H), 6.98 (d, J = 8.5Hz, 1H), 3.96 (s, 3H), 3.82 (s, 3H) | 400 (M⁺), 251 (base) |

TABLE 162

| Aldehyde compound | Ketone compound | Example | ¹H-NMR | Mass, m/z |
|---|---|---|---|---|
| | | Example 22-9 | | |
| 4-Hydroxy-3,5-dimethyl benzaldehyde | 1-(4-Chloro-2-methoxy phenyl) ethanone | | (DMSO-$d_6$) δ : 13.86 and 13.47 (two s, 1H), 11.67 and 11.40 (two s, 1H), 8.69 and 8.76 (two s, 1H), 8.35 and 8.29 (two s, 1H), 7.95 (d, J = 7.7Hz, 1H), 7.77 (d, J = 8.5Hz, 1H), 7.33 and 7.29 (two s, 2H), 7.27 (d, J = 1.9Hz, 1H), 7.18-7.12 (m, 1H), 3.96 (s, 3H), 2.21 (s, 6H) | 398 (M⁺), 235 (base |
| | | Example 22-10 | | |
| 1-Methyl-1H-benzimida-zole-5-carboxy-aldehyde | 1-(4-Chloro-2-methoxy phenyl) ethanone | | (DMSO-$d_6$) δ : 11.55 (s, 1H), 8.64 (s, 1H), 8.25 (s, 1H), 7.97-7.92 (m, 1H), 7.89 (s, 1H), 7.80-7.75 (m, 2H), 7.66 (d, J = 8.1Hz, 1H), 7.28 (d, J = 1.9Hz, 1H), 7.18~7.14 (m, 2H), 3.97 (s, 3H), 3.88 (s, 3H) | 407 (M⁺), 251 (base) |

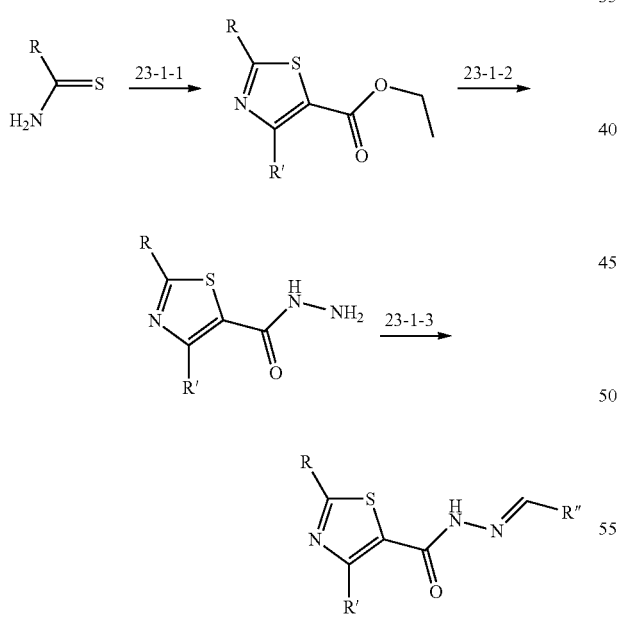

Synthesis scheme 23

In the formulae, R represents an alkyl group, or a carbocyclic (homocyclic) or heterocyclic group which may have a substituent (such as a halogen atom, an alkyl group, a haloalkyl group, a hydroxyl group, or an alkoxy group); R' represents a hydrogen atom, an alkyl group, a haloalkyl group, or a cycloalkyl or aryl group which may have a substituent (such as an alkoxy group); and R" represents a carbocyclic (homocyclic) or heterocyclic group which may have a substituent (such as a halogen atom, an alkyl group, a hydroxyl group, an alkoxy group, an aryloxy group, an aralkyloxy group, an alkylthio group, an amino group, an N-alkyl-substituted amino group, or a nitro group).

Example 23-1

Step 23-1-1

Ethyl 2-(2,4-dichlorophenyl)-4-methylthiazole-5-carboxylate

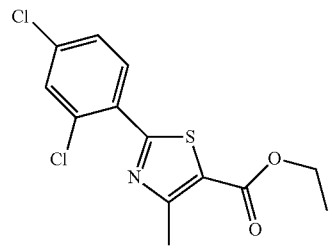 [SMILES: CCOC(=O)c1sc(-c2ccc(Cl)cc2Cl)nc1C]

In ethanol (10 ml), 2,4-dichlorothiobenzamide (378 mg) was dissolved, and ethyl 2-chloroacetoacetate (302 mg) was added thereto. The mixture was heated under reflux for 25 hours. After the mixture was allowed to cool, the precipitated crystal was separated by filtration, washed with water, and dried to give ethyl 2-(2,4-dichlorophenyl)-4-methylthiazole-5-carboxylate (368 mg, 64%).

¹H-NMR (CDCl₃) δ: 8.08 (d, J=1.9 Hz, 1H), 7.76 (dd, J=2.0, 8.5 Hz, 1H), 7.51 (d, J=8.1 Hz, 1H), 4.35 (q, J=7.3 Hz, 2H), 1.38 (t, J=7.3 Hz, 3H)

Mass, m/z: 315 (M⁺), 71 (base)

Step 23-1-2

2-(2,4-Dichlorophenyl)-4-methylthiazole-5-carboxylic acid hydrazide

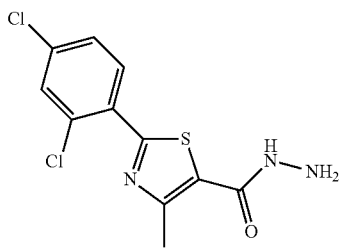 [SMILES: Cc1nc(-c2ccc(Cl)cc2Cl)sc1C(=O)NN]

Ethyl 2-(2,4-dichlorophenyl)-4-methylthiazole-5-carboxylate (250 mg) prepared in the Step 23-1-1 was dissolved in ethanol (10 ml), and hydrazine monohydrate (794 mg) was added thereto. The mixture was heated under reflux for 23 hours. After the mixture was allowed to cool, the precipitated crystal was separated by filtration, washed with water, and dried to give 2-(2,4-dichlorophenyl)-4-methylthiazole-5-carboxylic acid hydrazide (211 mg, 88%).

¹H-NMR (DMSO-d₆) δ: 9.62 (brs, 1H), 8.13 (d, J=1.9 Hz, 1H), 7.89 (dd, J=2.3, 8.5 Hz, 1H), 7.78 (d, J=8.5 Hz, 1H), 4.56 (brs, 2H), 2.60 (s, 3H)

Mass, m/z: 301 (M⁺), 71 (base)

Step 23-1-3

2-(2,4-Dichlorophenyl)-4-methylthiazole-5-carboxylic acid[1-(3-hydroxy-4-methoxyphenyl)methylidene]hydrazide

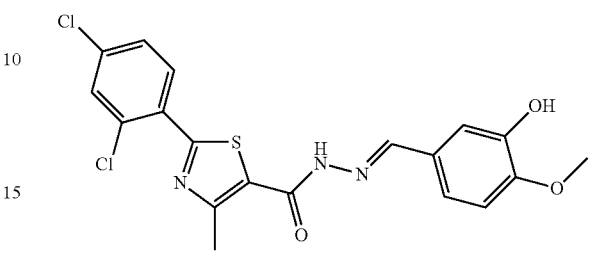

In ethanol (5 ml), 2-(2,4-dichlorophenyl)-4-methylthiazole-5-carboxylic acid hydrazide (34 mg) and 3-hydroxy-4-methoxybenzaldehyde (19 mg) was heated under reflux for 25 hours. After the mixture was allowed to cool, the precipitated crystal was separated by filtration to give the title compound (42 mg, 86%).

¹H-NMR (DMSO-d₆) δ: 11.74 (s, 1H), 9.39 (s, 1H), 8.21 (s, 1H), 8.00 (d, J=7.3 Hz, 1H), 7.99 (s, 1H), 7.82 (d, J=8.5 Hz, 1H), 7.31 (s, 1H), 7.09 (dd, J=1.5, 8.5 Hz, 1H), 7.00 (d, J=8.5 Hz, 1H), 3.82 (s, 3H), 2.77 (s, 3H)

Mass, m/z: 435 (M⁺), 71 (base)

Examples 23-2 to 23-165 and 23-171 to 23-172

The objective compounds were obtained according to the same procedure as in Example 23-1 except that compounds shown in the following tables were used instead of 2,4-dichlorothiobenzamide as a thioamide compound, 3-hydroxy-4-methoxybenzaldehyde as an aldehyde compound, or ethyl 2-chloroacetoacetate as a ring-forming component.

TABLE 163

| Thioamide compound | Aldehyde compound | Ring-forming component | Example | ¹H-NMR | Mass, m/z |
|---|---|---|---|---|---|
| 2-Chloro thiobenzamide | — | — | Example 23-2 | (DMSO-d₆) δ : 11.75 (s, 1H), 9.11 (s, 1H), 8.39-8.20 (m, 1H), 7.99 (s, 1H), 7.72-7.67 (m, 1H), 7.59-7.51 (m, 2H), 7.30 (s, 1H), 7.14 (d, J = 7.7Hz, 1H), 6.99 (d, J = 8.5Hz, 1H), 3.83 (s, 3H), 2.80 (s, 3H) | 401 (M⁺), 71 (base) |
| 2-Chloro thiobenzamide | 4-Hydroxy-3-methyl benzaldehyde | — | Example 23-3 | (DMSO-d₆) δ : 11.71 (s, 1H), 9.89 (s, 1H), 8.43-8.34 (m, 1H), 8.00 (s, 1H), 7.75-7.68 (m, 1H), 7.59 (s, 1H), 7.58-7.51 (m, 2H), 7.40 (dd, J = 0.8, 7.7Hz, 1H), 6.84 (d, J = 8.5Hz, 1H), 2.81 (s, 3H), 2.17 (s, 3H) | 385 (M⁺), 71 (base) |

TABLE 163-continued

| Thioamide compound | Aldehyde compound | Ring-forming component | Example | ¹H-NMR | Mass, m/z |
|---|---|---|---|---|---|
| | | | Example 23-4 | | |
| 2-Chloro thio-benzamide | 2-Chloro-3-hydroxy-4-methoxy benzaldehyde | — | | (DMSO-$d_6$) δ: 11.95 (s, 1H), 9.63 (s, 1H), 8.47 (s, 1H), 8.37-8.27 (m, 1H), 7.72-7.68 (m, 1H), 7.63-7.52 (m, 3H), 7.04 (d, J = 8.9Hz, 1H), 3.89 (s, 3H), 2.80 (s, 3H) | 435 (M⁺), 71 (base) |
| | | | Example 23-5 | | |
| 2-Chloro thio-benzamide | 3-Hydroxy-4,5-dimethoxy benzaldehyde | — | | (DMSO-$d_6$) δ: 11.85 (s, 1H), 9.31 (s, 1H), 8.31-8.25 (m, 2H), 7.98 (s, 1H), 7.71-7.66 (m, 1H), 7.59-7.51 (m, 2H), 6.93 and 6.89 (two s, 1H), 3.80 (s, 3H), 3.72 (s, 3H), 2.80 (s, 3H) | 431 (M⁺), 71 (base) |

TABLE 164

| Thioamide compound | Aldehyde compound | Ring-forming component | Example | ¹H-NMR | Mass, m/z |
|---|---|---|---|---|---|
| | | | Example 23-6 | | |
| 4-Chloro thio-benzamide | 4-Hydroxy benzaldehyde | – | | (DMSO-$d_6$) δ: 11.68 (s, 1H), 9.95 (s, 1H), 8.04 (d, J = 8.1Hz, 2H), 8.03 (s, 1H), 7.61 (dt, J = 1.9, 2.7, 8.5Hz, 4H), 6.88 (d, J = 8.1Hz, 2H), 2.77 (s, 3H) | 371 (M⁺), 71 (base) |
| | | | Example 23-7 | | |
| 4-Chloro thio-benzamide | – | – | | (DMSO-$d_6$) δ: 11.69 (s, 1H), 9.37 (s, 1H), 8.05 (d, J = 7.7Hz, 2H), 7.99 (s, 1H), 7.61 (dt, J = 1.9, 2.3, 8.8Hz, 2H), 7.28 (d, J = 1.9Hz, 1H), 7.10 (d, J = 8.1Hz, 1H), 7.01 (d, J = 8.5Hz, 1H), 3.82 (s, 3H), 2.77 (s, 3H) | 401 (M⁺), 71 (base) |

TABLE 164-continued

| Thioamide compound | Aldehyde compound | Ring-forming component | Example | ¹H-NMR | Mass, m/z |
|---|---|---|---|---|---|

Example 23-8

| 4-Chloro thio-benzamide | 4-Hydroxy-3,5-dimethyl benzaldehyde | — | | (DMSO-$d_6$) δ: 11.68 (s, 1H), 8.78 (s, 1H), 8.01 (d, J = 8.1Hz, 2H), 7.96 (s, 1H), 7.62 (d, J = 8.1Hz, 2H), 7.36 (s, 2H), 2.22 (s, 6H) | 399 (M⁺), 71 (base) |

Example 23-9

| 4-Chloro thio-benzamide | 3-Hydroxy benzaldehyde | — | | (DMSO-$d_6$) δ: 11.81 (s, 1H), 9.68 (s, 1H), 8.05 (s, 1H), 8.04 (d, J = 7.0Hz, 2H), 7.62 (dt, J = 1.9, 2.7, 8.5Hz, 2H), 7.29 (dd, J = 7.7, 8.1Hz, 1H), 7.20 (dd, J = 1.6, 2.3Hz, 1H), 7.14 (d, J = 7.3Hz, 1H), 6.85 (ddd, J = 1.2, 2.7, 8.1Hz, 1H), 2.77 (s, 3H) | 371 (M⁺), 71 (base) |

TABLE 165

| Thioamide compound | Aldehyde compound | Ring-forming component | Example | ¹H-NMR | Mass, m/z |
|---|---|---|---|---|---|

Example 23-10

| 4-Chloro thio-benzamide | 3,4-Dihydroxy benzaldehyde | — | | (DMSO-$d_6$) δ: 11.62 (s, 1H), 9.41 (s, 1H), 9.33 (s, 1H), 8.06 (d, J = 8.1Hz, 2H), 7.95 (s, 1H), 7.61 (dt, J = 1.9, 2.7, 8.5Hz, 2H), 7.25 (d, J = 1.9Hz, 1H), 6.97 (d, J = 7.7Hz, 1H), 6.82 (d, J = 8.1Hz, 1H), 2.77 (s, 3H) | 387 (M⁺), 71 (base) |

Example 23-11

| 4-Chloro thio-benzamide | 4-hydroxy-3-methyl benzaldehyde | — | | (DMSO-$d_6$) δ: 11.67 (s, 1H), 9.87 (s, 1H), 8.03 (d, J = 8.1Hz, 2H), 7.99 (s, 1H), 7.62 (d, J = 8.5Hz, 2H), 7.50 (s, 1H), 7.43 (d, J = 7.3Hz, 1H), 6.88 (d, J = 8.1Hz, 1H), 2.77 (s, 3H), 2.18 (s, 3H) | 385 (M⁺), 71 (base) |

TABLE 165-continued

| Thioamide compound | Aldehyde compound | Ring-forming component | Example | ¹H-NMR | Mass, m/z |
|---|---|---|---|---|---|
| | | | Example 23-12 | | |
| 2-Methyl thio-benzamide | – | – | (structure) | (DMSO-d$_6$) δ: 11.68 (s, 1H), 9.24 (s, 1H), 7.98 (s, 1H), 7.89 (d, J = 7.4Hz, 1H), 7.47-7.34 (m, 3H), 7.25 (d, J = 1.6Hz, 1H), 7.09 (d, J = 8.1Hz, 1H), 6.99 (d, J = 8.1Hz, 1H), 3.81 (s, 3H), 2.79 (s, 3H), 2.61 (s, 3H) | 381 (M$^+$), 216 (base) |
| | | | Example 23-13 | | |
| 2-Trifluoromethyl thio-benzamide | – | – | (structure) | (DMSO-d$_6$) δ: 11.74 (s, 1H), 9.21 (s, 1H), 8.01-7.94 (m, 2H), 7.87-7.76 (m, 3H), 7.18 (s, 1H), 7.08 (dd, J = 1.9, 8.5Hz, 1H), 6.97 (d, J = 8.5Hz, 1H), 3.79 (s, 3H), 2.78 (s, 3H) | 435 (M$^+$), 71 (base) |

TABLE 166

| Thioamide compound | Aldehyde compound | Ring-forming component | Example | ¹H-NMR | Mass, m/z |
|---|---|---|---|---|---|
| | | | Example 23-14 | | |
| 2-Methoxy thio-benzamide | — | — | (structure) | (DMSO-d$_6$) δ: 11.59 (s, 1H), 9.16 (brs, 1H), 8.37 (d, J = 7.7 Hz, 1H), 7.99 (brs, 1H), 7.55-7.49 (m, 1H), 7.35-7.26 (m, 2H), 7.21-7.09 (m, 2H), 7.03 (d, J = 7.7 Hz, 1H), 4.10 (s, 3H), 3.84 (s, 3H), 2.78 (s, 3H) | 397 (M$^+$), 232 (base) |
| | | | Example 23-15 | | |
| 2,3-Dichloro thio-benzamide | — | — | (structure) | (DMSO-d$_6$) δ: 11.78 (s, 1H), 9.15 (brs, 1H), 8.27 (d, J = 7.7 Hz, 1H), 8.00 (s, 1H), 7.84 (dd, J = 1.6, 8.1Hz, 1H), 7.56 (t, J = 8.1Hz, 1H), 7.30 (s, 1H), 7.11 (d, J = 7.7Hz, 1H), 7.00 (d, J = 8.5Hz, 1H), 3.82 (s, 3H), 2.80 (s, 3H) | 435 (M$^+$), 71 (base) |

TABLE 166-continued

| Thioamide compound | Aldehyde compound | Ring-forming component | Example | ¹H-NMR | Mass, m/z |
|---|---|---|---|---|---|
| | | | Example 23-16 | | |
| 4-Chloro thio-benzamide | — | Ethyl 2-chloro-3-oxo-propionate | [structure] | (DMSO-$d_6$) δ: 11.90 (s, 1H), 9.45 (s, 1H), 8.69 (s, 1H), 8.32-7.98 (m, 3H), 7.69-7.57 (m, 2H), 7.34 (d, J = 0.8Hz, 1H), 7.13 (dd, J = 1.6, 8.5Hz, 1H), 7.03 (d, J = 8.1Hz, 1H), 3.83 (s, 3H) | 387 (M⁺), 57 (base) |
| | | | Example 23-17 | | |
| 4-Chloro thio-benzamide | 4-Hydroxy-3,5-dimethyl benzalde-hyde | Ethyl 2-chloro-3-oxo-propionate | [structure] | (DMSO-$d_6$) δ: 11.88 (s, 1H), 8.82 (s, 1H), 8.28-7.98 (m, 3H), 7.69-7.58 (m, 2H), 7.39 (d, 2H), 2.25 (s, 6H) | 385 (M⁺), 57 (base) |

TABLE 167

| Thioamide compound | Aldehyde compound | Ring-forming component | Example | ¹H-NMR | Mass, m/z |
|---|---|---|---|---|---|
| | | | Example 23-18 | | |
| 4-Chloro thio-benzamide | — | Ethyl 2-chloro-4,4,4-trifluoro-3-oxo-butyrate | [structure] | (DMSO-$d_6$) δ: 12.22 (s, 1H), 9.27 (s, 1H), 8.17-7.98 (m, 1H), 8.08 (d, J = 8.9Hz, 2H), 7.66 (dt, J = 1.9, 2.3, 8.8Hz, 2H), 7.13-6.93 (m, 3H), 3.79 (s, 3H) | 455 (M⁺), 149 (base) |
| | | | Example 23-19 | | |
| 4-Chloro thio-benzamide | 4-Hydroxy-3,5-dimethyl benzaldehyde | Ethyl 2-chloro-4,4,4-trifluoro-3-oxo-butyrate | [structure] | (DMSO-$d_6$) δ: 12.18 and 12.14 (two s, 1H), 8.83 and 8.79 (two s, 1H), 8.14-7.97 (m, 3H), 7.69-7.63 (m, 2H), 7.34 and 7.22 (two s, 2H), 2.21 and 2.16 (two s, 6H) | 453 (M⁺), 147 (base) |

TABLE 167-continued

| Thioamide compound | Aldehyde compound | Ring-forming component | Example | ¹H-NMR | Mass, m/z |
|---|---|---|---|---|---|
| | | | Example 23-20 | | |
| 4-Chloro thio-benzamide | — | Ethyl 2-chloro-4,4-dimethyl-3-oxo-pentanoate | | (DMSO-$d_6$) δ: 9.33 (s, 1H), 8.22-7.25 (m, 1H), 7.89 (d, J = 6.6Hz, 2H), 7.40 (dt, J = 1.9, 2.3, 8.5Hz, 2H), 7.29-6.77 (m, 3H), 5.62 (s, 1H), 3.91 (s, 3H), 1.49 (s, 9H) | 443 ($M^+$), 278 (base) |

TABLE 168

| Thioamide compound | Aldehyde compound | Ring-forming component | Example | ¹H-NMR | Mass, m/z |
|---|---|---|---|---|---|
| | | | Example 23-21 | | |
| 4-Chloro thio-benzamide | 4-Hydroxy-3,5-dimethyl benz-aldehyde | Methyl 2-Chloro-4,4-dimethyl-3-oxo-pentanoate | | (DMSO-$d_6$) δ: 11.91 (brs, 1H), 8.77 (s, 1H), 8.10 (s, 1H), 7.97 (d, J = 8.5Hz, 2H), 7.59 (d, J = 8.5Hz, 2H), 7.30 (s, 2H), 2.20 (s, 6H), 1.42 (s, 9H) | 441 ($M^+$), 278 (base) |
| | | | Example 23-22 | | |
| 2,3-Dimethyl thio-benzamide | — | — | | (DMSO-$d_6$) δ: 11.65 (s, 1H), 9.25 (s, 1H), 7.98 (s, 1H), 7.50 (d, J = 7.3Hz, 1H), 7.35 (d, J = 7.3Hz, 1H), 7.24 (t, J = 7.3, 7.7Hz, 1H), 7.21 (s, 1H), 7.07 (dd, J = 2.0, 8.1Hz, 1H), 6.99 (d, J = 8.5Hz, 1H), 3.80 (s, 3H), 2.78 (s, 3H), 2.41 (s, 3H), 2.35 (s, 3H) | 395 ($M^+$), 230 (base) |
| | | | Example 23-23 | | |
| 2,3-Dimethyl thio-benzamide | 4-Hydroxy-3,5-dimethyl benz-aldehyde | — | | (DMSO-$d_6$) δ: 11.65 (s, 1H), 8.76 (s, 1H), 7.96 (s, 1H), 7.58 (d, J = 7.3Hz, 1H), 7.35 (d, J = 7.7Hz, 1H), 7.32 (s, 2H), 7.25 (t, J = 7.4, 7.7Hz, 1H), 2.78 (s, 3H), 2.47 (s, 3H), 2.35 (s, 3H), 2.19 (s, 6H) | 393 ($M^+$), 230 (base) |

TABLE 168-continued

| Thioamide compound | Aldehyde compound | Ring-forming component | Example | $^1$H-NMR | Mass, m/z |
|---|---|---|---|---|---|
| | | | Example 23-24 | | |
| 2,3-Dimethyl thio-benzamide | — | — | 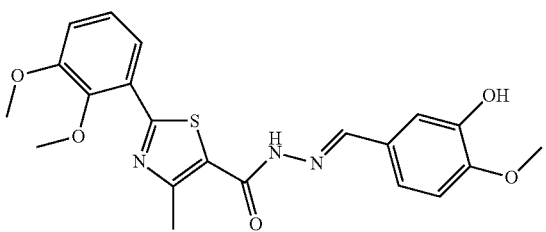 | (DMSO-d$_6$) δ : 11.62 (s, 1H), 9.09 (s, 1H), 8.00 (s, 1H), 7.89 (d, J = 4.2Hz, 1H), 7.27 (d, J = 1.9Hz, 1H), 7.23 (s, 1H), 7.21 (d, J = 1.2Hz, 1H), 7.20-7.14 (m, 1 H), 7.01 (d, J = 8.1Hz, 1H), 4.00 (s, 3H), 3.90 (s, 3H), 3.84 (s, 3H), 2.76 (s, 3H) | 427 (M$^+$), 262 (base) |

Table 169

| Thioamide compound | Aldehyde compound | Ring-forming component | Example | $^1$H-NMR | Mass, m/z |
|---|---|---|---|---|---|
| | | | Example 23-25 | | |
| 2,3-Dimethoxy thio-benzamide | 4-Hydroxy-3,5-dimethyl benz-aldehyde | — | | (DMSO-d$_6$) δ : 11.58 (s, 1H), 8.76 (s, 1H), 7.97 (s, 1H), 7.95-7.80 (m, 1H), 7.39 (s, 2H), 7.23 (d, J = 0.8Hz, 1 H), 7.22 (s, 1H), 3.94 (s, 3H), 3.91 (s, 3H), 2.77 (s, 3H), 2.22 (s, 6H) | 425 (M$^+$), 262 (base) |
| | | | Example 23-26 | | |
| 3-Methyl pyridine-2-carbo-thioamide | — | — | | (DMSO-d$_6$) δ : 11.66 and 11.61 (two s, 1H), 9.29 and 9.18 (two s, 1H), 8.52 (d, J = 4.2Hz, 1H), 8.25 and 7.99 (two s, 1H), 7.83 (d, J = 7.3Hz, 1H), 7.44 (dd, J = 4.6, 7.7Hz, 1H), 7.32-6.94 (m, 3H), 3.82 (s, 3H), 2.77 (s, 3H), 2.75 and 2.68 (two brs, 2H) | 382 (M$^+$), 217 (base) |
| | | | Example 23-27 | | |
| Isoquin-oline-1-carbo-thioamide | — | — | 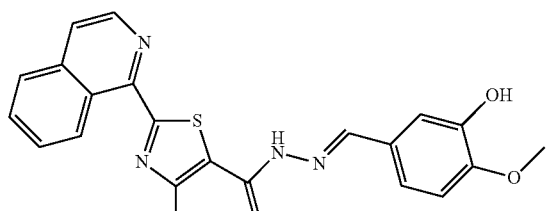 | (DMSO-d$_6$) δ : 11.75 and 11.71 (two s, 1H), 9.79-9.73 (m, 1H), 9.30 and 9.20 (two s, 1H), 8.64 (d, J = 5.4Hz, 1H), 8.33-8.00 (m, 3H), 7.92-7.83 (m, 2 H), 7.34-7.96 (m, 3H), 3.82 (s, 3H), 2.85 and 2.78 (two s, 3H) | 418 (M$^+$), 253 (base) |

Table 169-continued

| Thioamide compound | Aldehyde compound | Ring-forming component | Example | $^1$H-NMR | Mass, m/z |
|---|---|---|---|---|---|
| | | | Example 23-28 | | |
| Pyridine-2-carbo-thioamide | — | — | | (DMSO-d$_6$) δ: 11.69 (s, 1H), 9.21 (s, 1H), 8.68 (d, J = 4.2Hz, 1H), 8.32-7.92 (m, 3H), 7.55 (ddd, J = 1.2, 5.0, 7.3Hz, 1H), 7.40-7.04 (m, 2H), 7.02 (d, J = 8.5 Hz, 1H), 3.83 (s, 3H), 2.75 (s, 3H) | 368 (M$^+$), 203 (base) |

TABLE 170

| Thioamide compound | Aldehyde compound | Ring-forming component | Example | $^1$H-NMR | Mass, m/z |
|---|---|---|---|---|---|
| | | | Example 23-29 | | |
| Pyridine-2-carbo-thioamide | 4-Hydroxy-3,5-dimethyl benz-aldehyde | — | | (DMSO-d$_6$) δ: 11.68 (s, 1H), 8.77 (s, 1H), 8.70-8.64 (m, 1H), 8.28-7.89 (m, 1H), 8.17 (d, J = 7.7Hz, 1H), 7.98 (td, J = 1.5, 7.7Hz, 1H), 7.55 (ddd, J = 0.8, 5.0, 7.4Hz, 1H), 7.40 (s, 2H), 2.78 (s, 3H), 2.23 (s, 6H) | 366 (M$^+$), 203 (base) |
| | | | Example 23-30 | | |
| 4-Chloro thio-benzamide | — | Methyl 2-chloro-3-oxo-nonanoate | | (DMSO-d$_6$) δ: 11.66 (s, 1H), 9.35 (s, 1H), 8.04 (d, J = 7.7Hz, 2H), 7.99 (s, 1H), 7.61 (dt, J = 1.9, 2.3, 8.9Hz, 2H), 7.26 (d, J = 1.9Hz, 1H), 7.09 (d, J = 7.4Hz, 1H), 7.00 (d, J = 8.5Hz, 1H), 3.82 (s, 3H), 3.29-3.00 (m, 2H), 1.72 (quintet, J = 7.3Hz, 2H), 1.40-1.23 (m, 6H), 0.85 (t, J = 7.3Hz, 3H) | 471 (M$^+$), 71 (base) |
| | | | Example 23-31 | | |
| 4-Chloro thio-benzamide | 4-Hydroxy-3,5-dimethyl benz-aldehyde | Methyl 2-chloro-3-oxo-nonanoate | | (DMSO-d$_6$) δ: 11.64 (s, 1H), 8.77 (s, 1H), 8.26-7.91 (m, 1H), 8.01 (d, J = 8.1Hz, 2H), 7.62 (d, J = 8.5Hz, 2H), 7.35 (s, 2H), 3.29-3.16 (m, 2H), 1.72 (quintet, J = 7.3Hz, 2H), 1.42-1.21 (m, 6H), 0.85 (t, J = 6.5, 7.0Hz, 3H) | 469 (M$^+$), 71 (base) |

TABLE 171

| Thioamide compound | Aldehyde compound | Ring-forming component | Example | ¹H-NMR | Mass, m/z |
|---|---|---|---|---|---|
| | | | Example 23-32 | | |
| 4-Chloro thio-benzamide | 2-Furalde-hyde | — | (structure) | (DMSO-$d_6$) δ : 11.83 (brs, 1H), 8.02 (d, J = 8.5Hz, 2H + 1H), 7.88 (s, 1H), 7.61 (dt, J = 1.9, 2.0, 2.3, 8.9Hz, 2H), 6.99 (d, J = 2.7Hz, 1H), 6.77 (dd, J = 1.6, 3.1Hz, 1H), 2.75 (s, 3H) | 345 (M⁺), 71 (base) |
| | | | Example 23-33 | | |
| 4-Chloro thio-benzamide | 3-Furalde-hyde | — | (structure) | (DMSO-$d_6$) δ : 11.78 (brs, 1H), 8.19 (s, 1H), 8.10-8.00 (m, 3H), 7.80 (s, 1H), 7.60 (dt, J = 1.9, 2.7, 8.5Hz, 2H), 6.91 (s, 1H), 2.77 (s, 3H) | 345 (M⁺), 71 (base) |
| | | | Example 23-34 | | |
| 4-Chloro thio-benzamide | 3,4-(Methylene dioxy) benz-aldehyde | — | (structure) | (DMSO-$d_6$) δ : 11.79 (brs, 1H), 8.04 (s, 1H), 8.01 (d, J = 8.5 Hz, 2H), 7.61 (dt, J = 1.6, 1.9, 8.5Hz, 2H), 7.32 (s, 1H), 7.21 (d, J = 8.1Hz, 1H), 7.02 (d, J = 7.7Hz, 1H), 6.11 (s, 2H), 2.76 (s, 3H) | 399 (M⁺), 71 (base) |
| | | | Example 23-35 | | |
| 4-Chloro thio-benzamide | 3-Hydroxy-4-methyl benz-aldehyde | — | (structure) | (DMSO-$d_6$) δ : 11.74 (brs, 1H), 9.64 (brs, 1H), 8.07 (d, J = 7.3Hz, 2H), 8.01 (s, 1H), 7.61 (dt, J = 1.6, 1.9, 2.3, 2.7, 8.5Hz, 2H), 7.25 (s, 1H), 7.17 (d, J = 7.7Hz, 1H), 7.03 (d, J = 6.6Hz, 1H), 2.77 (s, 3H), 2.16 (s, 3H) | 385 (M⁺), 236 (base) |

TABLE 172

| Thioamide compound | Aldehyde compound | Ring-forming component | Example | ¹H-NMR | Mass, m/z |
|---|---|---|---|---|---|
| 2-Methoxy-thio-benzamide | 2-Fur-aldehyde | — | Example 23-36 | (DMSO-d$_6$) δ: 11.72 (s, 1H), 8.35 (d, J = 7.7 Hz, 1H), 8.00 (br s, 1H), 7.90 (br s, 1H), 7.52 (td, J = 1.5, 8.5 Hz, 1H), 7.30 (d, J = 8.5 Hz, 1H), 7.13 (t, J = 7.7 Hz, 1H), 6.96 (d, J = 3.1 Hz, 1H), 6.69 (s, 1H), 4.08 (s, 3H), 2.75 (s, 3H) | 341 (M$^+$), 232 (base) |
| Octane-thioamide | — | — | Example 23-37 | (DMSO-d$_6$) δ: 9.11 (br s, 1H), 7.73 (br s, 1H), 7.38 (d, J = 1.9 Hz, 1H), 7.16 (d, J = 7.3 Hz, 1H), 6.89 (d, J = 8.1 Hz, 1H), 5.71 (s, 1H), 3.94 (s, 3H), 3.00 (d, J = 7.7 Hz, 2H), 2.81 (s, 3H), 1.83 (quintet, J = 7.4, 7.7 Hz, 2H), 1.48-1.22 (m, 8H), 0.87 (t, J = 6.6, 7.3 Hz, 3H) | 389 (M$^+$), 224 (base) |
| 1-Benzo-thiophene-3-carbo-thioamide | — | — | Example 23-38 | (DMSO-d$_6$) δ: 11.70 (s, 1H), 9.32 (s, 1H), 8.75 (d, J = 8.1 Hz, 1H), 8.61 (s, 1H), 8.14 (d, J = 8.1 Hz, 1H), 8.01 (s, 1H), 7.61 (t, J = 7.3, 7.7 Hz, 1H), 7.52 (td, J = 0.8, 8.1 Hz, 1H), 7.33 (s, 1H), 7.14 (d, J = 7.7 Hz, 1H), 7.02 (d, J = 8.1 Hz, 1H), 3.83 (s, 3H), 2.84 (s, 3H) | 423 (M$^+$), 258 (base) |
| 1-Benzo-thiophene-3-carbo-thioamide | 4-Hydroxy-3-methyl-benz-aldehyde | — | Example 23-39 | (DMSO-d$_6$) δ: 11.67 (s, 1H), 9.87 (s, 1H), 8.72 (d, J = 7.7 Hz, 1H), 8.61 (s, 1H), 8.15 (d, J = 8.1 Hz, 1H), 8.02 (s, 1H), 7.62-7.44 (m, 4H), 6.90 (d, J = 8.1 Hz, 1H), 2.84 (s, 3H), 2.18 (s, 3H) | 407 (M$^+$), 258 (base) |

TABLE 173

| Thioamide compound | Aldehyde compound | Ring-forming component | Example | ¹H-NMR | Mass, m/z |
|---|---|---|---|---|---|
| Pyridine-4-carbothioamide | — | — | Example 23-40 | (DMSO-d$_6$) δ: 11.78 (s, 1H), 9.40 (s, 1H), 8.76 (dd, J = 1.6, 4.2 Hz, 2H), 8.30-7.87 (m, 1H), 7.97 (d, J = 4.6 Hz, 2H), 7.29 (d, J = 2.0 Hz, 1H), 7.12 (d, J = 8.1 Hz, 1H), 7.02 (d, J = 8.5 Hz, 1H), 3.82 (s, 3H), 2.80 (s, 3H) | 368 (M$^+$), 203 (base) |

TABLE 173-continued

| Thioamide compound | Aldehyde compound | Ring-forming component | Example | ¹H-NMR | Mass, m/z |
|---|---|---|---|---|---|
| Pyridine-3-carbothioamide | — | — | Example 23-41 | (DMSO-d₆) δ: 11.72 (s, 1H), 9.41 (s, 1H), 9.22 (s, 1H), 8.73 (dd, J = 1.6, 4.6 Hz, 1H), 8.39 (d, J = 7.0 Hz, 1H), 8.00 (s, 1H), 7.59 (dd, J = 4.6, 8.1 Hz, 1H), 7.31 (s, 1H), 7.10 (d, J = 7.7 Hz, 1H), 7.02 (d, J = 8.5 Hz, 1H), 3.82 (s, 3H), 2.80 (s, 3H) | 368 (M⁺), 203 (base) |
| 4-Chloro-thiobenzamide | 3,4-Dimethoxy-benzaldehyde | — | Example 23-42 | (DMSO-d₆) δ: 11.81 (s, 1H), 8.05 (br s, 1H), 8.05 (d, J = 7.7 Hz, 2H), 8.01 (dt, J = 1.9, 2.0, 2.7, 8.5 Hz, 2H), 7.61 (dt, J = 1.9, 2.0, 2.7, 8.5 Hz, 2H), 7.48 (s, 1H), 7.22 (dd, J = 1.9, 8.5 Hz, 1H), 7.05 (d, J = 8.1 Hz, 1H), 3.87 (s, 3H), 3.82 (s, 3H), 2.79 (s, 3H) | 415 (M⁺), 71 (base) |
| 2,3-Dimethyl-thiobenzamide | 3,4-Methylene-dioxy-benzaldehyde | — | Example 23-43 | (DMSO-d₆) δ: 11.76 (br s, 1H), 8.03 (s, 1H), 7.49 (d, J = 7.4 Hz, 1H), 7.35 (d, J = 7.3 Hz, 1H), 7.29 (d, J = 1.5 Hz, 1H), 7.24 (d, J = 7.7 Hz, 1H), 7.17 (dd, J = 1.2, 7.7 Hz, 1H), 7.00 (d, J = 8.1 Hz, 1H), 6.08 (s, 2H), 2.76 (s, 3H), 2.41 (s, 3H), 2.35 (s, 3H) | 393 (M⁺), 230 (base) |

TABLE 174

| Thioamide compound | Aldehyde compound | Ring-forming component | Example | ¹H-NMR | Mass, m/z |
|---|---|---|---|---|---|
| 2,4-Dimethyl-thiobenzamide | — | — | Example 23-44 | (DMSO-d₆) δ: 11.65 (s, 1H), 9.23 (s, 1H), 7.97 (s, 1H), 7.80 (d, J = 6.9 Hz, 1H), 7.25 (d, J = 2.0 Hz, 1H), 7.23 (s, 1H), 7.18 (d, J = 8.1 Hz, 1H), 7.09 (d, J = 8.1 Hz, 1H), 6.99 (d, J = 8.1 Hz, 1H), 3.81 (s, 3H), 2.77 (s, 3H), 2.59 (s, 3H), 2.35 (s, 3H) | 395 (M⁺), 71 (base) |
| 2,4-Dimethyl-thiobenzamide | 4-Hydroxy-3-methyl-benz-aldehyde | — | Example 23-45 | (DMSO-d₆) δ: 11.62 (s, 1H), 9.86 (s, 1H), 7.98 (s, 1H), 7.87 (d, J = 7.7 Hz, 1H), 7.53 (s, 1H), 7.37 (dd, J = 1.9, 8.5 Hz, 1H), 7.24 (s, 1H), 7.18 (d, J = 8.1 Hz, 1H), 6.85 (d, J = 8.5 Hz, 1H), 2.78 (s, 3H), 2.63 (s, 3H), 2.35 (s, 3H), 2.16 (s, 3H) | 379 (M⁺), 230 (base) |

TABLE 174-continued

| Thioamide compound | Aldehyde compound | Ring-forming component | Example | ¹H-NMR | Mass, m/z |
|---|---|---|---|---|---|
| 4-Chloro-2-methyl-thiobenzamide | — | — | Example 23-46 | (DMSO-d$_6$) δ: 11.70 (s, 1H), 9.25 (s, 1H), 7.98 (s, 1H), 7.94 (d, J = 7.7 Hz, 1H), 7.54 (d, J = 1.9 Hz, 1H), 7.44 (dd, J = 2.3, 8.5 Hz, 1H), 7.25 (d, J = 1.2 Hz, 1H), 7.09 (d, J = 8.5 Hz, 1H), 6.99 (d, J = 8.1 Hz, 1H), 3.81 (s, 3H), 2.79 (s, 3H), 2.62 (s, 3H) | 415 (M$^+$), 71 (base) |
| 4-Chloro-2-methyl-thiobenzamide | 4-Hydroxy-3-methyl-benz-aldehyde | — | Example 23-47 | (DMSO-d$_6$) δ: 11.67 (s, 1H), 9.87 (s, 1H), 8.30-7.79 (m, 2H), 7.55 (s, 1H), 7.52 (s, 1H), 7.44 (dd, J = 1.9, 8.1 Hz, 1H), 7.38 (dd, J = 1.6, 8.5 Hz, 1H), 6.85 (d, J = 8.5 Hz, 1H), 2.79 (s, 3H), 2.66 (s, 3H), 2.16 (s, 3H) | 399 (M$^+$), 71 (base) |

TABLE 175

| Thioamide compound | Aldehyde compound | Ring-forming component | Example | ¹H-NMR | Mass, m/z |
|---|---|---|---|---|---|
| 2-Propyl-oxythio-benzamide | — | — | Example 23-48 | (DMSO-d$_6$) δ: 11.57 (s, 1H), 9.16 (br s, 1H), 8.35 (d, J = 7.7 Hz, 1H), 7.99 (br s, 1H), 7.52-7.45 (m, 1H), 7.27 (d, J = 8.1 Hz, 1H), 7.24 (br s, 1H), 7.11 (td, J = 0.8, 7.7 Hz, 2H), 6.99 (d, J = 8.1 Hz, 1H), 4.26 (t, J = 6.6 Hz, 2H), 3.82 (s, 3H), 2.73 (s, 3H), 1.78 (br s, 2H), 0.85 (br s, 3H) | 425 (M$^+$), 260 (base) |
| 2-Propyl-oxythio-benzamide | 2-Fur-aldehyde | — | Example 23-49 | (DMSO-d$_6$) δ: 11.69 (s, 1H), 8.35 (dd, J = 1.6, 7.7 Hz, 1H), 7.84 (s, 1H), 7.49 (td, J = 1.6, 8.5 Hz, 1H), 7.26 (d, J = 8.1 Hz, 1H), 7.11 (td, J = 0.8, 8.1 Hz, 1H), 6.93 (d, J = 3.1 Hz, 1H), 6.65 (dd, J = 1.6, 3.5 Hz, 1H), 4.24 (t, J = 6.5 Hz, 2H), 2.71 (s, 3H), 1.89 (br s, 2H), 0.95 (br s, 3H) | 369 (M$^+$), 260 (base) |
| 2-Methyl-thio-benzamide | — | Ethyl 2-chloro-3-oxo-propionate | Example 23-50 | (DMSO-d$_6$) δ: 11.89 (s, 1H), 9.32 (s, 1H), 8.71 (s, 1H), 8.02 (s, 1H), 7.89 (d, J = 7.7 Hz, 1H), 7.50-7.34 (m, 3H), 7.31 (d, J = 2.0 Hz, 1H), 7.12 (dd, J = 1.9, 8.5 Hz, 1H) 7.01 (d, J = 8.1 Hz, 1H), 3.82 (s, 3H), 2.61 (s, 3H) | 367 (M$^+$), 174 (base) |

TABLE 175-continued

| Thioamide compound | Aldehyde compound | Ring-forming component | Example | ¹H-NMR | Mass, m/z |
|---|---|---|---|---|---|
| 2-Methyl-thio-benzamide | 4-Hydroxy-3-methyl-benz-aldehyde | Ethyl 2-chloro-3-oxo-propionate | Example 23-51 | (DMSO-$d_6$) δ: 11.86 (s, 1H), 9.90 (s, 1H), 8.70 (s, 1H), 8.03 (s, 1H), 7.97 (d, J = 7.7 Hz, 1H), 7.56 (s, 1H), 7.47-7.35 (m, 4H), 6.87 (d, J = 8.1 Hz, 1H), 2.65 (s, 3H), 2.17 (s, 3H) | 351 (M⁺), 174 (base) |

TABLE 176

| Thioamide compound | Aldehyde compound | Ring-forming component | Example | ¹H-NMR | Mass, m/z |
|---|---|---|---|---|---|
| 2-Methylthio-benzamide | 3,4-Methylene-dioxy-benz-aldehyde | Ethyl 2-chloro-3-oxo-propionate | Example 23-52 | (DMSO-$d_6$) δ: 11.98 (s, 1H), 8.71 (s, 1H), 8.08 (s, 1H), 7.91 (d, J = 7.3 Hz, 1H), 7.49-7.30 (m, 4H), 7.22 (dd, J = 1.5, 8.1 Hz, 1H), 7.02 (d, J = 7.7 Hz, 1H), 6.11 (s, 2H), 2.62 (s, 3H) | 365 (M⁺), 174 (base) |
| Thio-benzamide | — | — | Example 23-53 | (DMSO-$d_6$) δ: 11.67 (s, 1H), 9.36 (s, 1H), 8.04 (br s, 2H), 7.99 (s, 1H), 7.58-7.53 (m, 3H), 7.28 (d, J = 1.6 Hz, 1H), 7.10 (d, J = 8.1 Hz, 1H), 7.02 (d, J = 8.5 Hz, 1H), 3.82 (s, 3H), 2.77 (s, 3H) | 367 (M⁺), 202 (base) |
| Thio-benzamide | 4-Hydroxy-3-methyl-benz-aldehyde | — | Example 23-54 | (DMSO-$d_6$) δ: 11.65 (br s, 1H), 9.86 (s, 1H), 8.10-7.90 (m, 3H), 7.59-7.47 (m, 5H), 6.88 (d, J = 8.5 Hz, 1H), 2.77 and 2.67 (two s, 3H), 2.18 (s, 3H) | 351 (M⁺), 202 (base) |
| 2-Propyloxy-thio-benzamide | 4-Hydroxy-3,5-dimethyl-benz-aldehyde | — | Example 23-55 | (DMSO-$d_6$) δ: 11.53 (s, 1H), 8.73 (s, 1H), 8.34 (d, J = 7.7 Hz, 1H), 7.97 (s, 1H), 7.52-7.45 (m, 1H), 7.32 (s, 2H), 7.26 (d, J = 8.5 Hz, 1H), 7.12 (t, J = 7.3, 7.7 Hz, 1H), 4.21 (s, 2H), 2.73 (s, 3H), 2.19 (s, 6H), 1.75 (br s, 2H), 0.84 (s, 3H) | 423 (M⁺), 260 (base) |

TABLE 177

| Thioamide compound | Aldehyde compound | Ring-forming component | Example | ¹H-NMR | Mass, m/z |
|---|---|---|---|---|---|
| 2-Hydroxy-thiobenzamide | 4-Hydroxy-3,5-dimethyl-benz-aldehyde | — | Example 23-56 | (DMSO-$d_6$) δ: 11.57 (br s, 1H), 11.27 (s, 1H), 8.16 (dd, J = 1.5, 7.7 Hz, 1H), 7.96 (br s, 1H), 7.43-7.27 (m, 3H), 7.09 (d, J = 7.7 Hz, 1H), 6.99 (d, J = 7.7 Hz, 1H), 2.76 (s, 3H), 2.23 (s, 6H) | 381 (M$^+$), 218 (base) |
| 2-Hydroxy-thiobenzamide | — | — | Example 23-57 | (DMSO-$d_6$) δ: 11.61 (s, 1H), 11.46 (s, 1H), 8.15 (d, J = 7.7 Hz, 1H), 7.98 (br s, 1H), 7.37 (td, J = 1.5, 8.5 Hz, 1H), 7.32-6.98 (m, 3H), 7.07 (d, J = 8.1 Hz, 1H), 6.99 (t, J = 7.7 Hz, 1H) 3.83 (s, 3H), 2.75 (s, 3H) | 383 (M$^+$), 218 (base) |
| 4-Chloro-thiobenzamide | 3-Chloro-4-hydroxy-benz-aldehyde | — | Example 23-58 | (DMSO-$d_6$) δ: 11.80 (br s, 1H), 10.74 (s, 1 H), 8.33-7.90 (m, 3H), 7.77 (s, 1H), 7.61 (d, J = 8.5 Hz, 2H), 7.57 (d, J = 8.1 Hz, 1H), 7.08 (d, J = 8.1 Hz, 1H), 2.76 (s, 3H), 2.18 (s, 3H) | 405 (M$^+$), 71 (base) |
| 4-Chloro-thiobenzamide | 2-Hydroxy-benz-aldehyde | — | Example 23-59 | (DMSO-$d_6$) δ: 12.01 and 11.81 (two br s, 1H), 11.08 and 10.06 (two s, 1H), 8.62 and 8.46 (two s, 1H), 8.01 (d, J = 8.5 Hz, 2H), 7.90-7.50 (m, 1H), 7.61 (d, J = 8.5 Hz, 2H), 7.28 (s, 1H), 6.94 (t, J = 7.3, 7.7 Hz, 2H), 2.76 and 2.70 (two s, 3H) | 371 (M$^+$), 71 (base) |

TABLE 178

| Thioamide compound | Aldehyde compound | Ring-forming component | Example | ¹H-NMR | Mass, m/z |
|---|---|---|---|---|---|
| 4-Chloro-thiobenzamide | 2-Hydroxy-3-methoxy-benz-aldehyde | — | Example 23-60 | (DMSO-$d_6$) δ: 11.98 and 11.82 (two br s, 1H), 10.72 and 9.31 (two s, 1H), 8.63 and 8.49 (two s, 1H), 8.01 (d, J = 8.1 Hz, 2H), 7.61 (dt, J = 1.9, 2.0, 2.7, 8.5 Hz, 2H), 7.45 and 7.18 (two br s, 1H), 7.04 (d, J = 7.7 Hz, 1H), 6.90 (t, J = 7.0, 6.9 Hz, 1H), 3.83 (s, 3H), 2.76 and 2.70 (two s, 3H) | 401 (M$^+$), 71 (base) |

TABLE 178-continued

| Thioamide compound | Aldehyde compound | Ring-forming component | Example | ¹H-NMR | Mass, m/z |
|---|---|---|---|---|---|
| 4-Chloro-thiobenzamide | 2-Chloro-3-hydroxy-4-methoxy-benz-aldehyde | — | Example 23-61 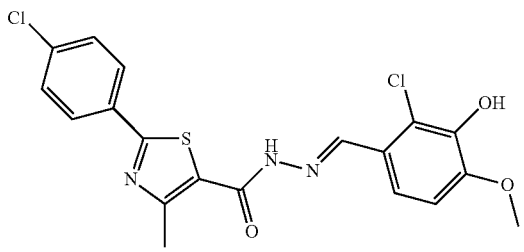 | (DMSO-d₆) δ: 11.91 (br s, 1H), 9.62 (br s, 1H), 8.47 (s, 1H), 8.03 (d, J = 8.1 Hz, 2H), 7.61 (dt, J = 1.9, 2.0, 2.7, 8.5 Hz, 2H), 7.57 (d, J = 7.7 Hz, 1H), 7.15 (d, J = 7.7 Hz, 1H), 3.90 (s, 3H), 2.77 (s, 3H) | 435 (M⁺), 71 (base) |
| 4-Chloro-thiobenzamide | 3,5-Dibromo-4-hydroxy-benz-aldehyde | — | Example 23-62 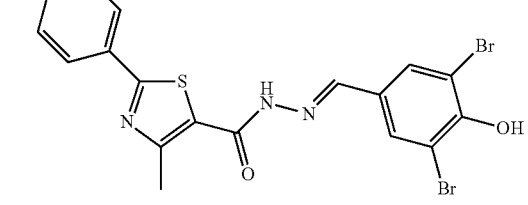 | (DMSO-d₆) δ: 11.96 (br s, 1H), 10.46 (br s, 1H), 8.10-7.88 (m, 5H), 7.65 (d, J = 8.1 Hz, 2H), 2.77 (s, 3H) | 529 (M⁺), 71 (base) |
| 4-Chloro-thiobenzamide | 2-Hydroxy-1-naphth-aldehyde | — | Example 23-63 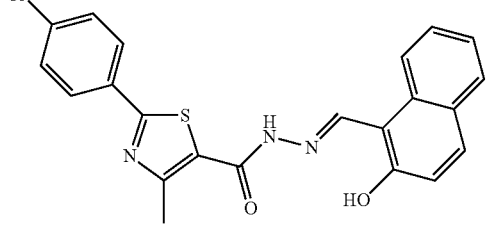 | (DMSO-d₆) δ: 12.54 (s, 1H), 12.09 (s, 1H), 9.45 (s, 1H), 8.30 (d, J = 8.5 Hz, 1H), 8.15-7.79 (m, 4H), 7.62 (d, J = 7.3 Hz, 2H + 1H), 7.42 (t, J = 6.6, 6.9 Hz, 1H), 7.24 (d, J = 8.8 Hz, 1H), 2.74 (s, 3H) | 421 (M⁺), 71 (base) |

TABLE 179

| Thioamide compound | Aldehyde compound | Ring-forming component | Example | ¹H-NMR | Mass, m/z |
|---|---|---|---|---|---|
| 4-Chloro-thio-benzamide | 3-Hydroxy-4-nitro-benzaldehyde | — | Example 23-64 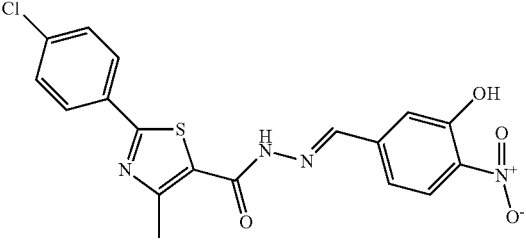 | (DMSO-d₆) δ: 12.07 (s, 1H), 11.23 (br s, 1H), 8.19-7.91 (m, 4H), 7.62 (d, J = 8.5 Hz, 2H), 7.49 (s, 1H), 7.36 (d, J = 7.3 Hz, 1H), 2.76 (s, 3H) | 416 (M⁺), 71 (base) |

TABLE 179-continued

| Thioamide compound | Aldehyde compound | Ring-forming component | Example | ¹H-NMR | Mass, m/z |
|---|---|---|---|---|---|
| 2-Fluoro-thio-benzamide | 4-Methoxy-benzaldehyde | — | Example 23-65 | (DMSO-d$_6$) δ: 11.79 (br s, 1H), 8.32-8.30 (m, 1H), 8.09 (s, 1H), 7.82 (d, J = 8.9 Hz, 1H), 7.74 (d, J = 8.5 Hz, 2H), 7.62-7.58 (m, 1H), 7.52-7.47 (m, 1H), 7.44-7.40 (m, 1H), 7.07-7.04 (m, 2H), 3.83 (s, 3H), 2.81 (s, 3H) | 369 (M$^+$), 220, 71 (base) |
| 3-Fluoro-thio-benzamide | 4-Methoxy-benzaldehyde | — | Example 23-66 | (DMSO-d$_6$) δ: 11.78 (br s, 1H), 8.09 (s, 1H), 7.87 (d, J = 7.6 Hz, 1H), 7.82 (d, J = 8.9 Hz, 2H), 7.73 (d, J = 8.1 Hz, 1H), 7.64-7.59 (m, 1H), 7.44-7.39 (m, 1H), 7.09-7.05 (m, 2H), 3.83 (s, 3H), 2.78 (s, 3H) | 369 (M$^+$), 220 (base) |
| 4-Fluoro-thio-benzamide | 4-Methoxy-benzaldehyde | — | Example 23-67 | (DMSO-d$_6$) δ: 11.74 (br s, 1H), 8.64 (s, 1H), 8.08 (br s, 2H), 7.72 (d, J = 8.1 Hz, 2H), 7.41-7.37 (m, 2H), 7.08-7.05 (m, 2H), 3.84 and 3.83 (two s, 3H), 2.77 and 2.50 (two s, 3H) | 369 (m$^+$), 220 (base) |

TABLE 180

| Thioamide compound | Aldehyde compound | Ring-forming component | Example | ¹H-NMR | Mass, m/z |
|---|---|---|---|---|---|
| 2-Methoxy-thio-benzamide | 3-Fluoro-4-methoxy-benzaldehyde | — | Example 23-68 | (DMSO-d$_6$) δ: 11.77 (br s, 1H), 8.38 (d, J = 8.1 Hz, 1H), 8.07 (s, 1H), 7.75-7.68 (m, 2H), 7.56-7.51 (m, 2H), 7.33-7.27 (m, 2H), 7.17-7.13 (m, 1H), 4.09 (s, 3H), 3.92 (s, 3H), 2.79 (s, 3H) | 399 (m$^+$), 232 (base) |
| 2-Methoxy-thio-benzamide | 4-Benzyloxy benzaldehyde | — | Example 23-69 | (DMSO-d$_6$) δ: 11.67 (br s, 1H), 8.38 (d, J = 7.3 Hz, 1H), 8.07 (s, 1H), 7.79 (d, J = 7.7 Hz, 2H), 7.53 (ddd, J = 1.5, 6.9, 8.5 Hz, 1H), 7.49-7.47 (m, 2H), 7.44-7.40 (m, 2H), 7.37-7.35 (m, 1H), 7.33-7.29 (m, 1H), 7.16-7.12 (m, 3H), 5.20 (s, 2H), 4.07 (s, 3H), 2.78 (s, 3H) | 457 (m$^+$), 232 (base) |

TABLE 180-continued

| Thioamide compound | Aldehyde compound | Ring-forming component | Example | 1H-NMR | Mass, m/z |
|---|---|---|---|---|---|
| 2-Methoxy-thiobenz-amide | 4-(Methyl-thio)benz-aldehyde | — | Example 23-70 | (DMSO-d6) δ: 11.76 (br s, 1H), 8.38 (d, J = 7.7 Hz, 1H), 8.09 (s, 1H), 7.77 (d, J = 8.1 Hz, 2H), 7.56-7.52 (m, 1H), 7.39 (d, J = 8.1 Hz, 2H), 7.31 (d, J = 7.7 Hz, 1H), 7.17-7.13 (m, 1H), 4.11 (s, 3H), 2.78 (s, 3H), 2.54 (s, 3H) | 397 (m+), 232 (base) |
| 2-Fluoro-thiobenz-amide | — | — | Example 23-71 | (DMSO-d6) δ: 11.73 (br s, 1H), 8.35-8.25 (m, 1H), 8.00 (s, 1H), 7.65-7.55 (m, 1H), 7.51-7.35 (m, 2H), 7.29-7.22 (m, 1H), 7.20-7.12 (m, 1H), 7.03-7.00 (m, 1H), 3.84 (s, 3H), 2.80 (s, 3H) | 385 (m+), 220 (base) |

TABLE 181

| Thioamide compound | Aldehyde compound | Ring-forming component | Example | 1H-NMR | Mass, m/z |
|---|---|---|---|---|---|
| 3-Fluoro-thiobenz-amide | — | — | Example 23-72 | (DMSO-d6) δ: 9.40 and 9.29 (two s, 1H), 8.51 and 8.00 (two s, 1H), 7.90-7.80 (m, 1H), 7.78-7.72 (m, 1H), 7.64-7.55 (m, 1H), 7.43-7.37 (m, 1H), 7.35-7.30 (m, 1H), 7.25-7.09 (m, 1H), 7.02 (d, J = 8.5 Hz, 1H), 3.84 and 3.82 (two s, 3H), 2.78 and 2.61 (two s, 3H) | 385 (m+), 220 (base) |
| 4-Fluoro-thiobenz-amide | — | — | Example 23-73 | (DMSO-d6) δ: 11.68 (br s, 1H), 9.38 (br s, 1H), 9.28 and 8.51 (two s, 1H), 8.10-7.99 (m, 2H), 7.42-7.28 (m, 3H), 7.24-7.10 (m, 1H), 7.03-7.01 (m, 1H), 3.84 and 3.82 (two s, 3H), 2.77 and 2.68 (two s, 3H) | 385 (m+), 220 (base) |

TABLE 181-continued

| Thioamide compound | Aldehyde compound | Ring-forming component | Example | ¹H-NMR | Mass, m/z |
|---|---|---|---|---|---|
| 4-Chloro-2-methoxy-thio-benzamide | — | — | Example 23-74 | (DMSO-$d_6$) δ: 11.61 (s, 1H), 9.17 (s, 1H), 8.36 (d, J = 8.5 Hz, 1H), 7.99 (s, 1H), 7.42 (d, J = 1.9 Hz, 1H), 7.32 (s,1H), 7.20 (dd, J = 1.9, 8.5 Hz, 1H), 7.15 (d, J = 8.1 Hz, 1H), 7.02 (d, J = 8.1 Hz, 1H), 4.13 (s, 3H), 3.84 (s, 3H), 2.77 (s, 3H) | 431 (M⁺), 71 (base) |
| 4-Chloro-2-methoxy-thio-benzamide | 4-Hydroxy-benz-aldehyde | — | Example 23-75 | (DMSO-$d_6$) δ: 11.62 (s, 1H), 9.97 (s, 1H), 8.37 and 8.27 (two d, J = 8.5 Hz, 1H), 8.02 (s, 1H), 7.67 (d, J = 8.1 Hz, 2H), 7.42 and 7.38 (two d, J = 1.6 Hz, 1H), 7.21 and 7.18 (two dd, J = 1.9, 8.5 Hz, 1H), 6.90 (d, J = 8.1 Hz, 2H), 4.13 (s, 3H), 2.78 (s, 3H) | 401 (M⁺), 266 (base) |

TABLE 182

| Thioamide compound | Aldehyde compound | Ring-forming component | Example | ¹H-NMR | Mass, m/z |
|---|---|---|---|---|---|
| 4-Chloro-2-methoxy-thiobenzamide | 4-Hydroxy-3-methyl-benz-aldehyde | — | Example 23-76 | (DMSO-$d_6$) δ: 11.59 (s, 1H), 9.87 (s, 1H), 8.37 (d, J = 8.5 Hz, 1H), 8.00 (s, 1H), 7.56 (br d, J = 7.0 Hz, 1H), 7.46 (br s, 1H), 7.43 (d, J = 1.5 Hz, 1H), 7.21 (dd, J = 1.9, 8.5 Hz, 1H), 6.91 (d, J = 8.8 Hz, 1H), 4.11 (s, 3H), 2.77 (s, 3H), 2.17 (s, 3H) | 415 (M⁺), 266 (base) |
| 4-Chloro-2-methoxy-thiobenzamide | 3,4-Dihydroxy-benz-aldehyde | — | Example 23-77 | (DMSO-$d_6$) δ: 11.55 (s, 1H), 9.59 (s, 1H), 9.07 (s, 1H), 8.36 (d, J = 8.5 Hz, 1H), 7.95 (s, 1H), 7.42 (d, J = 1.9 Hz, 1H), 7.24 (d, J = 1.9 Hz, 1H), 7.20 (dd, J = 1.9, 8.5 Hz, 1H), 7.09 (br d, J = 7.7 Hz, 1H), 6.85 (d, J = 7.7 Hz, 1H), 4.13 (s, 3H), 2.78 (s, 3H) | 417 (M⁺), 71 (base) |

TABLE 182-continued

| Thioamide compound | Aldehyde compound | Ring-forming component | Example | ¹H-NMR | Mass, m/z |
|---|---|---|---|---|---|
| 4-Chloro-2-methoxy-thiobenzamide | 3,4-Dimethoxy-benzaldehyde | — | Example 23-78 | (DMSO-d$_6$) δ: 11.57 (s, 1H), 8.77 (s, 1H), 8.35 (d, J = 8.5 Hz, 1H), 7.97 (s, 1H), 7.41 (d, J = 2.0 Hz, 1H), 7.36 (br s, 2H), 7.21 (dd, J = 1.9, 8.5 Hz, 1H), 4.06 (s, 3H), 2.76 (s, 3H), 2.22 (s, 6H) | 429 (M$^+$), 266 (base) |
| 4-Chloro-2-methoxy-thiobenzamide | 4-Methoxy-benzaldehyde | — | Example 23-79 | (DMSO-d$_6$) δ: 11.69 (s, 1H), 8.36 (d, J = 8.5 Hz, 1H), 8.07 (s, 1H), 7.78 (d, J = 7.7 Hz, 2H), 7.41 (d, J = 2.0 Hz, 1H), 7.21 (dd, J = 1.9, 8.5 Hz, 1H), 7.08 (d, J = 7.4 Hz, 2H), 4.13 (s, 3H), 3.83 (s, 3H), 2.78 (s, 3H) | 415 (M$^+$), 266 (base) |

TABLE 183

| Thioamide compound | Aldehyde compound | Ring-forming component | Example | ¹H-NMR | Mass, m/z |
|---|---|---|---|---|---|
| 4-Chloro-2-methoxy-thiobenzamide | 3-Methoxy-benzaldehyde | — | Example 23-80 | (DMSO-d$_6$) δ: 11.83 (s, 1H), 8.36 (d, J = 8.5 Hz, 1H), 8.09 (s, 1H), 7.43 (br s, 2H), 7.41 (d, J = 1.9 Hz, 1H), 7.36 (br s, 1H), 7.21 (dd, J = 1.9, 8.5 Hz, 1H), 7.06 (d, J = 7.0 Hz, 1H), 4.11 (s, 3H), 3.81 (s, 3H), 2.77 (s, 3H) | 415 (M$^+$), 266 (base) |
| 4-Chloro-2-methoxy-thiobenzamide | 4-Hydroxy-3-methoxy-benzaldehyde | — | Example 23-81 | (DMSO-d$_6$) δ: 11.69 (s, 1H), 9.56 (s, 1H), 8.35 (d, J = 8.9 Hz, 1H), 8.01 (s, 1H), 7.42 (d, J = 1.5 Hz, 1H), 7.32 (br s, 2H), 7.21 (dd, J = 1.9, 8.5 Hz, 1H), 6.91 (d, J = 7.4 Hz, 1H), 4.07 (s, 3H), 3.80 (s, 3H), 2.77 (s, 3H) | 431 (M$^+$), 266 (base) |

TABLE 183-continued

| Thioamide compound | Aldehyde compound | Ring-forming component | Example | ¹H-NMR | Mass, m/z |
|---|---|---|---|---|---|
| 4-Chloro-2-methoxy-thiobenzamide | 4-Methoxy-3-methyl-benzaldehyde | — | Example 23-82 | (DMSO-d$_6$) δ: 11.66 (s, 1H), 8.36 (d, J = 8.1 Hz, 1H), 8.04 (s, 1H), 7.66 (br d, J = 7.7 Hz, 1H), 7.57 (br s, 1H), 7.42 (d, J = 1.9 Hz, 1H), 7.21 (dd, J = 1.9, 8.5 Hz, 1H), 7.07 (d, J = 8.5 Hz, 1H), 4.10 (s, 3H), 3.86 (s, 3H), 2.77 (s, 3H), 2.21 (s, 3H) | 429 (M⁺), 266 (base) |
| 4-Chloro-2-methoxy-thiobenzamide | 2,3-Dihydro-benzofuran-5-carbaldehyde | — | Example 23-83 | (DMSO-d$_6$) δ: 11.62 (s, 1H), 8.36 (d, J = 8.5 Hz, 1H), 8.06 (s, 1H), 7.68 (s, 1H), 7.57 (br d, J = 8.1 Hz, 1H), 7.41 (d, J = 1.5 Hz, 1H), 7.21 (dd, J = 1.9, 8.5 Hz, 1H), 6.90 (d, J = 8.5 Hz, 1H), 4.62 (t, J = 8.5 Hz, 2H), 4.12 (s, 3H), 3.26 (t, J = 8.5 Hz, 2H), 2.78 (s, 3H) | 427 (M⁺), 266 (base) |

TABLE 184

| Thioamide compound | Aldehyde compound | Ring-forming component | Example | ¹H-NMR | Mass, m/z |
|---|---|---|---|---|---|
| 4-Chloro-2-methoxy-thiobenzamide | 4-Hydroxy-3,5-dimethyl-benzaldehyde | — | Example 23-84 | (DMSO-d$_6$) δ: 11.58 (s, 1H), 8.78 (s, 1H), 8.35 (d, J = 7.7 Hz, 1H), 7.98 (s, 1H), 7.42 (d, J = 1.9 Hz, 1H), 7.36 (br s, 2H), 7.21 (dd, J = 1.9, 8.5 Hz, 1H), 4.07 (s, 3H), 2.77 (s, 3H), 2.22 (s, 6H) | 429 (M⁺), 266 (base) |
| 4-Chloro-2-methoxy-thiobenzamide | 6-Methoxy-3-pyridine-carbaldehyde | — | Example 23-85 | (DMSO-d$_6$) δ: 11.86 (s, 1H), 8.61 (s, 1H), 8.37 (d, J = 8.8 Hz, 1H), 8.18 (d, J = 9.3 Hz, 1H), 8.11 (s, 1H), 7.42 (d, J = 1.9 Hz, 1H), 7.21 (dd, J = 1.9, 8.8 Hz, 1H), 7.00 (d, J = 9.6 Hz, 1H), 4.16 (s, 3H), 3.93 (s, 3H), 2.78 (s, 3H) | 416 (M⁺), 266 (base) |

TABLE 184-continued

| Thioamide compound | Aldehyde compound | Ring-forming component | Example | ¹H-NMR | Mass, m/z |
|---|---|---|---|---|---|
| 2-Methoxy-thiobenzamide | 2-Hydroxy-4-methoxy-benzaldehyde | — | Example 23-86 | (DMSO-d₆) δ: 11.87 and 11.58 (two br s, 1H), 11.52 and 10.16 (two br s, 1H), 8.54 and 8.36 (two br s, 2H), 7.88-7.42 (m, 1H), 7.52 (d, J = 6.9 Hz, 1H), 7.30 (d, J = 8.5 Hz, 1H), 7.16-7.13 (m, 1H), 6.56 (br s, 1H), 6.50 (s, 1H), 4.09 (s, 3H), 3.78 (s, 3H), 2.77 and 2.69 (two s, 3H) | 397 (m⁺), 232 (base) |
| 2-Methoxy-thiobenzamide | 4-Formyl-benzoic acid | — | Example 23-87 | (DMSO-d₆) δ: 13.10 (br s, 1H), 11.94 (br s, 1H), 8.38 (d, J = 8.1 Hz, 1H), 8.21 (s, 2H), 8.00-7.85 (m, 2H), 7.57-7.54 (m, 1H), 7.32 (d, J = 8.1 Hz, 1H), 7.17-7.14 (m, 1H), 4.12 (s, 3H), 2.79 (s, 3H) | 395 (m⁺), 232 (base) |

TABLE 185

| Thioamide compound | Aldehyde compound | Ring-forming component | Example | ¹H-NMR | Mass, m/z |
|---|---|---|---|---|---|
| 2-Methoxy-thiobenzamide | 4-Dimethyl-amino-benz-aldehyde | — | Example 23-88 | (DMSO-d₆) δ: 11.51 (br s, 1H), 8.38 (d, J = 6.9 Hz, 1H), 7.99 (s, 1H), 7.66 (d, J = 7.7 Hz, 2H), 7.55-7.51 (m, 1H), 7.31 (d, J = 8.1 Hz, 1H), 7.16-7.13 (m, 1H), 6.81 (d, J = 8.5 Hz, 2H), 4.13 (s, 3H), 3.00 (s, 6H), 2.79 and 2.68 (two s, 3H) | 394 (m⁺), 232 (base) |
| 2-Methoxy-thiobenzamide | 4-(4-Morpho-linyl)benz-aldehyde | — | Example 23-89 | (DMSO-d₆) δ: 11.59 (br s, 1H), 8.38 (d, J = 7.3 Hz, 1H), 8.02 (s, 1H), 7.71 (d, J = 8.1 Hz, 2H), 7.56-7.51 (m, 1H), 7.30 (d, J = 8.1 Hz, 1H), 7.17-7.13 (m, 1H), 7.05 (d, J = 8.1 Hz, 2H), 4.12 (s, 3H), 3.76 (t, J = 5.0 Hz, 4H), 3.24 (t, J = 5.0 Hz, 4H), 2.79 and 2.68 (two s, 3H) | 436 (m⁺), 232 (base) |

TABLE 185-continued

| Thioamide compound | Aldehyde compound | Ring-forming component | Example | ¹H-NMR | Mass, m/z |
|---|---|---|---|---|---|
| 2-Methoxy-thiobenzamide | 1H-Indole-5-carbaldehyde | — | Example 23-90 | (DMSO-d₆) δ: 11.60 (br s, 1H), 11.34 (br s, 1H), 8.42-8.35 (m, 1H), 8.21 (s, 1H), 7.92 (s, 1H), 7.80-7.70 (m, 1H), 7.60-7.50 (m, 2H), 7.43 (s, 1H), 7.33 (d, J = 8.5 Hz, 1H), 7.16 (t, J = 7.3 Hz, 1H), 6.54 (s, 1H), 4.16 (s, 3H), 2.80 (s, 3H) | 390 (m⁺), 232 (base) |
| 2-Methoxy-thiobenzamide | 1H-Indole-6-carbaldehyde | — | Example 23-91 | (DMSO-d₆) δ: 11.63 (br s, 1H), 11.33 (br s, 1H), 8.39 (d, J = 7.3 Hz, 1H), 8.21 (s, 1H), 7.71-7.68 (m, 3H), 7.56-7.52 (m, 1H), 7.48-7.47 (m, 1H), 7.32 (d, J = 8.5 Hz, 1H), 7.17-7.13 (m, 1H), 6.51 (s, 1H), 4.12 (s, 3H), 2.80 (s, 3H) | 390 (m⁺), 232 (base) |

TABLE 186

| Thioamide compound | Aldehyde compound | Ring-forming component | Example | ¹H-NMR | Mass, m/z |
|---|---|---|---|---|---|
| 2-Methoxy-thiobenzamide | 1-Methyl-1H-indole-5-carbaldehyde | — | Example 23-92 | (DMSO-d₆) δ: 11.61 (br s, 1H), 8.40 (d, J = 8.1 Hz, 1H), 8.21 (s, 1H), 7.92 (s, 1H), 7.80 (d, J = 8.5 Hz, 1H), 7.59 (d, J = 8.9 Hz, 1H), 7.55 (t, J = 6.9 Hz, 1H), 7.41 (d, J = 3.1 Hz, 1H), 7.33 (d, J = 8.5 Hz, 1H), 7.16 (t, J = 7.3 Hz, 1H), 6.53 (d, J = 3.1 Hz, 1H), 4.16 (s, 3H), 3.85 (s, 3H), 2.80 and 2.68 (two s, 3H) | 404 (m⁺), 232 (base) |
| 2-Methoxy-thiobenzamide | 1-Methyl-1H-indole-6-carbaldehyde | — | Example 23-93 | (DMSO-d₆) δ: 11.73 (br s, 1H), 8.39 (d, J = 7.7 Hz, 1H), 8.24 (s, 1H), 7.84 (d, J = 6.6 Hz, 1H), 7.71 (br s, 2H), 7.56-7.52 (m, 1H), 7.46 (d, J = 3.1 Hz, 1H), 7.32 (d, J = 8.5 Hz, 1H), 7.17-7.14 (m, 1H), 6.51 (d, J = 2.7 Hz, 1H), 4.13 (s, 3H), 3.85 (s, 3H), 2.80 (s, 3H) | 404 (m⁺), 232 (base) |

TABLE 186-continued

| Thioamide compound | Aldehyde compound | Ring-forming component | Example | ¹H-NMR | Mass, m/z |
|---|---|---|---|---|---|
| 4-Chloro-2-methoxy-thiobenzamide | 1H-Indole-4-carbaldehyde | — | Example 23-94 | (DMSO-d$_6$) δ: 11.68 (br s, 1H), 9.49 (s, 1H), 8.28 (s, 1H), 8.26 (s, 1H), 7.53 (d, J = 8.1 Hz, 1H), 7.50-7.49 (m, 1H), 7.41-7.38 (m, 2H), 7.23-7.17 (m, 3H), 4.07 (s, 3H), 3.85 (s, 3H), 2.60 (s, 3H) | 424 (m$^+$), 266 (base) |
| 4-Chloro-2-methoxy-thiobenzamide | 1-Methyl-1H-indole-4-carbaldehyde | — | Example 23-95 | (DMSO-d$_6$) δ: 11.70 (br s, 1H), 8.37 (d, J = 7.7 Hz, 1H), 7.59-7.57 (m, 2H), 7.48 (d, J = 3.1 Hz, 1H), 7.41-7.37 (m, 1H), 7.29 (br s, 1H), 7.22 (dd, J = 1.9, 8.5 Hz, 1H), 7.18 (dd, J = 1.9, 8.5 Hz, 1H), 6.86 (br s, 1H), 4.06 (s, 3H), 3.85 (s, 3H), 2.76 (s, 3H) | 438 (m$^+$), 266 (base) |

TABLE 187

| Thioamide compound | Aldehyde compound | Ring-forming component | Example | ¹H-NMR | Mass, m/z |
|---|---|---|---|---|---|
| 4-Chloro-2-methoxy thiobenzamide | 1-Methyl-1H-indole-7-carbaldehyde | — | Example 23-96 | (DMSO-d$_6$) δ: 8.43-8.35 (m, 1H), 8.00-7.92 (m, 1H), 7.73-7.67 (m, 1H), 7.41 (s, 1H), 7.35 (d, J = 3.1 Hz, 1H), 7.23-7.17 (m, 3H), 6.51 (d, J = 3.1 Hz, 1H), 4.11 (s, 3H), 4.04 (s, 3H), 2.80 (s, 3H) | 438 (m$^+$), 266 (base) |
| 2-Methoxy thiobenzamide | Quinoline-6-carbaldehyde | — | Example 23-97 | (DMSO-d$_6$) δ: 11.94 (brs, 1H), 8.95 (dd, J = 1.5, 4.2 Hz, 1H), 8.46-8.43 (m, 2H), 8.40 (d, J = 7.7 Hz, 1H), 8.35 (s, 1H), 8.23 (d, J = 1.5 Hz, 1H), 8.15 (d, J = 8.1 Hz, 1H), 7.61 (dd, J = 4.2, 8.1 Hz, 1H), 7.57-7.53 (m, 1H), 7.34 (d, J = 8.5 Hz, 1H), 7.18-7.14 (m, 1H), 4.15 (s, 3H), 2.80 (s, 3H) | 402 (m$^+$), 232 (base) |

TABLE 187-continued

| Thioamide compound | Aldehyde compound | Ring-forming component | Example | ¹H-NMR | Mass, m/z |
|---|---|---|---|---|---|
| 2-Methoxy thiobenzamide | 4-Methyl-3,4-dihydro-2H-1,4-benzoxazine-7-carbaldehyde | — | Example 23-98 | (DMSO-$d_6$) δ: 11.51 (brs, 1H), 8.38 (d, J = 7.3 Hz, 1H), 7.94 (s, 1H), 7.52 (dt, J = 1.5, 8.5 Hz, 1H), 7.31-7.29 (m, 2H), 7.16-7.12 (m, 1H), 6.74 (d, J = 8.5 Hz, 1H), 4.26-4.24 (m, 2H), 4.13 (s, 3H), 3.35 (t, J = 4.2 Hz, 2H), 2.93 (s, 3H), 2.78 (s, 3H) | 422 (m⁺), 232, 174 (base) |
| 2-Methoxy thiobenzamide | Coumarin-6-carbaldehyde | — | Example 23-99 | (DMSO-$d_6$) δ: 11.87 (brs, 1H), 8.37 (d, J = 7.3 Hz, 1H), 8.32 (d, J = 1.9 Hz, 1H), 8.21 (d, J = 9.6 Hz, 1H), 8.12 (dd, J = 1.5, 8.5 Hz, 1H), 8.02 (s, 1H), 7.60 (d, J = 8.9 Hz, 1H), 7.56-7.52 (m, 1H), 7.31 (d, J = 8.1 Hz, 1H), 7.17-7.13 (m, 1H), 6.57 (d, J = 9.6 Hz, 1H), 4.07 (s, 3H), 2.78 (s, 3H) | 419 (m⁺), 232 (base) |

TABLE 108

| Thioamide compound | Aldehyde compound | Ring-forming component | Example | ¹H-NMR | Mass, m/z |
|---|---|---|---|---|---|
| 4-Chloro thiobenzamide | — | Ethyl 2-chloro-3-oxo-pentanoate | Example 23-100 | (DMSO-$d_6$) δ: 11.69 (s, 1H), 9.36 (s, 1H), 8.30-7.90 (m, 3H), 7.62 (dt, J = 1.6 Hz, J = 2.3 Hz, J = 8.5 Hz, 2H), 7.27 (d, J = 1.9 Hz, 1H), 7.10 (d, J = 8.5 Hz, 1H), 7.01 (d, J = 8.1 Hz, 1H), 3.82 (s, 3H), 3.28-3.16 (m, 2H), 1.29 (t, J = 7.3 Hz, 3H) | 415 (M⁺), 250 (base) |
| 4-Chloro thiobenzamide | — | Methyl 2-chloro-3-cyclopropyl-3-oxo-propionate | Example 23-101 | (DMSO-$d_6$) δ: 11.70 (s, 1H), 9.35 (s, 1H), 8.31-7.82 (m, 3H), 7.60 (dt, J = 1.9 Hz, J = 2.3 Hz, J = 8.9 Hz, 2H), 7.27 (d, J = 2.0 Hz, 1H), 7.10 (d, J = 7.7 Hz, 1H), 7.01 (d, J = 8.1 Hz, 1H), 3.82 (s, 3H), 3.30-3.20 (m, 1H), 1.20-0.98 (m, 4H) | 427 (M⁺), 97 (base) |

TABLE 108-continued

| Thioamide compound | Aldehyde compound | Ring-forming component | Example | ¹H-NMR | Mass, m/z |
|---|---|---|---|---|---|
| 4-Chloro thiobenzamide | — | Ethyl 2-chloro-3-oxo-hexanoate | Example 23-102 | (DMSO-d₆) δ: 11.66 (s, 1H), 9.36 (s, 1H), 8.30-7.90 (m, 3H), 7.61 (dt, J = 1.9 Hz, J = 8.5 Hz, 2H), 7.26 (d, J = 1.9 Hz, 1H), 7.09 (d, J = 8.1 Hz, 1H), 7.01 (d, J = 8.5 Hz, 1H), 3.82 (s, 3H), 3.27-2.96 (m, 2H), 1.76 (sextet, J = 7.3 Hz, J = 7.7 Hz, 2H), 0.95 (t, J = 7.3 Hz, 3H) | 429 (M⁺), 65 (base) |

TABLE 189

| Thioamide compound | Aldehyde compound | Ring-forming component | Example | ¹H-NMR | Mass, m/z |
|---|---|---|---|---|---|
| 4-Methoxy thiobenzamide | — | — | Example 23-103 | (DMSO-d₆) δ: 11.60 (s, 1H), 9.36 (br, 1H), 8.32-7.78 (m, 3H), 7.28 (s, 1H), 7.10 (d, J = 8.9 Hz, 2H + 1H), 7.01 (d, J = 8.1 Hz, 1H), 3.85 (s, 3H), 3.82 (s, 3H), 2.74 (s, 3H) | 397 (M⁺), 232 (base) |
| 4-Methoxy thiobenzamide | 4-Hydroxy-3,5-dimethyl benzaldehyde | — | Example 23-104 | (DMSO-d₆) δ: 11.59 (s, 1H), 8.77 (s, 1H), 7.95 (d, J = 7.7 Hz, 3H), 7.37 (br, 2H), 7.10 (d, J = 8.5 Hz, 2H), 3.85 (s, 3H), 2.75 (s, 3H), 2.23 (s, 6H) | 395 (M⁺), 232 (base) |

TABLE 189-continued

| Thioamide compound | Aldehyde compound | Ring-forming component | Example | ¹H-NMR | Mass, m/z |
|---|---|---|---|---|---|
| 4-Chlorothiobenzamide | 4-Hexyloxy-3-hydroxybenzaldehyde | — | Example 23-105 | (DMSO-d$_6$) δ: 11.69 (s, 1H), 9.25 (s, 1H), 8.05 (d, J = 8.1 Hz, 2H), 7.98 (s, 1H), 7.61 (dt, J = 1.9, 2.3, 8.8 Hz, 2H), 7.28 (d, J = 2.0 Hz, 1H), 7.08 (d, J = 8.1 Hz, 1H), 6.99 (d, J = 8.1 Hz, 1H), 4.00 (t, J = 6.6 Hz, 2H), 2.77 (s, 3H), 1.73 (quintet, J = 6.6, 7.0, 7.7 Hz, 2H), 1.44 (quintet, J = 7.0, 7.3, 7.7 Hz, 2H), 1.38-1.25 (m, 4H), 0.92-0.84 (m, 3H) | 471 (M⁺), 71 (base) |

TABLE 190

| Thioamide compound | Aldehyde compound | Ring-forming component | Example | ¹H-NMR | Mass, m/z |
|---|---|---|---|---|---|
| 4-Chlorothiobenzamide | 4-Hydroxy-3,5-dimethylbenzaldehyde | Ethyl 2-chloro-3-oxopentanoate | Example 23-106 | (DMSO-d$_6$) δ: 11.68 (s, 1H), 8.78 (s, 1H), 8.02 (d, J = 8.1 Hz, 2H), 7.97 (s, 1H), 7.62 (d, J = 8.5 Hz, 1H), 7.35 (s, 1H), 3.27-3.17 (m, 2H), 2.22 (s, 6H), 1.28 (t, J = 7.3 Hz, 3H) | 431 (M⁺), 250 (base) |
| 4-Chlorothiobenzamide | 4-Hydroxy-3,5-dimethylbenzaldehyde | Ethyl 2-chloro-3-oxopentanoate | Example 23-107 | (DMSO-d$_6$) δ: 11.65 (s, 1H), 8.77 (s, 1H), 8.01 (d, J = 8.5 Hz, 2H), 7.97 (s, 1H), 7.62 (d, J = 8.5 Hz, 2H), 7.35 (s, 2H), 3.25-3.15 (m, 2H), 2.22 (s, 6H), 1.75 (sextet, J = 7.3 Hz, 2H), 0.95 (t, J = 7.3 Hz, 3H) | 427 (M⁺), 264 (base) |
| 4-Chlorothiobenzamide | 4-Hydroxy-3-methylbenzaldehyde | Ethyl 2-chloro-3-oxopentanoate | Example 23-108 | (DMSO-d$_6$) δ: 11.66 (s, 1H), 9.78 (s, 1H), 8.03 (d, J = 8.1 Hz, 2H), 7.99 (s, 1H), 7.62 (d, J = 8.5 Hz, 2H), 7.50 (s, 1H), 7.42 (d, J = 7.3 Hz, 1H), 6.88 (d, J = 8.1 Hz, 1H), 3.27-3.17 (m, 2H), 2.18 (s, 3H), 1.28 (t, J = 7.3 Hz, 3H) | 399 (M⁺), 250 (base) |

TABLE 191

| Thioamide compound | Aldehyde compound | Ring-forming component | Example | 1H-NMR | Mass, m/z |
|---|---|---|---|---|---|
| 4-Chloro thiobenzamide | 4-Hydroxy-3,5-dimethoxy benzaldehyde | — | Example 23-109 | (DMSO-d6) δ: 11.83 (s, 1H), 8.93 (s, 1H), 7.99 (dt, J = 1.9, 2.0, 2.3, 2.7, 8.5 Hz, 2H + 1), 7.61 (dt, J = 1.9, 2.7, 8.5 Hz, 2H), 7.09 (s, 2H), 3.85 (s, 6H), 2.79 (s, 3H) | 431 (M+), 71 (base) |
| 4-Chloro thiobenzamide | 4-Hydroxy-1-naphthaldehyde | — | Example 23-110 | (DMSO-d6) δ: 11.70 (s, 1H), 10.82 (s, 1H), 8.76 (s, 1H), 8.52 (d, J = 7.7 Hz, 1H), 8.25 (dd, J = 0.8, 8.1 Hz, 1H), 8.02 (d, J = 8.5 Hz, 2H), 7.93-7.52 (m, 3H), 7.61 (dt, J = 1.9, 2.0, 2.7, 8.5 Hz, 2H), 7.03 (d, J = 7.0 Hz, 1H), 2.78 (s, 3H) | 421 (M+), 71 base |
| 4-Chloro thiobenzamide | 4-Hydroxy-3-methoxy benzaldehyde | — | Example 23-111 | (DMSO-d6) δ: 11.74 (s, 1H), 9.59 (s, 1H), 8.01 (d, J = 8.5 Hz, 2H + 1H), 7.61 (dt, J = 1.9, 2.7, 8.5 Hz, 4H), 7.45 (s, 1H), 7.10 (dd, J = 1.9, 8.1 Hz, 1H), 6.86 (d, J = 8.1 Hz, 1H), 3.88 (s, 3H), 2.78 (s, 3H) | 401 (M+), 71 base |

TABLE 192

| Thioamide compound | Aldehyde compound | Ring-forming component | Example | 1H-NMR | Mass, m/z |
|---|---|---|---|---|---|
| 4-Methoxy thiobenzamide | 4-Hydroxy-3,5-dimethoxy benzaldehyde | — | Example 23-122 | (DMSO-d6) δ: 11.74 (s, 1H), 8.91 (s, 1H), 7.99 (s, 1H), 7.92 (dt, J = 2.7, 8.9 Hz, 2H), 7.09 (s, 2H), 7.08 (d, J = 8.5 Hz, 2H), 3.86 (s, 3H), 3.85 (s, 6H), 2.77 (s, 3H) | 427 (M+), 232 (base) |

TABLE 192-continued

| Thioamide compound | Aldehyde compound | Ring-forming component | Example | ¹H-NMR | Mass, m/z |
|---|---|---|---|---|---|
| 4-Methoxy thiobenzamide | 4-Hydroxy-1-naphthaldehyde | — | Example 23-123 | (DMSO-d₆) δ: 11.61 (s, 1H), 10.80 (s, 1H), 8.74 (s, 1H), 8.56 (t, J = 3.5 Hz, 1H), 8.25 (d, J = 8.9 Hz, 1H), 7.95 (d, J = 8.5 Hz, 2H), 7.87-7.75 (m, 1H), 7.62 (s, 1H), 7.55 (t, J = 6.9 Hz, 1H), 7.10 (dt, J = 1.9, 2.7, 3.1, 8.8 Hz, 2H), 7.02 (d, J = 5.8 Hz, 1H), 3.85 (s, 3H), 2.75 (s, 3H) | 417 (M⁺), 232 (base) |
| 4-Methoxy thiobenzamide | — | — | Example 23-124 | (DMSO-d₆) δ: 11.65 (s, 1H), 9.57 (s, 1H), 7.99 (s, 1H), 7.93 (d, J = 8.9 Hz, 2H), 7.47 (s, 1H), 7.09 (dt, J = 2.7, 3.1, 8.9 Hz, 2H + 1H), 6.86 (d, J = 8.1 Hz, 1H), 3.88 (s, 3H), 3.85 (s, 3H), 2.76 (s, 3H) | 397 (M⁺), 232 (base) |

TABLE 193

| Thioamide compound | Aldehyde compound | Ring-forming component | Example | ¹H-NMR | Mass, m/z |
|---|---|---|---|---|---|
| 4-Chloro thiobenzamide | 4-Difluoro methoxy-3-hydroxy benzaldehyde | — | Example 23-115 | (DMSO-d₆) δ: 11.83 (br, 1H), 10.26 (br, 1H), 8.06 (t, J = 7.3 Hz, J = 7.7 Hz, 3H), 7.61 (dt, J = 1.9 Hz, J = 2.7 Hz, J = 8.5 Hz, 2H), 7.42 (d, J = 2.0 Hz, 1H), 7.22 (d, J = 8.1 Hz, 1H), 7.16 (d, J = 8.5 Hz, 1H), 7.12 (t, J = 74.8 Hz, 1H), 2.77 (s, 3H) | 397 (M⁺), 232 (base) |
| 2-Chloro thiobenzamide | 4-Difluoro methoxy-3-hydroxy benzaldehyde | — | Example 23-116 | (DMSO-d₆) δ: 11.89 (br, 1H), 10.07 (br, 1H), 8.37-8.23 (m, 1H), 8.04 (s, 1H), 7.73-7.66 (m, 1H), 7.59-7.51 (m, 2H), 7.36 (s, 1H), 7.24 (d, J = 8.5 Hz, 1H), 7.18 (d, J = 8.1 Hz, 1H), 7.12 (t, J = 74.8 Hz, 1H), 2.80 (s, 3H) | 437 (M⁺), 71 (base) |

TABLE 193-continued

| Thioamide compound | Aldehyde compound | Ring-forming component | Example | ¹H-NMR | Mass, m/z |
|---|---|---|---|---|---|
| 2,3-Dimethyl thiobenzamide | 4-Difluoro methoxy-3-hydroxy benzaldehyde | — | Example 23-117 | (DMSO-d₆) δ: 11.79 (br, 1H), 10.19 (br, 1H), 8.03 (s, 2H), 7.52 (d, J = 7.3 Hz, 1H), 7.35 (d, J = 7.3 Hz, 2H), 7.28-7.11 (m, 3H), 7.10 (t, J = 74.8 Hz, 1H), 2.78 (s, 3H), 2.42 (s, 3H), 2.35 (s, 3H) | 431 (M⁺), 230 (base) |
| 2-Trifluoro methyl thiobenzamide | 4-Difluoro methoxy-3-hydroxy benzaldehyde | — | Example 23-118 | (DMSO-d₆) δ: 11.87 (s, 1H), 10.16 (s, 1H), 8.04 (s, 1H), 7.97 (d, J = 7.7 Hz, 1H), 7.88-7.76 (m, 3H), 7.33 (s, 1H), 7.21-7.11 (m, 2H), 7.10 (t, J = 74.8 Hz, 1H), 2.78 (s, 3H) | 471 (M⁺), 71 (base) |

TABLE 194

| Thioamide compound | Aldehyde compound | Ring-forming component | Example | ¹H-NMR | Mass, m/z |
|---|---|---|---|---|---|
| 3-Methyl pyridine-2-carbothioamide | 4-Hydroxy-3,5-dimethyl benzaldehyde | — | Example 23-119 | (DMSO-d₆) δ: 11.66 (s, 1H), 8.76 (s, 1H), 8.51 (dd, J = 0.8, 4.6 Hz, 1H), 7.95 (s, 1H), 7.83 (d, J = 7.7 Hz, 1H), 7.44 (dd, J = 4.6, 8.1 Hz, 1H), 7.41 (s, 1H), 7.31 (s, 1H), 2.78 (s, 6H), 2.22 (s, 6H) | 380 (M⁺), 217 (base) |
| 2-Methoxy thiobenzamide | 4-Hydroxy-3,5-dimethyl benzaldehyde | — | Example 23-120 | (DMSO-d₆) δ: 11.54 (s, 1H), 8.77 (s, 1H), 8.36 (d, J = 6.6 Hz, 1H), 7.98 (s, 1H), 7.52 (ddd, J = 1.5, 7.3, 8.8 Hz, 1H), 7.37 (s, 2H), 7.30 (d, J = 8.1 Hz, 1H), 7.14 (t, J = 7.3 Hz, 1H), 4.04 (s, 3H), 2.76 (s, 3H), 2.22 (s, 6H) | 395 (M⁺), 232 (base) |

TABLE 194-continued

| Thioamide compound | Aldehyde compound | Ring-forming component | Example | $^1$H-NMR | Mass, m/z |
|---|---|---|---|---|---|
| 2-Methoxy thiobenzamide | 4-Hydroxy-3-methyl benzaldehyde | — | Example 23-121 | (DMSO-d$_6$) δ: 11.56 (s, 1H), 9.85 (s, 1H), 8.37 (d, J = 7.3 Hz, 1H), 8.00 (s, 1H), 7.57 (d, J = 7.3 Hz, 1H), 7.53 (ddd, J = 1.9, 7.3, 8.5 Hz, 1H), 7.47 (d, J = 1.5 Hz, 1H), 7.31 (t, J = 8.5 Hz, 1H), 7.14 (td, J = 0.8, 7.7 Hz, 1H), 6.91 (d, J = 8.1 Hz, 1H), 4.08 (s, 3H), 2.78 (s, 3H), 2.18 (s, 3H) | 381 (M$^+$), 232 (base) |
| 2,4-Dimethyl thiobenzamide | 4-Hydroxy-3,5-dimethyl benzaldehyde | — | Example 23-122 | (DMSO-d$_6$) δ: 11.62 (s, 1H), 8.77 (s, 1H), 7.96 (s, 1H), 7.91 (d, J = 8.1 Hz, 1H), 7.35 (s, 2H), 7.24 (s, 1H), 7.18 (d, J = 8.1 Hz, 1H), 2.78 (s, 3H), 2.65 (s, 3H), 2.35 (s, 3H), 2.20 (s, 6H) | 393 (M$^+$), 230 (base) |

TABLE 195

| Thioamide compound | Aldehyde compound | Ring-forming component | Example | $^1$H-NMR | Mass, m/z |
|---|---|---|---|---|---|
| 4-Chloro-2-methyl thiobenzamide | 4-Hydroxy-3,5-dimethyl benzaldehyde | — | Example 23-123 | (DMSO-d$_6$) δ: 11.67 (s, 1H), 8.78 (s, 1H), 8.04 (d, J = 8.5 Hz, 1H), 7.96 (s, 1H), 7.55 (s, 1H), 7.44 (dd, J = 2.0 Hz, J = 8.5 Hz, 1H), 7.34 (s, 2H), 2.79 (s, 3H), 2.69 (s, 3H), 2.20 (s, 6H) | 413 (M$^+$), 71 (base) |
| 2-Methyl thiobenzamide | 4-Hydroxy-3,5-dimethyl benzaldehyde | Ethyl 2-chloro-3-oxopropionate | Example 23-124 | (DMSO-d$_6$) δ: 11.86 (s, 1H), 8.81 (s, 1H), 8.70 (s, 1H), 8.02 (s, 1H), 8.01 (s, 1H), 7.48-7.32 (m, 5H), 2.68 (s, 3H), 2.22 (s, 6H) | 365 (M$^+$), 174 (base) |

TABLE 195-continued

| Thioamide compound | Aldehyde compound | Ring-forming component | Example | ¹H-NMR | Mass, m/z |
|---|---|---|---|---|---|
| 3-Chloro-2-methyl thiobenzamide | — | — | Example 23-125 | (DMSO-d₆) δ: 11.72 (s, 1H), 9.27 (s, 1H), 8.00 (s, 1H), 7.71 (d, J = 7.7 Hz, 1H), 7.64 (d, J = 7.7 Hz, 1H), 7.39 (t, J = 7.3, 8.1 Hz, 1H), 7.23 (s, 1H), 7.08 (dd, J = 1.9, 8.5 Hz, 1H), 6.99 (d, J = 8.5 Hz, 1H), 3.81 (s, 3H), 2.79 (s, 3H), 2.58 (s, 3H) | 415 (M⁺), 71 (base) |
| 2,5-Dimethyl thiobenzamide | — | — | Example 23-126 | (DMSO-d₆) δ: 11.68 (s, 1H), 9.23 (s, 1H), 7.98 (s, 1H), 7.73 (s, 1H), 7.33-7.26 (m, 2H), 7.24 (dd, J = 1.6, 7.7 Hz, 1H), 7.09 (dd, J = 1.2, 8.1 Hz, 1H), 6.99 (d, J = 8.5 Hz, 1H), 3.81 (s, 3H), 2.78 (s, 3H), 2.57 (s, 3H), 2.36 (s, 3H) | 395 (M⁺), 230 (base) |

TABLE 196

| Thioamide compound | Aldehyde compound | Ring-forming component | Example | ¹H-NMR | Mass, m/z |
|---|---|---|---|---|---|
| 2,5-Dimethyl thiobenzamide | 4-Hydroxy-3,5-dimethyl benzaldehyde | — | Example 23-127 | (DMSO d₆) δ: 11.65 (s, 1H), 8.77 (s, 1H), 7.96 (s, 1H), 7.82 (s, 1H), 7.36 (s, 2H), 7.31 (d, J = 7.7 Hz, 1H), 7.24 (dd, J = 1.6, 8.1 Hz, 1H), 2.80 (s, 3H), 2.63 (s, 3H), 2.36 (s, 3H), 2.21 (s, 6H) | 393 (M⁺), 230 (base) |
| Cyclohexane carbothiamide | — | — | Example 23-128 | (DMSO-d₆) δ: 11.51 (s, 1H), 9.26 (s, 1H), 7.94 (s, 1H), 7.22 (s, 1H), 7.07 (d, J = 8.1 Hz, 1H), 6.99 (d, J = 8.1 Hz, 1H), 3.82 (s, 3H), 3.05-2.93 (m, 1H), 2.66 (s, 3H), 2.08 (s, 1H), 2.06 (s, 1H), 1.80 (dd, J = 2.7, 9.6 Hz, 1H), 1.70 (d, J = 12.7 Hz, 1H), 1.64-1.34 (m, 4H), 1.28 (d, J = 12.0, 12.3 Hz, 1H) | 373 (M⁺), 208 (base) |

TABLE 196-continued

| Thioamide compound | Aldehyde compound | Ring-forming component | Example | 1H-NMR | Mass, m/z |
|---|---|---|---|---|---|
| Cyclohexane carbothiamide | 4-Hydroxy-3,5-dimethyl benzaldehyde | — | Example 23-129 | (DMSO-$d_6$) δ: 11.51 (s, 1H), 8.74 (s, 1H), 7.91 (s, 1H), 7.32 (s, 2H), 3.05-2.92 (m, 1H), 2.66 (s, 3H), 2.20 (s, 6H), 2.11 (d, J = 8.9 Hz, 2H), 1.79 (dt, J = 2.7, 3.1, 3.5, 12.7 Hz, 2H), 1.69 (d, J = 12.4 Hz, 1H), 1.61-1.19 (m, 5H) | 371 ($M^+$), 156 (base) |
| 3-Methoxy-2-methyl thiobenzamide | — | — | Example 23-130 | (DMSO-$d_6$) δ: 11.67 (s, 1H), 9.24 (s, 1H), 7.98 (s, 1H), 7.39-7.28 (m, 2H), 7.23 (s, 1H), 7.15 (d, J = 9.3 Hz, 1H), 7.08 (dd, J = 1.5, 8.5 Hz, 1H), 6.99 (d, J = 8.1 Hz, 1H), 3.87 (s, 3H), 3.81 (s, 3H), 2.78 (s, 3H), 2.40 (s, 3H) | 411 ($M^+$), 246 (base) |

TABLE 197

| Thioamide compound | Aldehyde compound | Ring-forming component | Example | 1H-NMR | Mass, m/z |
|---|---|---|---|---|---|
| 3-Methoxy-2-methyl thiobenzamide | 4-Hydroxy-3,5-dimethyl benzaldehyde | — | Example 23-131 | (DMSO-$d_6$) δ: 11.65 (s, 1H), 8.77 (s, 1H), 7.96 (s, 1H), 7.43 (d, J = 7.3 Hz, 1H), 7.37-7.29 (m, 3H), 7.15 (d, J = 8.9 Hz, 1H), 3.87 (s, 3H), 2.79 (s, 3H), 2.46 (s, 3H), 2.19 (s, 6H) | 409 ($M^+$), 71 (base) |
| Thioacetamide | — | — | Example 23-132 | (DMSO-$d_6$) δ: 11.53 (br s, 1H), 9.33 (s, 1H), 7.93 (br s, 1H), 7.26 (s, 1H), 7.06 (d, J = 8.8 Hz, 1H), 6.98 (d, J = 8.5 Hz, 1H), 3.81 (s, 3H), 2.67 (s, 3H), 2.66 (s, 3H) | 305 ($M^+$), 140 (base) |
| Thioacetamide | 4-Hydroxy-3,5-dimethyl benzaldehyde | — | Example 23-133 | (DMSO-$d_6$) δ: 11.49 (br s, 1H), 8.75 (s, 1H), 7.92 (br s, 1H), 7.30 (s, 2H), 2.66 (s, 6H), 2.21 (s, 6H) | 303 ($M^+$), 140 (base) |

TABLE 197-continued

| Thioamide compound | Aldehyde compound | Ring-forming component | Example | ¹H-NMR | Mass, m/z |
|---|---|---|---|---|---|
| 2,4-Dimethyl thiazole-5-carbothioamide | — | — | Example 23-134 | (DMSO-d₆) δ: 11.73 (s, 1H), 9.18 (s, 1H), 7.98 (s, 1H), 7.31 (s, 1H), 7.12 (d, J = 8.1 Hz, 1H), 7.00 (d, J = 8.5 Hz, 1H), 3.83 (s, 3H), 2.73 (s, 3H), 2.69 (s, 3H), 2.67 (s, 3H) | 402 (M⁺), 71 (base) |

TABLE 198

| Thioamide compound | Aldehyde compound | Ring-forming component | Example | ¹H-NMR | Mass, m/z |
|---|---|---|---|---|---|
| 4-Methyl pyridine-3-carbothioamide | — | — | Example 23-135 | (DMSO-d₆) δ: 11.74 (s, 1H), 9.29 (s, 1H), 9.00 (s, 1H), 8.56 (d, J = 5.0 Hz, 1H), 7.99 (s, 1H), 7.46 (d, J = 5.0 Hz, 1H), 7.28 (d, J = 2.0 Hz, 1H), 7.09 (dd, J = 1.6, 8.5 Hz, 1H), 6.99 (d, J = 8.1 Hz, 1H), 3.81 (s, 3H), 2.81 (s, 3H), 2.64 (s, 3H) | 382 (M⁺), 71 (base) |
| 4-Methyl pyridine-3-carbothioamide | 4-Hydroxy-3,5-dimethyl benzaldehyde | — | Example 23-136 | (DMSO-d₆) δ: 11.71 (s, 1H), 9.09 (s, 1H), 8.78 (s, 1H), 8.55 (d, J = 5.0 Hz, 1H), 7.97 (s, 1H), 7.47 (d, J = 5.0 Hz, 1H), 7.35 (s, 2H), 2.82 (s, 3H), 2.70 (s, 3H), 2.20 (s, 6H) | 380 (M⁺), 71 (base) |
| 4-Methyl thiazole-5-carbothioamide | — | — | Example 23-137 | (DMSO-d₆) δ: 11.76 (s, 1H), 9.19 (s, 1H), 9.15 (s, 1H), 7.98 (s, 1H), 7.32 (s, 1H), 7.13 (d, J = 6.5 Hz, 1H), 7.00 (d, J = 8.1 Hz, 1H), 3.83 (s, 3H), 2.78 (s, 3H), 2.76 (s, 3H) | 388 (M⁺), 223 (base) |

TABLE 198-continued

| Thioamide compound | Aldehyde compound | Ring-forming component | Example | ¹H-NMR | Mass, m/z |
|---|---|---|---|---|---|
| 3-Chloro pyridine-2-carbothioamide | 4-Methoxy benzaldehyde | — | Example 23-138 | (DMSO-d$_6$) δ: 11.81 (s, 1H), 8.69 (s, 1H), 8.14 (dd, J = 1.2, 8.1 Hz, 1H), 8.09 (s, 1H), 7.69 (d, J = 8.8 Hz, 2H), 7.58 (dd, J = 4.6, 8.1 Hz, 1H), 7.04 (d, J = 8.9 Hz, 2H), 3.82 (s, 3H), 2.78 (s, 3H) | 386 (M⁺), 71 (base) |

TABLE 199

| Thioamide compound | Aldehyde compound | Ring-forming component | Example | ¹H-NMR | Mass, m/z |
|---|---|---|---|---|---|
| 3-Chloro pyridine-2-carbothioamide | — | — | Example 23-139 | (DMSO-d$_6$) δ: 11.75 (s, 1H), 9.20 (s, 1H), 8.67 (d, J = 3.8 Hz, 1H), 8.15 (dd, J = 1.6, 8.1 Hz, 1H), 8.00 (s, 1H), 7.58 (dd, J = 4.6, 8.1 Hz, 1H), 7.19 (s, 1H), 7.11 (d, J = 8.1 Hz, 1H), 7.00 (d, J = 8.1 Hz, 1H), 3.82 (s, 3H), 2.77 (s, 3H) | 402 (M⁺), 71 (base) |
| 4-Chloro thiobenzamide | 5-Formyl-2-methoxyphenyl boronic acid | — | Example 23-140 | (DMSO-d$_6$) δ: 11.76 (s, 1H), 8.30 (s, 1H), 8.13-8.04 (m, 2H), 8.02 (d, J = 8.5 Hz, 1H), 7.91 (s, 2H), 7.76-7.64 (m, 2H), 7.60 (dt, J = 1.9, 2.0, 2.7, 8.5 Hz, 1H), 7.09 (d, J = 8.9 Hz, 1H), 3.88 (s, 3H), 2.79 (s, 3H) | 61 (base) |
| 2-Methyl thiobenzamide | 4-Methoxy benzaldehyde | Ethyl 2-chloro-3-oxopropionate | Example 23-141 | (DMSO-d$_6$) δ: 11.95 (s, 1H), 8.71 (s, 1H), 8.12 (s, 1H), 7.89 (d, J = 7.7 Hz, 1H), 7.74 (d, J = 8.8 Hz, 1H), 7.74-7.68 (m, 1H), 7.49-7.34 (m, 3H), 7.06 (d, J = 8.5 Hz, 2H), 3.82 (s, 3H), 2.61 (s, 3H) | 351 (M⁺), 174 (base) |
| 2-Chloro thiobenzamide | — | Ethyl 2-chloro-3-oxopropionate | Example 23-142 | (DMSO-d$_6$) δ: 11.96 (s, 1H), 9.19 (s, 1H), 8.75 (s, 1H), 8.38-8.32 (m, 1H), 8.03 (s, 1H), 7.74-7.69 (m, 1H), 7.61-7.53 (m, 2H), 7.35 (d, J = 1.9 Hz, 1H), 7.16 (dd, J = 1.9, 8.5 Hz, 1H), 7.01 (d, J = 8.1 Hz, 1H), 3.84 (s, 3H) | 387 (M⁺), 57 (base) |

TABLE 200

| Thioamide compound | Aldehyde compound | Ring-forming component | Example | ¹H-NMR | Mass, m/z |
|---|---|---|---|---|---|
| 2-Chloro thiobenzamide | 4-Hydroxy-3,5-dimethyl benzaldehyde | Ethyl 2-chloro-3-oxopropionate | Example 23-143 | (DMSO-$d_6$) δ: 11.91 (s, 1H), 8.83 (s, 1H), 8.73 (s, 1H), 8.46-8.40 (m, 1H), 8.01 (s, 1H), 7.77-7.70 (m, 1H), 7.60-7.53 (m, 2H), 7.41 (s, 2H), 2.23 (s, 6H) | 385 (M$^+$), 238 (base) |
| 2,5-Dimethyl-2H-pyrazole-3-carbothioamide | — | — | Example 23-144 | (DMSO-$d_6$) δ: 11.58 (s, 1H), 9.23 (s, 1H), 7.97 (s, 1H), 7.18 (s, 1H), 7.10 (s, 1H), 7.01 (d, J = 6.9 Hz, 1H), 6.61 (s, 1H), 3.83 (s, 3H), 3.82 (s, 3H), 2.70 (s, 3H), 2.32 (s, 3H) | 385 (M$^+$), 220 (base) |
| 2-Methoxy thiobenzamide | 4-Methoxy benzaldehyde | — | Example 23-145 | (DMSO-$d_6$) δ: 11.66 (s, 1H), 8.69 (s, 1H), 8.38 (d, J = 7.3 Hz, 1H), 8.08 (s, 1H), 7.79 (d, J = 7.7 Hz, 2H), 7.53 (ddd, J = 2.0 Hz, J = 7.4 Hz, J = 8.8 Hz, 1H), 7.30 (d, J = 7.7 Hz, 1H), 7.14 (td, J = 1.2 Hz, J = 8.1 Hz, 1H), 7.08 (d, J = 8.1 Hz, 1H), 4.10 (s, 3H), 3.83 (s, 3H), 2.78 (s, 3H) | 381 (M$^+$), 232 (base) |
| 2,5-Dimethyl-2H-pyrazole-3-carbothioamide | 4-Hydroxy-3,5-dimethyl benzaldehyde | — | Example 23-146 | (DMSO-$d_6$) δ: 11.58 (s, 1H), 8.76 (s, 1H), 7.93 (s, 1H), 7.38 (s, 2H), 6.60 (d, J = 0.8 Hz, 1H), 3.81 (s, 3H), 2.72 (s, 3H), 2.32 (s, 3H), 2.23 (s, 6H) | 383 (M$^+$), 220 (base) |

TABLE 201

| Thioamide compound | Aldehyde compound | Ring-forming component | Example | | $^1$H-NMR | Mass, m/z |
|---|---|---|---|---|---|---|
| 2-Chloro thiobenzamide | 4-Methoxy benzaldehyde | Ethyl 2-chloro-3-oxopropionate | Example 23-147 | | (DMSO-$d_6$) δ: 12.02 (s, 1H), 8.75 (s, 1H), 8.38-8.32 (m, 1H), 8.12 (s, 1H), 7.78 (d, J = 8.5 Hz, 2H), 7.75-7.65 (m, 1H), 7.61-7.53 (m, 2H), 7.05 (dt, J = 1.9, 2.7, 8.9 Hz, 2H), 3.83 (s, 3H) | 371 (M$^+$), 238 (base) |
| 2-Chloro thiobenzamide | 4-(1,3,2-Dioxaborinan-2-yl) benzaldehyde | — | Example 23-148 | | (DMSO-$d_6$) δ: 11.90 (s, 1H), 8.13 (s, 1H), 8.04 (d, J = 8.1 Hz, 2H), 7.79 (d, J = 7.3 Hz, 2H), 7.73 (d, J = 7.7 Hz, 2H), 7.62 (d, J = 8.5 Hz, 2H), 4.13 (t, J = 5.4 Hz, 4H), 2.77 (s, 3H), 2.03 (quintet, J = 5.4 Hz, 2H) | 439 (M$^+$), 236 (base) |
| 2-Propyloxy thiobenzamide | 4-Methoxy benzaldehyde | — | Example 23-149 | | (DMSO-$d_6$) δ: 11.64 (s, 1H), 8.36 (d, J = 7.7 Hz, 1H), 8.09 (br, 1H), 7.70 (d, J = 8.9 Hz, 2H), 7.49 (ddd, J = 1.9, 7.3, 8.5 Hz, 1H), 7.27 (d, J = 8.1 Hz, 1H), 7.14-7.08 (m, 1H), 7.03 (dt, J = 2.0, 2.7, 3.1, 8.5 Hz, 2H), 4.26 (t, J = 6.6 Hz, 2H), 3.82 (s, 3H), 2.75 (s, 3H), 1.79 (br, 2H), 0.87 (br, 3H) | 409 (M$^+$), 260 (base) |
| 3-Methyl pyridine-2-carbothioamide | 4-Methoxy benzaldehyde | — | Example 23-150 | | (DMSO-$d_6$) δ: 11.74 (s, 1H), 8.54 (s, 1H), 8.08 (s, 1H), 7.83 (d, J = 7.7 Hz, 1H), 7.69 (d, J = 8.9 Hz, 2H), 7.44 (dd, J = 4.6, 7.7 Hz, 1H), 7.04 (d, J = 8.9 Hz, 2H), 3.82 (s, 3H), 2.77 (s, 3H) | 366 (M$^+$), 217 (base) |

TABLE 202

| Thioamide compound | Aldehyde compound | Ring-forming component | Example | | ¹H-NMR | Mass, m/z |
|---|---|---|---|---|---|---|
| 2-Chloro thiobenzamide | 3-Formyl-phenylboronic acid | — | Example 23-151 | 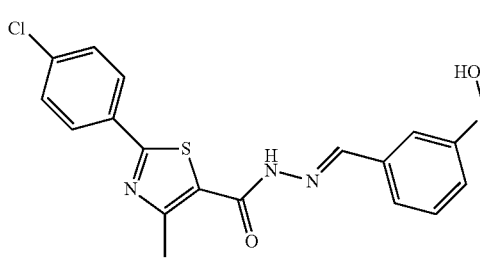 | (DMSO-d₆) δ: 11.87 (s, 1H), 8.41 (s, 1H), 8.25 (s, 1H), 8.25-7.98 (m, 4H), 7.90 (d, J = 7.3 Hz, 1H), 7.78-7.57 (m, 3H), 7.47 (t, J = 7.3 Hz, 1H), 2.80 (s, 2H) | 59 (base) |
| 2-Chloro thiobenzamide | 2,3-Dihydro benzofuran-5-carbaldehyde | — | Example 23-152 | 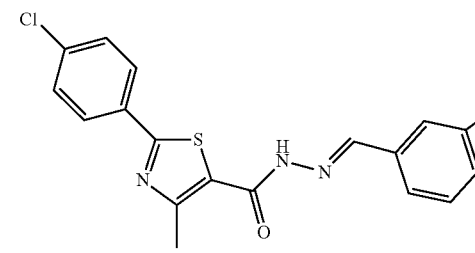 | (DMSO-d₆) δ: 11.71 (s, 1H), 8.05 (s, 1H), 8.03 (d, J = 8.1 Hz, 2H), 7.67 (s, 1H), 7.61 (d, J = 8.5 Hz, 2H), 7.50 (d, J = 7.3 Hz, 1H), 6.88 (d, J = 7.7 Hz, 1H), 4.61 (t, J = 8.9 Hz, 2H), 3.26 (t, J = 8.5 Hz, 2H), 2.77 (s, 3H) | 397 (M⁺), 71 (base) |
| 2-Methoxy thiobenzamide | 2,3-Dihydro benzofuran-5-carbaldehyde | — | Example 23-153 | 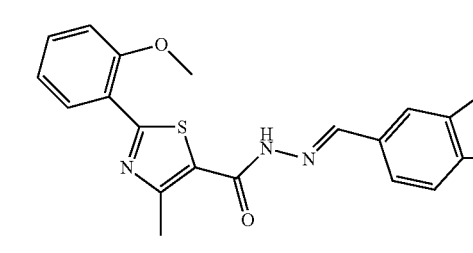 | (DMSO-d₆) δ: 11.59 (s, 1H), 8.37 (d, J = 7.3 Hz, 1H), 8.06 (s, 1H), 7.70 (s, 1H), 7.57 (d, J = 6.9 Hz, 1H), 7.53 (td, J = 1.6, 8.9 Hz, 1H), 7.30 (d, J = 8.5 Hz, 1H), 7.14 (t, J = 7.3 Hz, 1H), 6.90 (t, J = 8.1 Hz, 1H), 4.61 (t, J = 8.8, 8.9 Hz, 2H), 4.09 (s, 3H), 3.26 (t, J = 8.5, 8.9 Hz, 2H), 2.78 (s, 3H) | 393 (M⁺), 232 (base) |

TABLE 203

| Thioamide compound | Aldehyde compound | Ring-forming component | Example | | ¹H-NMR | Mass, m/z |
|---|---|---|---|---|---|---|
| 2,3-Dihydro benzo[1,4] dioxin-5-carbothioamide | — | — | Example 23-154 | 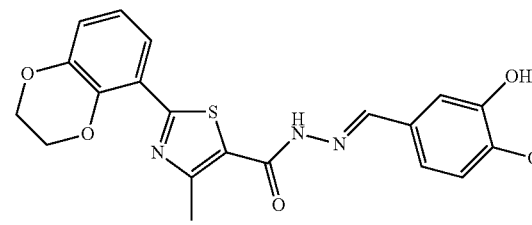 | (DMSO-d₆) δ: 11.63 (s, 1H), 9.15 (br, 1H), 7.98 (s, 1H), 7.89 (d, J = 7.0 Hz, 1H), 7.36 (d, J = 7.0 Hz, 1H), 7.14 (d, J = 7.7 Hz, 1H), 7.05-7.00 (m, 1H), 7.03 (dd, J = 1.9, 7.7 Hz, 1H), 6.99 (d, J = 7.7, 7.7 Hz, 1H), 4.60 (br, 2H), 4.44-4.34 (m, 2H), 3.84 (s, 3H), 2.78 (s, 3H) | 425 (M⁺), 260 (base) |

TABLE 203-continued

| Thioamide compound | Aldehyde compound | Ring-forming component | Example | ¹H-NMR | Mass, m/z |
|---|---|---|---|---|---|
| 2,3-Dihydro benzo[1,4]dioxin-5-carbothioamide | 4-Methoxy benzaldehyde | — | Example 23-155 | (DMSO-d₆) δ: 11.68 (s, 1H), 8.07 (s, 1H), 7.90 (d, J = 6.9 Hz, 1H), 7.77 (d, J = 7.7 Hz, 2H), 7.09 (d, J = 8.1 Hz, 1H), 7.08-7.02 (m, 1H), 7.03 (dd, J = 1.9, 8.1 Hz, 1H), 6.99 (t, J = 7.7 Hz, 1H), 4.58 (s, 2H), 4.42 (s, 2H), 3.83 (s, 3H), 2.78 (s, 3H) | 409 (M⁺), 260 (base) |
| 2-Chloro thiobenzamide | 4-Methoxy benzaldehyde | Ethyl 2-chloro-3-oxopropionate | Example 23-156 | (DMSO-d₆) δ: 11.96 (s, 1H), 8.68 (s, 1H), 8.12 (s, 1H), 8.09 (d, J = 8.5 Hz, 2H), 7.77 (d, J = 8.5 Hz, 2H), 7.63 (d, J = 8.5 Hz, 2H), 7.10 (d, J = 8.9 Hz, 2H), 3.84 (s, 3H) | 371 (M⁺), 238 (base) |

TABLE 204

| Thioamide compound | Aldehyde compound | Ring-forming component | Example | ¹H-NMR | Mass, m/z |
|---|---|---|---|---|---|
| 2-Methoxy thiobenzamide | 4-Methoxy benzaldehyde | Ethyl 2-chloro-3-oxopropionate | Example 23-157 | (DMSO-d₆) δ: 11.81 (s, 1H), 8.69 (s, 1H), 8.14 (dd, J = 1.2, 8.1 Hz, 1H), 8.09 (s, 1H), 7.69 (d, J = 8.8 Hz, 2H), 7.58 (dd, J = 4.6, 8.1 Hz, 1H), 7.04 (d, J = 8.9 Hz, 2H), 3.82 (s, 3H), 2.78 (s, 3H) | 367 (M⁺), 218 (base) |
| 4-Chloro-2-methoxy thiobenzamide | 4-Methoxy benzaldehyde | Ethyl 2-chloro-3-oxopropionate | Example 23-158 | (DMSO-d₆) δ: 11.90 (s, 1H), 8.68 (s, 1H), 8.38 (d, J = 8.1 Hz, 1H), 8.11 (s, 1H), 7.81 (d, J = 8.1 Hz, 2H), 7.44 (s, 1H), 7.23 (dd, J = 1.2, 8.5 Hz, 1H), 7.10 (d, J = 8.5 Hz, 2H), 4.16 (s, 3H), 3.84 (br, 3H) | 401 (M⁺), 252 (base) |

TABLE 204-continued

| Thioamide compound | Aldehyde compound | Ring-forming component | Example | ¹H-NMR | Mass, m/z |
|---|---|---|---|---|---|
| 2-Methoxy thiobenzamide | Benzofuran-5-carbaldehyde | — | Example 23-159 | (DMSO-$d_6$) δ: 11.75 (s, 1H), 8.39 (d, J = 7.3 Hz, 1H), 8.24 (br, 1H), 8.09 (d, J = 1.9 Hz, 1H), 8.04 (s, 1H), 7.92 (d, J = 6.9 Hz, 1H), 7.77 (d, J = 8.5 Hz, 1H), 7.54 (ddd, J = 1.5, 7.3, 8.5 Hz, 1H), 7.31 (d, J = 8.1 Hz, 1H), 7.15 (td, J = 1.2, 8.1 Hz, 1H), 7.06 (td, J = 0.8, 1.9 Hz, 1H), 4.11 (s, 3H), 2.80 (s, 3H) | 391 (M⁺), 232 (base) |
| 2-Methoxy thiobenzamide | 5-Formyl-2-methoxy phenylboronic acid | — | Example 23-160 | (DMSO-$d_6$) δ: 11.62 (s, 1H), 8.36 (d, J = 6.6 Hz, 1H), 8.24-7.76 (m, 5H), 7.56-7.49 (m, 1H), 7.30 (ddd, J = 0.8, 2.7, 8.5 Hz, 1H), 7.14 (td, J = 0.8, 7.7 Hz, 1H), 7.13-7.06 (m, 1H), 4.08 and 4.06 (two s, 3H), 3.87 and 3.85 (two s, 3H), 2.77 (s, 3H) | 232 (base) |

TABLE 205

| Thioamide compound | Aldehyde compound | Ring-forming component | Example | ¹H-NMR | Mass, m/z |
|---|---|---|---|---|---|
| 4-Chloro thiobenzamide | Benzofuran-5-carbaldehyde | — | Example 23-161 | (DMSO-$d_6$) δ: 11.85 (s, 1H), 8.24 (br, 1H), 8.08 (d, J = 2.3 Hz, 1H), 8.06 (d, J = 8.5 Hz, 2H), 8.02 (d, J = 1.5 Hz, 1H), 7.82 (d, J = 8.1 Hz, 1H), 7.74 (d, J = 8.1 Hz, 1H), 7.63 (d, J = 8.5 Hz, 2H), 7.07 (s, 1H), 2.78 (s, 3H) | 395 (M⁺), 236 (base) |
| 2-Methyl thiobenzamide | 4-Hydroxy-3,5-dimethyl benzaldehyde | Ethyl 2-chloro-3-(4-methoxy-phenyl)-3-oxopropionate | Example 23-162 | (DMSO-$d_6$) δ: 11.84 and 11.77 (two s. 1H), 8.79 and 8.71 (two s, 1H), 8.03-7.82 (m, 2H), 7.80 and 7.71 (two d, J = 8.1 Hz, 2H), 7.46-7.37 (m, 3H), 7.29 (s, 1H), 7.12 (s, 1H), 7.04 and 6.98 (two d, J = 8.9 Hz, 2H), 3.80 and 3.78 (two s, 3H), 2.69 and 2.60 (two s, 3H), 2.16 and 2.20 (two s, 6H) | 471 (M⁺), 323, 308, 163 (base) |

TABLE 205-continued

| Thioamide compound | Aldehyde compound | Ring-forming component | Example | 1H-NMR | Mass, m/z |
|---|---|---|---|---|---|
| 2-Methyl thiobenz-amide | 4-Methoxy benzaldehyde | Ethyl 2-chloro-3-(4-methoxy-phenyl)-3-oxopropionate | Example 23-163 | (DMSO-d$_6$) δ: 11.93 and 11.87 (two s, 1H), 8.15 and 8.02 (two s, 1H), 7.79-7.89 (m, 2H), 7.71-7.66 (m, 2H), 7.51-7.38 (m, 4H), 7.06-6.97 (m, 4H), 3.80 (s, 3H), 3.78 (s, 3H), 2.66 (s, 3H) | 457 (M$^+$), 323, 308, 163 (base) |

TABLE 206

| Thioamide compound | Aldehyde compound | Ring-forming component | Example | 1H-NMR | Mass, m/z |
|---|---|---|---|---|---|
| 4-Chloro-2-methoxy thiobenz-amide | 4'-Methoxy acetophenone | — | Example 23-164 | (DMSO-d$_6$) δ: 10.77 (s, 1H), 8.35 (d, J = 8.5 Hz, 1H), 7.88 (d, J = 8.9 Hz, 2H), 7.37 (d, J = 1.5 Hz, 1H), 7.20 (dd, J = 1.9, 8.5 Hz, 1H), 7.04 (d, J = 8.9 Hz, 2H), 4.00 (s, 3H), 3.82 (s, 3H), 2.77 (s, 3H), 2.34 (s, 3H) | 429 (M$^+$), 266 (base) |
| 4-Chloro-2-methoxy thiobenz-amide | 5-Methoxy indan-1-one | — | Example 23-165 | (DMSO-d$_6$) δ: 10.78 (s, 1H), 8.37 (d, J = 8.5 Hz, 1H), 7.80 (brs, 1H), 7.41 (d, J = 2.2 Hz, 1H), 7.21 (dd, J = 2.0, 8.5 Hz, 1H), 7.01 (brs, 2H), 4.13 (s, 3H), 3.83 (s, 3H), 3.10 (t, J = 6.2 Hz, 2H), 2.90 (t, J = 6.2 Hz, 2H), 2.79 (s, 3H) | 441 (M$^+$), 266 (base) |
| 4-Chloro-2-methoxy thiobenz-amide | 1-Methyl-1H-benzimidazol-5-carboxy aldehyde | — | Example 23-171 | (DMSO-d$_6$) δ: 11.73 (brs, 1H), 8.39 (d, J = 8.9 Hz, 1H), 8.29 (s, 1H), 8.25 (brs, 1H), 8.16 (brs, 1H), 7.77 (d, J = 8.9 Hz, 1H), 7.71 (d, J = 8.1 Hz, 1H), 7.45 (s, 1H), 7.22 (dd, J = 1.9, J = 8.7 Hz, 1H), 4.27 (s, 2H), 3.89 (s, 4H), 2.80 (s, 3H) | 439 (M$^+$), 266 (base) |

TABLE 207

| Thioamide compound | Aldehyde compound | Ring-forming component | | Example | ¹H-NMR | Mass, m/z |
|---|---|---|---|---|---|---|
| 4-Chloro-2-methoxy thio-benzamide | Example 48-2 | — | | Example 23-172 | (DMSO-d₆) δ: 11.73 (brs, 1H), 8.39 (d, J = 7.7 Hz, 1H), 8.24 (s, 1H), 8.08 (s, 1H), 7.75 (d, J = 8.1 Hz, 1H), 7.67 (d, J = 8.5 Hz, 1H), 7.44 (s, 1H), 7.22 (dd, J = 1.9, J = 8.5 Hz, 1H), 5.00 (s, 2H), 4.26-4.18 (m, 7H), 2.80 (s, 3H) | 481 (M⁺), 238 (base) |

Example 23-166

5-(4-Chlorophenyl)-2-methylfuran-3-carboxylic acid [1-(3-hydroxy-4-methoxyphenyl)methylidene]hydrazide

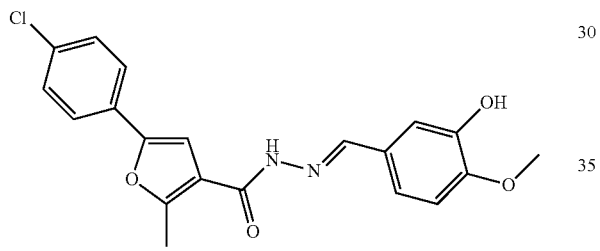

The title compound was obtained according to the same procedure as in Example 23-1 except that methyl 5-(4-chlorophenyl)-2-methylfuran-3-carboxylate was used instead of ethyl 2-(2,4-dichlorophenyl)-4-methylthiazole-5-carboxylate.

¹H-NMR (DMSO-d₆) δ: 11.29 (s, 1H), 9.28 (s, 1H), 8.25 (s, 1H), 7.67 (d, J=8.1 Hz, 2H), 7.53 (d, J=8.5 Hz, 2H), 7.36 (s, 1H), 7.26 (brs, 1H), 7.06 (d, J=8.1 Hz, 1H), 6.98 (d, J=8.5 Hz, 1H), 3.82 (s, 3H), 2.63 (s, 3H)

Mass, m/z: 384 (M⁺), 219 (base)

Example 23-167

5-(4-Chlorophenyl)-2-methylfuran-3-carboxylic acid [1-(4-hydroxy-3,5-dimethylphenyl)methylidene]hydrazide

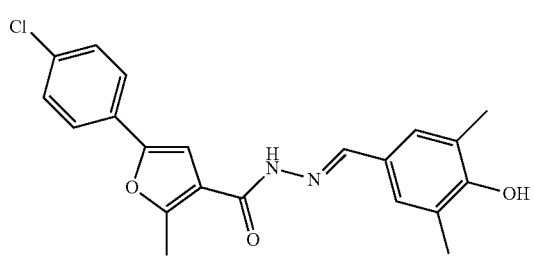 [SMILES: Cc1cc(/C=N/NC(=O)c2cc(-c3ccc(Cl)cc3)oc2C)cc(C)c1O]

The title compound was obtained according to the same procedure as in Example 23-1 except that methyl 5-(4-chlorophenyl)-2-methylfuran-3-carboxylate and 4-hydroxy-3,5-dimethylbenzaldehyde were used instead of ethyl 2-(2,4-dichlorophenyl)-4-methylthiazole-5-carboxylate and 3-hydroxy-4-methoxybenzaldehyde, respectively.

¹H-NMR (DMSO-d₆) δ: 11.26 (s, 1H), 8.71 (s, 1H), 8.22 (s, 1H), 7.68 (d, J=8.1 Hz, 2H), 7.53 (d, J=8.9 Hz, 2H), 7.36 (s, 1H), 7.30 (s, 2H), 2.62 (s, 3H), 2.21 (s, 6H)

Mass, m/z: 382 (M⁺), 219 (base)

Example 23-168

4-(4-Chloro-2-methoxyphenyl)-1-methyl-1H-pyrrole-2-carboxylic acid (4-methoxybenzylidene)hydrazide

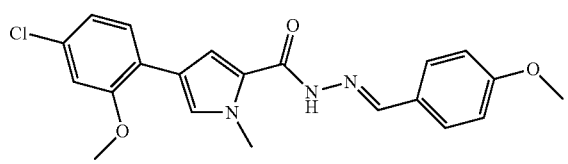 [SMILES: COc1ccc(/C=N/NC(=O)c2cc(-c3ccc(Cl)cc3OC)cn2C)cc1]

The title compound was obtained according to the same procedure as in Example 23-1 except that ethyl 4-(4-chloro-2-methoxyphenyl)-1-methyl-1H-pyrrole-2-carboxylate prepared in the Step 10-1-3 and 4-methoxybenzaldehyde were used instead of ethyl 2-(2,4-dichlorophenyl)-4-methylthiazole-5-carboxylate and 3-hydroxy-4-methoxybenzaldehyde, respectively.

¹H-NMR (DMSO-d₆) δ: 11.37 (brs, 1H), 8.31 (brs, 1H), 7.65 (d, J=8.9 Hz, 2H), 7.52 (s, 1H), 7.39 (s, 1H), 7.12 (d, J=1.9 Hz, 1H), 7.06 to 7.01 (m, 3H), 3.91 (s, 6H), 3.82 (s, 3H)

Mass, m/z: 397 (m⁺), 248 (base)

Example 23-169

4-(4-Chloro-2-methoxyphenyl)-1-methyl-1H-pyrrole-2-carboxylic acid (4-hydroxy-3,5-dimethylbenzylidene)hydrazide

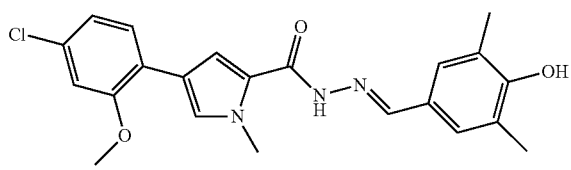 [SMILES: COc1cc(Cl)ccc1-c1cc(C(=O)N/N=C/c2cc(C)c(O)c(C)c2)n(C)c1]

The title compound was obtained according to the same procedure as in Example 23-1 except that ethyl 4-(4-chloro-2-methoxyphenyl)-1-methyl-1H-pyrrole-2-carboxylate prepared in the Step 10-1-3 and 4-hydroxy-3,5-dimethylbenzaldehyde were used instead of ethyl 2-(2,4-dichlorophenyl)-4-methylthiazole-5-carboxylate and 3-hydroxy-4-methoxybenzaldehyde, respectively.

$^1$H-NMR (DMSO-d$_6$) δ: 11.29 (brs, 1H), 8.67 (s, 1H), 8.19 (s, 1H), 7.51 (d, J=2.7 Hz, 1H), 7.28 (s, 2H), 7.12 (d, J=2.3 Hz, 2H), 7.03 (dd, J=2.3, 8.5 Hz, 1H), 3.91 (s, 3H), 2.21 (s, 3H)

Mass, m/z: 411 (m$^+$), 248 (base)

Example 23-170

4-(4-Chloro-2-methoxyphenyl)-1-methyl-1H-pyrrole-2-carboxylic acid (3-hydroxy-4-methoxybenzylidene)hydrazide

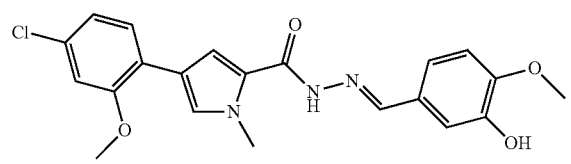 [SMILES: COc1ccc(/C=N/NC(=O)c2cc(-c3ccc(Cl)cc3OC)cn2C)cc1O]

The title compound was obtained according to the same procedure as in Example 23-1 except that ethyl 4-(4-chloro-2-methoxyphenyl)-1-methyl-1H-pyrrole-2-carboxylate prepared in the Step 10-1-3 was used instead of ethyl 2-(2,4-dichlorophenyl)-4-methylthiazole-5-carboxylate.

$^1$H-NMR (DMSO-d$_6$) δ: 11.31 (brs, 1H), 9.24 (s, 1H), 8.22 (s, 1H), 7.52 (s, 1H), 7.37 (s, 1H), 7.24 (d, J=1.5 Hz, 1H), 7.12 (d, J=1.9 Hz, 1H), 7.04 (d, J=2.3 Hz, 1H), 7.02 (d, J=1.9 Hz, 1H), 6.98 (d, J=8.5 Hz, 1H), 3.91 (s, 6H), 3.81 (s, 3H)

Mass, m/z: 413 (m$^+$), 248 (base)

Synthesis scheme 24

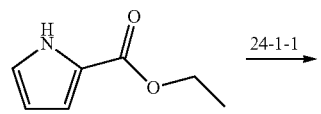

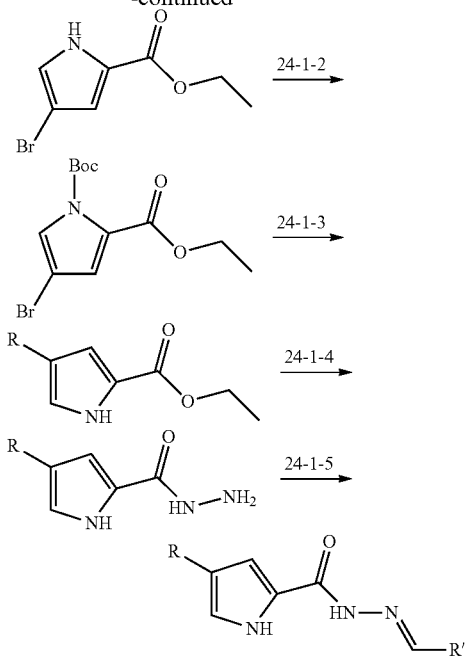

In the formulae, Boc represents a protecting group (t-butoxycarbonyl group), and R and R' are the same or different and each represent an aryl group which may have a substituent (such as an alkyl group, a hydroxyl group, or an alkoxy group).

Example 24-1

Step 24-1-1

Ethyl 4-bromo-1H-pyrrole-2-carboxylate

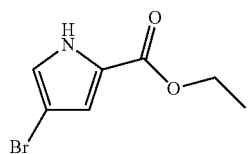

To a solution of ethyl 1H-pyrrole-2-carboxylate (1.17 g) in carbon tetrachloride (40 ml), a solution of bromine (1.48 g) in carbon tetrachloride (80 ml) was added dropwise at −15° C., and the mixture was stirred for one hour. The mixture was warmed to a room temperature, and a 2-N sodium hydroxide aqueous solution (80 ml) was added thereto. The resulting mixture was subjected to extraction with ethyl acetate, and the organic layer was dried over anhydrous magnesium sulfate and concentrated under a reduced pressure. The residue was purified by silica gel column chromatography (ethyl acetate:n-hexane=1:6) to give ethyl 4-bromo-1H-pyrrole-2-carboxylate (700 mg, 38%).

$^1$H-NMR (CDCl$_3$) δ: 9.16 (brs, 1H), 6.93 (dd, J=1.5, 2.7 Hz, 1H), 6.89 (dd, J=1.5, 2.7 Hz, 1H), 4.31 (q, J=6.9 Hz, 2H), 1.35 (t, J=6.9 Hz, 3H)

Mass, m/z: 217 (M$^+$), 189, 173 (base)

Step 24-1-2

4-bromopyrrole-1,2-dicarboxylic acid 1-tert-butyl ester 2-ethyl ester

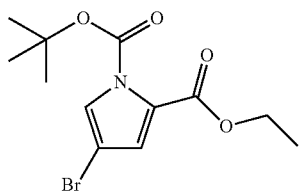 [SMILES: CCOC(=O)c1cc(Br)cn1C(=O)OC(C)(C)C]

To a solution of ethyl 4-bromo-1H-pyrrole-2-carboxylate (700 mg) obtained in the Step 24-1-1 in acetonitrile (5 ml), di-tert-butyl dicarbonate (917 mg) and 4-dimethylaminopyridine (39 mg) were added, and the mixture was stirred for 20 hours. Ethyl ether was added thereto, and the resulting mixture was washed with a 1 mol/L potassium bisulfate aqueous solution and a saturated sodium bicarbonate solution in order, and the organic layer was dried over anhydrous magnesium sulfate and concentrated under a reduced pressure. The residue was purified by silica gel column chromatography (ethyl acetate:n-hexane=5:1) to give 4-bromopyrrole-1,2-carboxylic acid 1-tert-butyl ester 2-ethyl ester (893 mg, 88%).

$^1$H-NMR (CDCl$_3$) δ: 7.29 (d, J=1.9 Hz, 1H), 6.78 (d, J=1.9 Hz, 1H), 4.29 (q, J=7.3 Hz, 2H), 1.57 (s, 9H), 1.34 (t, J=7.3 Hz, 3H)

Mass, m/z: 317 (M$^+$), 297, 217, 57 (base)

Step 24-1-3

Ethyl 4-(2,3-dimethylphenyl)-1H-pyrrole-2-carboxylate

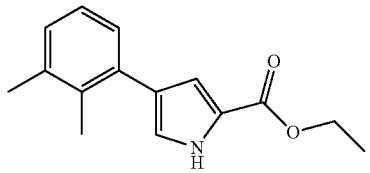 [SMILES: CCOC(=O)c1cc(-c2cccc(C)c2C)c[nH]1]

Dimethylformamide (3 ml) and a sodium carbonate aqueous solution (2 mol/l, 0.5 ml) were added to 4-bromo-pyrrole-1,2-carboxylic acid 1-tert-butyl ester 2-ethyl ester (100 mg) obtained in the Step 24-1-2, 2,3-dimethylphenylboronic acid (141 mg) and tetrakis(triphenylphosphine)palladium(0) (36 mg) at 110° C. After the mixture was heated and stirred for 2 hours, water was added thereto, and the resulting mixture was subjected to extraction with ethyl acetate. The organic layer was washed with water, and then dried over anhydrous magnesium sulfate and concentrated under a reduced pressure. The residue was purified by silica gel thin-layer chromatography (ethyl acetate:n-hexane=1:5) to give ethyl 4-(2,3-dimethylphenyl)-1H-pyrrole-2-carboxylate (50 mg, 65%).

$^1$H-NMR (DMSO-d$_6$) δ: 11.98 (brs, 1H), 7.12-7.03 (m, 4H), 6.84 (dd, J=1.5, 2.7 Hz, 1H), 4.26 (q, J=6.9 Hz, 2H), 2.27 (s, 3H), 2.24 (s, 3H), 1.30 (t, J=6.9 Hz, 3H)

Mass, m/z: 243 (M$^+$) (base), 197, 129

Step 24-1-4

4-(2,3-Dimethylphenyl)-1H-pyrrole-2-carboxylic acid hydrazide

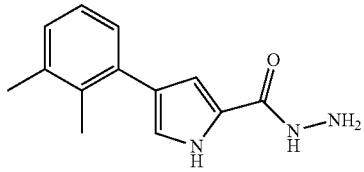 [SMILES: Cc1cccc(-c2c[nH]c(C(=O)NN)c2)c1C]

According to the same procedure as in the Step 22-1-3 except that ethyl 4-(2,3-dimethylphenyl)-1H-pyrrole-2-carboxylate obtained in the Step 24-1-3 was used instead of methyl 5-(2-chlorophenyl)-2H-pyrazole-3-carboxylate, the title compound (25 mg, 59%) was obtained.

$^1$H-NMR (DMSO-d$_6$) δ: 11.56 (brs, 1H), 9.29 (brs, 1H), 7.09-7.03 (m, 3H), 6.92 (dd, J=1.5, 2.7 Hz, 1H), 6.87 (s, 1H), 4.32 (d, J=3.9 Hz, 2H), 2.27 (s, 3H), 2.24 (s, 3H)

Mass, m/z: 229 (M$^+$), 198 (base)

Step 24-1-5

4-(2,3-Dimethylphenyl)-1H-pyrrole-2-carboxylic acid [1-(4-hydroxy-3,5-dimethylphenyl)methylidene]hydrazide

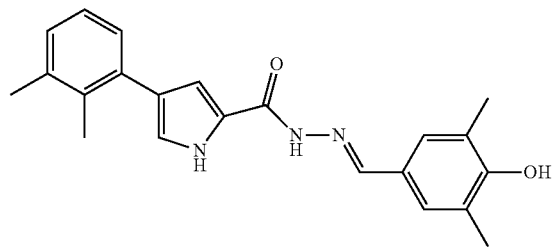 [SMILES: Cc1cccc(-c2c[nH]c(C(=O)N/N=C/c3cc(C)c(O)c(C)c3)c2)c1C]

The title compound was obtained according to the same procedure as in the Step 22-1-4 except that 4-(2,3-dimethylphenyl)-2H-pyrazole-2-carboxylic acid hydrazide obtained in the Step 24-1-4 and 4-hydroxy-3,5-dimethylbenzaldehyde were used instead of 5-(2-chlorophenyl)-2H-pyrazole-3-carboxylic acid hydrazide and 3-hydroxy-4-methoxybenzaldehyde, respectively.

$^1$H-NMR (DMSO-d$_6$) δ: 11.81 (brs, 1H), 11.25 (s, 1H), 8.68 (s, 1H), 8.20 (brs, 1H), 7.30 (s, 2H), 7.20-6.97 (m, 5H), 2.30 (s, 6H), 2.21 (s, 6H)

Mass, m/z: 361 (M$^+$), 164 (base)

Example 24-2

4-(4-Chlorophenyl)-1H-pyrrole-2-carboxylic acid [1-(3-hydroxy-4-methoxyphenyl)methylidene]hydrazide

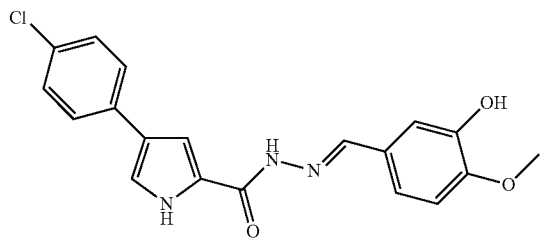 [SMILES: COc1ccc(/C=N/NC(=O)c2cc(-c3ccc(Cl)cc3)c[nH]2)cc1O]

The title compound was obtained according to the same procedure as in Example 24-1 except that 4-chlorophenylboronic acid was used instead of 2,3-dimethylphenylboronic acid in the Step 24-1-3.

$^1$H-NMR (DMSO-d$_6$) δ: 11.93 (s, 1H), 11.35 (s, 1H), 9.27 (s, 1H), 8.22 (s, 1H), 7.60 (d, J=8.1 Hz, 2H), 7.49 (dd, J=1.5, 2.7 Hz, 1H), 7.40 (d, J=8.5 Hz, 2H), 7.27 (brd, J=1.2 Hz, 1H), 7.06 (dd, J=1.9, 8.5 Hz, 1H), 6.99 (d, J=8.5 Hz, 1H), 3.82 (s, 3H)

Mass, m/z: 369 (M$^+$), 166 (base)

Example 24-3

4-(4-Chlorophenyl)-1H-pyrrole-2-carboxylic acid[1-(4-hydroxy-3,5-dimethylphenyl)methylidene]hydrazide

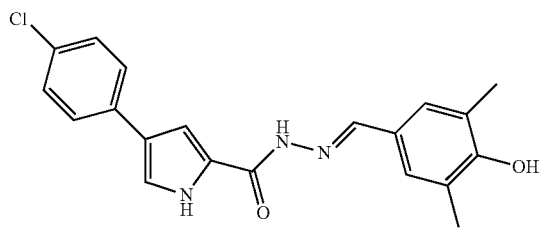 [SMILES: Cc1cc(/C=N/NC(=O)c2cc(-c3ccc(Cl)cc3)c[nH]2)cc(C)c1O]

The title compound was obtained according to the same procedure as in Example 24-1 except that 4-chlorophenylboronic acid and 4-hydroxy-3,5-dimethylbenzaldehyde were used instead of 2,3-dimethylphenylboronic acid and 3-hydroxy-4-methoxybenzaldehyde, respectively, in the Step 24-1-3.

$^1$H-NMR (DMSO-d$_6$) δ: 11.92 (s, 1H), 11.31 (s, 1H), 8.69 (s, 1H), 8.19 (s, 1H), 7.60 (d, J=8.5 Hz, 2H), 7.49 (s, 1H), 7.40 (d, J=8.9 Hz, 2H), 7.31 (s, 3H), 2.22 (s, 6H)

Mass, m/z: 367 (M$^+$), 164 (base)

Synthesis scheme 25

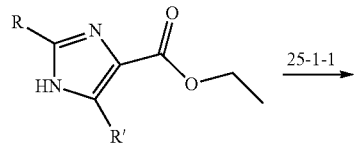

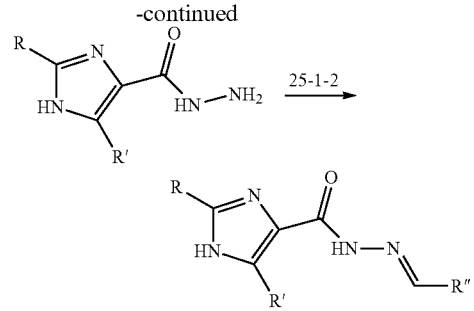

In the formulae, R and R″ are the same or different and each represent an aryl group which may have a substituent (such as a halogen atom, an alkyl group, a hydroxyl group, or an alkoxy group), and R′ represents a hydrogen atom or an alkyl group.

Example 25-1

Step 25-1-1

2-(4-Chlorophenyl)-1H-imidazole-4-carboxylic acid hydrazide

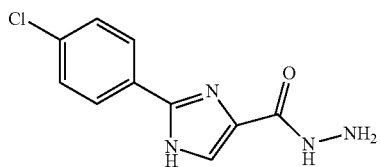 [SMILES: NNC(=O)c1c[nH]c(-c2ccc(Cl)cc2)n1]

The title compound was obtained according to the same procedure as in the Step 22-1-3 except that methyl 2-(4-chlorophenyl)-1H-imidazole-4-carboxylate was used instead of methyl 5-(2-chlorophenyl)-2H-pyrazole-3-carboxylate.

$^1$H-NMR (CDCl$_3$) δ: 7.75 (d, J=8.9 Hz, 2H), 7.44 (d, J=8.5 Hz, 2H), 7.01 (s, 1H), 4.03 (brs, 2H)

Mass, m/z: 236 (M$^+$), 205 (base)

Step 25-1-2

2-(4-Chlorophenyl)-3H-imidazole-4-carboxylic acid [1-(3-hydroxy-4-methoxyphenyl)methylidene]hydrazide

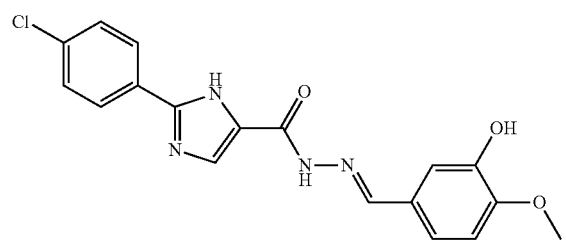 [SMILES: COc1ccc(/C=N/NC(=O)c2cnc(-c3ccc(Cl)cc3)[nH]2)cc1O]

The title compound was obtained according to the same procedure as in the Step 22-1-4 except that 2-(4-chlorophenyl)-1H-imidazole-4-carboxylic acid hydrazide prepared in the Step 25-1-1 was used instead of 5-(2-chlorophenyl)-2H-pyrazole-3-carboxylic acid hydrazide.

$^1$H-NMR (CDCl$_3$) δ: 13.18 (brs, 1H), 11.18 (s, 1H), 9.26 (s, 1H), 8.40 (s, 1H), 8.06 (d, J=8.5 Hz, 2H), 7.95 (s, 1H), 7.59 (d, J=8.9 Hz, 2H), 7.26 (s, 1H), 7.04 (dd, J=1.9, 8.5 Hz, 1H), 6.98 (d, J=8.9 Hz, 1H), 3.81 (s, 3H)

Mass, m/z: 370 (M$^+$), 166 (base)

Example 25-2

2-(2-Methylphenyl)-3H-imidazole-4-carboxylic acid [1-(4-hydroxy-3,5-dimethylphenyl)methylidene]hydrazide

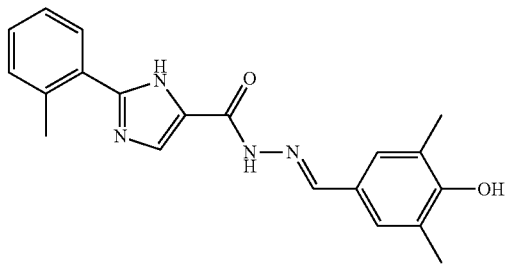 [SMILES: Cc1ccccc1-c1ncc(C(=O)N/N=C/c2cc(C)c(O)c(C)c2)[nH]1]

The title compound was obtained according to the same procedure as in Example 25-1 except that methyl 2-(2-methylphenyl)-1H-imidazole-4-carboxylate and 4-hydroxy-3,5-dimethylbenzaldehyde were used instead of methyl 2-(4-chlorophenyl)-1H-imidazole-4-carboxylate and 3-hydroxy-4-methoxybenzaldehyde, respectively.

$^1$H-NMR (CDCl$_3$) δ: 12.76 (brs, 1H), 11.05 (s, 1H), 8.66 (s, 1H), 8.34 (s, 1H), 7.90 (s, 1H), 7.59 (d, J=7.3 Hz, 1H), 7.35-7.27 (m, 5H), 2.50 (s, 6H), 2.21 (s, 3H)

Mass, m/z: 348 (M$^+$), 164 (base)

Example 25-3

2-(2-Methylphenyl)-3H-imidazole-4-carboxylic acid [1-(3-hydroxy-4-methoxyphenyl)methylidene]hydrazide

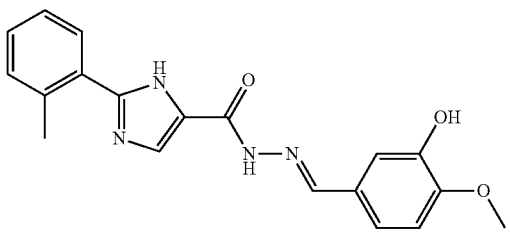 [SMILES: COc1ccc(/C=N/NC(=O)c2cnc(-c3ccccc3C)[nH]2)cc1O]

The title compound was obtained according to the same procedure as in Example 25-1 except that methyl 2-(2-methylphenyl)-1H-imidazole-4-carboxylate was used instead of methyl 2-(4-chlorophenyl)-1H-imidazole-4-carboxylate.

$^1$H-NMR (CDCl$_3$) δ: 12.78 (brs, 1H), 11.09 (s, 1H), 9.25 (s, 1H), 8.38 (s, 1H), 7.91 (s, 1H), 7.59 (d, J=6.9 Hz, 1H), 7.35-7.25 (m, 4H), 7.03-6.96 (m, 2H), 3.81 (s, 3H), 2.53 (s, 3H)

Mass, m/z: 350 (M$^+$), 164 (base)

Example 25-4

2-(2-Methylphenyl)-3H-imidazole-4-carboxylic acid [1-(4-hydroxy-3-methylphenyl)methylidene]hydrazide

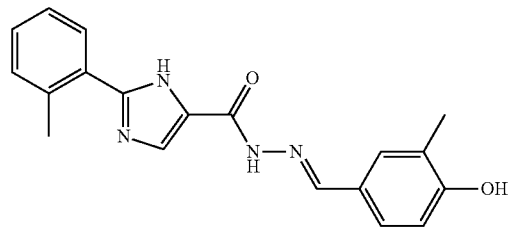 [SMILES: Cc1cc(/C=N/NC(=O)c2cnc(-c3ccccc3C)[nH]2)ccc1O]

The title compound was obtained according to the same procedure as in Example 25-1 except that methyl 2-(2-methylphenyl)-1H-imidazole-4-carboxylate and 4-hydroxy-3-methylbenzaldehyde were used instead of methyl 2-(4-chlorophenyl)-1H-imidazole-4-carboxylate and 3-hydroxy-4-methoxybenzaldehyde, respectively.

$^1$H-NMR (CDCl$_3$) δ: 12.76 (brs, 1H), 11.04 (s, 1H), 9.75 (s, 1H), 8.37 (s, 1H), 7.90 (s, 1H), 7.59 (d, J=7.3 Hz, 1H), 7.44 (s, 1H), 7.35-7.30 (m, 3H), 6.84 (d, J=8.1 Hz, 1H), 2.53 (s, 3H), 2.16 (s, 3H)

Mass, m/z: 334 (M$^+$), 185 (base)

Example 25-5

2-(4-Chlorophenyl)-5-methyl-3H-imidazole-4-carboxylic acid[1-(3-hydroxy-4-methoxyphenyl)methylidene]hydrazide

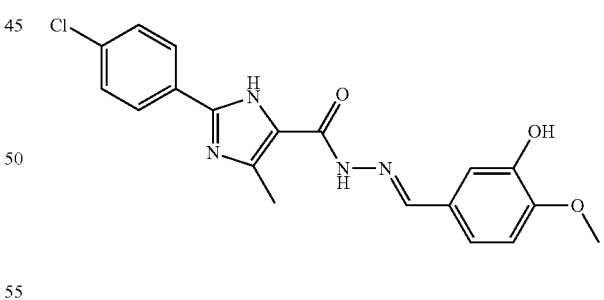

The title compound was obtained according to the same procedure as in Example 25-1 except that methyl 2-(4-chlorophenyl)-5-methyl-1H-imidazole-4-carboxylate was used instead of methyl 2-(4-chlorophenyl)-1H-imidazole-4-carboxylate.

$^1$H-NMR (CDCl$_3$) δ: 12.88 (brs, 1H), 11.03 (s, 1H), 9.25 (s, 1H), 8.38 (s, 1H), 8.02 (d, J=8.1 Hz, 2H), 7.58 (d, J=8.5 Hz, 2H), 7.24 (d, J=1.9 Hz, 1H), 7.02 (dd, J=1.9, 8.5 Hz, 1H), 6.98 (d, J=8.1 Hz, 1H), 3.81 (s, 3H), 2.56 (s, 3H)

Mass, m/z: 384 (M$^+$), 166 (base)

Synthesis scheme 26

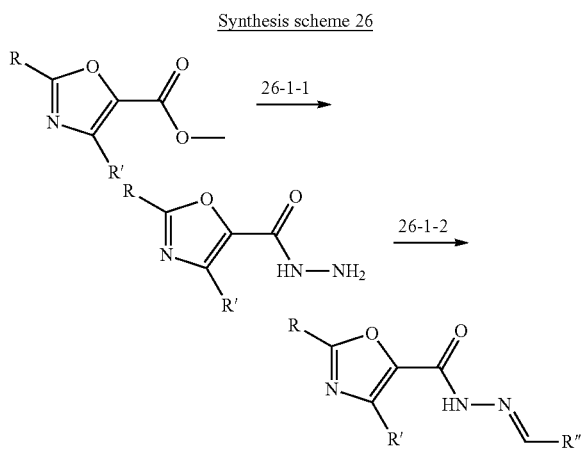

In the formulae, R and R" are the same or different and each represent an aryl group which may have a substituent (such as a halogen atom, an alkyl group, a hydroxyl group, or an alkoxy group), and R' represents an alkyl group.

Example 26-1

Step 26-1-1

2-(4-Chlorophenyl)-4-methyloxazole-5-carboxylic acid hydrazide

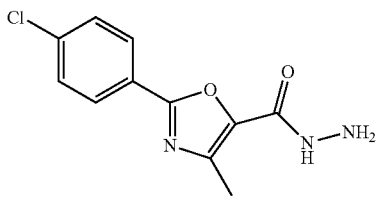 [SMILES: Cc1nc(-c2ccc(Cl)cc2)oc1C(=O)NN]

The title compound was obtained according to the same procedure as in the Step 22-1-3 except that methyl 2-(4-chlorophenyl)-4-methyloxazole-5-carboxylate was used instead of methyl 5-(2-chlorophenyl)-2H-pyrazole-3-carboxylate.

$^1$H-NMR (CDCl$_3$) δ: 9.89 (brs, 1H), 8.17 (d, J=8.5 Hz, 2H), 7.64 (d, J=8.5 Hz, 2H), 4.50 (brs, 2H), 2.44 (s, 3H)
Mass, m/z: 251 (M$^+$), 164 (base)

Step 26-1-2

2-(4-Chlorophenyl)-4-methyloxazole-5-carboxylic acid[N'-(4-hydroxy-3,5-dimethylphenyl)methylidene]hydrazide

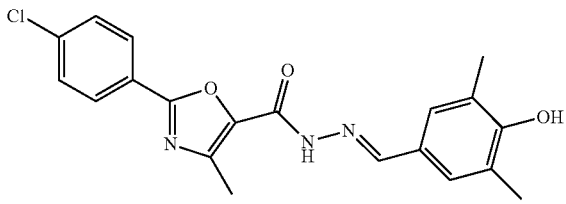 [SMILES: Cc1cc(/C=N/NC(=O)c2oc(-c3ccc(Cl)cc3)nc2C)cc(C)c1O]

The title compound was obtained according to the same procedure as in the Step 22-1-4 except that 2-(4-chlorophenyl)-4-methyloxazole-5-carboxylic acid hydrazide prepared in the Step 26-1-1 and 4-hydroxy-3,5-dimethylbenzaldehyde were used instead of 5-(2-chlorophenyl)-2H-pyrazole-3-carboxylic acid hydrazide and 3-hydroxy-4-methoxybenzaldehyde, respectively.

$^1$H-NMR (CDCl$_3$) δ: 11.63 (brs, 1H), 8.77 (s, 1H), 8.35 (s, 1H), 8.20 (d, J=8.5 Hz, 2H), 7.69 (d, J=8.5 Hz, 2H), 7.32 (s, 1H), 2.50 (s, 6H), 2.22 (s, 3H)
Mass, m/z: 383 (M$^+$), 236 (base)

Example 26-2

2-(2-Methoxyphenyl)-4-methyloxazole-5-carboxylic acid[N'-(3-hydroxy-4-methoxylphenyl)methylidene]hydrazide

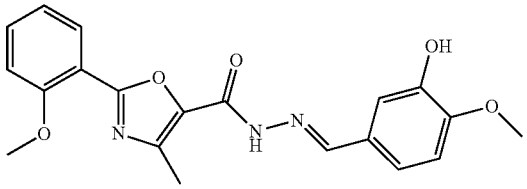 [SMILES: COc1ccc(/C=N/NC(=O)c2oc(-c3ccccc3OC)nc2C)cc1O]

The title compound was obtained according to the same procedure as in Example 26-1 except that 2-(2-methoxyphenyl)-4-methyloxazole-5-carboxylic acid hydrazide and 3-hydroxy-4-methoxybenzaldehyde were used instead of 2-(4-chlorophenyl)-4-methyloxazole-5-carboxylic acid hydrazide and 4-hydroxy-3,5-dimethylbenzaldehyde, respectively.

$^1$H-NMR (CDCl$_3$) δ: 11.52 (brs, 1H), 9.29 (s, 1H), 8.36 (brs, 1H), 8.04 (d, J=8.1 Hz, 1H), 7.60-7.55 (m, 1H), 7.26-7.23 (m, 2H), 7.13 (t, J=7.3 Hz, 1H), 7.06 (dd, J=1.9, 8.5 Hz, 1H), 6.99 (d, J=8.5 Hz, 1H), 3.90 (s, 3H), 3.82 (s, 3H), 2.47 (s, 3H)
Mass, m/z: 381 (M$^+$), 160 (base)

Example 26-3

2-(2-Methoxyphenyl)-4-methyloxazole-5-carboxylic acid[N'-(4-methoxy-3-methoxylphenyl)methylidene]hydrazide

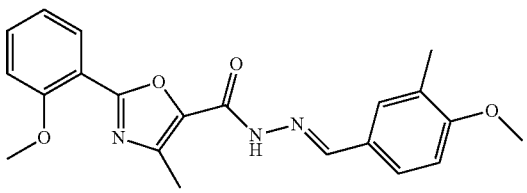 [SMILES: COc1ccc(/C=N/NC(=O)c2oc(-c3ccccc3OC)nc2C)cc1C]

The title compound was obtained according to the same procedure as in Example 26-1 except that 2-(2-methoxyphenyl)-4-methyloxazole-5-carboxylic acid hydrazide and 4-methoxy-3-methylbenzaldehyde were used instead of 2-(4-chlorophenyl)-4-methyloxazole-5-carboxylic acid hydrazide and 4-hydroxy-3,5-dimethylbenzaldehyde, respectively.

$^1$H-NMR (CDCl$_3$) δ: 11.49 (brs, 1H), 9.84 (s, 1H), 8.36 (brs, 1H), 8.03 (d, J=7.3 Hz, 1H), 7.59-7.55 (m, 1H), 7.47 (s, 1H), 7.37 (d, J=7.3 Hz, 1H), 7.24 (d, J=8.1 Hz, 1H), 7.12 (t, J=7.3 Hz, 1H), 6.85 (d, J=8.1 Hz, 1H), 3.90 (s, 3H), 2.47 (s, 3H), 2.16 (s, 3H)
Mass, m/z: 365 (M$^+$), 160 (base)

Synthesis scheme 27

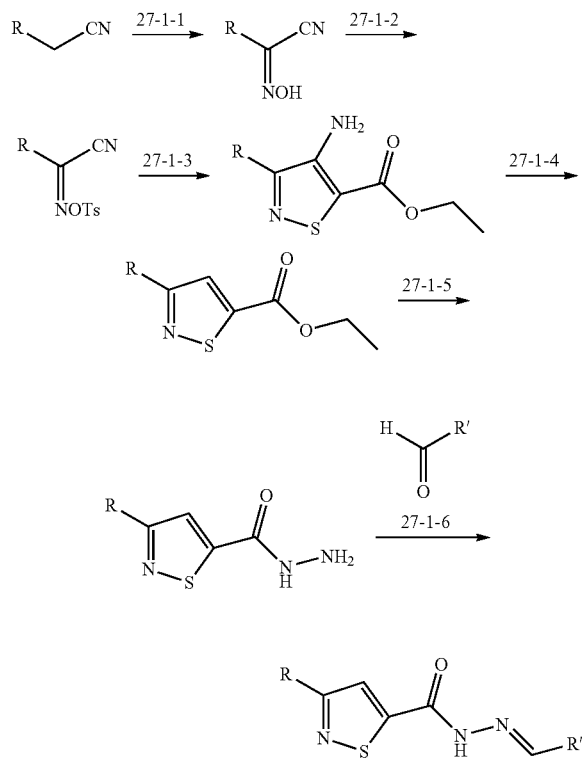

In the formulae, R and R' are the same or different and each represent an aryl or heterocyclic group which may have a substituent (such as a halogen atom, an alkyl group, a hydroxyl group, an alkoxy group, or a haloalkoxy group), and Ts represents a tosyl group.

Example 27-1

Step 27-1-1

(2,4-Dichlorophenyl)-hydroxyiminoacetonitrile

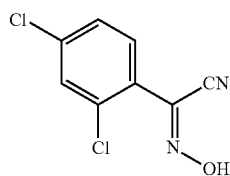 [SMILES: N#C/C(=N\O)c1ccc(Cl)cc1Cl]

Under an ice cooling, sodium methoxide (2.70 g) was dissolved in methanol (100 ml), and 2,4-dichlorophenylacetonitrile (9.30 g, 50 mmol) and isoamyl nitrite (5.85 g) were added thereto. The mixture was stirred for 18 hours at a room temperature. The solvent was distilled off, and the residue was crystallized by adding diethyl ether (100 ml) to the residue. The resulting crystal was separated by filtration and azeotropically dried with benzene to give the title compound (9.68 g, 90%).

$^1$H-NMR (DMSO-d$_6$) δ: 7.70 (d, J=8.9 Hz, 1H), 7.48 (d, J=2.3 Hz, 1H), 7.32 (dd, J=2.3, 8.5 Hz, 1H)

Step 27-1-2

(2,4-Dichlorophenyl)-O-(p-toluenesulfonyl)oxyiminoacetonitrile

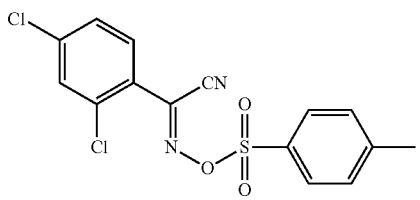 [SMILES: Cc1ccc(S(=O)(=O)O/N=C(\C#N)c2ccc(Cl)cc2Cl)cc1]

To toluene (200 ml), (2,4-dichlorophenyl)-hydroxyiminoacetonitrile (8.60 g, 40 mmol) prepared in the Step 27-1-1, tosyl chloride (9.50 g) and triethylamine (5.0 g) were added, and the mixture was heated under reflux for 5 hours. After being allowed to cool, the mixture was washed with water and dried over anhydrous magnesium sulfate. The resulting residue was purified by silica gel column chromatography (ethyl acetate:n-hexane=1:3) to give the title compound (11.4 g, 77%).

Step 27-1-3

Ethyl 4-amino-3-(2,4-dichlorophenyl)isothiazole-5-carboxylate

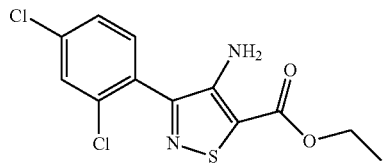 [SMILES: CCOC(=O)c1snc(-c2ccc(Cl)cc2Cl)c1N]

In ethanol (100 ml), (2,4-dichlorophenyl)-O-(p-toluenesulfonyl)hydroxyiminoacetonitrile (10.0 g, 27.1 mmol) prepared in the Step 27-1-2 was dissolved, and triethylamine (3.0 g) and ethyl thioglycolate (4.72 g) were added thereto. The mixture was stirred for one hour at a room temperature. The solvent was distilled off. The residue was dissolved in diethyl ether, washed with water, and dried over anhydrous magnesium sulfate. The resulting residue was purified by silica gel column chromatography (ethyl acetate:n-hexane=1:3) to give the title compound (4.81 g, 56%).

Step 27-1-4

Ethyl 3-(2,4-dichlorophenyl)isothiazole-5-carboxylate

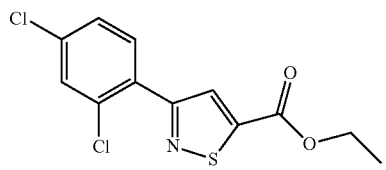 [SMILES: CCOC(=O)c1cc(-c2ccc(Cl)cc2Cl)ns1]

Ethyl 4-amino-3-(2,4-dichlorophenyl)isothiazole-5-carboxylate (3.17 g, 10.0 mmol) prepared in the Step 27-1-3 was dissolved in tetrahydrofuran (50 ml), and isoamyl nitrite (3.20 g) was added thereto. The mixture was heated and stirred for one hour. The solvent was distilled off, and the resulting residue was purified by silica gel column chromatography (ethyl acetate:n-hexane=1:3) to give the title compound (2.26 g, 75%).

$^1$H-NMR (DMSO-$d_6$) δ: 8.25 (s, 1H), 7.82 (d, J=2.3 Hz, 1H), 7.80 (d, J=8.1 Hz, 1H), 7.59 (dd, J=2.3 Hz, 1H), 4.40 (q, J=7.3 Hz, 1H), 1.34 (t, J=7.3 Hz, 1H)

Mass, m/z: 301 (M$^+$, base)

Step 27-1-5

3-(2,4-Dichlorophenyl)isothiazole-5-carboxylic acid hydrazide

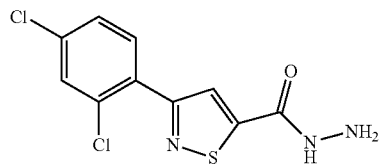 [SMILES: NNC(=O)c1cc(-c2ccc(Cl)cc2Cl)ns1]

The title compound was obtained according to the same procedure as in the Step 22-1-3 except that ethyl 3-(2,4-dichlorophenyl)isothiazole-5-carboxylate prepared in the Step 27-1-4 was used instead of methyl 5-(2-chlorophenyl)-2H-pyrazole-3-carboxylate.

$^1$H-NMR (CDCl$_3$) δ: 10.29 and 9.48 (two brs, 1H), 8.24 and 8.22 (two s, 1H), 7.81-7.76 (m, 2H), 7.60-7.54 (m, 1H), 5.26 and 4.68 (two brs, 2H)

Mass, m/z: 287 (M$^+$), 256 (base)

Step 27-1-6

3-(2,4-Dichlorophenyl)isothiazole-5-carboxylic acid [1-(4-dimethylaminophenyl)methylidene]hydrazide

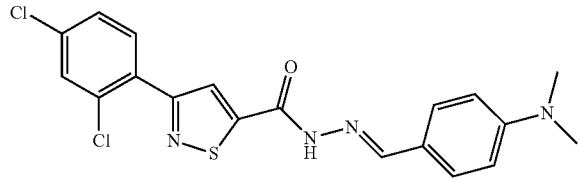 [SMILES: CN(C)c1ccc(/C=N/NC(=O)c2cc(-c3ccc(Cl)cc3Cl)ns2)cc1]

The title compound was obtained according to the same procedure as in the Step 22-1-4 except that 3-(2,4-dichlorophenyl)isothiazole-5-carboxylic acid hydrazide prepared in the Step 27-1-5 and 4-dimethylaminobenzaldehyde were used instead of 5-(2-chlorophenyl)-2H-pyrazole-3-carboxylic acid hydrazide and 3-hydroxy-4-methoxybenzaldehyde, respectively.

$^1$H-NMR (DMSO-$d_6$) δ: 12.17 (s, 1H), 8.36 (s, 1H), 8.08 (s, 1H), 7.84 (d, J=8.5 Hz, 1H), 7.81 (d, J=2.3 Hz, 1H), 7.68 (d, J=8.9 Hz, 2H), 7.59 (dd, J=2.3, 8.5 Hz, 1H), 6.84 (d, J=8.9 Hz, 2H), 3.26 (s, 6H)

Mass, m/z: 418 (M$^+$), 256, 162, 146 (base)

Examples 27-2 to 27-13

The objective compounds were obtained according to the same procedure as in Example 27-1 except that any one of aldehyde compounds or any one of acetonitrile compounds shown in the following tables were used instead of 4-dimethylaminobenzaldehyde or 2,4-dichlorophenylacetonitrile.

TABLE 208

| Aldehyde compound | Acetonitrile compound | Example | $^1$H-NMR | Mass, m/z |
|---|---|---|---|---|
| 4-Difluoromethoxy-3-hydroxy benzaldehyde | — | Example 27-2 | (DMSO-$d_6$) δ: 12.39 (brs, 1H), 10.44 (brs, 1H), 8.37 (s, 1H), 8.12 (s, 1H), 7.84 (d, J = 8.1 Hz, 1H), 7.82 (d, J = 1.9 Hz, 1H), 7.65 (d, J = 1.5 Hz, 1H), 7.59 (dd, J = 1.9, 8.5 Hz, 1H), 7.24 (d, J = 8.1 Hz, 1H), 7.20 (dd, J = 1.9, 8.5 Hz, 1H), 7.15 (t, J = 74.8 Hz, 1H) | 457 (M$^+$), 272, 256, 57 (base) |
| 4-Hydroxy-3-methyl benzaldehyde | — | Example 27-3 | (DMSO-$d_6$) δ: 12.23 (brs, 1H) 10.00 (brs, 1H), 8.37 (s, 1H), 8.09 (s, 1H), 7.84 (d, J = 8.1 Hz, 1H), 7.81 (d, J = 2.3 Hz, 1H), 7.59 (dd, J = 1.9, 8.5 Hz, 1H), 7.56 (s, 1H), 7.55 (d, J = 7.7 Hz, 1H), 6.94 (d, J = 8.1 Hz, 1H), 2.20 (s, 3H) | 405 (M$^+$), 272, 256, 133, 57 (base) |

TABLE 208-continued

| Aldehyde compound | Acetonitrile compound | Example | ¹H-NMR | Mass, m/z |
|---|---|---|---|---|
| 4-Hydroxy-3,5-dimethyl benzaldehyde | — | Example 27-4 | (DMSO-d₆) δ: 12.23 (s, 1H), 8.90 (s, 1H), 8.37 (s, 1H), 8.07 (s, 1H), 7.85 (d, J = 8.5 Hz, 1H), 7.81 (d, J = 2.3 Hz, 1H), 7.59 (dd, J = 2.3, 8.5 Hz, 1H), 7.44 (s, 2H), 2.25 (s, 6H) | 419 (M⁺), 272, 256, 147 (base) |
| 3-Hydroxy-4-methoxy benzaldehyde | — | Example 27-5 | (DMSO-d₆) δ: 12.26 (s, 1H), 9.55 (s, 1H), 8.36 (s, 1H), 8.07 (s, 1H), 7.84 (d, J = 8.5 Hz, 1H), 7.81 (d, J = 1.9 Hz, 1H), 7.59 (dd, J = 1.9, 8.5 Hz, 1H), 7.49 (d, J = 1.9 Hz, 1H), 7.15 (dd, J = 1.9, 8.5 Hz, 1H), 7.04 (d, J = 8.5 Hz, 1H), 3.83 (s, 3H) | 421 (M⁺), 272, 256, 149 (base) |

TABLE 209

| Aldehyde compound | Acetonitrile compound | Example | ¹H-NMR | Mass, m/z |
|---|---|---|---|---|
| 4-Hydroxy-3-methyl benzaldehyde | 2-Methoxy-phenyl acetonitrile | Example 27-6 | (DMS0-d₆) δ: 12.14 (s, 1H), 9.97 (s, 1H), 8.48 (s, 1H), 8.07 (s, 1H), 7.98 (dd, J = 1.9, 8.5 Hz, 1H), 7.57 (s, 1H), 7.55 (dd, J = 1.9, 7.7 Hz, 1H), 7.47 (dt, J = 1.9, 7.7 Hz, 1H), 7.22 (d, J = 8.1 Hz, 1H), 7.10 (t, J = 7.7 Hz, 1H), 6.94 (d, J = 8.1 Hz, 1H), 3.93 (s, 3H), 2.21 (s, 3H) | 367 (M⁺), 218, 205 (base), 190 |
| 3-Hydroxy-4-methyl benzaldehyde | 2-Methoxy-phenyl acetonitrile | Example 27-7 | (DMS0-d₆) δ: 12.17 (s, 1H), 9.53 (s, 1H), 8.48 (s, 1H), 8.06 (s, 1H), 7.99 (dd, J = 1.9, 7.7 Hz, 1H), 7.49 (d, J = 1.9 Hz, 1H), 7.47 (dt, J = 1.9, 7.7 Hz, 1H), 7.22 (d, J = 8.5 Hz, 1H), 7.15 (dd, J = 1.9, 8.5 Hz, 1H), 7.10 (t, J = 7.7 Hz, 1H), 7.04 (d, J = 8.5 Hz, 1H), 3.94 (s, 3H), 3.84 (s, 3H) | 383 (M⁺) (base), 218, 205, 190 |

TABLE 209-continued

| Aldehyde compound | Acetonitrile compound | Example | ¹H-NMR | Mass, m/z |
|---|---|---|---|---|
| 4-Hydroxy-3,5-dimethyl benzaldehyde | 2-Methoxy-phenyl acetonitrile | Example 27-8 | (DMS0-d₆) δ: 12.44 (s, 1H), 8.88 (s, 1H), 8.47 (s, 1H), 8.05 (s, 1H), 7.99 (dd, J = 1.9, 7.7 Hz, 1H), 7.49-7.45 (m, 1H), 7.44 (s, 2H), 7.22 (d, J = 7.7 Hz, 1H), 7.09 (dt, J = 1.2, 7.7 Hz, 1H), 3.93 (s, 3H), 2.25 (s, 6H) | 381 (M⁺), 218, 205 (base), 190 |
| 3-Hydroxy-4-methoxy benzaldehyde | 2-Methoxy-phenyl acetonitrile | Example 27-9 | (DMS0-d₆) δ: 12.19 (s, 1H), 9.54 (s, 1H), 8.20 (s, 1H), 8.07 (s, 1H), 7.63 (d, J = 7.3 Hz, 1H), 7.49 (d, J = 1.9 Hz, 1H), 7.40-7.28 (m, 3H), 7.15 (dd, J = 1.9, 8.5 Hz, 1H), 7.04 (d, J = 8.5 Hz, 1H), 3.83 (s, 3H), 2.48 (s, 3H) | 367 (M⁺) (base), 219, 202, 175, 149 |

TABLE 210

| Aldehyde compound | Acetonitrile compound | Example | ¹H-NMR | Mass, m/z |
|---|---|---|---|---|
| 4-Hydroxy-3,5-dimethyl benzaldehyde | 2-Methoxy-phenyl acetonitrile | Example 27-10 | (DMSO-d₆) δ: 12.16 (s, 1H), 8.89 (s, 1H), 8.20 (s, 1H), 8.06 (s, 1H), 7.62 (d, J = 7.3 Hz, 1H), 7.44 (s, 2H), 7.40-7.29 (m, 3H), 2.47 (s, 3H), 2.25 (s, 6H) | 365 (M⁺) (base), 219, 202 174, 147 |
| 4-Hydroxy-3-methyl benzaldehyde | 2-Methoxy-phenyl acetonitrile | Example 27-11 | (DMSO-d₆) δ: 12.16 (s, 1H), 9.98 (s, 1H), 8.20 (s, 1H), 8.08 (s, 1H), 7.63 (d, J = 7.3 Hz, 1H), 7.59-7.54 (m, 2H), 7.39-7.29 (m, 3H), 6.94 (d, J = 8.9 Hz, 1 H), 2.48 (s, 3H), 2.20 (s, 3H) | 351 (M⁺), 281, 207 (base), 133 |
| 4-Hydroxy-3,5-dimethyl benzaldehyde | 2-Pyridyl acetonitrile | Example 27-12 | (DMSO-d₆) δ: 12.19 (s, 1H), 8.90 (s, 1H), 8.71 (dd, J = 1.2, 5.2 Hz, 1H), 8.63 (s, 1H), 8.24 (d, J = 8.1 Hz, 1 H), 8.07 (s, 1H), 7.98 (dt, J = 1.5, 7.7 Hz, 1H), 7.51-7.47 (m, 1H), 7.44 (s, 2H), 2.26 (s, 6H) | 352 (M⁺), 206, 147, 105 (base) |

TABLE 210-continued

| Aldehyde compound | Acetonitrile compound | Example | ¹H-NMR | Mass, m/z |
|---|---|---|---|---|
| 4-Hydroxy-3,5-dimethyl benzaldehyde | (3-Methyl-pyridin-2-yl) acetonitrile | Example 27-13 | (DMSO-d₆) δ: 12.15 (s, 1H), 8.89 (s, 1H), 8.56 (s, 1H), 8.55 (d, J = 3.5 Hz, 1H), 8.07 (s, 1H), 7.80 (d, J = 7.7 Hz, 1H), 7.44 (s, 2H), 7.40 (dd, J = 5.0, 7.7 Hz, 1H), 2.69 (s, 3H), 2.26 (s, 6H) | 366 (M⁺), 220, 175, 119 (base) |

4-Amino-3-(2,4-dichlorophenyl)isothiazole-5-carboxylic acid[1-(4-hydroxy-3-methylphenyl)methylidene]hydrazide

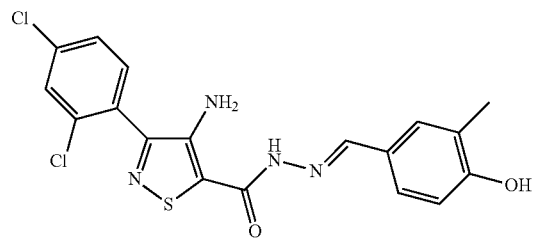 [SMILES: Cc1cc(/C=N/NC(=O)c2snc(-c3ccc(Cl)cc3Cl)c2N)ccc1O]

The title compound was obtained according to the same procedure as in Example 22-1 except that ethyl 4-amino-3-(2,4-dichlorophenyl)isothiazole-5-carboxylate prepared in the Step 27-1-3 and 4-hydroxy-3-methylbenzaldehyde were used instead of methyl 5-(2-chlorophenyl)-2H-pyrazole-3-carboxylate and 3-hydroxy-4-methoxybenzaldehyde, respectively.
¹H-NMR (DMSO-d₆) δ: 11.72 (s, 1H), 9.90 (s, 1H), 8.00 (s, 1H), 7.79 (d, J=1.9 Hz, 1H), 7.57 (dd, J=1.9, 8.5 Hz, 1H), 7.53 (s, 1H), 7.51 (d, J=8.1 Hz, 1H), 7.48 (d, J=8.5 Hz, 1H), 6.91 (d, 1H), 6.47 (s, 2H), 2.19 (s, 3H)
Mass, m/z: 420 (M⁺), 271, 235, 150, 72 (base)

Example 27-15

4-Amino-3-(2,4-dichlorophenyl)isothiazole-5-carboxylic acid[1-(4-hydroxy-3,5-dimethylphenyl)methylidene]hydrazide

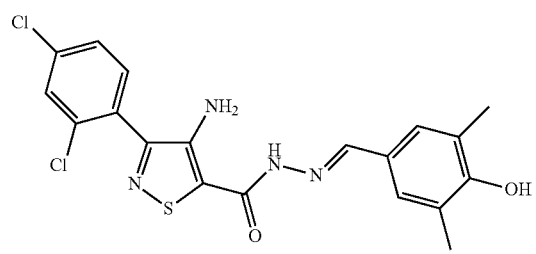 [SMILES: Cc1cc(/C=N/NC(=O)c2snc(-c3ccc(Cl)cc3Cl)c2N)cc(C)c1O]

The title compound was obtained according to the same procedure as in Example 22-1 except that ethyl 4-amino-3-(2,4-dichlorophenyl)isothiazole-5-carboxylate prepared in the Step 27-1-3 and 4-hydroxy-3,5-dimethylbenzaldehyde were used instead of methyl 5-(2-chlorophenyl)-2H-pyrazole-3-carboxylate and 3-hydroxy-4-methoxybenzaldehyde, respectively.

¹H-NMR (DMSO-d₆) δ: 11.72 (s, 1H), 9.81 (s, 1H), 7.98 (s, 1H), 7.79 (d, J=1.9 Hz, 1H), 7.56 (d, J=2.3 Hz, 1H), 7.48 (d, J=8.1 Hz, 1H), 7.41 (s, 2H), 6.47 (s, 2H), 2.23 (s, 6H)
Mass, m/z: 434 (M⁺), 271, 235, 164, 72 (base)

Synthesis scheme 28

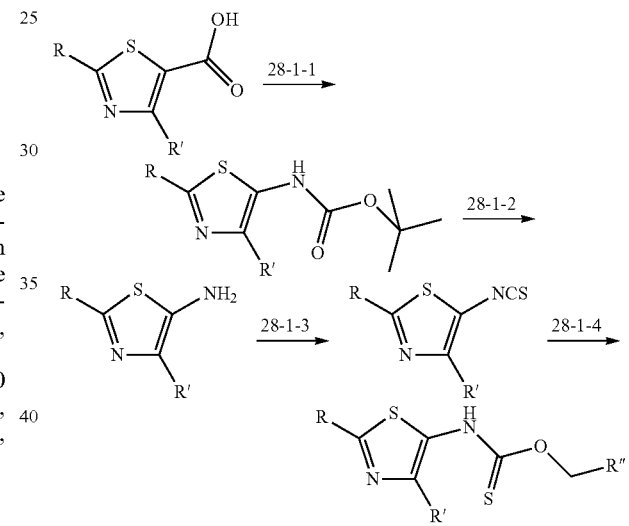

In the formulae, R and R″ are the same or different and each represent an aryl group which may have a substituent (such as a halogen atom or an alkoxy group), and R' represents an alkyl group.

Example 28-1

Step 28-1-1

[2-(4-Chloro-2-methoxyphenyl)-4-methylthiazol-5-yl]carbamic acid tert-butyl ester

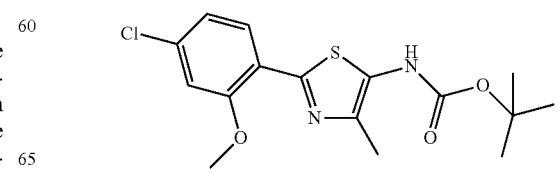

In tert-butanol (10 ml), 2-(4-chloro-2-methoxyphenyl)-4-methylthiazole-5-carboxylic acid (567 mg, 2.00 mmol) prepared in Example 7-1 was suspended, and triethylamine (243 mg, 2.40 mmol) and then diphenylphosphoryl azide (605 mg, 2.20 mmol) were added thereto. The mixture was heated under reflux for 16 hours. After being allowed to cool, the mixture was concentrated under a reduced pressure, and dissolved in chloroform. The resulting solution was washed with a saturated sodium bicarbonate solution, and then dried over anhydrous magnesium sulfate and concentrated. The concentrate was purified by silica gel column chromatography (n-hexane:ethyl acetate=1:1) to give the title compound (1.04 g, quantitative) as a white powder.

$^1$H-NMR (DMSO-d$_6$) δ: 8.16 (d, J=8.5 Hz, 1H), 7.34-7.27 (m, 1H), 7.17-7.12 (m, 1H), 4.02 (s, 3H), 2.32 (s, 3H), 1.94 (s, 9H)

Mass, m/z: 354 (M$^+$), 298

Step 28-1-2

5-Amino-2-(4-chloro-2-methoxyphenyl)-4-methylthiazole

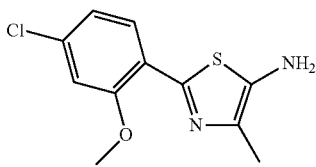 [SMILES: COc1cc(Cl)ccc1-c1nc(C)c(N)s1]

In methanol (25 ml), [2-(4-chloro-2-methoxyphenyl)-4-methylthiazol-5-yl]carbamic acid tert-butyl ester (1.02 g, 2.87 mmol) prepared in the Step 28-1-1 was dissolved, and a 4-N hydrogen chloride-dioxane solution (25 ml) was added thereto. The mixture was stirred at a room temperature for 16 hours. Chloroform was added to the mixture, and the resulting mixture was neutralized with a saturated sodium bicarbonate solution. The resulting mixture was subjected to extraction with chloroform. The extract was dried over anhydrous magnesium sulfate and then concentrated. The concentrate was purified by silica gel column chromatography (chloroform:methanol=20:1) to give the title compound (474 mg, 65%) as a light-brown powder.

$^1$H-NMR (DMSO-d$_6$) δ: 8.04 (d, J=8.5 Hz, 1H), 7.20 (d, J=2.3 Hz, 1H), 7.05 (dd, J=2.3, 8.5 Hz, 1H), 5.36 (brs, 2H), 3.96 (s, 3H), 2.18 (s, 3H)

Mass, m/z: 254 (M$^+$)

Step 28-1-3

2-(4-Chloro-2-methoxyphenyl)-5-isocyanate-4-methylthiazole

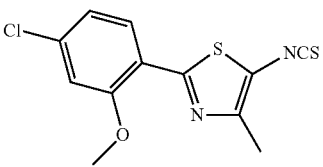

Sodium hydrogen carbonate (240 mg, 2.79 mmol) was dissolved in purified water (10 ml). To this solution, a solution (5 ml) of thiophosgene (240 mg, 2.05 mmol) in chloroform was added. Under stirring, a solution (5 ml) of 5-amino-2-(4-chloro-2-methoxyphenyl)-4-methylthiazole (474 mg, 1.86 mmol) prepared in the Step 28-1-2 in chloroform was added dropwise thereto, and the mixture was stirred at a room temperature for 4 hours. Chloroform was added to the mixture. The resulting mixture was washed with a saturated sodium bicarbonate solution, and then dried over anhydrous magnesium sulfate and concentrated. The concentrate was purified by silica gel column chromatography (n-hexane:ethyl acetate=4:1), crystallized from ethyl acetate-n-hexane, and separated by filtration. By drying the separated product under a reduced pressure, the title compound (480 mg, 87%) as a light-brown powder was obtained.

$^1$H-NMR (DMSO-d$_6$) δ: 8.21 (d, J=8.9 Hz, 1H), 7.38 (d, J=2.3 Hz, 1H), 7.19 (dd, J=1.9, 8.5 Hz, 1H), 4.06 (s, 3H), 2.42 (s, 3H)

Mass, m/z: 296 (M$^+$, base)

Step 28-1-4

[2-(4-Chloro-2-methoxyphenyl)-4-methylthiazol-5-yl]thiocarbamic acid O-(4-methoxybenzyl)ester

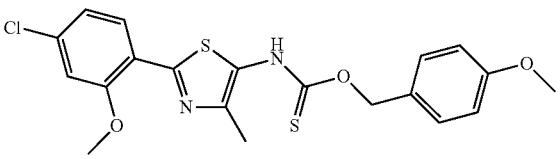 [SMILES: COc1ccc(COC(=S)Nc2sc(-c3ccc(Cl)cc3OC)nc2C)cc1]

In tetrahydrofuran (10 ml), 2-(4-chloro-2-methoxyphenyl)-5-isocyanate-4-methylthiazole (100 mg, 0.34 mmol) prepared in the Step 28-1-3 was dissolved, and 4-methoxybenzyl alcohol (70 mg, 0.51 mmol) was added thereto. The mixture was heated under reflux for 15 hours. After being allowed to cool, the mixture was purified by silica gel column chromatography (chloroform:methanol=20:1) to give the title compound (50 mg, 34%) as a white powder.

$^1$H-NMR (DMSO-d$_6$) δ: 8.21 (d, J=8.5 Hz, 1H), 7.32-7.28 (m, 1H), 7.23 (d, J=8.9 Hz, 2H), 7.13 (dd, J=1.9, 8.5 Hz, 1H), 6.88 (d, J=8.9 Hz, 2H), 4.16 (s, 2H), 4.04 (s, 3H), 3.28 (s, 3H), 2.34 (s, 3H)

Mass, m/z: 434 (M$^+$), 121 (base)

Synthesis scheme 29

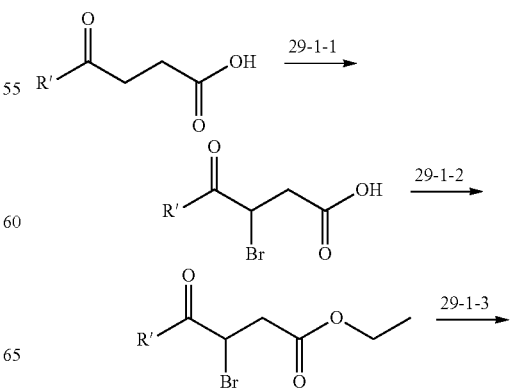

-continued

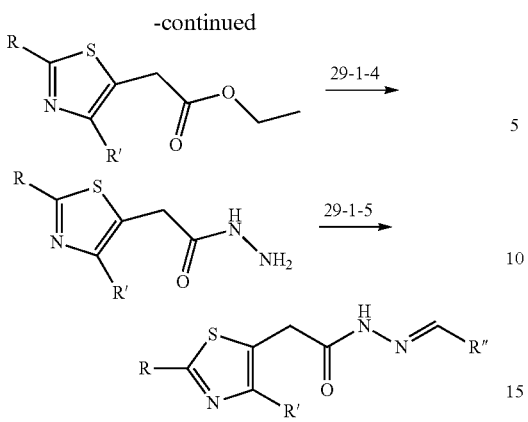

In the formulae, R and R″ are the same or different and each represent an aryl group which may have a substituent (such as a halogen atom or an alkoxy group), and R′ represents an alkyl group.

Example 29-1

Step 29-1-1

3-Bromo-4-oxopentanoic acid

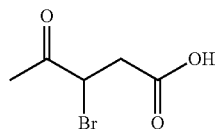

Concentrated hydrochloric acid (20 ml) was added to 4-oxopentanoic acid (5.0 g), and bromine was added dropwise thereto at −15° C. The mixture was stirred at a room temperature. After 4 hours, the reaction solution was poured into ice water (45 ml). The reaction solution was subjected to extraction with ethyl ether, and the organic layer was washed with a saturated saline solution, dried over anhydrous magnesium sulfate and then concentrated under a reduced pressure to give the title compound (7.06 g, 84%).

$^1$H-NMR (CDCl$_3$) δ: 4.61 (dd, J=5.4, 8.9 Hz, 1H), 3.32 (dd, J=8.9, 17.7 Hz, 1H), 2.94 (dd, J=5.4, 17.7 Hz, 1H), 2.42 (s, 3H)

Mass, m/z: 194 (M$^+$), 55 (base)

Step 29-1-2

Ethyl 3-bromo-4-oxopentanoate

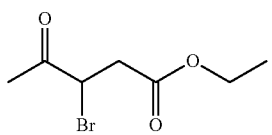

Ethanol (100 ml) and concentrated hydrochloric acid (0.05 ml) were added to 4-oxopentanoic acid (3.0 g) obtained in the Step 29-1-1, and the mixture was heated under reflux. After 10 hours, the mixture was neutralized with a 1-N sodium hydroxide aqueous solution and concentrated under a reduced pressure. Ethyl acetate was added to the residue, and the resulting mixture was filtered. The filtrate was concentrated under a reduced pressure. The residue was purified by silica gel column chromatography (ethyl acetate:n-hexane=1: 8) to give the title compound (1.42 g, 47%).

$^1$H-NMR (CDCl$_3$) δ: 4.64 (dd, J=5.8, 8.9 Hz, 1H), 4.14 (q, J=7.3 Hz, 2H), 3.25 (dd, J=8.9, 17.0 Hz, 1H), 2.88 (dd, J=5.8, 17.0 Hz, 1H), 2.41 (s, 3H), 1.25 (t, J=7.3 Hz, 3H)

Mass, m/z: 221 (M$^+$), 101 (base)

Step 29-1-3

Ethyl [2-(4-chloro-2-methoxyphenyl)-4-methylthiazol-5-yl]acetate

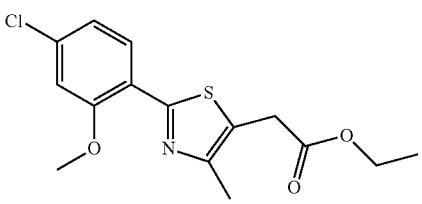 [SMILES: CCOC(=O)Cc1sc(-c2ccc(Cl)cc2OC)nc1C]

The title compound was obtained according to the same procedure as in the Step 23-1-1 except that ethyl 3-bromo-4-oxopentanoate obtained in the Step 29-1-2 and 4-chloro-2-methoxythiobenzamide were used instead of ethyl 2-chloroacetoacetate and 2,4-dichlorothiobenzamide, respectively.

$^1$H-NMR (CDCl$_3$) δ: 9.31 (d, J=8.5 Hz, 1H), 7.28 (dd, J=1.9, 8.5 Hz, 1H), 7.08 (d, J=1.9 Hz, 1H), 4.27 (q, J=7.3 Hz, 2H), 4.10 (s, 3H), 3.84 (s, 2H), 2.82 (s, 3H), 1.33 (t, J=7.3 Hz, 3H)

Mass, m/z: 325 (M$^+$), 252 (base)

Step 29-1-4

[2-(4-Chloro-2-methoxyphenyl)-4-methylthiazol-5-yl]acetic acid hydrazide

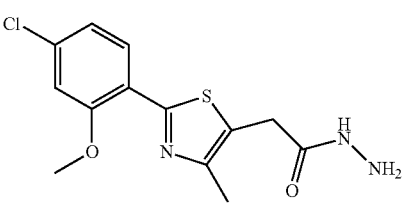 [SMILES: COc1cc(Cl)ccc1-c1nc(C)c(CC(=O)NN)s1]

The title compound was obtained according to the same procedure as in the Step 23-1-2 except that ethyl [2-(4-chloro-2-methoxyphenyl)-4-methylthiazol-5-yl]acetate obtained in the Step 29-1-3 was used instead of ethyl 2-(2,4-dichlorophenyl)-4-methylthiazole-5-carboxylate.

$^1$H-NMR (DMSO-d$_6$) δ: 9.27 (s, 1H), 8.20 (d, J=8.5 Hz, 1H), 7.32 (d, J=1.9 Hz, 1H), 7.13 (dd, J=1.9 Hz, 8.5 Hz, 1H), 4.27 (s, 2H), 4.03 (s, 3H), 3.58 (s, 3H), 2.50 (s, 3H)

Mass, m/z: 311 (M$^+$), 252 (base)

Step 29-1-5

[2-(4-Chloro-2-methoxyphenyl)-4-methylthiazol-5-yl]acetic acid[1-(4-methoxyphenyl)methylidene]hydrazide

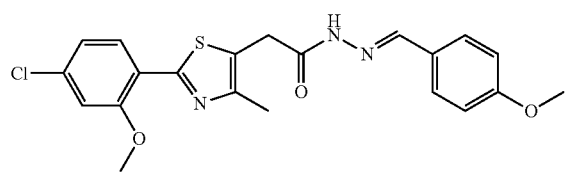 [SMILES: COc1ccc(/C=N/NC(=O)Cc2sc(-c3ccc(Cl)cc3OC)nc2C)cc1]

The title compound was obtained according to the same procedure as in the Step 23-1-3 except that [2-(4-chloro-2-methoxyphenyl)-4-methylthiazol-5-yl]acetic acid hydrazide obtained in the Step 29-1-4 and 4-methoxybenzaldehyde were used instead of 2-(2,4-dichlorophenyl)-4-methylthiazole-5-carboxylic acid hydrazide and 3-hydroxy-4-methoxybenzaldehyde, respectively.

$^1$H-NMR (DMSO-$d_6$) δ: 11.52 and 11.36 (two s, 1H), 8.22 and 8.21 (two d, J=8.5 Hz, 1H), 8.18 and 7.98 (two s, 1H), 7.70 and 7.64 (two d, J=8.9 Hz, 2H), 7.32 and 7.28 (d, J=2.3 Hz, 1H), 7.14 and 7.13 (two dd, J=2.3, 8.5 Hz, 1H), 7.04 and 7.01 (d, J=8.9 Hz, 2H), 4.16 and 4.03 (two s, 2H), 3.92 and 3.78 (two s, 3H), 3.82 and 3.80 (two s, 3H), 2.41 and 2.40 (s, 3H)

Mass, m/z: 429 (M$^+$), 295, 252, 128, 85 (base)

Example 29-2

[2-(4-Chloro-2-methoxyphenyl)-4-methylthiazol-5-yl]acetic acid[1-(4-hydroxy-3,5-dimethylphenyl)methylidene]hydrazide

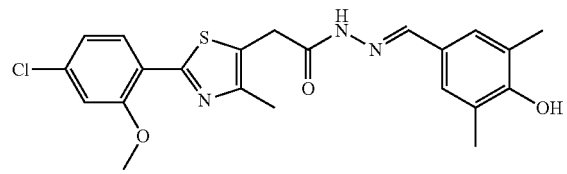 [SMILES: COc1cc(Cl)ccc1-c1nc(C)c(CC(=O)N/N=C/c2cc(C)c(O)c(C)c2)s1]

The title compound was obtained according to the same procedure as in Example 29-1 except that 4-hydroxy-3,5-dimethylbenzaldehyde was used instead of 4-methoxybenzaldehyde.

$^1$H-NMR (DMSO-$d_6$) δ: 11.43 and 11.26 (two s, 1H), 8.71 (s, 1H), 8.22 and 8.21 (two d, J=8.5 Hz, 1H), 8.04 and 7.87 (two s, 1H), 7.33-7.27 (m, 3H), 7.14 and 7.13 (two dd, J=2.3, 8.5 Hz, 1H), 4.15 and 4.03 (two s, 2H), 3.93 and 3.76 (two s, 3H), 2.41 and 2.39 (two s, 3H), 2.21 and 2.19 (two s, 6H)

Mass, m/z: 443 (M$^+$), 295, 252, 128, 85 (base)

Synthesis scheme 30

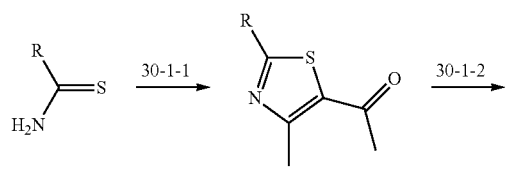

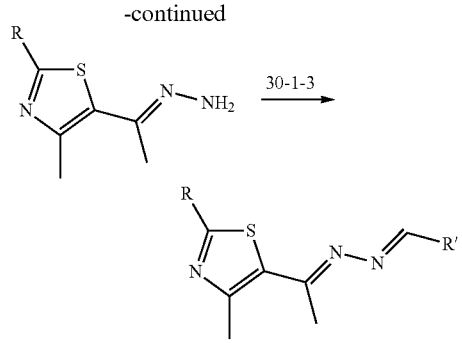

In the formulae, R and R' are the same or different and each represent an aryl group which may have a substituent (such as a halogen atom, an alkyl group, a hydroxyl group, or an alkoxy group).

Example 30-1

Step 30-1-1

1-[2-(4-Chlorophenyl)-4-methylthiazol-5-yl]-ethanone

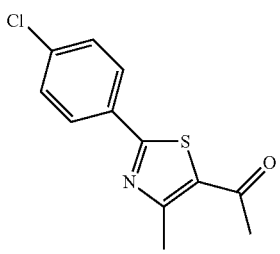 [SMILES: CC(=O)c1sc(-c2ccc(Cl)cc2)nc1C]

3-Chloro-pentane-2,4-dione (540 mg) 4-chloro-thiobenzamide (688 mg) were dissolved in ethanol (10 ml), and the mixture was heated under reflux for 21 hours. After the mixture was allowed to cool, the precipitated crystal was separated by filtration, washed with ethanol, and dried to give the title compound (582 mg, 58%).

$^1$H-NMR (CDCl$_3$) δ: 8.02 (dt, J=1.9, 2.7, 8.5 Hz, 2H), 7.60 (dt, J=1.9, 2.3, 2.7, 8.8 Hz, 2H), 2.72 (s, 3H), 2.58 (s, 3H)

Mass, m/z: 251 (M$^+$), 236 (base)

Step 30-1-2

{1-[2-(4-Chlorophenyl)-4-methylthiazol-5-yl]ethylidene}-hydrazine

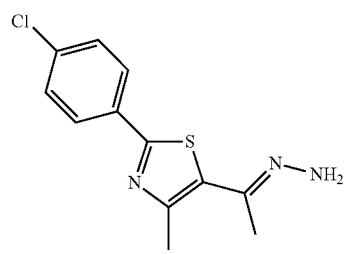 [SMILES: C/C(=N\N)c1sc(-c2ccc(Cl)cc2)nc1C]

507

In ethanol (10 ml), 1-[2-(4-chlorophenyl)-4-methylthiazol-5-yl]-ethanone (205 mg) prepared in the Step 30-1-1 was dissolved, and hydrazine monohydrate (1.2 g) was added thereto. The mixture was heated under reflux for 21 hours. The mixture was concentrated under a reduced pressure, and then water was added thereto. The precipitated crystal was separated by filtration, washed with water, and dried to give the title compound (196 mg, 91%).

¹H-NMR (DMSO-d₆) δ: 7.88 (dt, J=1.9, 2.7, 8.5 Hz, 2H), 7.53 (dt, J=1.9, 2.7, 8.5 Hz, 2H), 6.59 (br, 2H), 2.53 (s, 3H), 2.11 (s, 3H)

Mass, m/z: 265 (M⁺) (base)

Step 30-1-3

4-{[1-[2-(4-Chlorophenyl)-4-methylthiazol-5-yl]ethylidene]hydrazonomethyl}-2,6-dimethyl-phenol

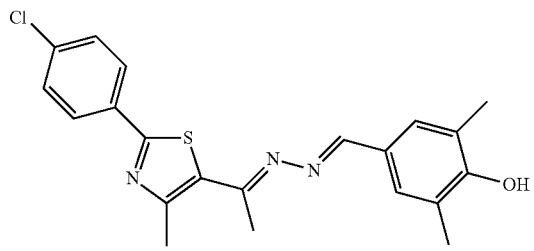 [SMILES: C/C(=N\N=C\c1cc(C)c(O)c(C)c1)c1sc(-c2ccc(Cl)cc2)nc1C]

In ethanol (3 ml), {1-[2-(4-chlorophenyl)-4-methylthiazol-5-yl]ethylidene}-hydrazine (40 mg) prepared in the Step 30-1-2 and 4-hydroxy-3,5-dimethylbenzaldehyde (29 mg) was heated under reflux for 20 hours. After the mixture was allowed to cool, the precipitated crystal was separated by filtration to give the title compound (23 mg, 38%).

¹H-NMR (DMSO-d₆) δ: 8.92 (s, 1H), 8.35 (s, 1H), 7.98 (dt, J=1.9, 2.7, 8.5 Hz, 2H), 7.57 (dt, J=1.9, 2.7, 8.5 Hz, 2H), 7.48 (s, 2H), 2.71 (s, 3H), 2.59 (s, 3H), 2.22 (s, 6H)

Mass, m/z: 397 (M⁺), 150 (base)

Example 30-2

4-{[1-[2-(4-Chlorophenyl)-4-methylthiazol-5-yl]ethylidene]hydrazonomethyl}-2,6-dimethyl-phenol

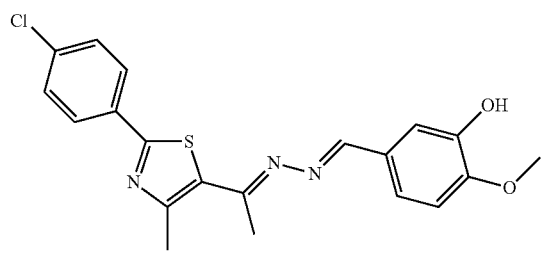 [SMILES: COc1ccc(/C=N/N=C(\C)c2sc(-c3ccc(Cl)cc3)nc2C)cc1O]

The title compound was obtained according to the same procedure as in Example 30-1 except that 3-hydroxy-4-methoxybenzaldehyde was used instead of 4-hydroxy-3,5-dimethylbenzaldehyde.

¹H-NMR (DMSO-d₆) δ: 9.31 (s, 1H), 8.38 (s, 1H), 7.98 (dt, J=2.0, 2.3, 2.7, 8.5 Hz, 2H), 7.58 (dt, J=1.9, 2.7, 8.5 Hz, 2H), 7.41 (d, J=1.9 Hz, 1H), 7.26 (dd, J=1.9, 8.1 Hz, 1H), 7.03 (d, J=8.5 Hz, 1H), 3.84 (s, 3H), 2.72 (s, 3H), 2.59 (s, 3H)

Mass, m/z: 399 (M⁺), 248 (base)

508

Example 30-3

2-Methoxy-5-{[1-[2-(2-methoxyphenyl)-4-methylthiazol-5-yl]ethylidene]hydrazonomethyl}phenol

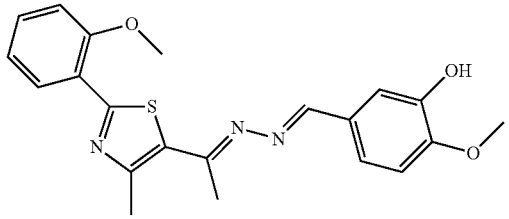 [SMILES: COc1ccc(/C=N/N=C(\C)c2sc(-c3ccccc3OC)nc2C)cc1O]

The title compound was obtained according to the same procedure as in Example 30-1 except that 2-methoxythiobenzamide and 3-hydroxy-4-methoxybenzaldehyde were used instead of 4-chlorothiobenzamide and 4-hydroxy-3,5-dimethylbenzaldehyde, respectively.

¹H-NMR (DMSO-d₆) δ: 9.29 (s, 1H), 8.41 (s, 1H), 8.31 (dd, J=1.6 Hz, J=7.7 Hz, 1H), 7.50 (ddd, J=1.6 Hz, J=7.3 Hz, J=8.5 Hz, 1H), 7.41 (d, J=2.3 Hz, 1H), 7.26 (dd, J=2.0 Hz, J=8.5 Hz, 2H), 7.12 (td, J=0.8 Hz, J=8.1 Hz, 1H), 7.03 (d, J=8.5 Hz, 1H), 4.05 (s, 3H), 3.84 (s, 3H), 2.72 (s, 3H), 2.59 (s, 3H)

Mass, m/z: 395 (M⁺) (base)

Synthesis scheme 31

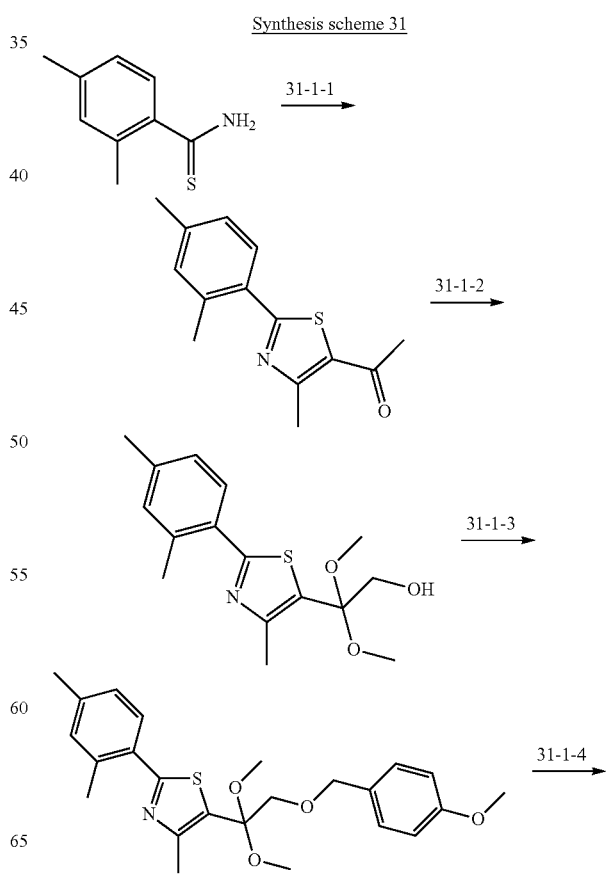

-continued

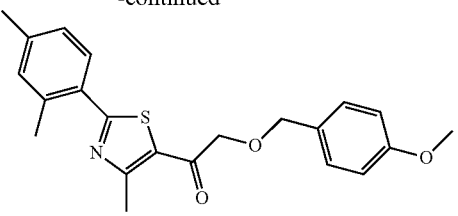

Example 31-1

Step 31-1-1

1-[2-(2,4-Dimethylphenyl)-4-methylthiazol-5-yl]ethanone

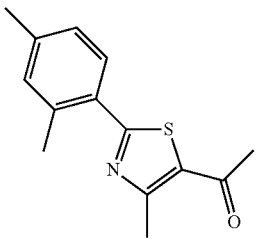 [SMILES: CC(=O)c1sc(-c2ccc(C)cc2C)nc1C]

To ethanol (20 ml), 2,4-dimethylthiobenzamide (2.00 g) and 3-chloropentane-2,4-dione (1.79 g) were added, and the mixture was stirred under heat reflux for 4 hours. After the mixture was allowed to cool to a room temperature, from the mixture ethanol was distilled off under a reduced pressure. To the resulting residue, ethyl acetate was added, and the mixture was heated and stirred. After the mixture was allowed to cool to a room temperature, the precipitate was separated by filtration, washed with ethyl acetate, and then dried under a reduced pressure to give the title compound (1.10 g, 37%).

$^1$H-NMR (CDCl$_3$) δ: 8.11 (d, J=7.7 Hz, 1H), 7.25 (d, J=6.2 Hz, 1H), 7.19 (s, 1H), 3.08 (s, 3H), 2.65 (s, 3H), 2.63 (s, 3H), 2.39 (s, 3H)

Mass, m/z: 245 (M$^+$, base)

Step 31-1-2

2-[2-(2,4-Dimethylphenyl)-4-methylthiazol-5-yl]-2,2-dimethoxyethanol

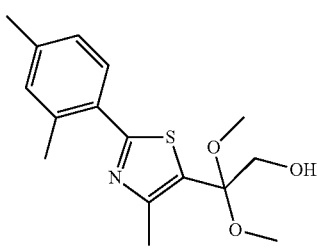 [SMILES: COC(CO)(OC)c1sc(-c2ccc(C)cc2C)nc1C]

To methanol (5 ml), 1-[2-(2,4-dimethylphenyl)-4-methylthiazol-5-yl]ethanone (981 mg) prepared in the Step 31-1-1 was added, and a solution of potassium hydroxide (673 mg) in methanol (10 ml) was added dropwise thereto under cooling by ice and stirring. Thereafter, iodobenzene diacetate (1.42 g) was added to the mixture, and then the resulting mixture was stirred at a room temperature for 22 hours. From the mixture methanol was distilled off under a reduced pressure, and water was added to the residue. The resulting mixture was subjected to extraction with dichloromethane. The extract was dried over anhydrous sodium sulfate, and then dichloromethane was distilled off under a reduced pressure. Hexane was added to the residue, the precipitate was separated by filtration, washed with hexane, and then dried under a reduced pressure to give the title compound (328 mg, 26%).

$^1$H-NMR (CDCl$_3$) δ: 7.64, 7.63 (two d, J=7.7 Hz, 1H), 7.07 (s, 1H), 7.05 (dd, J=1.2, 7.7 Hz, 1H), 3.89 (d, J=6.6 Hz, 2H), 3.31 (s, 6H), 2.54 (s, 3H), 2.48 (s, 3H), 2.34 (s, 3H), 1.74 (t, J=6.6 Hz, 1H)

Mass, m/z: 307 (M$^+$), 276 (base)

Step 31-1-3

5-[1,1-Dimethoxy-2-(4-methoxybenzyloxy)ethyl]-2-(2,4-dimethylphenyl)-4-methylthiazole

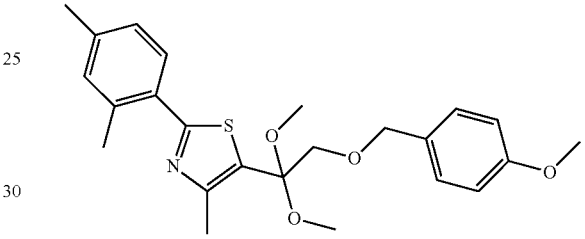

To N,N-dimethylformamide (2 ml), 2-[2-(2,4-dimethylphenyl)-4-methylthiazol-5-yl]-2,2-dimethoxyethanol (100 mg) prepared in the Step 31-1-2 and 4-methoxybenzyl chloride (61 mg) were added, and 60% sodium hydride suspension in oil (20 mg) was added thereto under an argon atmosphere. Then, the mixture was stirred at a room temperature for 4 hours. Ice water was added to the reaction solution, and then the mixture was subjected to extraction with ethyl acetate. The extract was dried over anhydrous sodium sulfate, and then concentrated under a reduced pressure. The residue was purified by thin-layer chromatography (hexane:ethyl acetate=3:1) to give the title compound (90 mg, 64%).

$^1$H-NMR (CDCl$_3$) δ: 7.64 (d, J=7.7 Hz, 1H), 7.09 to 7.04 (m, 4H), 6.78 (d, J=8.8 Hz, 2H), 4.40 (s, 2H), 3.76 (s, 3H), 3.70 (s, 2H), 3.27 (s, 6H), 2.56 (s, 3H), 2.34 (s, 6H)

Mass, m/z: 427 (M$^+$), 121 (base)

Step 31-1-4

1-[2-(2,4-Dimethylphenyl)-4-methylthiazol-5-yl]-2-(4-methoxybenzyloxy)ethanone

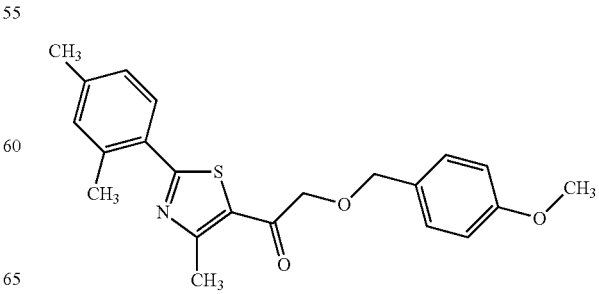

To dichloromethane (2 ml), 5-[1,1-dimethoxy-2-(4-methoxybenzyloxy)ethyl]-2-(2,4-dimethylphenyl)-4-methylthiazole (35 mg) prepared in the Step 31-1-3 was added, and trifluoroacetic acid (0.3 ml) and water (0.1 ml) were added thereto. Thereafter, the mixture was stirred at a room temperature for 5 hours. To the reaction solution, a saturated sodium bicarbonate solution was added, and then the resulting mixture was subjected to extraction with chloroform. The extract was washed with a saturated saline solution, and then dried over sodium sulfate and concentrated under a reduced pressure. The residue was purified by thin-layer chromatography (hexane:ethyl acetate=3:1, toluene:ethyl acetate=3:1) to give the title compound (18 mg, 57%).

$^1$H-NMR (CDCl$_3$) δ: 7.71 (d, J=8.1 Hz, 1H), 7.32 (d, J=8.5 Hz, 2H), 7.11 (s, 1H), 7.09 (d, J=8.1 Hz, 1H), 6.89 (d, J=8.9 Hz, 2H), 4.61 (s, 2H), 4.41 (s, 2H), 3.81 (s, 3H), 2.80 (s, 3H), 2.56 (s, 3H), 2.36 (s, 3H)

Mass, m/z: 383 (M$^+$), 245 (base)

Synthesis scheme 32

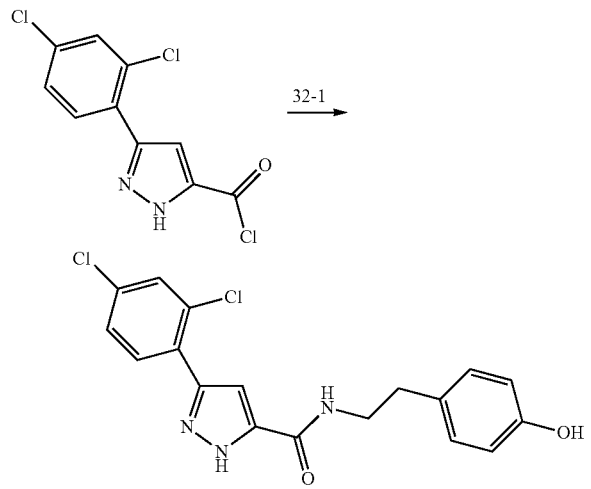

Example 32-1

Step 32-1

5-(2,4-Dichlorophenyl)-2H-pyrazole-3-carboxylic acid[2-(4-hydroxyphenyl)-ethyl]-amide

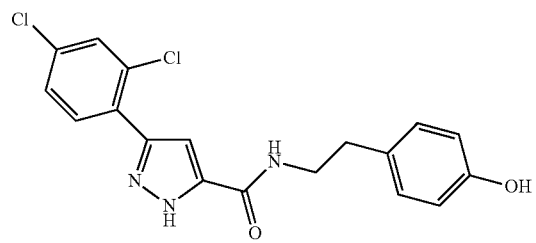 [SMILES: O=C(NCCc1ccc(O)cc1)c1cc(-c2ccc(Cl)cc2Cl)n[nH]1]

In pyridine (6 ml), 4-(2-amino-ethyl)-phenol (72 mg) was dissolved, and 5-(2,4-dichlorophenyl)-2H-pyrazole-3-carboxylic acid chloride (137 mg) was added thereto under an ice cooling while stirring. Thereafter, the mixture was stirred at a room temperature for 17 hours and then concentrated under a reduced pressure, and the concentrate was purified by silica gel column chromatography (5% methanol-chloroform) to give the title compound (132 mg, 70%).

$^1$H-NMR (DMSO-d$_6$): 13.84 and 13.62 (two s, 1H), 9.15 and 9.14 (two s, 1H), 8.62 and 8.16 (t, J=5.4 Hz, 1H), 7.86 and 7.68 (two d, J=8.5 Hz, 1H), 7.80 and 7.70 (two d, J=2.3 Hz, 1H), 7.58 and 7.50 (two dd, J=1.9, 8.5 Hz, 1H), 7.40 and 6.98 (two d, J=1.6 Hz, 1H), 7.03 (d, J=8.5 Hz, 2H), 6.68 (d, J=8.5 Hz, 2H), 3.42 (q, J=7.3 Hz, 2H), 2.73 (q, J=7.7 Hz, 2H)

Mass, m/z: 375 (M$^+$), 120 (base)

Synthesis scheme 33

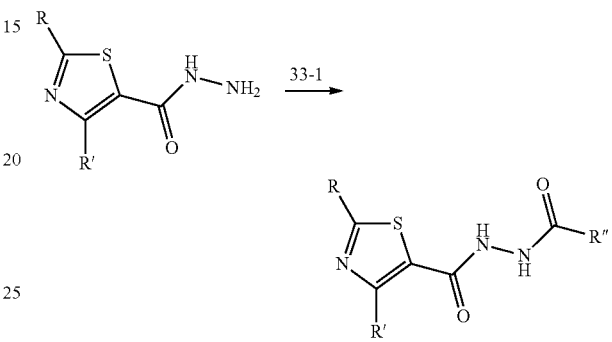

In the formulae, R and R" are the same or different and each represent an aryl group which may have a substituent (such as a halogen atom, an alkyl group, a hydroxyl group, or an alkoxy group), and R' represents an alkyl group.

Example 33-1

Step 33-1

3-Hydroxy-4-methoxy-benzoic acid N'-[2-(4-chlorophenyl)-4-methylthiazole-5-carbonyl]hydrazide

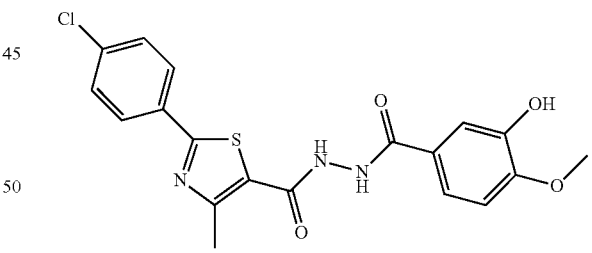

In pyridine (4 ml), 2-(4-chloro-phenyl)-4-methyl-thiazole-5-carboxylic acid hydrazide (120 mg) and 3-hydroxy-4-methoxy-benzoyl chloride (84 mg) were stirred for 24 hours at a room temperature. The mixture was concentrated under a reduced pressure, and then diluted hydrochloric acid was added thereto. The precipitated crystal was separated by filtration and dried, and the resulting crystal was recrystallized from ethanol to give the title compound (46 mg, 24%).

$^1$H-NMR (DMSO-d$_6$): 10.32 (s, 1H), 10.26 (s, 1H), 9.28 (s, 1H), 8.00 (d, J=8.5 Hz, 2H), 7.60 (d, J=8.5 Hz, 2H), 7.42 (dd, J=1.5, 8.1 Hz, 1H), 7.37 (s, 1H), 7.04 (d, J=8.5 Hz, 1H), 3.84 (s, 3H), 2.68 (s, 3H)

Mass, m/z: 417 (M$^+$), 151 (base)

Synthesis scheme 34

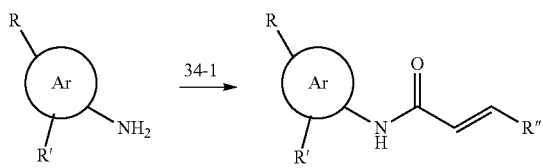

In the formulae, Ar represents a thiazole ring which may have an aryl group as a substituent; R and R' are the same or different and each represent a halogen atom, an alkyl group, a hydroxyl group or an alkoxy group; R" represents an aryl group which may have a substituent (such as an alkoxy group).

Example 34-1

Step 34-1

N-[2-(4-Chloro-2-methoxyphenyl)-4-methylthiazol-5-yl]-3-(4-methoxyphenyl)acrylamide

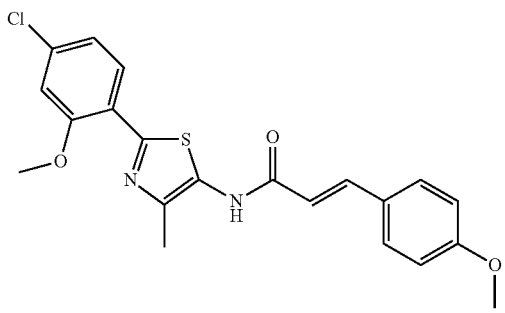

4-Methoxycinnamic acid (178 mg, 1.0 mmol) and thionyl chloride (480 mg, 4.0 mmol) were heated under reflux for 2 hours. The excess thionyl chloride was distilled off. The resulting residue was dissolved in pyridine (1 ml). Under an ice cooling, the resulting solution was added to a solution of 5-amino-2-(4-chloro-2-methoxyphenyl)-4-methylthiazole (254 mg, 1.0 mmol) prepared in the Step 28-1-2 in pyridine (4 ml). After the removal of the ice bath, the mixture was stirred for 16 hours at a room temperature. To the mixture, 3.5% hydrochloric acid was added, and the resulting mixture was subjected to extraction with chloroform. The extract was washed with water. The washed product was dried over anhydrous magnesium sulfate, and the solvent was distilled off. The resulting residue was purified by silica gel column chromatography (chloroform:methanol=30:1) to give the title compound (54 mg, 13%).

$^1$H-NMR (CDCl$_3$) δ: 8.25 (d, J=8.5 Hz, 1H), 7.79 (d, J=15.4 Hz, 1H), 7.53 (s, 1H), 7.51 (d, 8.5 Hz, 2H), 7.02 (dd, J=1.9, 8.5 Hz, 1H), 6.98 (d, J=1.9 Hz, 1H), 6.91 (d, J=8.9 Hz, 2H), 6.48 (d, J=15.4 Hz, 1H), 4.01 (s, 3H), 3.84 (s, 3H), 2.47 (s, 3H)

Mass, m/z: 414 (M$^+$), 161 (base)

Synthesis scheme 35

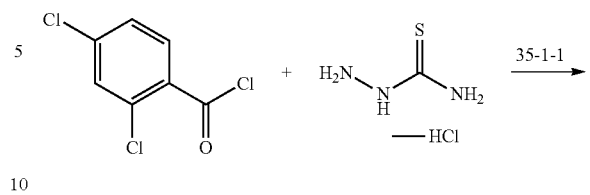

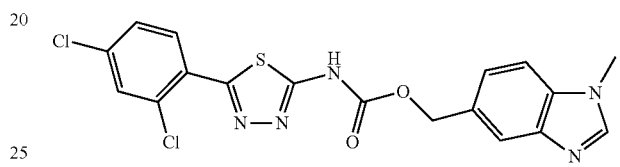

Example 35-1

Step 35-1-1

5-(2,4-Dichlorophenyl)-[1,3,4]thiadiazol-2-ylamine

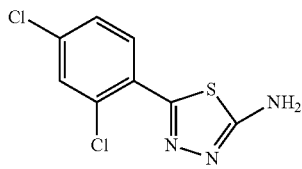 [SMILES: Nc1nnc(-c2ccc(Cl)cc2Cl)s1]

Thiosemicarbazide hydrochloride (2.55 g, 20.0 mmol) was mixed to pyridine (20 ml), and 2,4-dichlorobenzoyl chloride (2.81 ml) was added thereto. The mixture was stirred at a room temperature for 14 hours. The solvent was distilled off. Water was added to the resulting residue, and the mixture was stirred. The precipitate was separated by filtration. 2,4-Dichlorobenzoylthiosemicarbazide (2.11 g, 8.00 mmol) obtained from the precipitate by through circulation drying was mixed to toluene (25 ml), and methanesulfonic acid (0.78 ml) was added to the mixture. The resulting mixture was heated and stirred for 6 hours. The mixture was allowed to cool to a room temperature. Then, the precipitate was separated by filtration, neutralized with water and 25% ammonia water, and stirred for 30 minutes. The precipitate was separated by filtration, washed with water, and subjected to through circulation drying to give the title compound (1.14 g, 58%) as a white substance.

$^1$H-NMR (DMSO-d$_6$) δ: 8.03 (d, J=8.9 Hz, 1H), 7.79 (d, J=2.3 Hz, 1H), 7.55 (dd, J=2.3, 8.5 Hz, 1H), 7.49 (s, 2H)

Mass, m/z: 245, 247 (M$^+$), 74 (base)

Step 35-1-2

[5-(2,4-Dichlorophenyl)-[1,3,4]thiadiazol-2-yl]carbamic acid 1-methyl-1H-benzimidazol-5-ylmethyl ester

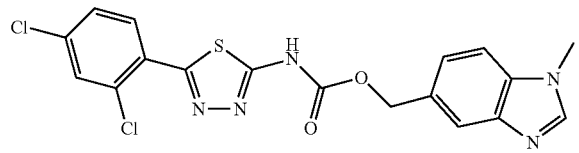 [SMILES: Cn1cnc2cc(COC(=O)Nc3nnc(-c4ccc(Cl)cc4Cl)s3)ccc21]

In tetrahydrofuran (20 ml), 5-(2,4-dichlorophenyl)-[1,3,4]thiadiazol-2-ylamine (80 mg, 0.33 mmol) was suspended, and phenyl chlorocarbonate (56 mg, 0.36 mmol) and triethylamine (36 mg, 0.36 mmol) were added thereto. The mixture was stirred at a room temperature for one hour. To the mixture, (1-methyl-1H-benzimidazol-5-yl)methanol (63 mg, 0.39 mmol) and 1,8-diazabicyclo[5.4.0]undec-7-ene (60 mg, 0.39 mmol) were added, and the resulting mixture was heated and stirred for one hour. After the resulting mixture was allowed to cool, the precipitate was washed with a small quantity of chloroform to give the title compound (20 mg, 14%) as a light-brown substance.

$^1$H-NMR (DMSO-d$_6$) δ: 12.47 (brs, 1H), 8.22 (s, 1H), 8.13 (d, J=8.5 Hz, 1H), 7.88 (d, J=2.3 Hz, 1H), 7.76 (s, 1H), 7.61 (dd, J=2.3, 8.5 Hz, 1H), 7.60 (d, J=8.1 Hz, 1H), 7.38 (dd, J=1.5, 8.5 Hz, 1H), 5.40 (s, 2H), 3.85 (s, 3H)

Mass, m/z: 389 (M$^+$-44), 133 (base)

Example 35-2

[5-(2,4-Dichlorophenyl)-[1,3,4]thiadiazol-2-yl]carbamic acid 1-methyl-1H-indazol-5-ylmethyl ester

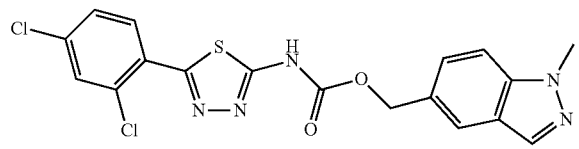 [SMILES: Cn1ncc2cc(COC(=O)Nc3nnc(-c4ccc(Cl)cc4Cl)s3)ccc21]

The title compound was obtained according to the same procedure as in Example 35-1 except that (1-methyl-1H-indazol-5-yl)methanol was used instead of (1-methyl-1H-benzimidazol-5-yl)methanol.

$^1$H-NMR (DMSO-d$_6$) δ: 12.47 (brs, 1H), 8.13 (d, J=8.5 Hz, 1H), 8.09 (d, J=8.5 Hz, 1H), 7.89 (d, J=2.3 Hz, 1H), 7.86 (s, 1H), 7.68 (d, J=8.9 Hz, 1H), 7.62 (dd, J=2.3, 8.5 Hz, 1H), 7.49 (dd, J=1.5, 8.5 Hz, 1H), 5.39 (s, 2H), 4.06 (s, 3H)

Mass, m/z: 433 (M$^+$), 389, 145 (base)

Synthesis scheme 36

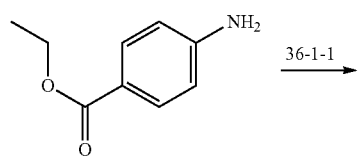

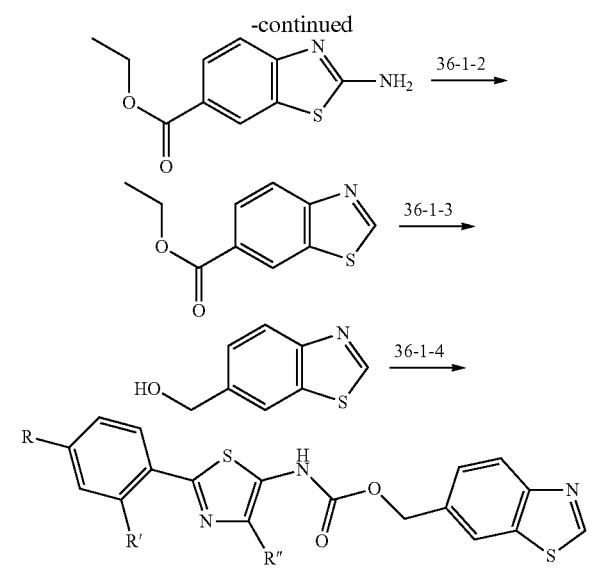

In the formulae, R and R' are the same or different and each represent a halogen atom, an alkyl group, a hydroxyl group or an alkoxy group; and R" represents an alkyl group.

Example 36-1

Step 36-1-1

Ethyl 2-aminobenzothiazole-6-carboxylate

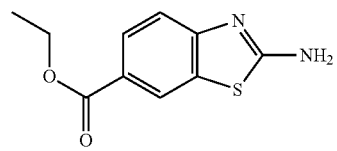

Ethyl 4-aminobenzoate (23.2 g, 140.4 mmol) and potassium thiocyanate (40.9 g, 420.9 mmol) were dissolved in acetic acid (280 ml), and under an ice cooling, bromine (22.4 g, 140.4 mmol) was slowly added thereto. The mixture was stirred under an ice cooling for 10 minutes and then stirred at a room temperature overnight. To the mixture, purified water was added and then ice was added. Thereafter, the resulting mixture was neutralized with ammonia water. The precipitate was separated by filtration, washed with purified water, and then subjected to through circulation drying to give the title compound (25.2 g, 81%) as a white powder.

$^1$H-NMR (DMSO-d$_6$) δ: 8.28 (d, J=1.5 Hz, 1H), 7.87 (brs, 2H), 7.82 (dd, J=1.9, 8.5 Hz, 1H), 7.37 (d, J=8.5 Hz, 1H), 4.29 (q, J=6.9 Hz, 2H), 1.32 (t, J=6.9 Hz, 3H)

Mass, m/z: 222 (M$^+$), 177 (base)

Step 36-1-2

Ethyl benzothiazole-6-carboxylate

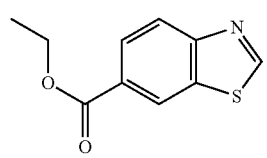

Ethyl 2-aminobenzothiazole-6-carboxylate (7.78 g, 35.0 mmol) prepared in the Step 36-1-1 was dissolved in tetrahydrofuran (100 ml). Amyl nitrite (8.2 g, 70.0 mmol) was added thereto, and the mixture was heated under reflux. After 1.5 hours, amyl nitrite (3.5 g, 30.0 mmol) was added thereto, and the resulting mixture was heated under reflux. After another 0.5 hours, amyl nitrite (2.6 g, 22.3 mmol) was added thereto, and the resulting mixture was heated under reflux. After being heated under reflux for another 3 hours, the resulting mixture was concentrated under a reduced pressure. The concentrate was purified by silica gel column chromatography (chloroform:methanol=100:1-20:1, and then n-hexane:ethyl acetate=3:1) to give the title compound (5.1 g, 70%) as a light-brown powder.

$^1$H-NMR (DMSO-d$_6$) δ: 9.60 (s, 1H), 8.84 (d, J=1.5 Hz, 1H), 8.29 (d, J=8.5 Hz, 1H), 8.11 (d, J=8.5 Hz, 1H), 4.37 (q, J=7.3 Hz, 2H), 1.36 (t, J=7.3 Hz, 3H)

Mass, m/z: 207 (M$^+$), 162

Step 36-1-3

Benzothiazol-6-ylmethanol

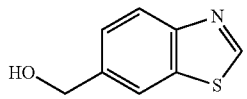 [SMILES: OCc1ccc2ncsc2c1]

Ethyl benzothiazole-6-carboxylate (2.10 g, 10.0 mmol) prepared in the Step 36-1-2 was dissolved in dichloromethane (80 ml), and under an ice cooling, a solution (1.5 mol/L) (20 ml, 30.0 mmol) of diisobutylaluminum hydride in hexane was slowly added thereto. The mixture was stirred at a room temperature for one hour, and then ethyl acetate (10 ml) and a saturated sodium bicarbonate solution were added to the mixture. Ethyl acetate and water were added thereto, the resulting mixture was subjected to extraction with ethyl acetate. The extract was dried over anhydrous magnesium sulfate and then concentrated. The residue was purified by silica gel column chromatography (n-hexane:ethyl acetate=1:1) to give the title compound (0.61 g, 37%) as a yellowish-brown oily substance.

$^1$H-NMR (DMSO-d$_6$) δ: 9.33 (s, 1H), 8.08 (s, 1H), 8.03 (d, J=8.5 Hz, 1H), 7.49 (dd, J=1.5, 8.1 Hz, 1H), 5.33 (t, J=5.8 Hz, 1H), 4.65 (d, J=5.8 Hz, 2H)

Mass, m/z: 165 (M$^+$), 136 (base)

Step 36-1-4

[2-(4-Chloro-2-methylphenyl)-4-methylthiazol-5-yl] carbamic acid benzothiazol-6-ylmethyl ester

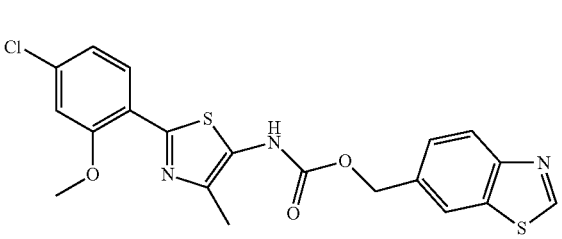 [SMILES: COc1cc(Cl)ccc1-c1nc(C)c(NC(=O)OCc2ccc3ncsc3c2)s1]

The title compound was obtained according to the same procedure as in Example 9-1 except that the compound prepared in Step 36-1-3 was used instead of (1,2,3,4-tetrahydrobenzo[4,5]imidazo[1,2-a]pyridin-7-ylmethanol.

$^1$H-NMR (DMSO-d$_6$) δ: 10.16 (brs, 1H), 9.43 (s, 1H), 8.26 (s, 1H), 8.17 (d, J=8.5 Hz, 1H), 8.13 (d, J=8.5 Hz, 1H), 7.63 (d, J=8.5 Hz, 1H), 7.30 (d, J=1.9 Hz, 1H), 7.12 (dd, J=1.9, 8.5 Hz, 1H), 5.36 (s, 2H), 4.01 (s, 3H), 2.32 (s, 3H)

Mass, m/z: 445 (M$^+$), 401

Examples 36-2 to 36-5

The objective compounds were obtained according to the same procedure as in Example 9-1 except that the carboxylic acids or hydroxy compounds obtained in Examples or Steps shown in the following table were used instead of 2-(4-chloro-2-methoxyphenyl)-4-methylthiazole-5-carboxylic acid or (1,2,3,4-tetrahydrobenzo[4,5]imidazo[1,2-a]pyridin-7-yl)methanol.

TABLE 211

| Carboxylic acid | Hydroxy compound | Example | $^1$H-NMR | Mass, m/z |
|---|---|---|---|---|
| Example 7-14 | Step 36-1-3 | Example 36-2 | (DMSO-d$_6$) δ: 10.15 (brs, 1H), 9.43 (s, 1H), 8.26 (s, 1 H), 8.13 (d, J = 8.5 Hz, 1H), 8.05 (d, J = 8.1 Hz, 1 H), 7.63 (d, J = 8.1 Hz, 1H), 7.02 (s, 1H), 6.88 (d, J = 8.1 Hz, 1H), 5.35 (s, 2H), 3.96 (s, 3H), 2.35 (s, 3H), 2.30 (s, 3H) | 425 (M$^+$), 381 |

TABLE 211-continued

| Carboxylic acid | Hydroxy compound | Example | ¹H-NMR | Mass, m/z |
|---|---|---|---|---|
| Example 7-15 | Step 36-1-3 | Example 36-3 | (DMSO-d$_6$) δ: 9.94 (brs, 1H), 9.43 (s, 1H), 8.25 (s, 1H), 8.13 (d, J = 8.5 Hz, 1H), 8.08 (d, J = 8.9 Hz, 1H), 7.62 (d, J = 8.5 Hz, 1H), 6.73 (d, J = 2.3 Hz, 1H), 6.66 (dd, J = 2.3, 8.5 Hz, 1H), 5.34 (s, 2H), 3.97 (s, 3H), 3.83 (s, 3H), 2.28 (s, 3H) | 441 (M$^+$), 395 |
| Example 7-16 | Step 36-1-3 | Example 36-4 | (DMSO-d$_6$) δ: 10.17 (brs, 1H), 9.24 (s, 1H), 8.26 (s, 1H), 8.13 (d, J = 8.5 Hz, 1H), 7.63 (d, J = 8.5 Hz, 1H), 7.55 (d, J = 8.1 Hz, 1H), 7.14 (s, 1H), 7.09 (d, J = 8.1 Hz, 1H), 5.36 (s, 2H), 2.31 (s, 3H), 2.31 (s, 3H) | 409 (M$^+$), 365 |
| Example 7-30 | Step 36-1-3 | Example 36-5 | (DMSO-d$_6$) δ: 10.22 (brs, 1H), 9.43 (s, 1H), 8.27 (s, 1H), 8.13 (d, J = 8.5 Hz, 1H), 7.69 (dd, J = 5.8, 8.5 Hz, 1H), 7.63 (d, J = 8.1 Hz, 1H), 7.21 (dd, J = 2.3, 10.0 Hz, 1H), 7.13 (dt, J = 3.1, 8.5 Hz, 1H), 5.36 (s, 2H), 2.69 (q, J = 7.3 Hz, 2H), 2.53 (s, 3H), 1.18 (t, J = 7.3 Hz, 3H) | 427 (M$^+$), 383 |

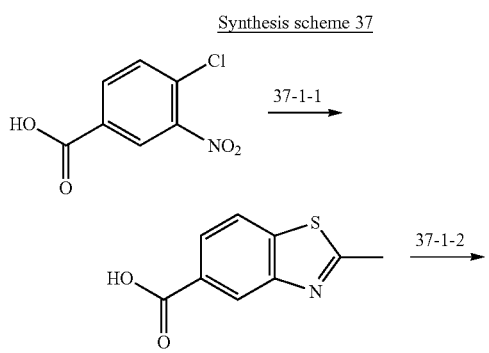

Synthesis scheme 37

In the formulae, R and R' are the same or different and each represent a halogen atom, an alkyl group, a hydroxyl group or an alkoxy group.

Example 37-1

Step 37-1-1

2-Methylbenzothiazole-5-carboxylic acid

4-Chloro-3-nitrobenzoic acid (2.02 g, 10.00 mmol), sodium sulfide nonahydrate (7.22 g, 30.00 mmol) and water (5 ml) were suspended, and the mixture was heated at about 100° C. for 30 minutes. After being allowed to cool, the mixture was cooled by ice, and acetic anhydride (18 ml) and acetic acid (10 ml) were added to the mixture. The resulting mixture was heated under reflux for 2 hours and stirred at a room temperature for 15 hours. To the mixture, tap water and then ethyl acetate were added, and sulfur was removed by filtration. The ethyl acetate layer was washed with a saturated saline solution, and then dried over anhydrous magnesium sulfate and concentrated to give the title compound (1.54 g, 80%) as a light-yellow powder.

$^1$H-NMR (DMSO-$d_6$) δ: 13.09 (brs, 1H), 8.40 (d, J=1.5 Hz, 1H), 8.16 (d, J=8.1 Hz, 1H), 7.95 (dd, J=1.5, 8.5 Hz, 1H), 2.84 (s, 3H)

Mass, m/z: 193 (M$^+$, base)

Step 37-1-2

(2-Methylbenzothiazol-5-yl)methanol

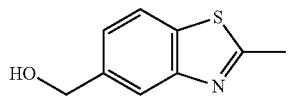

In tetrahydrofuran (20 ml), 2-methylbenzothiazole-5-carboxylic acid (0.97 g, 5.00 mmol) prepared in the Step 37-1-1 was dissolved, and triethylamine (0.66 g, 6.50 mmol) was added thereto. Under an ice cooling, ethyl chloroformate (0.71 g, 6.50 mmol) was added to the mixture. Under an ice cooling, the resulting mixture was stirred for 30 minutes. Under an ice cooling, sodium borohydride was suspended in ethanol (20 ml), and the above reaction solution was slowly added to the suspension. The mixture was allowed to warm to a room temperature and stirred for one hour. To the mixture, 3-N hydrochloric acid was added, and the resulting mixture was stirred for 10 minutes. Then, chloroform was added thereto, and the resulting mixture was neutralized with a saturated sodium bicarbonate solution. The chloroform layer was dried over anhydrous magnesium sulfate and then concentrated. The concentrate was purified by silica gel column chromatography (ethyl acetate:methanol=20:1 to 10:1) to give the title compound (0.52 g, 58%) as a light-yellow powder.

$^1$H-NMR (DMSO-$d_6$) δ: 7.95 (d, J=8.1 Hz, 1H), 7.84 (d, J=0.8 Hz, 1H), 7.35 (dd, J=1.5, 8.1 Hz, 1H), 5.28 (brs, 1H), 4.63 (s, 2H)

Mass, m/z: 179 (M$^+$), 150 (base)

Step 37-1-3

[2-(4-Chloro-2-methoxyphenyl)-4-methylthiazol-5-yl]carbamic acid 2-methylbenzothiazol-5-ylmethyl ester

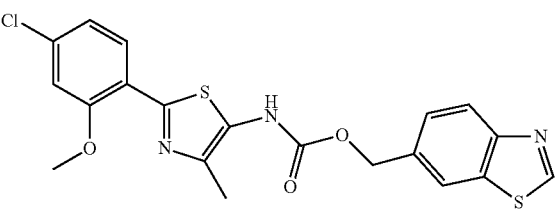 [SMILES: COc1cc(Cl)ccc1-c1nc(C)c(NC(=O)OCc2ccc3ncsc3c2)s1]

The title compound was obtained according to the same procedure as in Example 9-1 except that the compound prepared in the Step 37-1-2 was used instead of (1,2,3,4-tetrahydrobenzo[4,5]imidazo[1,2-a]pyridin-7-ylmethanol.

$^1$H-NMR (DMSO-$d_6$) δ: 10.16 (s, 1H), 8.17 (d, J=8.5 Hz, 1H), 8.06 (d, J=8.1 Hz, 1H), 7.99 (s, 1H), 7.47 (d, J=8.1 Hz, 1H), 7.30 (d, J=1.9 Hz, 1H), 7.12 (dd, J=1.9, 8.5 Hz, 1H), 5.34 (s, 2H), 4.02 (s, 3H), 2.81 (s, 3H), 2.32 (s, 3H)

Mass, m/z: 459 (M$^+$), 415, 162 (base)

Examples 37-2 to 37-4

The objective compounds were obtained according to the same procedure as in Example 9-1 except that the carboxylic acids or hydroxy compounds obtained in Examples or Steps shown in the following table were used instead of 2-(4-chloro-2-methoxyphenyl)-4-methylthiazole-5-carboxylic acid or (1,2,3,4-tetrahydrobenzo[4,5]imidazo[1,2-a]pyridin-7-yl)methanol.

TABLE 212

| Carboxylic acid | Hydroxy compound | Example | $^1$H-NMR | Mass, m/z |
|---|---|---|---|---|
| Example 7-14 | Step 37-1-2 | Example 37-2 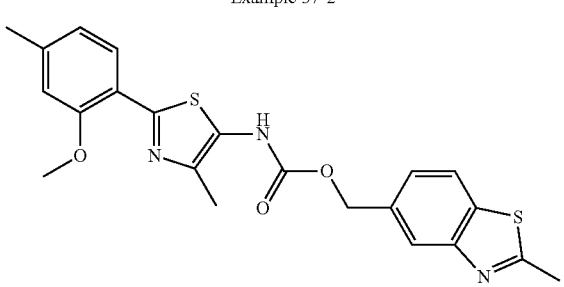 | (DMSO-$d_6$) δ: 10.02 (brs, 1H), 8.07-8.04 (m, 2H), 7.99 (s, 1H), 7.47 (d, J = 7.7 Hz, 1H), 7.02 (s, 1H), 6.87 (d, J = 8.1 Hz, 1H), 5.33 (s, 2H), 3.95 (s, 3H), 2.81 (s, 3H), 2.35 (s, 3H), 2.30 (s, 3H) | 439 (M$^+$), 395, 162 (base) |

TABLE 212-continued
| Carboxylic acid | Hydroxy compound | Example | ¹H-NMR | Mass, m/z |
|---|---|---|---|---|
| Example 7-16 | Step 37-1-2 | Example 37-3 | (DMSO-d$_6$) δ: 10.18 (brs, 1H), 8.06 (d, J = 8.1 Hz, 1H), 7.99 (s, 1H), 7.55 (d, J = 7.7 Hz, 1H), 7.47 (d, J = 7.3 Hz, 1H), 7.14 (s, 1H), 7.09 (d, J = 7.7 Hz, 1H), 5.34 (s, 2H), 2.81 (s, 3H), 2.50 (s, 3H), 2.30 (s, 6H) | 423 (M⁺), 379, 162 (base) |
| Example 7-7 | Step 37-1-2 | Example 37-4 | (DMSO-d$_6$) δ: 10.31 (s, 1H), 8.06 (d, J = 8.1 Hz, 1H), 7.99 (s, 1H), 7.70 (d, J = 8.5 Hz, 1H), 7.47 (d, J = 8.5 Hz, 1H), 7.44 (d, J = 1.9 Hz, 1H), 7.35 (dd, J = 1.9, 8.5 Hz, 1H), 5.35 (s, 2H), 2.81 (s, 3H), 2.53 (s, 3H), 2.34 (s, 3H) | 443 (M⁺), 399, 162 (base) |
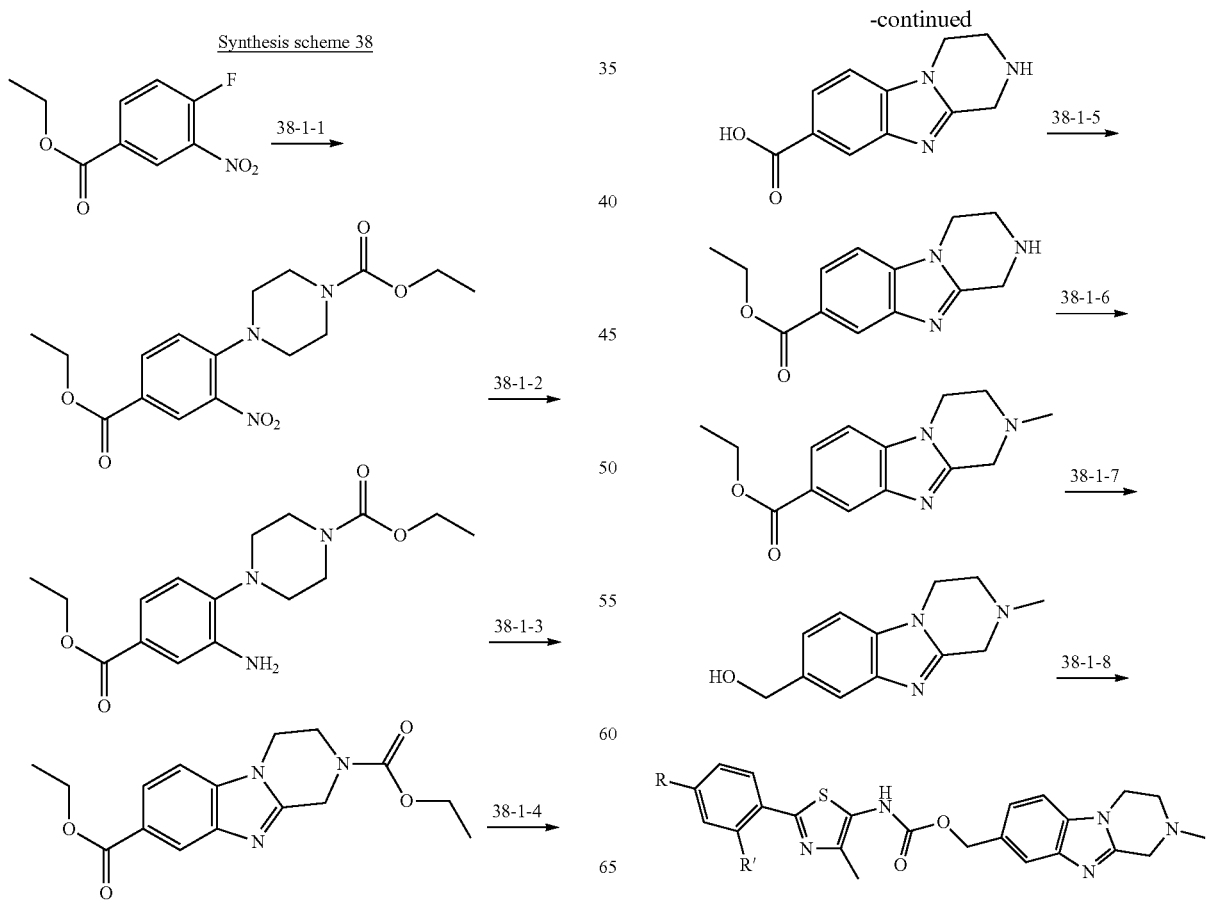

In the formulae, R and R' are the same or different and each represent a halogen atom, an alkyl group, a hydroxyl group or an alkoxy group.

Example 38-1

Step 38-1-1

Ethyl 4-(4-ethoxycarbonyl-2-nitrophenyl)piperidine-1-carboxylate

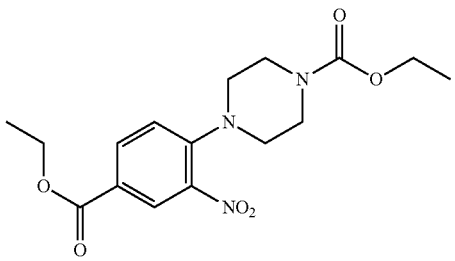 [SMILES: CCOC(=O)c1ccc(N2CCN(C(=O)OCC)CC2)c([N+](=O)[O-])c1]

Ethyl 4-fluoro-3-nitrobenzoate (10.0 g, 46.91 mmol) prepared in the Step 1-1-1 was dissolved in ethanol (100 ml). To the solution, triethylamine was added and then ethoxycarbonylpiperazine (49.26 mmol) was added, and the mixture was stirred at a room temperature for 18 hours. After the mixture was concentrated, ethyl acetate was added thereto. The resulting mixture was washed with a saturated sodium bicarbonate solution and a saturated saline solution in order. The washed product was dried over anhydrous magnesium sulfate and then concentrated. The concentrate was purified by silica gel column chromatography (n-hexane:ethyl acetate=2:1-1:1) to give the title compound (17.4 g, quantitative) as a yellowish-brown oily substance.

$^1$H-NMR (DMSO-$d_6$) δ: 8.31 (d, J=2.3 Hz, 1H), 8.04 (dd, J=1.9, 8.9 Hz, 1H), 7.36 (d, J=8.9 Hz, 1H), 4.31 (q, J=6.9 Hz, 1H), 4.07 (q, J=6.9 Hz, 2H), 3.53-3.50 (m, 4H), 3.20-3.18 (m, 4H), 1.32 (t, J=6.9 Hz, 3H), 1.20 (t, J=6.9 Hz, 3H)

Mass, m/z: 351 (M$^+$)

Step 38-1-2

Ethyl 4-(2-amino-4-ethoxycarbonylphenyl)piperazine-1-carboxylate

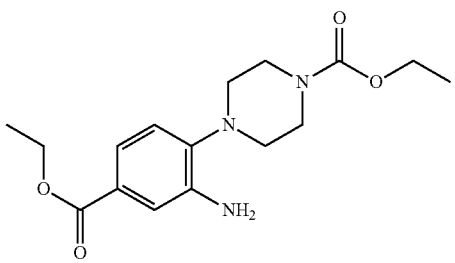 [SMILES: CCOC(=O)c1ccc(N2CCN(C(=O)OCC)CC2)c(N)c1]

Ethyl 4-(4-ethoxycarbonyl-2-nitrophenyl)piperidine-1-carboxylate (17.0 g, 48.4 mmol) prepared in the Step 38-1-1 was dissolved in methanol (100 ml), and palladium 5% on carbon (5.0 g) was added thereto. The mixture was stirred under a hydrogen flow for 16 hours. The mixture was filtered, and the filtrate was concentrated to give the title compound (15.2 g, 98%) as a light-black oily substance.

$^1$H-NMR (DMSO-$d_6$) δ: 7.33 (d, J=1.9 Hz, 1H), 7.18 (dd, J=1.9, 8.1 Hz, 1H), 6.93 (d, J=8.1 Hz, 1H), 5.03 (s, 2H), 4.24 (q, J=6.9 Hz, 2H), 4.07 (q, J=6.9 Hz, 2H), 3.56-3.53 (m, 4H), 2.81 (t, J=5.0 Hz, 4H), 1.29 (t, J=6.9 Hz, 3H), 1.20 (t, J=6.9 Hz, 3H)

Mass, m/z: 321 (M$^+$, base)

Step 38-1-3

Diethyl 3,4-dihydro-1H-benzo[4,5]imidazo[1,2-a]pyrazine-2,8-dicarboxylate

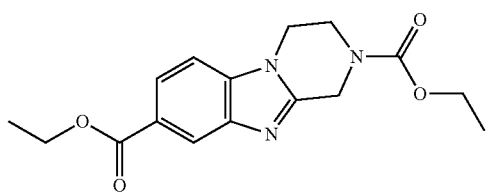 [SMILES: CCOC(=O)c1ccc2c(c1)nc1n2CCN(C(=O)OCC)C1]

Formic acid (0.29 g, 6.22 mmol) and purified water (5 ml) were added to ethyl 4-(2-amino-4-ethoxycarbonylphenyl)piperazine-1-carboxylate (2.0 g, 6.22 mmol) prepared in the Step 38-1-2. A 30% hydrogen peroxide solution (0.63 g, 18.67 mmol) was further added thereto, and the mixture was heated and stirred at 50° C. Formic acid (2 ml) and 2 ml of a 30% hydrogen peroxide solution were further added to the mixture. The resulting mixture was stirred for another one hour, then allowed to cool, and stirred. After being cooled to a room temperature, the mixture was neutralized with a saturated sodium bicarbonate solution and subjected to extraction with ethyl acetate. The extract was dried over anhydrous magnesium sulfate and then concentrated. The concentrate was purified by silica gel column chromatography (n-hexane: ethyl acetate=1:1 to 1:2) to give the title compound (0.22 g, 11%) as a white powder.

$^1$H-NMR (DMSO-$d_6$) δ: 8.19 (d, J=0.8 Hz, 1H), 7.89 (dd, J=1.5, 8.5 Hz, 1H), 7.63 (d, J=8.5 Hz, 1H), 4.87 (s, 2H), 4.33 (t, J=7.3 Hz, 2H), 4.25 (t, J=5.4 Hz, 2H), 4.14 (t, J=6.9 Hz, 2H), 1.35 (t, J=7.3 Hz, 3H), 1.24 (t, J=6.9 Hz, 3H)

Mass, m/z: 317 (M$^+$), 288 (base)

Step 38-1-4

1,2,3,4-Tetrahydrobenzo[4,5]imidazo[1,2-a]pyrazine-8-carboxylic acid

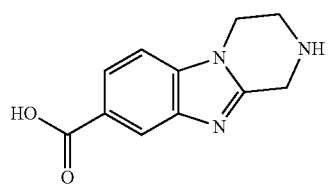 [SMILES: O=C(O)c1ccc2c(c1)nc1n2CCNC1]

Diethyl 3,4-dihydro-1H-benzo[4,5]imidazo[1,2-a]pyrazine-2,8-dicarboxylate (500 mg, 1.58 mmol) prepared in the Step 38-1-3 was suspended in ethanol (3.2 ml), and a 1 mol/L sodium hydroxide aqueous solution (1.6 ml) and then purified water (1.6 ml) were added thereto. The mixture was heated under reflux for 48 hours. After being allowed to cool, the mixture was neutralized with 3-N hydrochloric acid. The precipitate was separated by filtration and dried to give the title compound (230 mg, 67%) as a light-brown powder.

$^1$H-NMR (DMSO-$d_6$) δ: 8.13 (d, J=1.5 Hz, 1H), 7.84 (dd, J=1.5, 8.5 Hz, 1H), 7.54 (d, J=8.5 Hz, 1H), 4.10-4.08 (m, 4H), 3.21 (t, J=5.4 Hz, 2H)

Mass, m/z: 217 (M$^+$, base)

Step 38-1-5

Ethyl 1,2,3,4-tetrahydrobenzo[4,5]imidazo[1,2-a]pyrazine-8-carboxylate

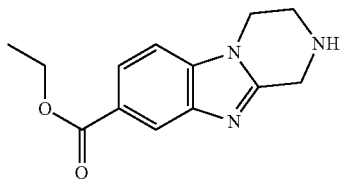 [SMILES: CCOC(=O)c1ccc2c(c1)nc1n2CCNC1]

In ethanol (200 ml), 1,2,3,4-tetrahydrobenzo[4,5]imidazo[1,2-a]pyrazine-8-carboxylic acid (2.94 g, 13.53 mmol) prepared in the Step 38-1-4 was suspended. Concentrated sulfuric acid (10 ml) was added thereto, and the mixture was heated under reflux for 72 hours. After being allowed to cool, the mixture was concentrated under a reduced pressure. The concentrate was neutralized with a saturated sodium bicarbonate solution and 25% ammonia water and then subjected to extraction with chloroform. The extract was dried over anhydrous magnesium sulfate and then concentrated under a reduced pressure. The concentrate was purified by silica gel column chromatography (chloroform:methanol=10:1) to give the title compound (2.78 g, 84%) as a light-yellow powder.

$^1$H-NMR (DMSO-$d_6$) δ: 8.15 (d, J=1.2 Hz, 1H), 7.85 (dd, J=1.5, 8.5 Hz, 1H), 7.58 (d, J=8.5 Hz, 1H), 4.33 (t, J=6.9 Hz, 2H), 4.11-4.08 (m, 4H), 3.22-3.19 (m, 2H), 1.35 (t, J=6.9 Hz, 3H)

Mass, m/z: 245 (M$^+$, base)

Step 38-1-6

Ethyl 2-methyl-1,2,3,4-tetrahydrobenzo[4,5]imidazo[1,2-a]pyrazine-8-carboxylate

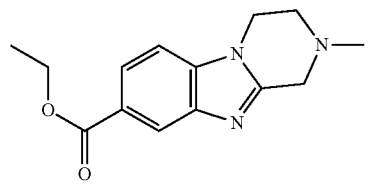 [SMILES: CCOC(=O)c1ccc2c(c1)nc1n2CCN(C)C1]

Ethyl 1,2,3,4-tetrahydrobenzo[4,5]imidazo[1,2-a]pyrazine-8-carboxylate (0.98 g, 4.00 mmol) prepared in the Step 38-1-5 was dissolved in methanol (100 ml), and acetic acid (1.00 ml) and a 37% formaldehyde aqueous solution (1.2 ml) were added thereto. Thereafter, sodium cyanoborohydride (0.57 g, 9.07 mmol) was added to the mixture, and the resulting mixture was stirred. After 30 minutes, the mixture was concentrated under a reduced pressure. Chloroform was added to the concentrate, and the resulting mixture was washed with a saturated sodium bicarbonate solution. The washed product was dried over anhydrous magnesium sulfate and concentrated. The concentrate was purified by silica gel column chromatography (chloroform:methanol=10:1) to give the title compound (958 mg, 92%) as a light-brown powder.

$^1$H-NMR (CDCl$_3$) δ: 8.42 (d, J=1.2 Hz, 1H), 7.89 (dd, J=1.5, 8.5 Hz, 1H), 7.32 (d, J=8.5 Hz, 1H), 4.39 (t, J=6.9 Hz, 2H), 4.16 (t, J=5.4 Hz, 2H), 3.88 (s, 2H), 2.98 (t, J=5.4 Hz, 2H), 2.55 (s, 3H), 1.41 (t, J=6.9 Hz, 3H)

Mass, m/z: 259 (M$^+$, base)

Step 38-1-7

(2-Methyl-1,2,3,4-tetrahydrobenzo[4,5]imidazo[1,2-a]pyrazin-8-yl)methanol

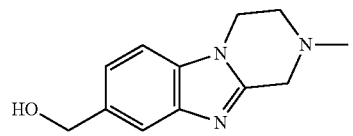 [SMILES: CN1CCn2c(nc3cc(CO)ccc32)C1]

lithium aluminum hydride (0.21 g, 5.40 mmol) was suspended in tetrahydrofuran (15 ml), and under an ice cooling, a solution (5 ml) of ethyl 2-methyl-1,2,3,4-tetrahydrobenzo[4,5]imidazo[1,2-a]pyrazine-8-carboxylate (0.70 g, 2.70 mmol) prepared in the Step 38-1-6 in tetrahydrofuran was slowly added dropwise to the suspension. After the mixture was stirred for 30 minutes under an ice cooling, and a saturated sodium bicarbonate solution was slowly added to the mixture under an ice cooling. Ethyl acetate was slowly added to the resulting mixture, and the precipitate was removed by filtration. The residue separated by filtration was carefully washed with chloroform. The washings and the filtrate were concentrated together. The concentrate was purified by silica gel column chromatography (chloroform:methanol=10:1 to 5:1) to give the title compound (0.56 g, 96%) as a white powder.

$^1$H-NMR (DMSO-$d_6$) δ: 7.49 (s, 1H), 7.41 (d, J=8.1 Hz, 1H), 7.17 (dd, J=1.2, 8.1 Hz, 1H), 5.10 (t, J=5.8 Hz, 1H), 4.58 (d, J=5.8 Hz, 2H), 4.11 (t, J=5.4 Hz, 2H), 3.74 (s, 2H), 2.92 (t, J=5.4 Hz, 2H), 2.45 (s, 3H)

Mass, m/z: 217 (M$^+$)

Step 38-1-8

[2-(4-Chloro-2-methoxyphenyl)-4-methylthiazol-5-yl]carbamic acid 2-methyl-1,2,3,4-tetrahydrobenzo[4,5]imidazo[1,2-a]pyrazin-8-ylmethyl ester

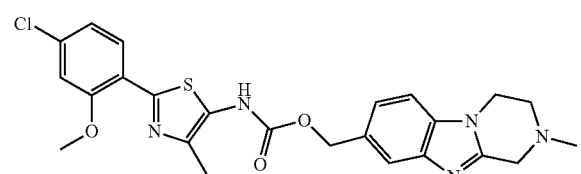

The title compound was obtained according to the same procedure as in Example 9-1 except that the compound prepared in the Step 38-1-7 was used instead of (1,2,3,4-tetrahydrobenzo[4,5]imidazo[1,2-a]pyridin-7-ylmethanol.

$^1$H-NMR (DMSO-$d_6$) δ: 10.11 (brs, 1H), 8.32 (s, 1H), 8.16 (d, J=8.5, 1H), 7.66 (s, 1H), 7.51 (d, J=8.5 Hz, 1H), 7.32-7.30 (m, 2H), 7.12 (dd, J=1.9, 8.5 Hz, 1H), 5.30 (s, 2H), 4.14 (t, J=5.8 Hz, 2H), 4.01 (s, 3H), 3.76 (s, 2H), 2.94 (t, J=5.8 Hz, 2H), 2.45 (s, 3H), 2.31 (s, 3H)

Mass, m/z: 454 (M$^+$-44), 260 (base)

Example 38-2

[2-(2-Methoxy-4-methylphenyl)-4-methylthiazol-5-yl]carbamic acid 2-methyl-1,2,3,4-tetrahydrobenzo[4,5]imidazo[1,2-a]pyrazin-8-ylmethyl ester

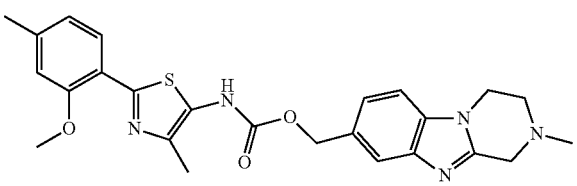

The title compound was obtained according to the same procedure as in Example 9-1 except that the compound of Example 7-14 and the compound prepared in the Step 38-1-7 were used instead of 2-(4-chloro-2-methoxyphenyl)-4-methylthiazole-5-carboxylic acid and (1,2,3,4-tetrahydrobenzo[4,5]imidazo[1,2-a]pyridin-7-ylmethanol, respectively.

$^1$H-NMR (DMSO-$d_6$) δ: 9.96 (brs, 1H), 8.04 (d, J=8.1 Hz, 1H), 7.65 (s, 1H), 7.51 (d, J=8.5 Hz, 1H), 7.30 (d, J=8.1 Hz, 1H), 7.02 (s, 1H), 6.87 (d, J=8.1 Hz, 1H), 5.29 (s, 2H), 4.13 (t, J=5.8 Hz, 2H), 3.96 (s, 3H), 3.75 (s, 2H), 2.93 (t, J=5.8 Hz, 2H), 2.45 (s, 3H), 2.35 (s, 3H), 1.99 (s, 3H)

Mass, m/z: 477 (M$^+$), 433, 260 (base)

Example 38-3

[2-(2,4-Dimethylphenyl)-4-methylthiazol-5-yl]carbamic acid 2-methyl-1,2,3,4-tetrahydrobenzo[4,5]imidazo[1,2-a]pyrazin-8-ylmethyl ester

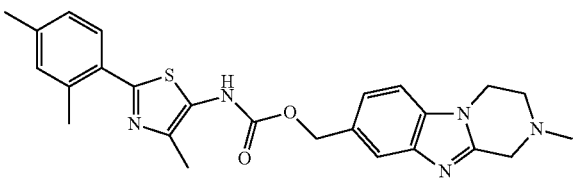

The title compound was obtained according to the same procedure as in Example 9-1 except that the compound of Example 7-16 and the compound prepared in the Step 38-1-7 were used instead of 2-(4-chloro-2-methoxyphenyl)-4-methylthiazole-5-carboxylic acid and (1,2,3,4-tetrahydrobenzo[4,5]imidazo[1,2-a]pyridin-7-ylmethanol, respectively.

$^1$H-NMR (DMSO-$d_6$) δ: 10.11 (brs, 1H), 7.65 (s, 1H), 7.55 (d, J=8.1 Hz, 1H), 7.50 (d, J=8.5 Hz, 1H), 7.30 (d, J=8.1 Hz, 1H), 7.14 (s, 1H), 7.09 (d, J=8.1 Hz, 1H), 5.29 (s, 2H), 4.14 (t, J=5.8 Hz, 2H), 3.76 (s, 3H), 2.93 (t, J=5.8 Hz, 2H), 2.45 (s, 3H), 2.31 (s, 6H)

Mass, m/z: 417 (M$^+$-44), 244 (base)

Synthesis scheme 39

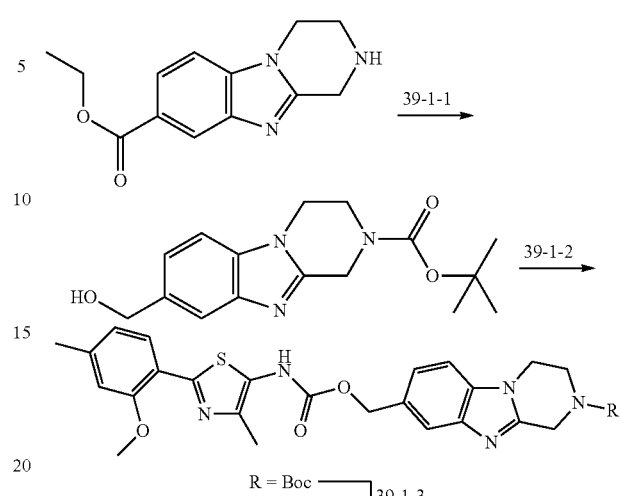

Example 39-1

Step 39-1-1 tert-Butyl(8-hydroxymethyl-3,4-dihydro-1H-benzo[4,5]imidazo[1,2-a]pyrazine-2-carboxylate

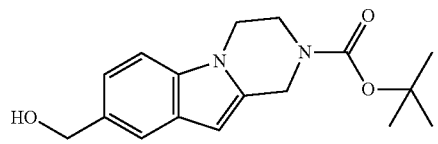 [SMILES: CC(C)(C)OC(=O)N1CCn2c(cc3cc(CO)ccc32)C1]

lithium aluminum hydride (0.16 g, 4.08 mmol) was suspended in tetrahydrofuran (5 ml), and under an ice cooling, a solution (5 ml) of ethyl 1,2,3,4-tetrahydrobenzo[4,5]imidazo[1,2-a]pyrazine-8-carboxylate (0.50 g, 2.04 mmol) prepared in the Step 38-1-5 in tetrahydrofuran was slowly added dropwise to the suspension. After the mixture was stirred for 30 minutes under an ice cooling, a saturated sodium bicarbonate solution was slowly added to the mixture under an ice cooling. Ethyl acetate was slowly added to the resulting mixture, and the precipitate was removed by filtration. The residue separated by filtration was carefully washed with chloroform-methanol. The washings and the filtrate were concentrated together. The concentrated residue was suspended in chloroform (50 ml), and di-tert-butyl dicarbonate (0.67 g, 3.06 mmol) and triethylamine (0.57 ml, 4.08 mmol) were added dropwise to the suspension. After being stirred at a room temperature for 15 hours, the mixture was concentrated under a reduced pressure. The concentrate was purified by silica gel column chromatography (chloroform:methanol=20:1) to give the title compound (0.38 g, 62%) as a white powder.

$^1$H-NMR (DMSO-$d_6$) δ: 7.52 (s, 1H), 7.43 (d, J=8.5 Hz, 1H), 7.19 (dd, J=1.5, 8.5 Hz, 1H), 5.12 (t, J=5.8 Hz, 1H), 4.67 (s, 2H), 4.58 (d, J=5.8 Hz, 2H), 4.15 (t, J=5.4 Hz, 2H), 3.91 (t, J=5.4 Hz, 2H), 1.46 (s, 9H)

Mass, m/z: 303 (M$^+$), 246 (base)

Step 39-1-2 tert-Butyl 8-[2-(2-methoxy-4-methylphenyl)-4-methylthiazol-5-ylcarbamoylmethyl]-3,4-dihydro-1H-benzo[4,5]imidazo[1,2-a]pyrazine-2-carboxylate

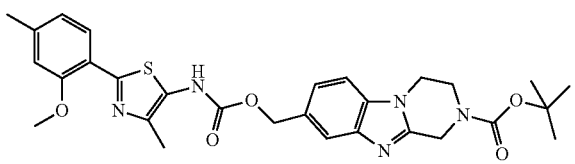 [SMILES: COc1cc(C)ccc1-c1nc(C)c(NC(=O)OCc2ccc3c(c2)nc2n3CCN(C(=O)OC(C)(C)C)C2)s1]

The title compound was obtained according to the same procedure as in Example 9-1 except that the compound of Example 7-14 and the compound prepared in the Step 39-1-1 were used instead of 2-(4-chloro-2-methoxyphenyl)-4-methylthiazole-5-carboxylic acid and (1,2,3,4-tetrahydrobenzo[4,5]imidazo[1,2-a]pyridin-7-ylmethanol, respectively.

$^1$H-NMR (DMSO-$d_6$) δ: 9.94 (brs, 1H), 8.04 (d, J=7.7 Hz, 1H), 7.68 (s, 1H), 7.53 (d, J=8.5 Hz, 1H), 7.32 (d, J=8.5 Hz, 1H), 7.02 (s, 1H), 6.87 (d, J=7.7 Hz, 1H), 5.29 (s, 2H), 4.79 (s, 2H), 4.79-4.59 (m, 2H), 3.96 (s, 3H), 3.93-3.91 (m, 2H), 2.35 (s, 3H), 2.28 (s, 3H), 1.46 (s, 9H)

Mass, m/z: 563 (M$^+$), 519, 260 (base)

Step 39-1-3

[2-(2-Methoxy-4-methylphenyl)-4-methylthiazol-5-yl]carbamic acid 1,2,3,4-tetrahydrobenzo[4,5]imidazo[1,2-a]pyrazin-8-ylmethyl ester

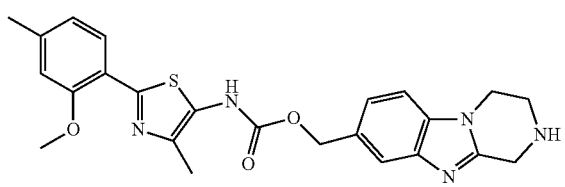 [SMILES: COc1cc(C)ccc1-c1nc(C)c(NC(=O)OCc2ccc3c(c2)nc2n3CCNC2)s1]

In ethyl acetate (5 ml), tert-butyl 8-[2-(2-methoxy-4-methylphenyl)-4-methylthiazol-5-ylcarbamoylmethyl]-3,4-dihydro-1H-benzo[4,5]imidazo[1,2-a]pyrazine-2-carboxylate (120 mg, 0.213 mmol) prepared in the Step 39-1-2 was dissolved, and a 4-N hydrochloric acid-dioxane solution (5 ml) was added thereto. The mixture was stirred at a room temperature for 2 hours. Ethyl acetate was added to the mixture, and the resulting mixture was neutralized with a saturated sodium bicarbonate solution. The resulting mixture was subjected to extraction with chloroform, and the extract was dried over anhydrous magnesium sulfate and then concentrated. The residue was lightly washed with ethyl acetate-n-hexane (1:1), separated by filtration, and dried to give the title compound (85 mg, 86%).

$^1$H-NMR (DMSO-$d_6$) δ: 9.96 (brs, 1H), 8.04 (d, J=7.7 Hz, 1H), 7.64 (s, 1H), 7.49 (d, J=8.1 Hz, 1H), 7.29 (d, J=7.7 Hz, 1H), 7.02 (s, 1H), 6.87 (d, J=8.1 Hz, 1H), 5.28 (s, 2H), 4.06 (brs, 3H), 3.96 (s, 3H), 3.32-3.29 (m, 2H), 3.20 (t, J=5.4 Hz, 2H), 2.35 (s, 3H), 2.28 (s, 3H)

Mass, m/z: 463 (M$^+$), 260 (base)

Synthesis scheme 40

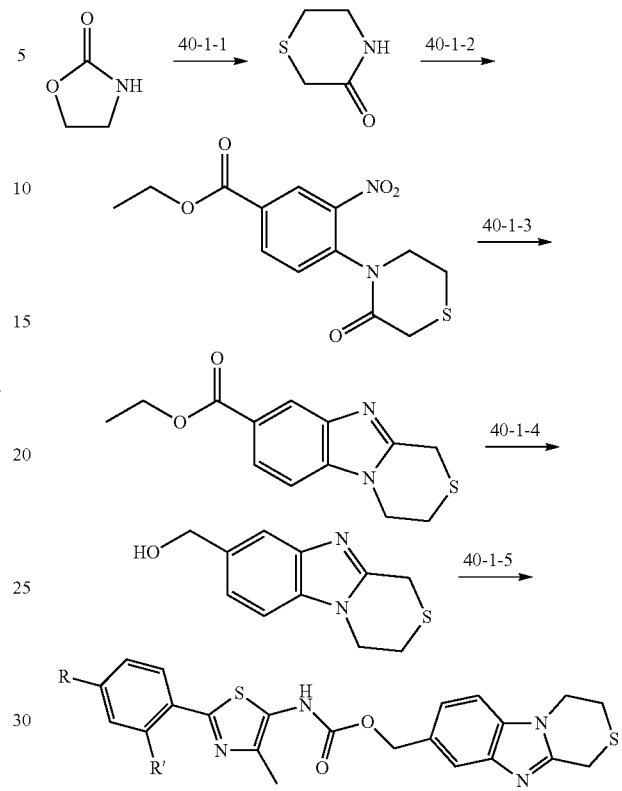

In the formulae, R and R' are the same or different and each represent a halogen atom, an alkyl group, a hydroxyl group or an alkoxy group.

Example 40-1

Step 40-1-1

Thiomorpholin-3-one

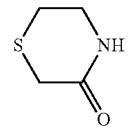

Under an argon flow and under an ice cooling, sodium hydride (60%, 2.0 g, 49.9 mmol) was added to n-propanol (100 ml). After being stirred for 5 minutes, the mixture was allowed to warm to a room temperature, and ethyl thioglycolate (8.0 g, 66.6 mmol) was added thereto. The resulting mixture was stirred for 30 minutes. To the mixture, 2-oxazolidone (2.9 g, 33.3 mmol) was added, and the resulting mixture was heated under reflux for 4 hours. The mixture was concentrated, and ethyl acetate was added to the concentrate. The resulting mixture was washed with a saturated sodium bicarbonate solution, dried over anhydrous magnesium sulfate, and concentrated. The resulting concentrate was purified by silica gel column chromatography (ethyl acetate:methanol=20:1) to give the title compound (1.0 g, 26%) as a white powder.

¹H-NMR (DMSO-d₆) δ: 7.79 (brs, 1H), 3.41-3.38 (m, 2H), 3.15 (s, 2H), 2.76 (t, J=5.8 Hz, 2H)

Mass, m/z: 117 (M⁺, base)

Step 40-1-2

Ethyl 3-nitro-4-(3-oxothiomorpholin-4-yl)benzoate

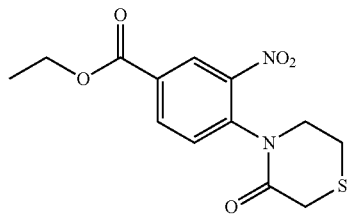 [SMILES: CCOC(=O)c1ccc(N2CCSCC2=O)c([N+](=O)[O-])c1]

Sodium hydride (60%, 171 mg, 4.27 mmol) was suspended in tetrahydrofuran (10 ml), and thiomorpholin-3-one (500 mg, 4.27 mmol) prepared in the Step 40-1-1 was added thereto. The mixture was stirred at a room temperature for 5 minutes, and a solution (10 ml) of ethyl 4-fluoro-3-nitrobenzoate (910 mg, 4.27 mmol) prepared in the Step 1-1-1 in tetrahydrofuran was slowly added to the mixture. The resulting mixture was stirred at a room temperature for 4 hours. The mixture was concentrated, and chloroform was added thereto. The resulting mixture was washed with a saturated sodium bicarbonate solution. The washed product was dried over anhydrous magnesium sulfate and then concentrated. The residue was purified by silica gel column chromatography (n-hexane:ethyl acetate=1:1) and washed with methanol to give the title compound (360 mg, 27%) as a yellow powder.

¹H-NMR (DMSO-d₆) δ: 8.39 (d, J=1.9 Hz, 1H), 8.30 (dd, J=1.9, 8.5 Hz, 1H), 7.76 (d, J=8.1 Hz, 1H), 4.38 (q, J=6.9 Hz, 2H), 4.14 (brs, 2H), 3.44 (s, 2H), 3.13 (t, J=5.4 Hz, 2H), 1.35 (t, J=6.9 Hz, 3H)

Mass, m/z: 310 (M⁺), 264 (base)

Step 40-1-3

Ethyl 3,4-dihydro-1H-2-thia-4a,9-diazafluorene-7-carboxylate

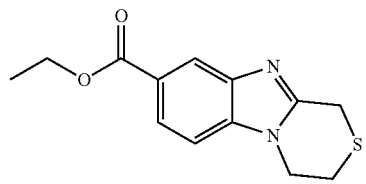 [SMILES: CCOC(=O)c1ccc2c(c1)nc1n2CCSC1]

Ethyl 3-nitro-4-(3-oxothiomorpholin-4-yl)benzoate (2.00 g, 6.44 mmol) prepared in the Step 40-1-2 was dissolved in ethanol (120 ml). Purified water (12 ml), iron powder (2.62 g, 47.04 mmol) and hydrochloric acid (0.5 ml) was added to the solution, and the mixture was heated under reflux for 4 hours. The mixture was concentrated, and a saturated sodium bicarbonate solution was added thereto, and the resulting mixture was subjected to extraction with chloroform. The extract was dried over anhydrous magnesium sulfate and then concentrated. The concentrate was purified by silica gel column chromatography (n-hexane:ethyl acetate=1:2) to give the title compound (0.90 g, 53%) as a light-yellow powder.

¹H-NMR (DMSO-d₆) δ: 8.17 (d, J=1.5 Hz, 1H), 7.88 (dd, J=1.5, 8.5 Hz, 1H), 7.61 (d, J=8.5 Hz, 1H), 4.40 (t, J=5.8 Hz, 2H), 4.33 (q, J=6.9 Hz, 2H), 4.14 (s, 2H), 3.27 (t, J=5.8 Hz, 2H), 1.35 (t, J=6.9 Hz, 3H)

Mass, m/z: 262 (M⁺), 217 (base)

Step 40-1-4

(3,4-Dihydro-1H-2-thia-4a,9-diazafluoren-7-yl)methanol

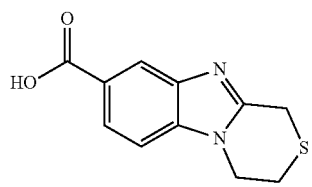 [SMILES: O=C(O)c1ccc2c(c1)nc1n2CCSC1]

Lithium aluminum hydride (76 mg, 2.00 mmol) was suspended in tetrahydrofuran (20 ml), and under an ice cooling, a solution (10 ml) of ethyl 3,4-dihydro-1H-2-thia-4a,9-diazafluorene-7-carboxylate (260 mg, 1.00 mmol) prepared in the Step 40-1-3 in tetrahydrofuran was slowly added to the suspension. After the mixture was stirred under an ice cooling for 30 minutes, under an ice cooling, a saturated sodium bicarbonate solution was slowly added to the mixture, and then ethyl acetate was added thereto. The resulting mixture was filtered, and the residue was washed with a mixture solution of chloroform and methanol. The filtrate was concentrated and purified by silica gel column chromatography (chloroform:methanol=50:1) to give the title compound (150 mg, 68%) as a white powder.

¹H-NMR (DMSO-d₆) δ: 7.50 (s, 1H), 7.42 (d, J=8.1 Hz, 1H), 7.19 (dd, J=1.2, 8.5 Hz, 1H), 5.12 (t, J=5.8 Hz, 1H), 4.59 (d, J=5.8 Hz, 2H), 4.32 (t, J=5.8 Hz, 2H), 4.08 (s, 2H), 3.24 (t, J=5.8 Hz, 2H)

Mass, m/z: 220 (M⁺, base), 191

Step 40-1-5

[2-(4-Chloro-2-methoxyphenyl)-4-methylthiazol-5-yl]carbamic acid 3,4-dihydro-1H-2-thia-4a,9-diazafluoren-7-ylmethyl ester

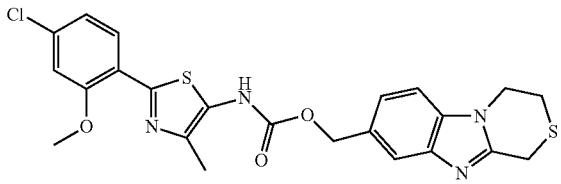 [SMILES: COc1cc(Cl)ccc1-c1nc(C)c(NC(=O)OCc2ccc3c(c2)nc2n3CCSC2)s1]

The title compound was obtained according to the same procedure as in Example 9-1 except that the compound prepared in the Step 40-1-4 was used instead of (1,2,3,4-tetrahydrobenzo[4,5]imidazo[1,2-a]pyridin-7-ylmethanol.

¹H-NMR (DMSO-d₆) δ: 10.10 (brs, 1H), 8.16 (d, J=8.5 Hz, 1H), 7.67 (s, 1H), 7.52 (d, J=8.5 Hz, 1H), 7.33 (d, J=8.1 Hz, 1H), 7.29 (d, J=1.9 Hz, 1H), 7.12 (dd, J=1.9, 8.5 Hz, 1H), 5.30

(s, 2H), 4.35 (t, J=5.8 Hz, 2H), 4.10 (s, 2H), 4.02 (s, 3H), 3.30-3.17 (m, 4H), 2.31 (s, 3H)

Mass, m/z: 500 (M⁺), 456, 280, 220 (base)

Example 40-2

[2-(2-Methoxy-4-methylphenyl)-4-methylthiazol-5-yl]carbamic acid 3,4-dihydro-1H-2-thia-4a,9-diazafluoren-7-ylmethyl ester

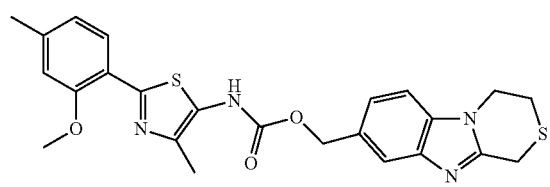 [SMILES: COc1cc(C)ccc1-c1nc(C)c(NC(=O)OCc2ccc3c(c2)nc2n3CCSC2)s1]

The title compound was obtained according to the same procedure as in Example 9-1 except that the compound of Example 7-14 and the compound prepared in the Step 40-1-4 were used instead of 2-(4-chloro-2-methoxyphenyl)-4-methylthiazole-5-carboxylic acid and (1,2,3,4-tetrahydrobenzo[4,5]imidazo[1,2-a]pyridin-7-ylmethanol, respectively.

¹H-NMR (DMSO-d₆) δ: 9.95 (brs, 1H), 8.04 (d, J=7.7 Hz, 1H), 7.66 (s, 1H), 7.52 (d, J=8.1 Hz, 1H), 7.32 (d, J=8.1 Hz, 1H), 7.02 (s, 1H), 6.87 (d, J=8.1 Hz, 1H), 5.29 (s, 2H), 4.35 (t, J=5.8 Hz, 2H), 4.10 (s, 2H), 3.96 (s, 3H), 3.31-3.24 (m, 4H), 2.35 (s, 3H), 2.28 (s, 3H)

Mass, m/z: 480 (M⁺), 436, 260 (base)

Example 40-3

[2-(4-Chloro-2-methylphenyl)-4-methylthiazol-5-yl]carbamic acid 3,4-dihydro-1H-2-thia-4a,9-diazafluoren-7-ylmethyl ester

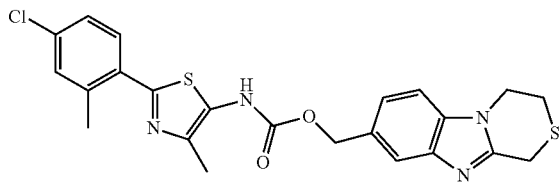

The title compound was obtained according to the same procedure as in Example 9-1 except that the compound of Example 7-7 and the compound prepared in the Step 40-1-4 were used instead of 2-(4-chloro-2-methoxyphenyl)-4-methylthiazole-5-carboxylic acid and (1,2,3,4-tetrahydrobenzo[4,5]imidazo[1,2-a]pyridin-7-ylmethanol, respectively.

¹H-NMR (DMSO-d₆) δ: 10.24 (brs, 1H), 7.71-7.68 (m, 1H), 7.55-7.44 (m, 3H), 7.36-7.32 (m, 2H), 5.31 (s, 2H), 4.36 (t, J=5.8 Hz, 2H), 4.11 (s, 2H), 3.32-3.25 (m, 4H), 2.53 (s, 3H), 2.32 (s, 3H)

Mass, m/z: 265, 220

Synthesis scheme 41

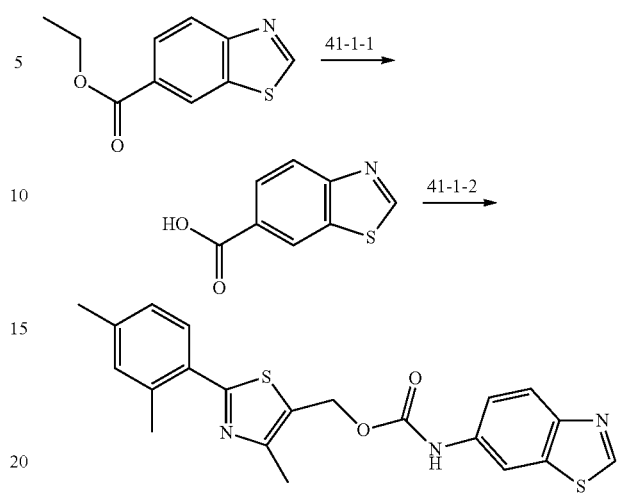

Example 41-1

Step 41-1-1

Benzothiazole-6-carboxylic acid

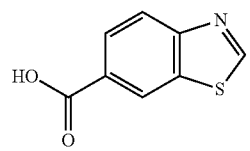 [SMILES: O=C(O)c1ccc2ncsc2c1]

Ethyl benzothiazole-6-carboxylate (1.30 g, 6.28 mmol) prepared in the Step 36-1-2 was suspended in ethanol (10 ml) and a 1 mol/L sodium hydroxide aqueous solution (10 ml), and the mixture was heated under reflux for 40 minutes. After the mixture was allowed to cool, concentrated hydrobromic acid was added to the mixture, and the resulting mixture was adjusted to pH 4. The precipitate was separated by filtration, washed with water, and then subjected to through circulation drying to give the title compound (1.10 g, 98%) as a light-brown powder.

¹H-NMR (DMSO-d₆) δ: 13.11 (brs, 1H), 9.58 (s, 1H), 8.81 (d, J=1.5 Hz, 1H), 8.17 (d, J=8.5 Hz, 1H), 8.09 (dd, J=1.5, 8.5 Hz, 1H)

Mass, m/z: 179 (M⁺, base), 162

Step 41-1-2

Benzothiazol-6-ylcarbamic acid 2-(2,4-dimethylphenyl)-4-methylthiazol-5-ylmethyl ester

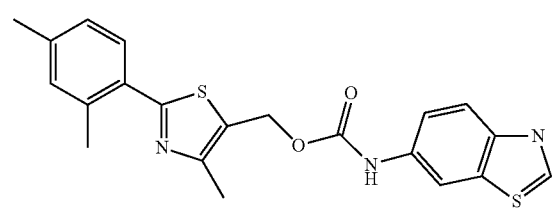

The title compound was obtained according to the same procedure as in Example 13-1 except that the compound of Example 12-6 and the compound of the Step 41-1-1 were used instead of [2-(2-methylphenyl)-4-methylthiazol-5-yl] methanol and 1-methyl-1H-benzimidazole-5-carboxylic acid, respectively.

¹H-NMR (DMSO-d₆) δ: 10.09 (brs, 1H), 9.23 (s, 1H), 8.32 (d, J=0.8 Hz, 1H), 7.99 (d, J=8.9 Hz, 1H), 7.62 (d, J=7.7 Hz, 1H), 7.54 (d, J=8.1 Hz, 1H), 7.17 (s, 1H), 7.12 (d, J=8.1 Hz, 1H), 5.41 (s, 2H), 2.50 (s, 6H), 2.32 (s, 3H)

Mass, m/z: 409 (M⁺), 365, 216 (base)

Synthesis scheme 42

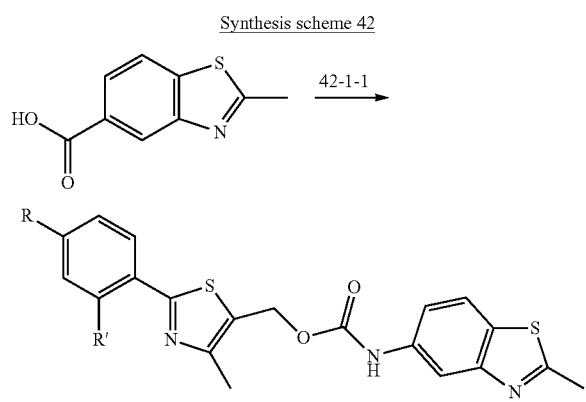

In the formulae, R and R' are the same or different and each represent a halogen atom, an alkyl group, a hydroxyl group or an alkoxy group.

Example 42-1

Step 42-1-1

(2-Methylbenzothiazol-5-yl)carbamic acid 2-(2,4-dimethylphenyl)-4-methylthiazol-5-ylmethyl ester

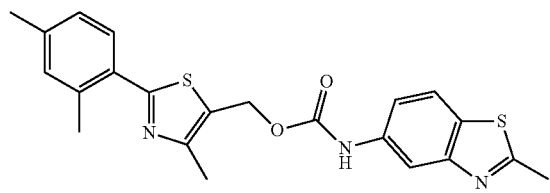

The title compound was obtained according to the same procedure as in Example 13-1 except that the compound of Example 12-6 and the compound of the Step 37-1-1 were used instead of [2-(2-methylphenyl)-4-methylthiazol-5-yl] methanol and 1-methyl-1H-benzimidazole-5-carboxylic acid, respectively.

¹H-NMR (DMSO-d₆) δ: 9.98 (brs, 1H), 8.10 (s, 1H), 7.90 (d, J=8.9 Hz, 1H), 7.62 (d, J=8.1 Hz, 1H), 7.46 (dd, J=1.9, 8.5 Hz, 1H), 7.17 (s, 1H), 7.12 (d, J=7.3 Hz, 1H), 5.40 (s, 2H), 2.77 (s, 3H), 2.47 (s, 3H), 2.50 (s, 3H), 2.32 (s, 3H)

Mass, m/z: 423 (M⁺), 379, 216 (base)

Example 42-2

(2-Methylbenzothiazol-5-yl)carbamic acid 2-(4-chloro-2-methylphenyl)-4-methylthiazol-5-ylmethyl ester

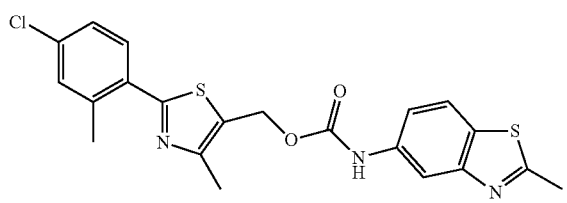 [SMILES: Cc1nc2cc(NC(=O)OCc3sc(-c4ccc(Cl)cc4C)nc3C)ccc2s1]

The title compound was obtained according to the same procedure as in Example 13-1 except that the compound of Example 12-8 and the compound of the Step 37-1-1 were used instead of [2-(2-methylphenyl)-4-methylthiazol-5-yl] methanol and 1-methyl-1H-benzimidazole-5-carboxylic acid, respectively.

¹H-NMR (DMSO-d₆) δ: 9.99 (brs, 1H), 8.10 (d, J=0.8 Hz, 1H), 7.90 (d, J=8.5 Hz, 1H), 7.76 (d, J=8.1 Hz, 1H), 7.48-7.44 (m, 2H), 7.38 (d, J=8.9 Hz, 1H), 5.41 (s, 2H), 2.77 (s, 3H), 2.55 (s, 3H), 2.50 (s, 3H)

Mass, m/z: 443 (M⁺), 399, 236 (base)

Synthesis scheme 43

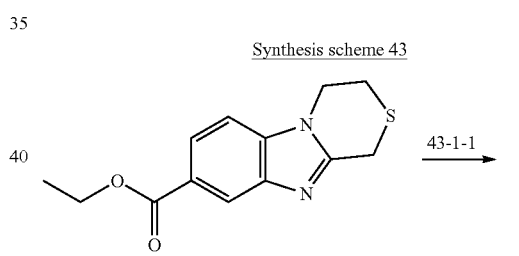

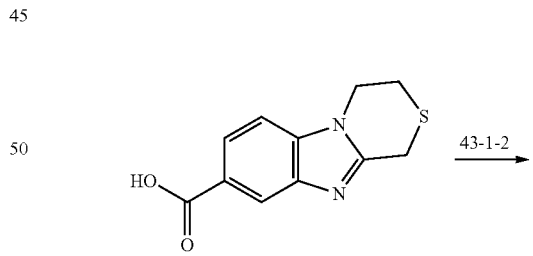

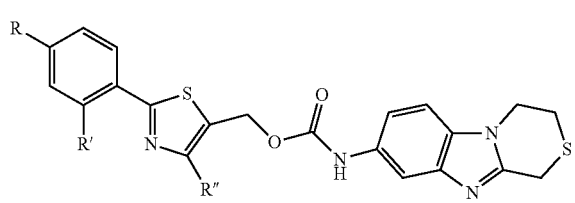

In the formulae, R and R' are the same or different and each represent a halogen atom, an alkyl group, a hydroxyl group or an alkoxy group; and R" represents an alkyl group.

Example 43-1

Step 43-1-1

3,4-Dihydro-1H-2-thia-4a,9-diazafluorene-7-carboxylic acid

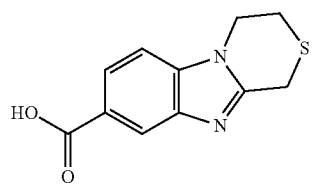 [SMILES: O=C(O)c1ccc2c(c1)nc1n2CCSC1]

Ethyl 3,4-dihydro-1H-thia-4a,9-diazafluorene-7-carboxylate (0.90 g, 3.43 mmol) prepared in the Step 40-1-3 was suspended in ethanol (116 ml) and a 1 mol/L sodium hydroxide aqueous solution (15 ml), and the mixture was heated under reflux for 50 minutes. After being allowed to cool, the mixture was adjusted to pH 5 with concentrated hydrobromic acid. The precipitate was separated by filtration, washed with water, and then subjected to through circulation drying to give the title compound (0.70 g, 88%) as a light-brown powder.
$^1$H-NMR (DMSO-$d_6$) δ: 12.70 (brs, 1H), 8.15 (d, J=1.2 Hz, 1H), 7.87 (dd, J=1.5 Hz, 8.5 Hz, 1H), 7.58 (d, J=8.5 Hz, 1H), 4.40 (t, J=5.8 Hz, 1H), 4.13 (s, 2H), 3.27 (t, J=5.8 Hz, 2H)
Mass, m/z: 234 (M$^+$, base)

Step 43-1-2

(3,4-Dihydro-1H-2-thia-4a,9-diazafluoren-7-yl)carbamic acid 2-(4-fluoro-2-methylphenyl)-4-methylthiazol-5-ylmethyl ester

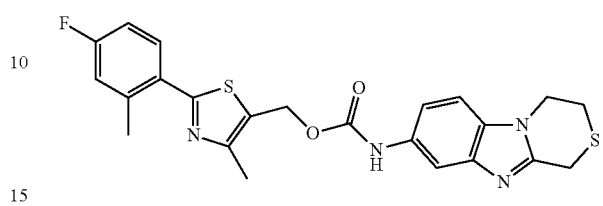

The title compound was obtained according to the same procedure as in Example 13-1 except that the compound of Example 12-7 and the compound of the Step 43-1-1 were used instead of [2-(2-methylphenyl)-4-methylthiazol-5-yl]methanol and 1-methyl-1H-benzimidazole-5-carboxylic acid, respectively.
$^1$H-NMR (DMSO-$d_6$) δ: 9.71 (brs, 1H), 7.79-7.75 (m, 2H), 7.39 (d, J=8.5 Hz, 1H), 7.29-7.23 (m, 2H), 7.15 (dt, J=2.7, 8.5 Hz, 1H), 5.38 (s, 2H), 4.29 (t, J=5.8 Hz, 2H), 4.06 (s, 2H), 3.30-3.22 (m, 4H), 2.54 (s, 3H), 2.50 (s, 3H)
Mass, m/z: 468 (M$^+$), 424, 231 (base)

Examples 43-2 to 43-4

The objective compounds were obtained according to the same procedure as in Example 13-1 except that the hydroxy compounds or carboxylic acids obtained in Examples or Steps shown in the following table were used instead of [2-(2-methylphenyl)-4-methylthiazol-5-yl]methanol or 1-methyl-1H-benzimidazole-5-carboxylic acid.

TABLE 213

| Hydroxy compound | Carboxylic acid | | Example | $^1$H-NMR | Mass, m/z |
|---|---|---|---|---|---|
| Example 12-8 | Step 43-1-1 | ![structure] | Example 43-2 | (DMSO-$d_6$) δ: 9.71 (brs, 1H), 7.77-7.74 (m, 2H), 7.48 (d, J = 1.9 Hz, 1H), 7.40-7.37 (m, 2H), 7.28 (dd, J = 1.2, 8.5 Hz, 1H), 5.38 (s, 2H), 4.29 (t, J = 5.8 Hz, 2H), 4.06 (s, 2H), 3.30-3.22 (m, 4H), 2.55 (s, 3H), 2.50 (s, 3H) | 484 (M$^+$), 440, 231 (base) |
| Example 12-6 | Step 43-1-1 | ![structure] | Example 43-3 | (DMSO-$d_6$) δ: 9.70 (brs, 1H), 7.74 (s, 1H), 7.62 (d, J = 8.1 Hz, 1H), 7.39 (d, J = 8.5 Hz, 1H), 7.28 (d, J = 8.1 Hz, 1H), 7.17 (s, 1H), 7.12 (d, J = 7.7 Hz, 1H), 5.37 (s, 2H), 4.29 (t, J = 5.8 Hz, 2H), 4.06 (s, 2H), 3.23 (t, J = 5.8 Hz, 2H), 2.50 (s, 3H), 2.48 (s, 3H), 2.32 (s, 3H) | 420 (M$^+$ − 44), 233 (base) |

TABLE 213-continued

| Hydroxy compound | Carboxylic acid | Example | ¹H-NMR | Mass, m/z |
|---|---|---|---|---|
| Example 12-34 | Step 43-1-1 | Example 43-4 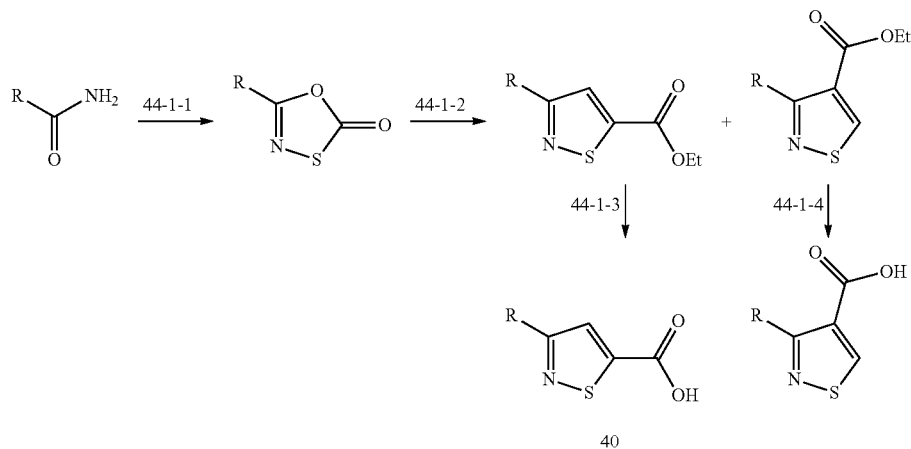 | (DMSO-$d_6$) δ: 9.70 (brs, 1H), 7.79-7.75 (m, 2H), 7.39 (d, J = 8.9 Hz, 1H), 7.29-7.24 (m, 2H), 7.15 (dt, J = 2.7, 8.5 Hz, 1H), 5.39 (s, 2H), 4.29 (t, J = 5.8 Hz, 2H), 4.06 (s, 2H), 3.30-3.22 (m, 4H), 2.85 (q, J = 7.7 Hz, 2H), 2.55 (s, 3H), 1.28 (t, J = 7.7 Hz, 3H) | 482 (M⁺), 438, 231 (base) |

Synthesis scheme 44

In the formulae, R represents an aryl group which may have a substituent (such as a halogen atom, an alkyl group, or an alkoxy group).

Example 44-1

Step 44-1-1

5-(4-Chloro-2-methoxyphenyl)-[1,3,4]oxathiazol-2-one

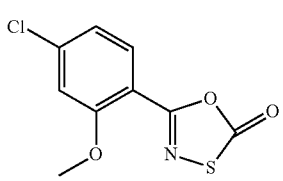

In tetrahydrofuran (100 ml), 4-chloro-2-methoxybenzamide (5.67 g, 30.5 mmol) prepared in the Step 7-1-1 and chlorocarbonylsulfenyl chloride (4.40 g, 33.6 mmol) were suspended, and the mixture was heated under reflux for 1.5 hours. After being allowed to cool, the mixture was subjected to extraction with ethyl acetate, and the extract was dried over anhydrous magnesium sulfate and then concentrated. The concentrate was purified by silica gel column chromatography (n-hexane:ethyl acetate=7:1) to give the title compound (5.33 g, 71%).

¹H-NMR (DMSO-$d_6$) δ: 7.76 (d, J=8.5 Hz, 1H), 7.36 (d, J=1.9 Hz, 1H), 7.18 (dd, J=1.9, 8.5 Hz, 1H), 3.30 (s, 3H)

Mass, m/z: 243 (M⁺), 169 (base)

Step 44-1-2

Ethyl 3-(4-chloro-2-methoxyphenyl)isothiazole-5-carboxylate and ethyl 3-(4-chloro-2-methoxyphenyl)isothiazole-4-carboxylate

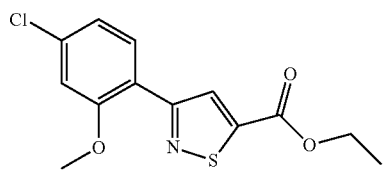

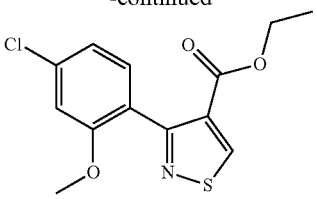

In toluene (35 ml), 5-(4-chloro-2-methoxyphenyl)-[1,3,4]oxathiazol-2-one (2.00 g, 8.21 mmol) prepared in the Step 44-1-1 and ethyl propiolate (4.00 g, 41.0 mmol) were suspended, and the mixture was heated under reflux for 72 hours. After being allowed to cool, the mixture was subjected to extraction with ethyl acetate, and the extract was dried over anhydrous magnesium sulfate and then concentrated. The concentrate was purified by silica gel column chromatography (n-hexane:ethyl acetate=20:1) to firstly give ethyl 3-(4-chloro-2-methoxyphenyl)isothiazole-5-carboxylate (1.00 g, 41%) and to secondly give ethyl 3-(4-chloro-2-methoxyphenyl)isothiazole-4-carboxylate (826 mg, 34%).

44-1-2-A: ethyl 3-(4-chloro-2-methoxyphenyl)isothiazole-5-carboxylate $^1$H-NMR (DMSO-$d_6$) δ: 8.25 (s, 1H), 7.93 (d, J=8.5 Hz, 1H), 7.30 (d, J=1.9 Hz, 1H), 7.16 (dd, J=1.9, 8.3 Hz, 1H), 4.39 (q, J=7.3 Hz, 2H), 3.29 (s, 3H), 1.34 (t, J=7.3 Hz, 3H)
Mass, m/z: 297 (M$^+$), 268 (base)

44-1-2-B: ethyl 3-(4-chloro-2-methoxyphenyl)isothiazole-4-carboxylate $^1$H-NMR (DMSO-$d_6$) δ: 9.60 (s, 1H), 7.41 (d, J=8.1 Hz, 1H), 7.18 (d, J=1.9 Hz, 1H), 7.11 (dd, J=1.9, 8.1 Hz, 1H), 4.14 (q, J=7.3 Hz, 2H), 3.71 (s, 3H), 1.13 (t, J=7.3 Hz, 3H)
Mass, m/z: 297 (M$^+$), 224 (base)

Step 44-1-3

3-(4-Chloro-2-methoxyphenyl)isothiazole-5-carboxylic acid

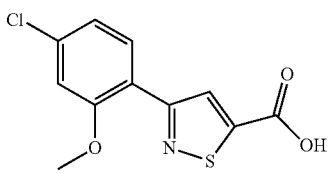 [SMILES: COc1cc(Cl)ccc1-c1cc(C(=O)O)sn1]

Ethyl 3-(4-chloro-2-methoxyphenyl)isothiazole-5-carboxylate (500 mg, 1.68 mmol) prepared in the Step 44-1-2-A was suspended in ethanol (10 ml), and 1 mol/L sodium hydroxide (10 ml) was added thereto. The mixture was heated under reflux for one hour. After being allowed to cool, the mixture was neutralized with hydrochloric acid, and then separated by filtration and washed with water. The washed product was subjected to through circulation drying to give the title compound (194 mg, 43%).
$^1$H-NMR (DMSO-$d_6$) δ: 14.11 (brs, 1H), 8.20 (s, 1H), 7.94 (d, J=8.5 Hz, 1H), 7.30 (d, J=1.9 Hz, 1H), 7.16 (dd, J=1.9, 8.1 Hz, 1H), 3.95 (s, 3H)
Mass, m/z: 269 (M$^+$), 240 (base)

Example 44-2

Step 44-1-4

3-(4-Chloro-2-methoxyphenyl)isothiazole-4-carboxylic acid

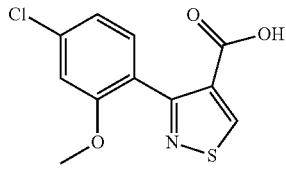 [SMILES: COc1cc(Cl)ccc1-c1nscc1C(=O)O]

The title compound was obtained according to the same procedure as in the Step 44-1-3 except that ethyl 3-(4-chloro-2-methoxyphenyl)isothiazole-4-carboxylate prepared in the Step 44-1-2-B was used instead of ethyl 3-(4-chloro-2-methoxyphenyl)isothiazole-5-carboxylate.
$^1$H-NMR (DMSO-$d_6$) δ: 14.11 (brs, 1H), 8.20 (s, 1H), 7.94 (d, J=8.5 Hz, 1H), 7.30 (d, J=1.9 Hz, 1H), 7.16 (dd, J=1.9, 8.1 Hz, 1H), 3.95 (s, 3H)
Mass, m/z: 269 (M$^+$), 240 (base)

Example 44-3

3-(2-Methoxy-4-methylphenyl)isothiazole-5-carboxylic acid

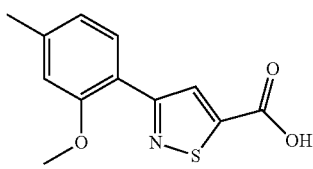 [SMILES: COc1cc(C)ccc1-c1cc(C(=O)O)sn1]

The title compound was obtained according to the same procedure as in Example 44-1 except that 4-methyl-2-methoxybenzamide was used instead of 4-chloro-2-methoxybenzamide.
$^1$H-NMR (DMSO-$d_6$) δ: 8.19 (s, 1H), 7.83 (d, J=7.8 Hz, 1H), 7.03 (s, 1H), 6.90 (d, J=7.7 Hz, 1H), 3.90 (s, 3H), 2.37 (s, 1H)
Mass, m/z: 249 (M$^+$), 220 (base)

Example 44-4

3-(2-Methoxyphenyl)isothiazole-5-carboxylic acid

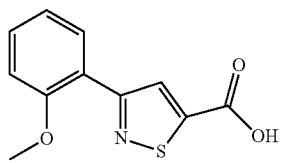 [SMILES: COc1ccccc1-c1cc(C(=O)O)sn1]

The title compound was obtained according to the same procedure as in Example 44-1 except that 2-methoxybenzamide was used instead of 4-chloro-2-methoxybenzamide.

$^1$H-NMR (DMSO-$d_6$) δ: 14.05 (brs, 1H), 8.22 (s, 1H), 7.91 (dd, J=1.5, 7.7 Hz, 1H), 7.48 (t, J=8.9 Hz, 1H), 7.21 (d, J=8.1 Hz, 1H), 7.09 (t, J=7.7 Hz, 1H), 3.92 (s, 3H)

Mass, m/z: 235 (M$^+$), 206 (base)

Example 44-5

3-(2-Methoxyphenyl)isothiazole-4-carboxylic acid

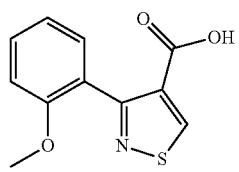 [SMILES: COc1ccccc1-c1nscc1C(=O)O]

The title compound was obtained according to the same procedure as in Example 44-2 except that 2-methoxybenzamide was used instead of 4-chloro-2-methoxybenzamide.

$^1$H-NMR (DMSO-$d_6$) δ: 12.70 (brs, 1H), 9.51 (s, 1H), 7.44-7.35 (m, 2H), 7.08-6.99 (m, 2H), 3.69 (s, 3H)

Mass, m/z: 235 (M$^+$, base)

Synthesis scheme 45

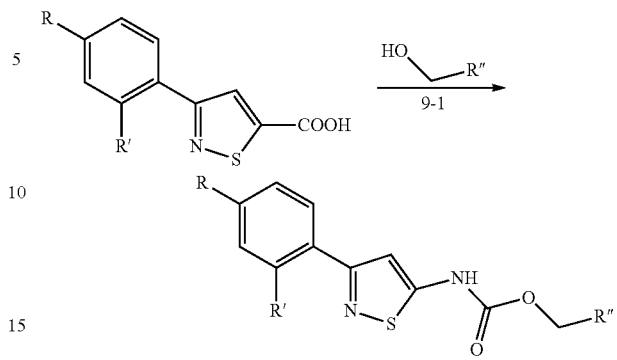

In the formulae, R and R' are the same or different and each represent a halogen atom, an alkyl group, a hydroxyl group or an alkoxy group.

Examples 45-1 to 45-7

The objective compounds were obtained according to the same procedure as in Example 9-1 except that the carboxylic acids or hydroxy compounds obtained in Examples shown in the following tables were used instead of 2-(4-chloro-2-methoxyphenyl)-4-methylthiazole-5-carboxylic acid or (1,2,3,4-tetrahydrobenzo[4,5]imidazo[1,2-a]pyridin-7-yl)methanol.

TABLE 214

| Carboxylic acid | Hydroxy compound | Example | $^1$H-NMR | Mass, m/z |
|---|---|---|---|---|
| Example 44-3 | Example 3-6 | Example 45-1 | (DMSO-$d_6$) δ: 11.5 (s, 1H), 7.78 (d, J = 7.7 Hz, 1H), 7.70 (s, 1 H), 7.56 (d, J = 8.1 Hz, 1H), 7.34 (dd, J = 1.3, 8.3 Hz, 1H), 7.29 (s, 1H), 6.96 (s, 1H), 6.85 (dd, J = 1.5, 8.4 Hz, 1H), 5.36 (s, 2H), 4.96 (s, 2H), 4.21-4.15 (m, 4H), 3.90-3.84 (m, 4H), 2.34 (s, 3H) | 406 (M$^+$ − 44), 187 (base) |
| Example 44-1 | Example 1-1 | Example 45-2 | (DMSO-$d_6$) δ: 11.6 (s, 1H), 8.21 (s, 1H), 7.90 (d, J = 8.5 Hz, 1 H), 7.75 (s, 1H), 7.60 (d, J = 8.5 Hz, 1H), 7.37 (dd, J = 1.3, 8.3 Hz, 1H), 7.29 (s, 1H), 7.22 (d, J = 1.9 Hz, 1H), 7.10 (dd, J = 1.9, 8.5 Hz, 1H), 5.37 (s, 2H), 3.89 (s, 3H), 3.85 (s, 3H) | 428 (M$^+$), 145 (base) |

TABLE 214-continued

| Carboxylic acid | Hydroxy compound | Example | ¹H-NMR | Mass, m/z |
|---|---|---|---|---|
| Example 44-1 | Example 1-2 | Example 45-3 | (DMSO-d₆) δ: 11.5 (s, 1H), 8.28 (s, 1H), 7.90 (d, J = 8.5 Hz, 1H), 7.75 (s, 1H), 7.64 (d, J = 8.5 Hz, 1H), 7.36 (dd, J = 1.2, 8.5 Hz, 1H), 7.29 (s, 1H), 7.23 (d, J = 1.9 Hz, 1H), 7.10 (dd, J = 1.9, 8.5 Hz, 1H), 4.29 (q, J = 7.3 Hz, 2H), 3.89 (s, 3H), 1.41 (t, J = 7.3 Hz, 3H) | 442 (M⁺), 159 (base) |
| Example 44-1 | Example 4-3 | Example 45-4 | (DMSO-d₆) δ: 11.6 (s, 1H), 8.09 (s, 1H), 7.90 (d, J = 8.5 Hz, 1H), 7.85 (s, 1H), 7.71 (d, J = 8.5 Hz, 1H), 7.47 (dd, J = 1.3, 8.7 Hz, 1H), 7.29 (s, 1H), 7.23 (d, J = 1.9 Hz, 1H), 7.09 (dd, J = 1.9, 8.5 Hz, 1H), 5.36 (s, 2H), 4.44 (q, J = 7.3 Hz, 2H), 3.89 (s, 3H), 1.39 (t, J = 7.3 Hz, 3H) | 442 (M⁺), 159 (base) |

TABLE 215

| Carboxylic acid | Hydroxy compound | Example | ¹H-NMR | Mass, m/z |
|---|---|---|---|---|
| Example 44-2 | Example 1-1 | Example 45-5 | (DMSO-d₆) δ: 9.06 (brs, 1H), 8.89 (s, 1H), 8.18 (s, 1H), 7.67 (s, 1H), 7.55 (d, J = 8.5 Hz, 1H), 7.29-7.25 (m, 2H), 7.17 (d, J = 1.9 Hz, 1H), 7.05 (dd, J = 1.9, 8.2 Hz, 1H), 5.22 (s, 2H), 3.83 (s, 3H), 3.71 (s, 3H) | 428 (M⁺), 145 (base) |
| Example 44-5 | Example 1-1 | Example 45-6 | (DMSO-d₆) δ: 8.88 (s, 1H), 8.81 (brs, 1H), 7.67 (s, 1H), 7.54 (d, J = 8.1 Hz, 1H), 7.46-7.41 (m, 1H), 7.30-7.26 (m, 2H), 7.11 (d, J = 8.5 Hz, 1H), 7.02 (t, J = 7.3 Hz, 1H), 5.22 (s, 2H), 3.83 (s, 3H), 3.70 (s, 3H) | 394 (M⁺), 145 (base) |

TABLE 215-continued

| Carboxylic acid | Hydroxy compound | Example | ¹H-NMR | Mass, m/z |
|---|---|---|---|---|
| Example 44-2 | Example 4-3 | Example 45-7 | (DMSO-$d_6$) δ: 9.05 (brs, 1H), 8.89 (s, 1H), 8.05 (s, 1H), 7.76 (s, 1H), 7.66 (d, J = 8.5 Hz, 1H), 7.38 (d, J = 8.5 Hz, 1H), 7.26 (d, J = 8.1 Hz, 1H), 7.17 (d, J = 1.9 Hz, 1H), 7.05 (dd, J = 1.9, 8.1 Hz, 1H), 5.21 (s, 2H), 4.43 (q, J = 7.3 Hz, 2H), 3.70 (s, 3H), 1.38 (t, J = 7.3 Hz, 3H) | 442 (M⁺), 159 (base) |

Synthesis scheme 46

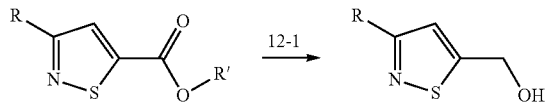

In the formulae, R represents an aryl group which may have a substituent (such as a halogen atom, an alkyl group, or an alkoxy group); and R' represents a hydrogen atom or an alkyl group.

Examples 46-1 to 46-4

The objective compounds were obtained according to the same procedure as in Example 12-1 except that the carboxylic acids or esters obtained in Examples shown in the following table were used instead of 2-(4-chloro-2-methoxyphenyl)-4-methylthiazole-5-carboxylic acid.

TABLE 216

| Carboxylic acid or ester | Example | ¹H-NMR | Mass, m/z |
|---|---|---|---|
| Example 27-1 | Example 46-1 | (DMSO-$d_6$) δ: 7.77-7.72 (m, 1H), 7.57-7.53 (m, 2H), 5.95 (t, J = 5.8 Hz, 1H), 4.88 (d, J = 5.8 Hz, 2H) | 259 (M⁺, base) |
| Example 44-1 | Example 46-2 | (DMSO-$d_6$) δ: 7.89 (d, J = 8.7 Hz, 1H), 7.65 (s, 1H), 7.25 (d, J = 1.9 Hz, 1H), 7.11 (dd, J = 1.9, 8.2 Hz, 1H), 5.87 (t, J = 5.8 Hz, 1H), 4.87-4.85 (m, 2H), 3.91 (s, 3H) | 255 (M⁺), 226 (base) |
| Example 44-3 | Example 46-3 | (DMSO-$d_6$) δ: 7.77 (d, J = 7.7 Hz, 1H), 7.62 (s, 1H), 6.98 (s, 1H), 6.86 (d, J = 7.7 Hz, 1H), 5.83 (br s, 1H), 4.85 (s, 2H), 3.86 (s, 3H), 2.36 (s, 3H) | 235 (M⁺), 206 (base) |

TABLE 216-continued

| Carboxylic acid or ester | Example | $^1$H-NMR | Mass, m/z |
|---|---|---|---|
| Example 44-4 | Example 46-4 | (DMSO-$d_6$) δ: 7.87 (dd, J = 1.9, 7.7 Hz, 1H), 7.65 (s, 1 H), 7.65-7.39 (m, 1H), 7.16 (d, J = 8.1 Hz, 1 H), 7.07-7.02 (m, 1H), 5.85 (t, J = 5.4 Hz, 1 H), 4.86 (d, J = 5.1 Hz, 2H), 3.30 (s, 3H) | 221 (M$^+$), 192 (base) |

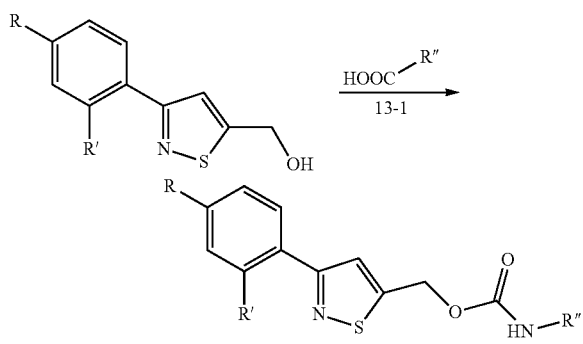

Synthesis scheme 47

In the formulae, R and R' are the same or different and each represent a halogen atom, an alkyl group, a hydroxyl group or an alkoxy group; and R" represents a heterocyclic group which may have a substituent (such as an alkyl group).

Examples 47-1 to 47-12

According to the production processes shown in the following tables, the hydroxy compounds or carboxylic acids obtained in Examples shown in the following tables were used instead of [2-(2-methylphenyl)-4-methylthiazol-5-yl]methanol or 1-methyl-1H-benzimidazole-5-carboxylic acid to give the objective compounds.

TABLE 217

| Hydroxy compound | Carboxylic acid | Production process | Example | $^1$H-NMR | Mass, m/z |
|---|---|---|---|---|---|
| Example 46-1 | — | Example 13-1 | Example 47-1 | (DMSO-$d_6$) δ: 9.84 (s, 1H), 8.12 (s, 1H), 7.84-7.74 (m, 4H), 7.56 (dd, J = 2.3, 8.5 Hz, 1H), 7.48 (d, J = 8.9 Hz, 1H), 7.34 (d, J = 8.1 Hz, 1H), 5.55 (s, 2H), 3.81 (s, 3H) | 432 (M$^+$), 173 (base) |
| Example 46-4 | — | Example 13-1 | Example 47-2 | (DMSO-$d_6$) δ: 9.82 (brs, 1H), 8.12 (s, 1H), 7.90 (s, 1 H), 7.88 (d, J = 1.9 Hz, 1H), 7.81 (brs, 1H), 7.48 (d, J = 8.5 Hz, 1H), 7.46-7.42 (m, 1H), 7.34 (d, J = 8.5 Hz, 1H), 7.18 (d, J = 8.1 Hz, 1H), 7.08-7.04 (m, 1H), 5.53 (s, 2H), 3.89 (s, 3H), 3.81 (s, 3H) | 394 (M$^+$), 173 (base) |

TABLE 217-continued

| Hydroxy compound | Carboxylic acid | Production process | Example | ¹H-NMR | Mass, m/z |
|---|---|---|---|---|---|
| Example 46-3 | — | Example 13-1 | Example 47-3 | (DMSO-d₆) δ: 9.80 (brs, 1H), 8.12 (s, 1H), 7.87 (s, 1H), 7.81 (brs, 1H), 7.79 (d, J = 7.7 Hz, 1H), 7.48 (d, J = 8.9 Hz, 1H), 7.34 (d, J = 8.5 Hz, 1H), 7.00 (s, 1H), 6.87 (d, J = 7.7 Hz, 1H), 5.52 (s, 2H), 3.88 (s, 3H), 3.81 (s, 3H), 2.36 (s, 3H) | 408 (M⁺), 173 (base) |
| Example 46-2 | — | Example 13-1 | Example 47-4 | (DMSO-d₆) δ: 9.82 (brs, 1H), 8.12 (s, 1H), 7.92 (d, J = 8.9 Hz, 1H), 7.81 (brs, 1H), 7.48 (d, J = 8.9 Hz, 1H), 7.34 (d, J = 7.7 Hz, 1H), 7.27 (d, J = 1.9 Hz, 1H), 7.12 (dd, J = 1.9, 8.5 Hz, 1H), 5.53 (s, 2H), 3.93 (s, 3H), 3.81 (s, 3H) | 428 (M⁺), 173 (base) |

TABLE 218

| Hydroxy compound | Carboxylic acid | Production process | Example | ¹H-NMR | Mass, m/z |
|---|---|---|---|---|---|
| Example 46-4 | Example 11-7 | Example 13-1 | Example 47-5 | (DMSO-d₆) δ: 9.75 (brs, 1H), 7.90-7.87 (m, 2H), 7.70 (brs, 1H), 7.46-7.41 (m, 1H), 7.36 (d, J = 8.5 Hz, 1H), 7.25 (d, J = 8.1 Hz, 1H), 7.18 (d, J = 8.1 Hz, 1H), 7.06 (t, J = 7.3 Hz, 1H), 5.52 (s, 2H), 4.06 (t, J = 6.2 Hz, 2H), 3.90 (s, 3H), 2.93 (t, J = 6.2 Hz, 2H), 2.06-1.88 (m, 4H) | 434 (M⁺), 213 (base) |
| Example 46-3 | Example 11-7 | Example 13-1 | Example 47-6 | (DMSO-d₆) δ: 9.75 (brs, 1H), 7.86 (s, 1H), 7.79 (d, J = 7.7 Hz, 1H), 7.70 (brs, 1H), 7.36 (d, J = 8.5 Hz, 1H), 7.25 (d, J = 8.1 Hz, 1H), 7.00 (s, 1H), 6.87 (d, J = 8.5 Hz, 1H), 5.51 (s, 2H), 4.05 (t, J = 6.2 Hz, 2H), 3.88 (s, 3H), 2.93 (t, J = 6.2 Hz, 2H), 2.36 (s, 3H), 2.06-1.88 (m, 4H) | 448 (M⁺), 213 (base) |

TABLE 218-continued

| Hydroxy compound | Carboxylic acid | Production process | Example | ¹H-NMR | Mass, m/z |
|---|---|---|---|---|---|
| Example 46-2 | Example 11-7 | Example 13-1 | Example 47-7 | (DMSO-d₆) δ: 9.76 (brs, 1H), 7.91 (d, J = 8.5 Hz, 1H), 7.89 (s, 1H), 7.70 (brs, 1H), 7.36 (d, J = 8.5 Hz, 1H), 7.27 (d, J = 1.9 Hz, 1H), 7.27-7.22 (m, 1H), 7.13 (dd, J = 1.9, 8.5 Hz, 1H), 5.52 (s, 2H), 4.05 (t, J = 6.2 Hz, 2H), 3.93 (s, 3H), 2.93 (t, J = 6.2 Hz, 2H), 2.06-1.88 (m, 4H) | 468 (M⁺), 213 (base) |
| Example 46-1 | Example 11-7 | Example 13-1 | Example 47-8 | (DMSO-d₆) δ: 9.78 (brs, 1H), 7.84 (s, 1H), 7.79 (d, J = 2.3 Hz, 1H), 7.76 (d, J = 8.1 Hz, 1H), 7.70 (s, 1H), 7.56 (dd, J = 2.3, 8.5 Hz, 1H), 7.36 (d, J = 8.5 Hz, 1H), 7.26-7.23 (m, 1H), 5.53 (s, 2H), 4.05 (t, J = 6.2 Hz, 2H), 2.93 (t, J = 6.2 Hz, 2H), 2.06-1.90 (m, 4H) | 472 (M⁺), 213 (base) |

TABLE 219

| Hydroxy compound | Carboxylic acid | Production process | Example | ¹H-NMR | Mass, m/z |
|---|---|---|---|---|---|
| Example 46-2 | Example 11-5 | Example 13-1 | Example 47-9 | (DMSO-d₆) δ: 9.82 (brs, 1H), 7.91 (d, J = 8.5 Hz, 1H), 7.89 (s, 1H), 7.77 (brs, 1H), 7.44 (d, J = 8.9 Hz, 1H), 7.31 (d, J = 8.9 Hz, 1H), 7.27 (d, J = 1.9 Hz, 1H), 7.13 (dd, J = 1.9, 8.5 Hz, 1H), 5.52 (s, 2H), 4.93 (s, 2H), 4.15 (s, 4H), 3.93 (s, 3H) | 471 (M⁺), 216 (base) |
| Example 46-4 | Example 11-11 | Example 13-1 | Example 47-10 | (DMSO-d₆) δ: 9.86 (brs, 1H), 7.99 (s, 1H), 7.90-7.87 (m, 3H), 7.61 (d, J = 8.9 Hz, 1H), 7.46-7.40 (m, 2H), 7.18 (d, J = 8.5 Hz, 1H), 7.06 (t, J = 7.3 Hz, 1H), 5.53 (s, 2H), 4.40 (q, J = 7.3 Hz, 2H), 3.89 (s, 3H), 1.38 (t, J = 7.3 Hz, 3H) | 408 (M⁺), 160 (base) |

TABLE 219-continued

| Hydroxy compound | Carboxylic acid | Production process | Example | ¹H-NMR | Mass, m/z |
|---|---|---|---|---|---|
| Example 46-2 | Example 11-11 | Example 13-1 | Example 47-11 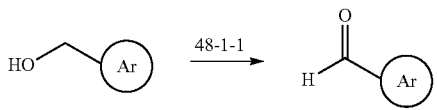 | (DMSO-d$_6$) δ: 9.86 (brs, 1H), 8.00-7.89 (m, 4H), 7.61 (d, J = 9.2 Hz, 1H), 7.41 (dd, J = 0.8, 8.5 Hz, 1H), 5.53 (s, 2H), 4.40 (q, J = 7.3 Hz, 2H), 3.93 (s, 3H), 1.38 (t, J = 7.3 Hz, 3H) | 442 (M$^+$), 160 (base) |
| Example 46-1 | Example 11-11 | Example 13-1 | Example 47-12 | (DMSO-d$_6$) δ: 9.88 (brs, 1H), 8.00 (s, 1H), 7.90 (brs, 1H), 7.84 (s, 1H), 7.79 (d, J = 1.9 Hz, 1H), 7.75 (d, J = 8.5 Hz, 1H), 7.61 (d, J = 9.2 Hz, 1H), 7.56 (dd, J = 1.9, 8.5 Hz, 1H), 7.43-7.40 (m, 1H), 5.55 (s, 2H), 4.40 (q, J = 7.3 Hz, 2H), 1.38 (t, J = 7.3 Hz, 3H) | 446 (M$^+$), 160 (base) |

Synthesis scheme 48

HO—Ar  →(48-1-1)  H(C=O)—Ar

In the formulae, Ar represents a heterocyclic ring which may have a substituent (such as an alkyl group).

Example 48-1

Step 48-1-1

1-Ethyl-1H-indazole-5-carbaldehyde

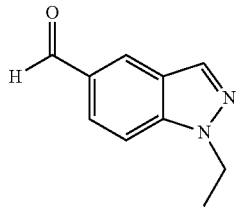

In dichloromethane (10 ml), (1-ethyl-1H-indazol-5-yl)methanol (0.3 g, 1.70 mmol) prepared in Example 4-3 was dissolved, and 1,1,1-triacetoxy-1,1-dihydro-1,2-benziodoxol-3(1H)-one (1.0 g, 2.38 mmol) was added thereto. The mixture was stirred for 2 hours. The mixture was subjected to extraction with chloroform, and the extract was dried over anhydrous magnesium sulfate and then concentrated. The concentrate was purified by silica gel column chromatography (dichloromethane:methanol=20:1) to give the title compound.

¹H-NMR (DMSO-d$_6$) δ: 10.03 (s, 1H), 8.43 (s, 1H), 8.33 (s, 1H), 7.85 (m, 2H), 4.49 (m, 2H), 1.42 (t, J=6.9 Hz, 3H)

Mass, m/z: 174 (M$^+$), 159 (base)

Example 48-2

3,4-Dihydro-1H-2-oxa-4a,9-diazafluorene-7-carbaldehyde

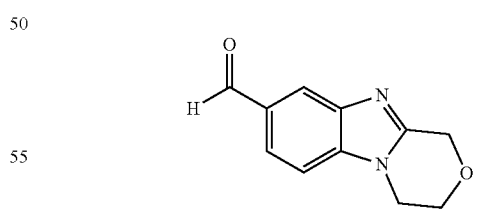

The title compound was obtained according to the same procedure as in Example 48-1 except that (3,4-dihydro-1H-2-oxa-4a,9-diazafluoren-7-yl)methanol prepared in Example 3-6 was used instead of (1-ethyl-1H-indazol-5-yl)methanol.

¹H-NMR (DMSO-d$_6$) δ: 10.06 (s, 1H), 8.19 (s, 1H), 7.82 (d, J=8.5 Hz, 1H), 7.72 (d, J=8.1 Hz, 1H), 5.01 (s, 2H), 4.28 (t, J=5.2 Hz, 2H), 4.19 (t, J=5.4 Hz, 2H)

Mass, m/z: 202 (M$^+$, base)

Synthesis scheme 49

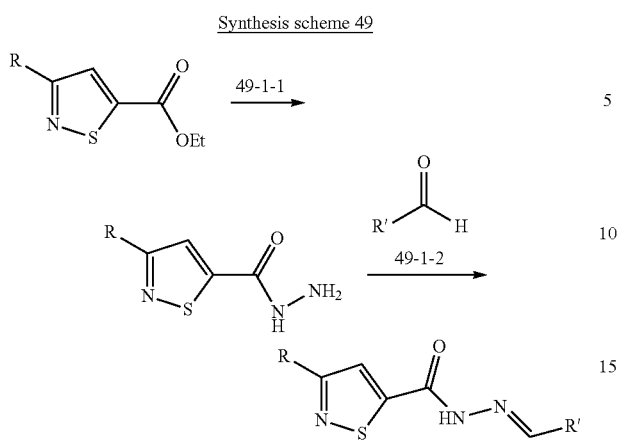

In the formulae, R represents an aryl group which may have a substituent (such as a halogen atom or an alkoxy group), and R' represents a heterocyclic group which may have a substituent (such as an alkyl group).

Example 49-1

Step 49-1-1

3-(4-Chloro-2-methoxyphenyl)isothiazole-5-carboxylic acid hydrazide

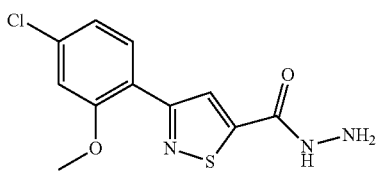 [SMILES: COc1cc(Cl)ccc1-c1cc(C(=O)NN)sn1]

The title compound was obtained according to the same procedure as in the Step 22-1-3 except that the compound prepared in the Step 44-1-2-A was used instead of methyl 5-(2-chlorophenyl)-2H-pyrazole-3-carboxylate.

$^1$H-NMR (DMSO-d$_6$) δ: 10.27 and 9.40 (two brs, 1H), 8.34 (d, J=17.0 Hz, 1H), 7.95 (t, J=8.5 Hz, 1H), 7.29-7.26 (m, 1H), 7.16-7.12 (m, 1H), 5.19 (s, 1H), 4.66 (s, 1H), 3.95 (s, 3H)

Mass, m/z: 283 (M$^+$), 252 (base)

Step 49-1-2

3-(4-Chloro-2-methoxyphenyl)isothiazole-5-carboxylic acid[1-methyl-1H-benzimidazol-5-yl)methylidene]hydrazide

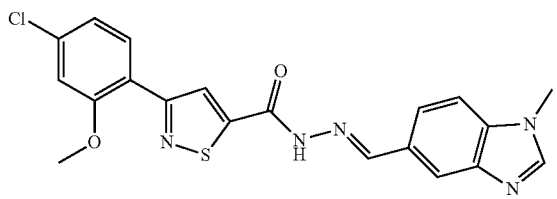 [SMILES: COc1cc(Cl)ccc1-c1cc(C(=O)N/N=C/c2ccc3c(c2)ncn3C)sn1]

The title compound was obtained according to the same procedure as in the Step 22-1-4 except that the compound prepared in the Step 49-1-1 and 1-methyl-1H-benzimidazole-5-carbaldehyde were used instead of 5-(2-chlorophenyl)-2H-pyrazole-3-carboxylic acid hydrazide and 3-hydroxy-4-methoxybenzaldehyde, respectively.

$^1$H-NMR (CD$_3$CO$_2$D) δ: 9.01 (s, 1H), 8.63 (s, 1H), 8.33-8.25 (m, 3H), 7.99 (d, J=8.5 Hz, 1H), 7.86 (d, J=8.9 Hz, 1H), 7.11 (d, J=1.9 Hz, 1H), 7.07 (dd, J=1.9, 8.5 Hz, 1H), 4.09 (s, 3H), 3.97 (s, 3H)

Mass, m/z: 425 (M$^+$), 157 (base)

Example 49-2

3-(2-Methoxyphenyl)isothiazole-5-carboxylic acid [1-(1-methyl-1H-benzimidazol-5-yl)methylidene] hydrazide

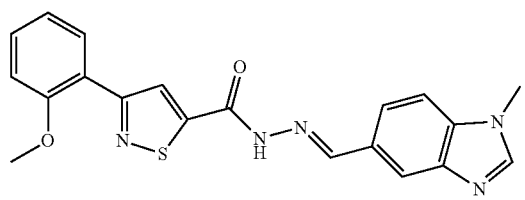 [SMILES: COc1ccccc1-c1cc(C(=O)N/N=C/c2ccc3c(c2)ncn3C)sn1]

The title compound was obtained according to the same procedure as in Example 49-1 except that the ester prepared in the process of the production of the compound of Example 44-4 was used instead of methyl 5-(2-chlorophenyl)-2H-pyrazole-3-carboxylate.

$^1$H-NMR (CD$_3$CO$_2$D) δ: 9.02 (s, 1H), 8.65 (d, J=2.3 Hz, 1H), 8.33-8.28 (m, 3H), 8.00 (dd, J=1.5, 7.7 Hz, 1H), 7.87 (d, J=8.5 Hz, 1H), 7.44-7.39 (m, 1H), 7.11-7.04 (m, 2H), 4.10 (s, 3H), 3.95 (s, 3H)

Mass, m/z: 391 (M$^+$), 204 (base)

Example 49-3

3-(2,4-Dichlorophenyl)isothiazole-5-carboxylic acid [3,4-dihydro-1H-2-oxa-4a,9-diazafluoren-7-yl)methylidene]hydrazide

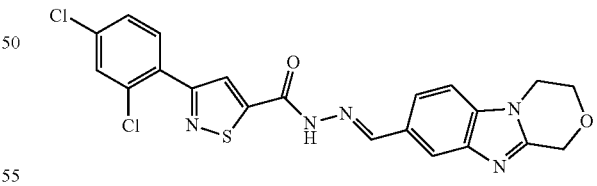

The title compound was obtained according to the same procedure as in the Step 22-1-4 except that the compound prepared in the Step 27-1-5 and the compound prepared in Example 48-2 were used instead of 5-(2-chlorophenyl)-2H-pyrazole-3-carboxylic acid hydrazide and 3-hydroxy-4-methoxybenzaldehyde, respectively.

$^1$H-NMR (CD$_3$CO$_2$D) δ: 12.39 (s, 1H), 8.40 (s, 1H), 8.35 (s, 1H), 8.05 (s, 1H), 7.84 (m, 2H), 7.72 (d, J=8.10 Hz, 1H), 7.60 (d, J=8.2 Hz, 1H), 5.00 (s, 2H), 4.26 (m, 2H), 4.19 (m, 2H)

Mass, m/z: 471 (M$^+$), 199 (base)

Example 49-4

3-(2-Methoxyphenyl)isothiazole-5-carboxylic acid [1-(3,4-dihydro-1H-2-oxa-4a,9-diazafluoren-7-yl)methylidene]hydrazide

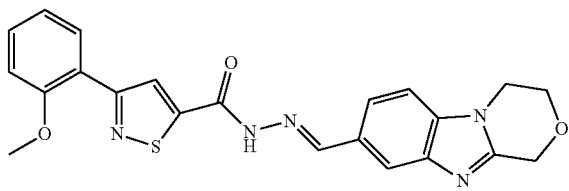 [SMILES: COc1ccccc1-c1cc(C(=O)N/N=C/c2ccc3c(c2)nc2n3CCOC2)sn1]

The title compound was obtained according to the same procedure as in Example 49-1 except that the ester prepared in the process of the production of the compound of Example 44-4 and the compound prepared in Example 48-2 were used instead of methyl 5-(2-chlorophenyl)-2H-pyrazole-3-carboxylate and 1-methyl-1H-benzimidazole-5-carbaldehyde, respectively.

$^1$H-NMR (CD$_3$CO$_2$D) δ: 8.63 (s, 1H), 8.28 (s, 1H), 8.18 (d, J=8.5 Hz, 1H), 8.14 (s, 1H), 8.00 (d, J=7.7 Hz, 1H), 7.71 (d, J=8.5 Hz, 1H), 7.42 (t, J=7.7 Hz, 1H), 7.11-7.04 (m, 2H), 5.17 (s, 2H), 4.33-4.27 (m, 4H), 3.95 (s, 3H)

Mass, m/z: 433 (M$^+$), 205 (base)

Example 49-5

3-(4-Chloro-2-methoxyphenyl)isothiazole-5-carboxylic acid[1-(3,4-dihydro-1H-2-oxa-4a,9-diazafluoren-7-yl)methylidene]hydrazide

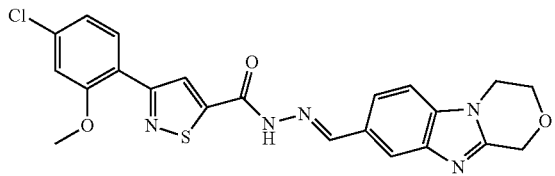 [SMILES: COc1cc(Cl)ccc1-c1cc(C(=O)N/N=C/c2ccc3c(c2)nc2n3CCOC2)sn1]

The title compound was obtained according to the same procedure as in Example 49-1 except that the compound prepared in Example 48-2 was used instead of 1-methyl-1H-benzimidazole-5-carbaldehyde.

$^1$H-NMR (CD$_3$CO$_2$D) δ: 8.64 (s, 1H), 8.32 (s, 1H), 8.21-8.18 (m, 2H), 8.00 (d, J=8.1 Hz, 1H), 7.73 (d, J=8.9 Hz, 1H), 7.12 (d, J=1.2 Hz, 1H), 7.08 (dd, J=1.7, 8.3 Hz, 1H), 5.18 (s, 2H), 4.35-4.27 (m, 4H), 3.97 (s, 3H)

Mass, m/z: 467 (M$^+$), 199 (base)

Example 49-6

3-(2,4-Dichlorophenyl)isothiazole-5-carboxylic acid [1-(1-ethyl-1H-indazol-5-yl)methylidene]hydrazide

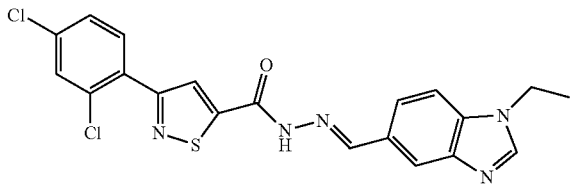 [SMILES: CCn1cnc2cc(/C=N/NC(=O)c3cc(-c4ccc(Cl)cc4Cl)ns3)ccc21]

The title compound was obtained according to the same procedure as in the Step 22-1-4 except that the compound prepared in the Step 27-1-5 and the compound prepared in Example 48-1 were used instead of 5-(2-chlorophenyl)-2H-pyrazole-3-carboxylic acid hydrazide and 3-hydroxy-4-methoxybenzaldehyde, respectively.

$^1$H-NMR (CD$_3$CO$_2$D) δ: 8.54 (s, 1H), 8.29 (s, 1H), 8.25 (s, 1H), 8.23 (dd, J=1.5 Hz, J=9.1 Hz, 1H), 8.17 (s, 1H), 7.81 (d, J=8.5 Hz, 1H), 7.72 (d, J=8.9 Hz, 1H), 7.59 (d, J=2.3 Hz, 1H), 7.44 (dd, J=1.9, 8.5 Hz, 1H), 4.55 (q, J=7.3 Hz, 2H), 1.50 (t, J=7.3 Hz, 3H)

Mass, m/z: 443 (M$^+$), 171 (base)

Example 49-7

3-(2-Methoxyphenyl)isothiazole-5-carboxylic acid [1-(1-ethyl-1H-indazol-5-yl)methylidene]hydrazide

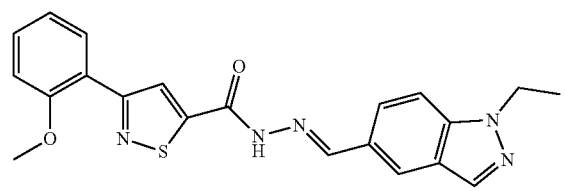 [SMILES: CCn1ncc2cc(/C=N/NC(=O)c3cc(-c4ccccc4OC)ns3)ccc21]

The title compound was obtained according to the same procedure as in Example 49-1 except that the ester in the process of the production of the compound of Example 44-4 and the compound prepared in Example 48-1 were used instead of methyl 5-(2-chlorophenyl)-2H-pyrazole-3-carboxylate and 1-methyl-1H-benzimidazole-5-carbaldehyde, respectively.

$^1$H-NMR (CD$_3$CO$_2$D) δ: 8.64 (s, 1H), 8.27-8.24 (m, 3H), 8.16 (s, 1H), 7.99 (dd, J=1.7, 7.5 Hz, 1H), 7.72 (d, J=8.9 Hz, 1H), 7.42 (m, 1H), 7.10 (d, J=8.9 Hz, 1H), 7.06 (d, J=7.7 Hz, 1H), 4.54 (q, J=7.3 Hz, 2H), 3.95 (s, 3H), 1.50 (t, J=7.3 Hz, 3H)

Mass, m/z: 405 (M$^+$), 171 (base)

Example 49-8

3-(4-Chloro-2-methoxyphenyl)isothiazole-5-carboxylic acid[1-ethyl-1H-indazol-5-yl)methylidene]hydrazide

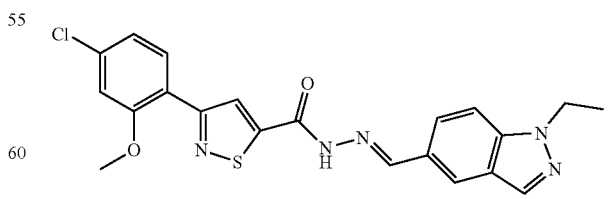

The title compound was obtained according to the same procedure as in Example 49-1 except that the compound prepared in Example 48-1 was used instead of 1-methyl-1H-benzimidazole-5-carbaldehyde.

$^1$H-NMR (CD$_3$CO$_2$D) δ: 8.63 (s, 1H), 8.27-8.22 (m, 3H), 8.16 (s, 1H), 8.00 (d, J=8.1 Hz, 1H), 7.72 (d, J=8.9 Hz, 1H), 7.11 (s, 1H), 7.08 (dd, J=1.5, 9.2 Hz, 1H), 4.54 (q, J=7.3 Hz, 2H), 3.97 (s, 3H), 1.50 (t, J=7.3 Hz, 3H)

Mass, m/z: 439 (M$^+$), 171 (base)

Pharmacological Test Procedure and Test Results

Hereinafter, the pharmacological test procedure for the validity (usefulness) of the heterocyclic compound or the salt thereof of the present invention and the results thereof will be explained.

Test Example 1

Measurement of Cell Death-Inducing Activity

The cell death-inducing activity of the compound represented by the formula (1) or the salt thereof was measured as follows.

Human prostate cancer cell lines (PC-3 cells) were seeded to 6-well plates at 1×10$^5$ cells/2 mL/well, and cultured in the presence of 5% CO$_2$ at 37° C. for 48 hours. Thereafter, each compound was added thereto so as to provide 10, 1, 0.1, 0.025 and 0.00625 μmol/L. As a control, DMSO was added. After the addition, the cells were continuously cultured for 48 hours. Then, typical 10 fields were observed in each well to qualitatively evaluate the cell death-inducing rate. When the cell death-inducing rate was not less than 40%, the compound was judged to have the cell death-inducing activity.

Results (1) Compounds (Example Number) Showing the Cell Death-Inducing Activity at a Concentration of 0.00625 μM Examples 9-15, 9-16, 9-24, 9-25, 9-38, 9-39, 9-40, 9-42, 9-48, 9-49, 9-58, 9-59, 9-60, 9-61, 9-62, 9-63, 9-64, 9-92, 9-93, 9-94, 9-96, 9-98, 9-103, 9-128, 9-129, 9-136, 9-137, 9-165, 9-169, 9-181, 9-221, 9-222, 9-223, 9-224, 9-226, 9-227, 9-228, 9-233, 9-235, 9-247, 9-249, 9-280, 9-300, 9-344, 9-372, 13-10, 13-26, 13-80, 13-84, 13-85, 13-86, 13-88, 13-89, 13-90, 13-92, 13-97, 13-99, 13-100, 13-101, 13-103, 13-106, 13-108, 13-109, 13-110, 13-111, 13-112, 13-113, 13-118, 13-133, 47-3, 47-4, 47-7, 47-9

(2) Compounds (Example Number) Showing Cell Death-Inducing Activity at a Concentration of 0.025 μM Examples 9-1, 9-13, 9-14, 9-17, 9-19, 9-20, 9-22, 9-23, 9-26, 9-27, 9-28, 9-33, 9-36, 9-37, 9-41, 9-47, 9-56, 9-57, 9-67, 9-71, 9-76, 9-77, 9-78, 9-81, 9-82, 9-86, 9-87, 9-91, 9-95, 9-97, 9-102, 9-106, 9-107, 9-108, 9-113, 9-130, 9-134, 9-135, 9-138, 9-139, 9-140, 9-141, 9-143, 9-144, 9-145, 9-147, 9-150, 9-153, 9-154, 9-155, 9-160, 9-161, 9-163, 9-164, 9-166, 9-167, 9-170, 9-171, 9-172, 9-173, 9-174, 9-176, 9-182, 9-207, 9-208, 9-209, 9-213, 9-217, 9-218, 9-219, 9-229, 9-230, 9-234, 9-239, 9-245, 9-248, 9-250, 9-251, 9-258, 9-259, 9-260, 9-261, 9-262, 9-267, 9-281, 9-283, 9-291, 9-292, 9-301, 9-340, 9-341, 9-345, 9-346, 9-349, 9-357, 9-358, 9-359, 9-360, 9-362, 9-364, 9-365, 9-373, 9-377, 13-8, 13-9, 13-11, 13-15, 13-16, 13-17, 13-18, 13-24, 13-25, 13-28, 13-34, 13-35, 13-50, 13-55, 13-76, 13-81, 13-82, 13-83, 13-87, 13-95, 13-98, 13-102, 13-104, 13-105, 13-107, 13-116, 13-119, 13-120, 13-121, 13-122, 13-123, 13-129, 13-149, 13-150, 17-2, 23-46, 23-92, 23-171, 40-1, 40-2, 43-2, 47-6, 49-1, 49-2

(3) Compounds (Example Number) Showing Cell Death-Inducing Activity at a Concentration of 0.1 μM Examples 9-3, 9-18, 9-35, 9-46, 9-53, 9-68, 9-70, 9-75, 9-79, 9-80, 9-83, 9-88, 9-90, 9-100, 9-101, 9-104, 9-111, 9-112, 9-115, 9-120, 9-126, 9-127, 9-131, 9-133, 9-142, 9-146, 9-152, 9-156, 9-157, 9-162, 9-168, 9-175, 9-177, 9-185, 9-210, 9-214, 9-215, 9-220, 9-236, 9-242, 9-243, 9-246, 9-252, 9-253, 9-256, 9-257, 9-268, 9-269, 9-270, 9-271, 9-284, 9-285, 9-286, 9-290, 9-293, 9-295, 9-302, 9-343, 9-348, 9-350, 9-352, 9-353, 9-356, 9-361, 9-366, 9-368, 9-370, 9-374, 9-375, 9-376, 13-1, 13-3, 13-5, 13-12, 13-13, 13-21, 13-30, 13-33, 13-44, 13-45, 13-48, 13-49, 13-53, 13-54, 13-56, 13-67, 13-77, 13-78, 13-91, 13-96, 13-114, 13-115, 13-117, 13-127, 13-135, 16-1, 16-6, 16-8, 16-11, 16-13, 16-19, 16-20, 16-24, 16-25, 17-1, 21-25, 22-9, 22-10, 23-2, 23-4, 23-7, 23-12, 23-14, 23-15, 23-16, 23-17, 23-44, 23-48, 23-50, 23-53, 23-68, 23-70, 23-73, 23-74, 23-78, 23-79, 23-82, 23-83, 23-84, 23-88, 23-90, 23-91, 23-93, 23-95, 23-97, 23-98, 23-120, 23-122, 23-123, 23-124, 23-145, 23-149, 23-153, 23-156, 23-157, 23-158, 23-159, 23-160, 24-3, 27-7, 27-8, 27-10, 27-13, 37-1, 39-1, 40-3, 43-1, 43-3, 45-5, 45-7, 47-1, 47-5, 47-11

(4) Compounds (Example Number) Showing Cell Death-Inducing Activity at a Concentration of 1 μM Examples 9-2, 9-12, 9-30, 9-31, 9-32, 9-43, 9-44, 9-45, 9-54, 9-66, 9-69, 9-72, 9-74, 9-84, 9-85, 9-99, 9-109, 9-110, 9-121, 9-122, 9-125, 9-148, 9-149, 9-151, 9-158, 9-183, 9-184, 9-186, 9-192, 9-193, 9-200, 9-203, 9-205, 9-216, 9-231, 9-240, 9-244, 9-254, 9-255, 9-263, 9-264, 9-265, 9-266, 9-274, 9-275, 9-276, 9-279, 9-288, 9-289, 9-294, 9-296, 9-303, 9-304, 9-305, 9-342, 9-347, 9-351, 9-354, 9-355, 9-363, 9-367, 9-369, 9-371, 10-2, 13-19, 13-20, 13-23, 13-27, 13-31, 13-39, 13-41, 13-57, 13-68, 13-71, 13-72, 13-93, 13-94, 13-125, 13-128, 13-130, 13-131, 13-132, 16-3, 16-4, 16-7, 16-10, 16-12, 16-15, 16-16, 16-17, 16-18, 16-21, 16-22, 16-23, 17-3, 18-1, 18-2, 21-7, 21-9, 21-11, 21-19, 21-20, 21-21, 21-22, 22-3, 22-6, 22-8, 23-8, 23-13, 23-22, 23-23, 23-26, 23-28, 23-34, 23-38, 23-41, 23-43, 23-45, 23-47, 23-52, 23-55, 23-61, 23-65, 23-66, 23-67, 23-71, 23-72, 23-75, 23-76, 23-77, 23-80, 23-85, 23-89, 23-94, 23-100, 23-104, 23-106, 23-110, 23-115, 23-116, 23-117, 23-118, 23-121, 23-125, 23-126, 23-127, 23-128, 23-130, 23-131, 23-134, 23-135, 23-136, 23-137, 23-139, 23-140, 23-141, 23-142, 23-143, 23-147, 23-161, 23-162, 23-165, 23-166, 23-167, 23-168, 23-171, 23-172, 24-1, 24-2, 27-4, 27-5, 27-9, 27-12, 29-1, 29-2, 30-2, 34-1, 36-1, 36-2, 37-2, 37-3, 37-4, 38-1, 42-1, 42-2, 43-4, 45-2, 45-6, 47-2, 47-8, 49-5, 49-6, 49-7, 49-8

(5) Compounds (Example Number) Showing Cell Death-Inducing Activity at a Concentration of 10 μM Examples 9-5, 9-7, 9-8, 9-11, 9-21, 9-29, 9-50, 9-55, 9-116, 9-118, 9-119, 9-124, 9-178, 9-179, 9-191, 9-195, 9-196, 9-204, 9-211, 9-212, 9-238, 9-241, 9-273, 9-277, 9-278, 9-297, 9-298, 9-306, 9-309, 9-311, 9-313, 9-320, 9-321, 9-324, 9-335, 9-337, 9-338, 9-339, 13-22, 13-36, 13-46, 13-61, 13-66, 13-70, 13-73, 13-124, 13-126, 13-137, 13-141, 13-144, 16-2, 16-5, 16-9, 16-14, 17-4, 19-1, 19-2, 20-1, 21-2, 21-6, 21-8, 21-13, 21-15, 21-17, 21-18, 22-1, 22-4, 22-7, 23-1, 23-5, 23-6, 23-10, 23-11, 23-18, 23-19, 23-20, 23-21, 23-24, 23-27, 23-30, 23-35, 23-40, 23-42, 23-51, 23-57, 23-59, 23-60, 23-81, 23-86, 23-101, 23-102, 23-103, 23-105, 23-107, 23-108, 23-113, 23-119, 23-129, 23-132, 23-133, 23-138, 23-150, 23-152, 23-154, 23-163, 23-169, 23-170, 25-1, 25-2, 25-3, 25-4, 25-5, 26-1, 26-2, 26-3, 27-1, 27-2, 27-3, 27-6, 27-11, 27-14, 27-15, 27-16, 28-1, 30-1, 31-1, 36-3, 36-4, 36-5, 38-2, 38-3, 41-1, 45-1, 45-3, 45-4, 47-10, 47-12, 49-3, 49-4

As apparent from the results, the compound represented by the formula (1) or the salt thereof showed the cell death-inducing activity at each concentration. Further, for the compound represented by the formula (1) or the salt thereof, the $IC_{50}$ values on various cancer cell lines can be calculated by the method of Test Example 2 or other methods.

Test Example 2

Calculation of $IC_{50}$ Value

Human prostate cancer cell lines (PC-3 cells) and human fibrosarcoma cell lines (HT1080 cells) were seeded to 96-well microplates so as to provide a density of 1,300 cells/well and that of 3,100 cells/well, respectively. In the presence of 5% $CO_2$ at 37° C., the PC-3 cells and the HT1080 cells were cultured for 48 hours and 24 hours, respectively. Thereafter, each one of test substances was added to each well. As a control of a medical agent, DMSO was added. After the addition, both cells were continuously cultured for 72 hours. Then, an XTT labeling reagent containing 1 mg/mL of sodium 3'-[1-(phenylaminocarbonyl)-3,4-tetrazolium]-bis (4-methoxy-6-nitro)benzenesulfonate hydrate (XTT) and an electronic coupling reagent containing 1.25 mM N-methyl dibenzopyrazine methyl sulfate (PMS) were mixed at a ratio of 50:1 to give an XTT labeling mixture. The XTT labeling mixture was added to each well in an amount of 50 µL per well, and the cells were cultured for another 4 hours. A culture solution containing a test substance was used as a blank, and the absorbencies of a culture solution containing the XTT labeling mixture at a measurement wavelength (450 nm) and a control wavelength (650 nm) were measured by a plate reader. The difference between these absorbencies was evaluated as an activity of dehydrogenase of mitochondria derived from living cells. With respect to the following model formula of sigmoid curve, the convergent solution of each variable (gain, range, base and $\alpha$) that minimize the residual sum of squares of the difference between these absorbencies and regressive prediction was determined, and then $IC_{50}$ ($=e^\alpha$) of each test substance was calculated.

$$\text{Difference between absorbencies} = \frac{\text{range}}{1 + e^{gain \cdot (ln(\text{Test substance concentration}) - \alpha)}} + \text{base}$$

The $IC_{50}$ values of the compounds represented by the formula (1) or the salts thereof on two cancer cell lines according to the method of Test Example 2 were calculated, and the results are shown in Table A.

TABLE A

| | Cell proliferation inhibitory activity ($IC_{50}$ value calculated from XTT assay) | |
|---|---|---|
| | Concentration showing 50% inhibitory activity (nmol/L) | |
| Compound number | Human prostate cancer cell lines (PC-3) | Human fibrosarcoma cell lines (HT1080) |
| 9-1 | 6.70 | 15.1 |
| 9-25 | 0.81 | 1.64 |
| 9-57 | 2.17 | — |
| 9-94 | 0.56 | 1.75 |
| 9-155 | 6.77 | — |
| 13-53 | 6.35 | — |
| 13-90 | 0.43 | — |
| 13-101 | 1.64 | 4.19 |

As apparent from Table A, the compounds represented by the formula (1) or the salts thereof have a strong cell proliferation inhibitory activity to the cancer cell lines, which suggests the usefulness of the compounds or salts thereof as antitumor agents.

Test Example 3

Measurement of Expression Kinetics of $p27^{Kip1}$ and Other Substrate Proteins

The possibility that $p21^{Cip1}$, $p57^{Kip2}$ and CyclinD1 are substrate proteins of $SCF^{Skp2}$ has been reported. While, there is also a report that gives a suggestion that these proteins may be substrates of another E3. The following suggestions about Nrf2 have been given: the progressive expression of Nrf2 is an index of the acquirement of resistance by an existing drug (anticancer agent), and Nrf2 is a substrate protein of another E3. Thus, in order to verify that the compounds represented by the formula (1) or the salts thereof are $p27^{Kip1}$-selective degradation inhibitors, these molecules in addition to $p27^{Kip1}$ were used as objects of analysis.

PC-3 cells in logarithmic growth phase (48 hours after seeding) were treated with 10 to 25 nmol/L of each test substance, then the cells were collected with time, and the protein was extracted and determined quantitatively. The protein groups contained in each extract (the amount of protein: 10 to 15 µg) were separated by polyacrylamide gel electrophoresis and then transferred to a PVDF (polyvinylidene difluoride) membrane. The proteins in the membrane were allowed to react with various primary antibodies to $p27^{Kip1}$, $p21^{Cip1}$, $p57^{Kip2}$, CyclinD1, Nrf2 and β-actin at a room temperature for about 2 hours, then allowed to further react with a biotinylated secondary antibody at a room temperature for one hour, and then allowed to react with streptavidin alkaline phosphatase at a room temperature for 30 minutes. As the final step, the proteins in the membrane were detected by allowing to react with a chemiluminescent substrate containing disodium 4-chloro-3-(methoxyspiro{1,2-dioxetadioxetane-3,2'-(5'-chloro)tricyclo[$3.3.1.1^{3,7}$]decan}-4-yl)phenylphosphate.

Results

Figure 2:
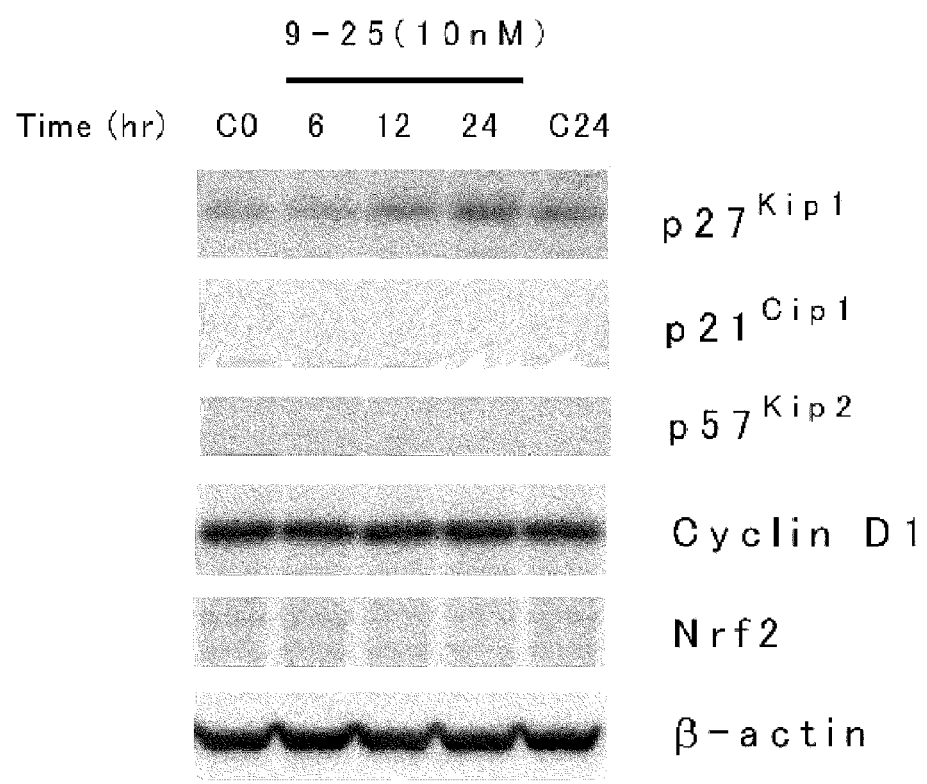
FIG. 2 shows results of the compound of Example 9-25 in Test Example 3.
Figure 3:
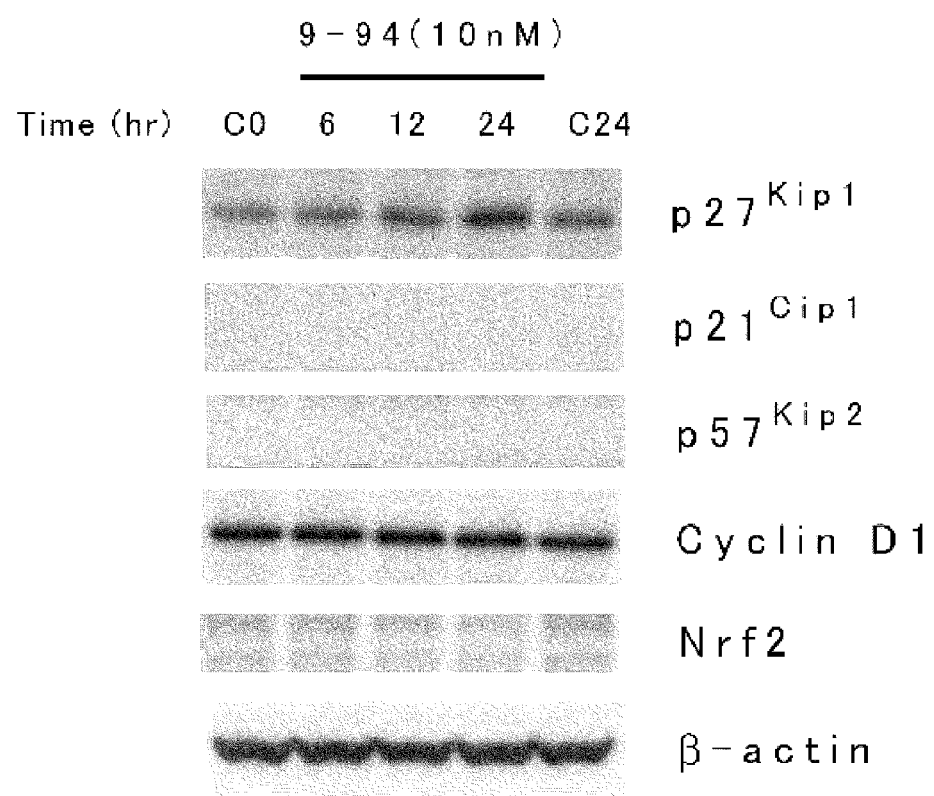
FIG. 3 shows results of the compound of Example 9-94 in Test Example 3.
Figure 4:
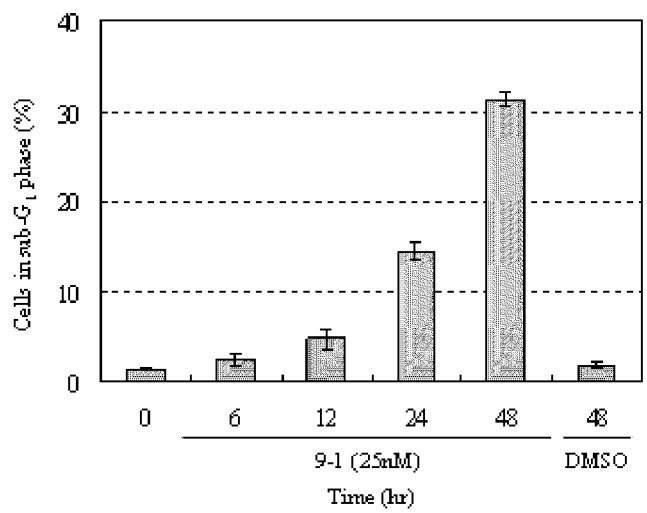
FIG. 4 is a graph showing results of the compound of Example 9-1 in Test Example 4.
Figure 5:
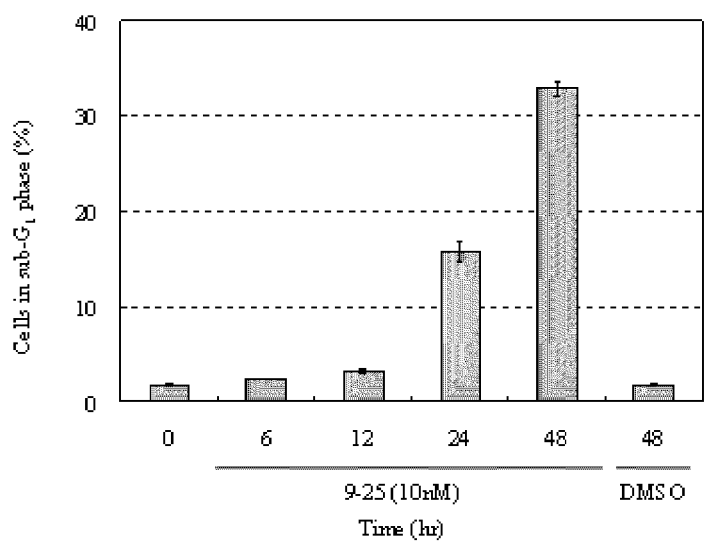
FIG. 5 is a graph showing results of the compound of Example 9-25 in Test Example 4.
Figure 6:
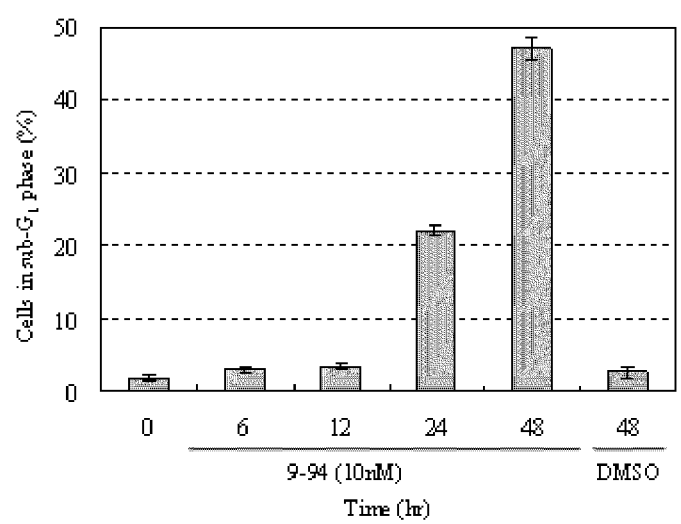
FIG. 6 is a graph showing results of the compound of Example 9-94 in Test Example 4.

As apparent from FIG. 1 to FIG. 3, the compounds represented by the formula (1) or the salts thereof increased only the expression amount of $p27^{Kip1}$ with time without affecting the expression amounts of other analyzed substrate proteins.

Test Example 4

Analysis of Cell Death-Inducing Action

Human prostate cancer cell lines (PC-3 cells) in logarithmic growth phase (48 hours after seeding) were treated with the compound represented by the formula (1) or the salt thereof, then the cells were collected with time and suspended in 70% ethanol. Thereafter, the cells in the suspension were allowed to stand at −20° C. overnight or more to be immobilized. The immobilized cells were washed with PBS twice, 100 µL of 192 mmol/L of disodium hydrogen phosphate and 4 mmol/L of a citric acid solution were added thereto, and the cells were suspended. The resulting suspension was gently stirred at a room temperature for 30 minutes. After centrifugation, the supernatant was removed. Then, 100 µL of a 100 µg/mL RNase/PBS solution was added to the residue, and the residue was suspended. The resulting suspension was incubated at 37° C. for 30 minutes. To the suspension, 850 µL of PBS was added, and then 50 µL of a 1 mg/mL propidium iodide/PBS solution were added thereto. The reaction was conducted at a room temperature for 30 minutes while gently stirring the mixture by inverting, and then the reaction mixture was filtered through a mesh filter to give an analysis sample. Using a flow cytometer, the ratio of sub-$G_1$ cells*, as an index of apoptosis cells, was analyzed.

*Darzynkiewicz Z, et al. Cytometry, 27: 1-20, (1997) (This paper defines that the sub-$G_1$ cell is an index of an apoptosis cell.)

Results

As apparent from FIG. 1 to FIG. 6, the results suggest that the compounds represented by the formula (1) or the salts thereof selectively increase the expression amount of $p27^{Kip1}$ and then induce apoptosis.

Test Example 5

Tumor Growth Inhibitory Effect Test Using Tumor Model 0.1 mL ($2 \times 10^5$ cells/body) of human prostate cancer cell lines PC-3 was transplanted into the right infra-axillary dermis of male 6-week-old nude mice. From 3 days after the transplantation, Vehicle or any one of the following compounds was orally administered repeatedly twice a day for 11 days. Fourteenth (14) days after the transplantation, the major axis and minor axis of the tumor were measured, and the efficacy of each compound was evaluated on the basis of the tumor volume (major axis×minor axis×height×0.5236).

Results

At a dose of not more than 1 mg/kg, the following compounds (Example numbers) showed an antitumor effect at an inhibitory ratio of not less than 50% compared with the Vehicle group.

Examples 9-1, 9-25, 9-57, 9-94, 9-145, 9-155, 9-157, 9-213, 9-247, 9-281, 13-53, 13-81, 13-90, 13-100, 13-101

Test Examples 1 to 5 suggest that the $p27^{Kip1}$ degradation inhibitor containing the compound represented by the formula (1) or the pharmaceutically acceptable salt thereof as an effective ingredient has a tumor growth inhibitory effect.

Preparation Examples

Solid Preparation for Oral Administration

| Formulation example: | mg/tablet |
|---|---|
| Active ingredient | 5.0 |
| Starch | 10.0 |
| Lactose | 73.0 |
| Carboxymethyl cellulose calcium | 10.0 |
| Talc | 1.0 |
| Magnesium stearate | 1.0 |
| Total amount | 100.0 |

Granule

The active ingredient [the compound represented by the formula (1) or the salt thereof] was pulverized to a grain size of not more than 70 μm, and a starch, a lactose and a carboxymethyl cellulose calcium were mixed with the pulverized powder fully. Thereafter, 10% starch glue was mixed with the mixture powder under stirring, and the resulting mixture was subjected to wet granulation to give a granule.

Tablet

The particle size of the granule obtained by the above step was sized around 1000 μm, and a talc and magnesium stearate were mixed thereto. The resulting mixture was subjected to tablet compression to give a tablet.

Capsule

The granule obtained by the above step was filled into a hard capsule shell to give a capsule.

Injectable Solution

The active ingredient [the compound represented by the formula (1) or the salt thereof] (50 mg) was dissolved in 100 ml of a physiological saline containing ethanol as a solubilizing agent, and the resulting solution was filled in a container. The container was sealed. Then, the sealed container was sterilized to give an injectable solution.

INDUSTRIAL APPLICABILITY

The compound or the salt thereof of the present invention specifically binds to Skp2 of ubiquitin ligase ($SCF^{Skp2}$) and, for example, inhibits the dissociation of $p27^{Kip1}$ from $SCF$-$^{Skp2}$ complex. Thus the compound or the salt thereof of the present invention is useful as an inhibitor for the ubiquitination and degradation of $p27^{Kip1}$. Moreover, since the compound or the salt thereof of the present invention can recover the expression amount of $p27^{Kip1}$ in cells having a decreased expression of $p27^{Kip1}$ to induce cell death (apoptosis), the compound or the salt thereof is also useful as an agent for preventing and/or treating a cell proliferative disease (for example, cancer, rheumatism, diabetes, adiposis, endometriosis, prostatomegaly, and inflammation). In particular, the possible application of the compound or the salt thereof as an anticancer agent to not only a cancer of the prostate but also a highly malignant solid cancer (e.g., a cancer of the lung, a cancer of the large intestine, a cancer of the liver, a cancer of the stomach, a cancer of the uterus, a cancer of the ovary, a cancer of the breast, and an oral squamous cell cancer, encephaloma) or a blood cancer is expected.

The invention claimed is:

1. A compound represented by formula (6-b) or formula (6-c):

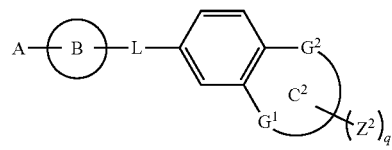

(6-b)

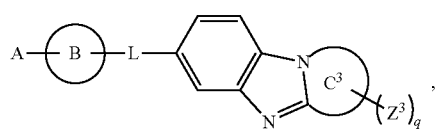

(6-c)

wherein A is a phenyl group having substituent(s) on the 2-position, the 4-position, or both of the 2-position and the 4-position independently selected from the group consisting of a halogen atom, an alkyl group, a haloalkyl group, a hydroxyl group, an alkoxy group, a haloalkoxy group, a mercapto group and an alkylthio group;

the ring B is a heterocyclic ring represented by any one of the following formulas (3-a), (3-b), (3-d), (3-h) and (3-k),

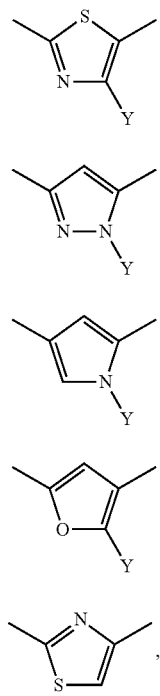

(3-a)

(3-b)

(3-d)

(3-h)

(3-k)

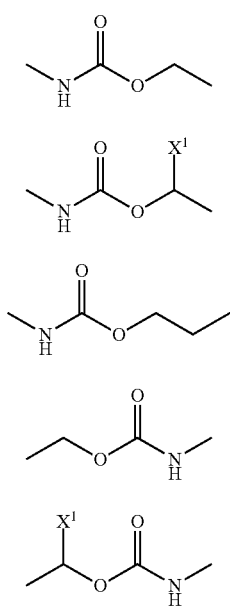

wherein Y is a hydrogen atom, an alkyl group, a haloalkyl group, a cycloalkyl group, an aryl group, an aralkyl group or an acyl group;

L is a linker represented by any one of the following formulas (1-a1), (1-a2), (1-a3), (1-a4), (1-a5), (1-a6), (1-b1), (1-b2), (1-c1), (1-c2) and (1-c3)

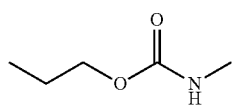

(1-a1)

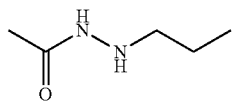

(1-a2)

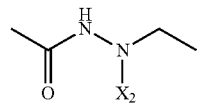

(1-a3)

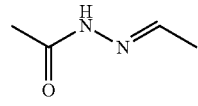

(1-a4)

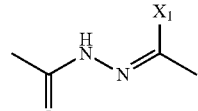

(1-a5)

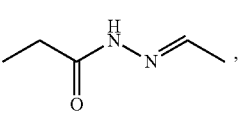

(1-a6)

(1-b1)

(1-b2)

(1-c1)

(1-c2)

(1-c3)

wherein $X^1$ is an alkyl group, and $X^2$ is an alkyl group or an acyl group;

the ring $C^2$ is a 5- to 8-membered heterocyclic ring containing $G^1$ and $G^2$, wherein the ring $C^2$ contains at least one heteroatom selected from the group consisting of N and O;

the ring $C^3$ is a 5- to 8-membered heterocyclic ring containing the N from the adjacent ring and optionally one or more additional heteroatoms selected from the group consisting of N and O;

$G^1$ is N, CH or $CH_2$;

$G^2$ is N, O or NH;

$Z^2$ is an alkyl group or an acyl group;

$Z^3$ is an alkyl group or an acyl group; and q is an integer of 0 to 6; or a pharmaceutically acceptable salt thereof.

2. The compound according to claim 1, wherein the ring B is a heterocyclic ring represented by any one of the following formulas (3-a), (3-b) and (3-d):

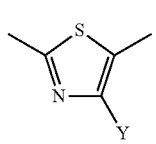

(3-a)

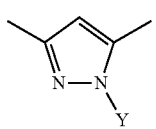

(3-b)

-continued

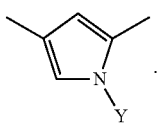
(3-d)

3. The compound according to claim 1, wherein the ring B is a heterocyclic ring represented by any one of the following formulas (3-a) and (3-b):

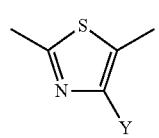
(3-a)

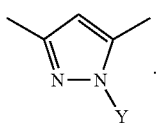
(3-b)

4. A pharmaceutical composition comprising:
a compound according to claim 1 or a pharmaceutically acceptable salt thereof, and a pharmaceutically acceptable carrier.

5. A $p27^{Kip1}$ ubiquitination inhibitor comprising, as an effective ingredient, a compound according to claim 1 or a pharmaceutically acceptable salt thereof.

6. A method for treating a cell proliferative disease, which comprises administering, as an effective ingredient, a compound according to claim 1, or a pharmaceutically acceptable salt thereof, to a subject having the cell proliferative disease,
wherein the cell proliferative disease is selected from the group consisting of cancer, rheumatism, diabetes, adiposis, endometriosis, prostatomegaly and inflammation, and
wherein the cancer is at least one selected from the group consisting of (1) prostate cancer, (2) fibrosarcoma, (3) an encephaloma, (4) an oral squamous cell cancer, (5) a lung cancer, (6) a cancer of the stomach, (7) a cancer of the large intestine, (8) a cancer of the liver, (9) a cancer of the bladder, (10) a cancer of the breast, (11) a cancer of the uterus, (12) a cancer of the uterine cervix, (13) a cancer of the ovary, and (14) a blood cancer.

7. A method for treating a cell proliferative disease, which comprises administering, as an effective ingredient, a compound according to claim 1, or a pharmaceutically acceptable salt thereof, to a subject having the cell proliferative disease in which cells have a decreased expression of $p27^{Kip1}$.

* * * * *